(12) United States Patent
Whitten et al.

(10) Patent No.: US 7,507,727 B2
(45) Date of Patent: Mar. 24, 2009

(54) SUBSTITUTED QUINOBENZOXAZINE ANALOGS AND METHODS OF USING THEREOF

(75) Inventors: Jeffrey P. Whitten, Santee, CA (US); Michael Schwaebe, San Diego, CA (US); Adam Siddiqui-Jain, San Diego, CA (US); Terence Moran, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 389 days.

(21) Appl. No.: 11/106,909

(22) Filed: Apr. 15, 2005

(65) Prior Publication Data
US 2006/0029950 A1  Feb. 9, 2006

Related U.S. Application Data

(63) Continuation-in-part of application No. 10/903,975, filed on Jul. 30, 2004, which is a continuation-in-part of application No. 10/821,243, filed on Apr. 7, 2004, now Pat. No. 7,141,565.

(60) Provisional application No. 60/461,271, filed on Apr. 7, 2003, provisional application No. 60/463,171, filed on Apr. 15, 2003, provisional application No. 60/519,535, filed on Nov. 12, 2003, provisional application No. 60/532,727, filed on Dec. 23, 2003.

(51) Int. Cl.
*A01N 43/00* (2006.01)
*A61K 49/00* (2006.01)
*C12Q 1/68* (2006.01)

(52) U.S. Cl. ............... 514/183; 435/6; 424/9.2
(58) Field of Classification Search ............ 435/6; 424/9.2; 514/183
See application file for complete search history.

(56) References Cited

U.S. PATENT DOCUMENTS
4,533,663 A   8/1985 Chu
(Continued)

FOREIGN PATENT DOCUMENTS
EP    0 160 284    11/1985
(Continued)

OTHER PUBLICATIONS
Banker et al., "Modern Pharmaceutics, 3rd ed." Marcel Dekker, New York (1996) pp. 451-596.
(Continued)

*Primary Examiner*—Jezia Riley
(74) *Attorney, Agent, or Firm*—Morrison & Foerster LLP

(57) ABSTRACT

The present invention relates to quinobenzoxazines analogs having the general formula:

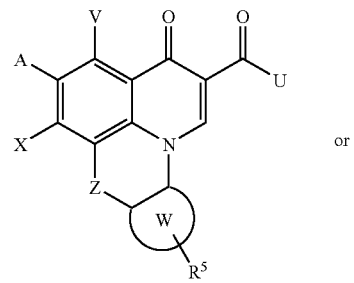

(1)

or

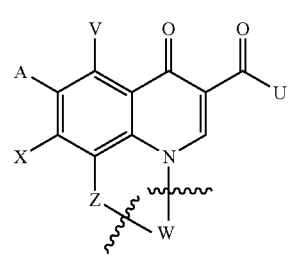

(2)

and pharmaceutically acceptable salts, esters and prodrugs thereof;
wherein V, A, X, Z, W, U and $R^5$ are substituents.

The present invention also relates to methods for using such compounds, such as in screening and for inducing apoptosis.

9 Claims, 16 Drawing Sheets

U.S. PATENT DOCUMENTS

| | | |
|---|---|---|
| 4,559,157 A | 12/1985 | Smith |
| 4,607,032 A | 8/1986 | Chu et al. |
| 4,608,392 A | 8/1986 | Jacquet |
| 4,725,595 A | 2/1988 | Schriewer et al. |
| 4,820,508 A | 4/1989 | Wortzman |
| 4,938,949 A | 7/1990 | Borch |
| 4,992,478 A | 2/1991 | Geria |
| 5,225,418 A | 7/1993 | Miller |
| 5,318,965 A | 6/1994 | Chu |
| 5,624,924 A | 4/1997 | Chu |
| 5,703,055 A | 12/1997 | Felgner |
| 6,214,560 B1 | 4/2001 | Yguerabide |
| 6,528,517 B1 | 3/2003 | Hurley |
| 6,645,981 B2 | 11/2003 | Ledoussal et al. |
| 6,750,224 B1 | 6/2004 | Patel et al. |
| 6,900,224 B2 | 5/2005 | Ledoussal et al. |
| 7,141,565 B1 | 11/2006 | Whitten et al. |
| 2002/0049223 A1 | 4/2002 | Elmore et al. |
| 2003/0232818 A1 | 12/2003 | Anderson et al. |
| 2004/0029882 A1 | 2/2004 | Ledoussal et al. |
| 2004/0072817 A1 | 4/2004 | Anderson et al. |
| 2005/0159423 A1 | 7/2005 | Anderson et al. |

FOREIGN PATENT DOCUMENTS

| | | |
|---|---|---|
| EP | 0 162 333 | 11/1985 |
| EP | 0 229 635 | 7/1987 |
| JP | 02040379 | 2/1990 |
| WO | WO-92/03136 | 3/1992 |
| WO | WO-99/40093 | 8/1999 |
| WO | WO-2004/014893 | 2/2004 |
| WO | WO-2004/091504 | 10/2004 |
| WO | WO-2004/091627 | 10/2004 |

OTHER PUBLICATIONS

Cecil Textbook of Medicine (20th Edition, vol. 2, 1996, pp. 1739-1747).
Dermer, Bio/Technology (1994) 12:320.
Freshney, "Culture of Animal Cells, A Manual of Basic Technique" Alan R. Liss, Inc., (1983) New York, p. 4.
Wolff, "Burger's Medicinal Chemistry, 5th ed., Part 1" John Wiley & Sons, 1995, pp. 975-977.
International Search Report for PCT/US2005/026977, mailed on Jul. 3, 2006, 5 pages.
Supplementary Partial European Search Report for EP 04759406.4, mailed on Nov. 14, 2006, 5 pages.
Supplementary European Search Report for EP 04 75 9406, mailed on Mar. 19, 2007; 5 pages.
Anantha et al., Biochemistry (1998) 37:2709-2714.
Ansell et al., Current Opinion in Biotechnology (1996) 7:89-94.
Berge et al., J. Pharm. Sci. (1977) 66:1-19.
Datta et al., JACS (2001) 123:9612-9619.
Gibson et al., Genome Res. (1996) 6:995-1001.
Han et al., Nucl. Acids Res. (1999) 27:537-542.
Han et al., Trends Pharm. Sci. (2000) 21:136-142.
He et al., Science (1998) 281:1509-1512.
Heid et al., Genome Res. (1996) 6:986-994.
Henegariu et al., Nature Biotech (2000) 18:345-348.
Jin and Pike, Mol. Endocrinol. (1996) 10:196-205.
Kim et al., J. of Medicinal Chemistry (2003) 46(4):571-583.
Kriz et al., Analytical Chemistry (1995) 67:2142-2144.
Qu and Chaires, Methods Enzymol (2000) 321:353-369.
Shea, Trends in Polymer Science (1994) 2:166-173.
Tomita et al., J. Med. Chem. (2002) 45:5564-5575.
Vaickus, Crit. Rev. in Oncol./Hemotol. (1991) 11:267-297.
Vlatakis et al., Nature (1993) 361:645-647.
Wang et al., Methods Cell Sci (1996) 18:249-255.
Weitzmann et al., J. Biol. Chem (1996) 271:20958-20964.
Zeng et al., J. Med. Chem. (1998) 41:4273-4278.

Selectivity Plot

Stop Plot

SUBSTITUTED QUINOBENZOXAZINE ANALOGS AND METHODS OF USING THEREOF

CROSS-REFERENCE TO RELATED APPLICATIONS

This application is a continuation-in-part of U.S. patent application Ser. No. 10/903,975, filed Jul. 30, 2004, which is a continuation-in-part of U.S. patent application Ser. No. 10/821,243, filed Apr. 7, 2004, which claims the benefit of U.S. provisional application 60/461,271, filed Apr. 7, 2003; U.S. provisional application 60/463,171, filed Apr. 15, 2003; U.S. provisional application 60/519,535, filed Nov. 12, 2003; and U.S. provisional application 60/532,727, filed Dec. 23, 2003. The contents of these documents are incorporated herein by reference.

FIELD OF THE INVENTION

The invention relates to substituted quinobenzoxazines analogs, and methods of using such compounds.

BACKGROUND

Quadruplexes can form in certain purine-rich strands of nucleic acids. In duplex nucleic acids, certain purine rich strands are capable of engaging in a slow equilibrium between a typical duplex helix structure and in unwound and non-B-form regions. These unwound and non-B forms can be referred to as "paranemic structures." Some forms are associated with sensitivity to S1 nuclease digestion, which can be referred to as "nuclease hypersensitivity elements" or "NHEs." A quadruplex is one type of paranemic structure and certain NHEs can adopt a quadruplex structure. Considerable circumstantial evidence suggests that quadruplex structures can exist in vivo in specific regions of the genome, including the telomeric ends of chromosomes and oncogene regulatory regions. (Han, et al., *Trends Pharm. Sci.* (2000) 21:136-142). Thus, quadruplex forming regions of DNA may be used as molecular targets for anticancer agents.

SUMMARY OF THE INVENTION

The present invention relates to compounds having formula 1, formula 1A, or formula 2, and methods of using the same. The present invention also encompasses derivatives of compounds having formula 1, formula 1A, or formula 2, with substituents independently selected from compounds in Table 1 (Tables 1A, 1B, 1C and 1D), and methods of using the same.

In one aspect, the present invention provides methods for determining interaction selectivity between a molecule and nucleic acids capable of forming a quadruplex structure, comprising: a) contacting a molecule in the absence of a competitor molecule with three or more nucleic acids capable of forming a quadruplex structure, wherein each nucleic acid is not a telomere nucleic acid; b) measuring a direct interaction between the molecule and said three or more nucleic acids; and c) determining interaction selectivity from a comparison of the interaction measurements. In one example, three or more nucleic acids comprise a nucleotide sequence located 5' of an oncogene nucleotide sequence. The oncogene may be MYC, HIF, VEGF, ABL, TGF, PDGFα, MYB, SPARC, HER, VAV, RET, H-RAS, EGF, SRC, BCL-1, BCL-2, DHFR, or HMGA.

In the above methods, the molecule may be separately contacted with each of said three or more nucleic acids in a different vessel. The interaction selectivity may be determined from a comparison of $IC_{50}$ values. In one example, the molecule may bind and/or stabilize a propeller quadruplex. Examples of propeller quadruplexes include but are not limited to H-RAS, RET, BCL-1, DHFR, TGF-β, HIF-1α, VEGF, c-Myc, or PDGFα. In another example, the molecule may bind and/or stabilize a chair-eller or a basket quadruplex. For example, the molecule may bind and/or stabilize BCL-2.

In one embodiment, the molecule comprises a nucleic acid or an antibody. The nucleic acid may be, for example, an antisense nucleic acid, a ribozyme, an RNAi or siRNA.

In another embodiment, the molecule comprises a compound having formula 1

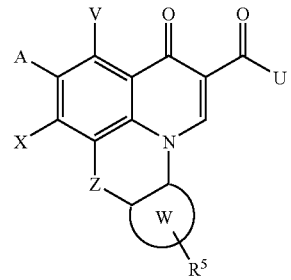

(1)

and pharmaceutically acceptable salts, esters and prodrugs thereof;
wherein V is H, halo, or $NR^1R^2$;
A is H, fluoro, or $NR^1_2$;
Z is O, S, $NR^1$ or $CH_2$;
U is $OR^2$ or $NR^1R^2$;
X is $OR^2$, $NR^1R^2$, halo, azido, or $SR^2$;
n is 1-3;
wherein in $NR^1R^2$, $R^1$ and $R^2$ may form a double bond or a ring, each of which is optionally substituted;
$R^1$ is H or a $C_{1-6}$ alkyl;
$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;
$R^5$ is a substituent at any position on W; and is H, $OR^2$, $C_{1-6}$ alkyl, $C_{2-6}$ alkenyl, each optionally substituted by halo, =O or one or more heteroatoms; or $R^5$ is an inorganic substituent; and
W is an optionally substituted aryl or heteroaryl, which may be monocyclic or fused with a single or multiple ring and optionally containing a heteroatom;
or a compound having formula (2)

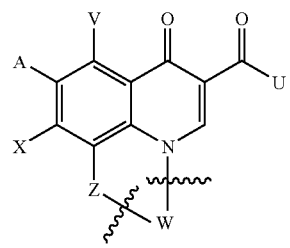

wherein V, A, X, Z and U are as defined in formula 1, and
W is selected from the group consisting of
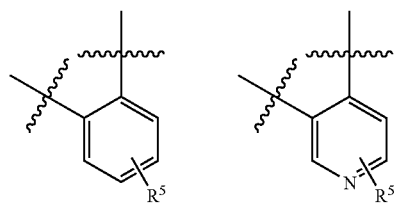
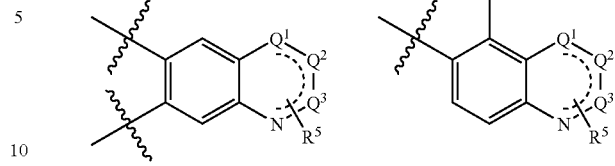
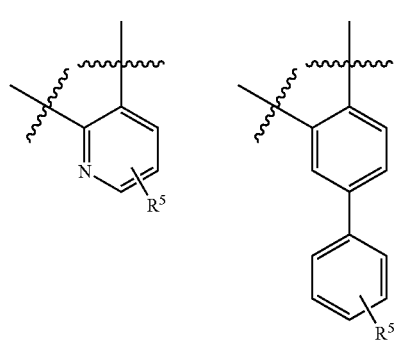
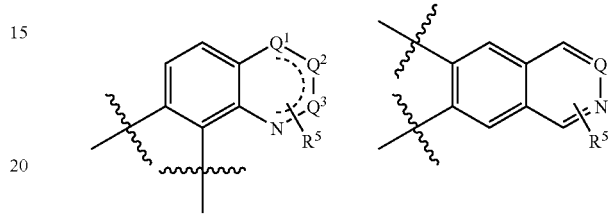
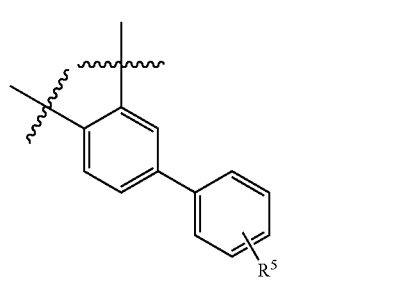
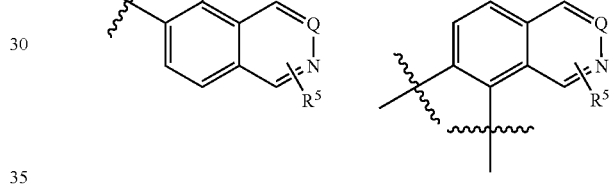
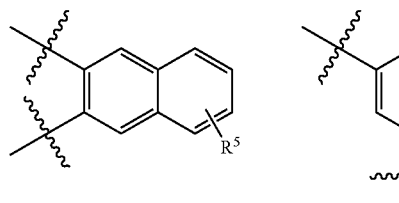
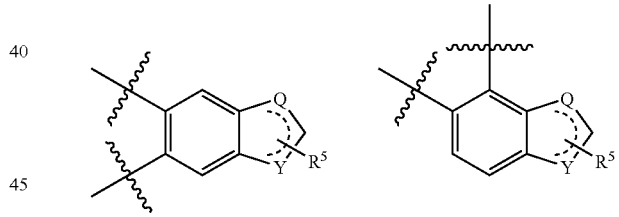
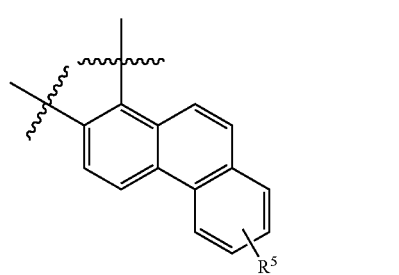
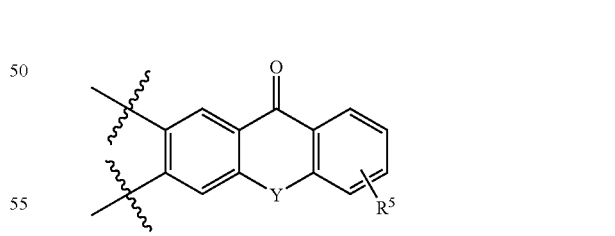
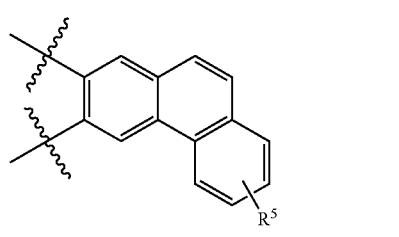
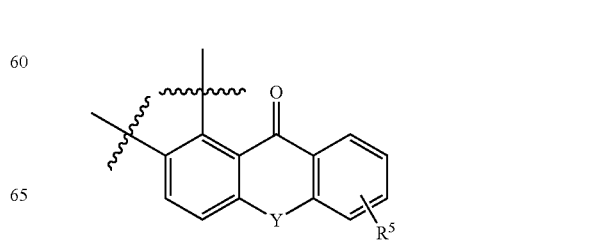

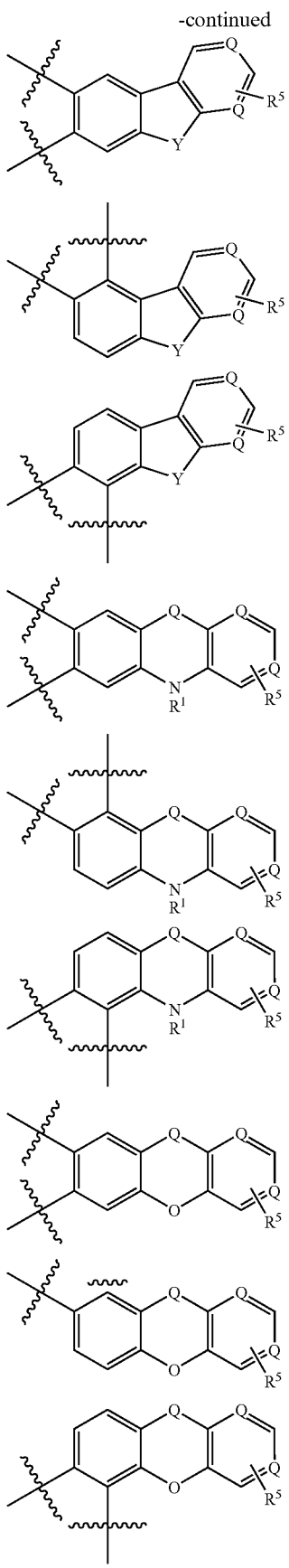

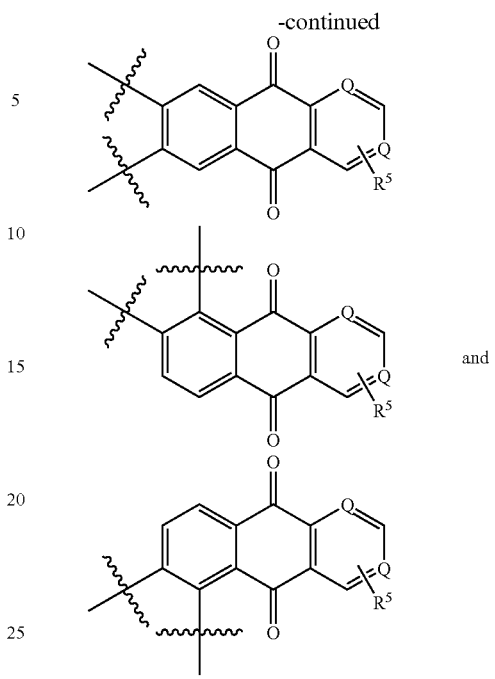

wherein Q, $Q^1$, $Q^2$, and $Q^3$ are independently CH or N;
Y is independently O, CH, =O or $NR^1$; and
$R^5$ is as defined in formula 1.

In yet another embodiment, the molecule comprises a compound having formula (1A)

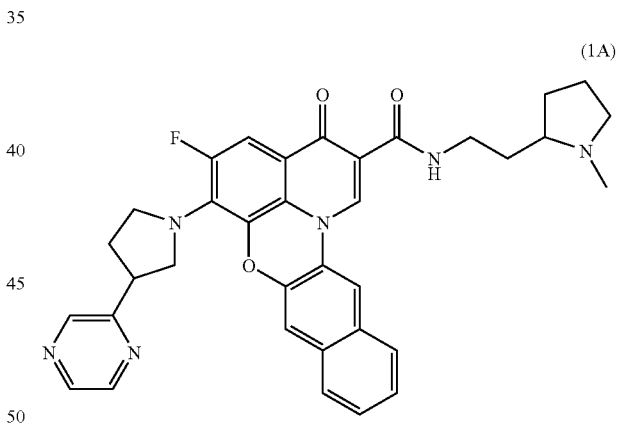

(1A)

and pharmaceutically acceptable salts, esters and prodrugs thereof.

The present invention also provides methods for inducing apoptosis, comprising administering to a system or a subject in need thereof an effective amount of a compound having formula 1, formula 1A, or formula 2, or a pharmaceutical composition thereof and optionally with a chemotherapeutic agent. The present invention also provides methods for treating or ameliorating a disorder mediated by c-Myc overexpression, comprising administering to a system or a subject in need thereof an effective amount of a compound having formula 1, formula 1A, or formula 2, or a pharmaceutical composition thereof and optionally with a chemotherapeutic agent. The subject may be human or an animal, and system may be a cell or a tissue.

Furthermore, the present invention provides pharmaceutical compositions comprising a compound having formula 1A, polyethylene glycol, and propylene glycol in a buffer solution. The polyethylene glycol may comprise PEG 300, for example with a concentration between 5% (w/w) and 10% (w/w). In one embodiment, the concentration of propylene glycol may be between 6% (w/w) and 12% (w/w). In yet another embodiment, the buffer comprises a phosphate buffer.

DEFINITIONS

Figure 1:
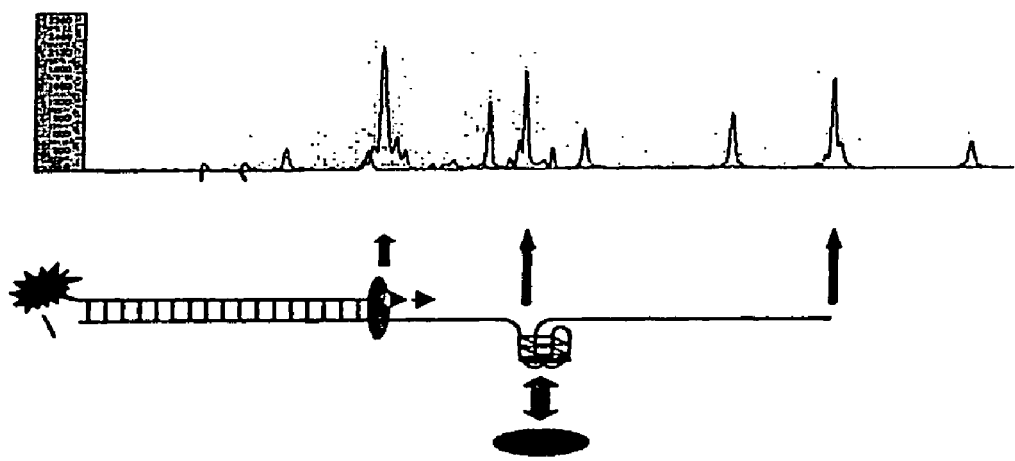
FIG. 1 shows a stop assay as a first pass screen for oncogene inhibitors.

As used herein, the term "alkyl" refers to a carbon-containing compound, and encompasses compounds containing one or more heteroatoms. The term "alkyl" also encompasses alkyls substituted with one or more substituents including but not limited to $OR^1$, amino, amido, halo, =O, aryl, heterocyclic groups, or inorganic substituents.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "aryl" refers to a polyunsaturated, typically aromatic hydrocarbon substituent, whereas a "heteroaryl" or "heteroaromatic" refer to an aromatic ring containing a heteroatom. The aryl and heteroaryl structures encompass compounds having monocyclic, bicyclic or multiple ring systems.

As used herein, the term "heteroatom" refers to any atom that is not carbon or hydrogen, such as nitrogen, oxygen or sulfur.

Illustrative examples of heterocycles-include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "bicyclic compound" refers to a compound having two rings which share a pair of bridgehead carbon atoms. Examples of bicyclic compounds include but are not limited to decalin, norbornane, camphor, and diazabicyclo[2.2.1]heptane.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "chemotherapeutic agent" refers to a therapeutic agent that may be used for treating or ameliorating a cell proliferative disorder such as tumors or cancer. Examples of chemotherapeutic agents include but are not limited to an antineoplastic agent, an alkylating agent, a plant alkaloid, an antimicrobial agent, a sulfonamide, an antiviral agent, a platinum agent, and other anticancer agents known in the art. Particular examples of chemotherapeutic agents include but are not limited to cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See e.g., Goodman & Gilman's, *The Pharmacological Basis of Therapeutics* (9th Ed) (Goodman, et al., eds.) (McGraw-Hill) (1996); and 1999 *Physician's Desk Reference* (1998)).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

DESCRIPTION OF THE INVENTION

The present invention relates to compounds having formula 1, 1A and 2, and pharmaceutically acceptable salts, esters, and prodrugs thereof. The present invention also relates to methods for using the compounds described herein, such as in screening and for inducing apoptosis. The compounds may interact with regions of DNA that can form quadruplexes, and may also be used for treatment of cell proliferative disorders.

In one aspect, the methods of the present invention relate to the use of compounds having formula 1 or 2:

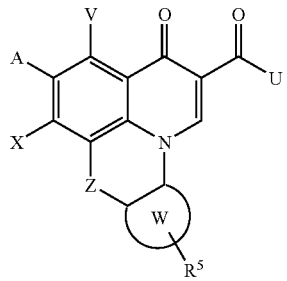

(1)

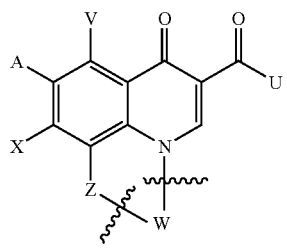

(2)

and pharmaceutically acceptable salts, esters and prodrugs thereof, where A, Z, V, X, W and U are previously described.

In the above formula 1 or 2, A and X may independently be halo. In one example, A and X may independently be fluoro.

In the above formula 1 or 2, V may be H. Alternatively, V may be $NH_2$ or a compound having the formula $NR^1$—$(CR^1_2)_n$—$NR^3R^4$;

wherein $R^1$ and $R^3$ are independently H or $C_{1-6}$ alkyl;
n is 1-6; and
$R^4$ is H, $C_{1-6}$ alkyl optionally substituted with a carbocyclic or heterocyclic ring, or aryl; and wherein in $NR^3R^4$, $R^3$ and $R^4$ may form an optionally substituted ring.

In the above formula 1 or 2, U and X may independently be $NR^1R^2$. In one example, $R^1$ is H and $R^2$ is a $C_{1-10}$ alkyl optionally containing one or more heteroatoms, and optionally substituted with a $C_{3-6}$ cycloalkyl, aryl or a 5-14 membered heterocyclic ring containing one or more N, O or S. In another example, $R^1$ is H and $R^2$ is an aryl or a 5-14 membered heterocyclic ring containing one or more N, O or S, each optionally substituted with an amino or another heterocyclic ring. In yet another example, $R^1$ and $R^2$ in $NR^1R^2$ form an optionally substituted 5-14 membered ring containing one or more N, O or S. For example, $NR^1R^2$ may form pyrrolidine, morpholine, thiomorpholine, piperazine, piperidine or diazepine.

In the above formula 1 or 2, U and X may independently have the formula $$NR^1\text{—}(CR^1_2)n\text{—}NR^3R^4 \qquad (3)$$

wherein $R^1$ and $R^3$ are independently H or $C_{1-6}$ alkyl;
n is 1-6; and
$R^4$ is H or a $C_{1-10}$ alkyl or $C_{2-10}$ alkenyl optionally containing one or more non-adjacent heteroatoms selected from N, O and S, and optionally substituted with a carbocyclic or heterocyclic ring; and wherein in $NR^3R^4$, $R^3$ and $R^4$ may form an optionally substituted ring.

In the above formula 3, n may be 2-3, and $NR^3R^4$ is an acyclic amine, or guanidinyl or a tautomer thereof; or $R^3$ and $R^4$ optionally form a substituted ring containing one or more N, O or S. In particular examples, $NR^3R^4$ is morpholine, thiomorpholine, imidazole, pyrrolidine, piperazine, pyridine or piperidine.

In the above formula 1 or 2, X may be $NR^1R^2$; and U has the formula $$NR^1\text{—}(CR^1_2)_n\text{—}NR^3R^4 \qquad (3)$$

wherein $R^1$ and $R^2$ are as defined in claim 1;
$R^3$ is H or $C_{1-6}$ alkyl;
n is 1-6; and
$R^4$ is H or a $C_{1-10}$ alkyl or $C_{2-10}$ alkenyl optionally containing one or more non-adjacent heteroatoms selected from N, O and S, and optionally substituted with a carbocyclic or heterocyclic ring; and
wherein in $NR^1R^2$ and $NR^3R^4$, $R^1$ and $R^2$, and $R^3$ and $R^4$ each independently may form a substituted ring.

In the above formula 1 or 2 where X is $NR^1R^2$ and U has the formula $NR^1$—$(CR^1_2)_n$—$NR^3R^4$ (2), the $R^1$ and $R^2$ in $NR^1R^2$, and $R^3$ and $R^4$ in $NR^3R^4$ each may independently form a substituted ring containing one or more N, O or S. For example, X is optionally substituted with amino, carbamate, a $C_{1-10}$ alkyl containing one or more non-adjacent N, O or S, and optionally substituted with a heterocyclic ring; aryl or a saturated or unsaturated heterocyclic ring, each of which is optionally substituted. In one example, X and $NR^3R^4$ are independently morpholine, thiomorpholine, imidazole, pyrrolidine, piperazine, pyridine or piperidine. In one example, X and $NR^3R^4$ are independently pyrrolidine. In another example, X is pyrrolidine substituted with pyrazine. In this example, V is H; A is fluoro; and W is naphthalenyl.

Examples of heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1] heptane, and 2,3,4,4a,9,9a-hexahydro-1H-β-carboline.

In the above formula 1 or 2, W may be benzene, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine.

In the above formula 1 or 2, U may be $OR^2$ and $R^2$ is a $C_{1-6}$ alkyl optionally substituted with a carbocyclic or heterocyclic ring.

In the above formula 1 or 2, each optionally substituted moiety is substituted with one or more halo, $OR^2$, $NR^1R^2$, carbamate, $C_{1-10}$ alkyl, $C_{2-10}$ alkenyl, each optionally substituted by halo, =O, aryl or one or more heteroatoms; inorganic substituents, aryl, carbocyclic or a heterocyclic ring.

In another aspect, the methods of the present invention relate to the use of a compound having formula 1A,

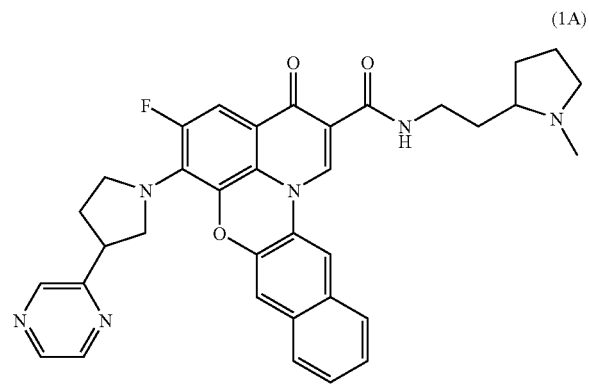

(1A)

which may also be designated as the compound CX-3543.

The compounds may be chiral or achiral. As used herein, a chiral compound is a compound that is different from its mirror image, and has an enantiomer. Methods of synthesizing chiral compounds and resolving a racemic mixture of enantiomers are well known to those skilled in the art. See, e.g., March, "*Advanced Organic Chemistry*," John Wiley and Sons, Inc., New York, (1985), which is incorporated herein by reference. Furthermore, the present invention provides pharmaceutical compositions comprising compounds having formula 1, formula 1A, or formula 2. Illustrative examples of compounds for use in the methods of the present invention are shown in Table 1 (1A, 1B, 1C and 1D).

TABLE 1A

| | Structure | Stop Data c-Myc μM | MTS Data Hella μM |
|---|---|---|---|
| 1 | 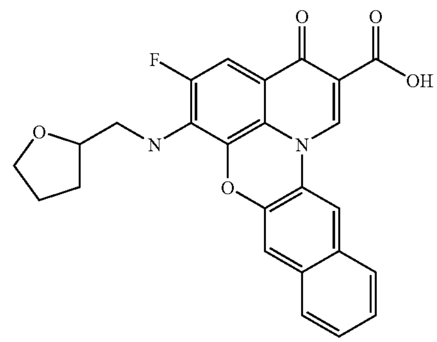 | 4 | |
| 2 | 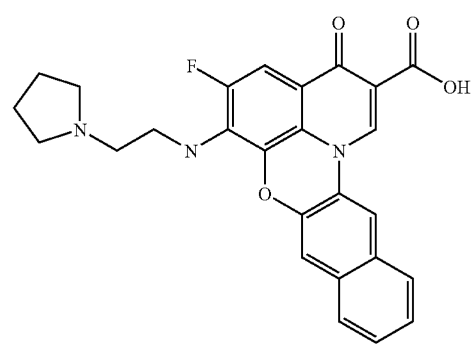 | 2.5 | |
| 3 | 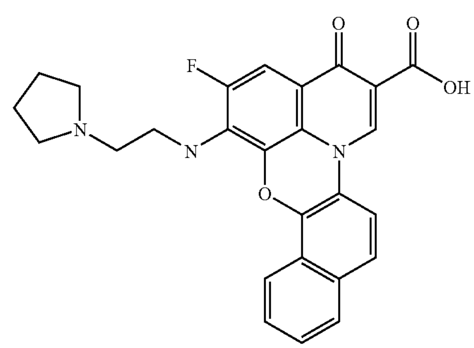 | 2.5 | |

TABLE 1A-continued

| Structure | Stop Data c-Myc μM | MTS Data Hella μM |
|---|---|---|
| 4 [structure] | 1.76 | |
| 5 [structure] | 1.75 | 7.20 |
| 6 [structure] | 1.75 | |
| 7 [structure] | 1.75 | |

TABLE 1A-continued

| Structure | Stop Data c-Myc µM | MTS Data Hella µM |
|---|---|---|
| 8 | | 1.75 |
| 9 | | 1.75 |
| 10 | | 1.75 |

TABLE 1A-continued
| Structure | Stop Data c-Myc μM | MTS Data Hella μM |
|---|---|---|
| 11 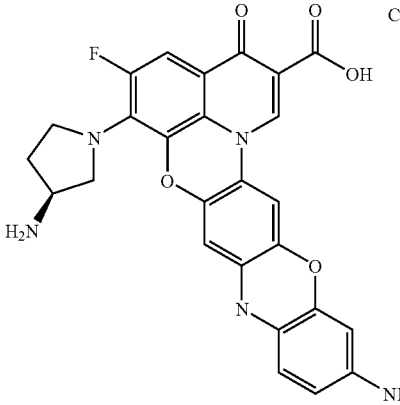 | | 1.75 |
| 12 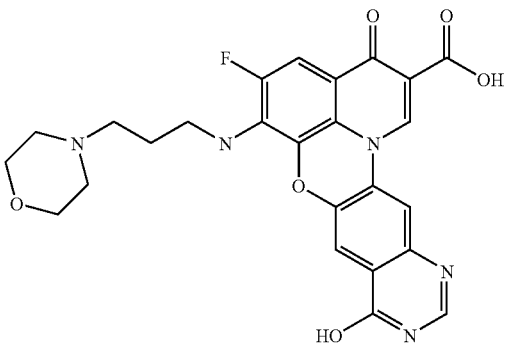 | | 1.75 |
| 13 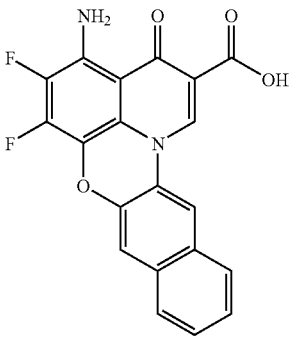 | | 1.75 |
| 14 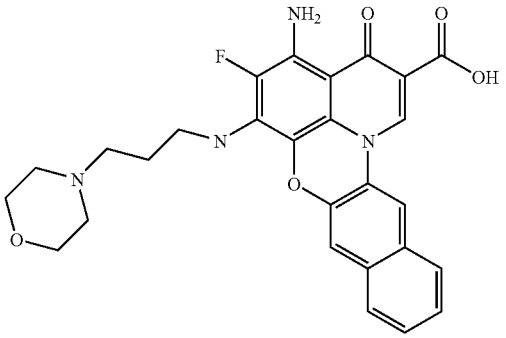 | | 1.75 |

TABLE 1A-continued

| Structure | Stop Data c-Myc µM | MTS Data Hella µM |
|---|---|---|
| 15 [structure] | 1.75 | |
| 16 [structure] | 0.9 | |
| 17 [structure] | 0.75 | |
| 18 [structure] | 0.75 | |

TABLE 1A-continued
| Structure | Stop Data c-Myc μM | MTS Data Hella μM |
|---|---|---|
| 19 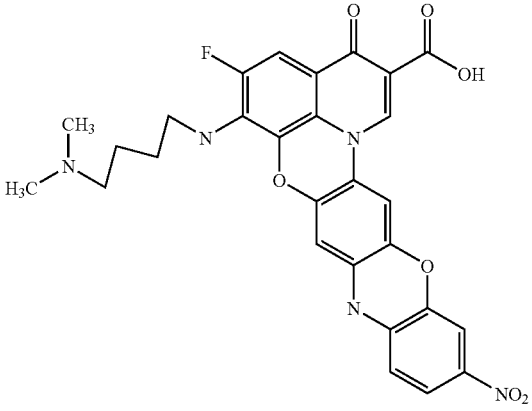 | | 0.75 |
| 20 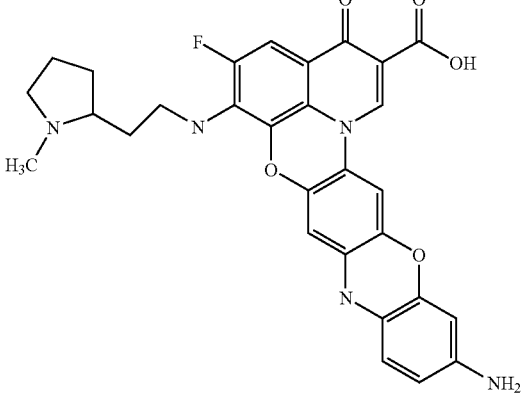 | | 0.75 |
| 21 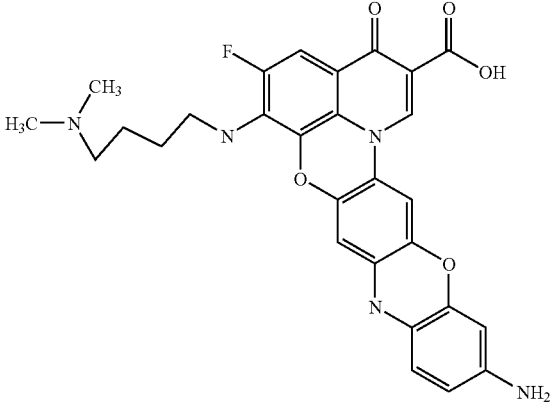 | | 0.75 |

TABLE 1A-continued

| Structure | Stop Data c-Myc μM | MTS Data Hella μM |
|---|---|---|
| 22 [structure] | 0.75 | |
| 23 [structure] | 0.75 | |
| 24 [structure, Chiral] | 0.5 | 7.00 |

TABLE 1A-continued
| Structure | Stop Data c-Myc μM | MTS Data Hella μM |
|---|---|---|
| 25 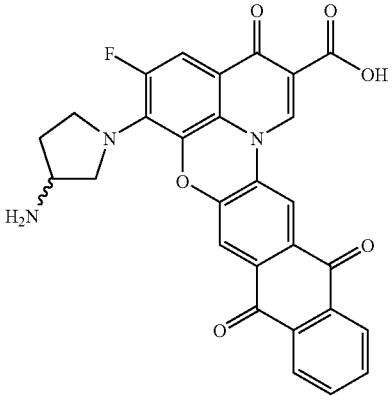 | 0.25 | 0.20 |
Table 1B
| Structure | | Stop Data c-Myc μM | MTS Data Hella μM |
|---|---|---|---|
| 26 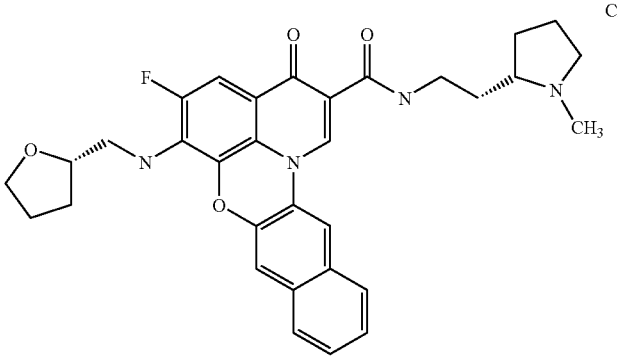 | Chiral | 4 | 0.73 |
| 27 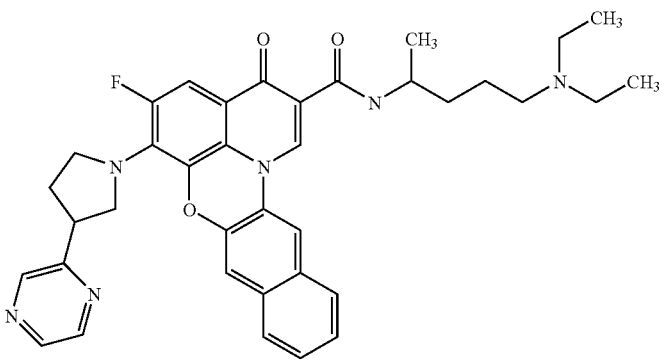 | | 3 | 3.80 |

-continued
| | | | |
|---|---|---|---|
| 28 | 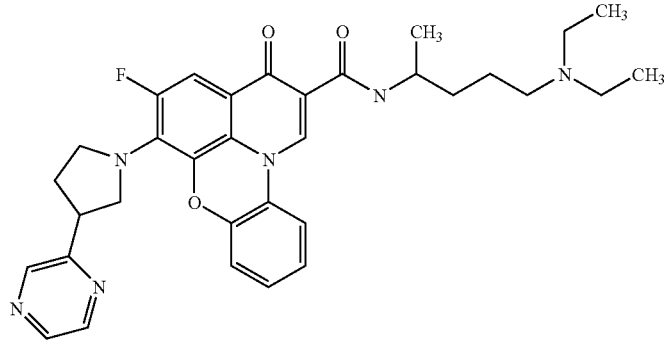 | 3 | 2.50 |
| 29 | 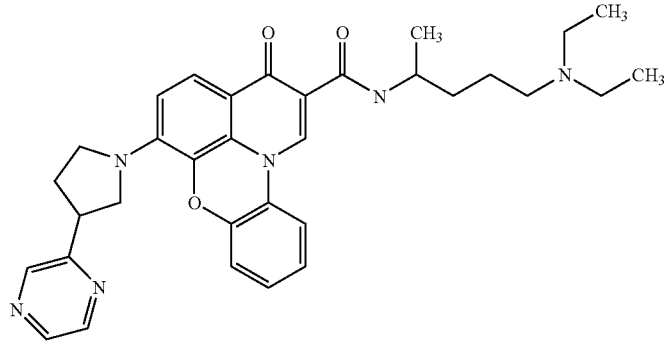 | 3 | 2.00 |
| 30 | 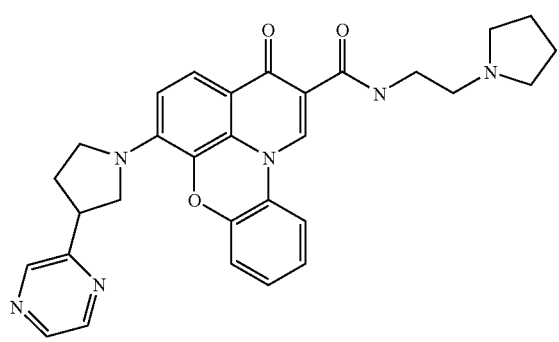 | 3 | 1.80 |
| 31 | 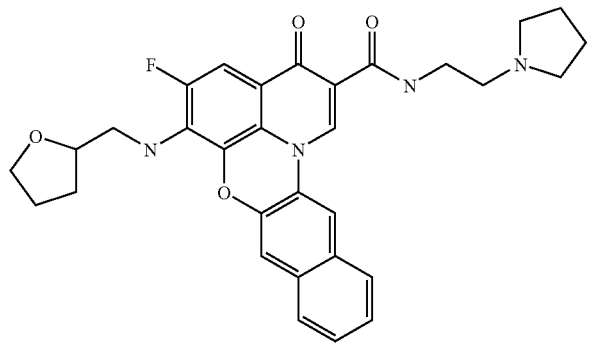 | 3 | 1.40 |

-continued
| | | | | |
|---|---|---|---|---|
| 32 | 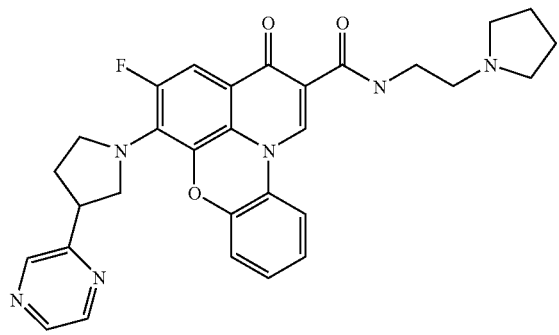 | | 3 | 0.60 |
| 33 | 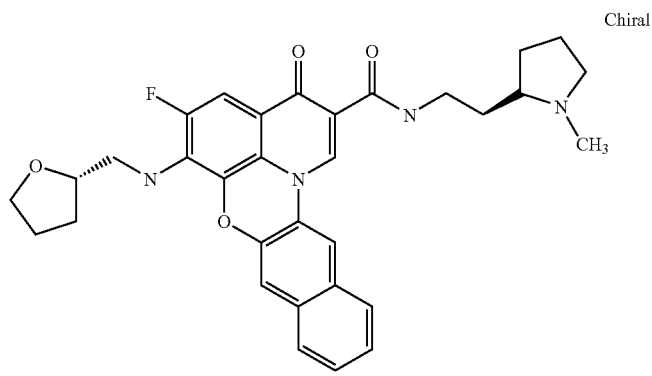 Chiral | | 3 | 0.29 |
| 34 | 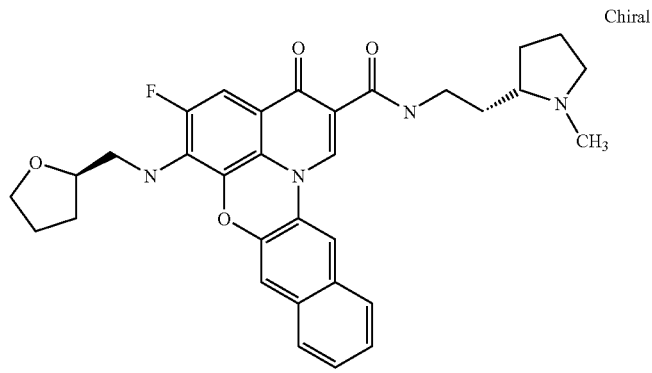 Chiral | | 3 | 0.28 |
| 35 | 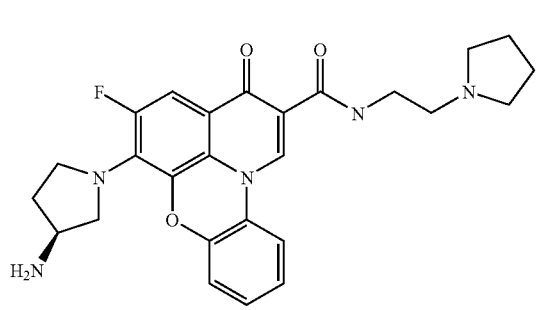 Chiral | | 3 | 0.21 |

-continued
| | | | | |
|---|---|---|---|---|
| 36 | 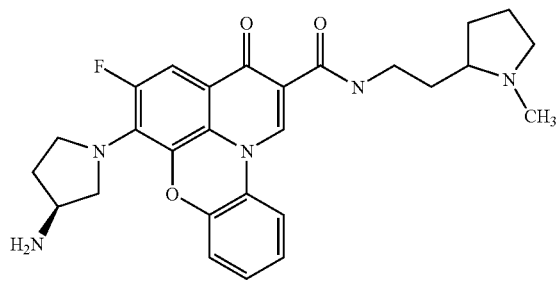 | Chiral | 3 | 0.16 |
| 37 | 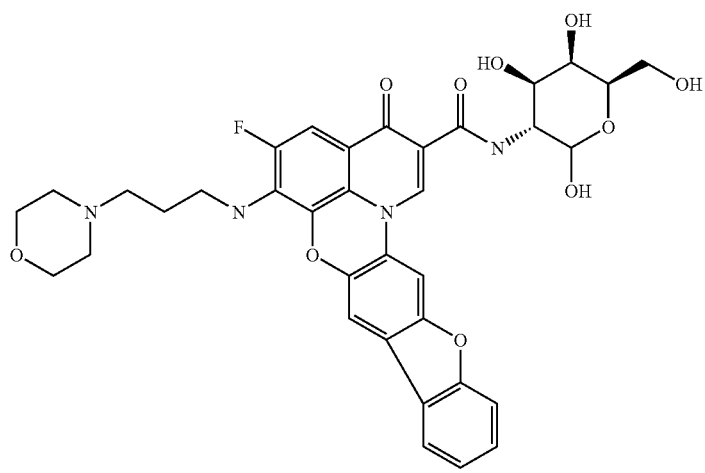 | | 2.5 | 2.80 |
| 38 | 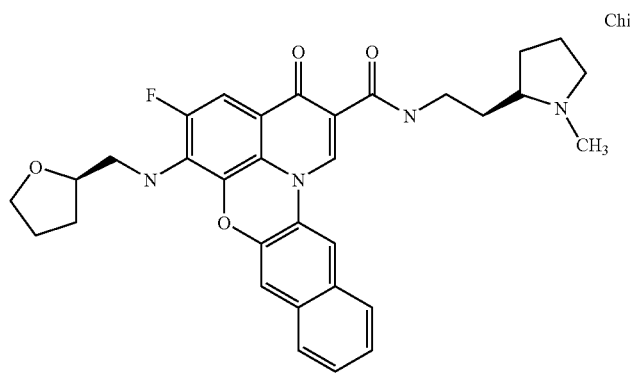 | Chiral | 2.5 | 0.26 |
| 39 | 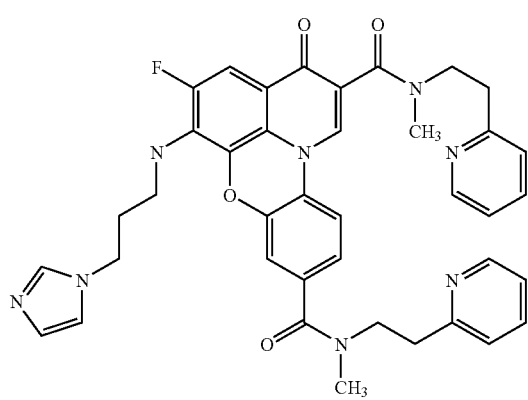 | | 2.5 | |

-continued
| | | | |
|---|---|---|---|
| 40 | 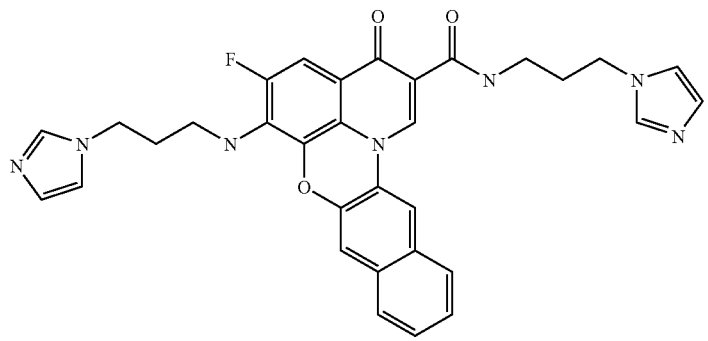 | | 2.5 |
| 41 | 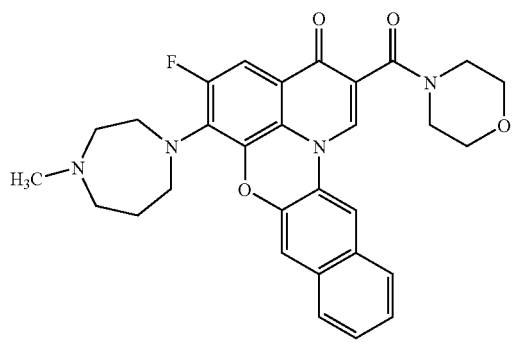 | | 2.5 |
| 42 | 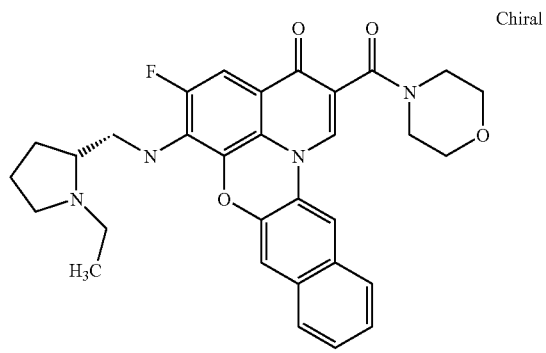 | Chiral | 2.5 |
| 43 | 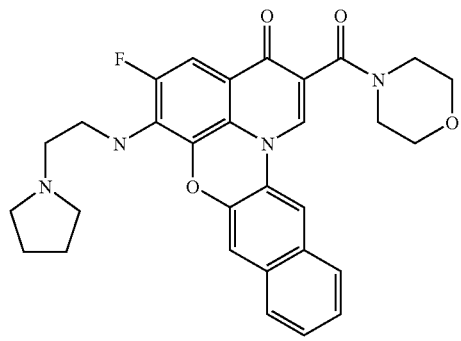 | | 2.5 |

-continued
| | | |
|---|---|---|
| 44 | 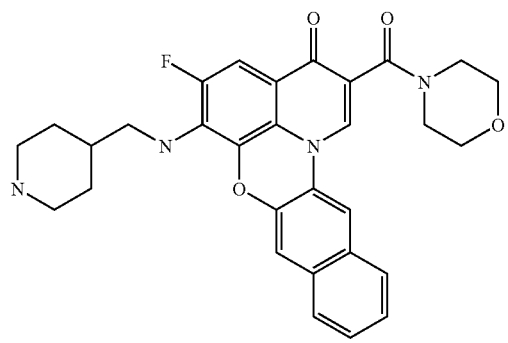 | 2.5 |
| 45 | 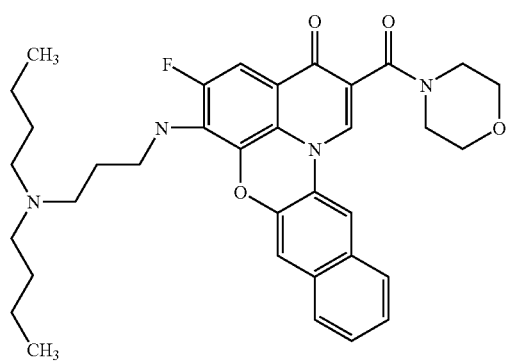 | 2.5 |
| 46 | 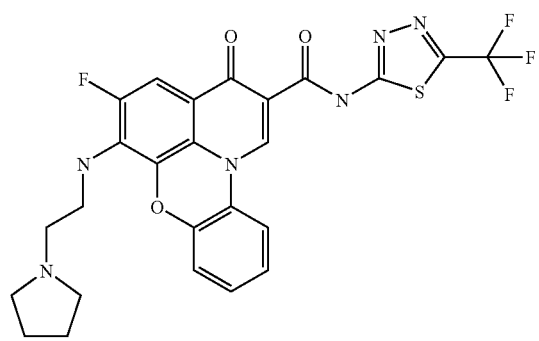 | 2.5 |
| 47 | 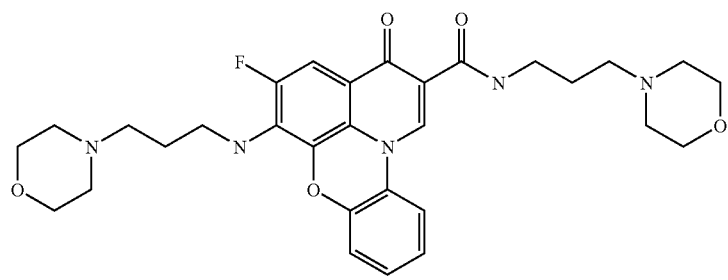 | 2.5 |

-continued
| 48 | 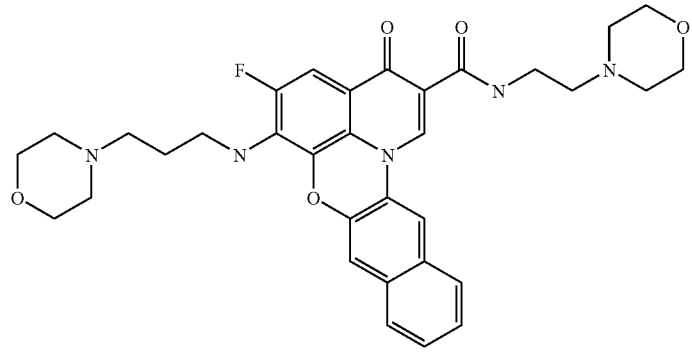 | 2.5 |
| --- | --- | --- |
| 49 | 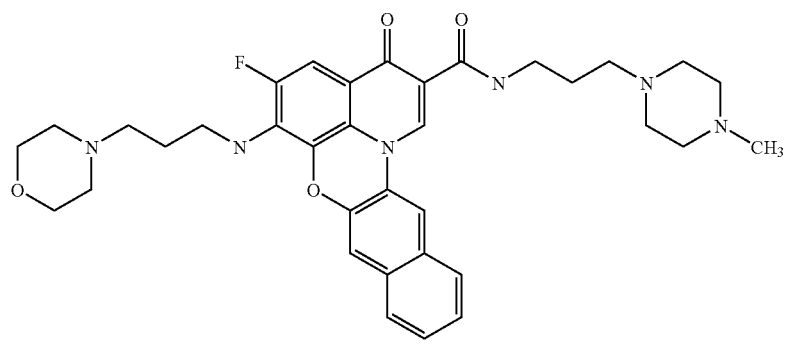 | 2.5 |
| 50 | 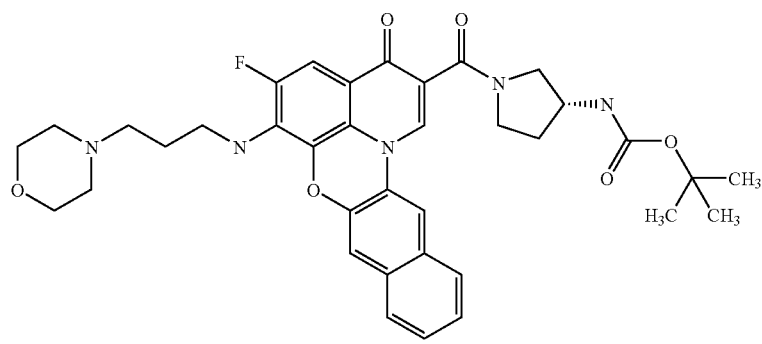 | 2.5 |
| 51 | 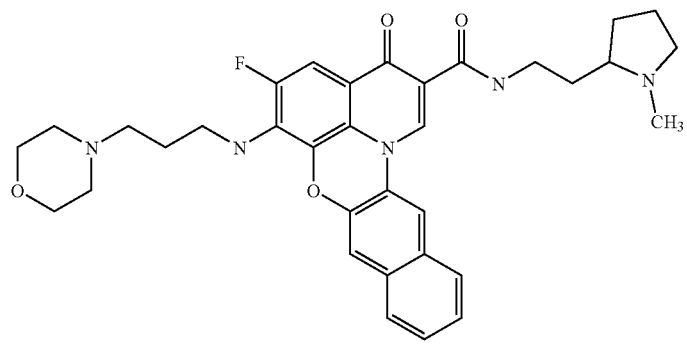 | 2.5 |

-continued
| | | |
|---|---|---|
| 52 | 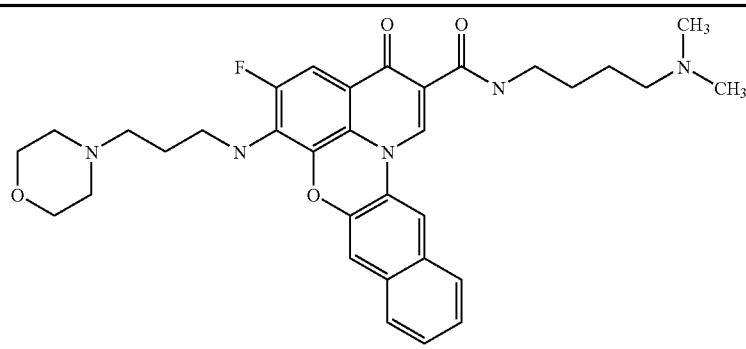 | 2.5 |
| 53 | 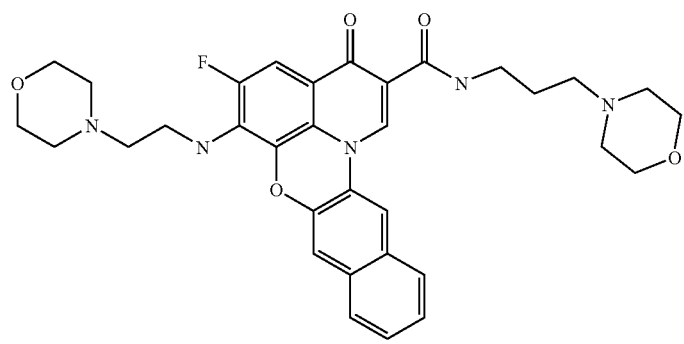 | 2.5 |
| 54 | 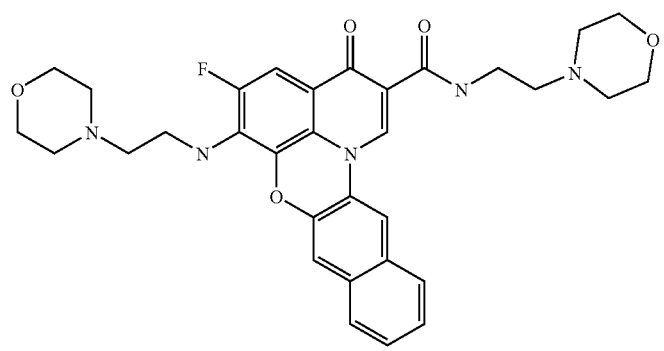 | 2.5 |
| 55 | 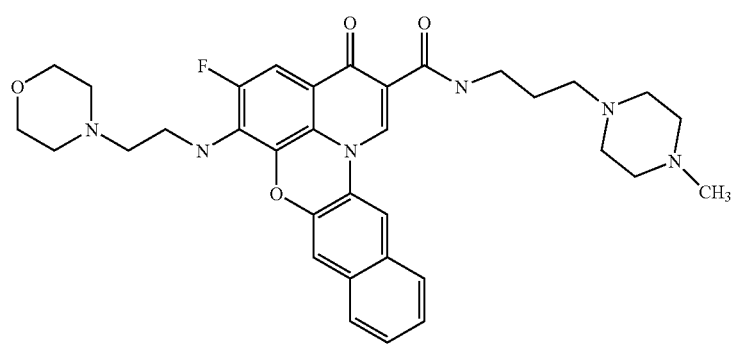 | 2.5 |

-continued
| | | |
|---|---|---|
| 56 | 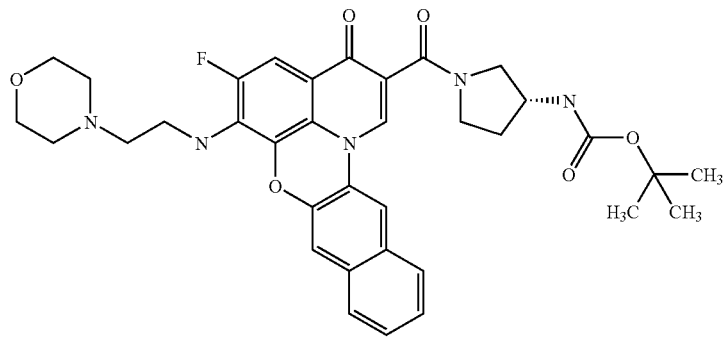 | 2.5 |
| 57 | 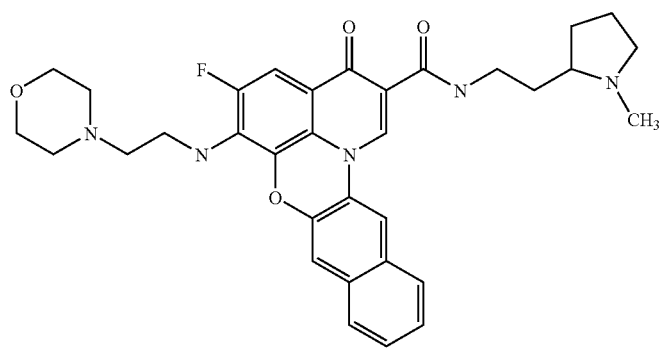 | 2.5 |
| 58 | 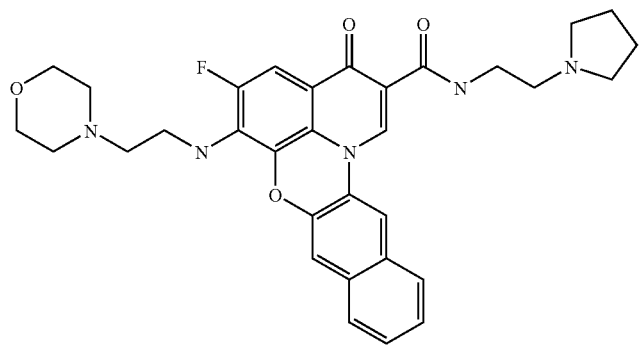 | 2.5 |
| 59 | 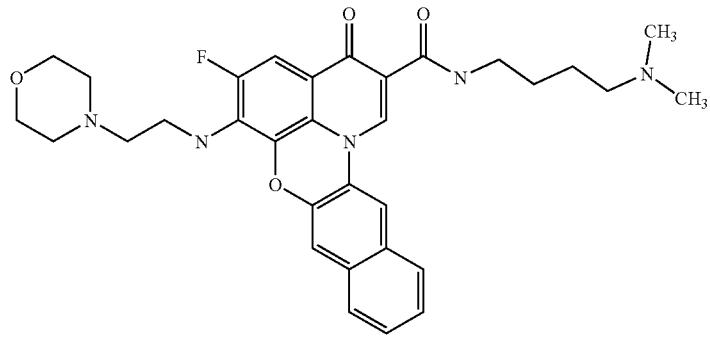 | 2.5 |

-continued
| | | |
|---|---|---|
| 60 | 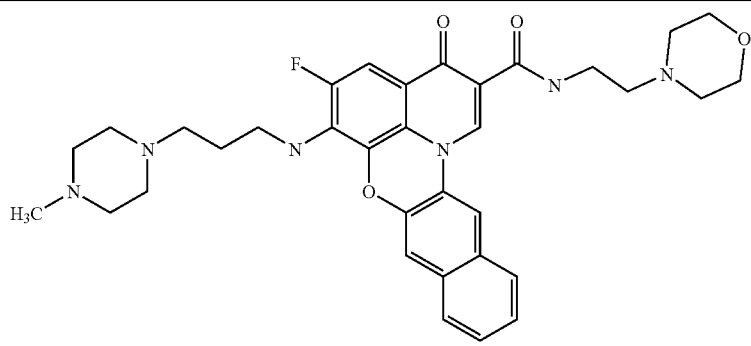 | 2.5 |
| 61 | 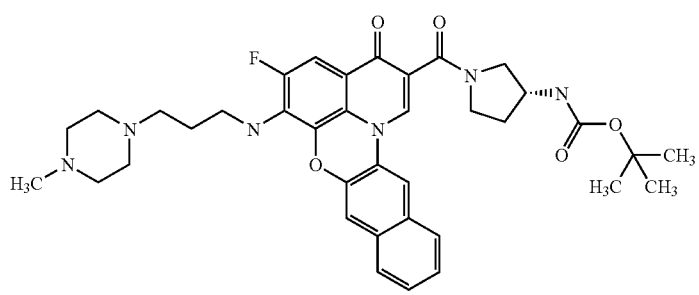 | 2.5 |
| 62 | 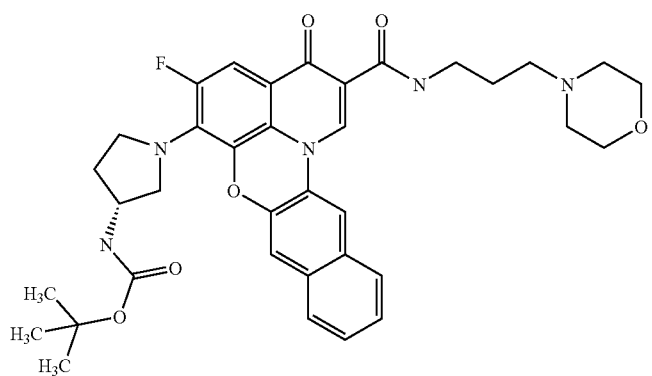 | 2.5 |
| 63 | 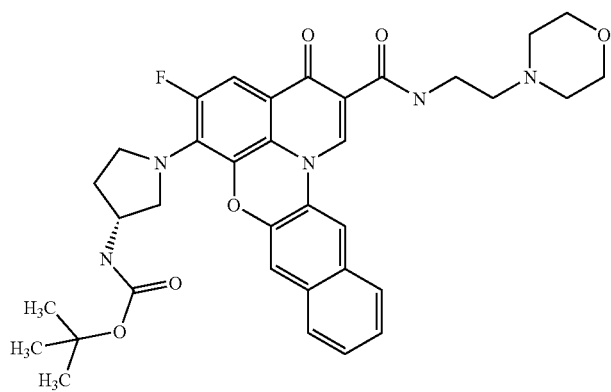 | 2.5 |

| | | |
|---|---|---|
| 64 | 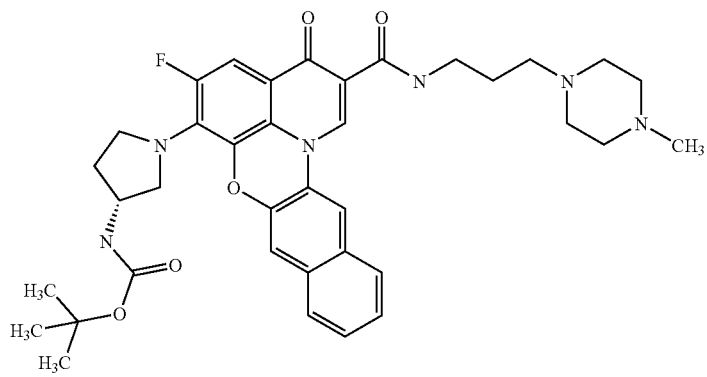 | 2.5 |
| 65 | 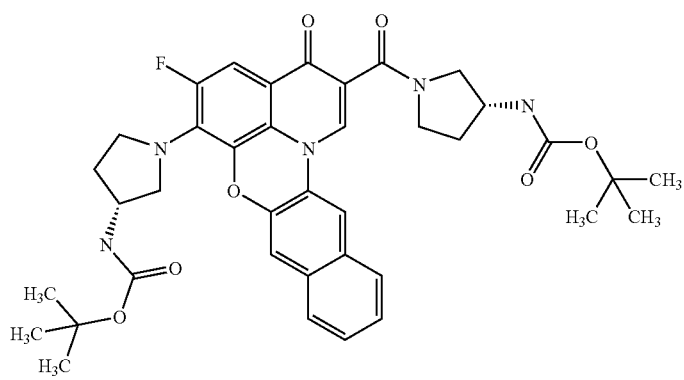 | 2.5 |
| 66 | 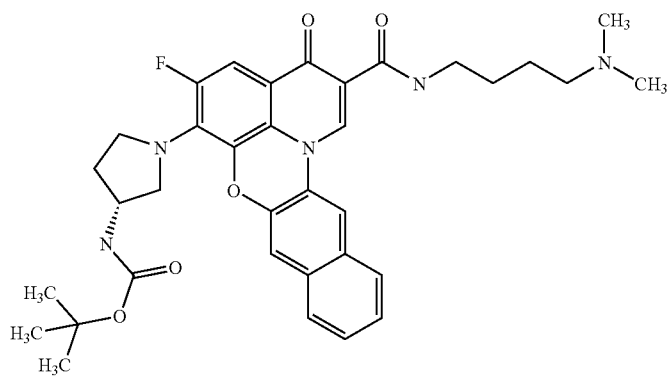 | 2.5 |
| 67 | 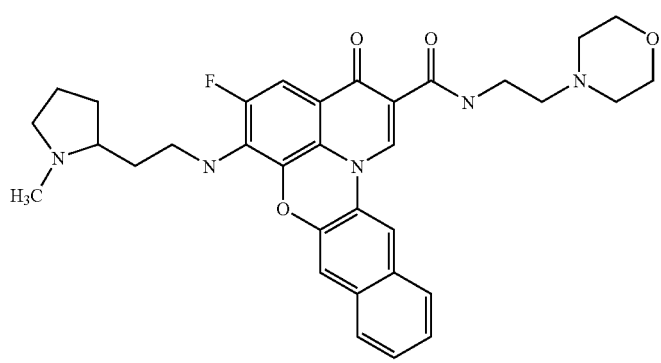 | 2.5 |

-continued
| | | |
|---|---|---|
| 68 | 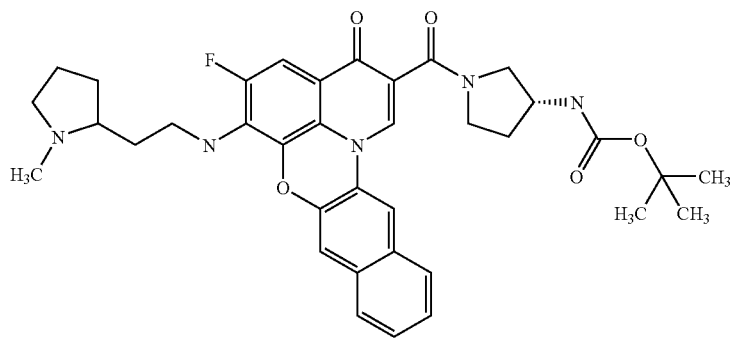 | 2.5 |
| 69 | 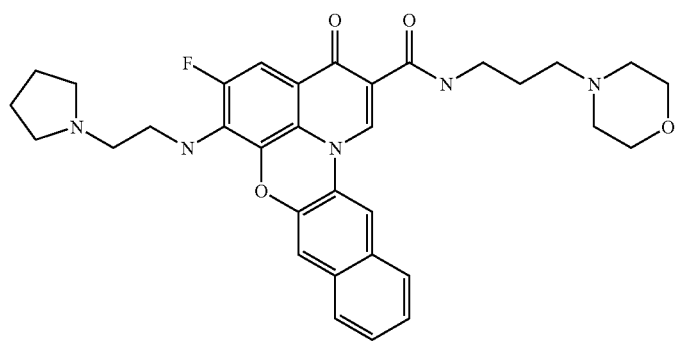 | 2.5 |
| 70 | 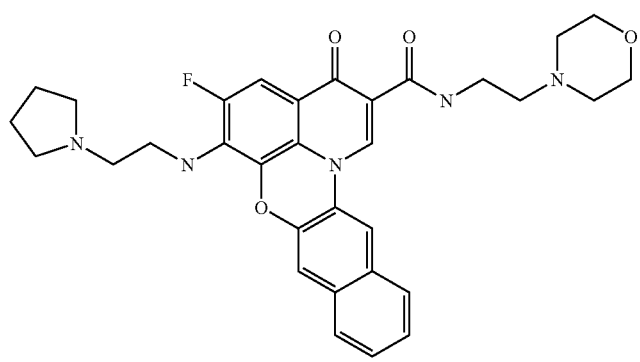 | 2.5 |
| 71 | 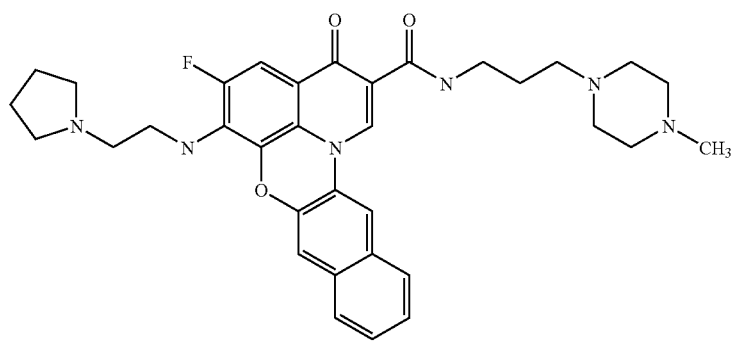 | 2.5 |

-continued
| | | |
|---|---|---|
| 72 | 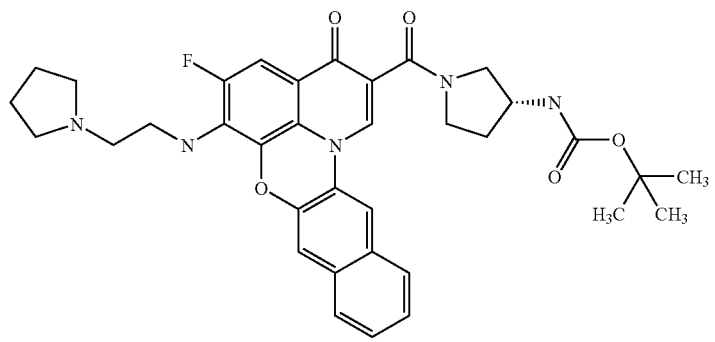 | 2.5 |
| 73 | 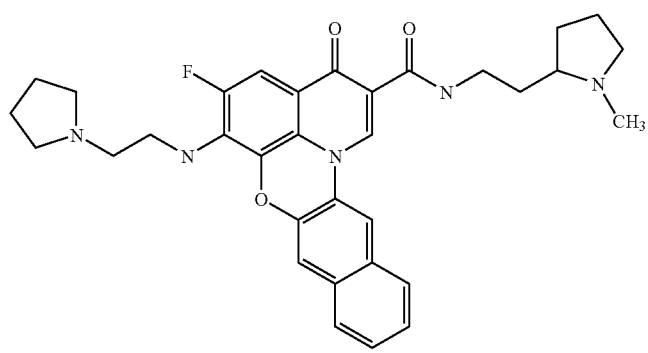 | 2.5 |
| 74 | 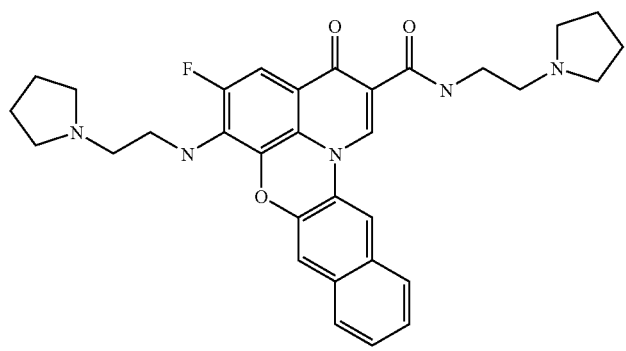 | 2.5 |
| 75 | 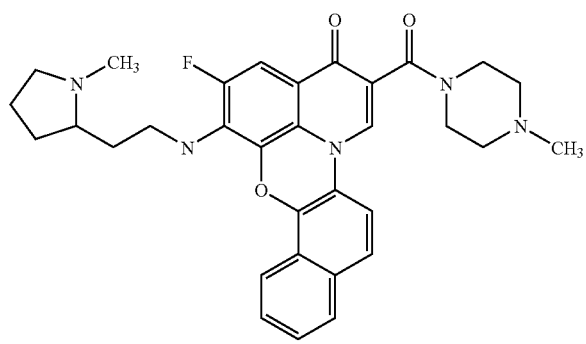 | 2.5 |

| | | |
|---|---|---|
| 76 | 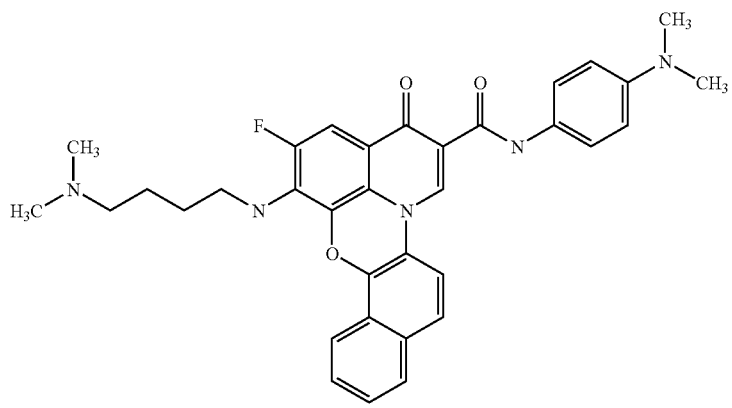 | 2.5 |
| 77 | 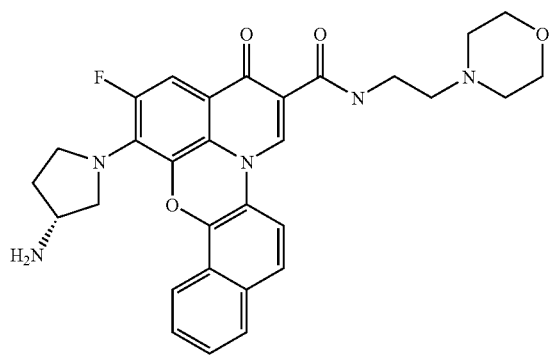 | 2.5 |
| 78 | 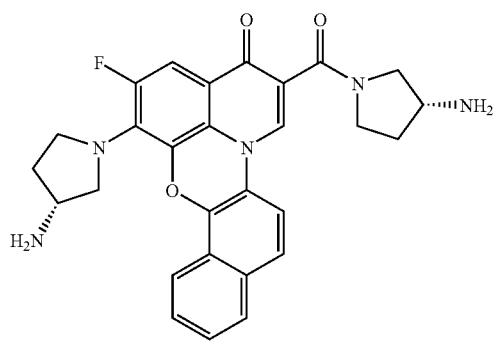 | 2.5 |
| 79 | 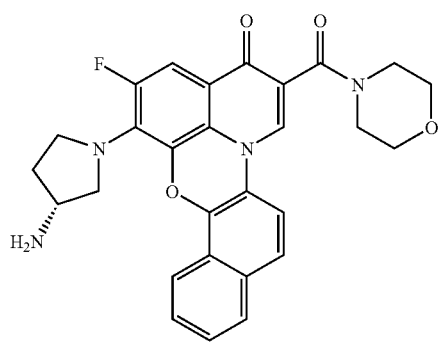 | 2.5 |

| | | |
|---|---|---|
| 80 | 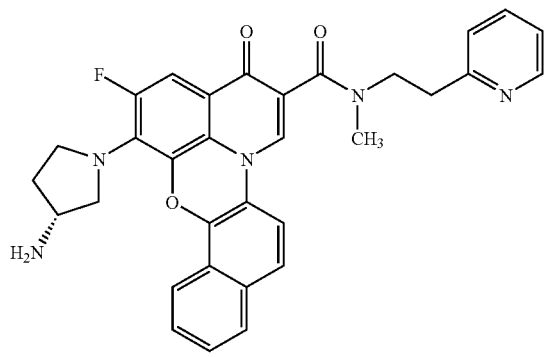 | 2.5 |
| 81 | 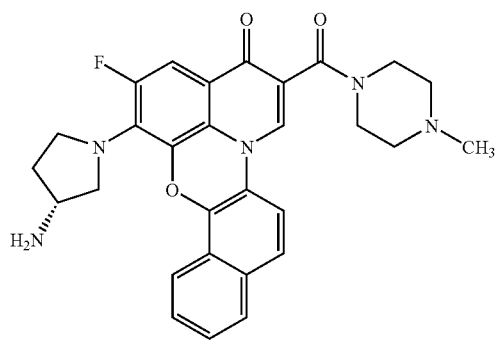 | 2.5 |
| 82 | 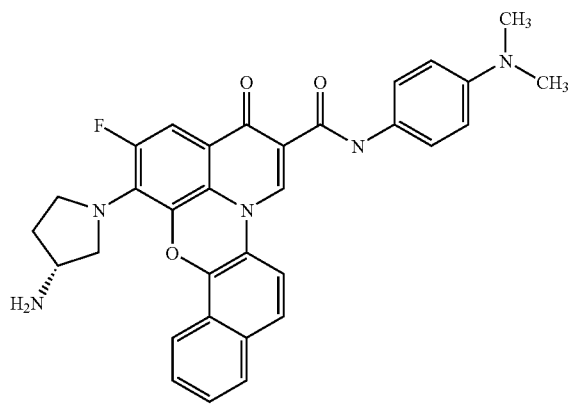 | 2.5 |
| 83 | 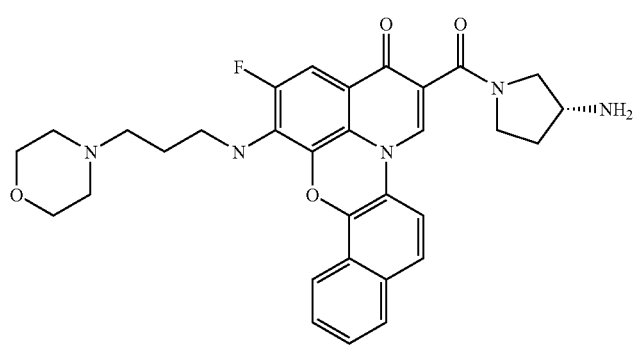 | 2.5 |

-continued
| | | |
|---|---|---|
| 84 | 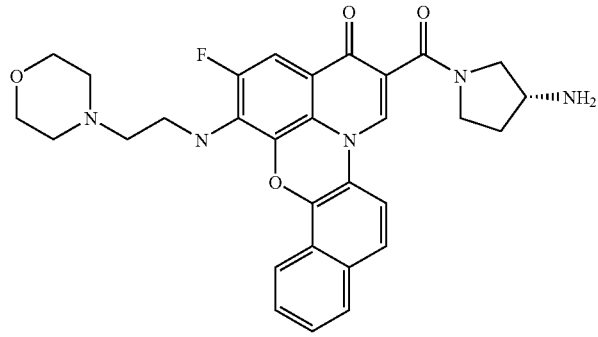 | 2.5 |
| 85 | 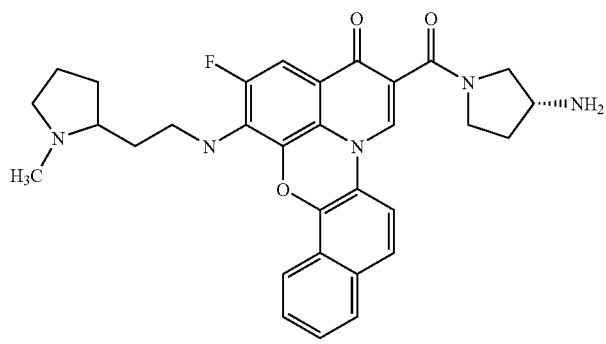 | 2.5 |
| 86 | 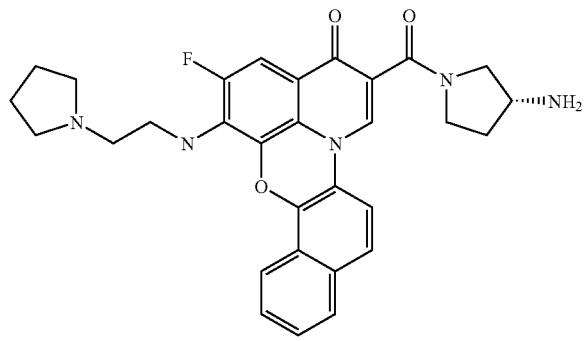 | 2.5 |
| 87 | 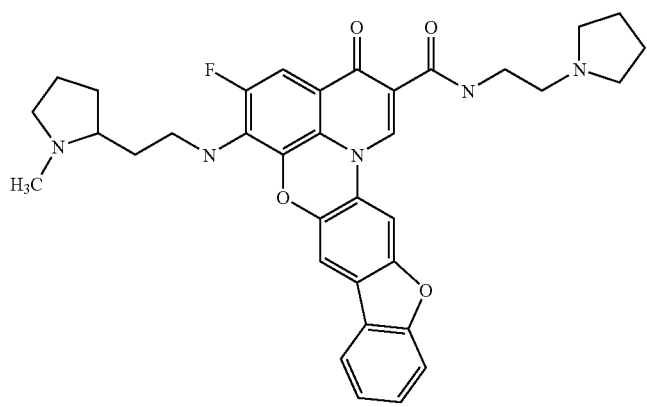 | 2.5 |

| | | |
|---|---|---|
| 88 | 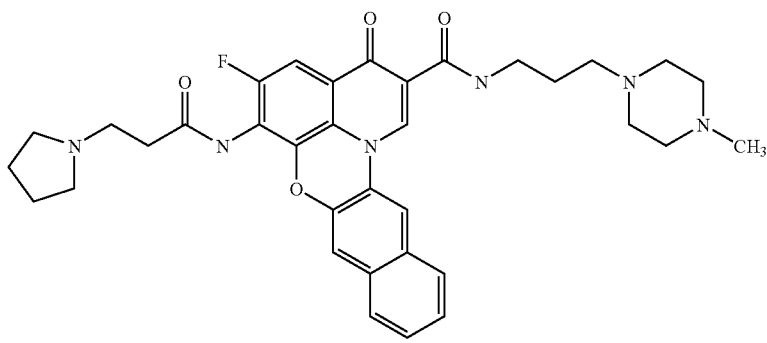 | 2.5 |
| 89 | 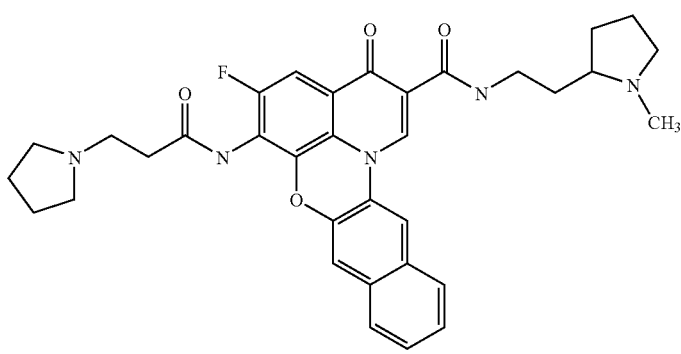 | 2.5 |
| 90 | 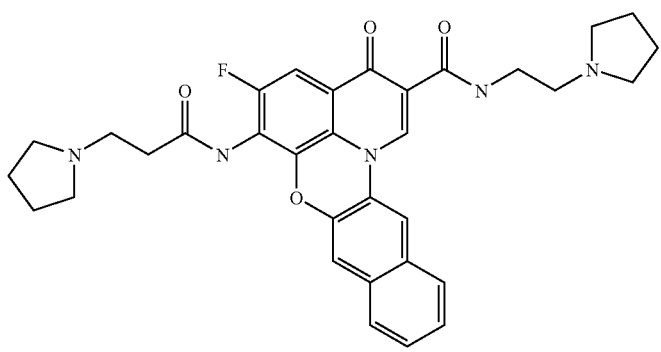 | 2.5 |
| 91 | 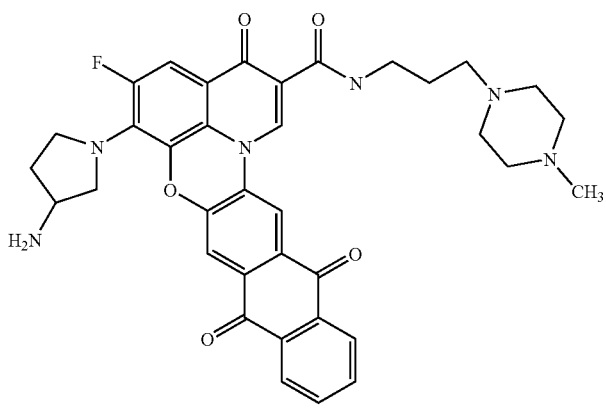 | 2.5 |

-continued
| | | |
|---|---|---|
| 92 | 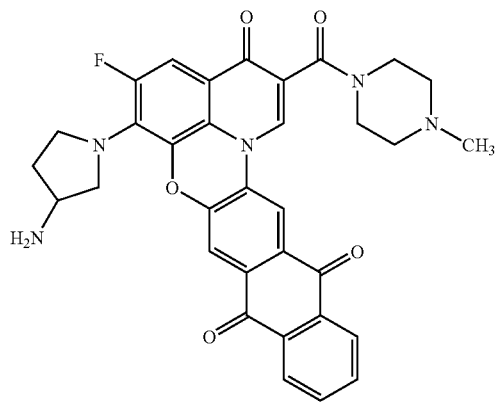 | 2.5 |
| 93 | 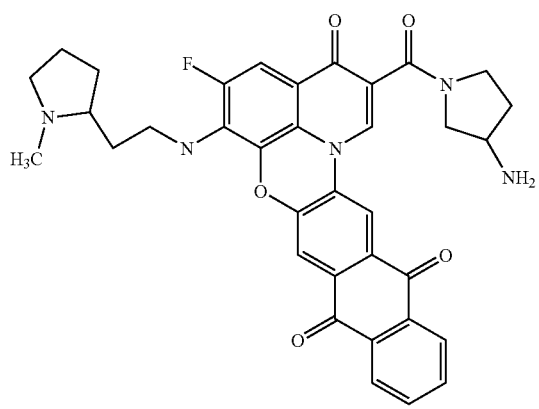 | 2.5 |
| 94 | 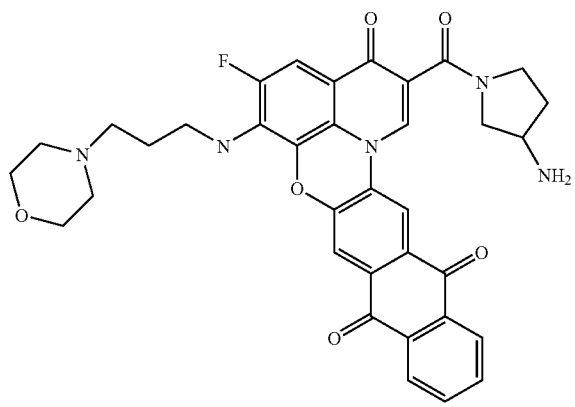 | 2.5 |
| 95 | 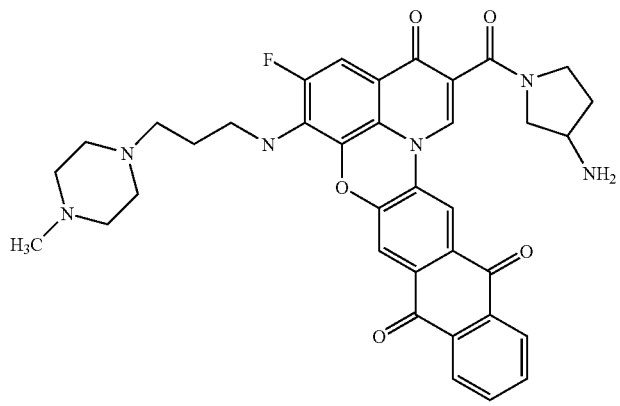 | 2.5 |

-continued
| 96 | 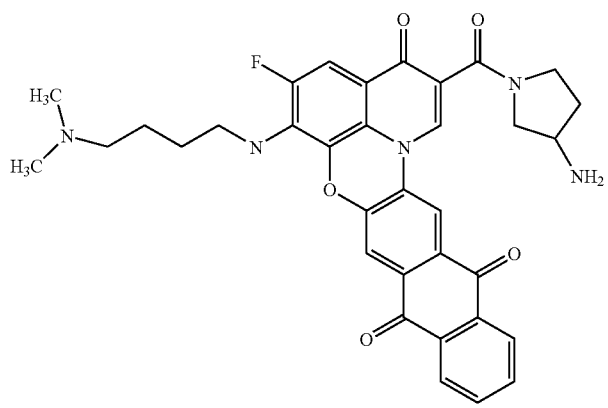 | 2.5 |
| 97 | 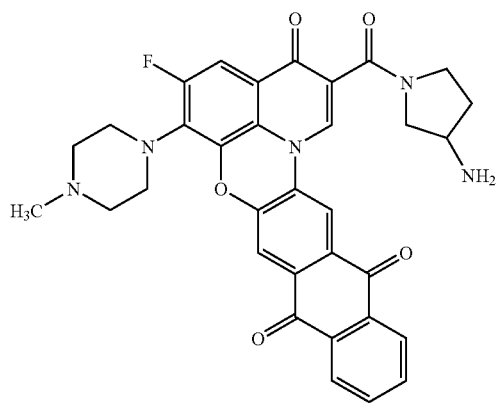 | 2.5 |
| 98 | 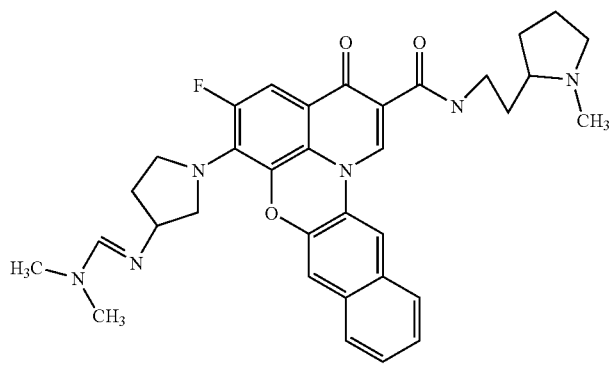 | 2.5 |
| 99 | 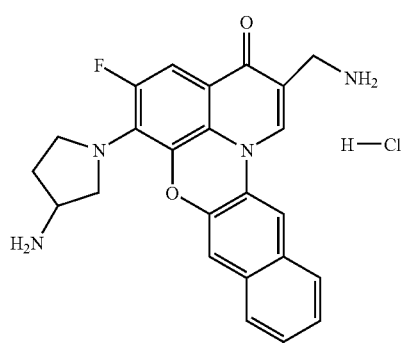 | 2.5 |

-continued
| | | | |
|---|---|---|---|
| 100 | 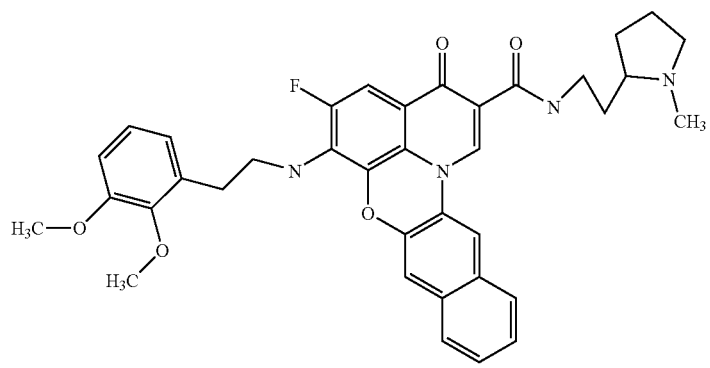 | 2.5 | |
| 101 | 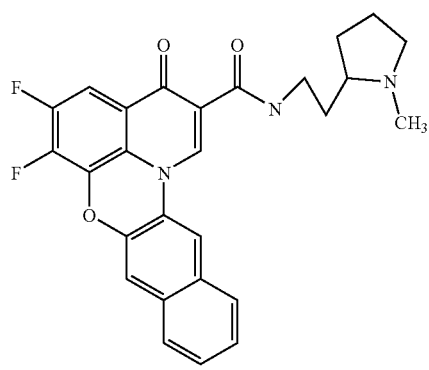 | 2.25 | |
| 102 | 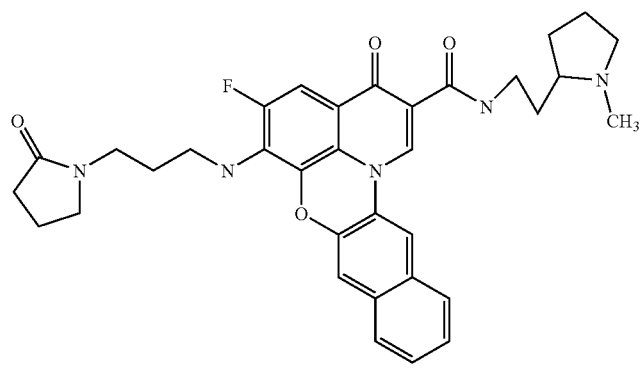 | 1.8 | 2.20 |
| 103 | 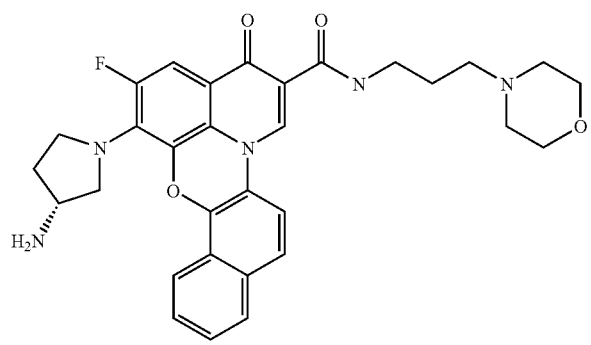 | 1.8 | |

-continued
| | | | |
|---|---|---|---|
| 104 | 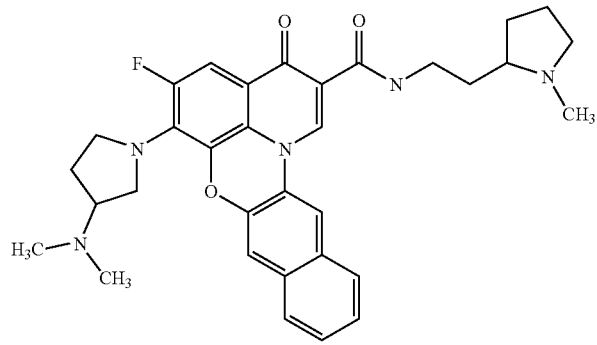 | 1.75 | 2.80 |
| 105 | 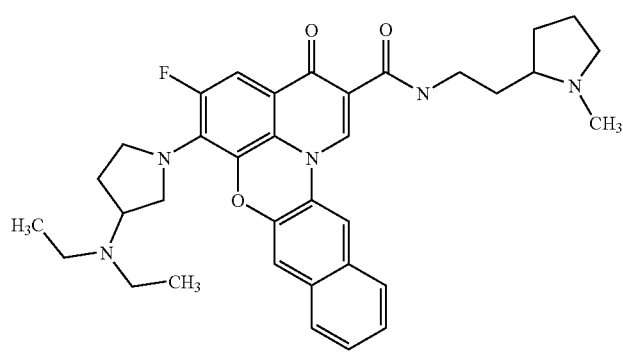 | 1.75 | 2.80 |
| 106 | 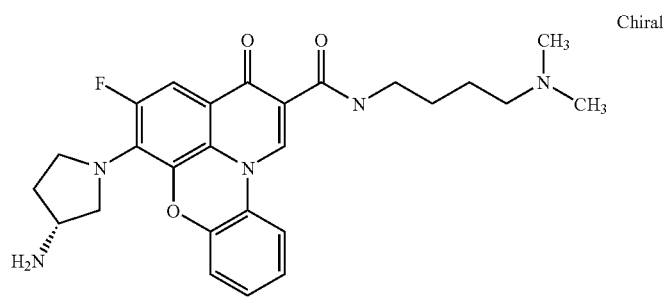 Chiral | 1.75 | 2.50 |
| 107 | 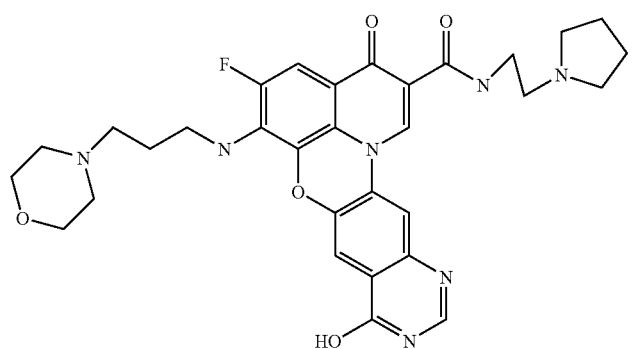 | 1.75 | 1.80 |

-continued
| | | | | |
|---|---|---|---|---|
| 108 | 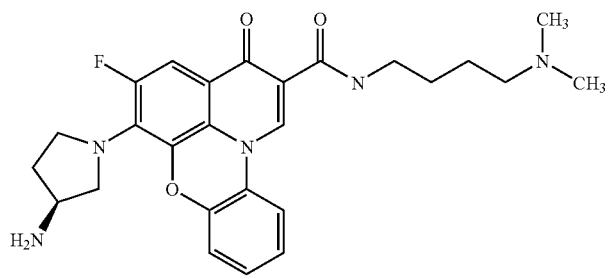 | Chiral | 1.75 | 0.46 |
| 109 | 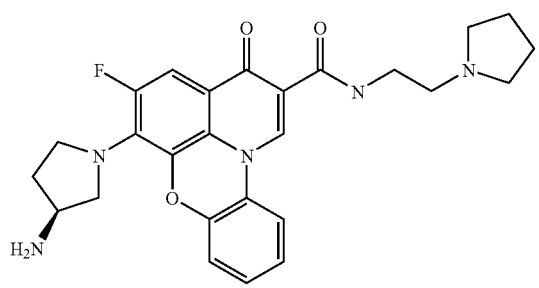 | Chiral | 1.75 | 0.31 |
| 110 | 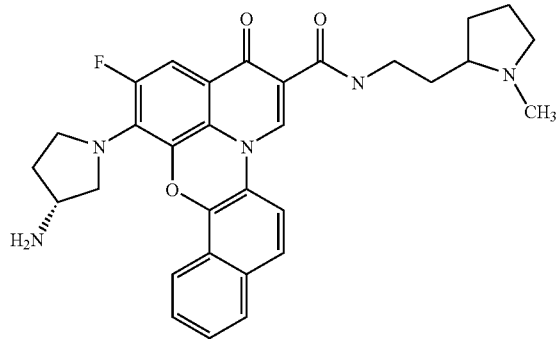 | | 1.75 | 0.25 |
| 111 | 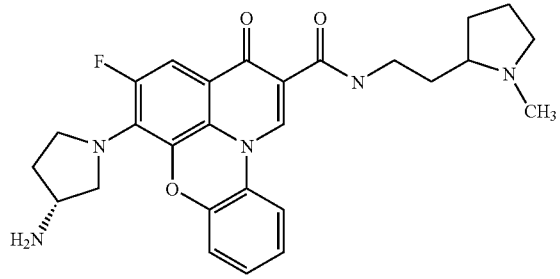 | Chiral | 1.75 | 0.22 |
| 112 | 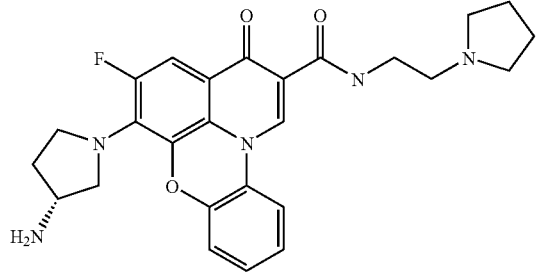 | Chiral | 1.75 | 0.22 |

-continued
| | | |
|---|---|---|
| 113 | 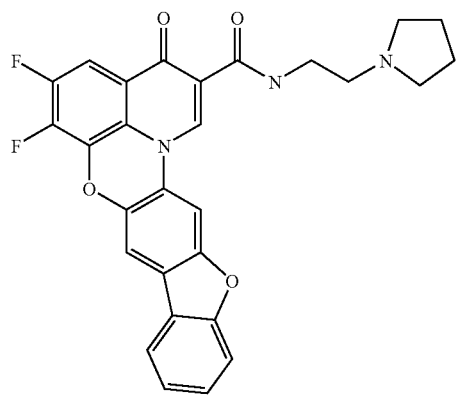 | 1.75 |
| 114 | 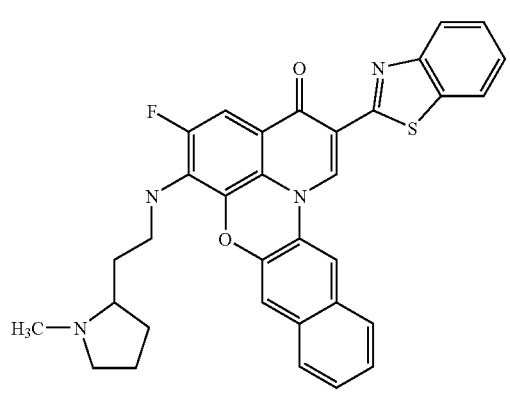 | 1.75 |
| 115 | 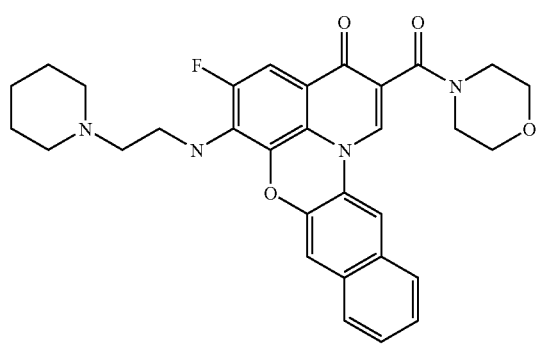 | 1.75 |
| 116 | 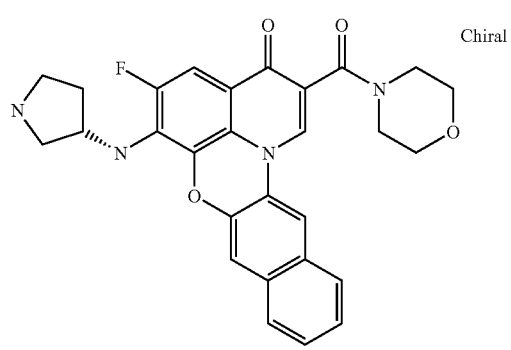 Chiral | 1.75 |

-continued
| | | |
|---|---|---|
| 117 | 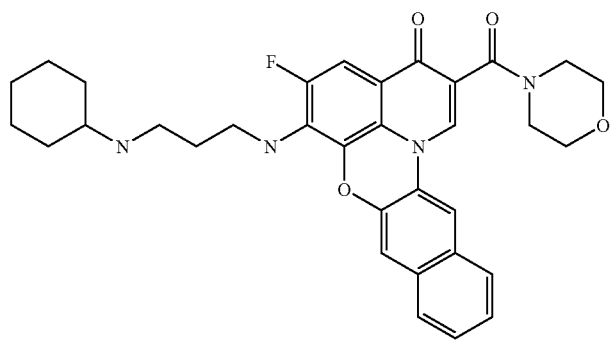 | 1.75 |
| 118 | 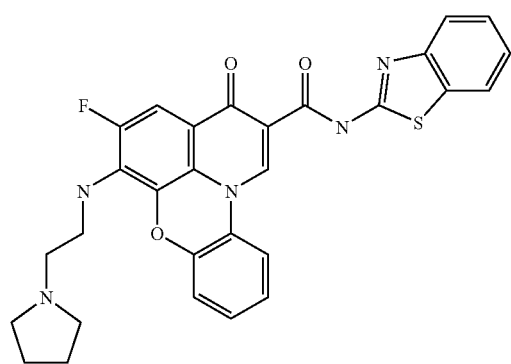 | 1.75 |
| 119 | 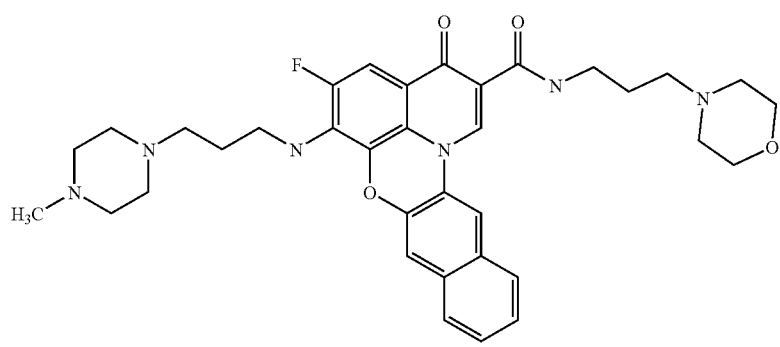 | 1.75 |
| 120 | 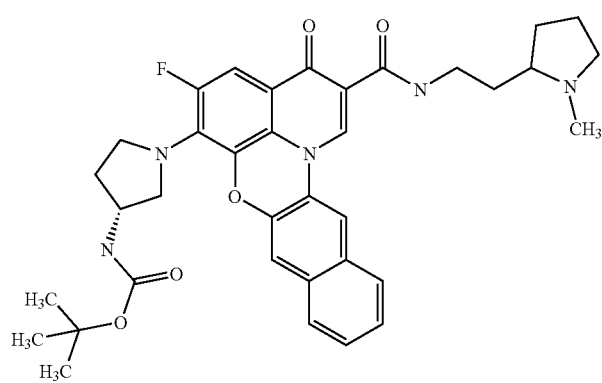 | 1.75 |

| 121 | 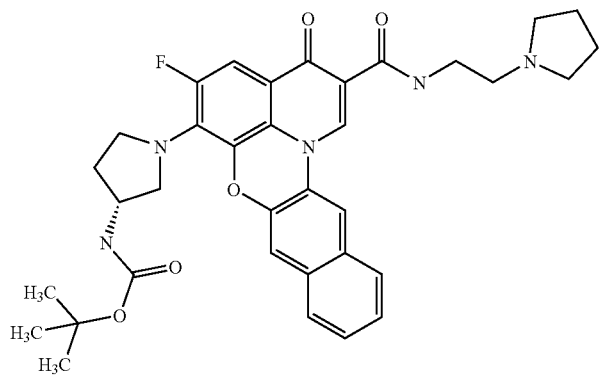 | 1.75 |
| 122 | 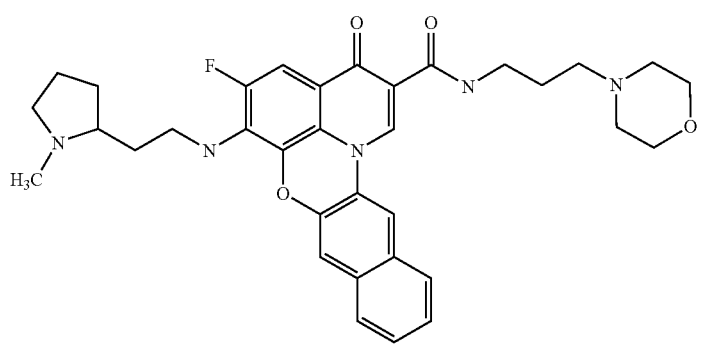 | 1.75 |
| 123 | 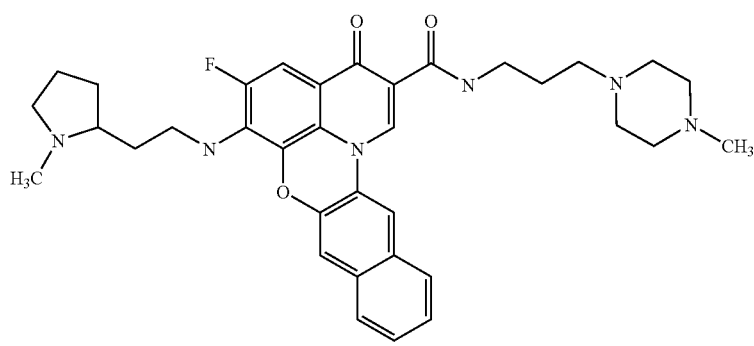 | 1.75 |
| 124 | 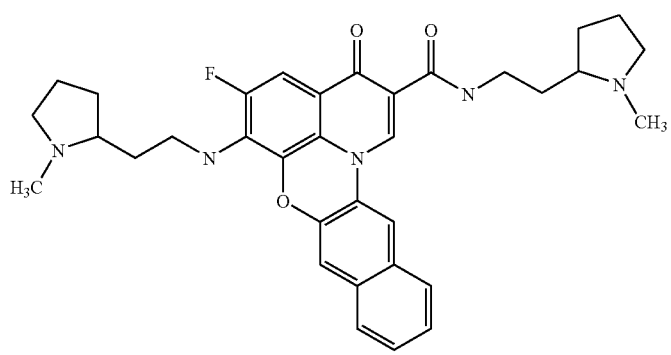 | 1.75 |

-continued
| | | |
|---|---|---|
| 125 | 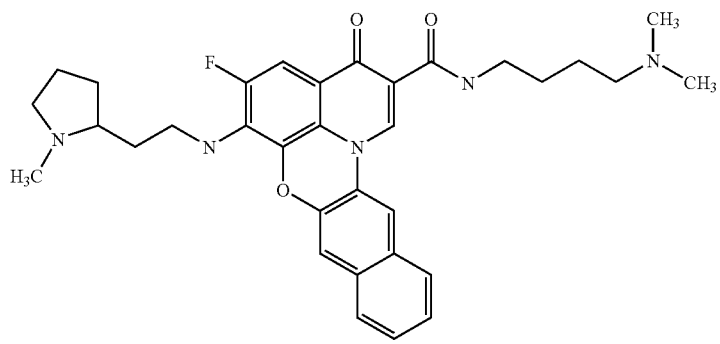 | 1.75 |
| 126 | 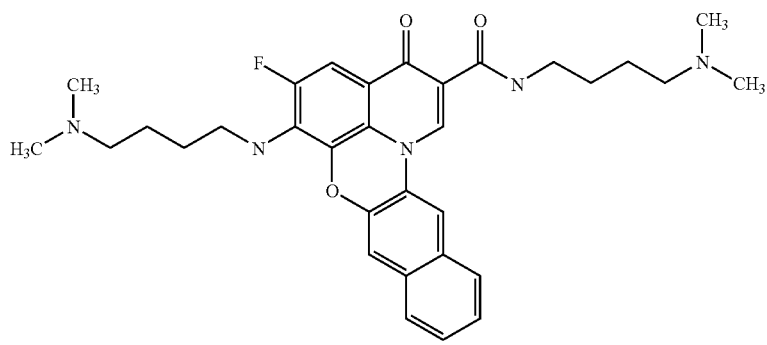 | 1.75 |
| 127 | 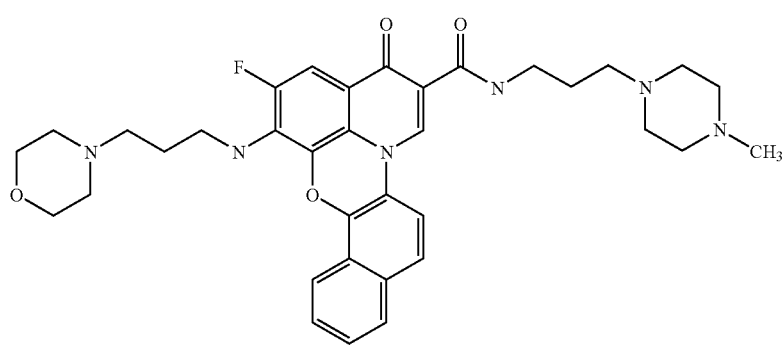 | 1.75 |
| 128 | 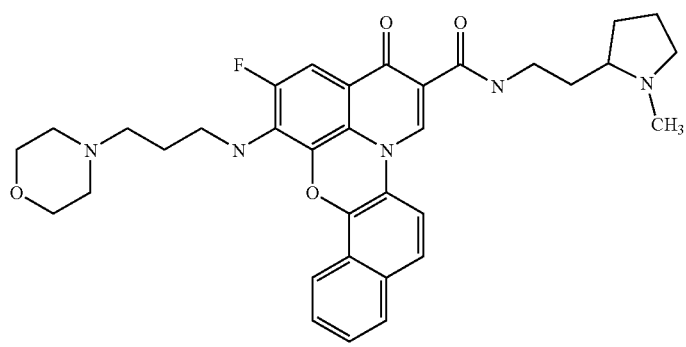 | 1.75 |

| | | |
|---|---|---|
| 129 | 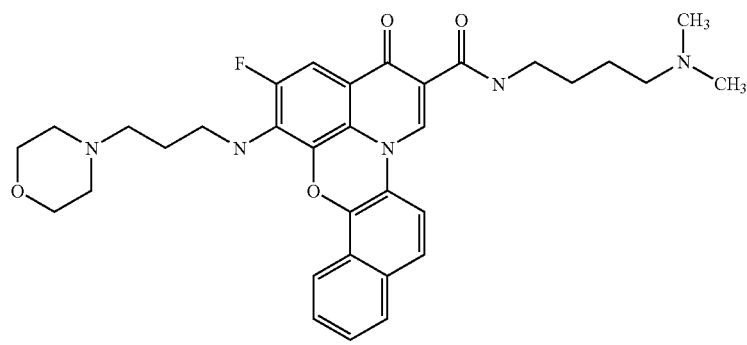 | 1.75 |
| 130 | 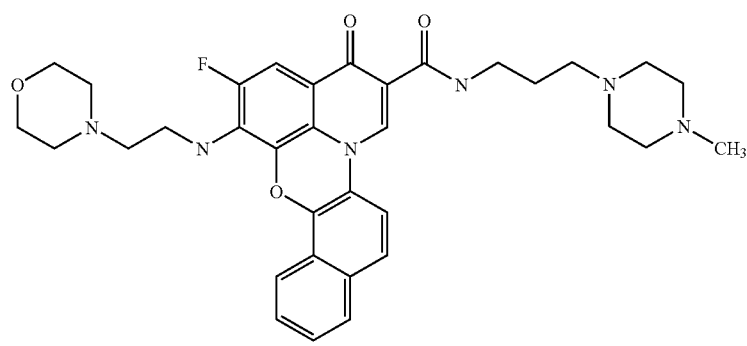 | 1.75 |
| 131 | 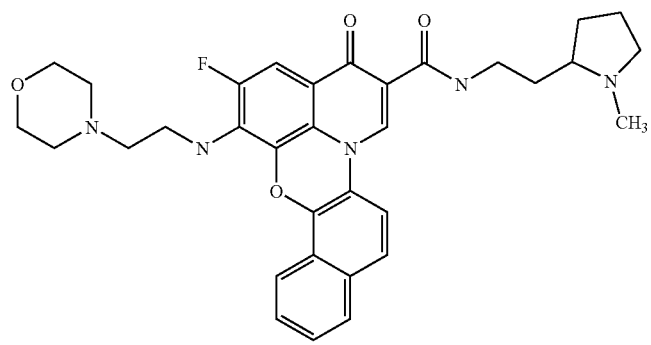 | 1.75 |
| 132 | 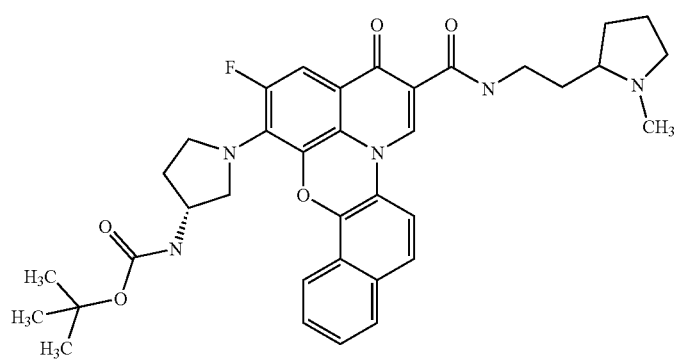 | 1.75 |

-continued
| | | |
|---|---|---|
| 133 | 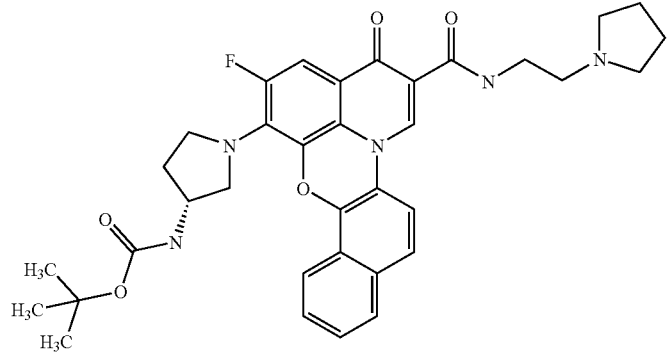 | 1.75 |
| 134 | 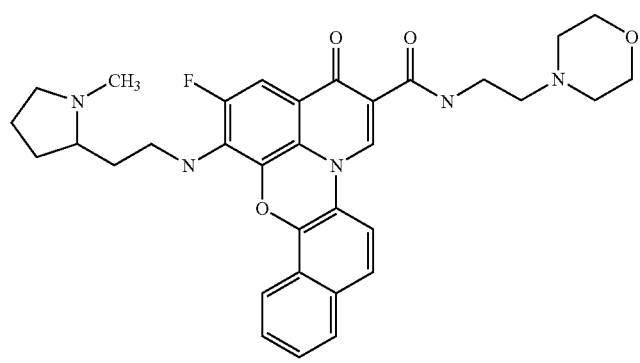 | 1.75 |
| 135 | 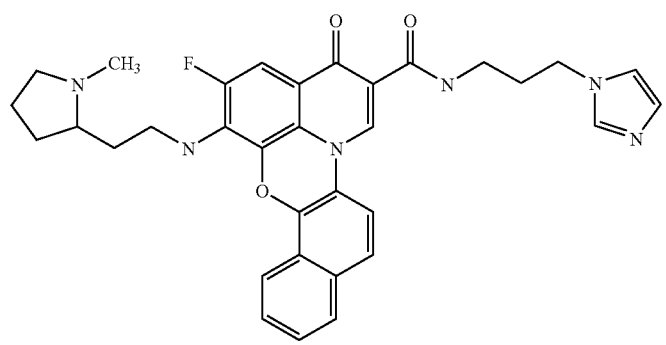 | 1.75 |
| 136 | 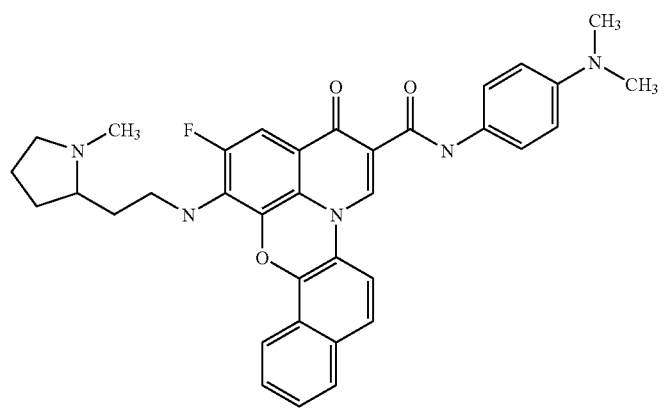 | 1.75 |

-continued
| | | |
|---|---|---|
| 137 | 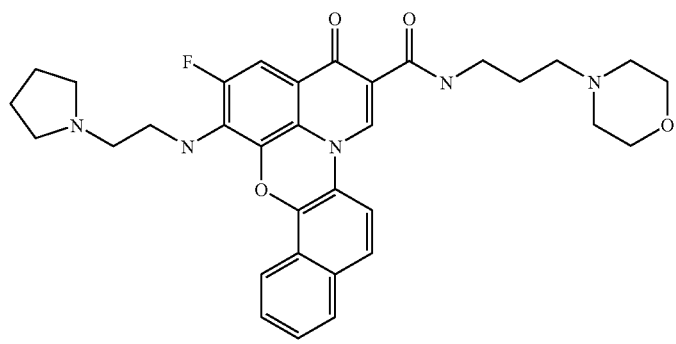 | 1.75 |
| 138 | 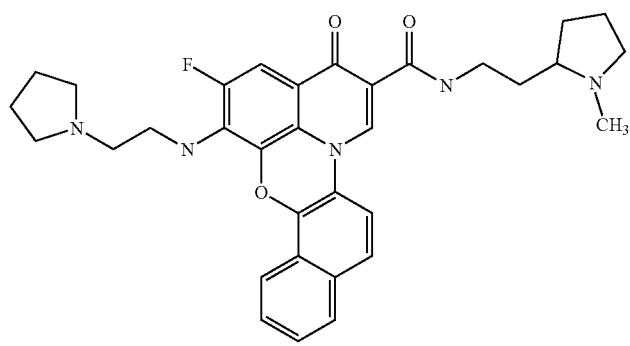 | 1.75 |
| 139 | 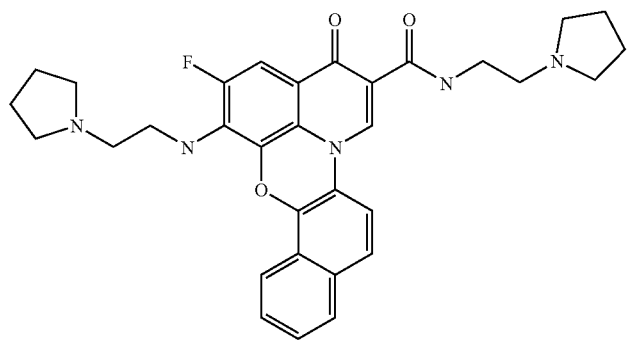 | 1.75 |
| 140 | 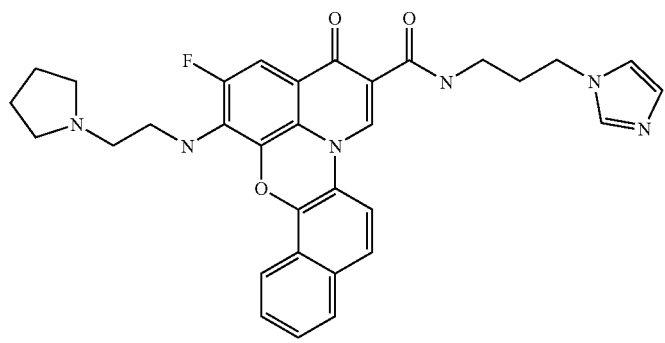 | 1.75 |

-continued
| | | |
|---|---|---|
| 141 | 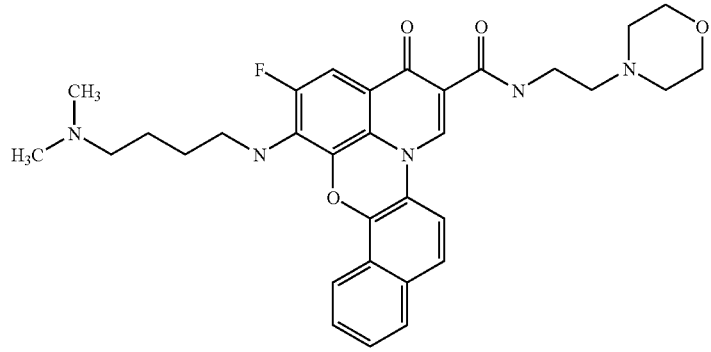 | 1.75 |
| 142 | 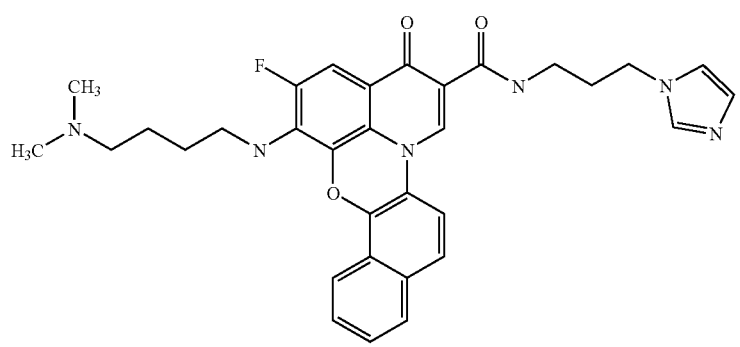 | 1.75 |
| 143 | 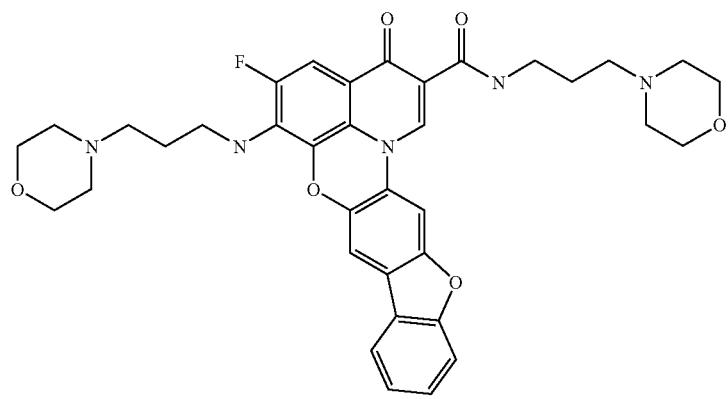 | 1.75 |
| 144 | 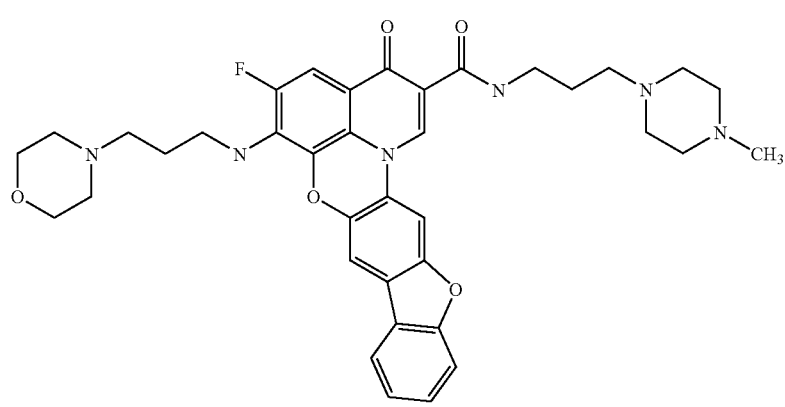 | 1.75 |

-continued
| 145 | 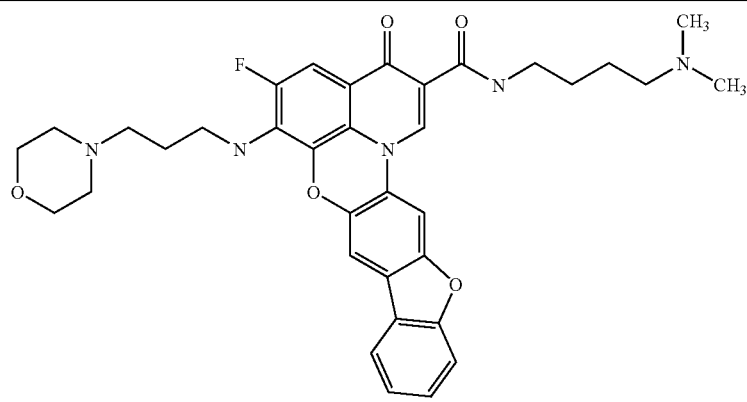 | 1.75 |
| 146 | 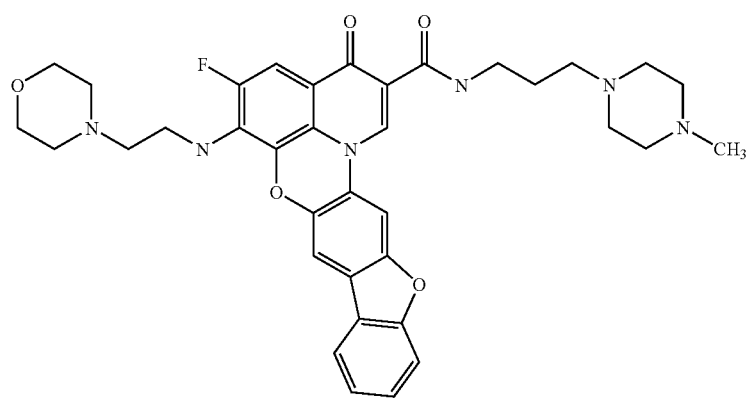 | 1.75 |
| 147 | 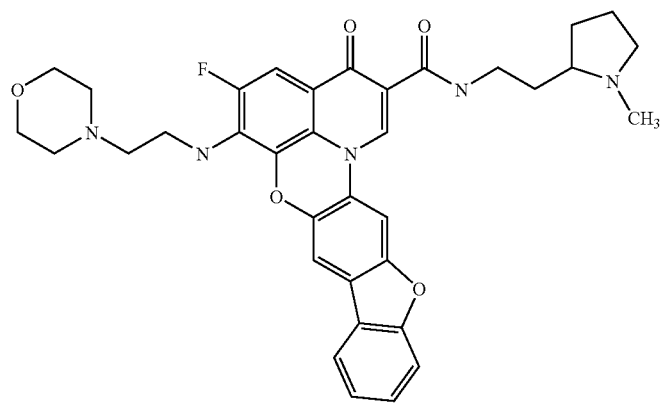 | 1.75 |
| 148 | 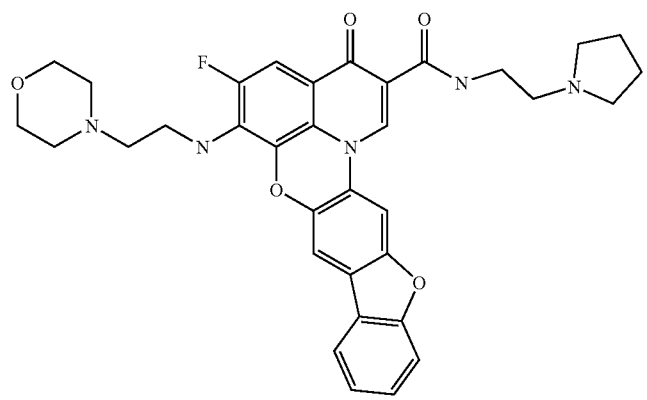 | 1.75 |

-continued
| | | |
|---|---|---|
| 149 | 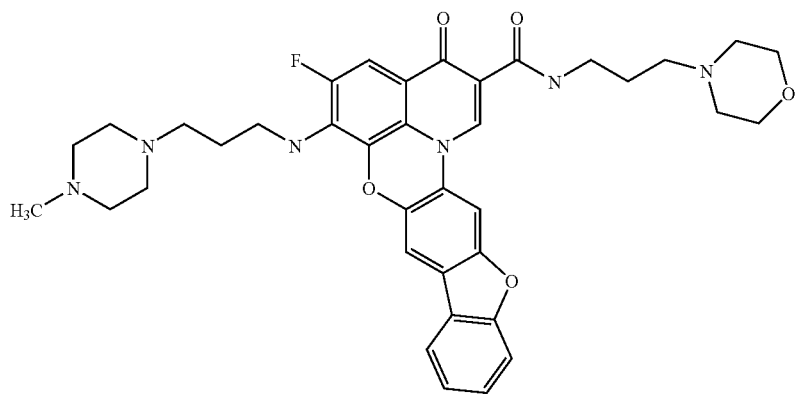 | 1.75 |
| 150 | 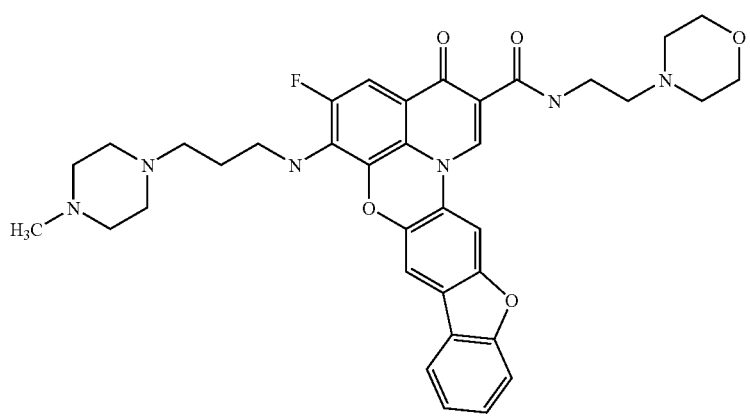 | 1.75 |
| 151 | 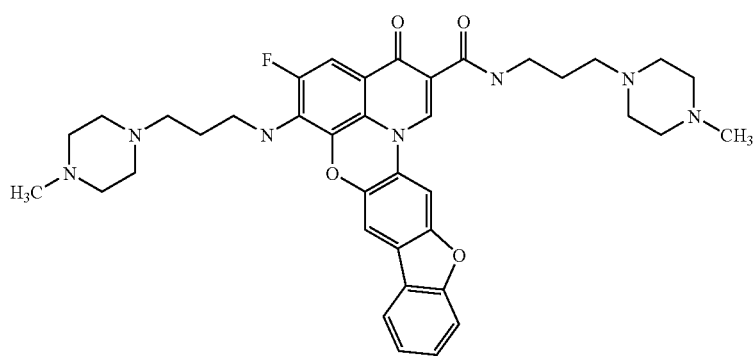 | 1.75 |
| 152 | 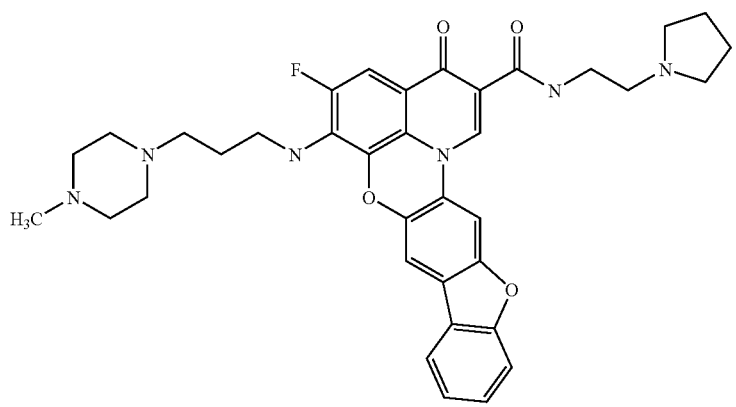 | 1.75 |

-continued
| | | |
|---|---|---|
| 153 | 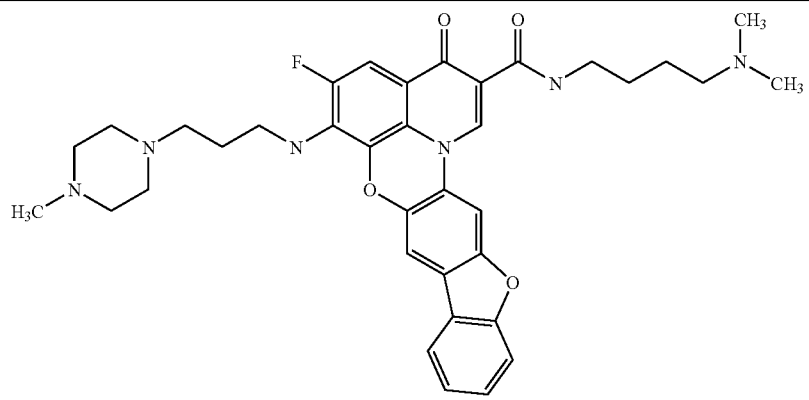 | 1.75 |
| 154 | 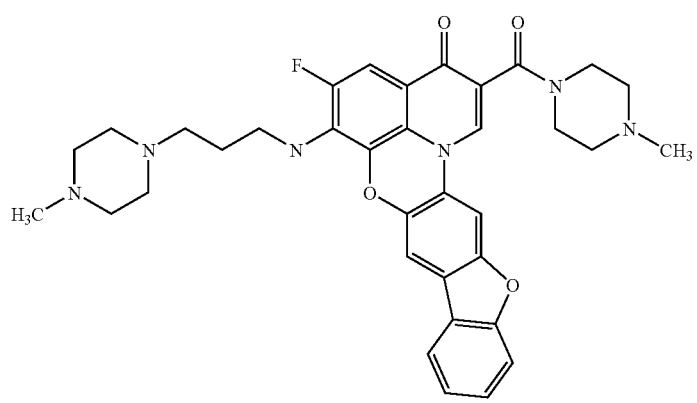 | 1.75 |
| 155 | 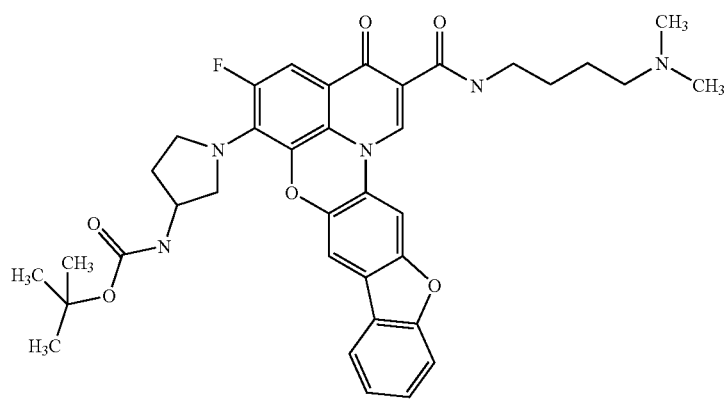 | 1.75 |
| 156 | 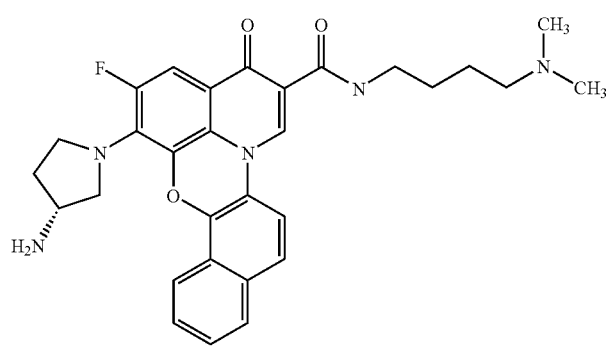 | 1.75 |

-continued
| | | |
|---|---|---|
| 157 | 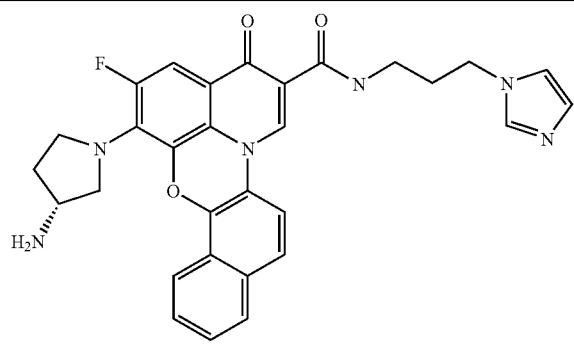 | 1.75 |
| 158 | 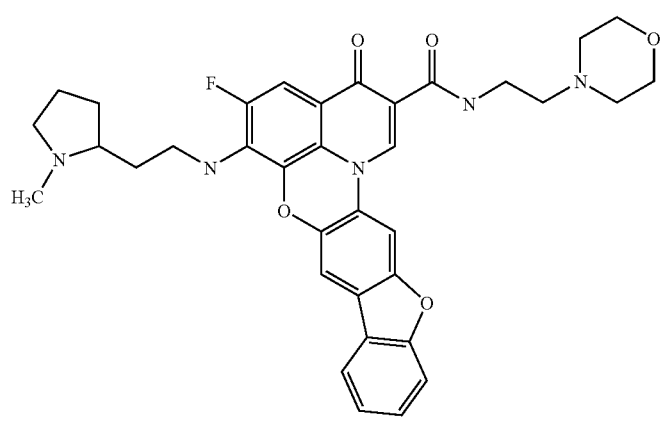 | 1.75 |
| 159 | 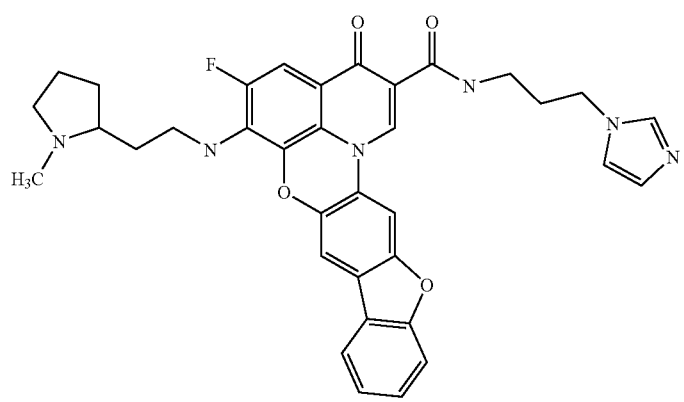 | 1.75 |
| 160 | 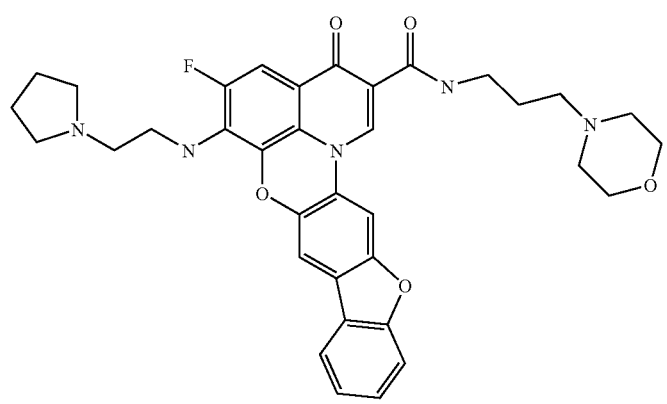 | 1.75 |

-continued
| | | |
|---|---|---|
| 161 | 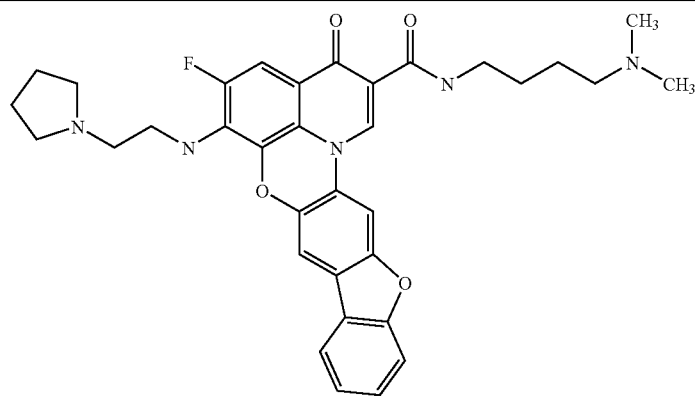 | 1.75 |
| 162 | 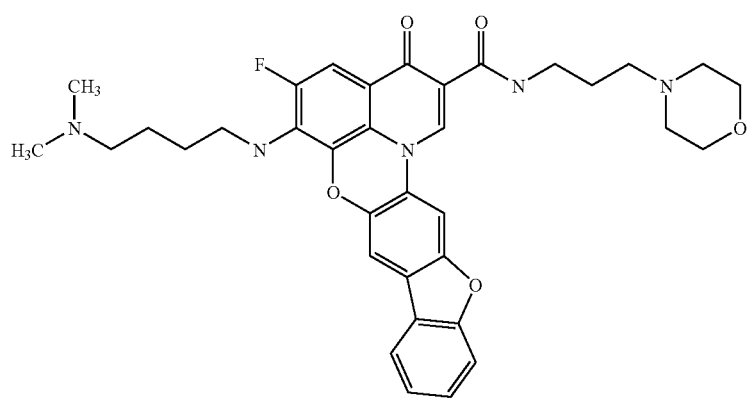 | 1.75 |
| 163 | 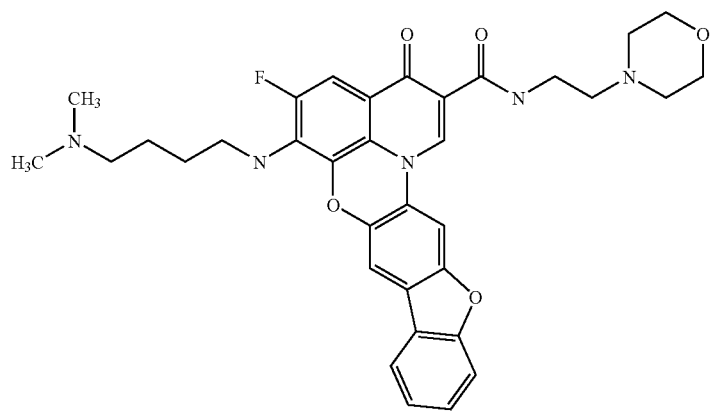 | 1.75 |
| 164 | 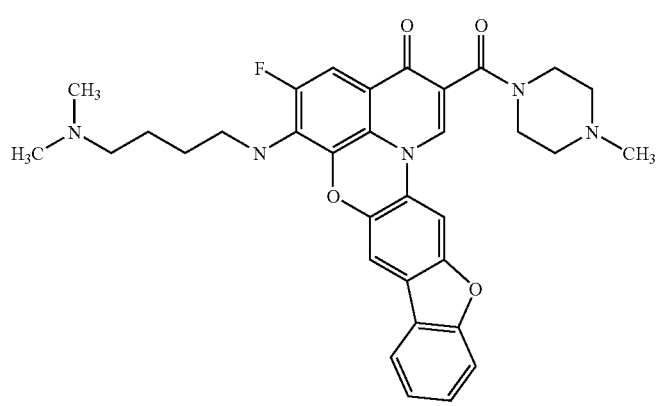 | 1.75 |

-continued
| | | |
|---|---|---|
| 165 | 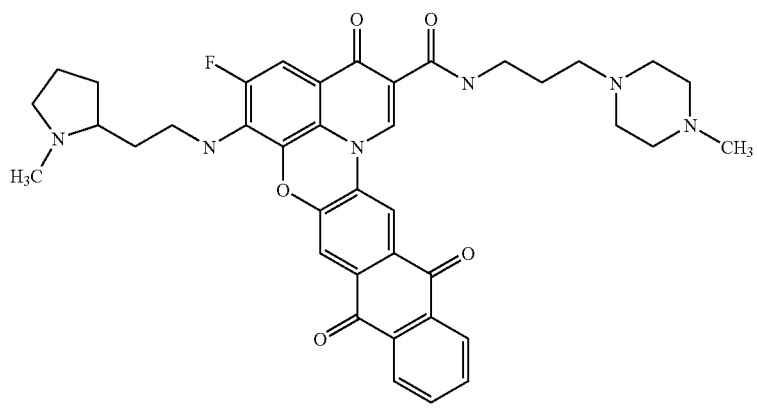 | 1.75 |
| 166 | 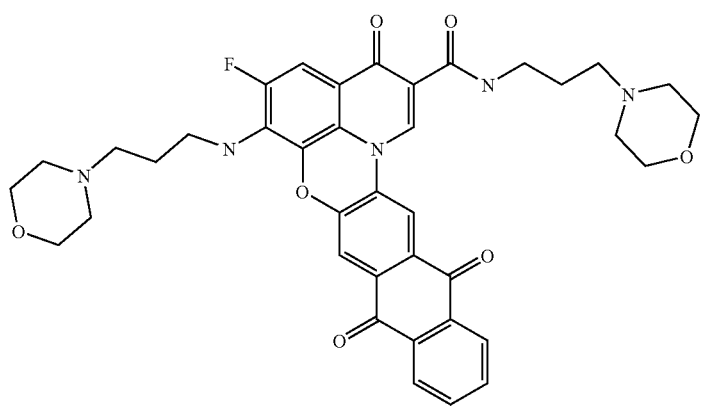 | 1.75 |
| 167 | 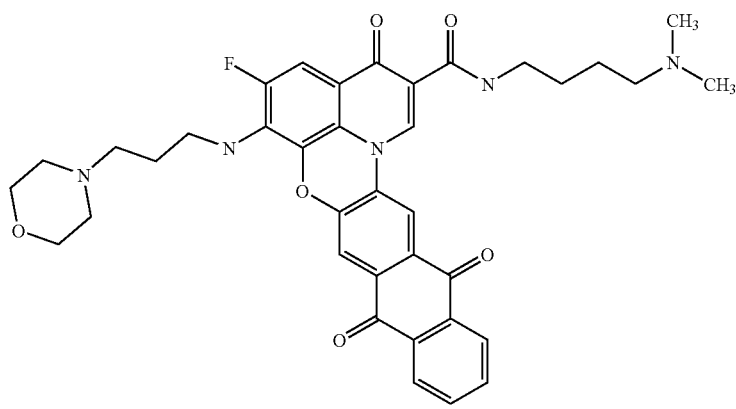 | 1.75 |

-continued
| | | |
|---|---|---|
| 168 | 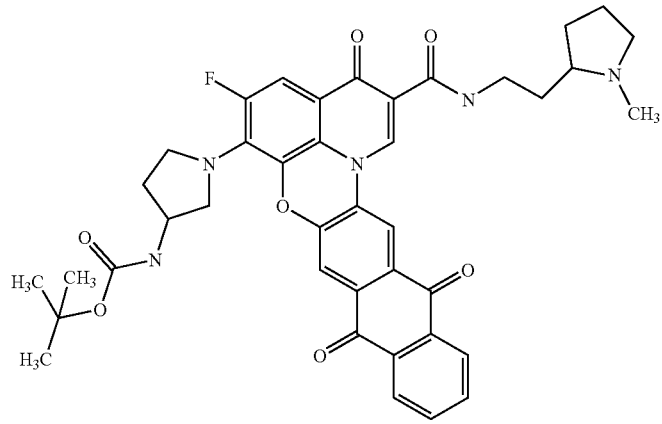 | 1.75 |
| 169 | 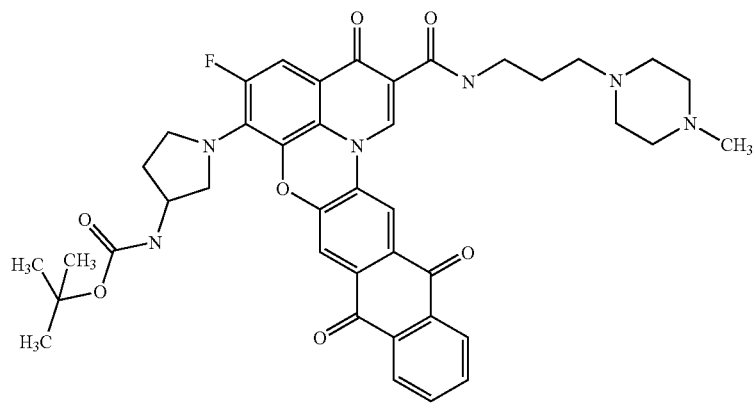 | 1.75 |
| 170 | 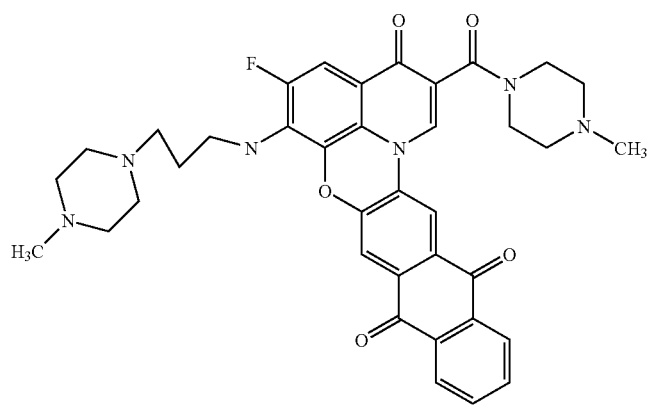 | 1.75 |

-continued
| | | |
|---|---|---|
| 171 | 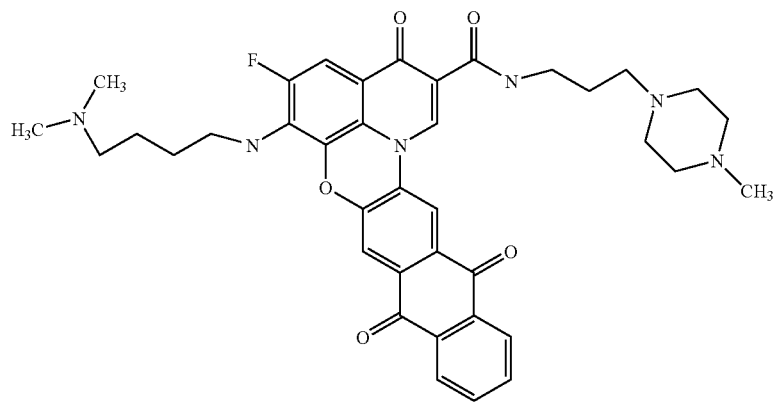 | 1.75 |
| 172 | 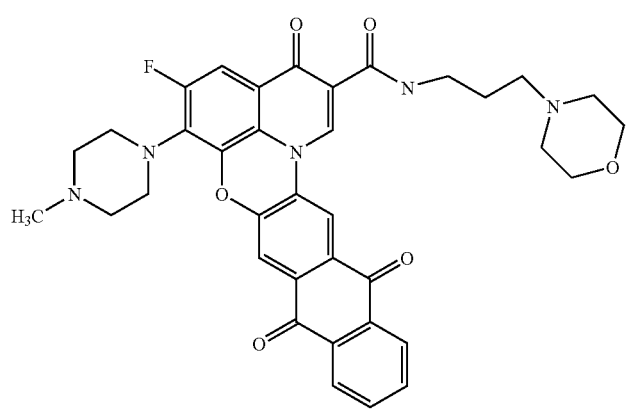 | 1.75 |
| 173 | 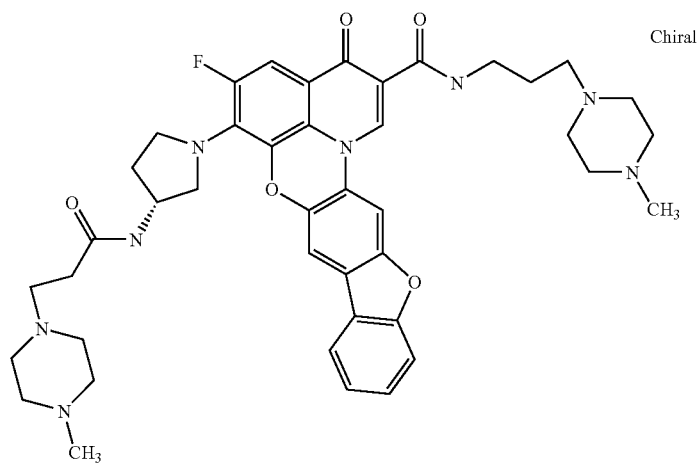 Chiral | 1.75 |

-continued
| | | |
|---|---|---|
| 174 | 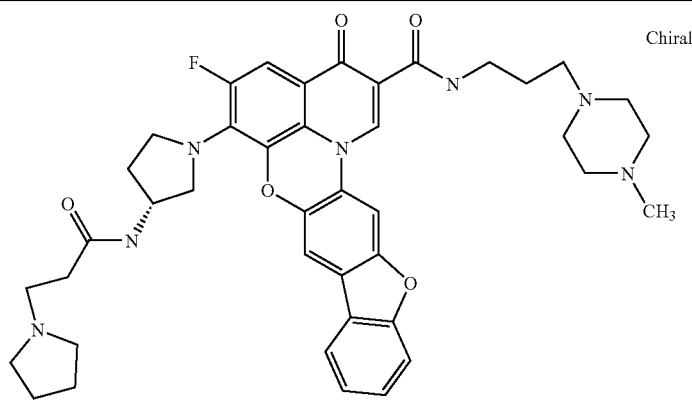 | 1.75 Chiral |
| 175 | 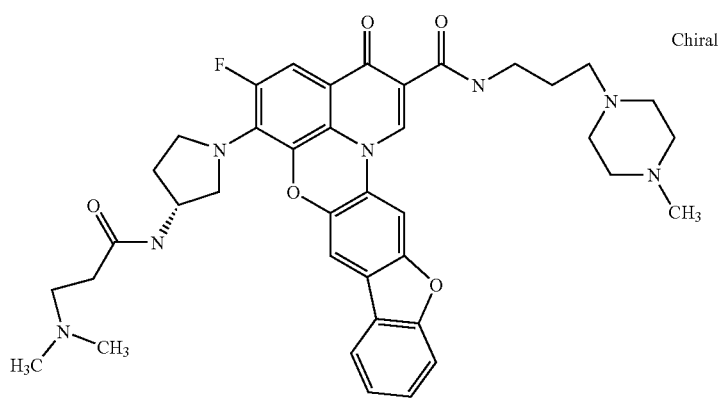 | 1.75 Chiral |
| 176 | 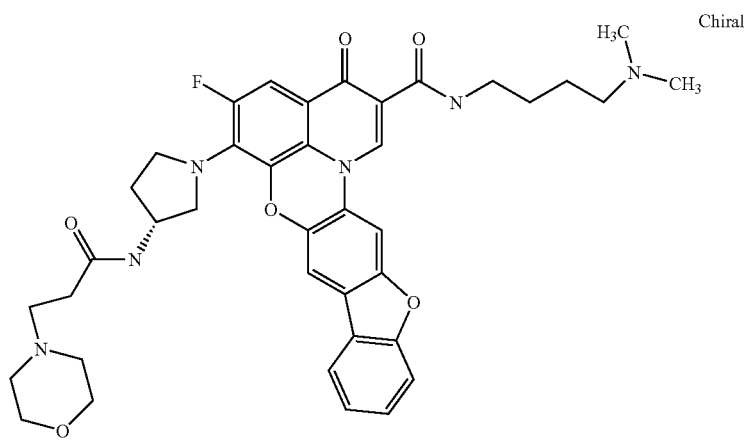 | 1.75 Chiral |
| 177 | 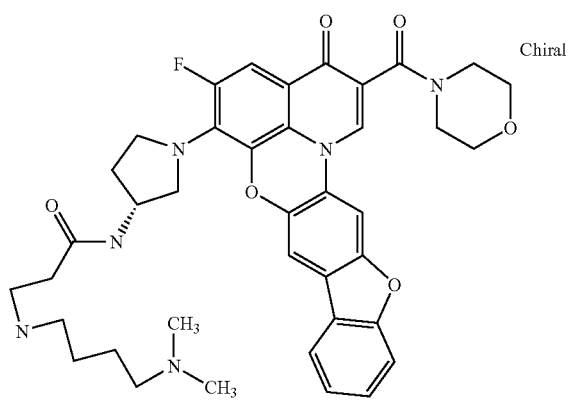 | 1.75 Chiral |

| | | -continued | |
|---|---|---|---|
| 178 | 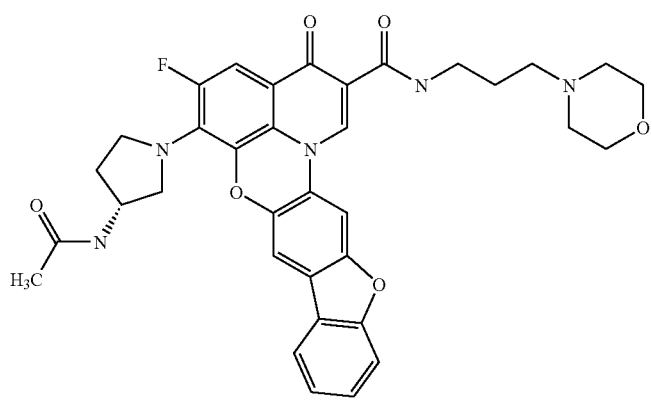 | | 1.75 |
| 179 | 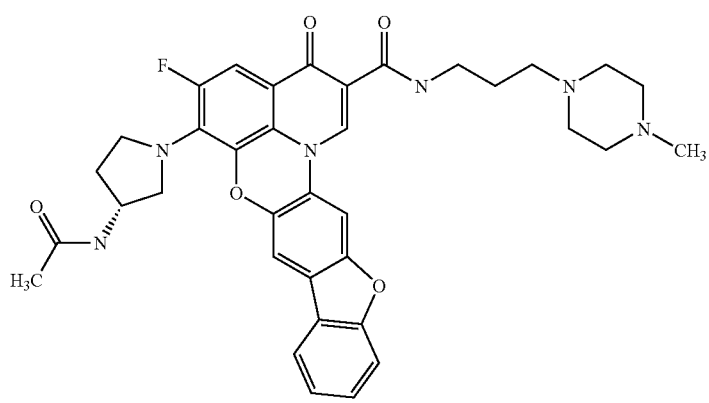 | | 1.75 |
| 180 | 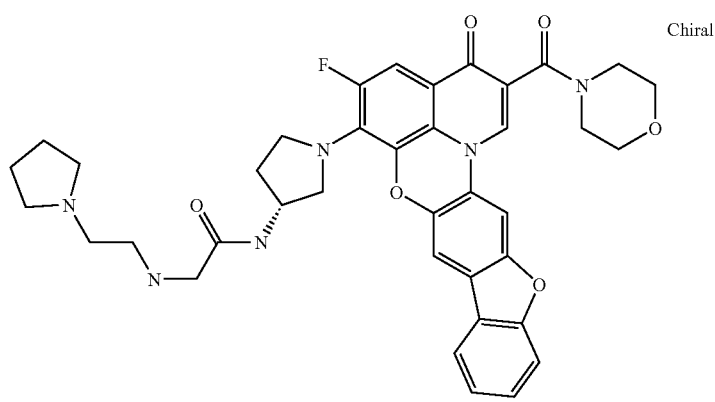 | Chiral | 1.75 |
| 181 | 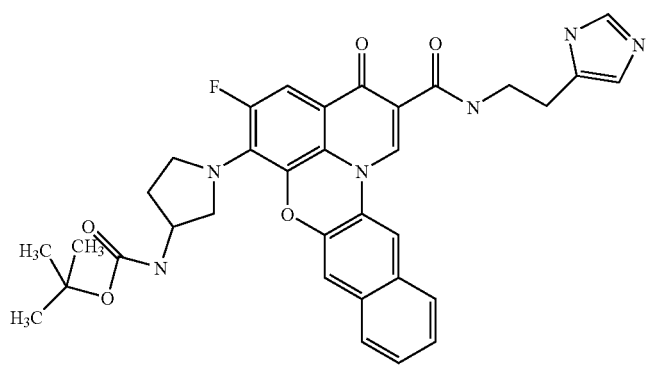 | | 1.75 |

-continued
| | | |
|---|---|---|
| 182 | 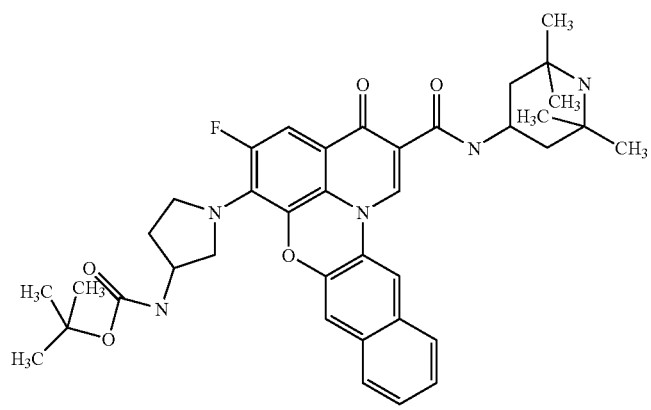 | 1.75 |
| 183 | 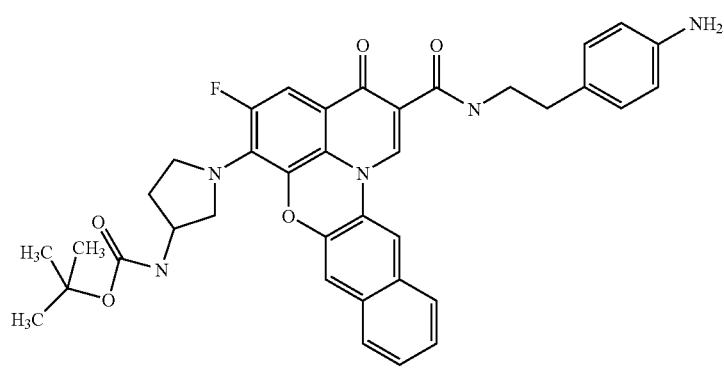 | 1.75 |
| 184 | 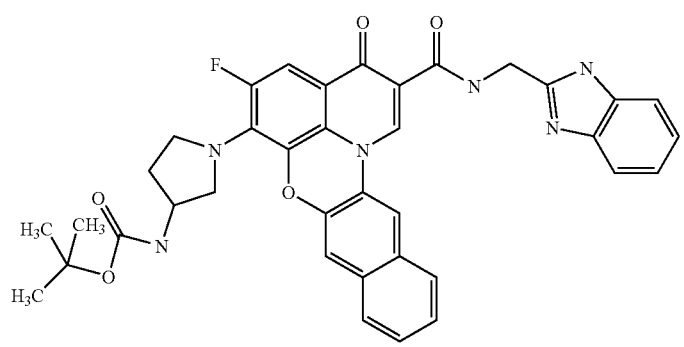 | 1.75 |
| 185 | 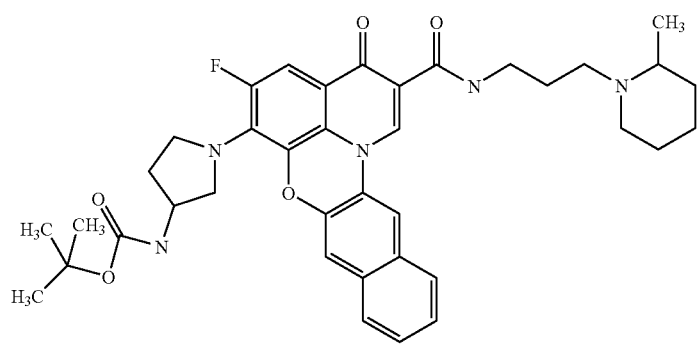 | 1.75 |

-continued
| | | |
|---|---|---|
| 186 | 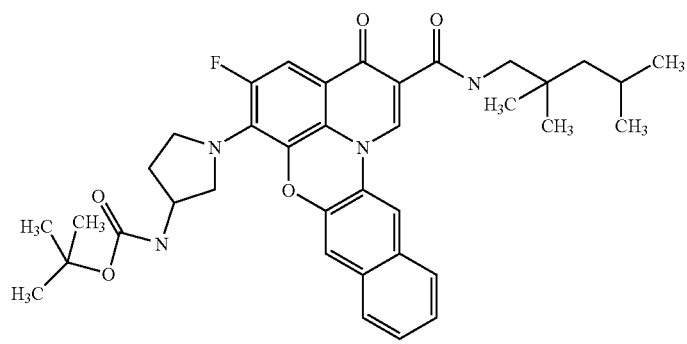 | 1.75 |
| 187 | 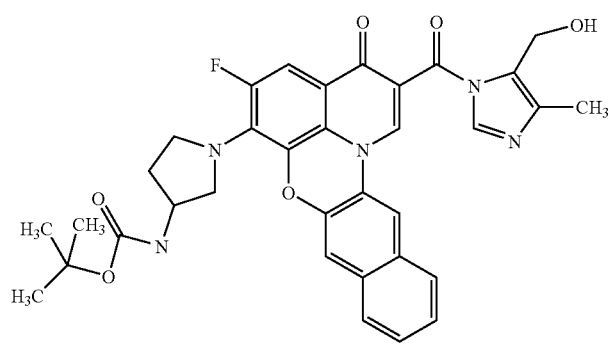 | 1.75 |
| 188 | 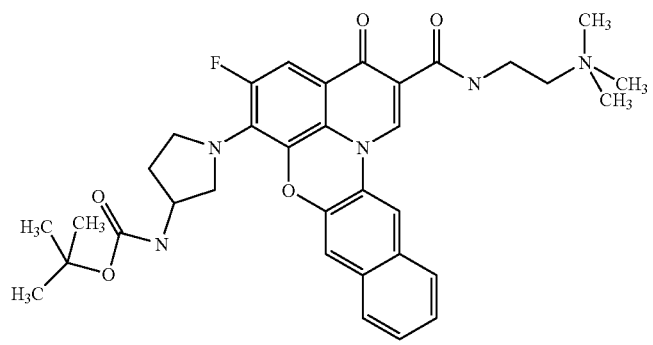 | 1.75 |
| 189 | 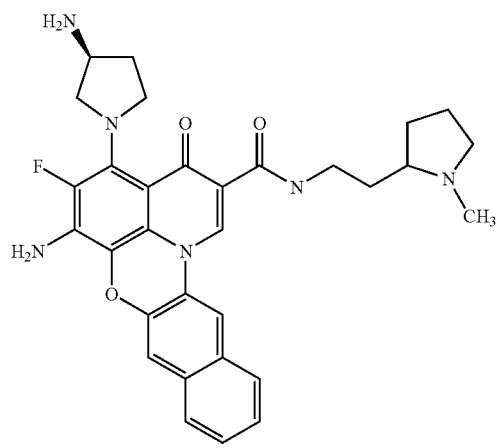 | 1.75 |

-continued
| | | |
|---|---|---|
| 190 | 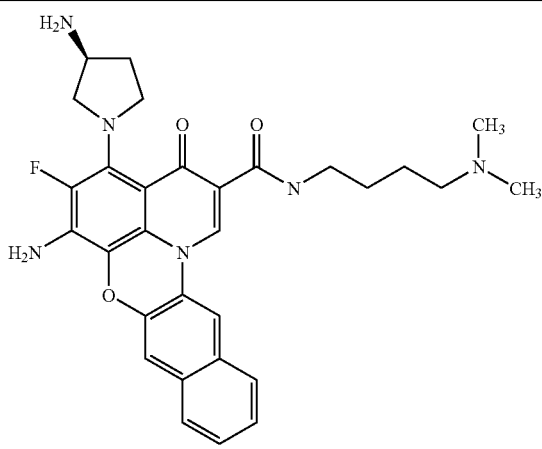 | 1.75 |
| 191 | 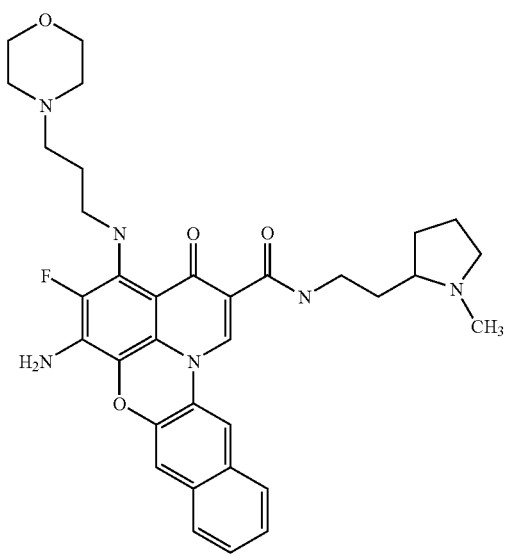 | 1.75 |
| 192 | 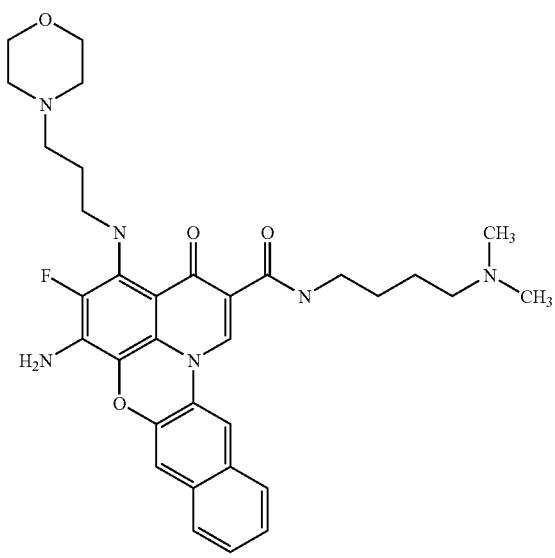 | 1.75 |

-continued
| | | |
|---|---|---|
| 193 | 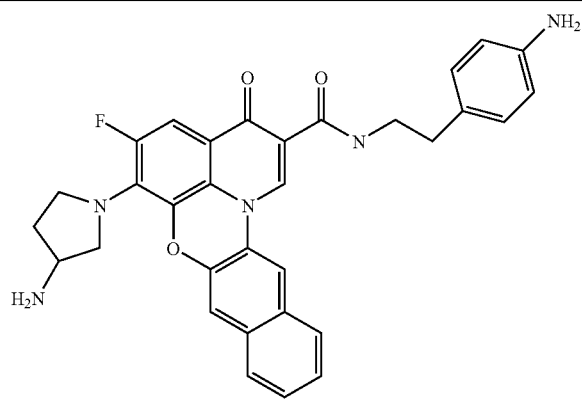 | 1.75 |
| 194 | 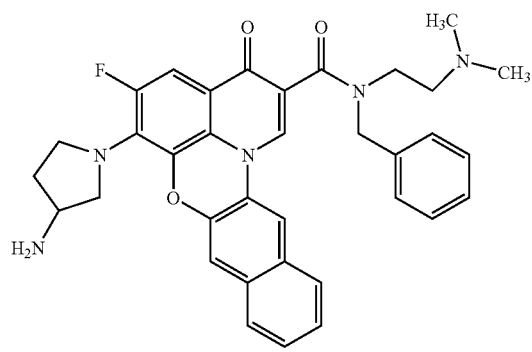 | 1.75 |
| 195 | 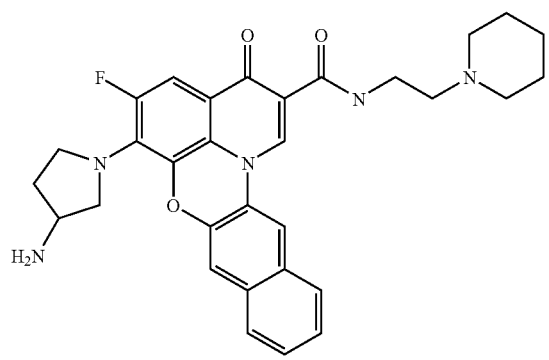 | 1.75 |
| 196 | 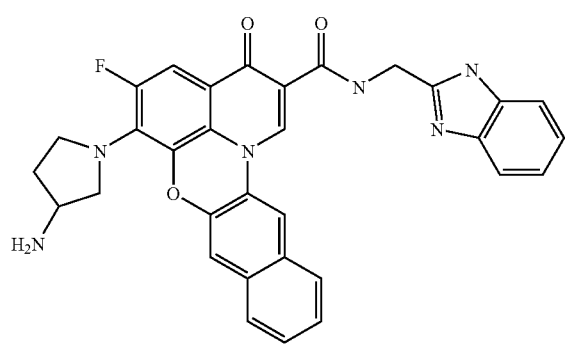 | 1.75 |

-continued
| | | |
|---|---|---|
| 197 | 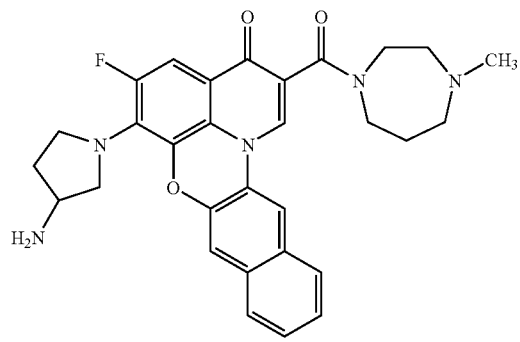 | 1.75 |
| 198 | 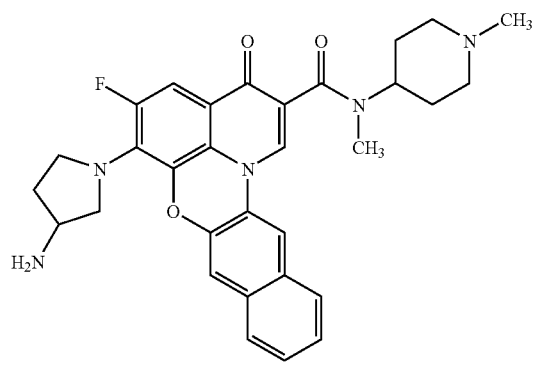 | 1.75 |
| 199 | 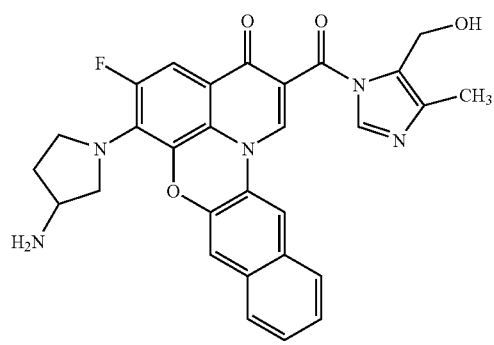 | 1.75 |
| 200 | 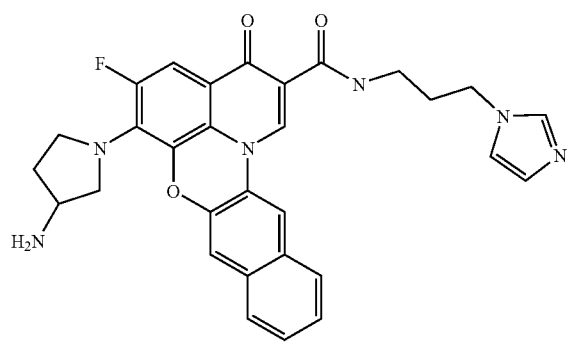 | 1.75 |

-continued
| | | |
|---|---|---|
| 201 | 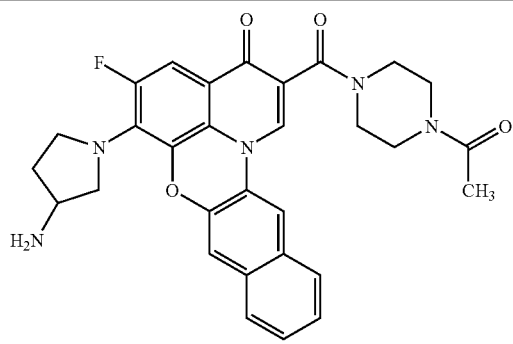 | 1.75 |
| 202 | 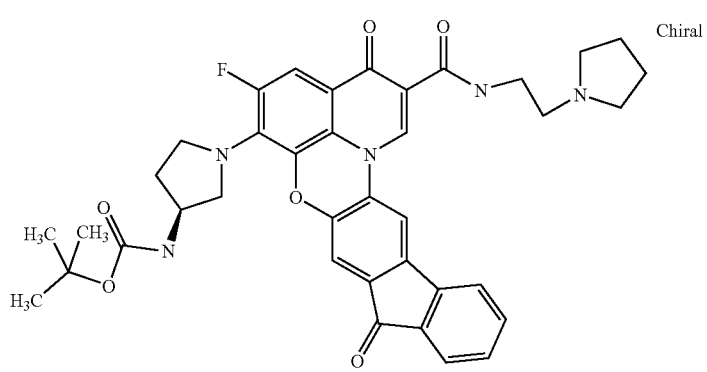 | 1.75 |
| 203 | 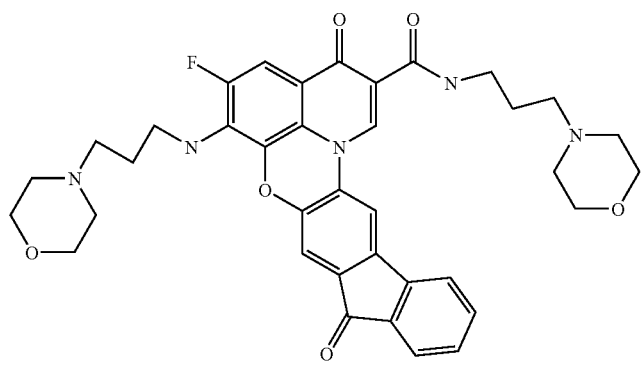 | 1.75 |
| 204 | 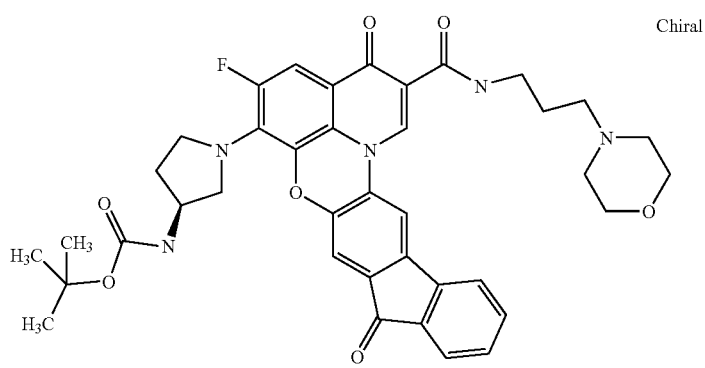 | 1.75 |

-continued
| | | | |
|---|---|---|---|
| 205 | 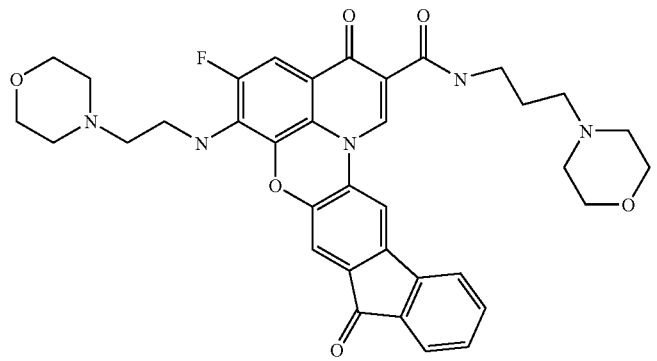 | | 1.75 |
| 206 | 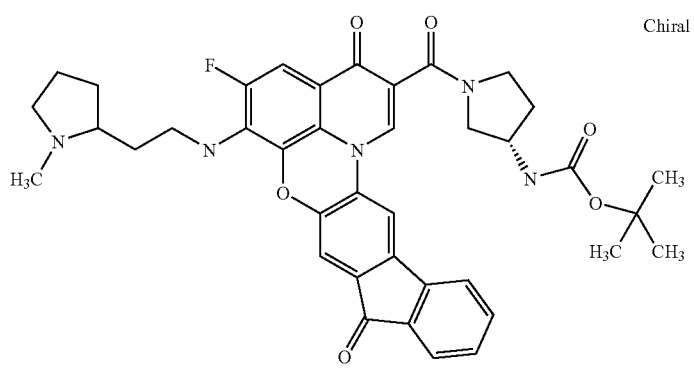 | Chiral | 1.75 |
| 207 | 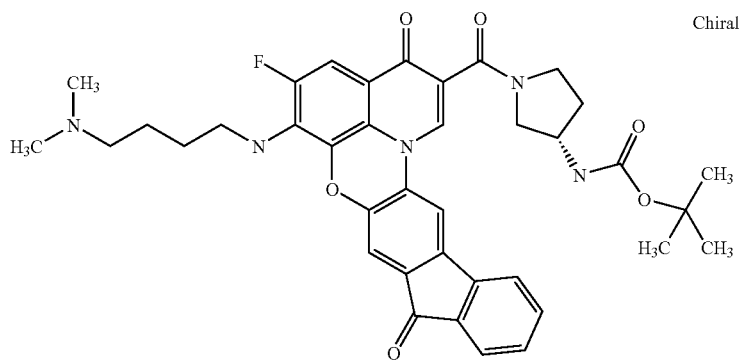 | Chiral | 1.75 |
| 208 | 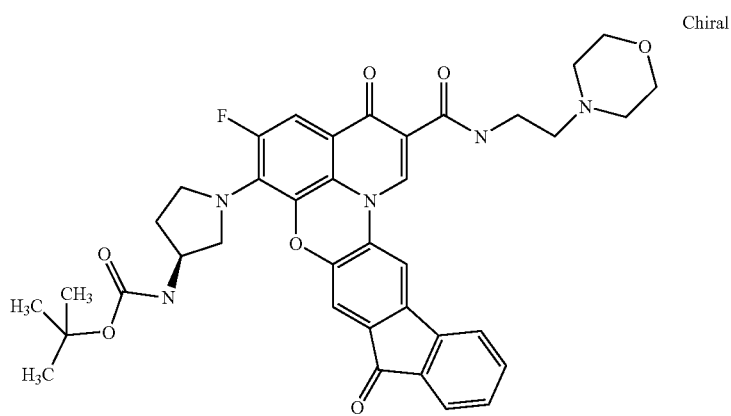 | Chiral | 1.75 |

-continued
| | | | |
|---|---|---|---|
| 209 | 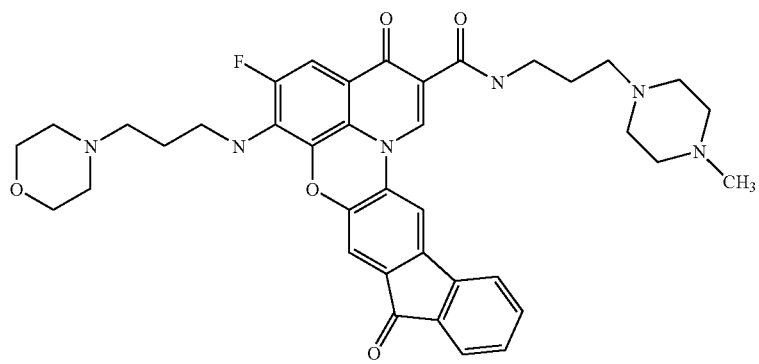 | | 1.75 |
| 210 | 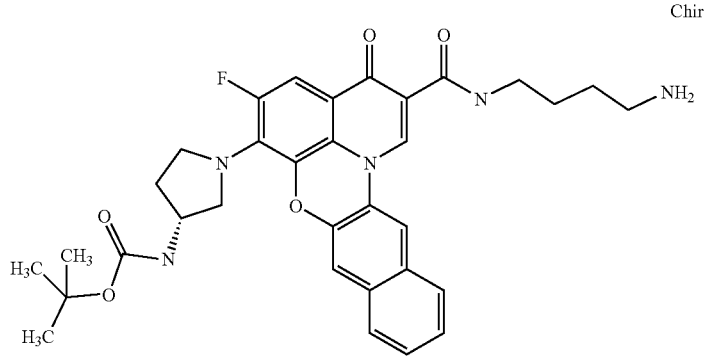 | Chiral | 1.75 |
| 211 | 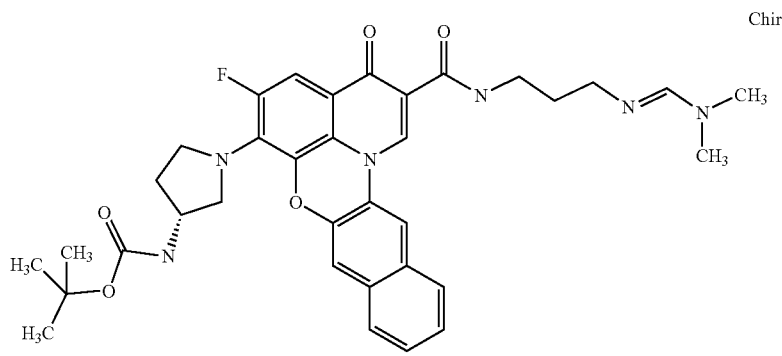 | Chiral | 1.75 |
| 212 | 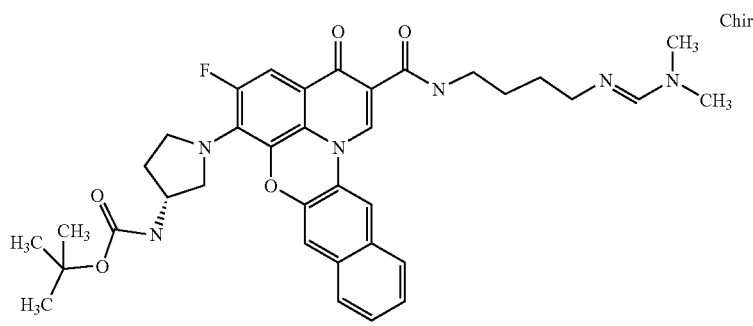 | Chiral | 1.75 |

-continued
| | | |
|---|---|---|
| 213 | 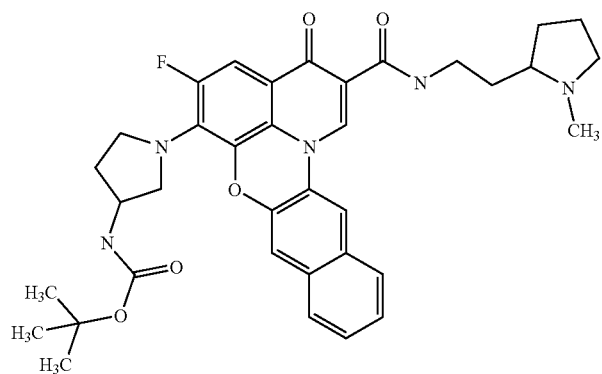 | 1.75 |
| 214 | 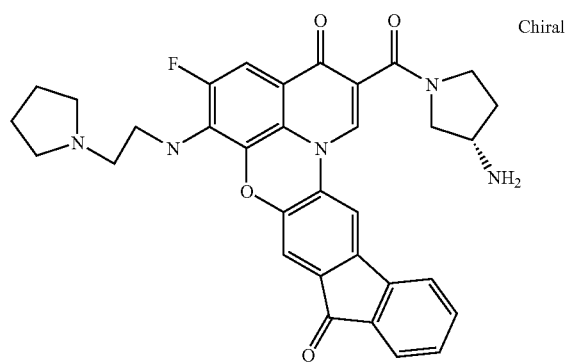 Chiral | 1.75 |
| 215 | 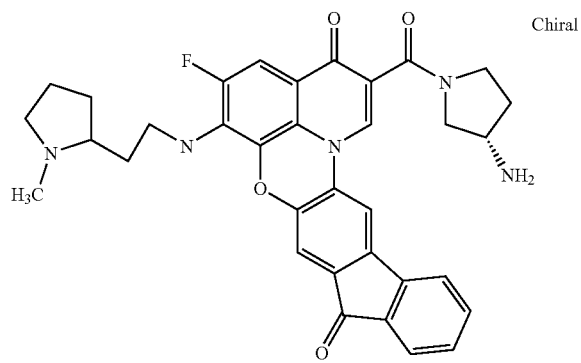 Chiral | 1.75 |
| 216 | 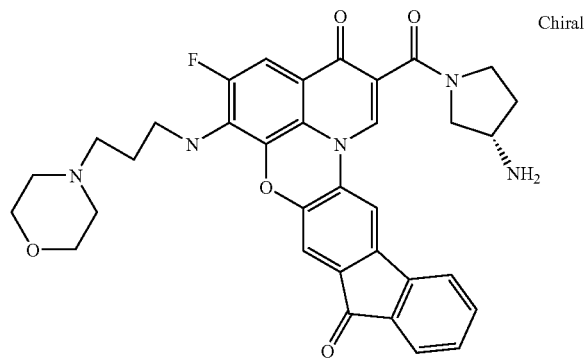 Chiral | 1.75 |

-continued
| 217 | 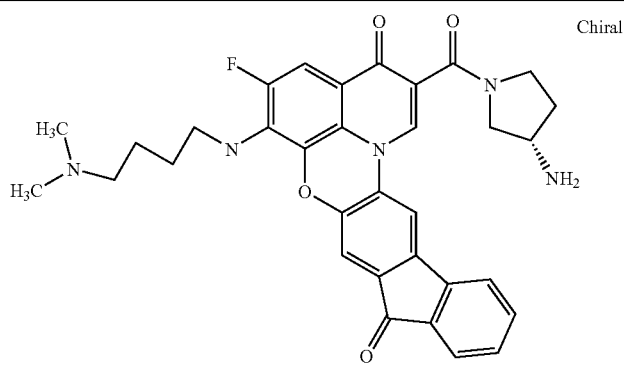 Chiral | 1.75 |
| --- | --- | --- |
| 218 | 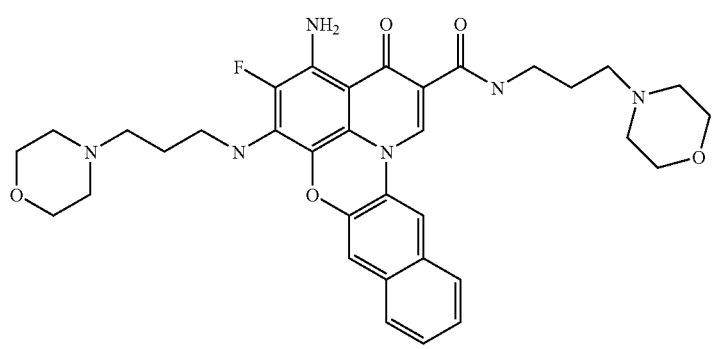 | 1.75 |
| 219 | 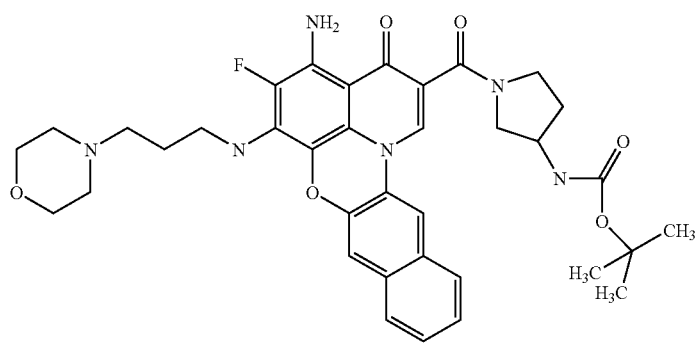 | 1.75 |
| 220 | 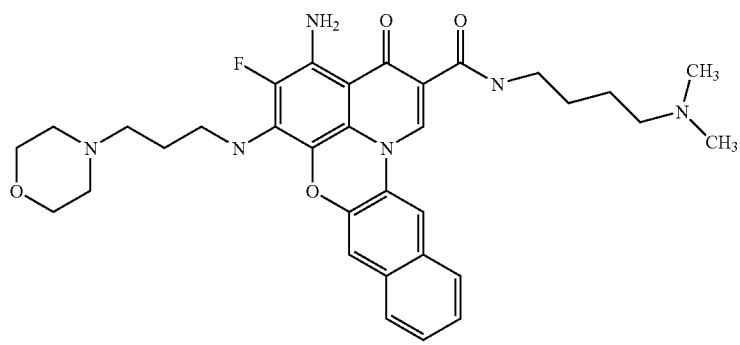 | 1.75 |

| | | |
|---|---|---|
| 221 | 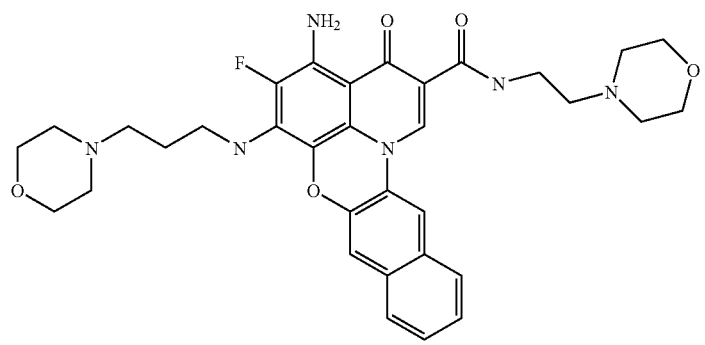 | 1.75 |
| 222 | 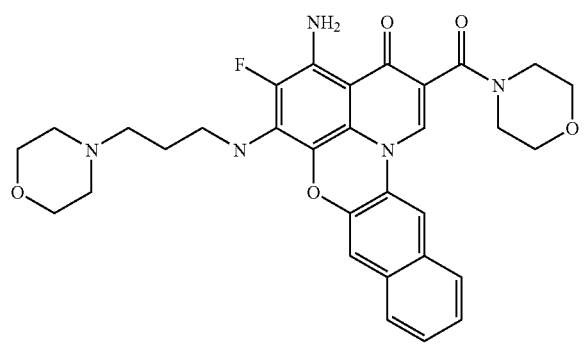 | 1.75 |
| 223 | 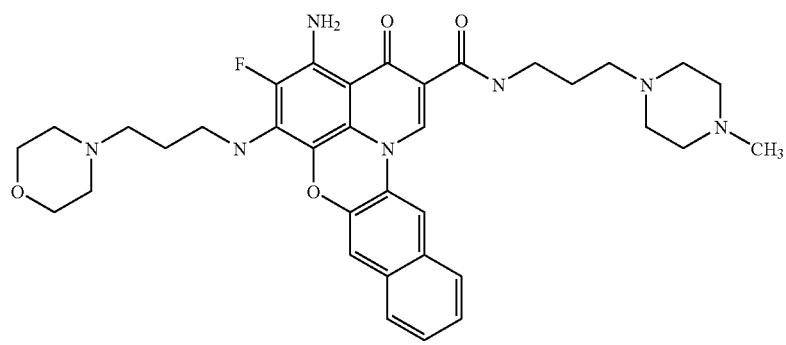 | 1.75 |
| 224 | 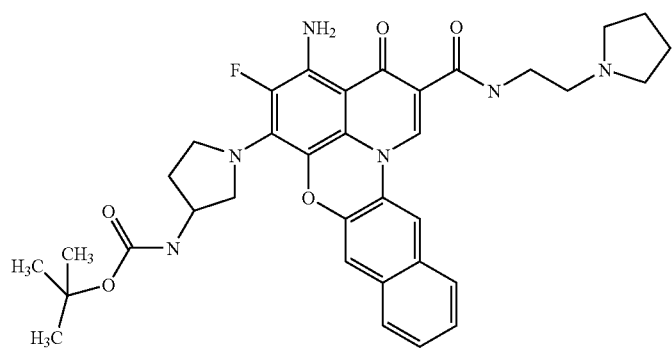 | 1.75 |

-continued
| | | |
|---|---|---|
| 225 | 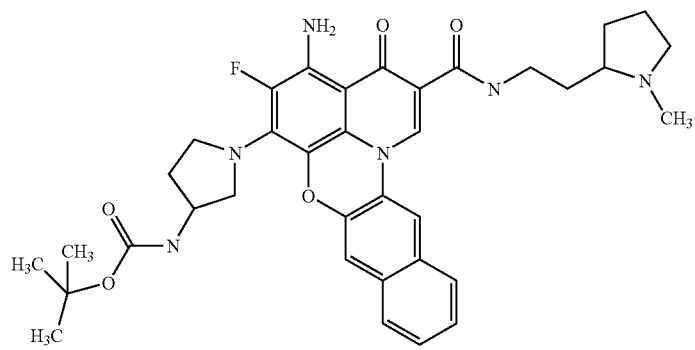 | 1.75 |
| 226 | 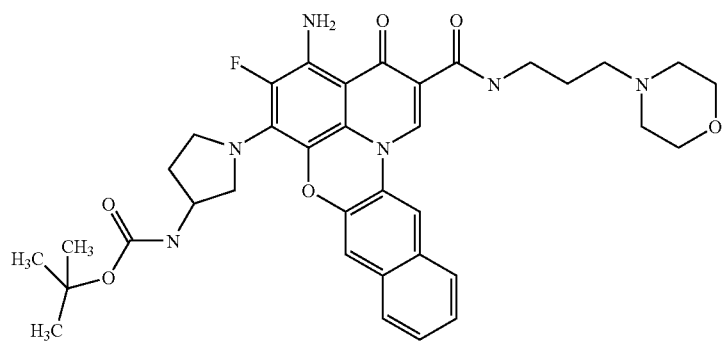 | 1.75 |
| 227 | 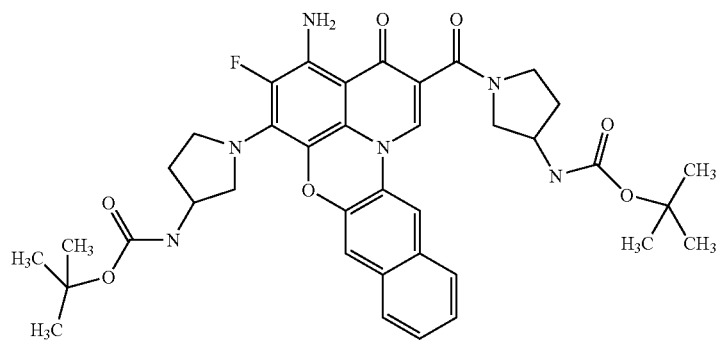 | 1.75 |
| 228 | 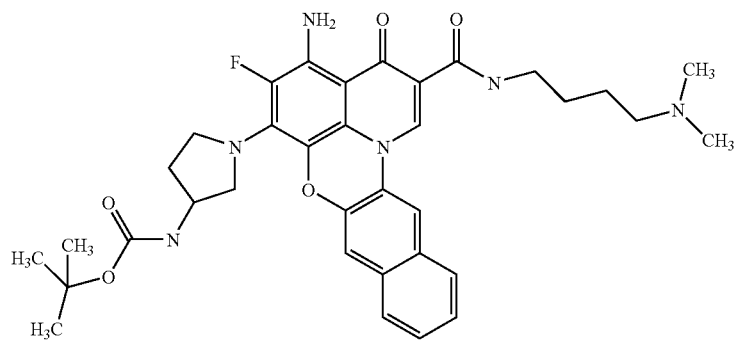 | 1.75 |

-continued
| | | |
|---|---|---|
| 229 | 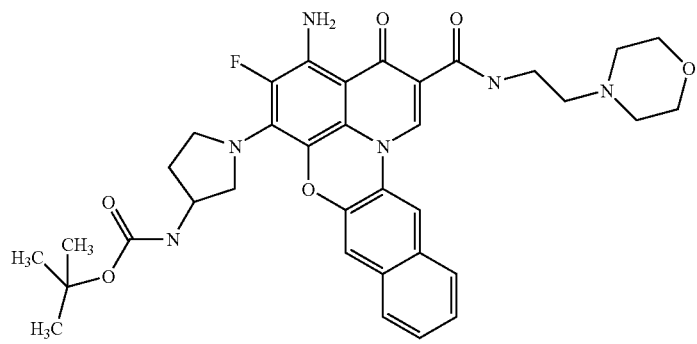 | 1.75 |
| 230 | 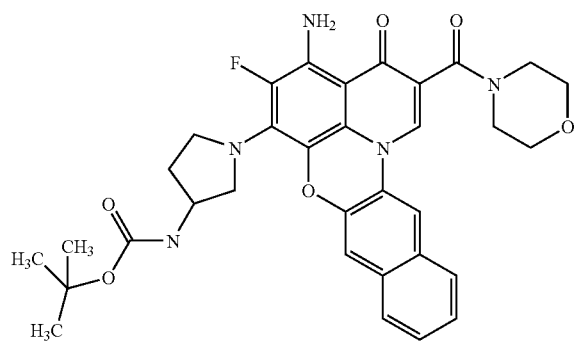 | 1.75 |
| 231 | 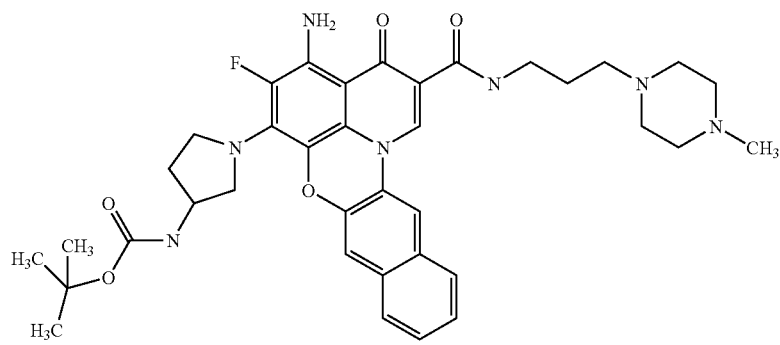 | 1.75 |
| 232 | 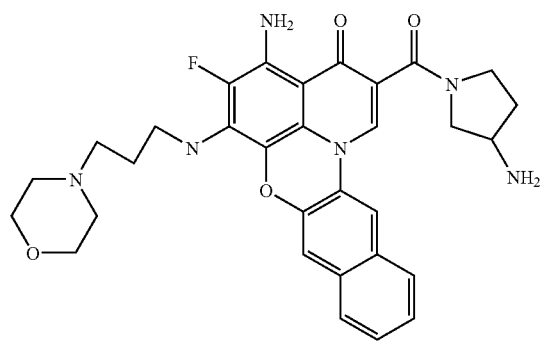 | 1.75 |

-continued
| | | |
|---|---|---|
| 233 | 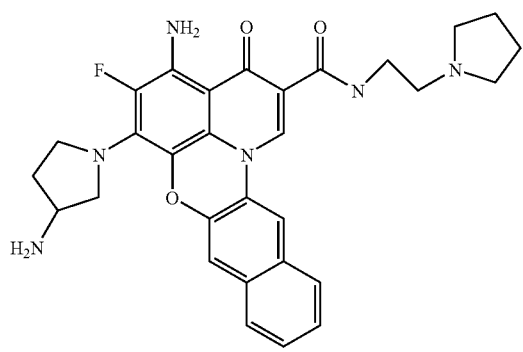 | 1.75 |
| 234 | 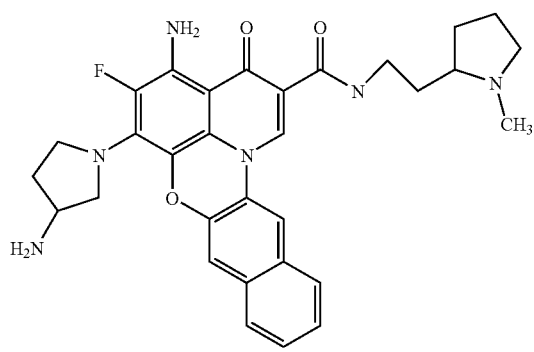 | 1.75 |
| 235 | 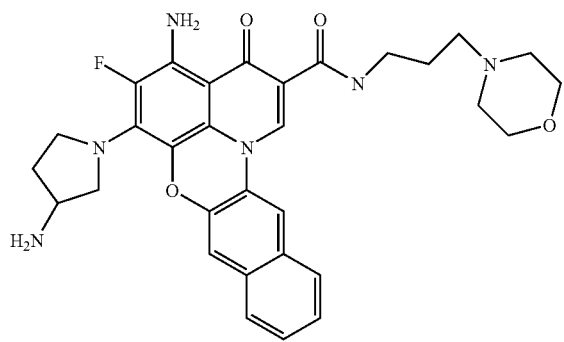 | 1.75 |
| 236 | 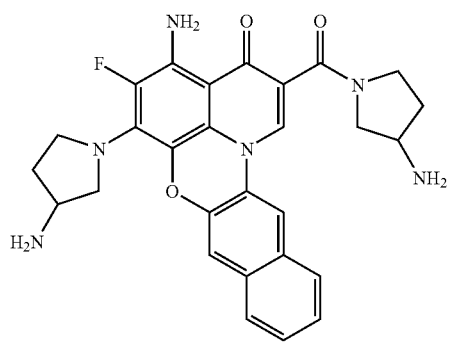 | 1.75 |

-continued
| | | |
|---|---|---|
| 237 | 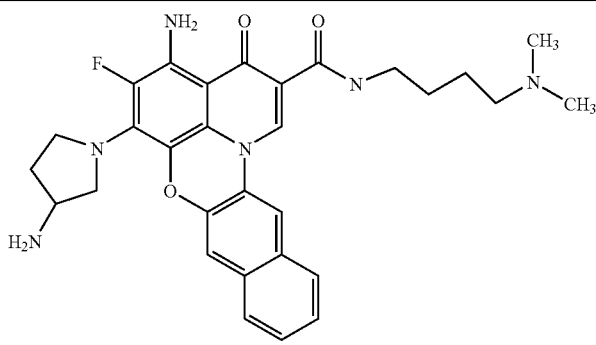 | 1.75 |
| 238 | 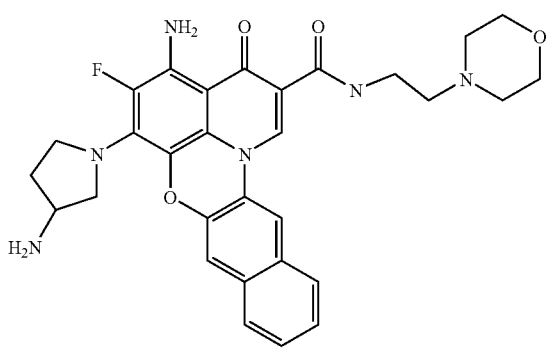 | 1.75 |
| 239 | 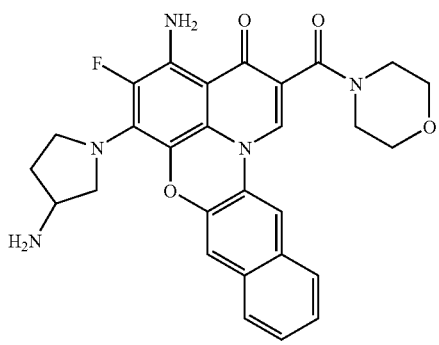 | 1.75 |
| 240 | 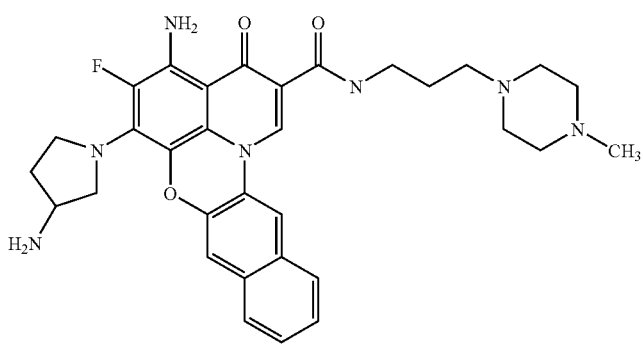 | 1.75 |

-continued
| | | |
|---|---|---|
| 241 | 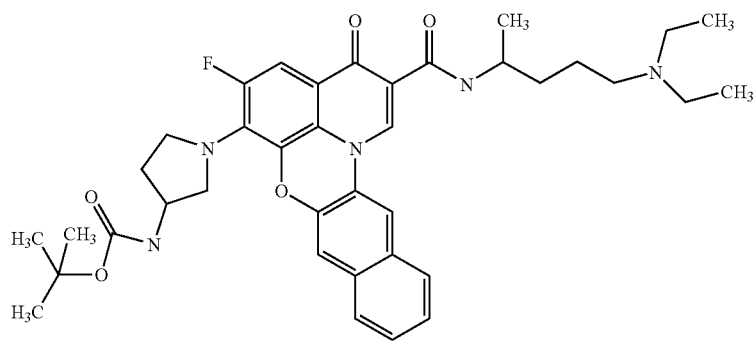 | 1.75 |
| 242 | 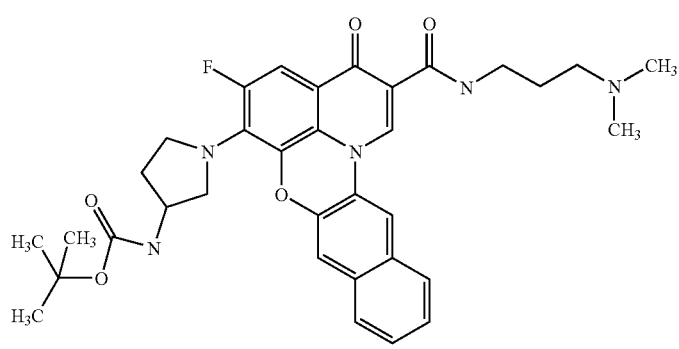 | 1.75 |
| 243 | 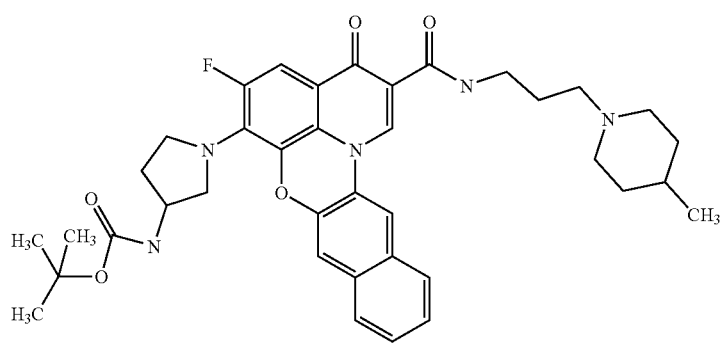 | 1.75 |
| 244 | 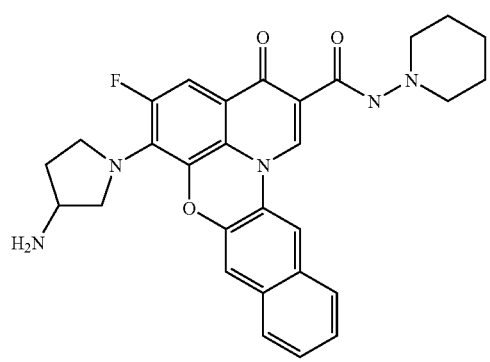 | 1.75 |

-continued
| | | |
|---|---|---|
| 245 | 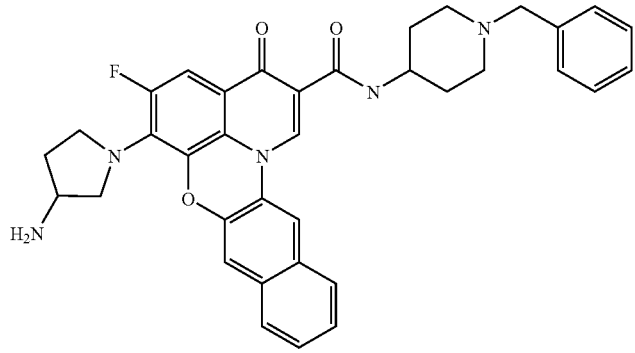 | 1.75 |
| 246 | 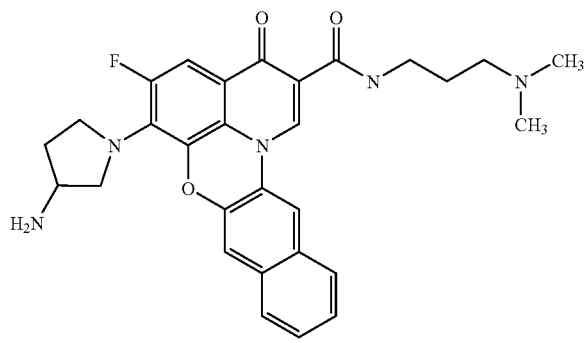 | 1.75 |
| 247 | 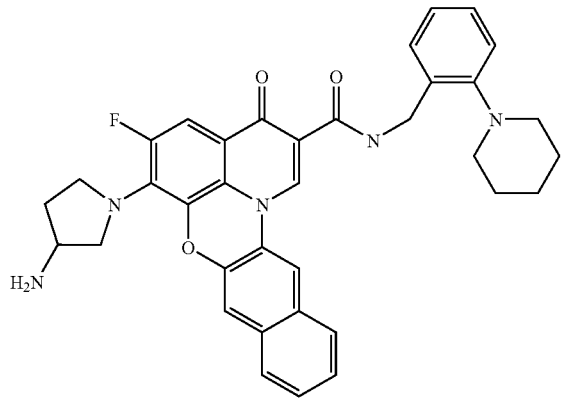 | 1.75 |
| 248 | 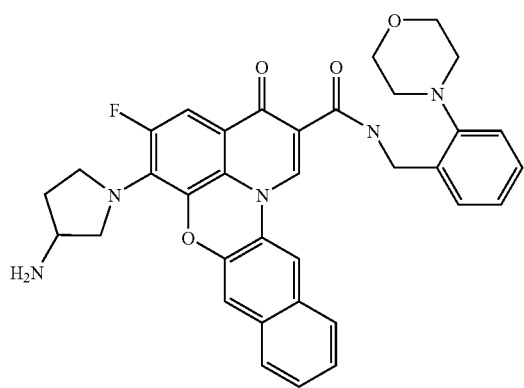 | 1.75 |

-continued
| | | |
|---|---|---|
| 249 | 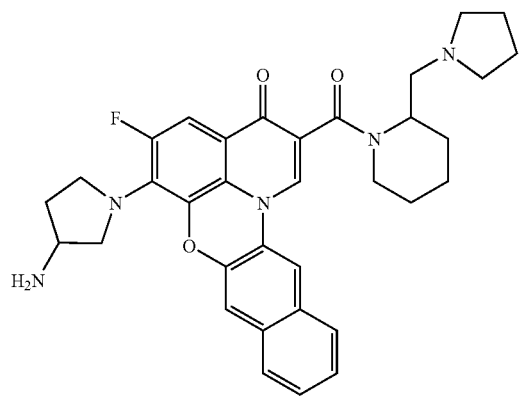 | 1.75 |
| 250 | 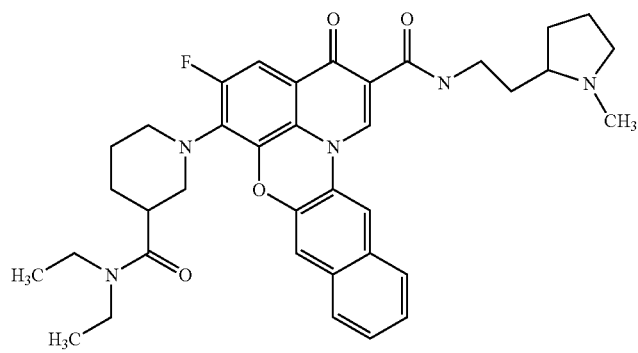 | 1.75 |
| 251 | 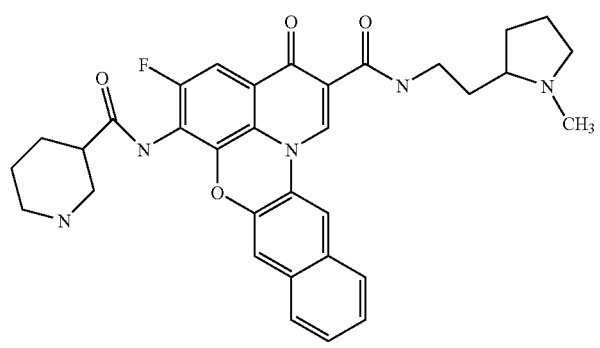 | 1.75 |
| 252 | 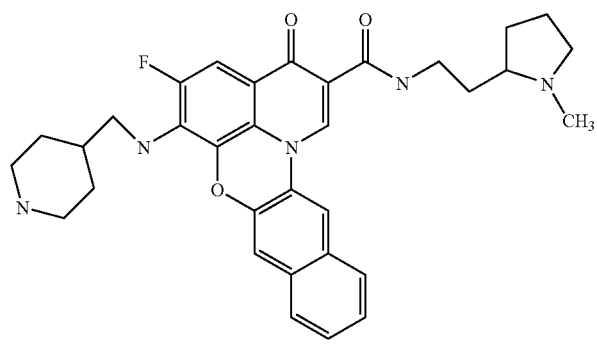 | 1.75 |

-continued
| | | |
|---|---|---|
| 253 | 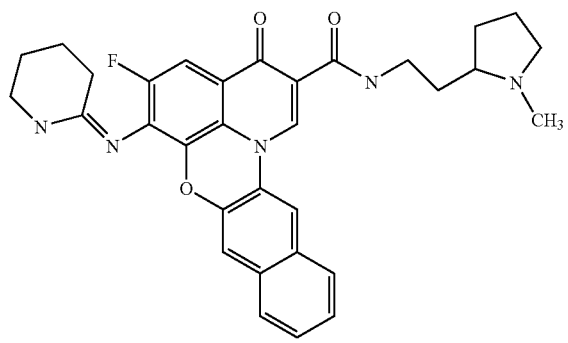 | 1.75 |
| 254 | 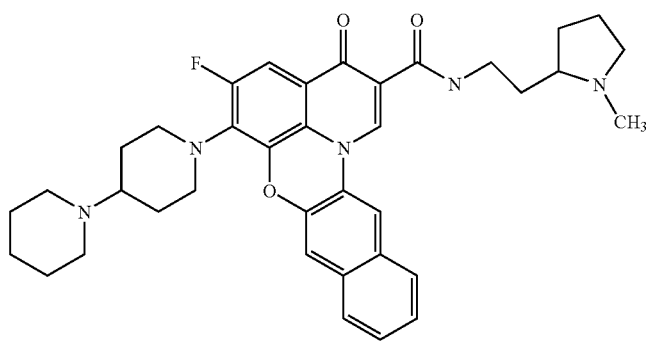 | 1.75 |
| 255 | 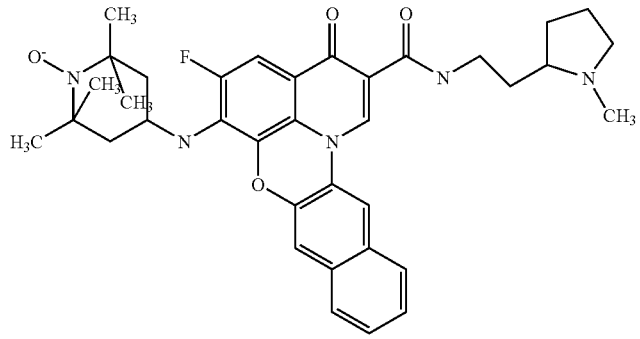 | 1.75 |
| 256 | 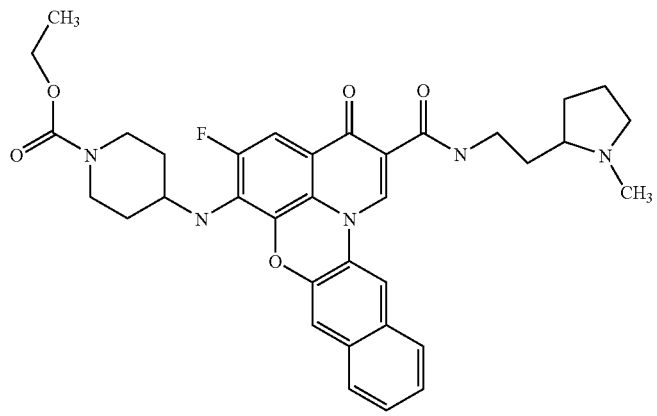 | 1.75 |

| | | |
|---|---|---|
| 257 | 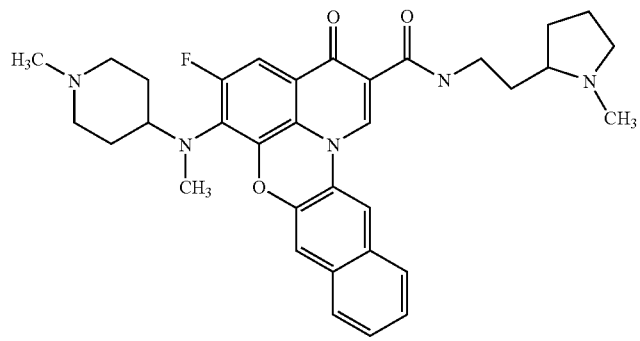 | 1.75 |
| 258 | 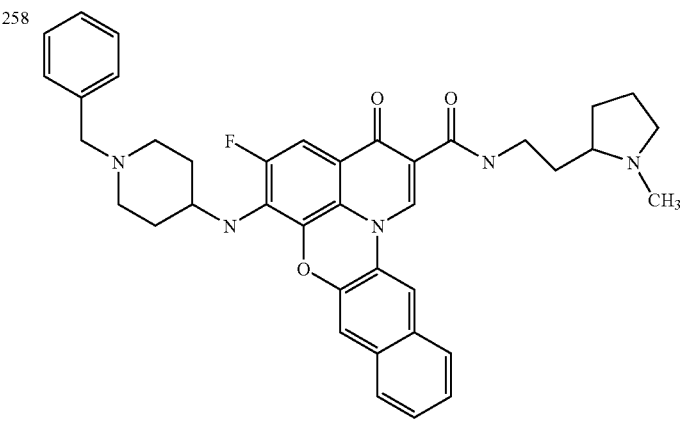 | 1.75 |
| 259 | 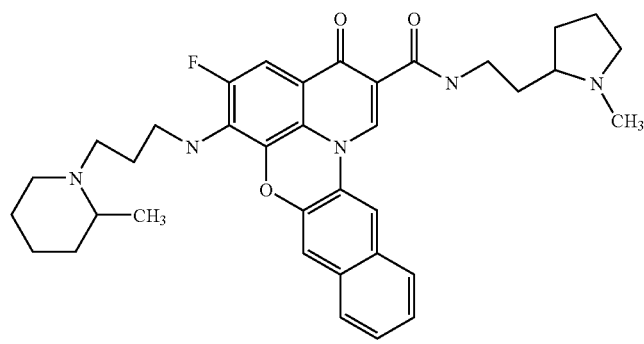 | 1.75 |
| 260 | 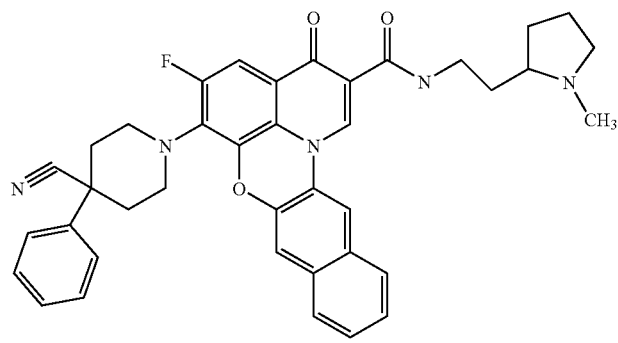 | 1.75 |

-continued
| 261 | 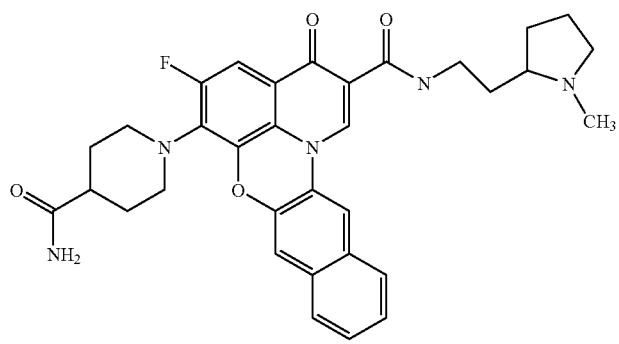 | 1.75 |
| 262 | 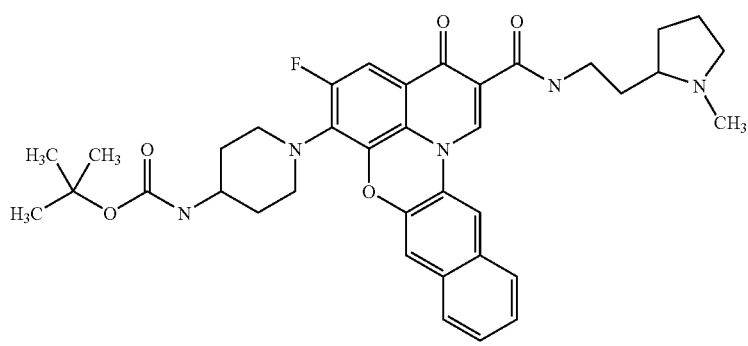 | 1.75 |
| 263 | 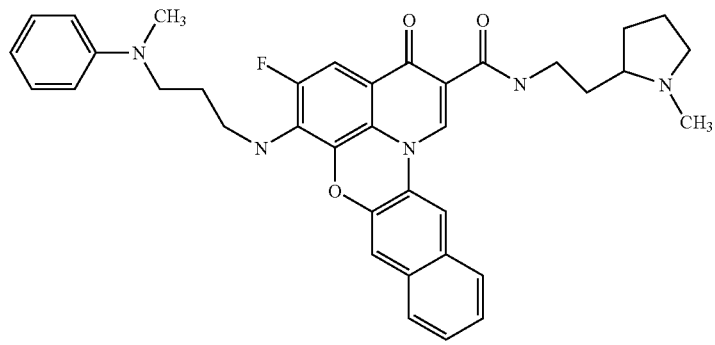 | 1.75 |
| 264 | 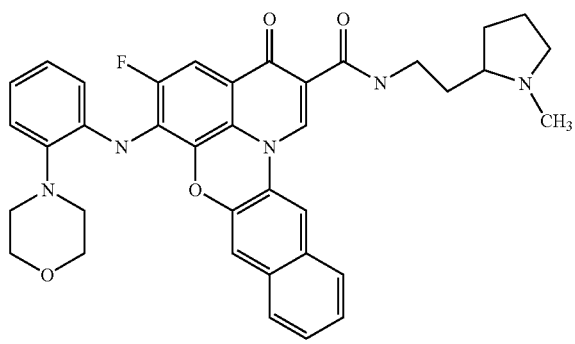 | 1.75 |

-continued
| 265 | 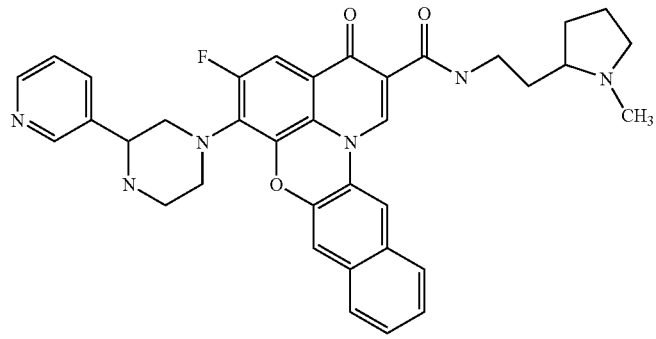 | 1.75 |
| 266 | 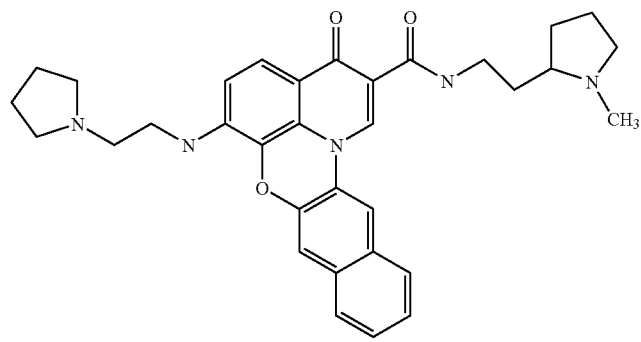 | 1.75 |
| 267 | 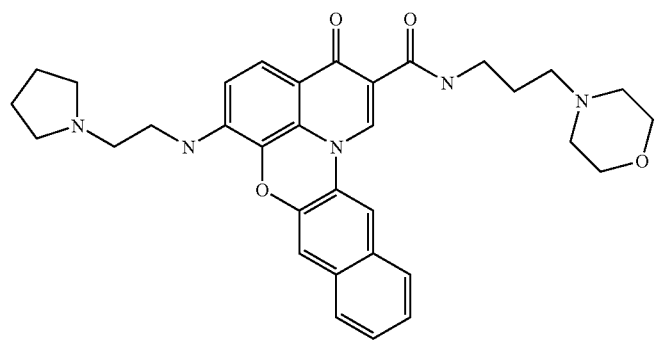 | 1.75 |
| 268 | 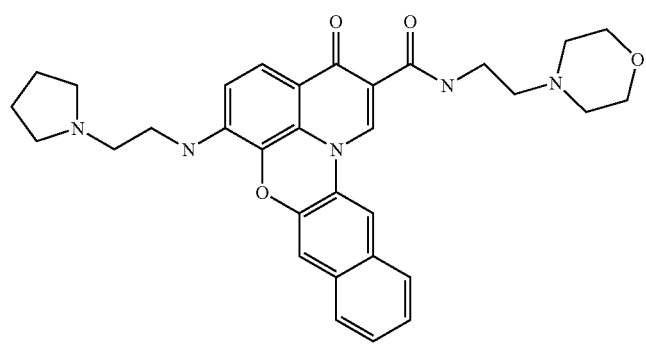 | 1.75 |

-continued
| | | |
|---|---|---|
| 269 | 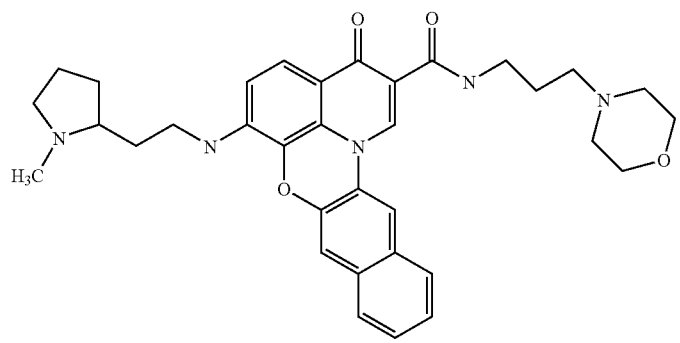 | 1.75 |
| 270 | 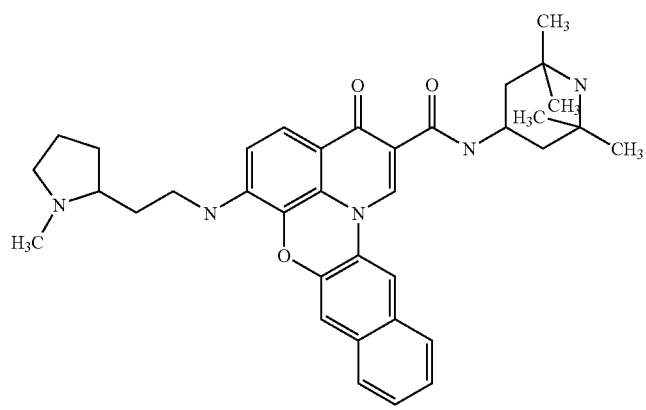 | 1.75 |
| 271 | 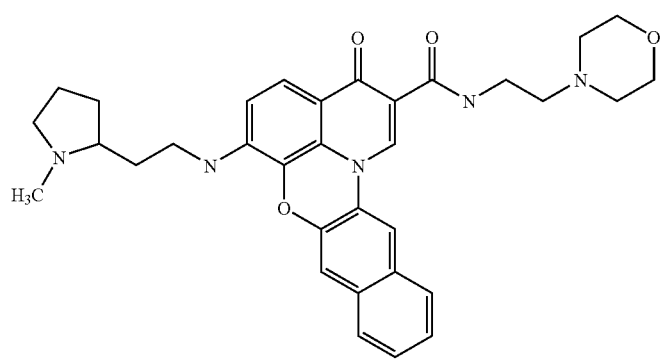 | 1.75 |
| 272 | 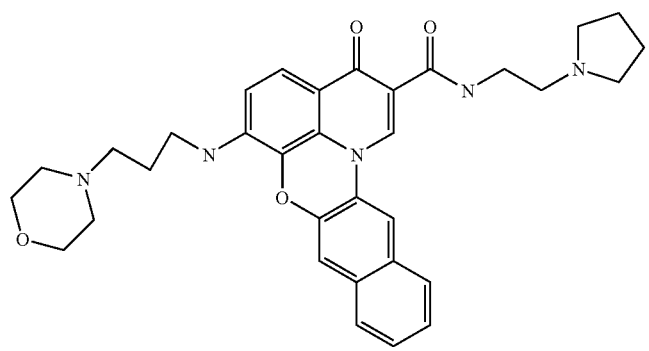 | 1.75 |

-continued
| | | |
|---|---|---|
| 273 | 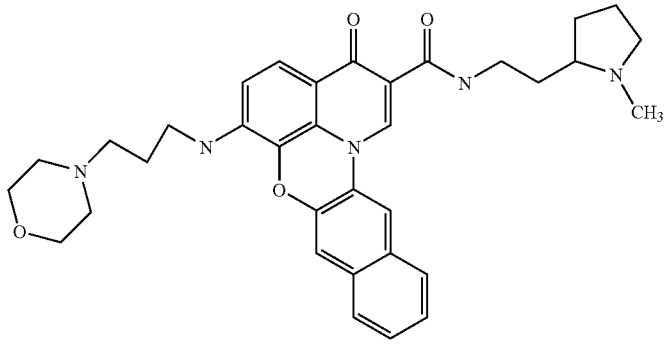 | 1.75 |
| 274 | 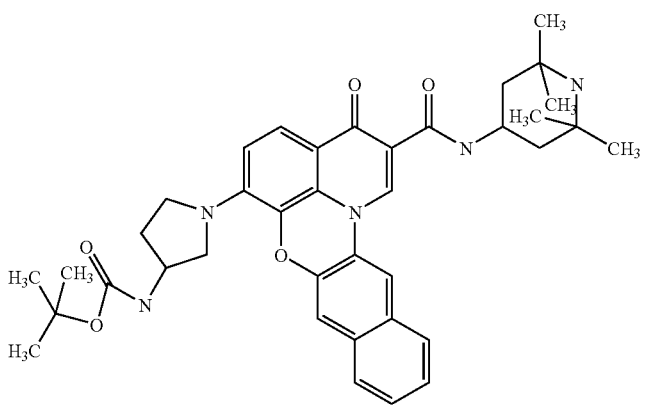 | 1.75 |
| 275 | 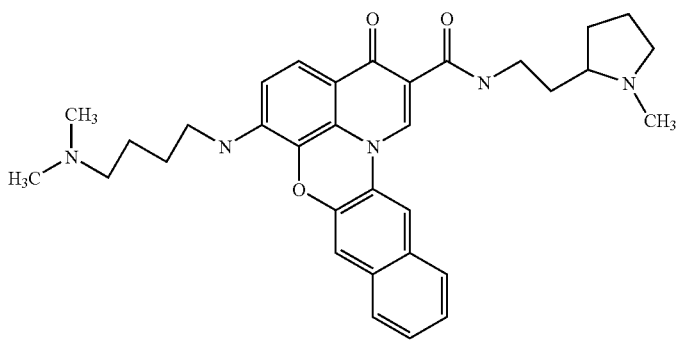 | 1.75 |
| 276 | 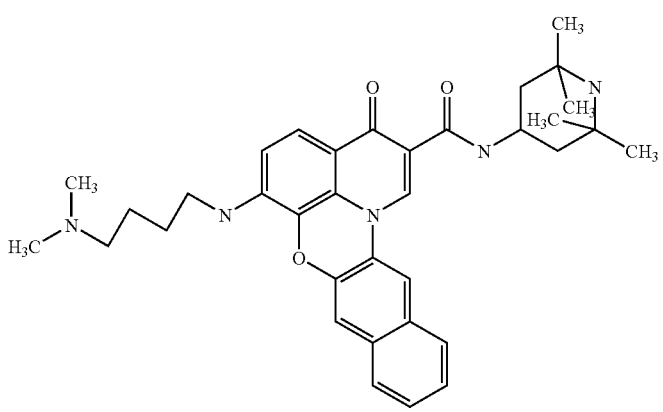 | 1.75 |

-continued
| | | |
|---|---|---|
| 277 | 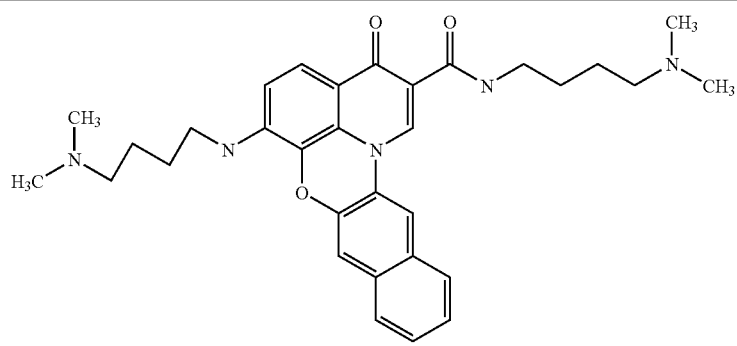 | 1.75 |
| 278 | 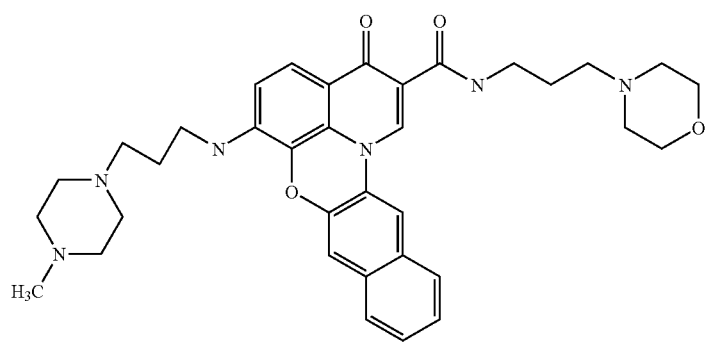 | 1.75 |
| 279 | 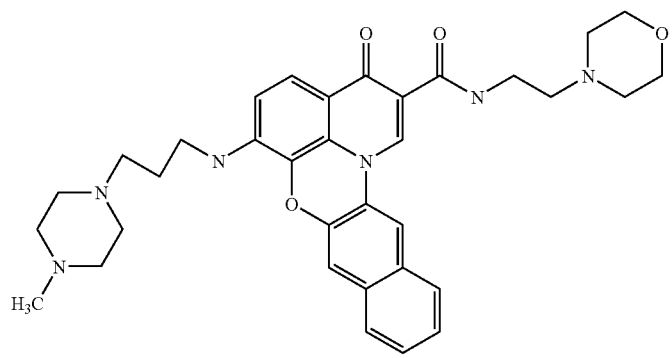 | 1.75 |
| 280 | 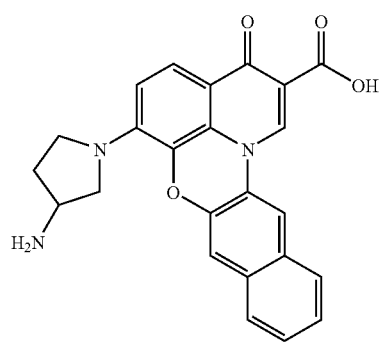 | 1.75 |

-continued
| | | |
|---|---|---|
| 281 | 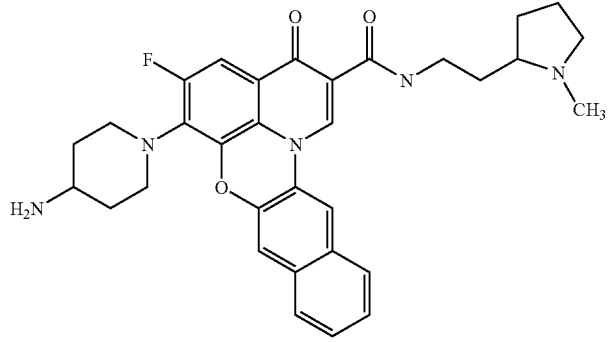 | 1.75 |
| 282 | 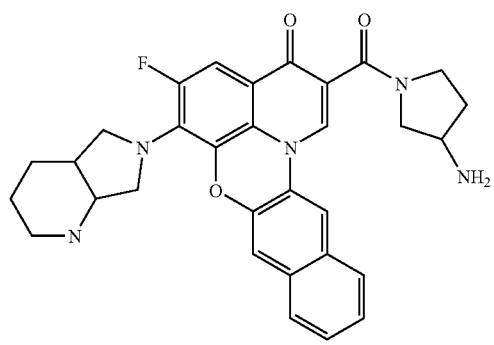 | 1.75 |
| 283 | 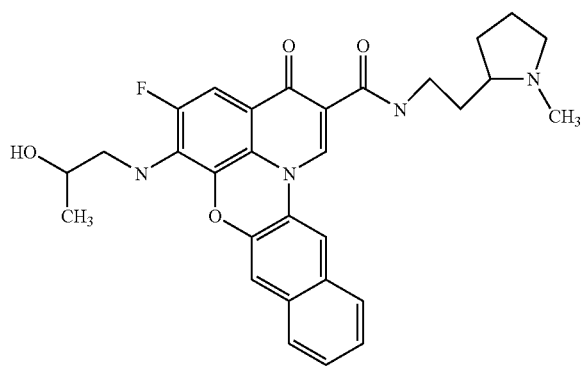 | 1.75 |
| 284 | 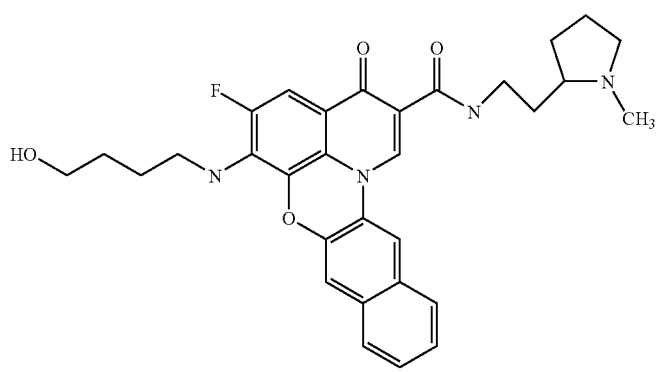 | 1.75 |

| | | |
|---|---|---|
| 285 | 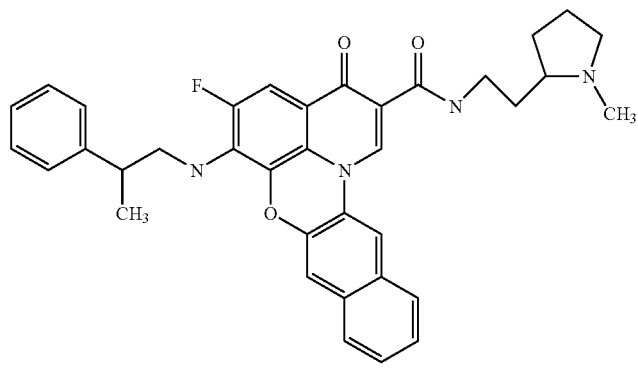 | 1.75 |
| 286 | 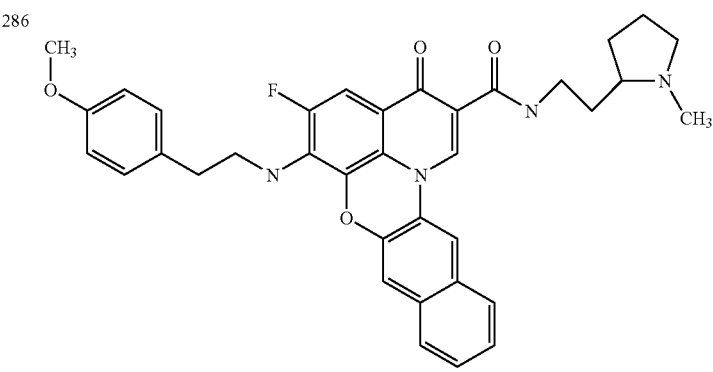 | 1.75 |
| 287 | 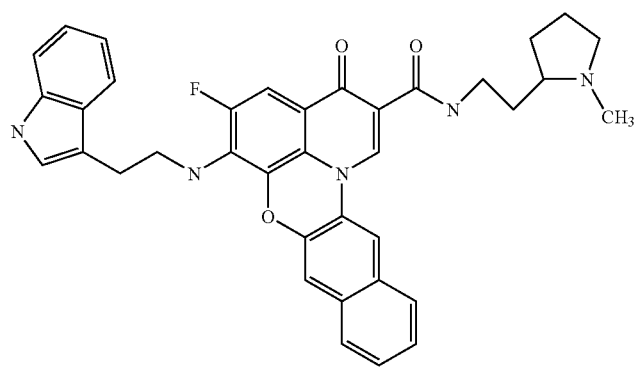 | 1.75 |
| 288 | 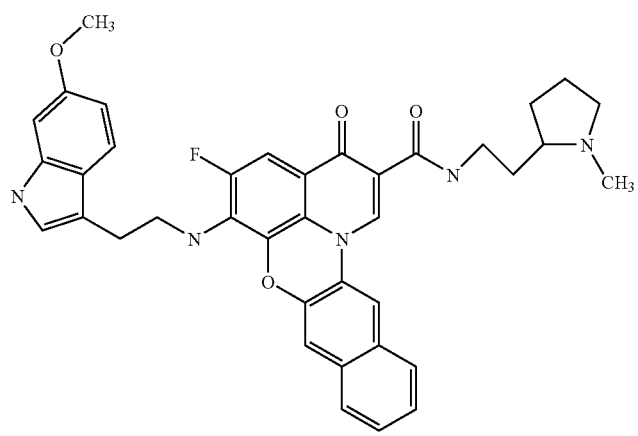 | 1.75 |

-continued
| | | |
|---|---|---|
| 289 | 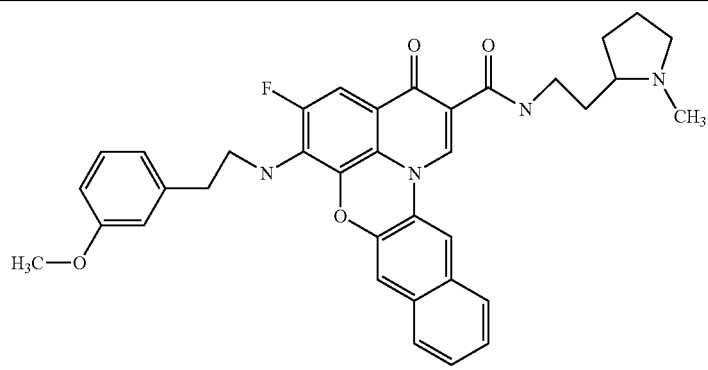 | 1.75 |
| 290 | 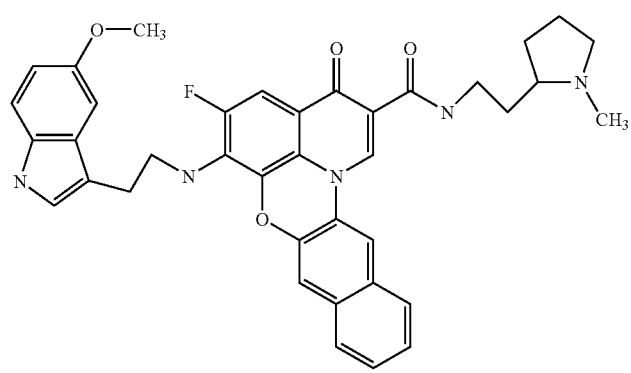 | 1.75 |
| 291 | 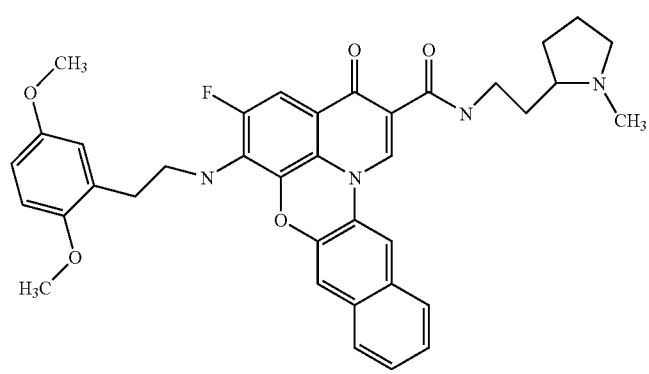 | 1.75 |
| 292 | 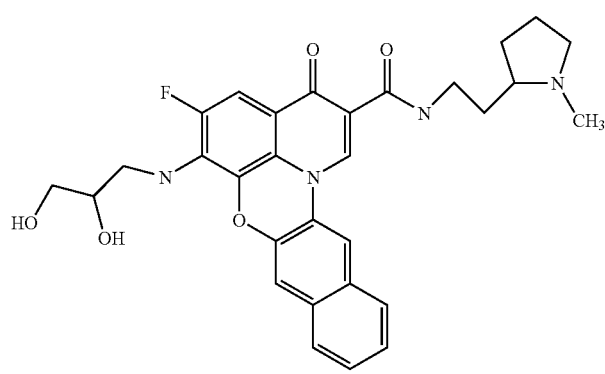 | 1.75 |

-continued
| | | |
|---|---|---|
| 293 | 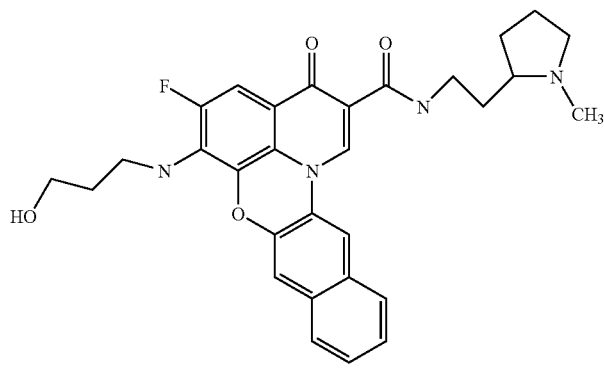 | 1.75 |
| 294 | 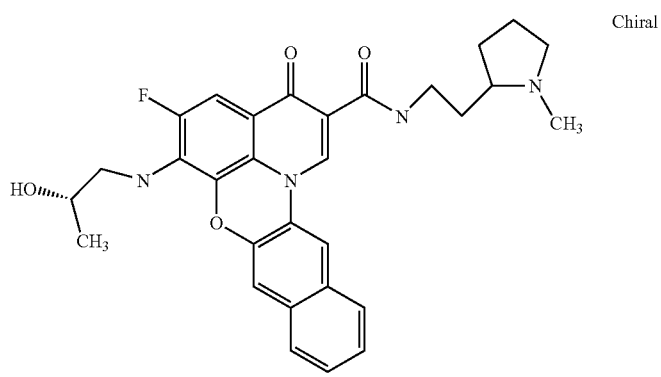 Chiral | 1.75 |
| 295 | 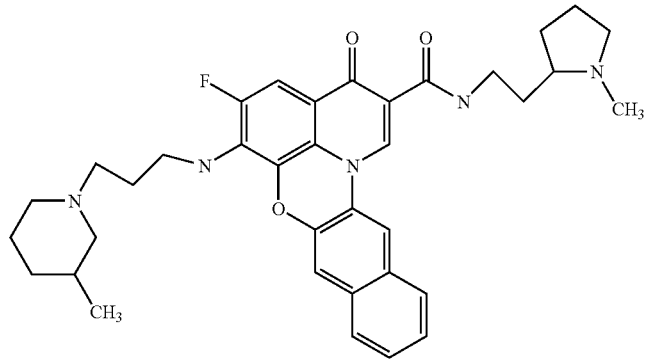 | 1.75 |
| 296 | 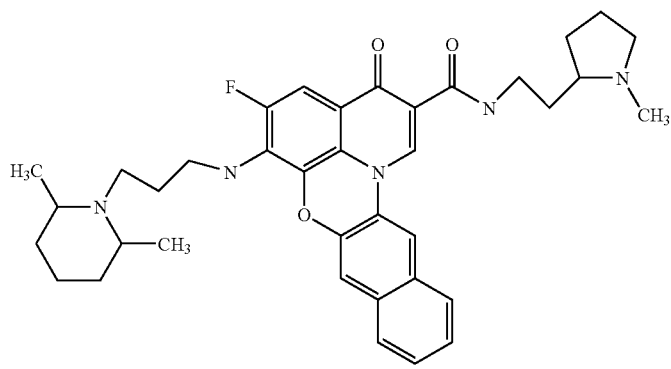 | 1.75 |

-continued
| | | |
|---|---|---|
| 297 | 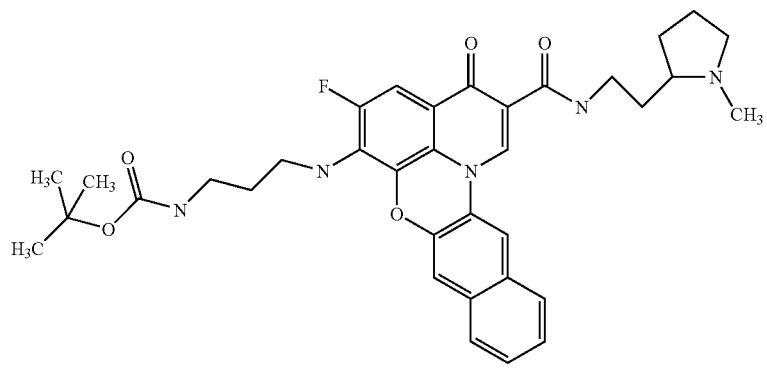 | 1.75 |
| 298 | 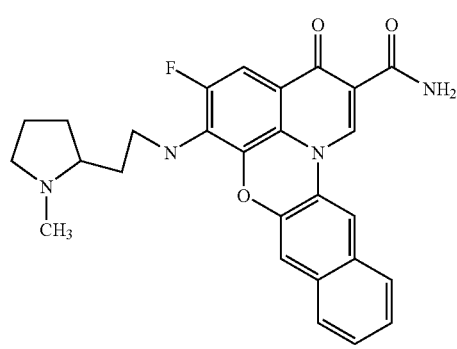 | 1.75 |
| 299 | 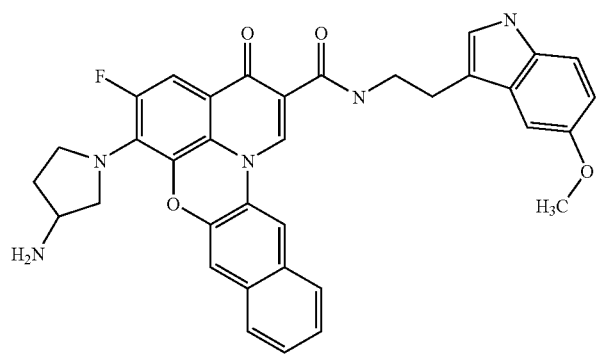 | 1.75 |
| 300 | 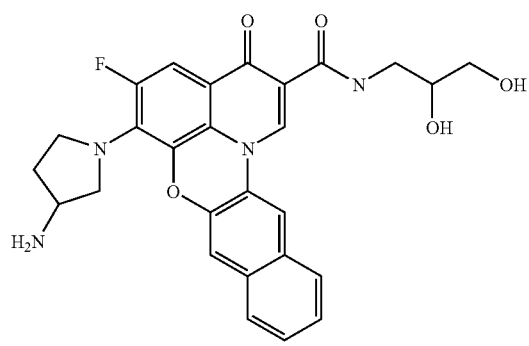 | 1.75 |

| | | | |
|---|---|---|---|
| 301 | 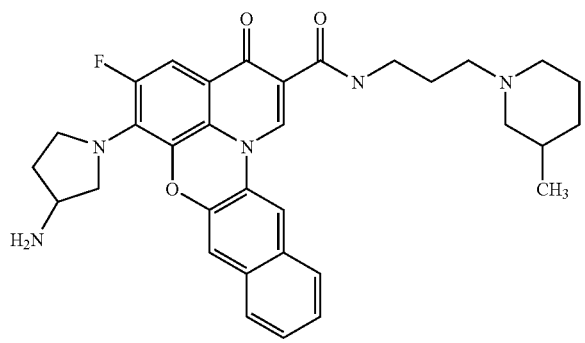 | 1.75 | |
| 302 | 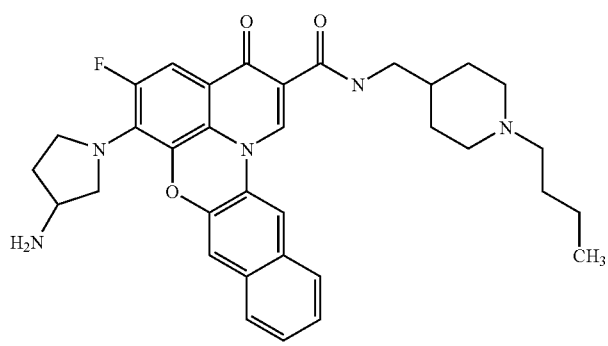 | 1.75 | |
| 303 | 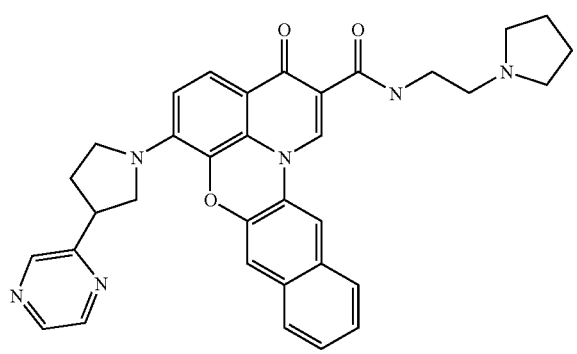 | 1.5 | 2.10 |
| 304 | 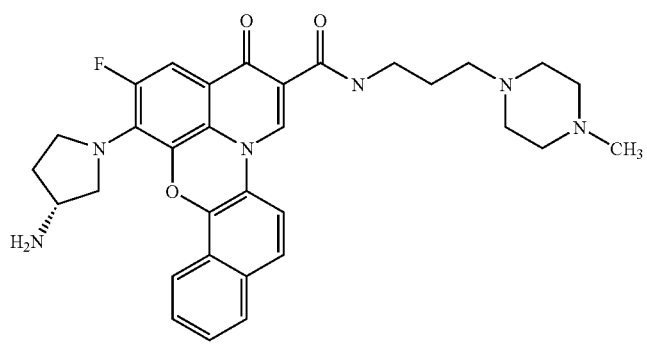 | 1.13 | |

-continued
| | | | |
|---|---|---|---|
| 305 | 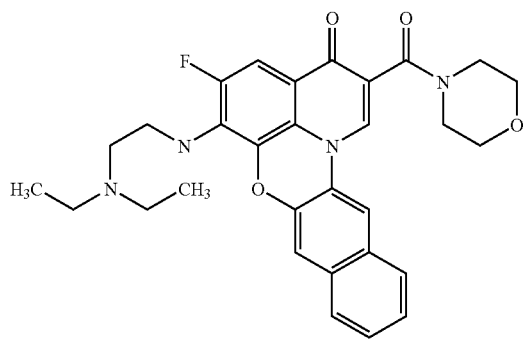 | 1.05 | |
| 306 | 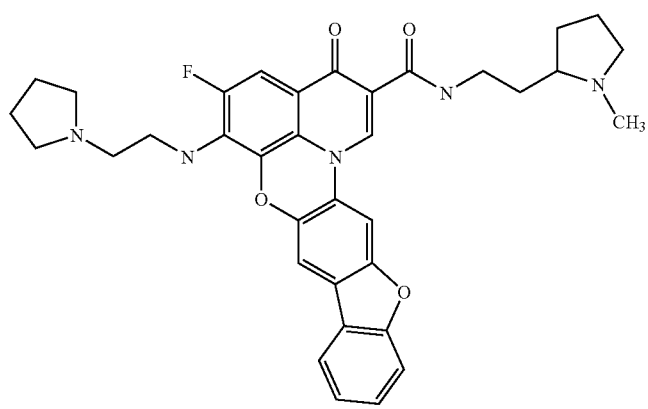 | 1 | 3.20 |
| 307 | 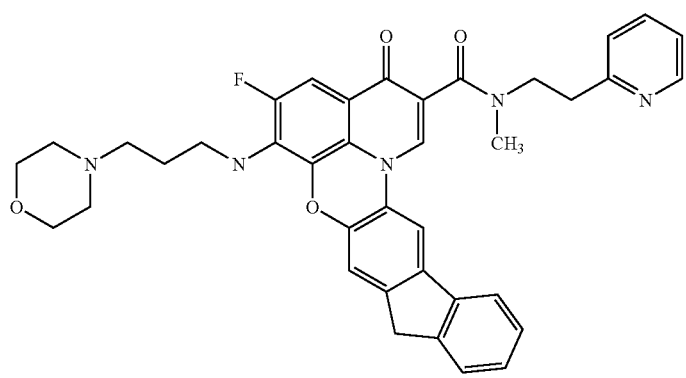 | 1 | 3.10 |
| 308 | 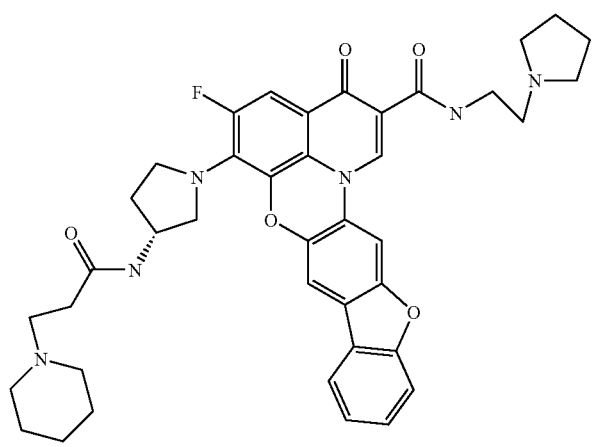 | 1 | 3.10 |

-continued
| | | | | |
|---|---|---|---|---|
| 309 | 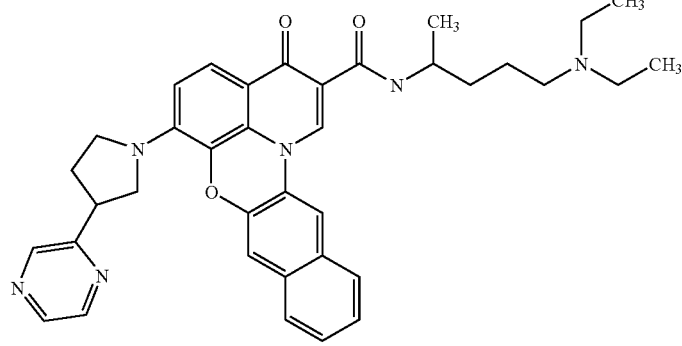 | | 1 | 3.00 |
| 310 | 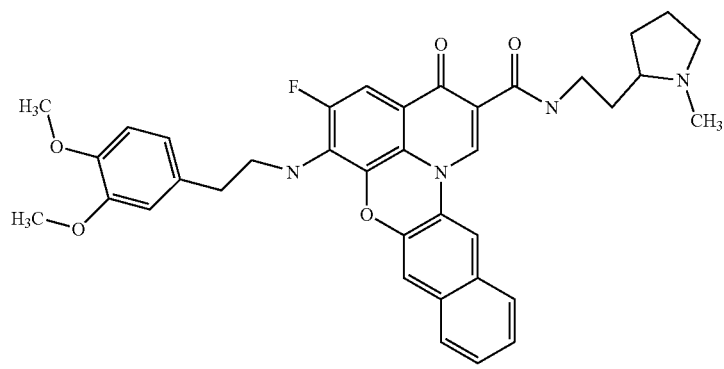 | | 1 | 2.30 |
| 311 | 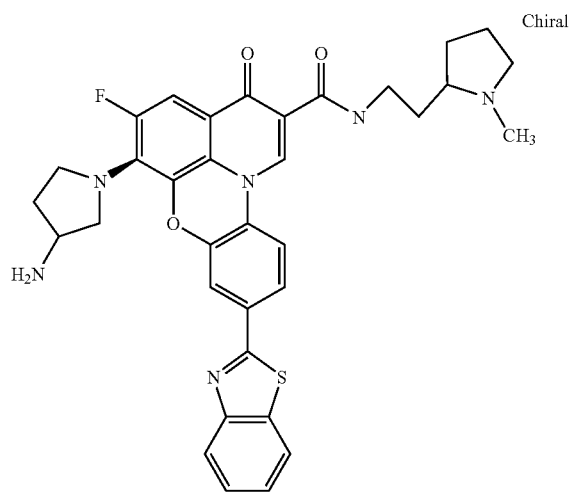 | Chiral | 1 | 2.10 |
| 312 | 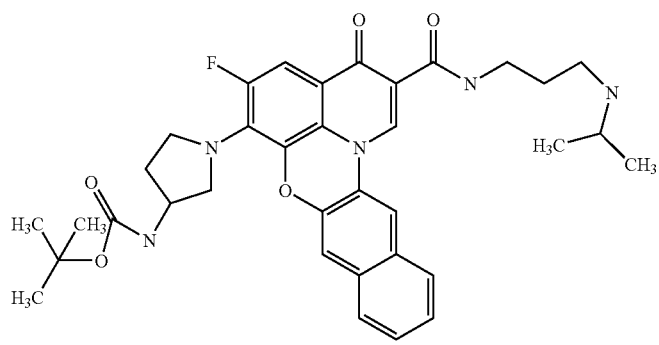 | | 1 | 1.90 |

-continued
| | | |
|---|---|---|
| 313 | 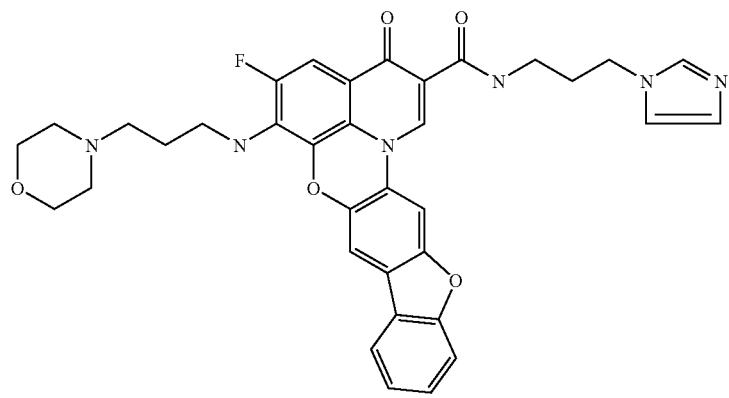 | 1 |
| 314 | 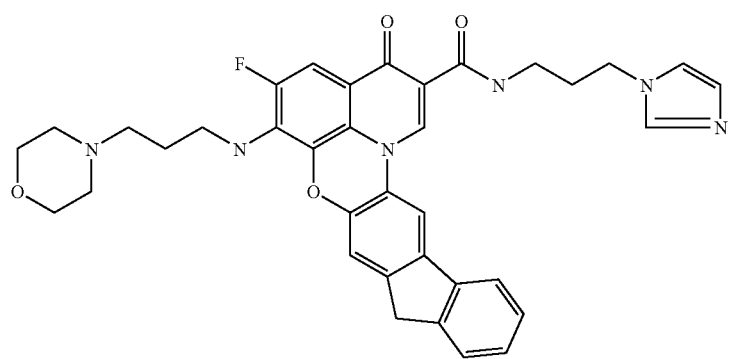 | 1 |
| 315 | 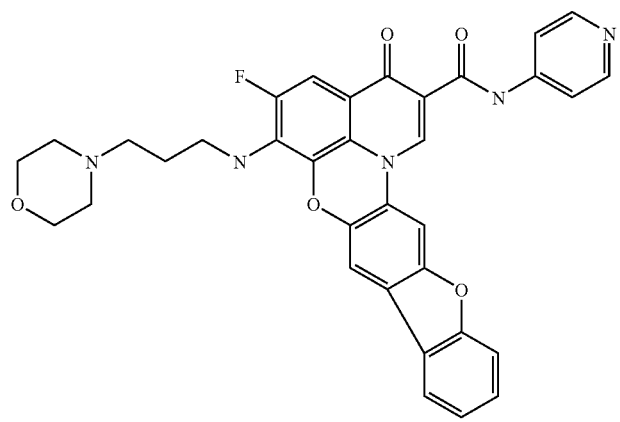 | 1 |
| 316 | 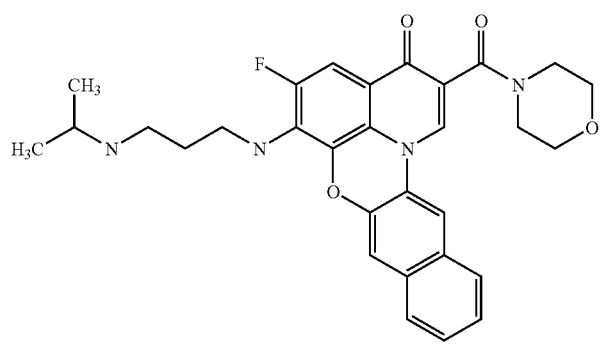 | 1 |

-continued
| | | |
|---|---|---|
| 317 | 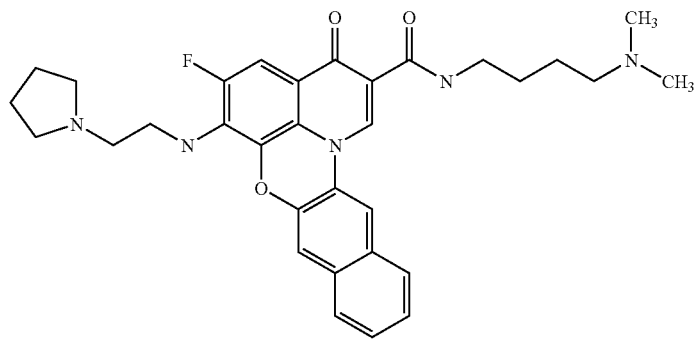 | 1 |
| 318 | 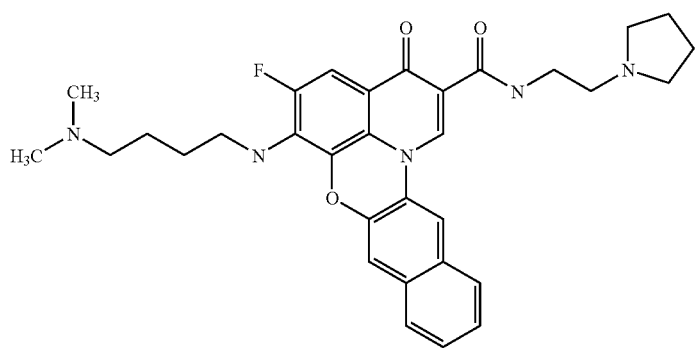 | 1 |
| 319 | 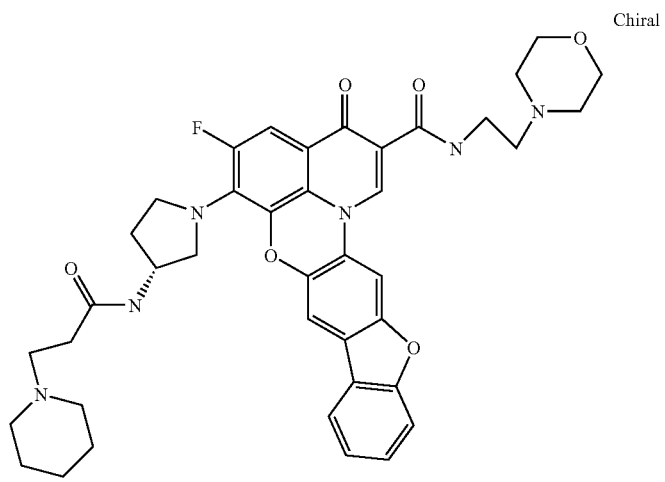 Chiral | 1 |
| 320 | 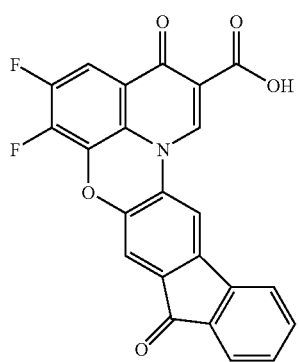 | 1 |

-continued
| | | |
|---|---|---|
| 321 | 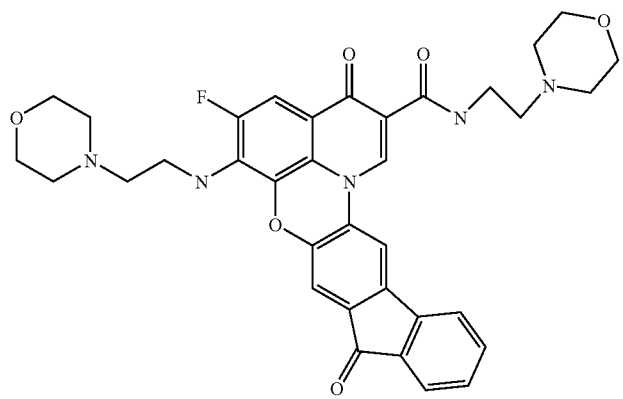 | 1 |
| 322 | 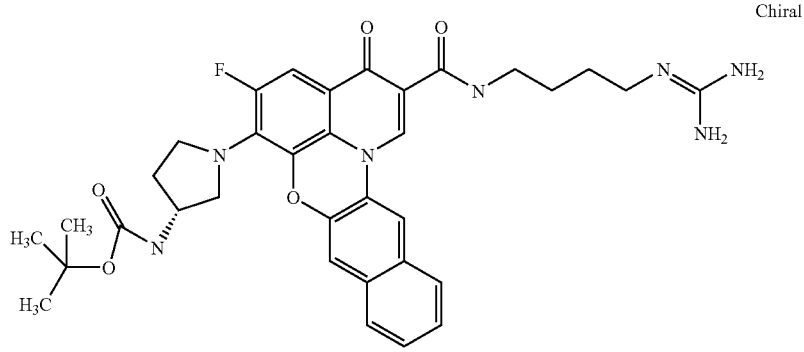 | Chiral 1 |
| 323 | 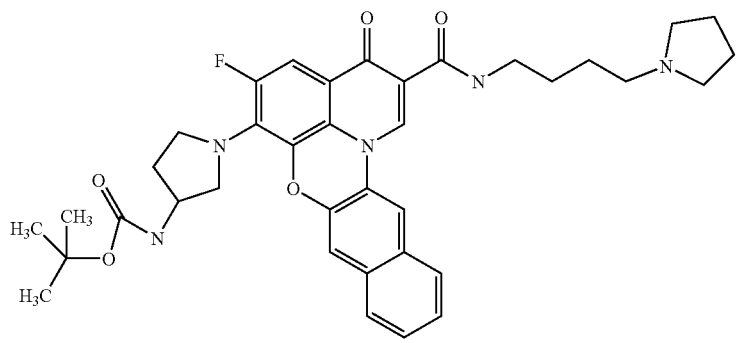 | 1 |
| 324 | 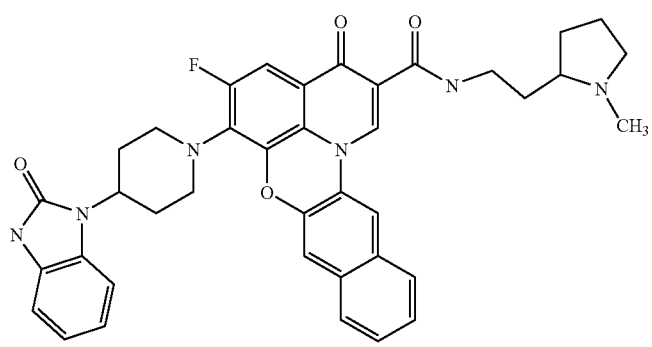 | 1 |

-continued
| | | |
|---|---|---|
| 325 | 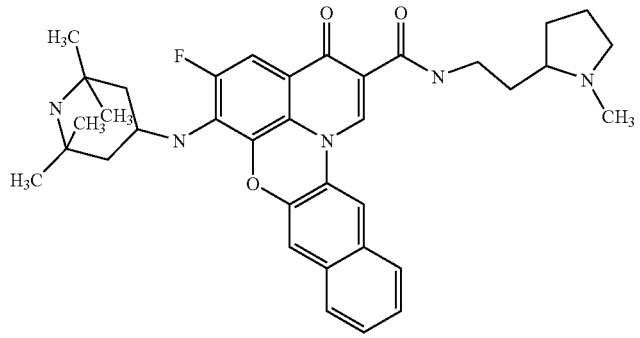 | 1 |
| 326 | 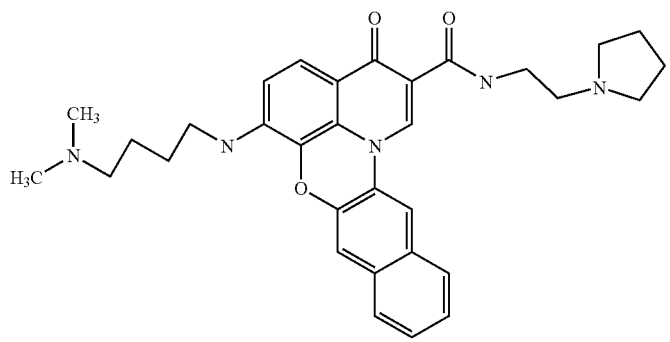 | 1 |
| 327 | 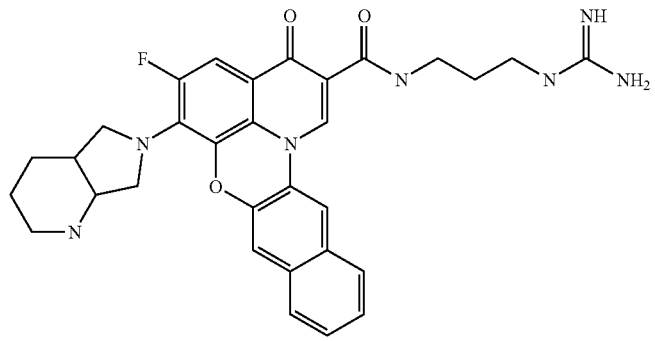 | 1 |
| 328 | 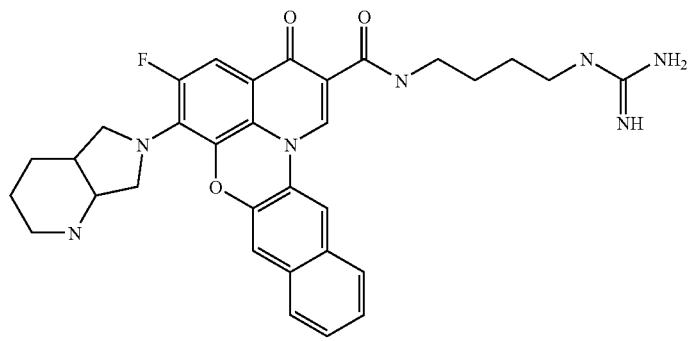 | 1 |

-continued
| | | |
|---|---|---|
| 329 | 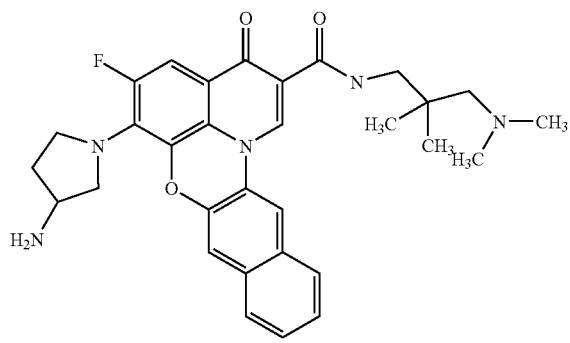 | 1 |
| 330 | 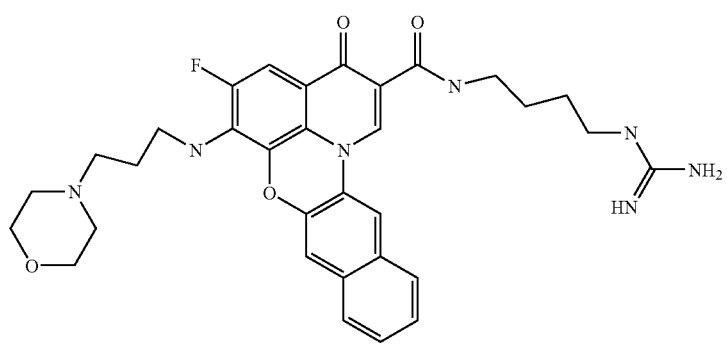 | 1 |
| 331 | 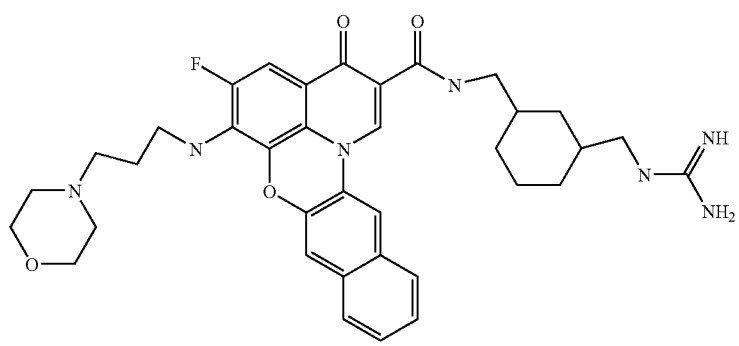 | 1 |
| 332 | 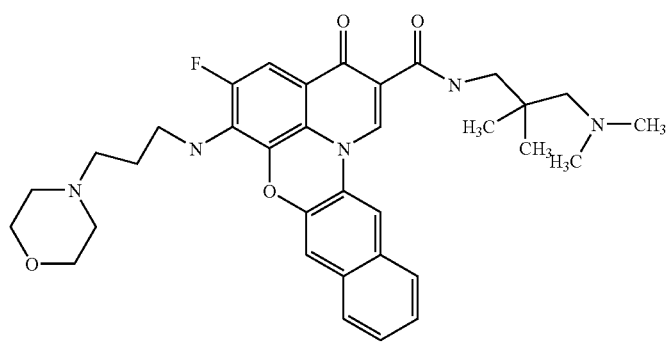 | 1 |

-continued
| | | |
|---|---|---|
| 333 | 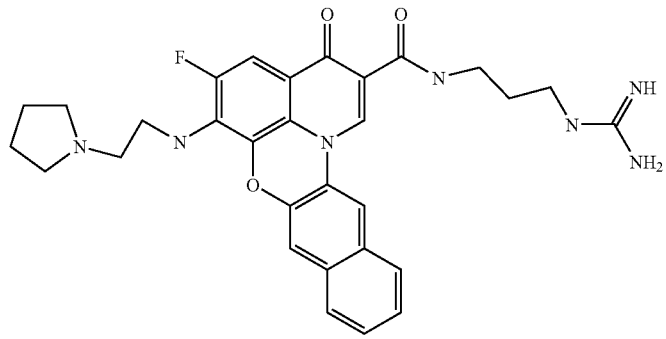 | 1 |
| 334 | 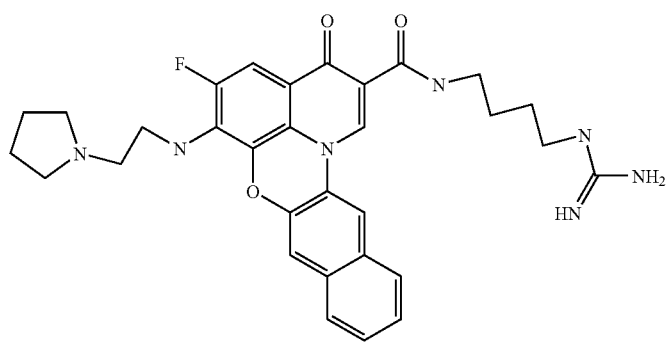 | 1 |
| 335 | 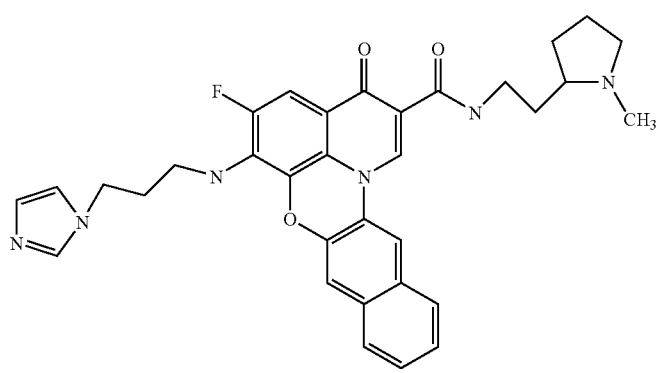 | 1 |
| 336 | 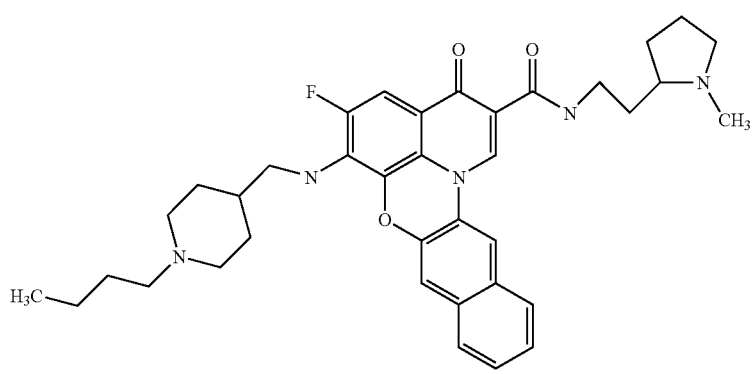 | 1 |

-continued
| | | |
|---|---|---|
| 337 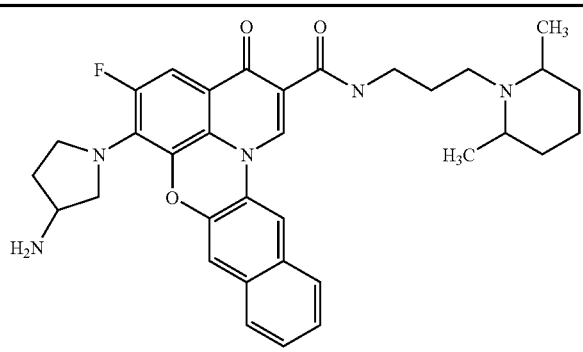 | 1 | |
| 338 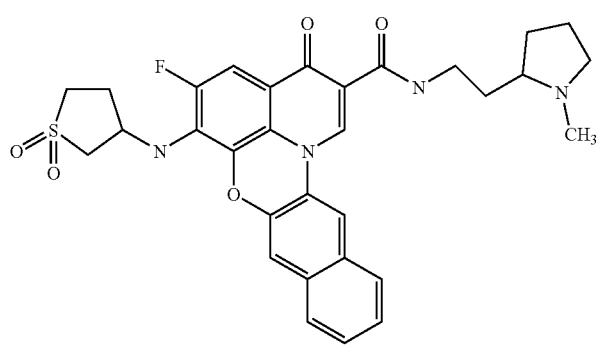 | 1 | |
| 339 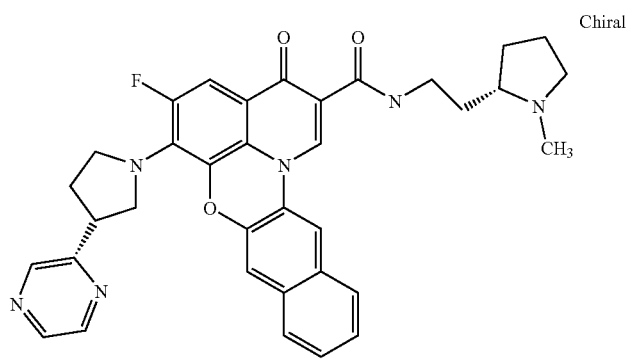 | 0.94 | |
| 340 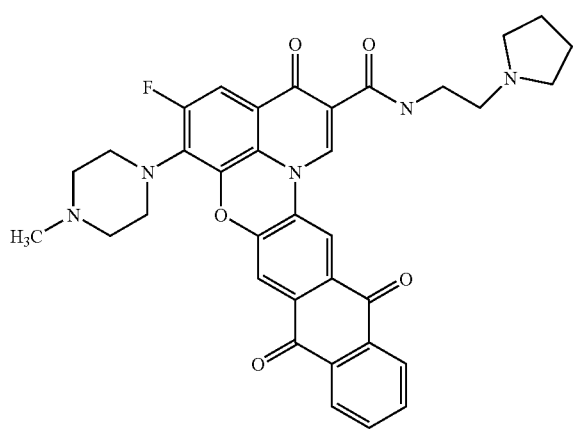 | 0.9 | 8.50 |

-continued
| 341 | 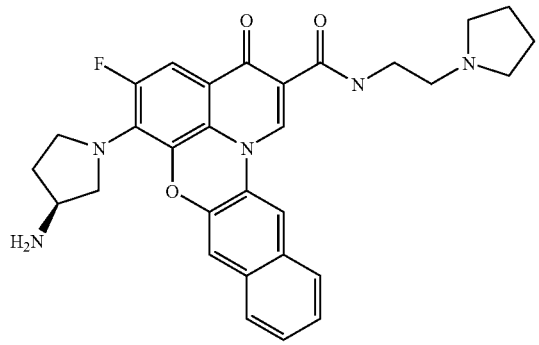 | Chiral | 0.9 | 0.28 |
| 342 | 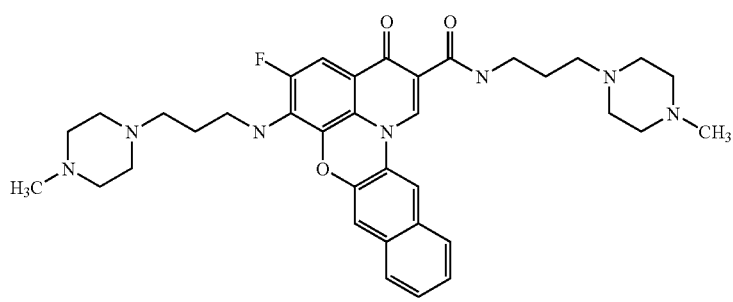 | | 0.9 | |
| 343 | 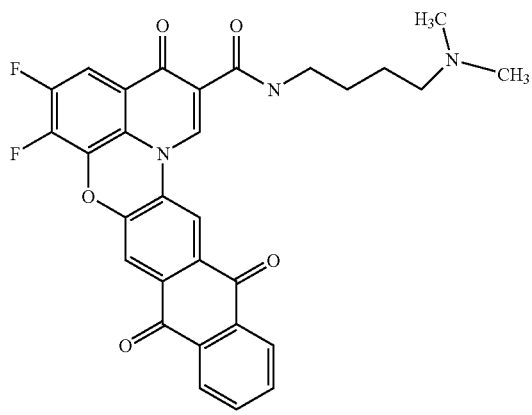 | | 0.9 | |
| 344 | 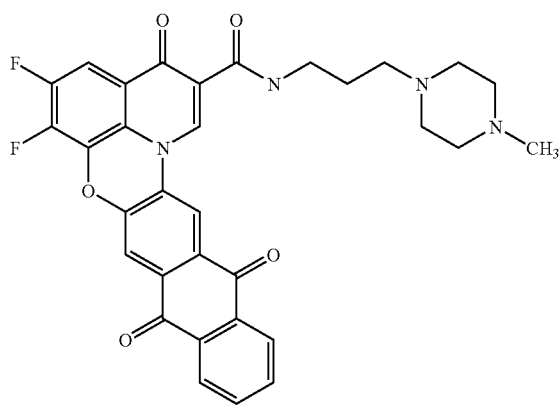 | | 0.9 | |

-continued
| | | |
|---|---|---|
| 345 | 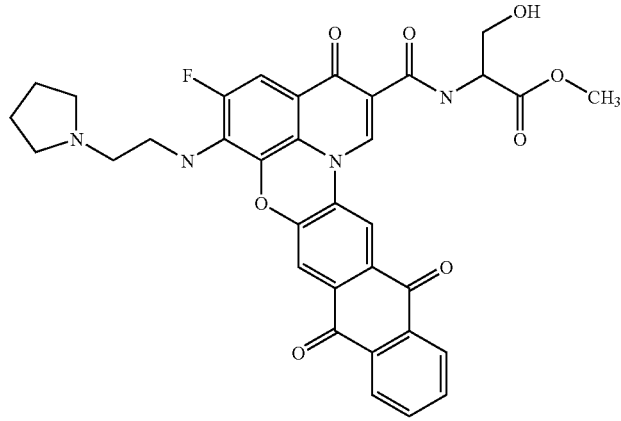 | 0.9 |
| 346 | 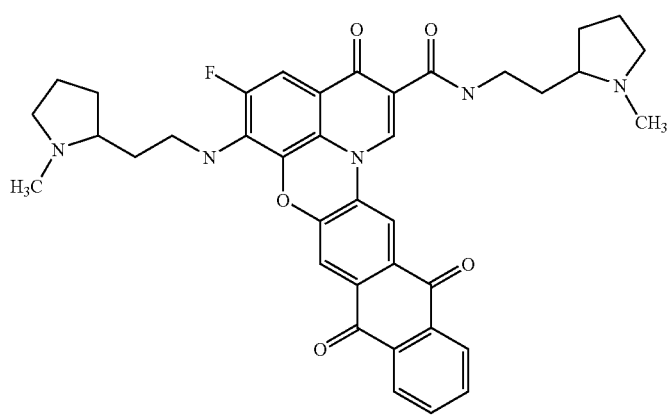 | 0.9 |
| 347 | 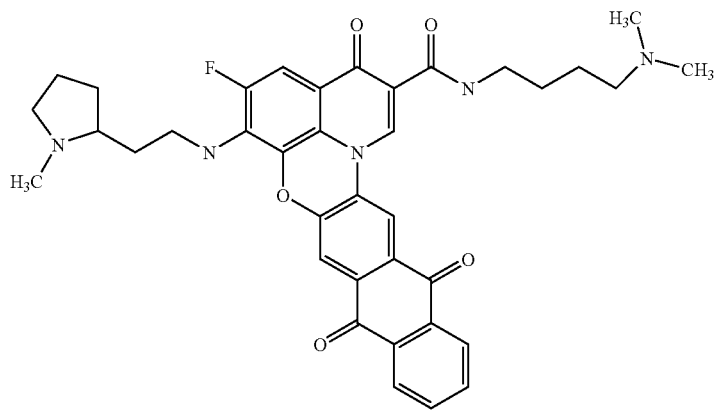 | 0.9 |

-continued
| 348 | 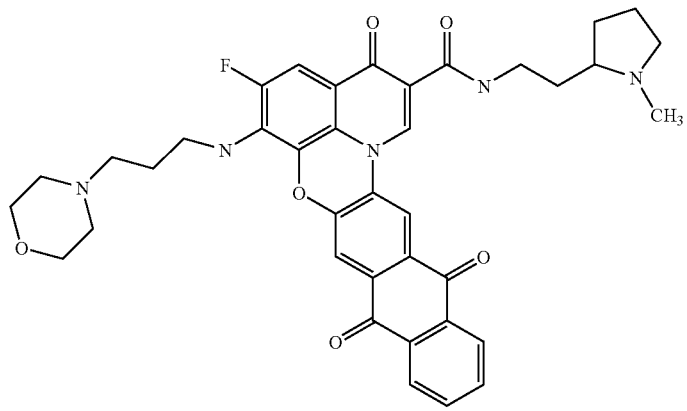 | 0.9 |
| 349 | 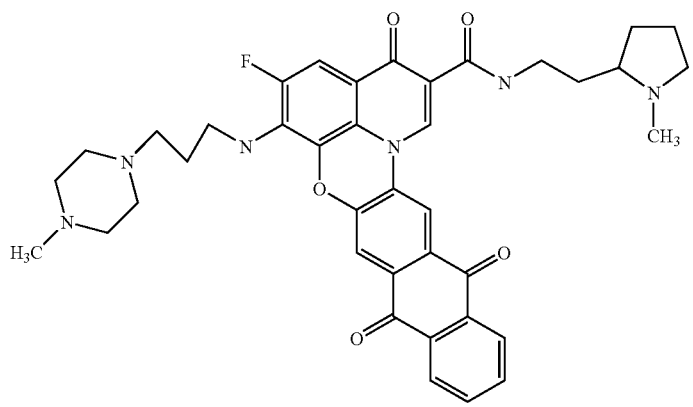 | 0.9 |
| 350 | 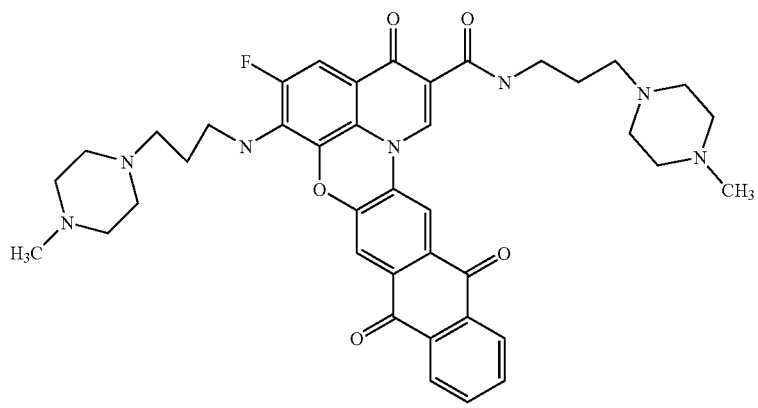 | 0.9 |

| | | |
|---|---|---|
| 351 | 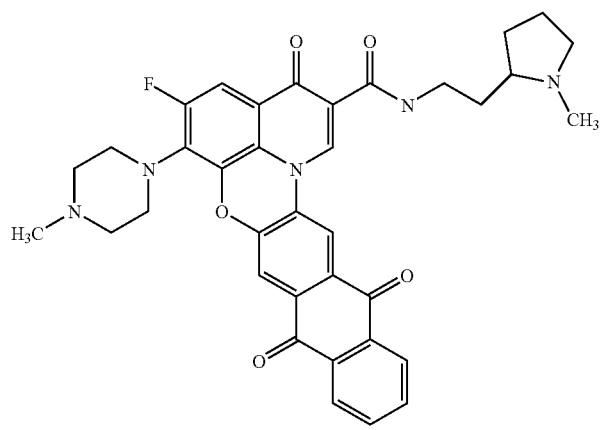 | 0.9 |
| 352 | 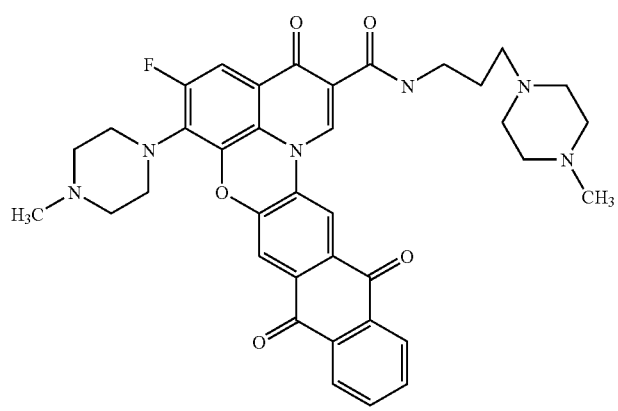 | 0.9 |
| 353 | 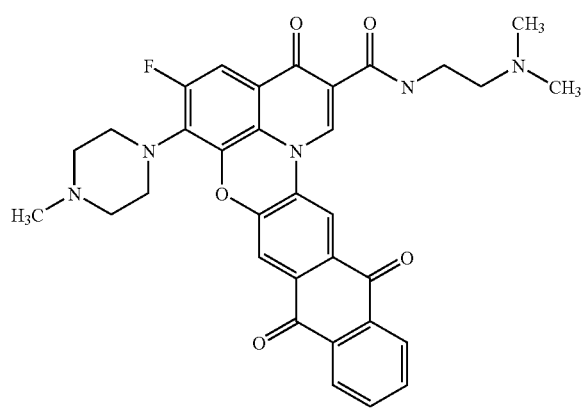 | 0.9 |

-continued
| | | | |
|---|---|---|---|
| 354 | 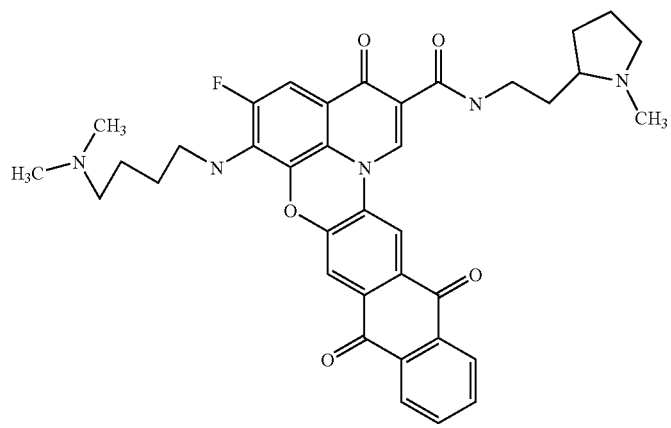 | | 0.9 |
| 355 | 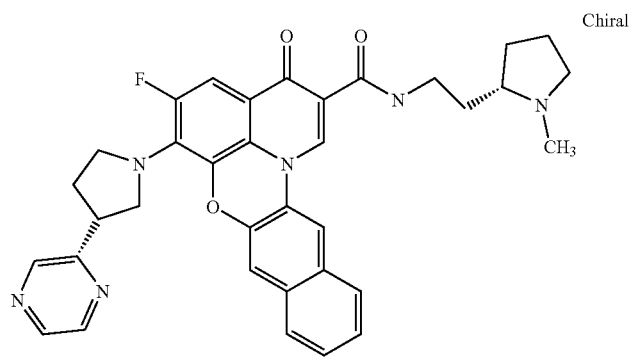 | Chiral | 0.89 |
| 356 | 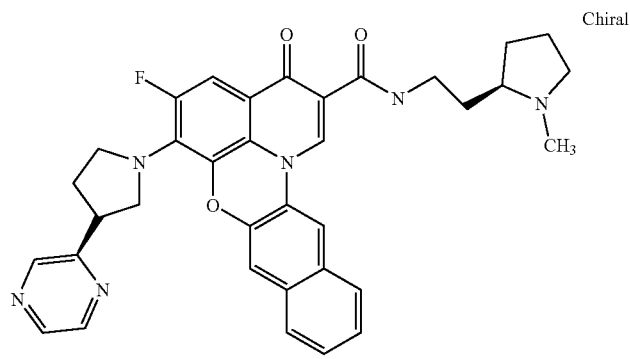 | Chiral | 0.85 |
| 357 | 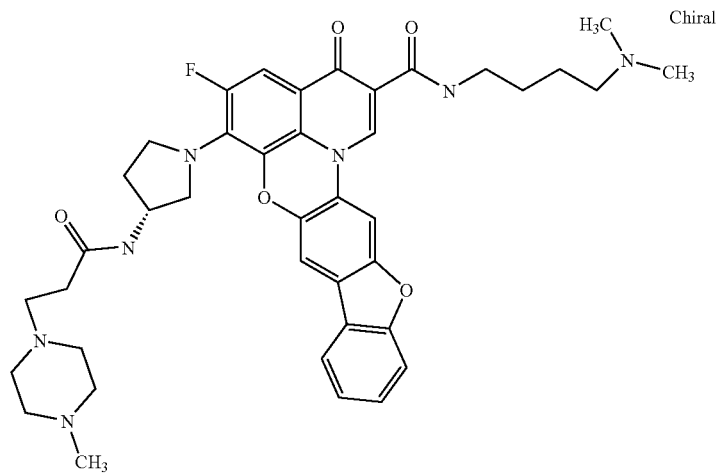 | Chiral | 0.75 8.60 |

-continued
| 358 | 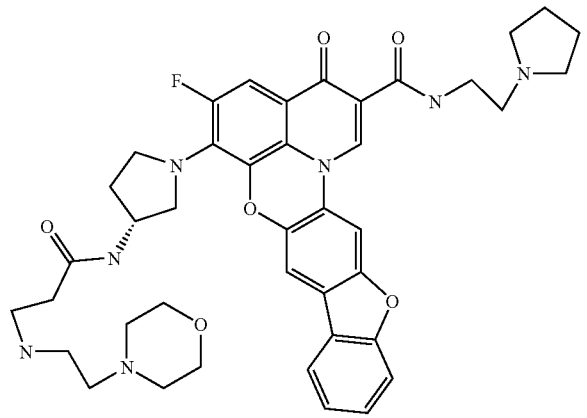 | Chiral | 0.75 | 5.70 |
| 359 | 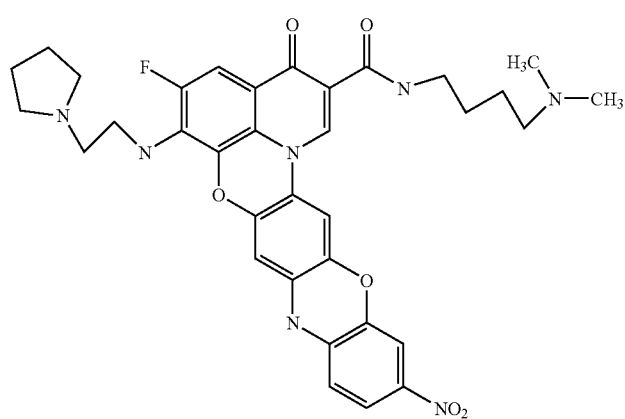 | | 0.75 | 4.80 |
| 360 | 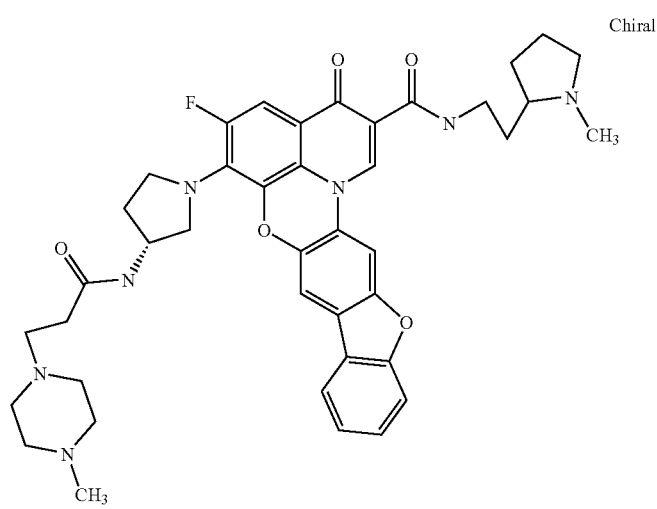 | Chiral | 0.75 | 4.50 |

-continued
| 361 | 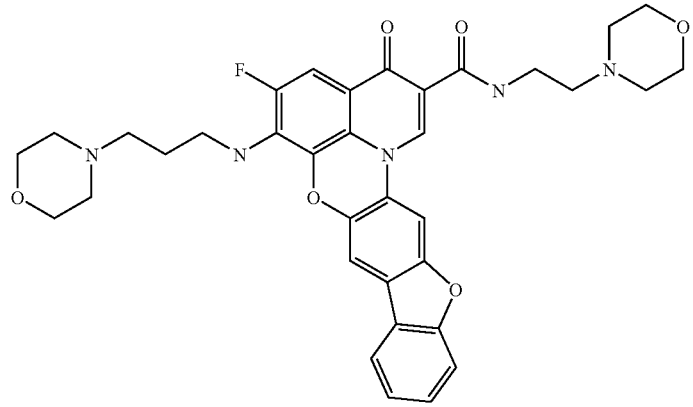 | 0.75 | 4.20 |
| 362 | 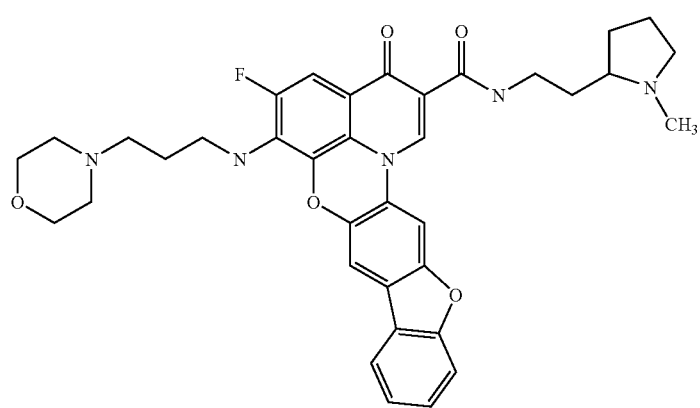 | 0.75 | 4.00 |
| 363 | 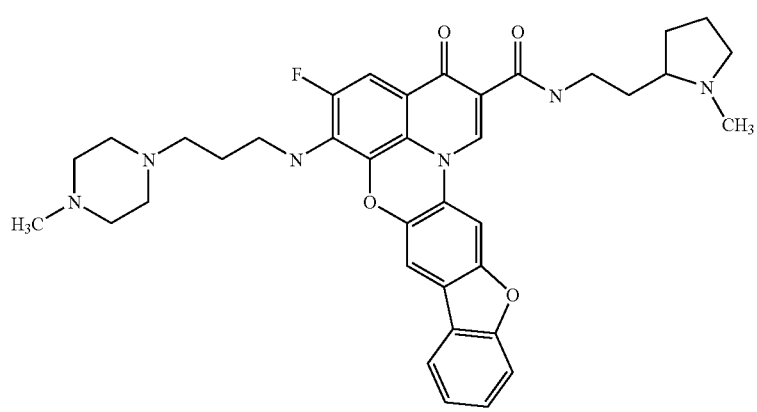 | 0.75 | 3.80 |
| 364 | 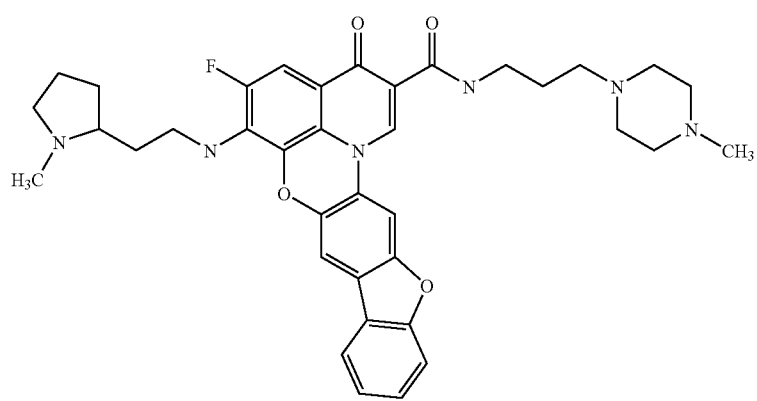 | 0.75 | 3.80 |

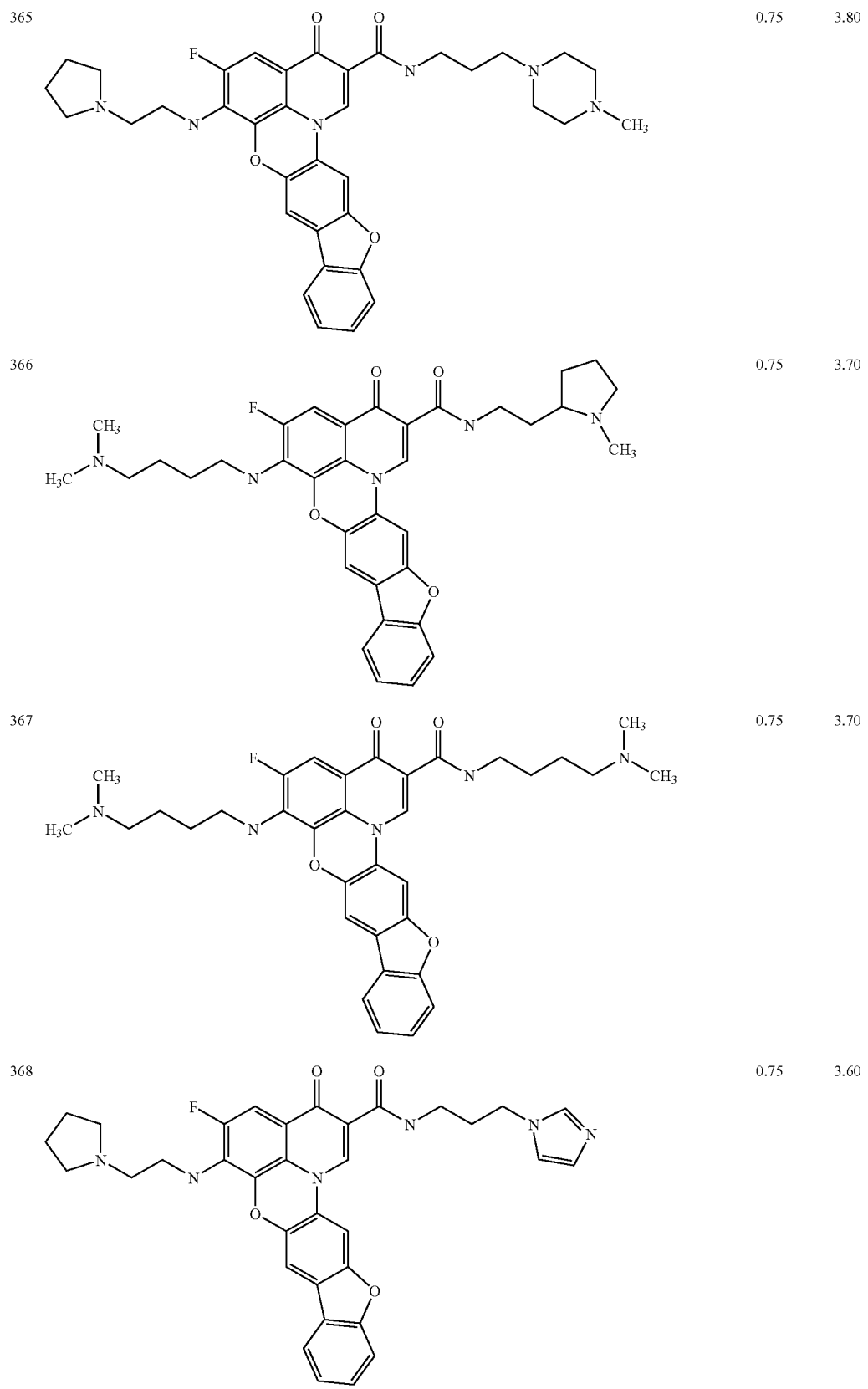

| | | | |
|---|---|---|---|
| 369 | 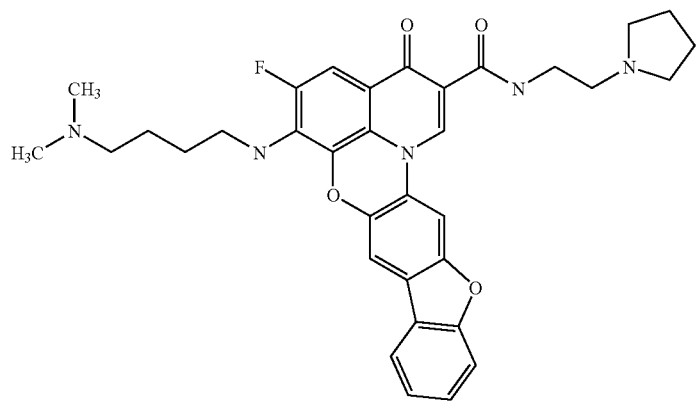 | 0.75 | 3.50 |
| 370 | 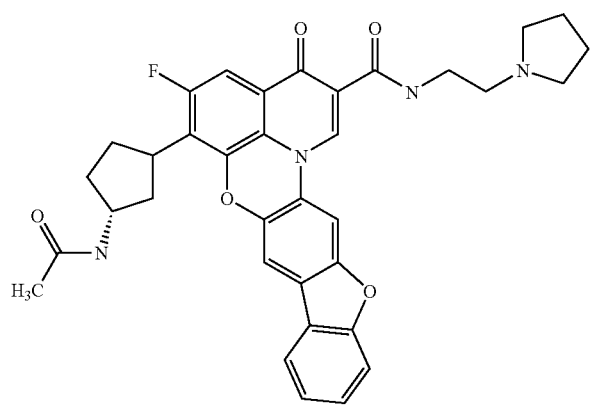 | 0.75 | 3.50 |
| 371 | 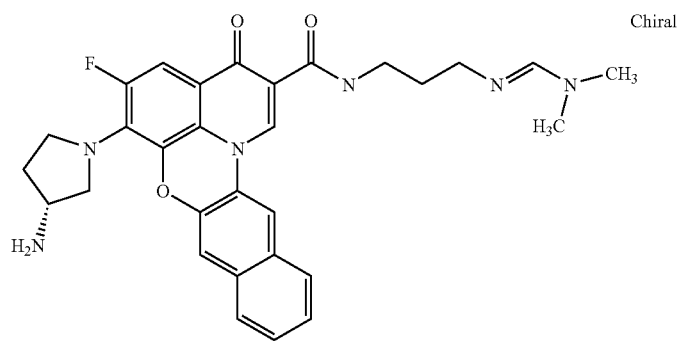 Chiral | 0.75 | 3.50 |
| 372 | 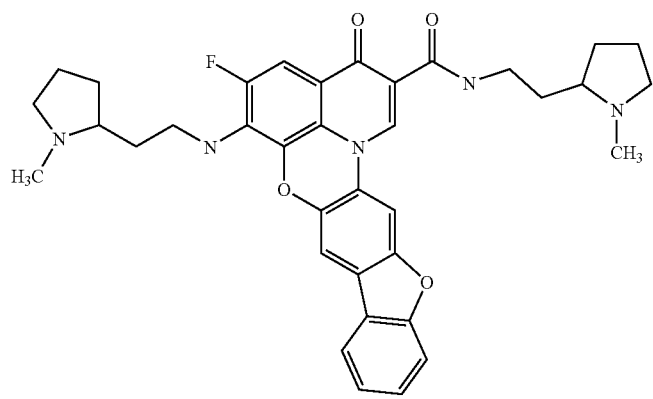 | 0.75 | 3.40 |

-continued
| | | | |
|---|---|---|---|
| 373 | 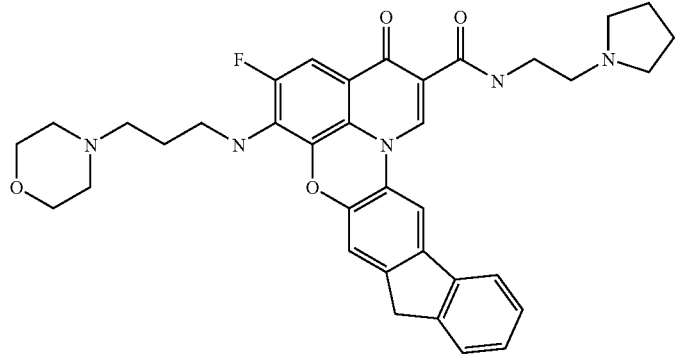 | 0.75 | 3.30 |
| 374 | 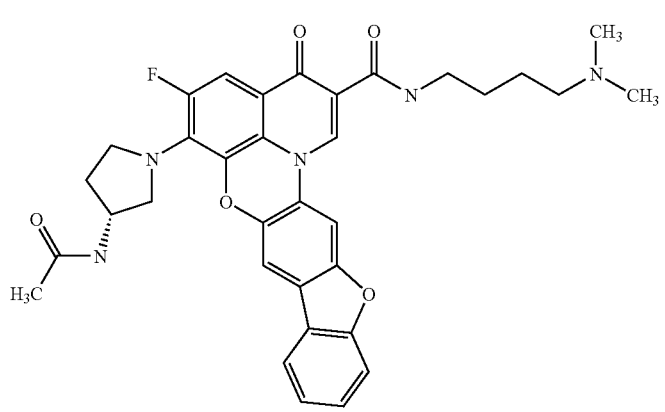 | 0.75 | 3.30 |
| 375 | 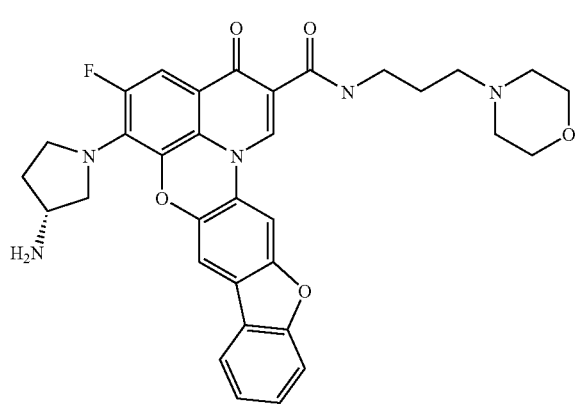 | 0.75 | 2.70 |
| 376 | 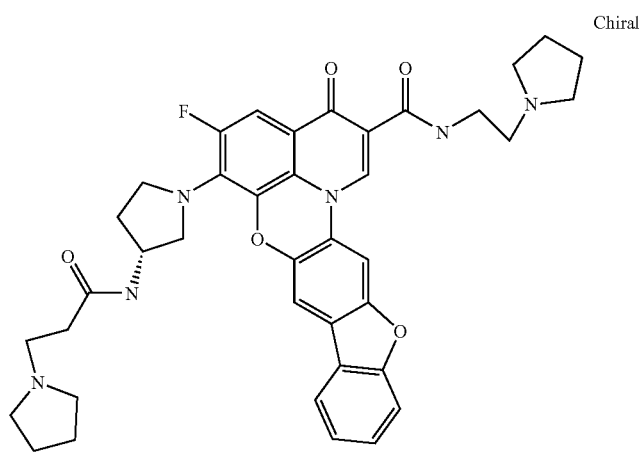 Chiral | 0.75 | 2.40 |

| | | | |
|---|---|---|---|
| 377 | 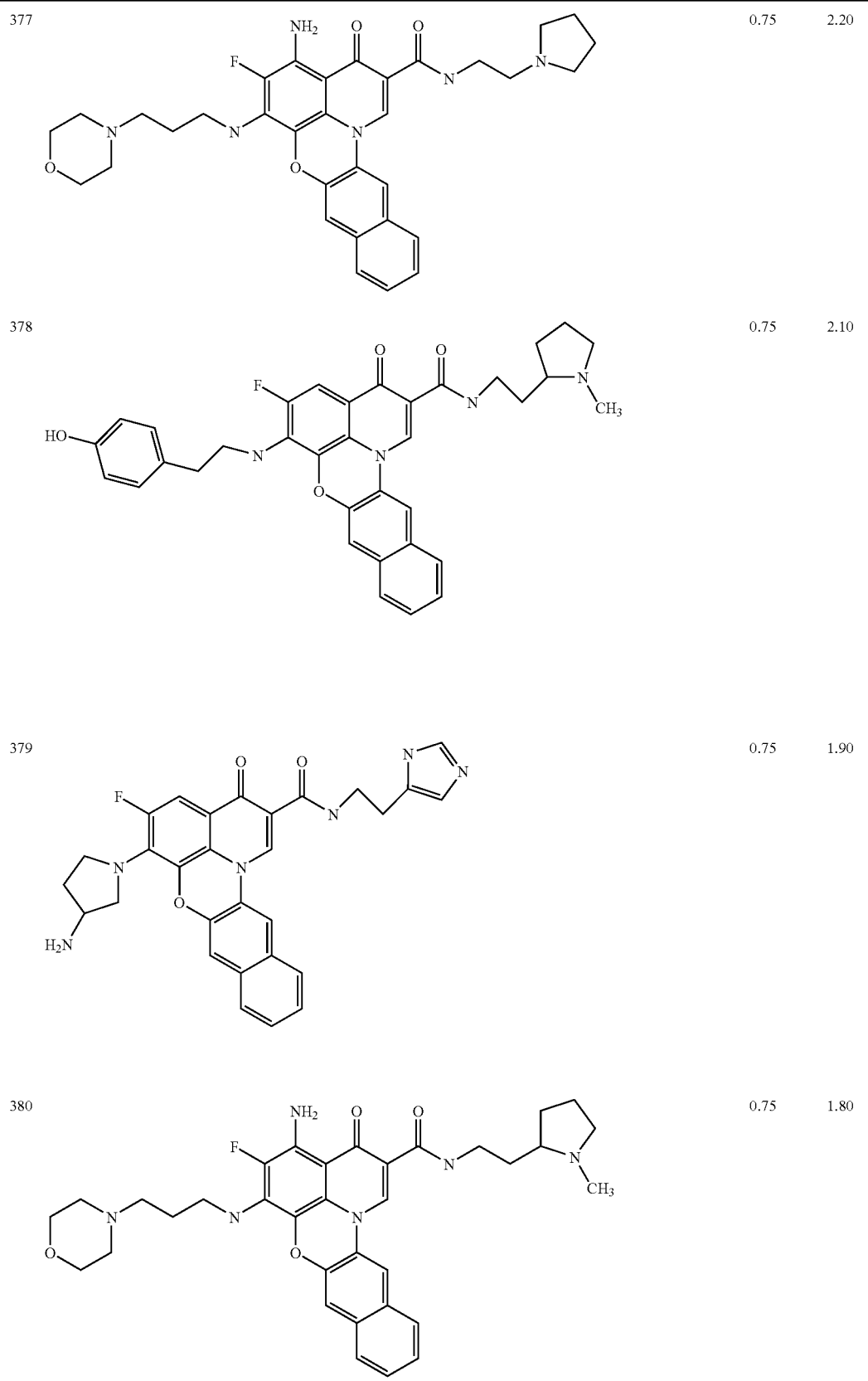 | 0.75 | 2.20 |
| 378 | | 0.75 | 2.10 |
| 379 | | 0.75 | 1.90 |
| 380 | | 0.75 | 1.80 |

-continued
| | | | |
|---|---|---|---|
| 381 | 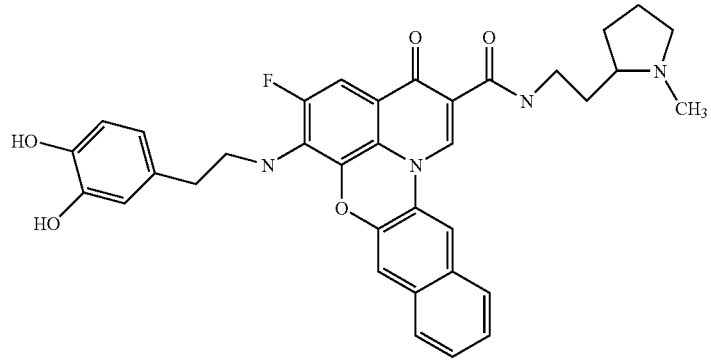 | 0.75 | 1.80 |
| 382 | 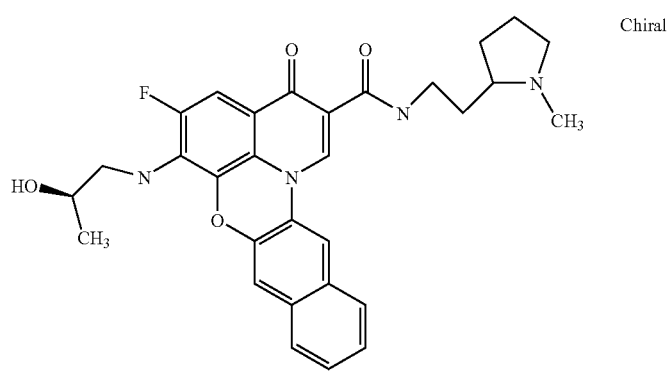 Chiral | 0.75 | 1.80 |
| 383 | 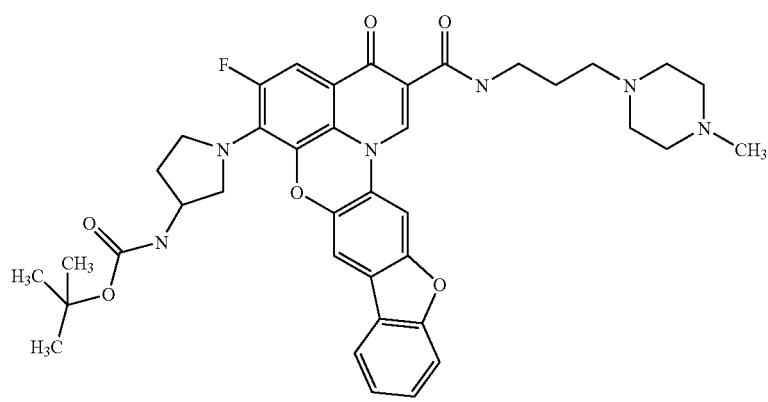 | 0.75 | 0.37 |
| 384 | 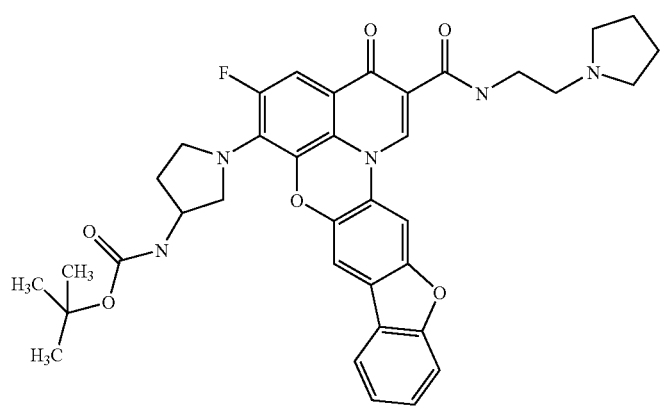 | 0.75 | 0.37 |

-continued
| | | | |
|---|---|---|---|
| 385 | 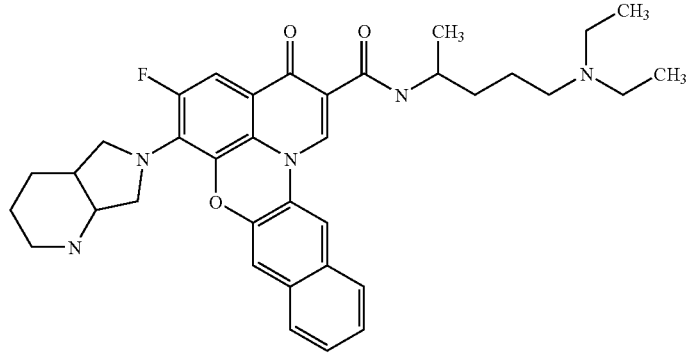 | 0.75 | 0.36 |
| 386 | 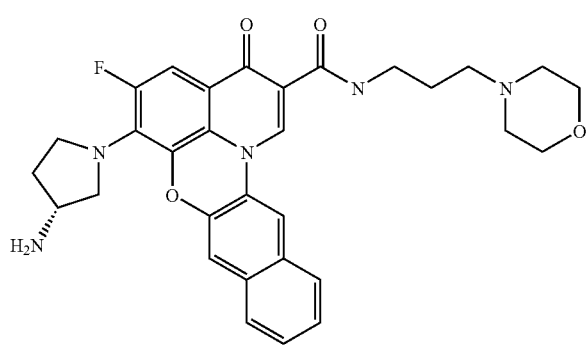 | 0.75 | 0.34 |
| 387 | 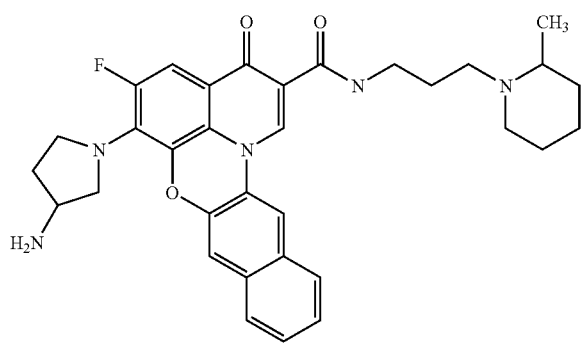 | 0.75 | 0.33 |
| 388 | 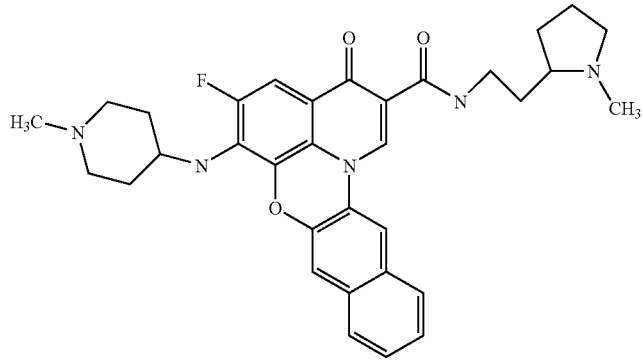 | 0.75 | 0.31 |

| | | | |
|---|---|---|---|
| 389 | 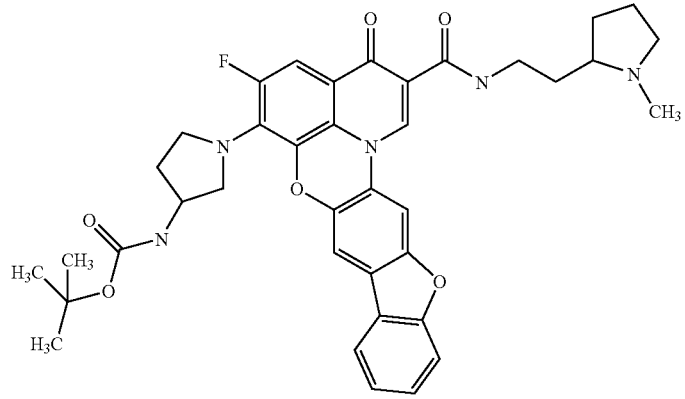 | 0.75 | 0.29 |
| 390 | 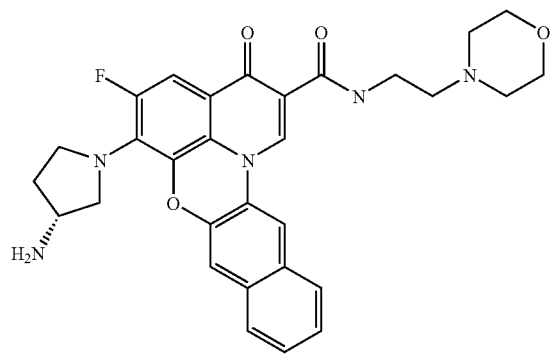 | 0.75 | 0.24 |
| 391 | 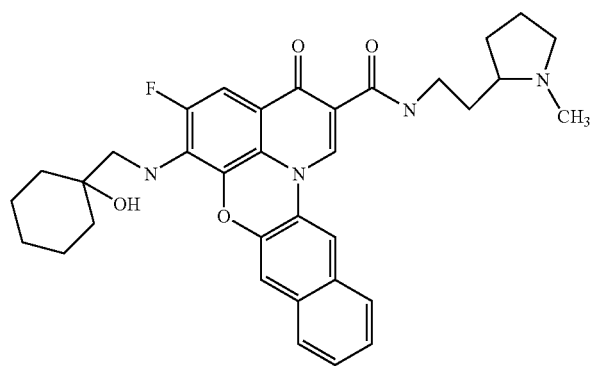 | 0.75 | 0.24 |
| 392 | 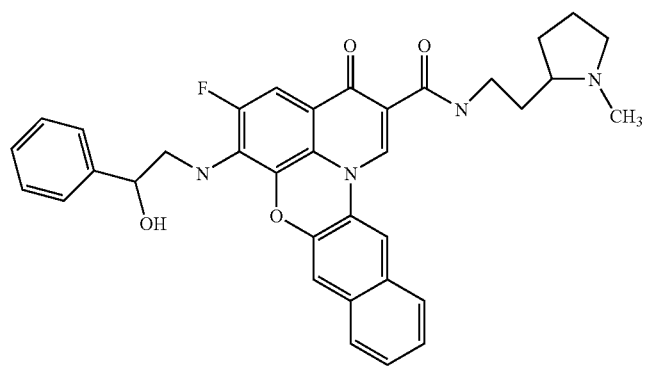 | 0.75 | 0.19 |

-continued
| | | |
|---|---|---|
| 393 | 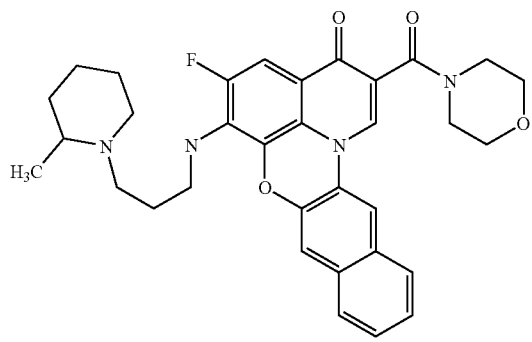 | 0.75 |
| 394 | 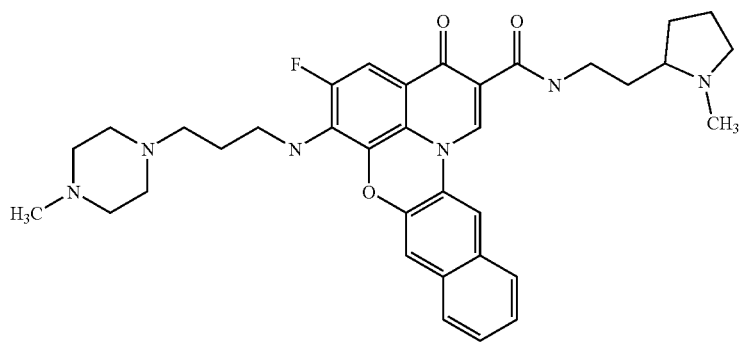 | 0.75 |
| 395 | 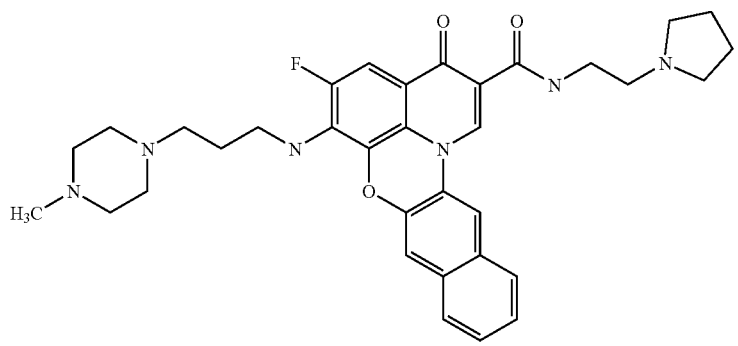 | 0.75 |
| 396 | 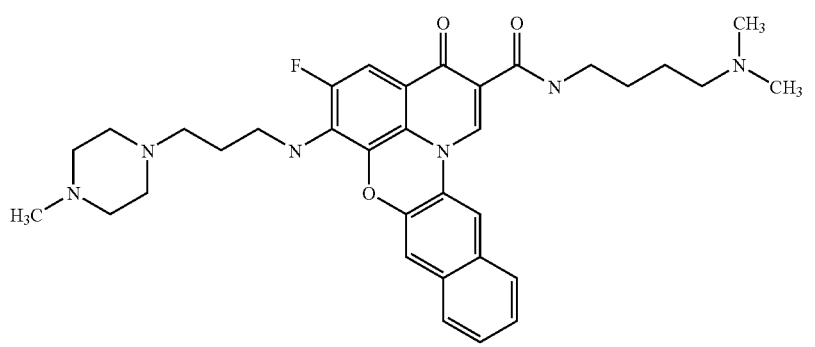 | 0.75 |

-continued
| | | |
|---|---|---|
| 397 | 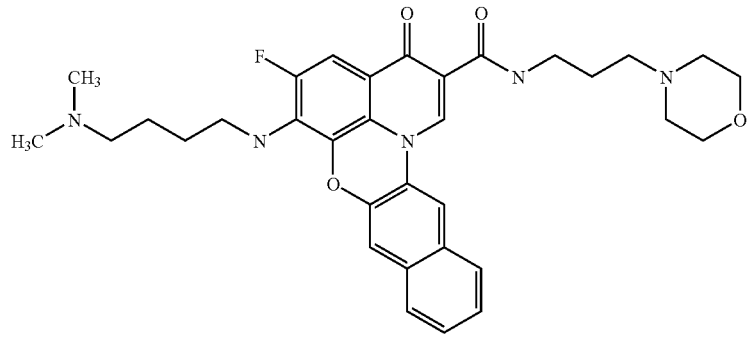 | 0.75 |
| 398 | 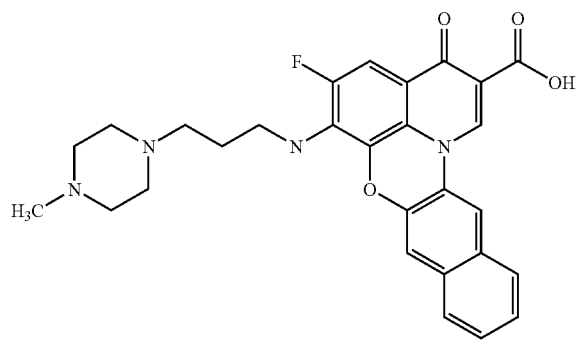 | 0.75 |
| 399 | 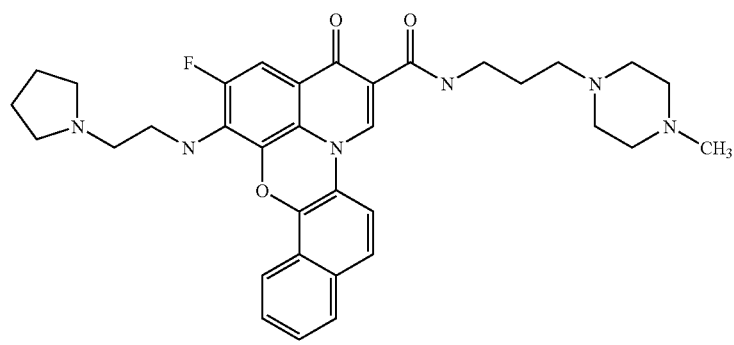 | 0.75 |
| 400 | 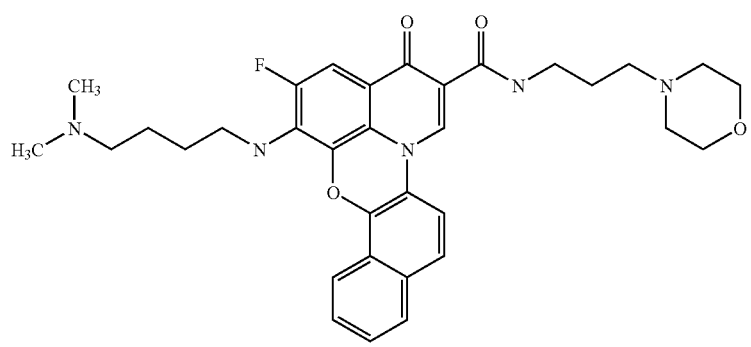 | 0.75 |

-continued
| | | | |
|---|---|---|---|
| 401 | 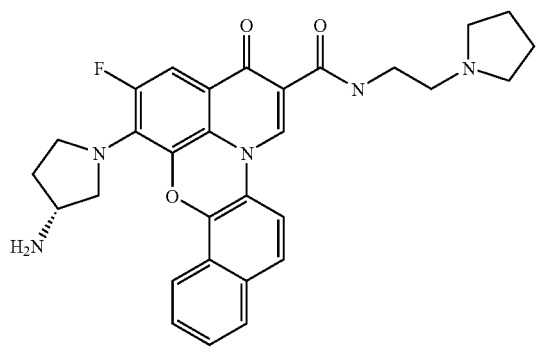 | | 0.75 |
| 402 | 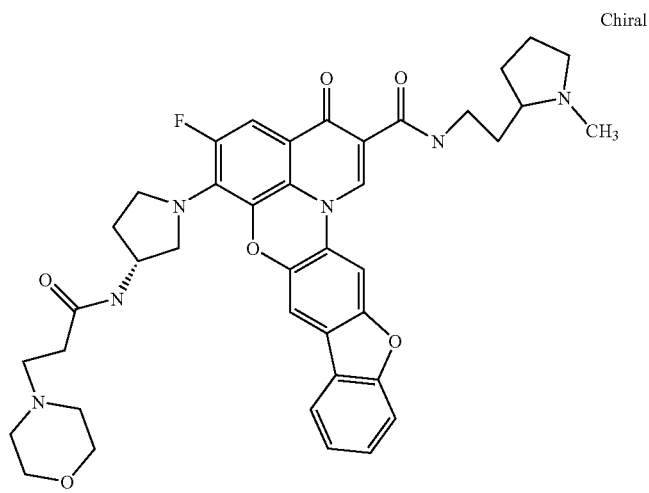 | Chiral | 0.75 |
| 403 | 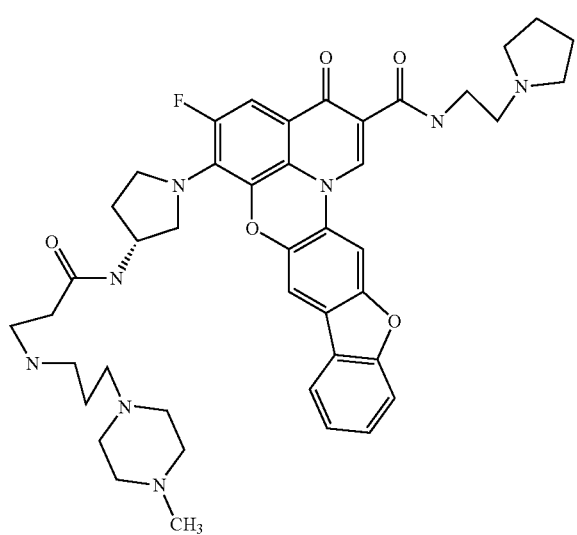 | Chiral | 0.75 |

-continued
| 404 | 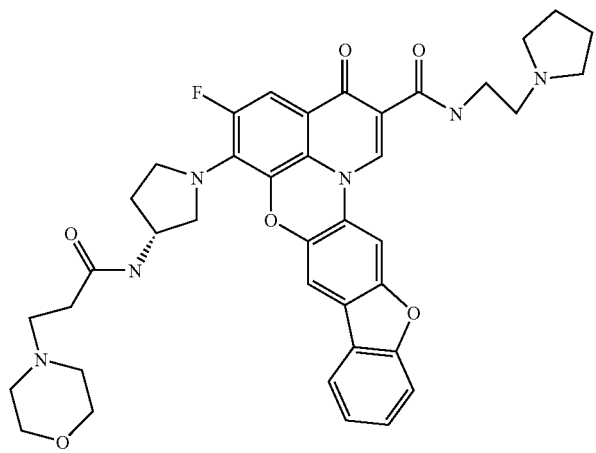 | Chiral | 0.75 |
| 405 | 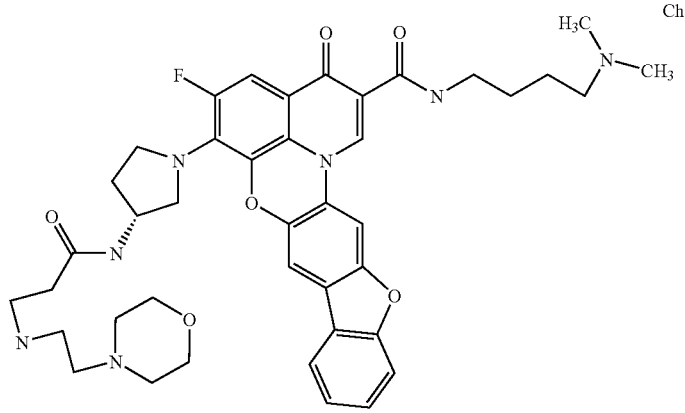 | Chiral | 0.75 |
| 406 | 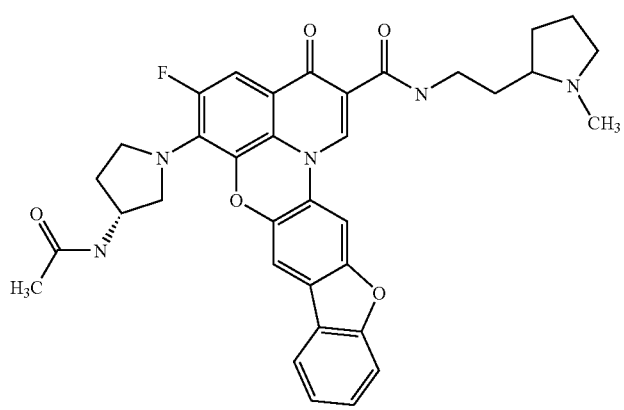 | | 0.75 |

| | | |
|---|---|---|
| 407 | 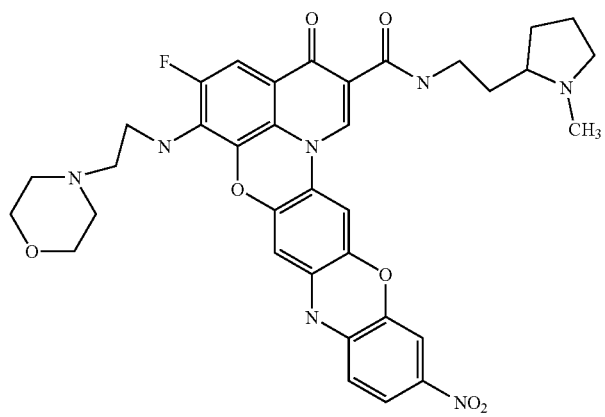 | 0.75 |
| 408 | 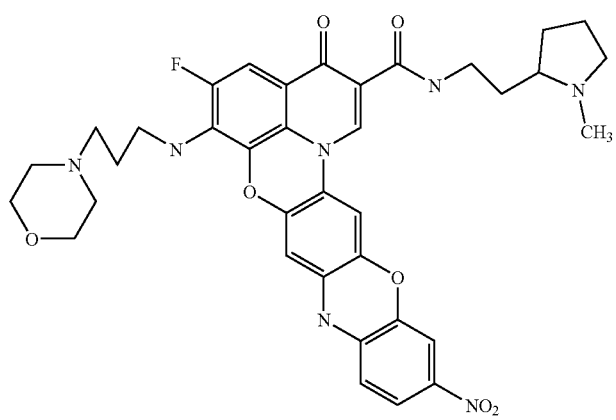 | 0.75 |
| 409 | 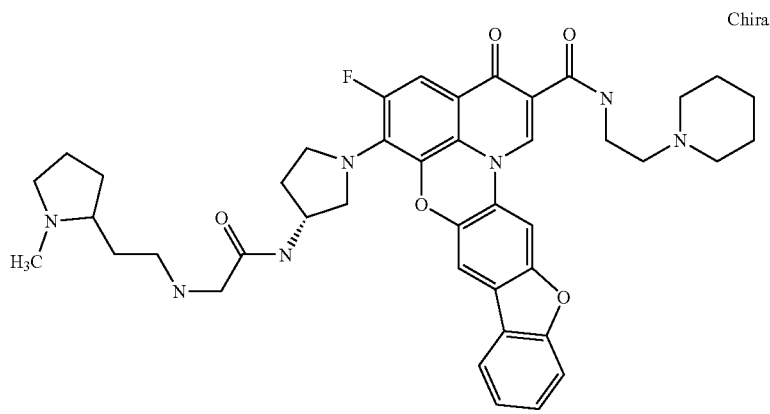 Chiral | 0.75 |

-continued
| 410 | 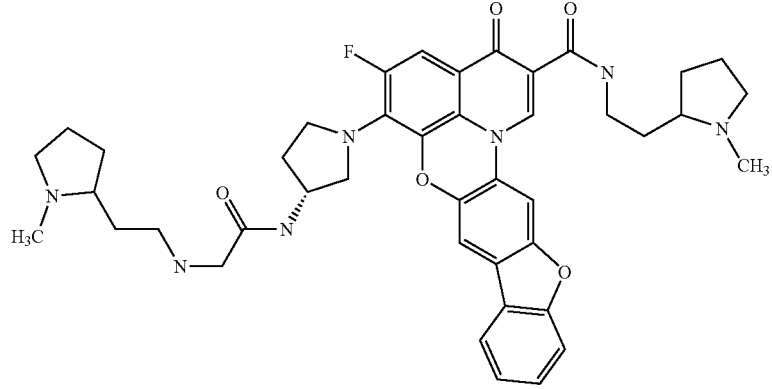 | Chiral | 0.75 |
| 411 | 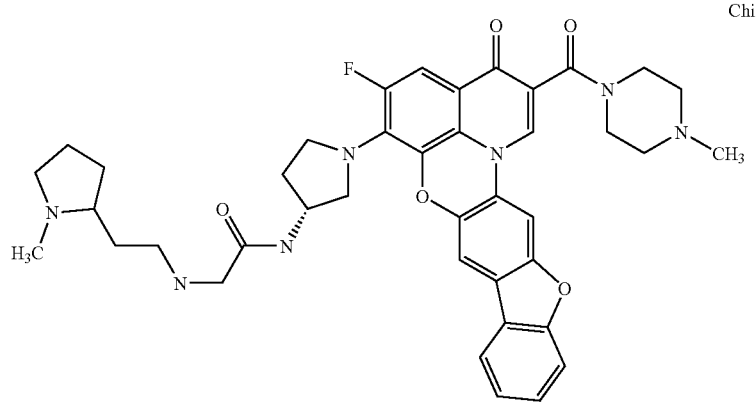 | Chiral | 0.75 |
| 412 | 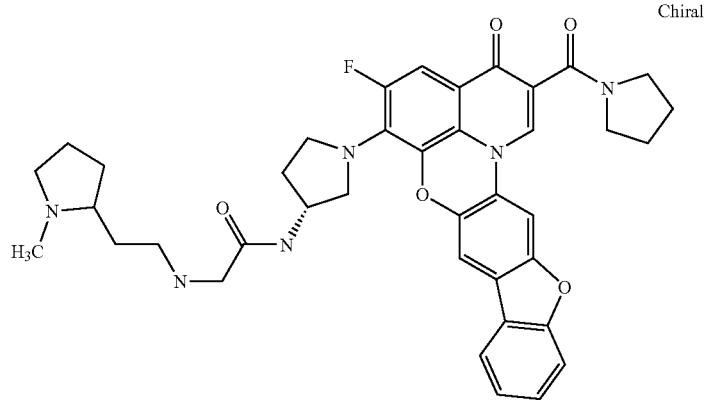 | Chiral | 0.75 |

-continued
| | | | |
|---|---|---|---|
| 413 | 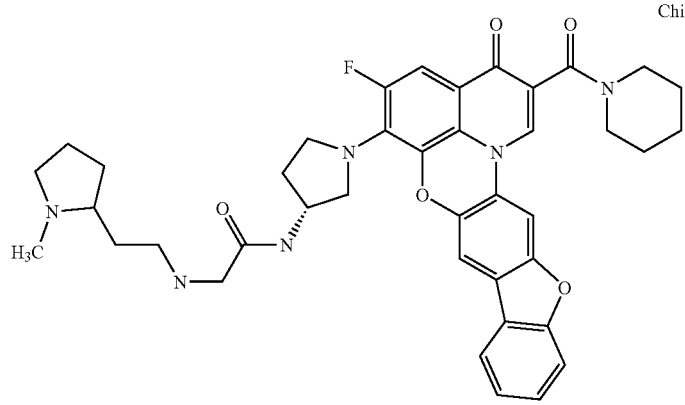 | Chiral | 0.75 |
| 414 | 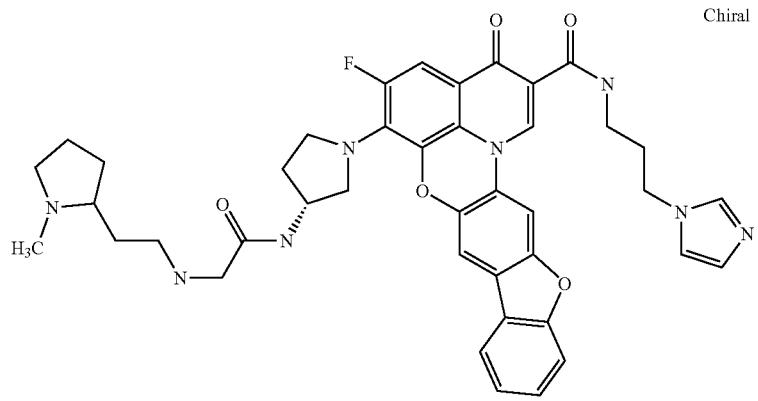 | Chiral | 0.75 |
| 415 | 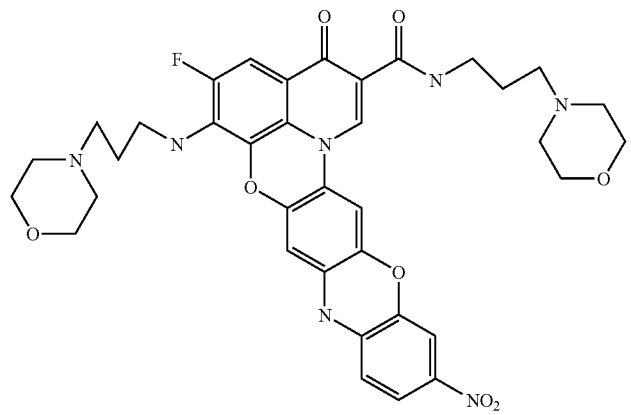 | | 0.75 |

| | | |
|---|---|---|
| 416 | 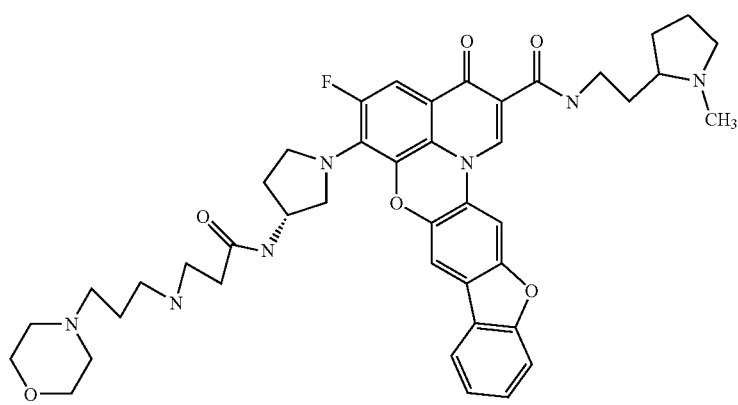 Chiral | 0.75 |
| 417 | 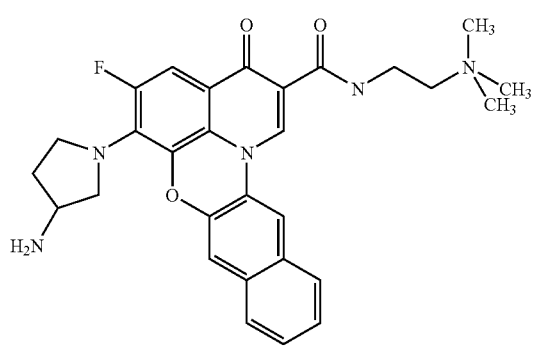 | 0.75 |
| 418 | 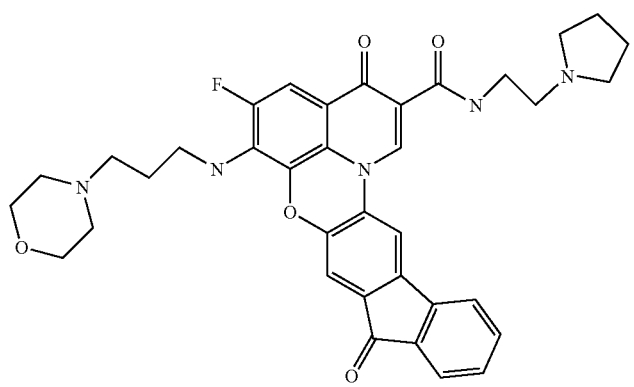 | 0.75 |
| 419 | 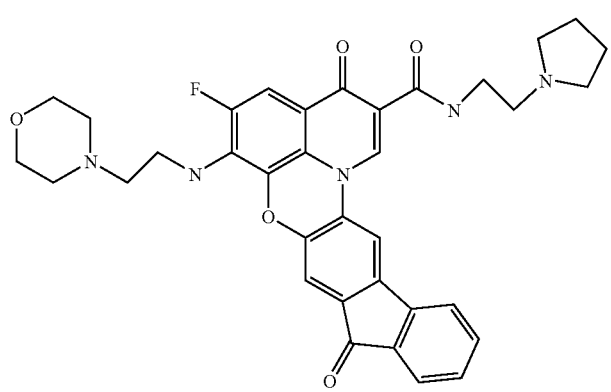 | 0.75 |

| | | |
|---|---|---|
| 420 | 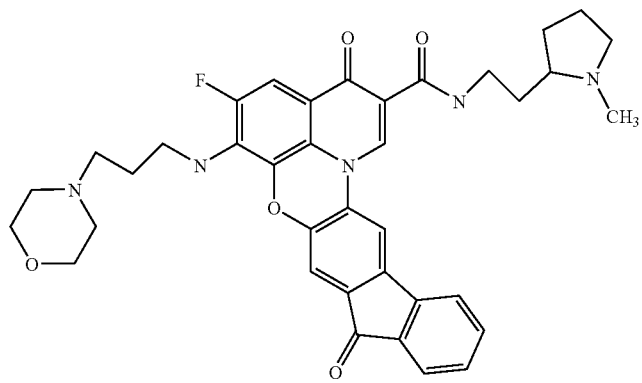 | 0.75 |
| 421 | 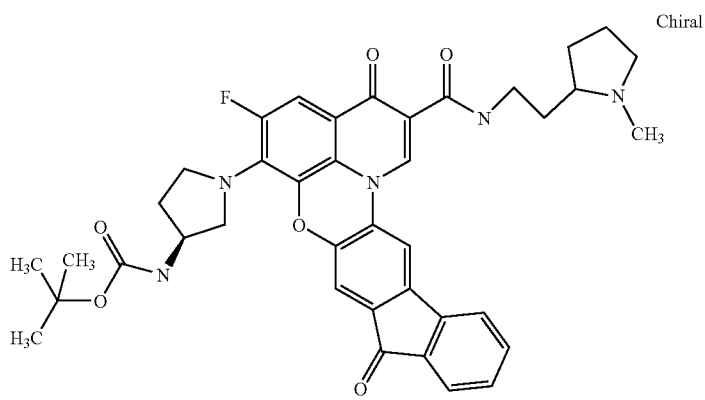 Chiral | 0.75 |
| 422 | 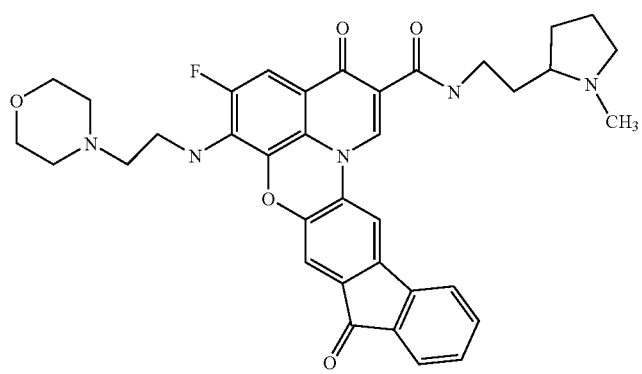 | 0.75 |
| 423 | 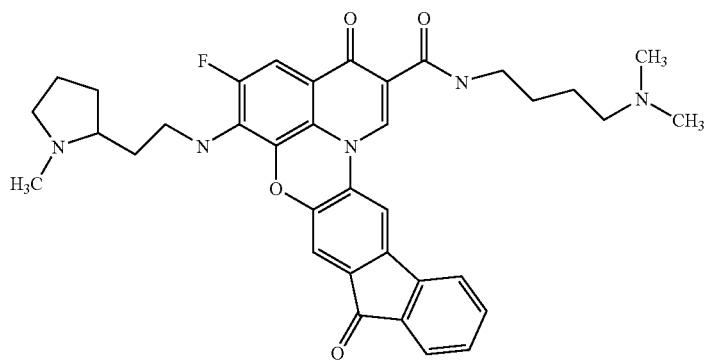 | 0.75 |

| | | |
|---|---|---|
| 424 | 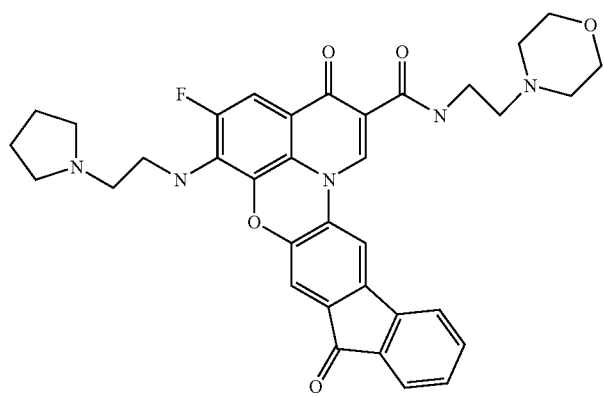 | 0.75 |
| 425 | 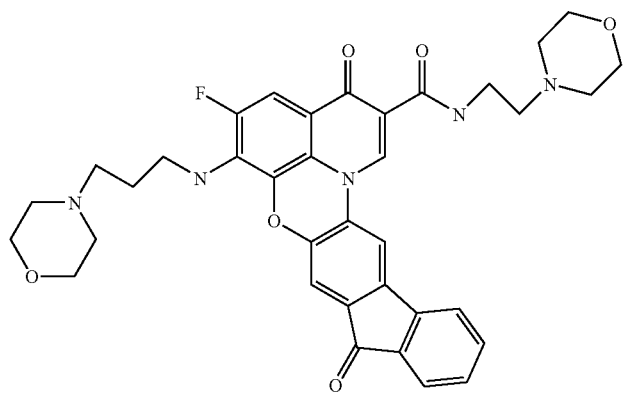 | 0.75 |
| 426 | 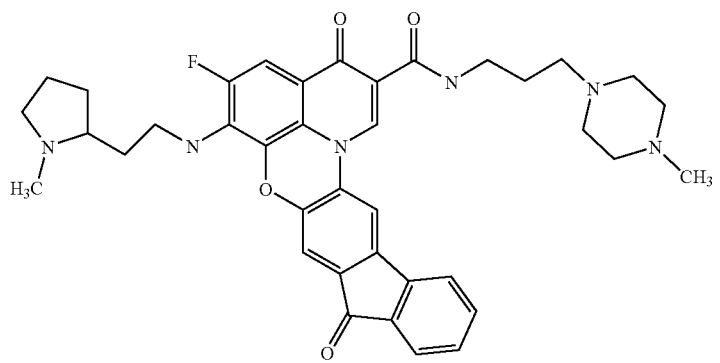 | 0.75 |
| 427 | 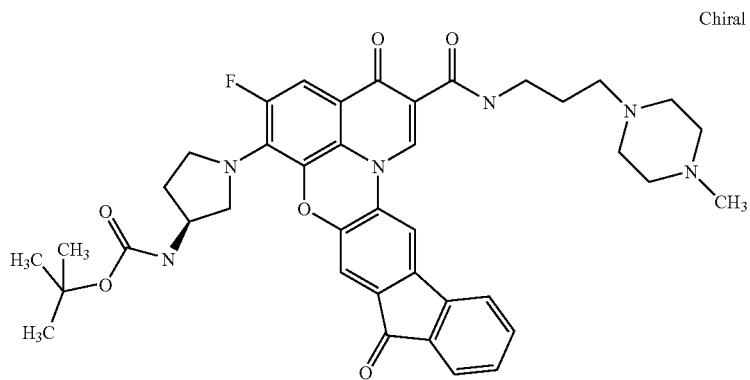 Chiral | 0.75 |

-continued
| | | | |
|---|---|---|---|
| 428 | 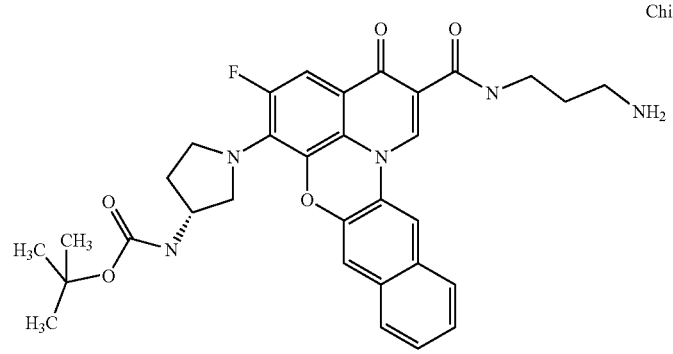 | Chiral | 0.75 |
| 429 | 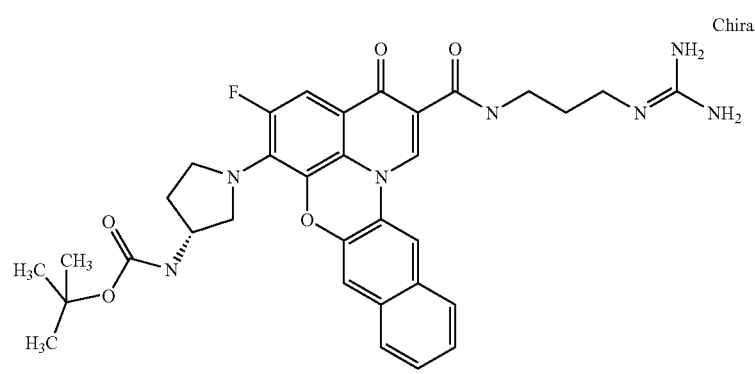 | Chiral | 0.75 |
| 430 | 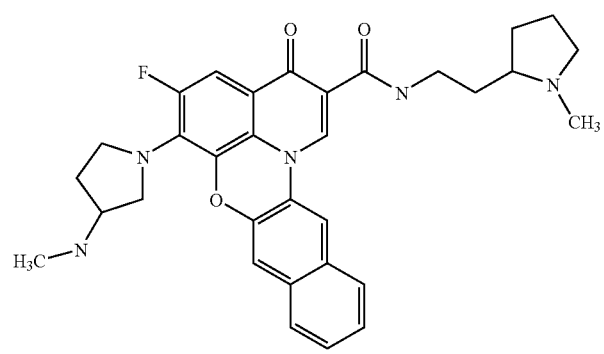 | | 0.75 |
| 431 | 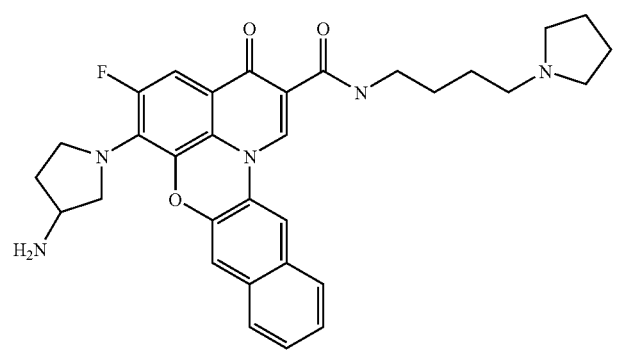 | | 0.75 |

-continued
| | | |
|---|---|---|
| 432 | 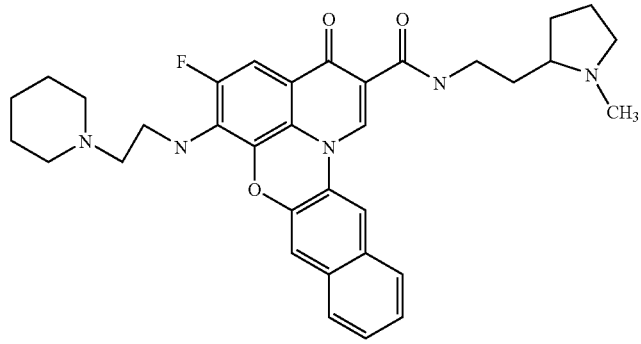 | 0.75 |
| 433 | 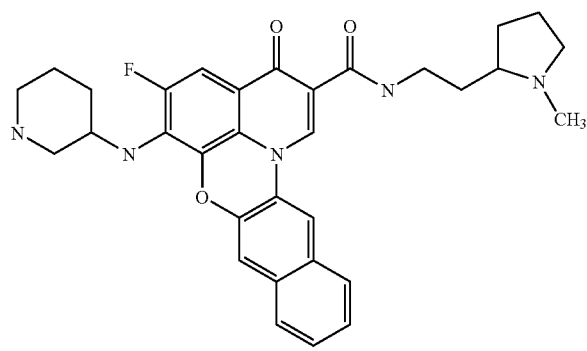 | 0.75 |
| 434 | 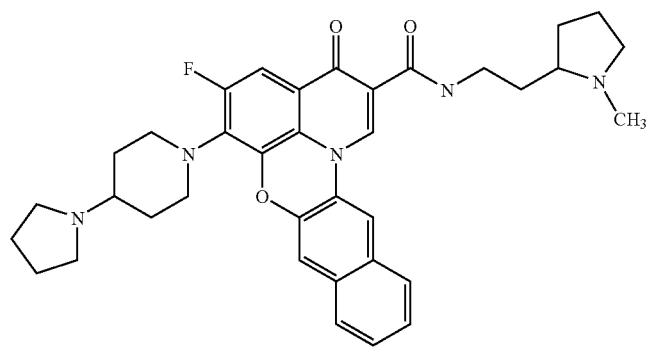 | 0.75 |
| 435 | 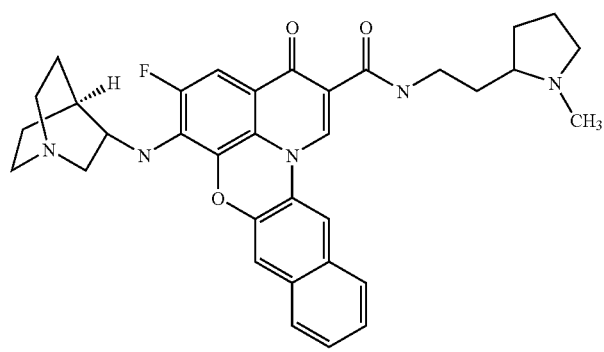 | 0.75 |

-continued
| | | |
|---|---|---|
| 436 | 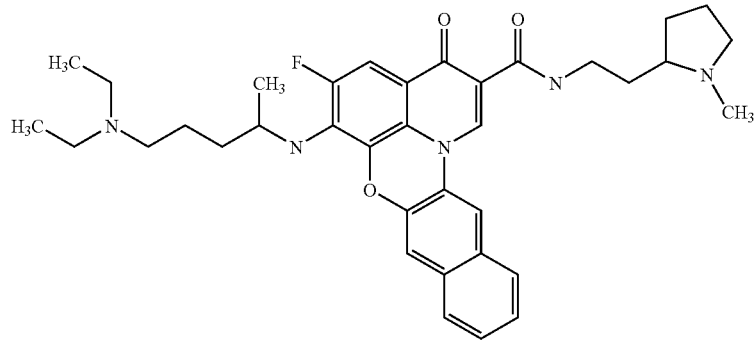 | 0.75 |
| 437 | 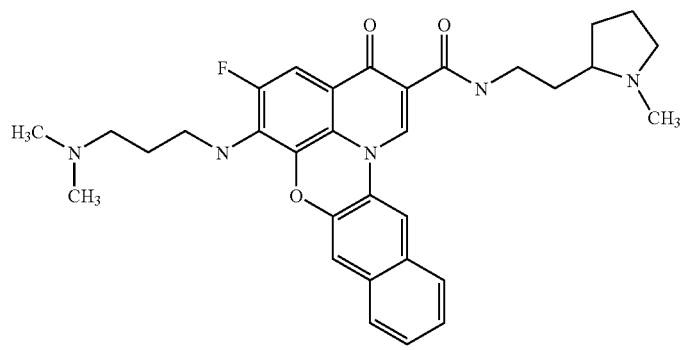 | 0.75 |
| 438 | 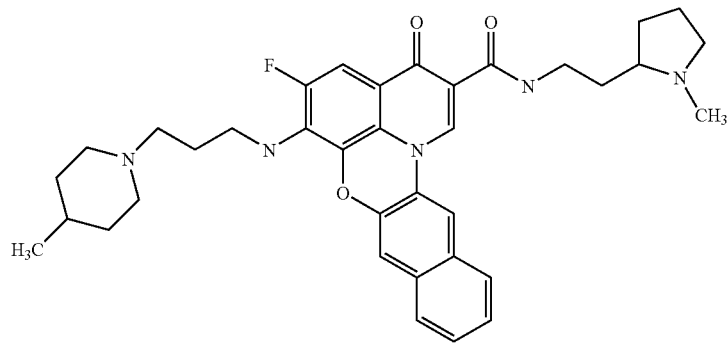 | 0.75 |
| 439 | 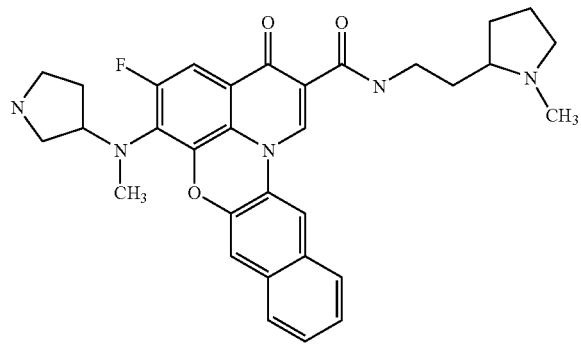 | 0.75 |

-continued
| | | |
|---|---|---|
| 440 | 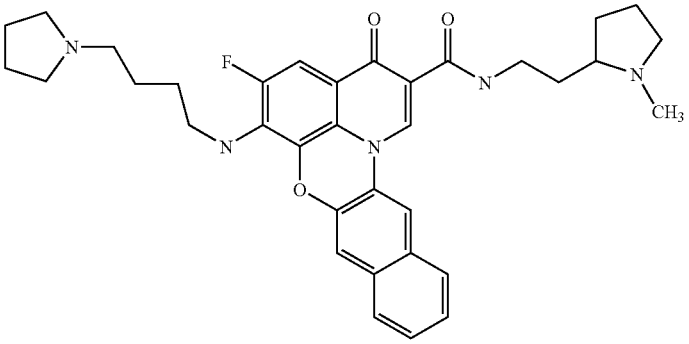 | 0.75 |
| 441 | 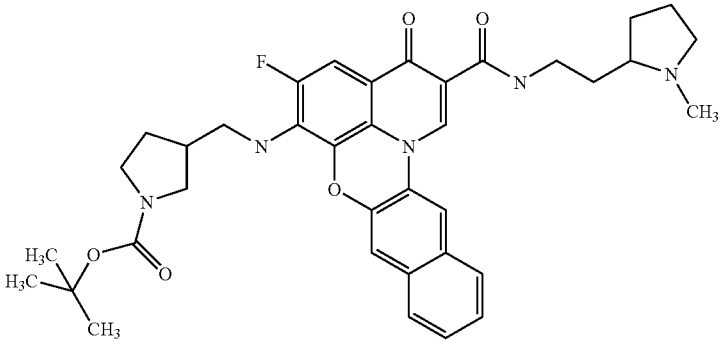 | 0.75 |
| 442 | 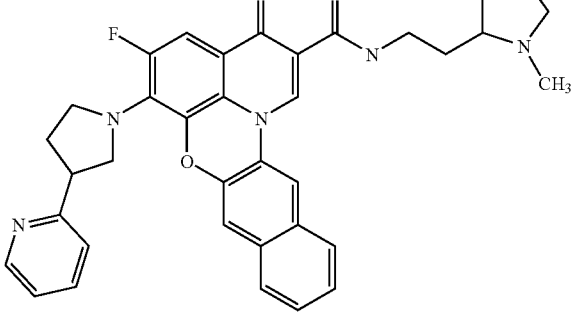 | 0.75 |
| 443 | 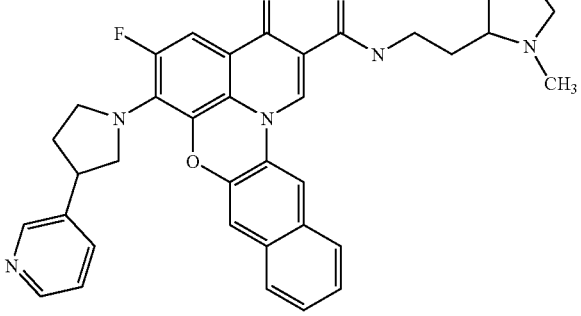 | 0.75 |

-continued
| | | |
|---|---|---|
| 444 | 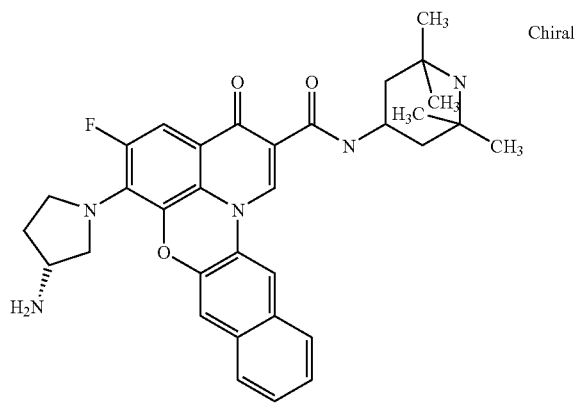 Chiral | 0.75 |
| 445 | 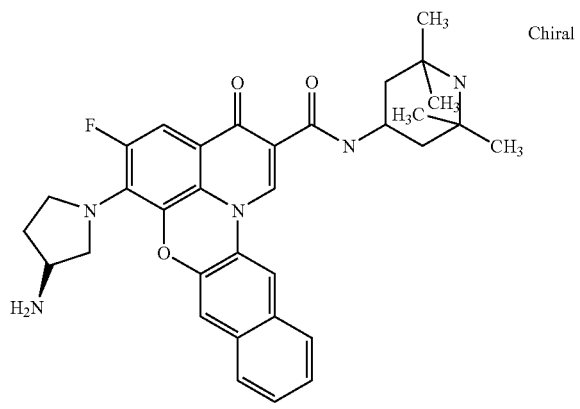 Chiral | 0.75 |
| 446 | 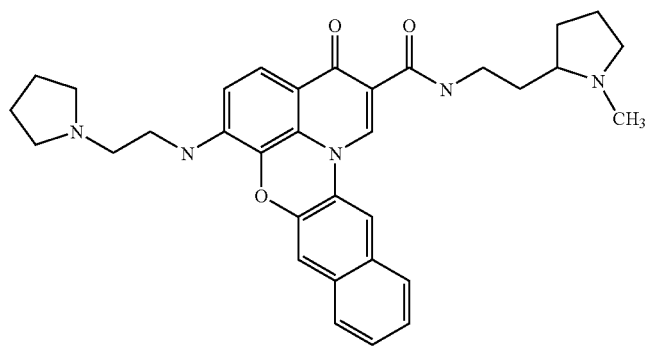 | 0.75 |
| 447 | 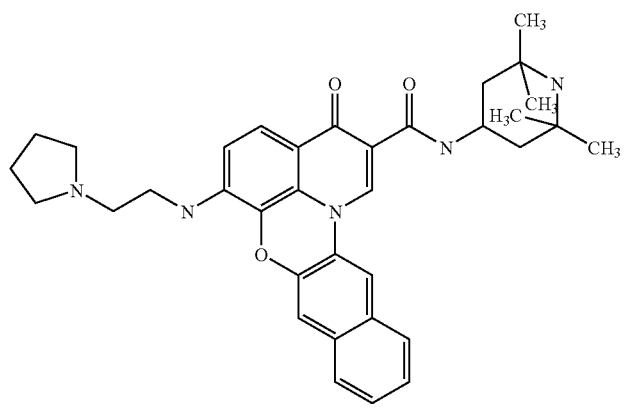 | 0.75 |

| | | |
|---|---|---|
| 448 | 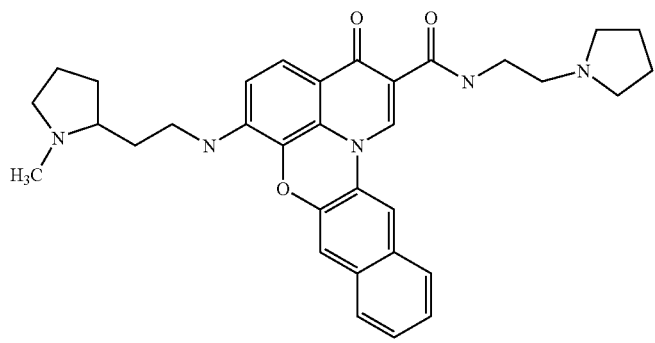 | 0.75 |
| 449 | 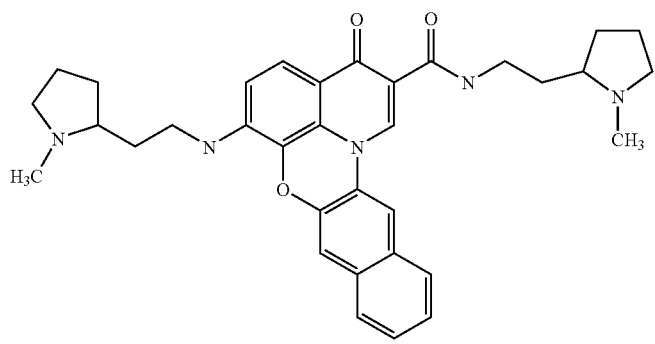 | 0.75 |
| 450 | 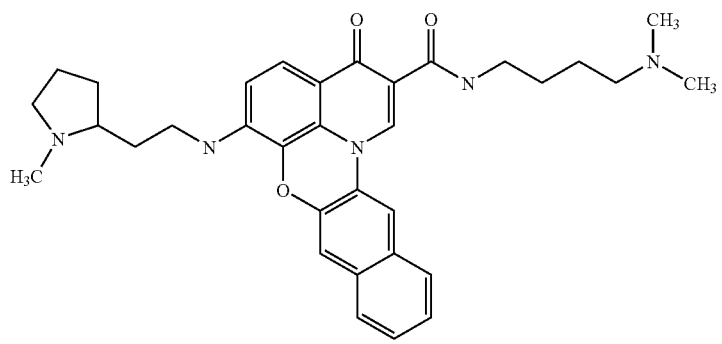 | 0.75 |
| 451 | 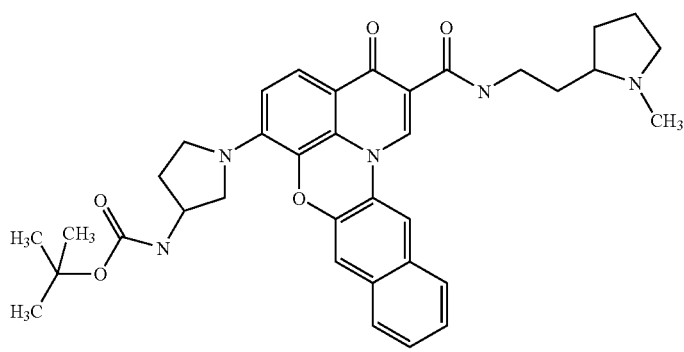 | 0.75 |

-continued
| | | |
|---|---|---|
| 452 | 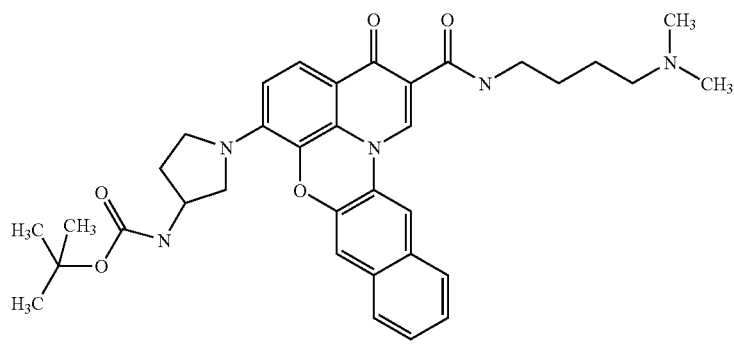 | 0.75 |
| 453 | 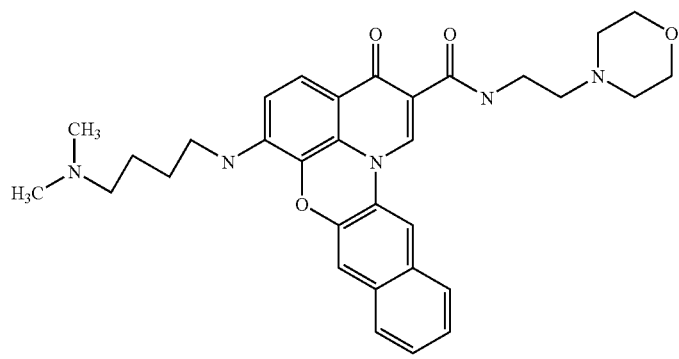 | 0.75 |
| 454 | 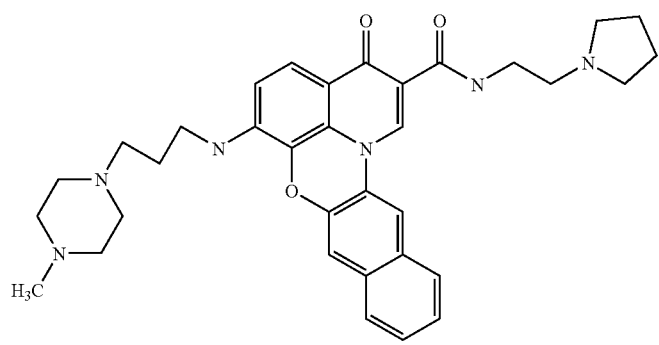 | 0.75 |
| 455 | 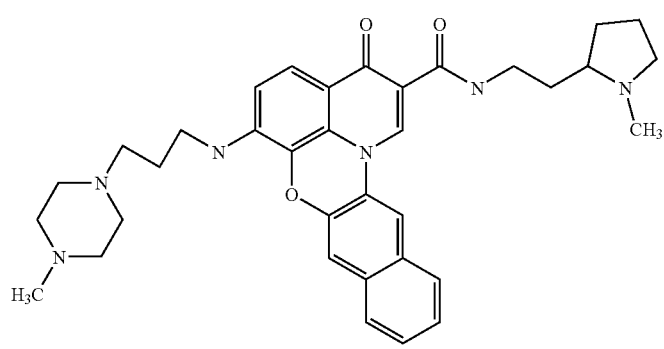 | 0.75 |

-continued
| | | |
|---|---|---|
| 456 | 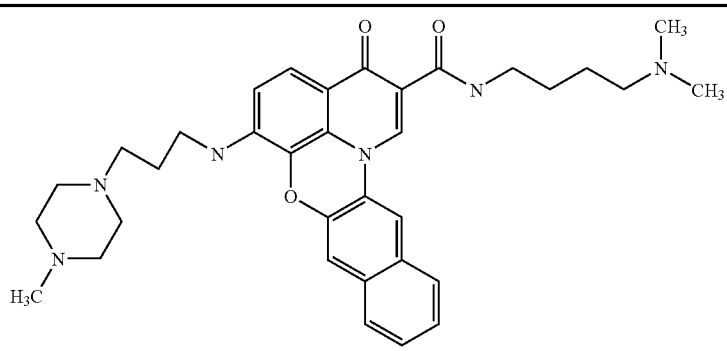 | 0.75 |
| 457 | 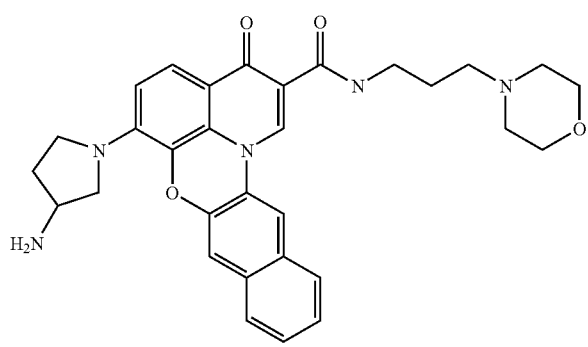 | 0.75 |
| 458 | 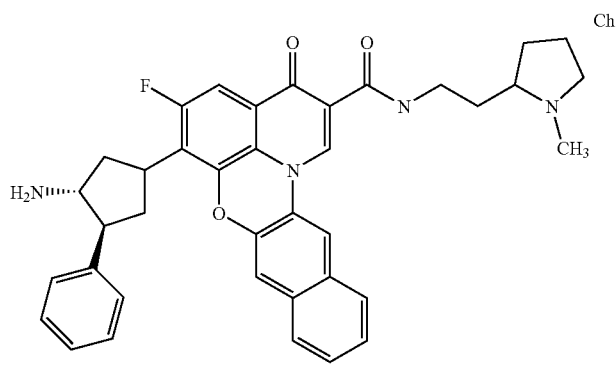 Chiral | 0.75 |
| 459 | 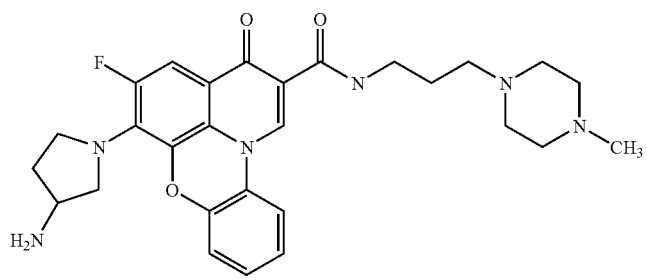 | 0.75 |
| 460 | 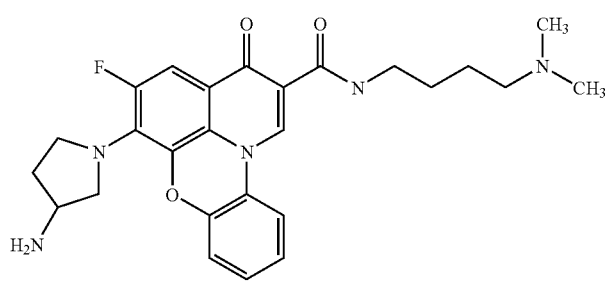 | 0.75 |

-continued
| | | |
|---|---|---|
| 461 | 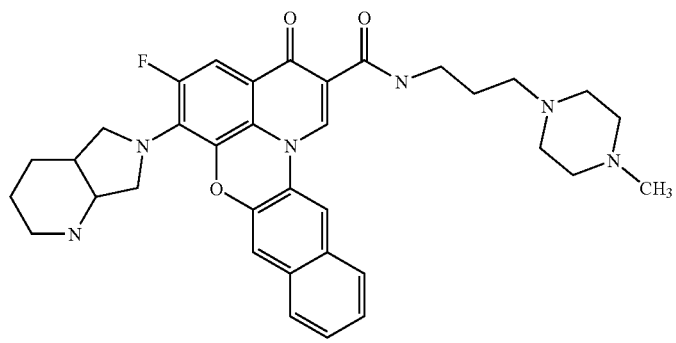 | 0.75 |
| 462 | 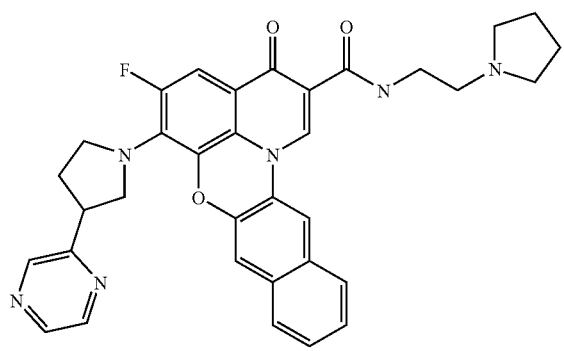 | 0.75 |
| 463 | 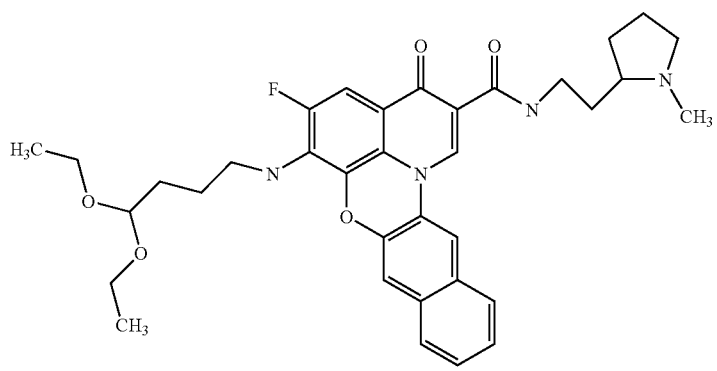 | 0.75 |
| 464 | 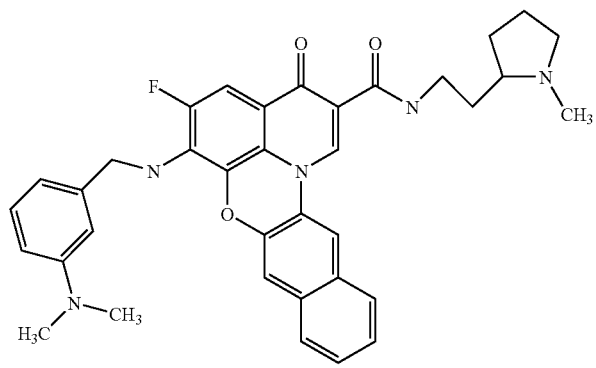 | 0.75 |

-continued
| | | |
|---|---|---|
| 465 | 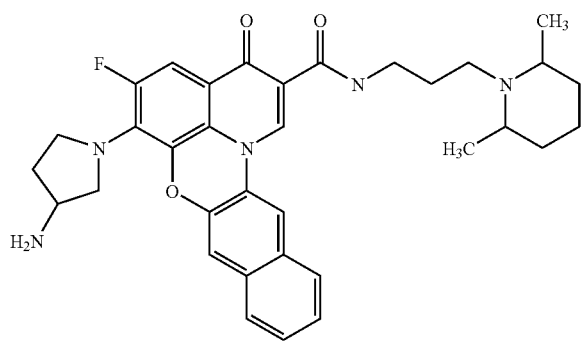 | 0.75 |
| 466 | 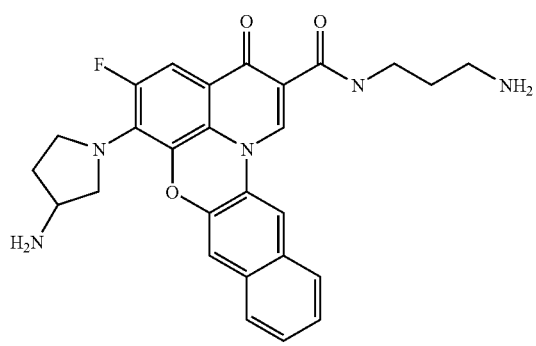 | 0.75 |
| 467 | 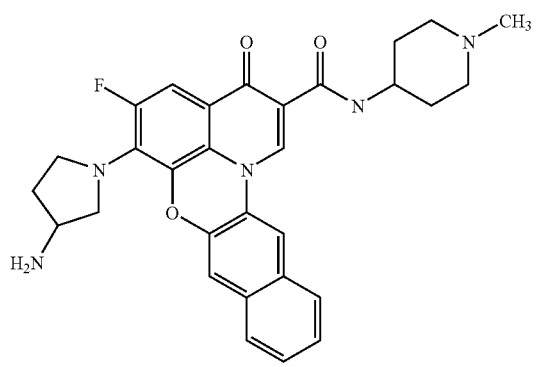 | 0.75 |
| 468 | 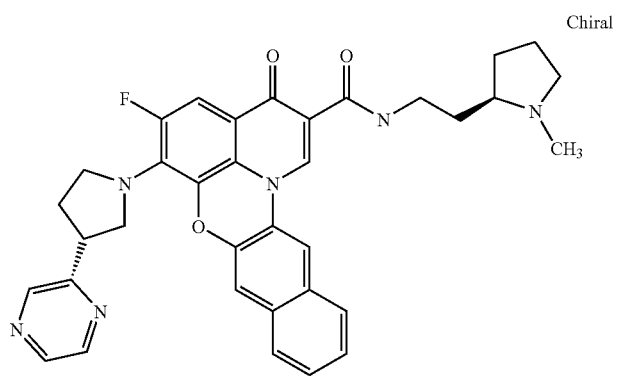 | 0.74 |

-continued
| | | | |
|---|---|---|---|
| 469 | 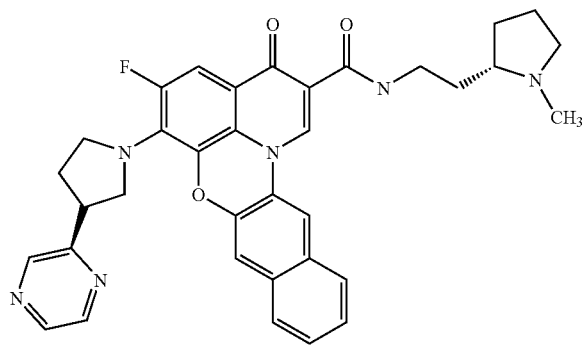 Chiral | 0.73 | |
| 470 | 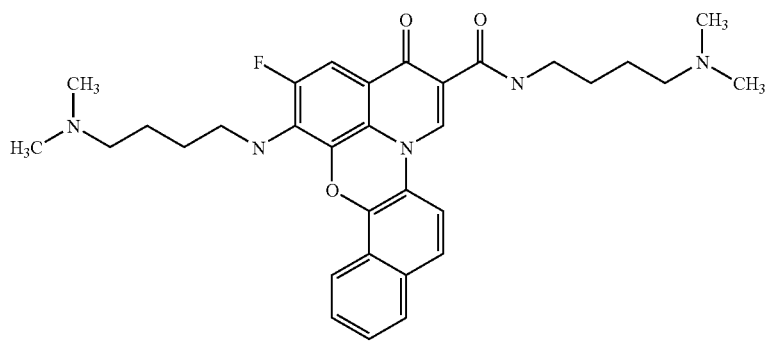 | 0.64 | |
| 471 | 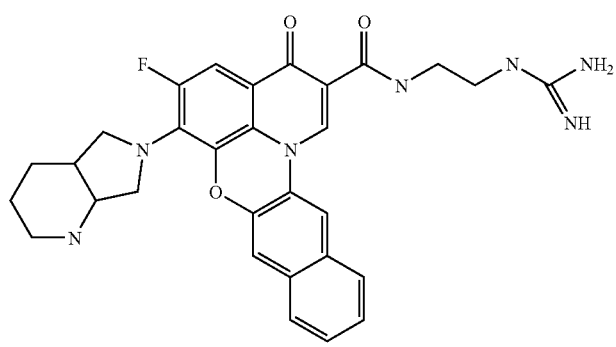 | 0.64 | |
| 472 | 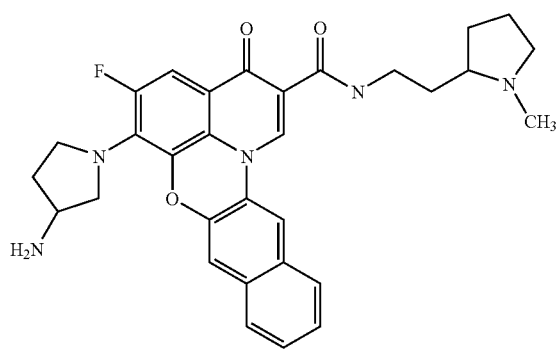 | 0.62 | 3.30 |

-continued
| | | | |
|---|---|---|---|
| 473 | 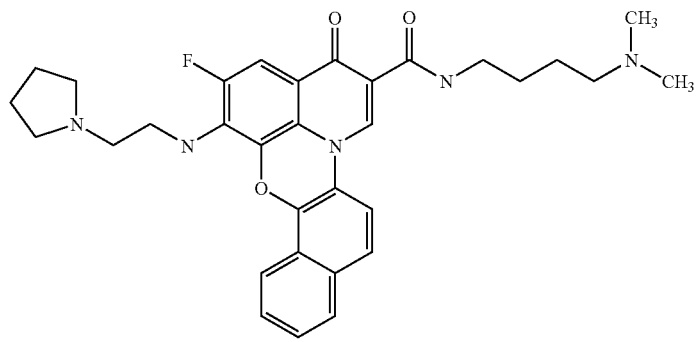 | 0.62 | |
| 474 | 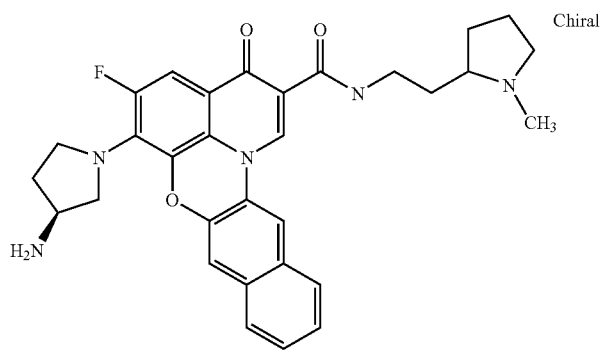 Chiral | 0.58 | 0.37 |
| 475 | 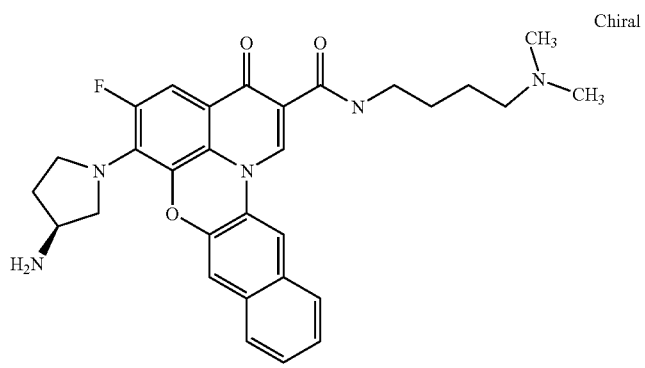 Chiral | 0.58 | 0.24 |
| 476 | 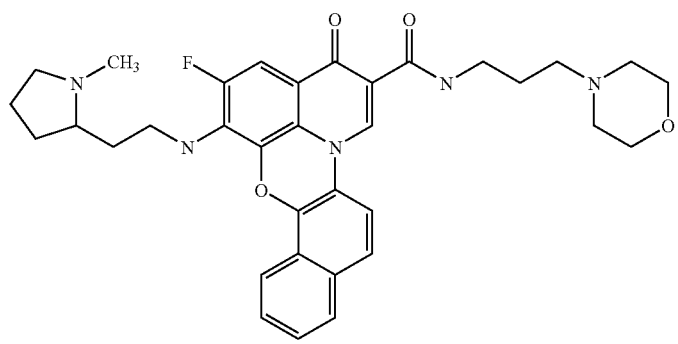 | 0.58 | |

-continued
| | | | |
|---|---|---|---|
| 477 | 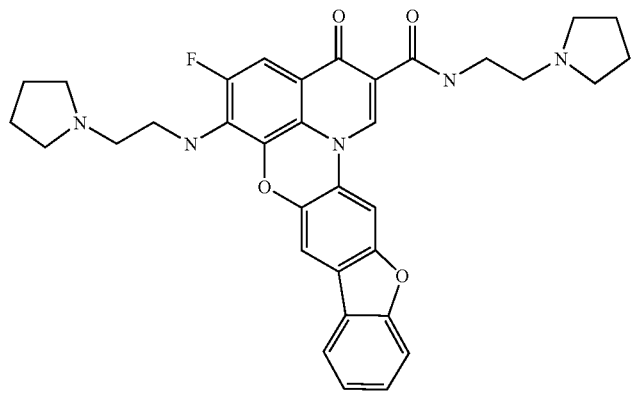 | 0.55 | 2.10 |
| 478 | 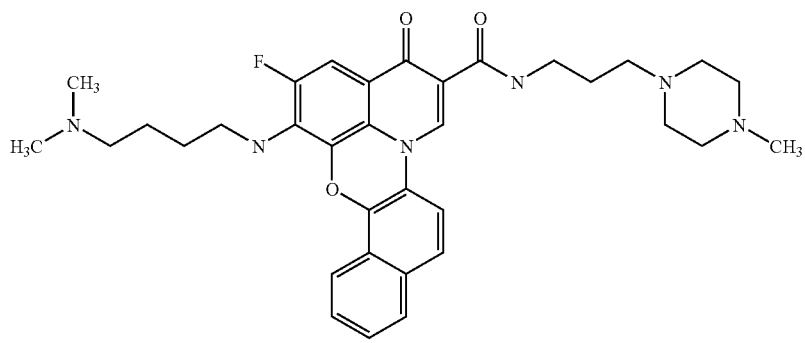 | 0.53 | |
| 479 | 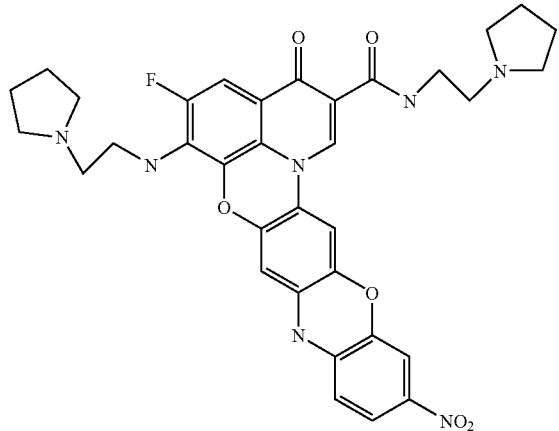 | 0.5 | 7.40 |
| 480 | 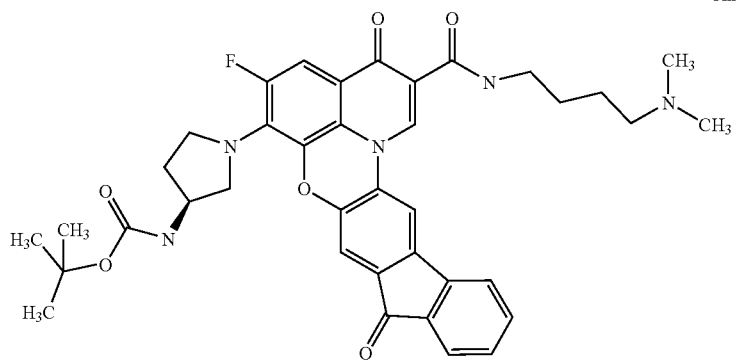 Chiral | 0.5 | 3.70 |

-continued
| | | | |
|---|---|---|---|
| 481 | 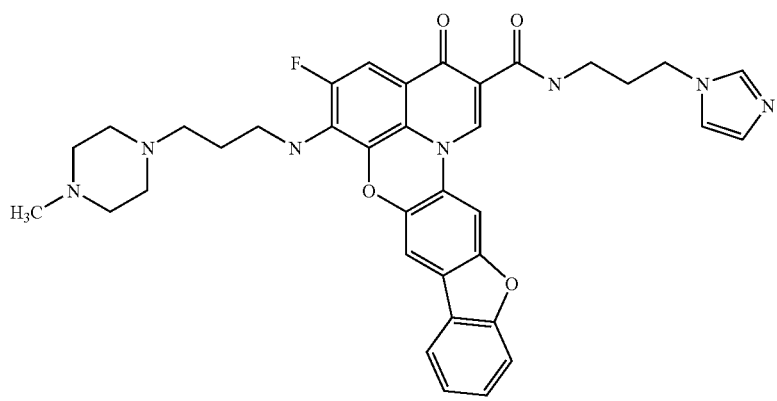 | 0.5 | 3.60 |
| 482 | 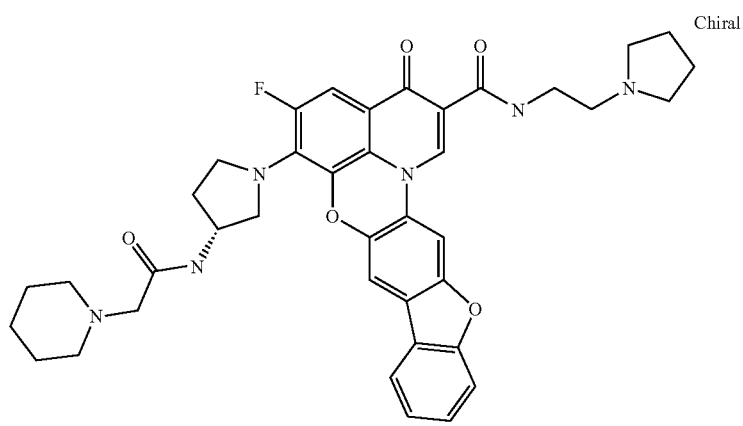 Chiral | 0.5 | 3.40 |
| 483 | 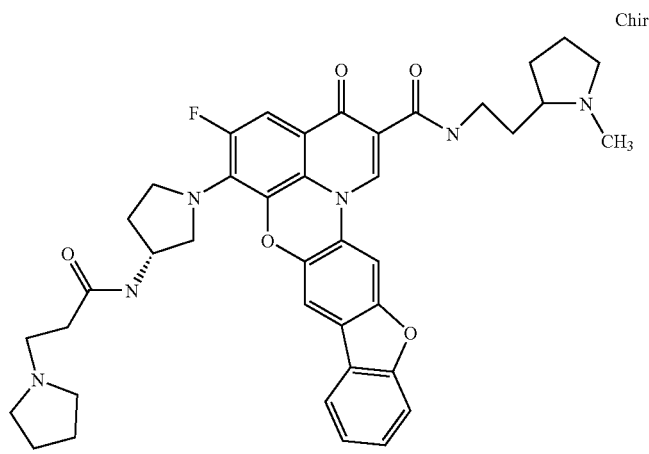 Chiral | 0.5 | 3.20 |

-continued
| | | | | |
|---|---|---|---|---|
| 484 | 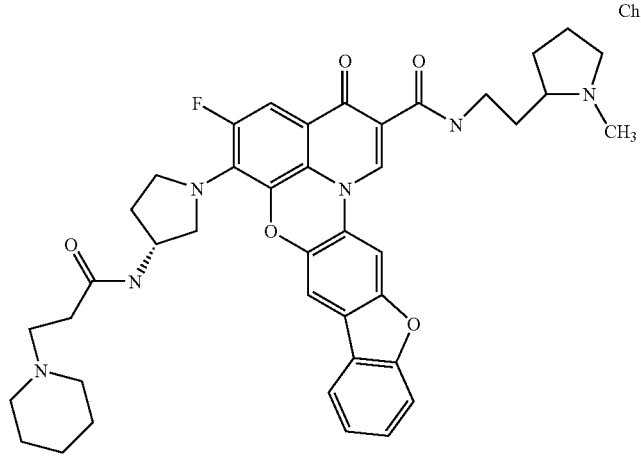 | Chiral | 0.5 | 3.10 |
| 485 | 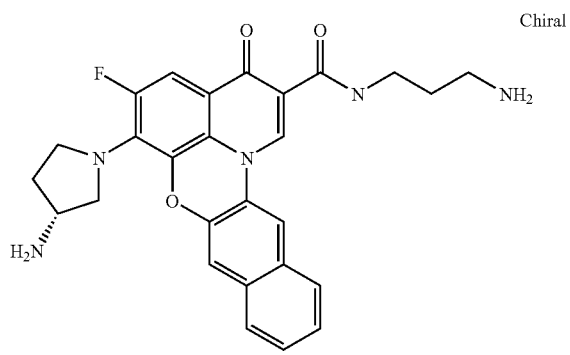 | Chiral | 0.5 | 0.50 |
| 486 | 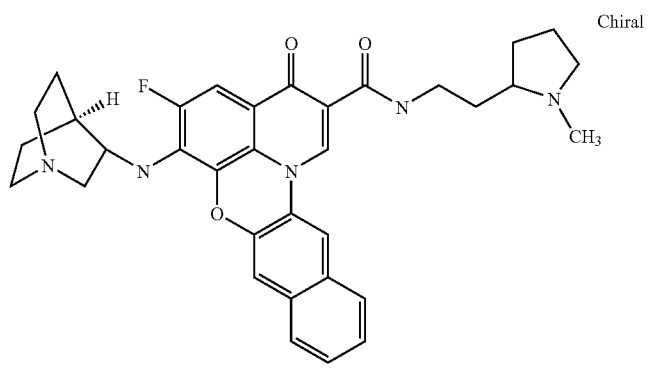 | Chiral | 0.5 | 0.39 |
| 487 | 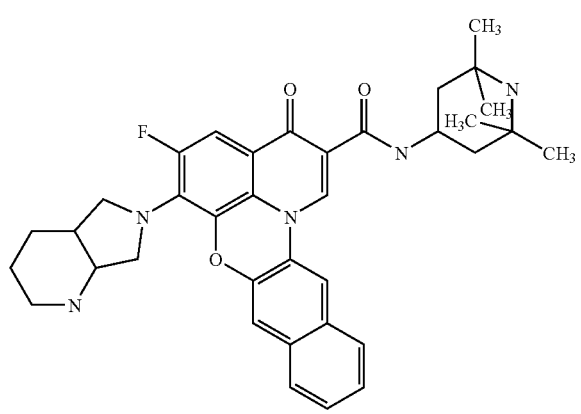 | | 0.5 | 0.18 |

-continued
| | | |
|---|---|---|
| 488 | 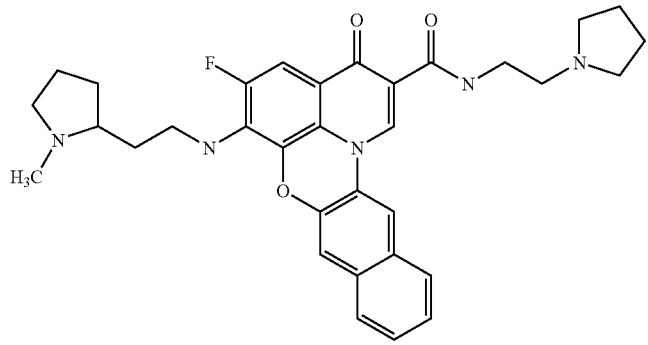 | 0.5 |
| 489 | 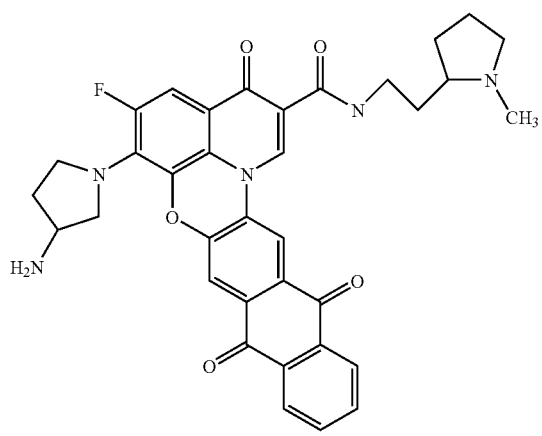 | 0.5 |
| 490 | 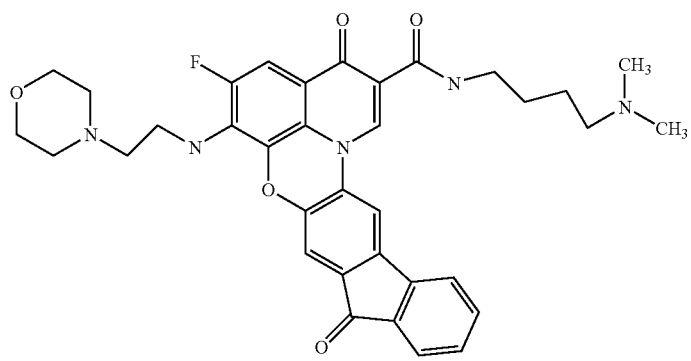 | 0.5 |
| 491 | 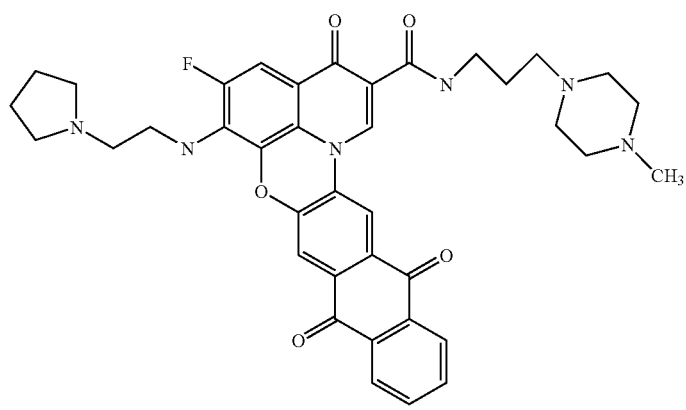 | 0.45 |

-continued
| | | |
|---|---|---|
| 492 | 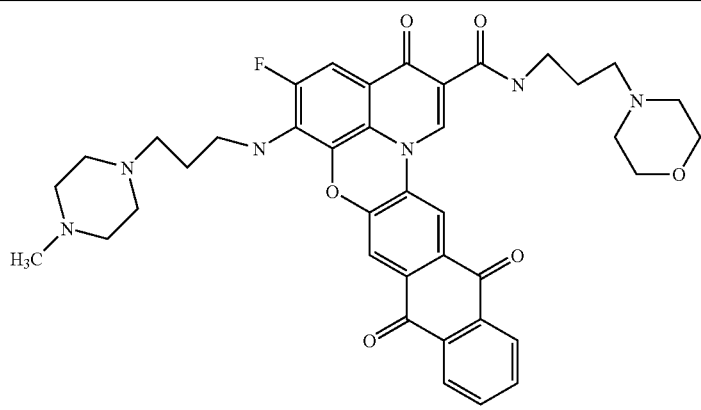 | 0.45 |
| 493 | 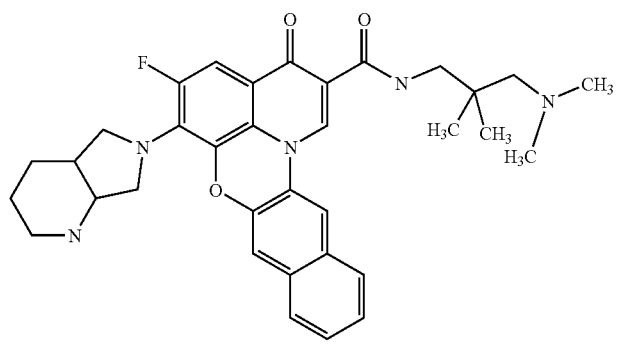 | 0.44 0.40 |
| 494 | 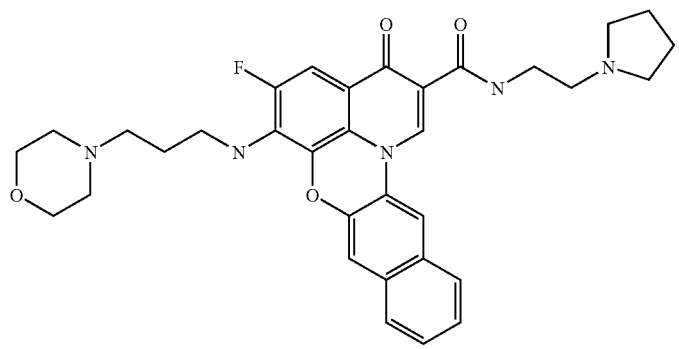 | 0.44 0.19 |
| 495 | 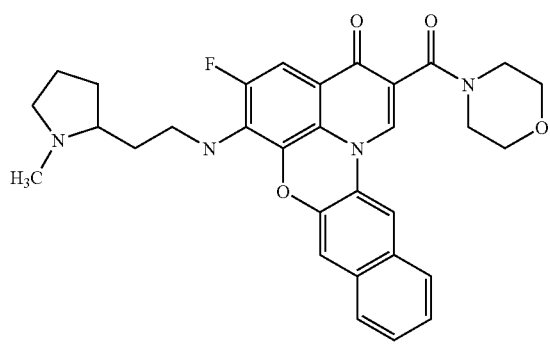 | 0.42 |

-continued
| | | | |
|---|---|---|---|
| 496 | 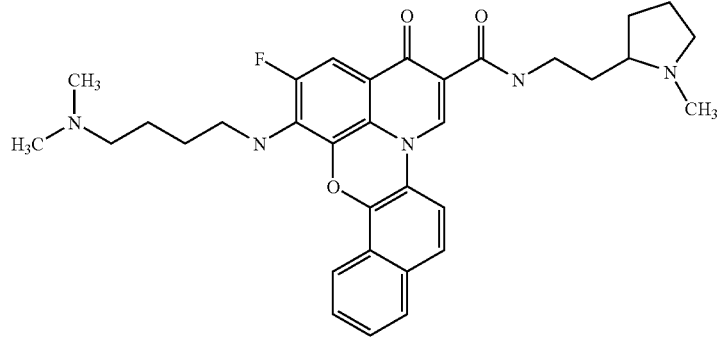 | 0.41 | 4.00 |
| 497 | 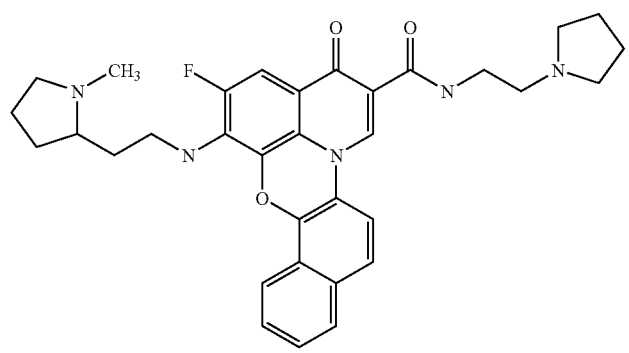 | 0.41 | 2.10 |
| 498 | 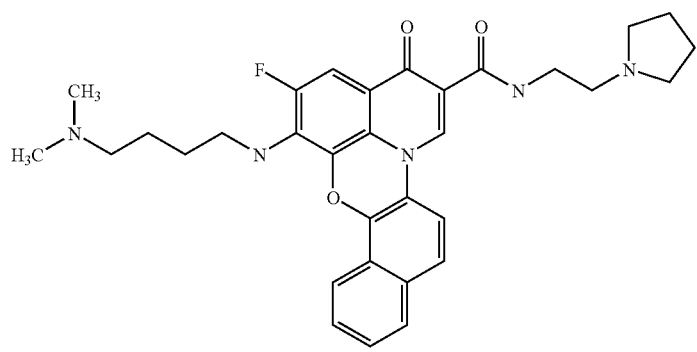 | 0.41 | |
| 499 | 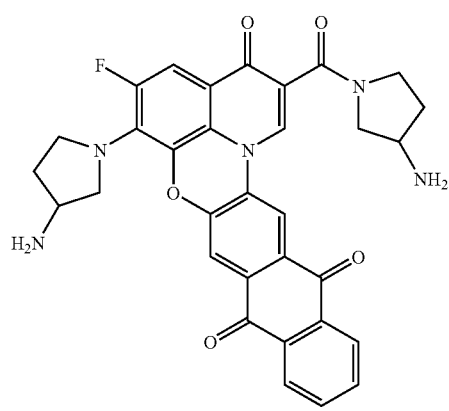 | 0.4 | |

-continued
| | | | | |
|---|---|---|---|---|
| 500 | 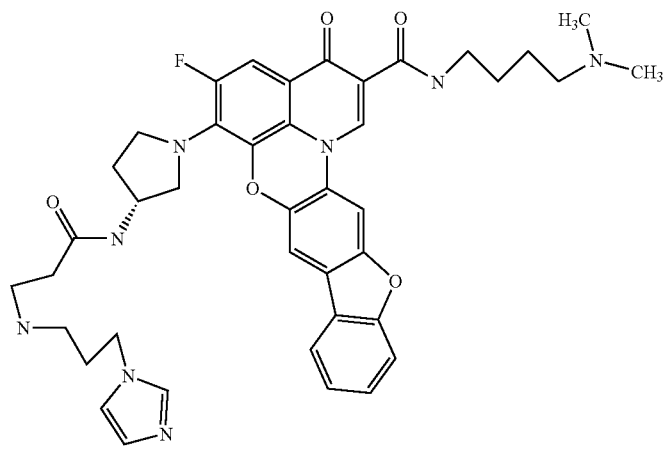 | Chiral | 0.375 | 5.60 |
| 501 | 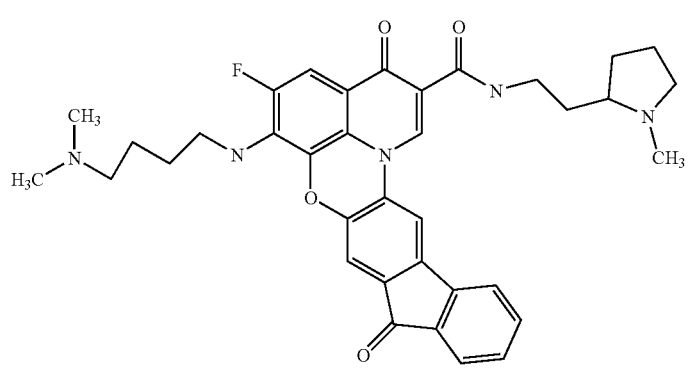 | | 0.375 | 4.20 |
| 502 | 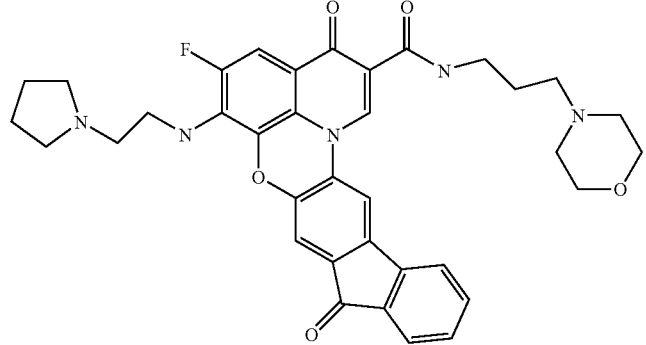 | | 0.375 | 4.00 |
| 503 | 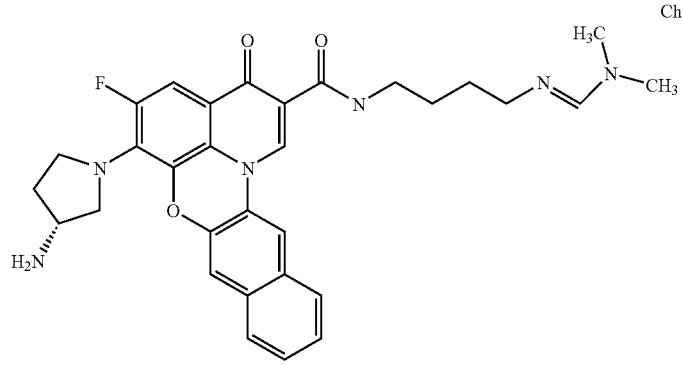 | Chiral | 0.375 | 4.00 |

| | | Chiral | 0.375 | 3.40 |
|---|---|---|---|---|
| 504 | 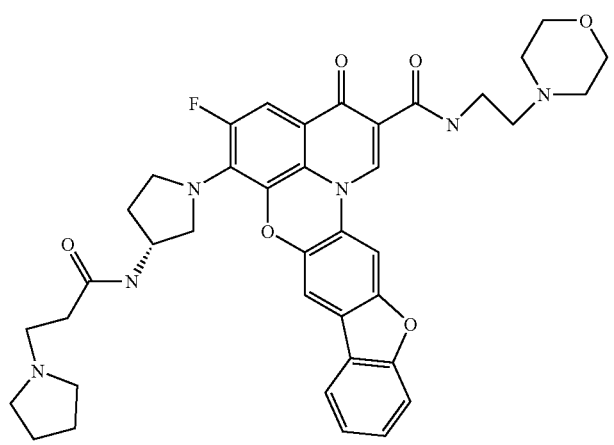 | | | |
| 505 | 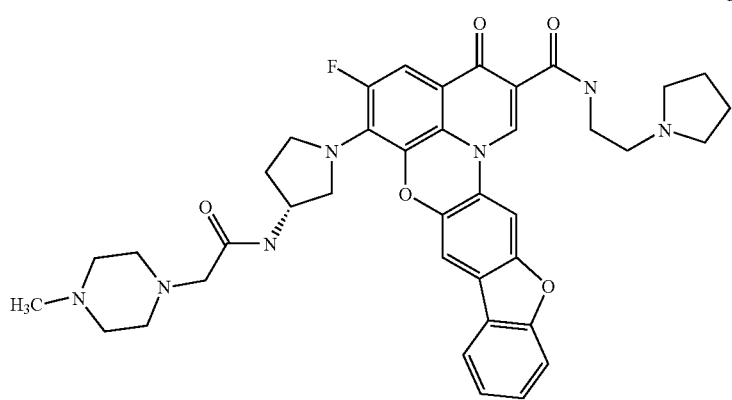 | Chiral | 0.375 | 3.40 |
| 506 | 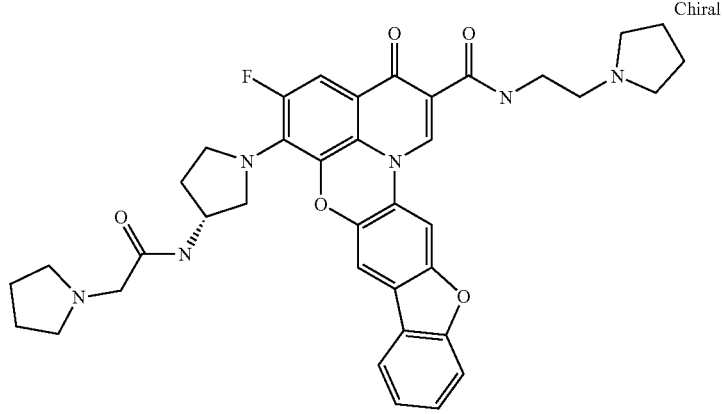 | Chiral | 0.375 | 3.40 |

-continued
| 507 | 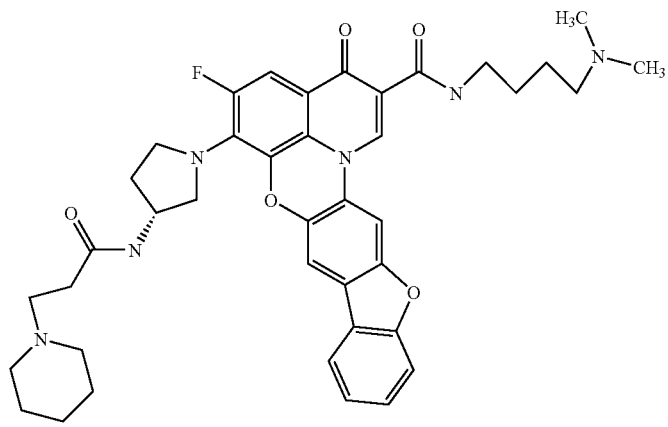 | Chiral | 0.375 | 3.30 |
| 508 | 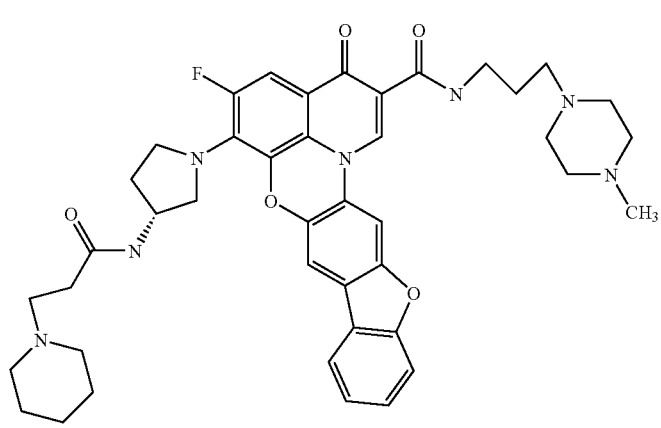 | Chiral | 0.375 | 3.20 |
| 509 | 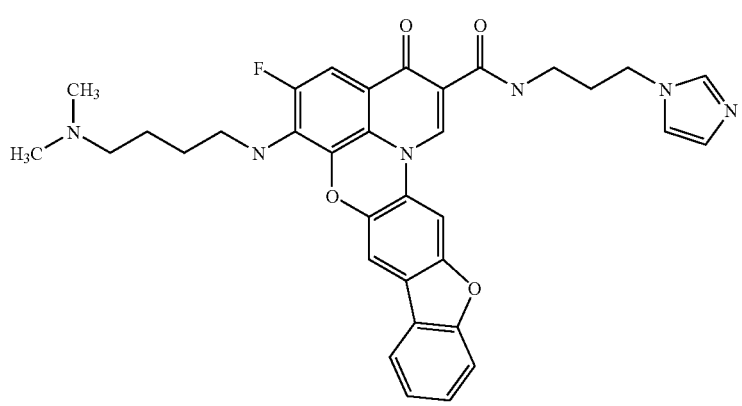 | | 0.375 | 3.10 |

-continued
| | | | |
|---|---|---|---|
| 510 | 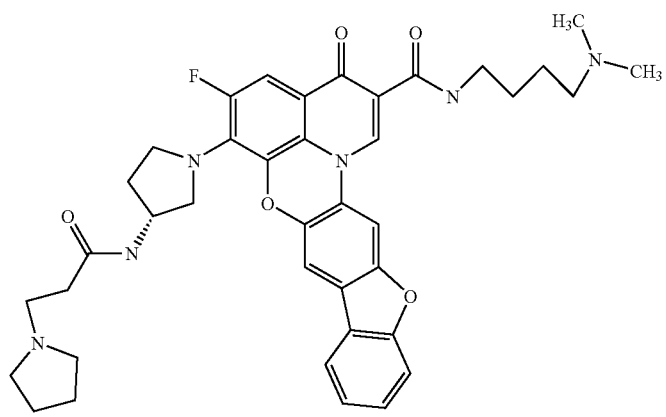 Chiral | 0.375 | 3.10 |
| 511 | 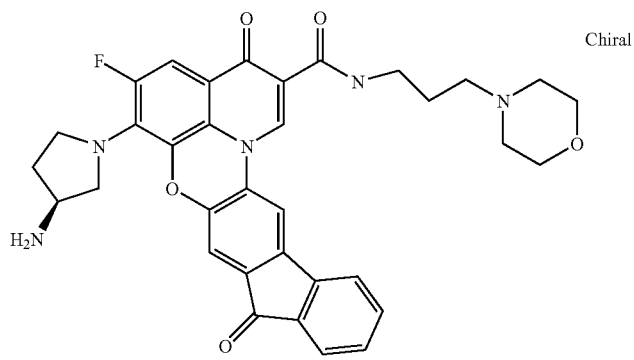 Chiral | 0.375 | 3.10 |
| 512 | 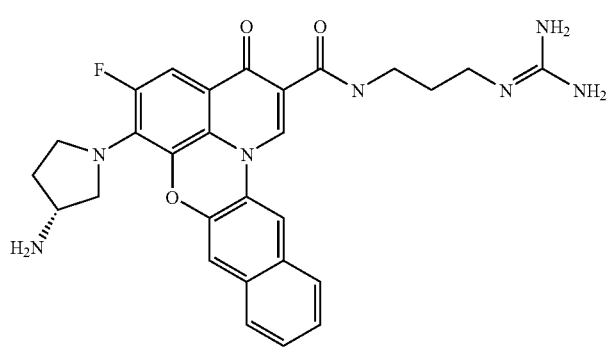 Chiral | 0.375 | 3.10 |
| 513 | 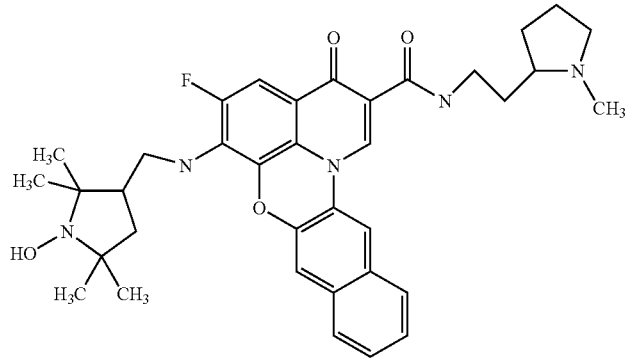 | 0.375 | 3.10 |

-continued
| | | | |
|---|---|---|---|
| 514 | 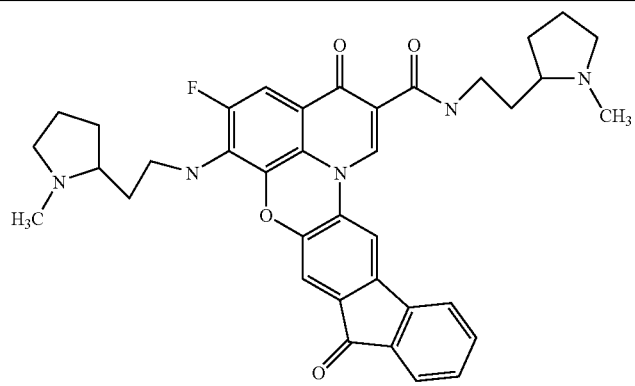 | 0.375 | 2.90 |
| 515 | 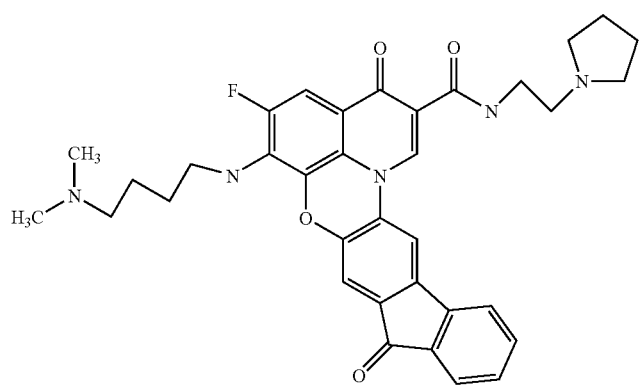 | 0.375 | 2.50 |
| 516 | 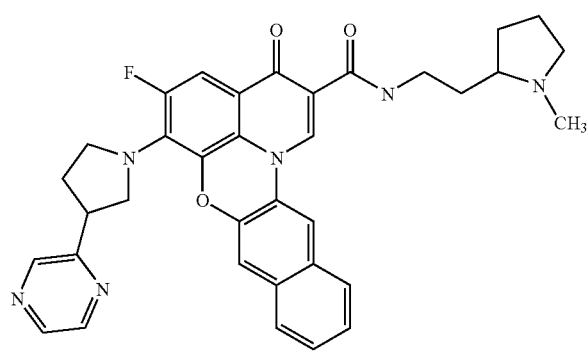 | 0.375 | 2.30 |
| 517 | 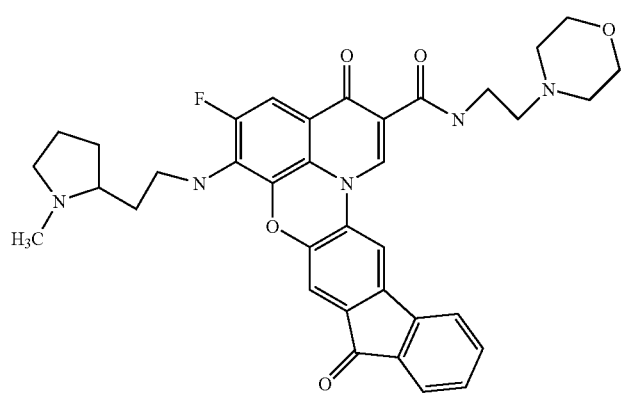 | 0.375 | 2.20 |

-continued
| | | | |
|---|---|---|---|
| 518 | 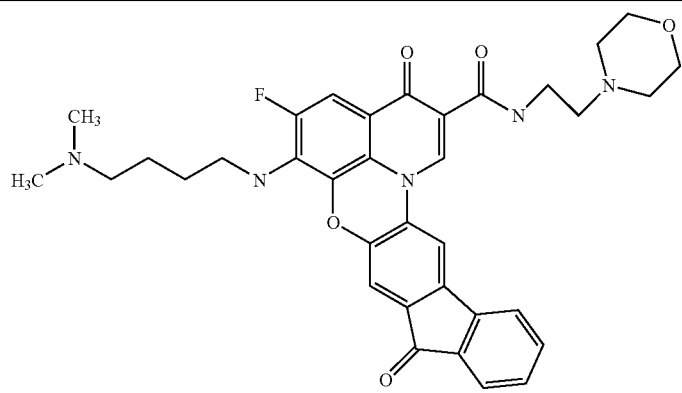 | 0.375 | 2.20 |
| 519 | 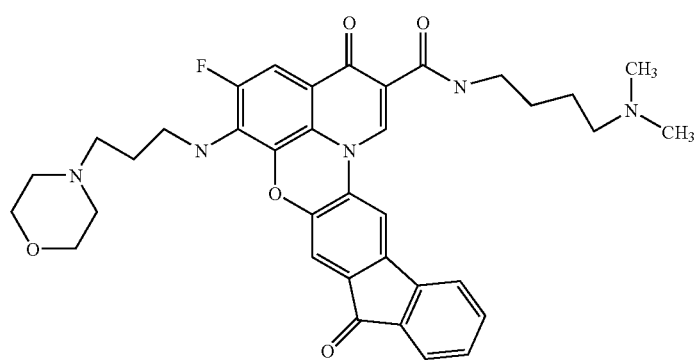 | 0.375 | 2.10 |
| 520 | 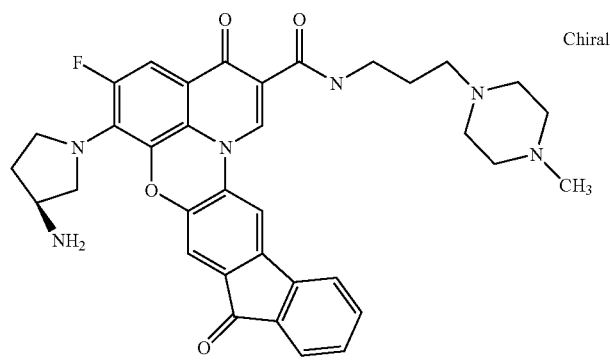 | 0.375 | 1.90 |
| 521 | 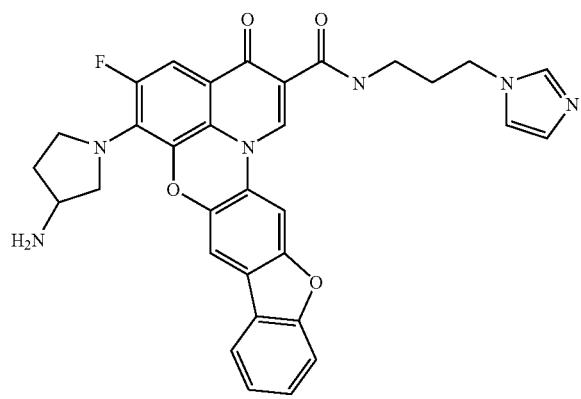 | 0.375 | 1.70 |

-continued
| | | |
|---|---|---|
| 522 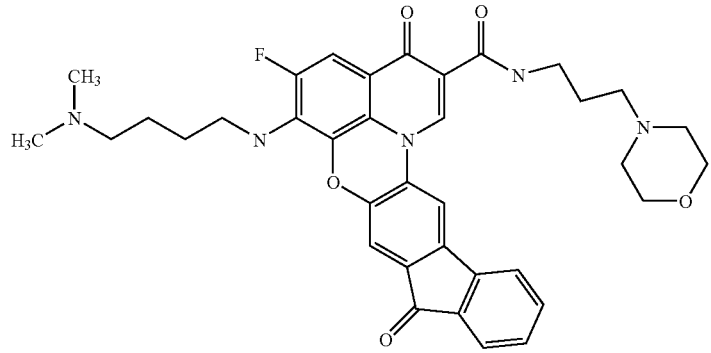 | 0.375 | 1.70 |
| 523 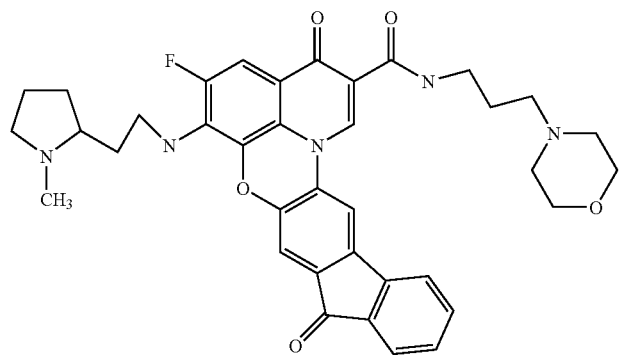 | 0.375 | 1.60 |
| 524 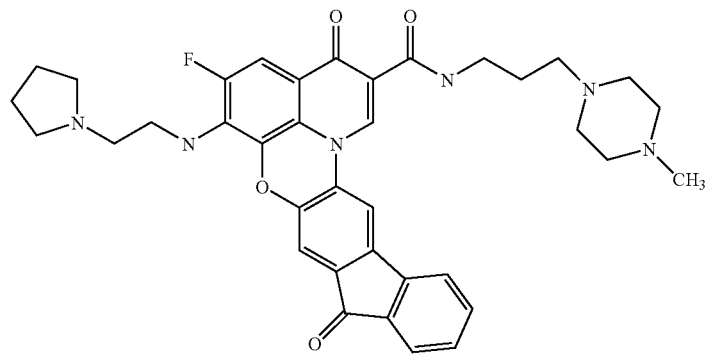 | 0.375 | 1.50 |
| 525 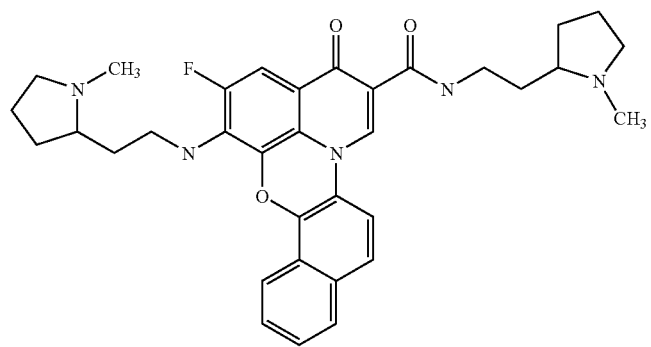 | 0.375 | 1., 2 |

-continued
| | | | |
|---|---|---|---|
| 526 | 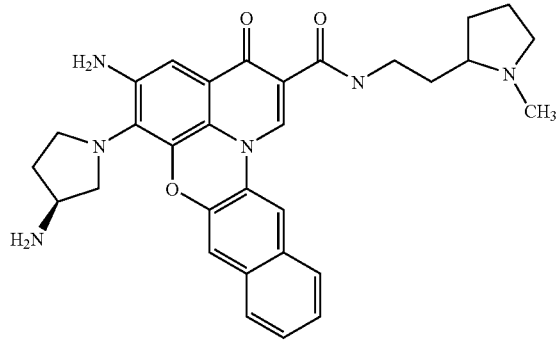 | 0.375 | 0.90 |
| 527 | 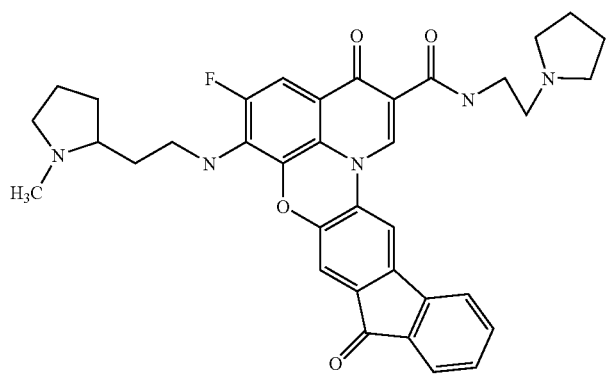 | 0.375 | 0.79 |
| 528 | 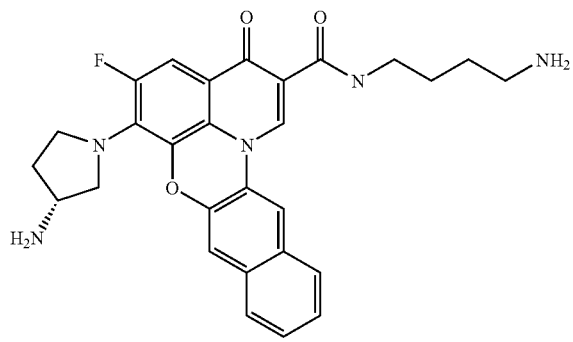 Chiral | 0.375 | 0.75 |
| 529 | 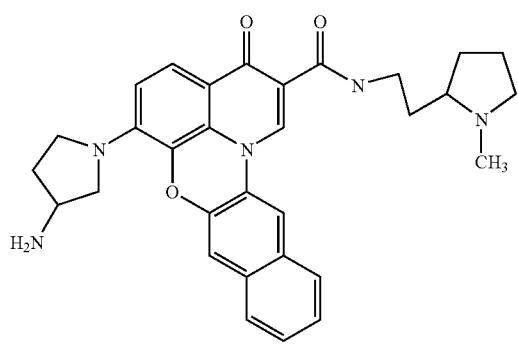 | 0.375 | 0.75 |

| | | | |
|---|---|---|---|
| 530 | 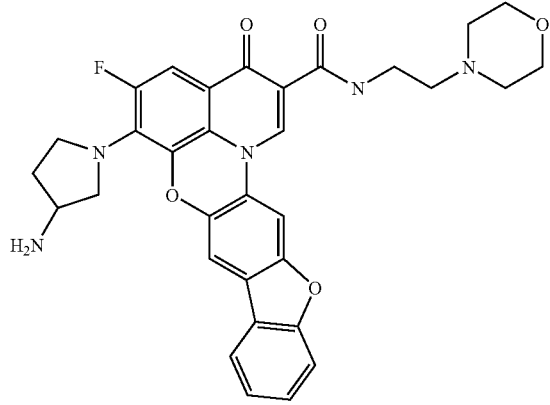 | 0.375 | 0.72 |
| 531 | 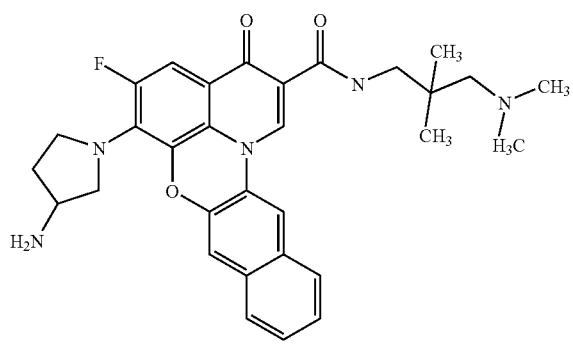 | 0.375 | 0.48 |
| 532 | 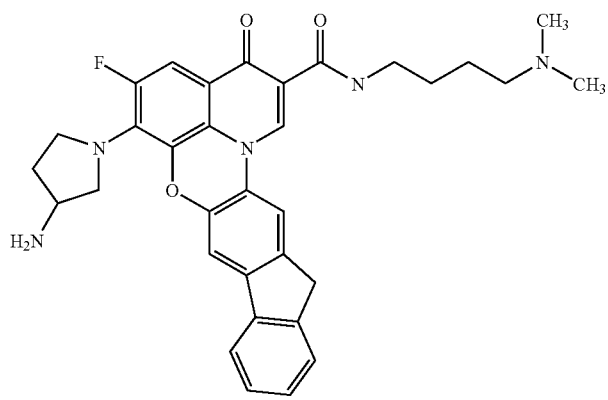 | 0.375 | 0.44 |

-continued
| | | | | |
|---|---|---|---|---|
| 533 | 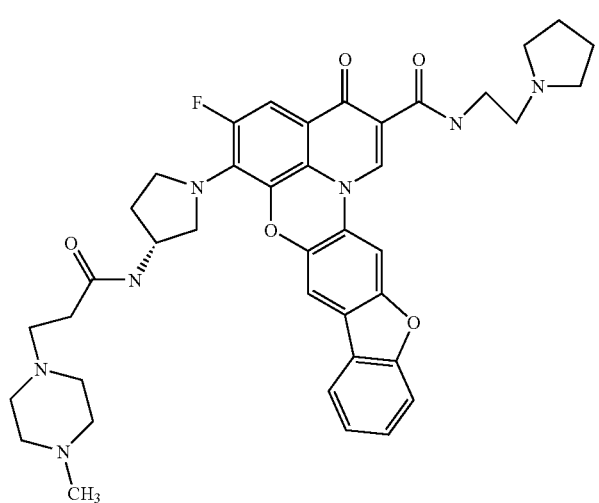 | Chiral | 0.375 | 0.40 |
| 534 | 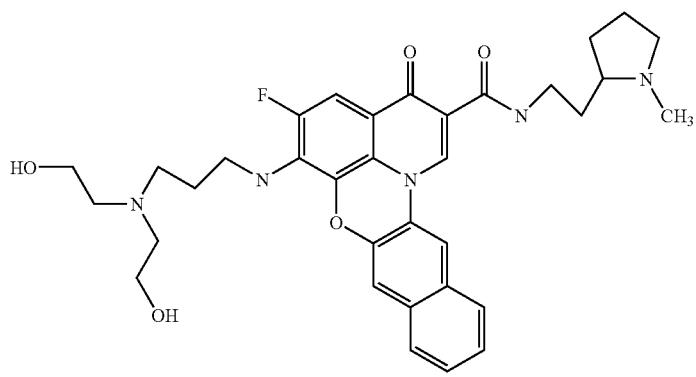 | | 0.375 | 0.40 |
| 535 | 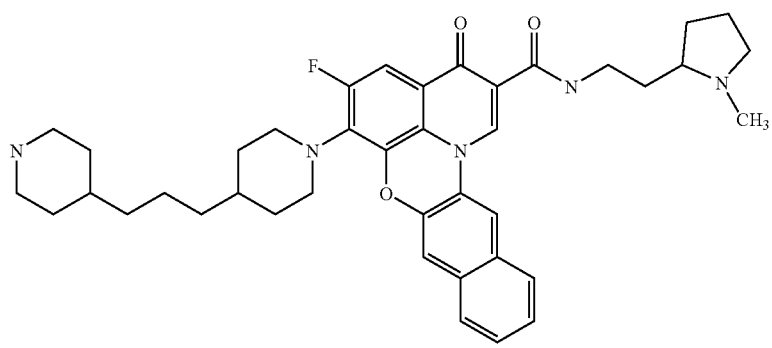 | | 0.375 | 0.31 |
| 536 | 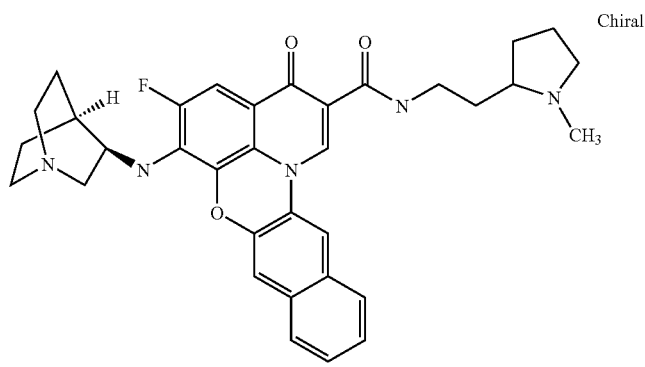 | Chiral | 0.375 | 0.31 |

-continued
| | | | |
|---|---|---|---|
| 537 | 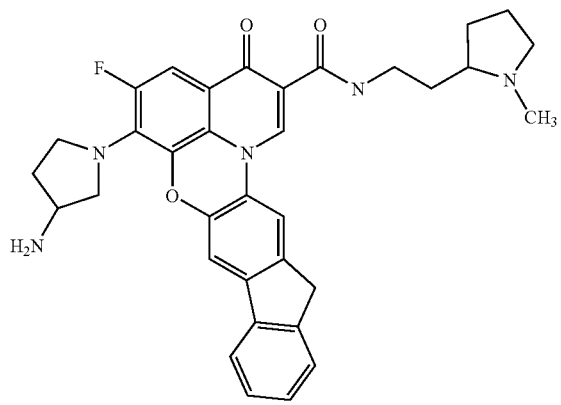 | 0.375 | 0.29 |
| 538 | 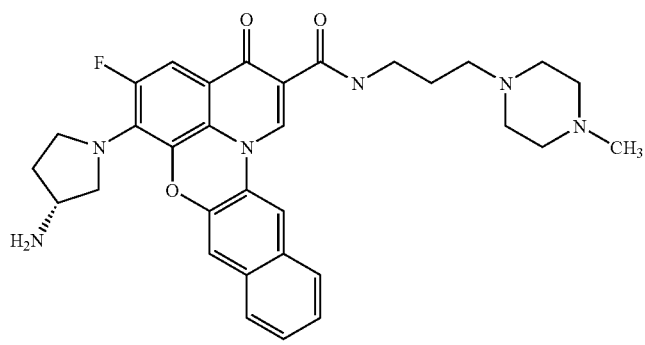 | 0.375 | 0.28 |
| 539 | 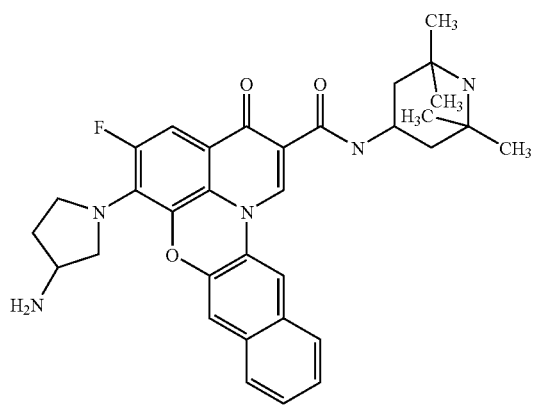 | 0.375 | 0.28 |
| 540 | 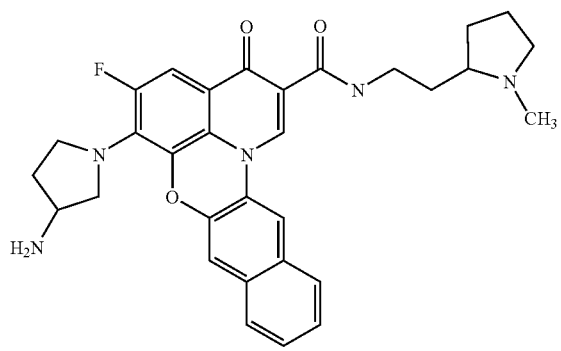 | 0.375 | 0.27 |

-continued
| | | | |
|---|---|---|---|
| 541 | 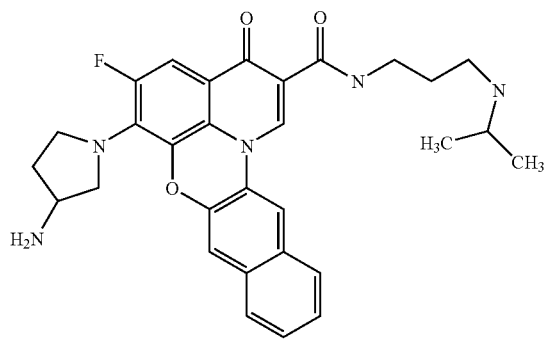 | 0.375 | 0.27 |
| 542 | 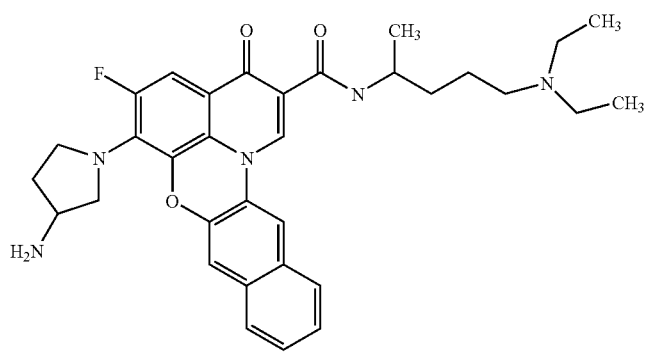 | 0.375 | 0.23 |
| 543 | 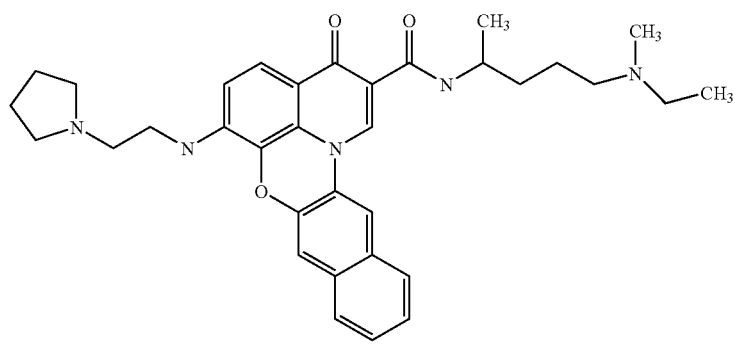 | 0.375 | 0.20 |
| 544 | 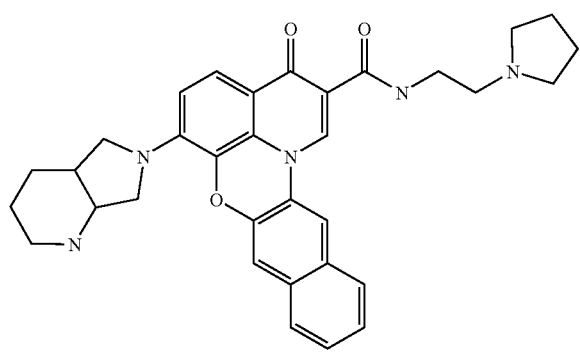 | 0.375 | 0.20 |

-continued
| | | | |
|---|---|---|---|
| 545 | 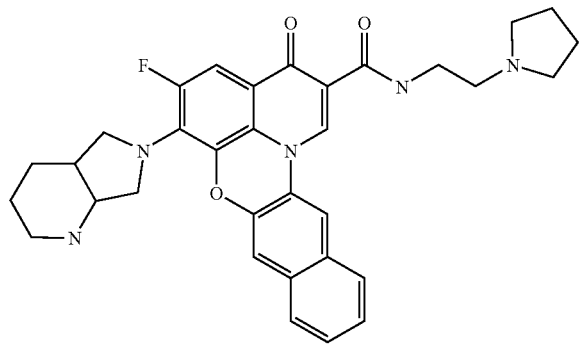 | 0.375 | 0.15 |
| 546 | 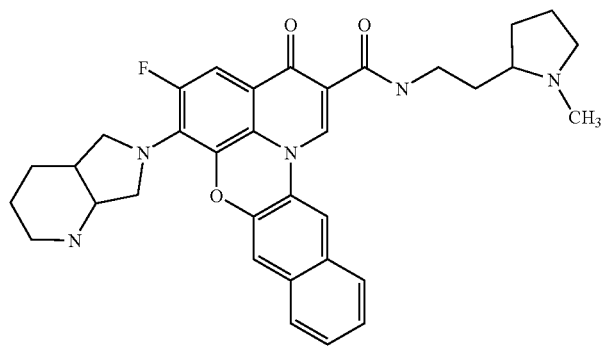 | 0.375 | 0.10 |
| 547 | 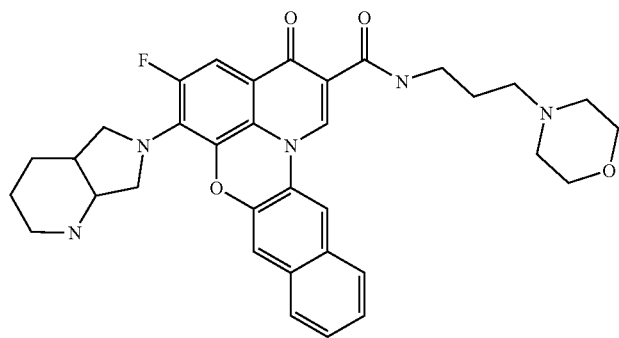 | 0.375 | 0.10 |
| 548 | 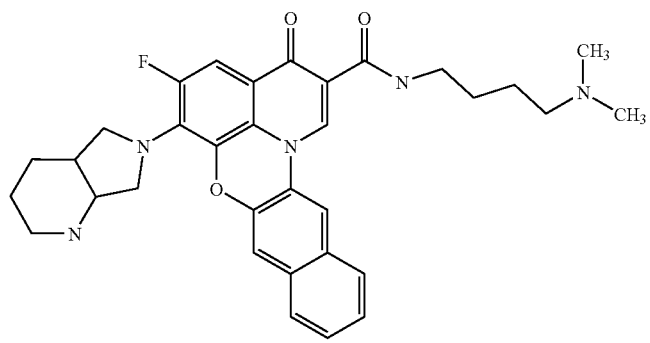 | 0.375 | 0.10 |

-continued
| 549 | 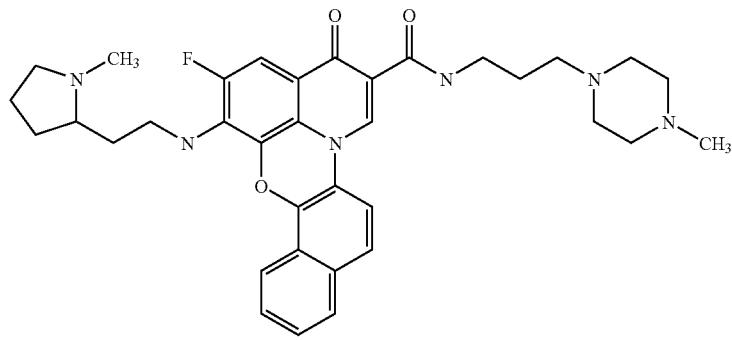 | 0.375 |
| 550 | 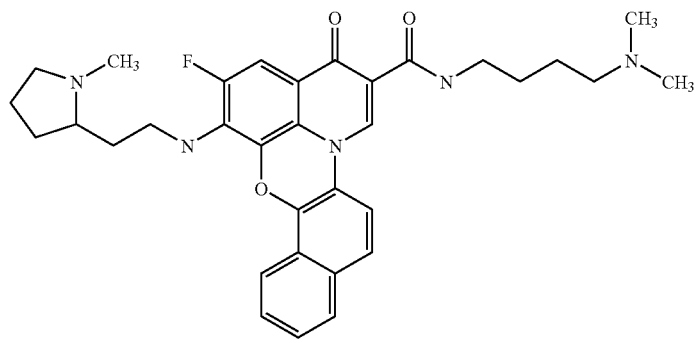 | 0.375 |
| 551 | 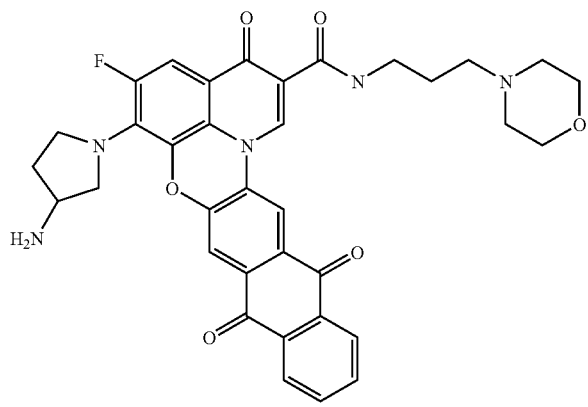 | 0.375 |
| 552 | 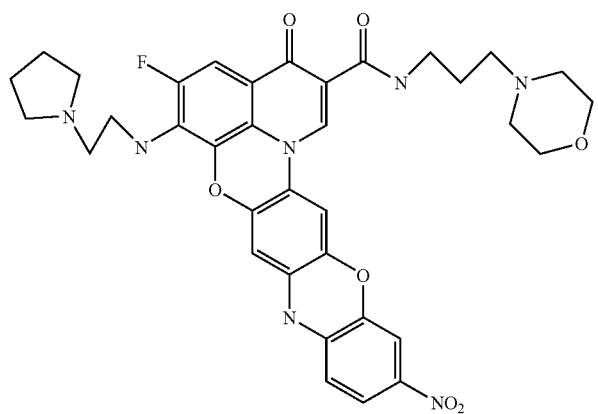 | 0.375 |

-continued
| | | |
|---|---|---|
| 553 | 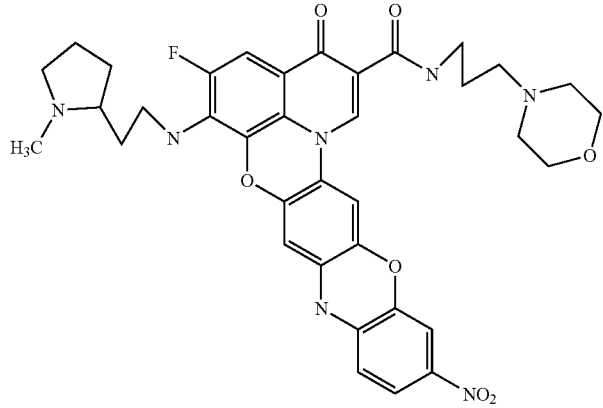 | 0.375 |
| 554 | 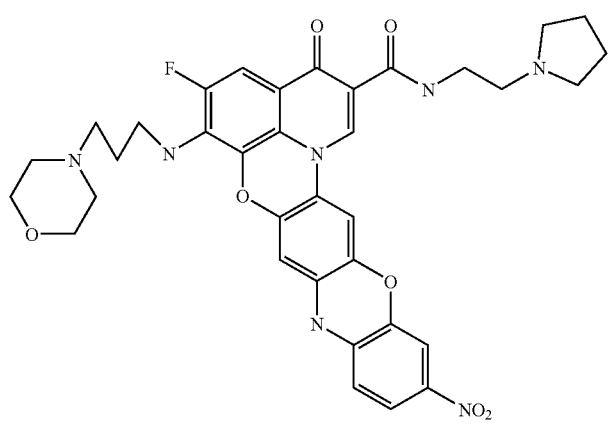 | 0.375 |
| 555 | 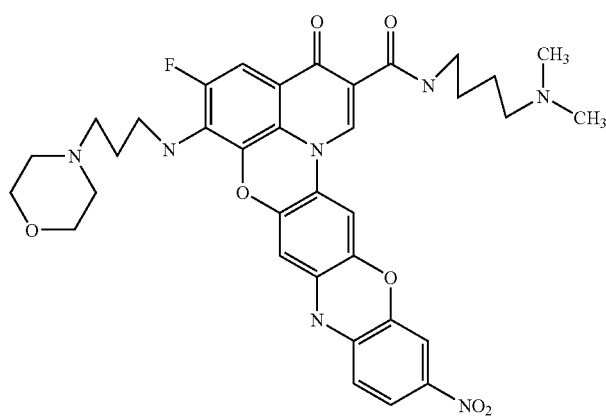 | 0.375 |

| | | |
|---|---|---|
| 556 | 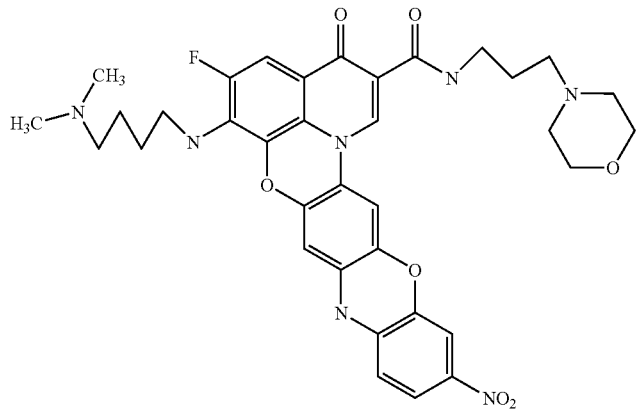 | 0.375 |
| 557 | 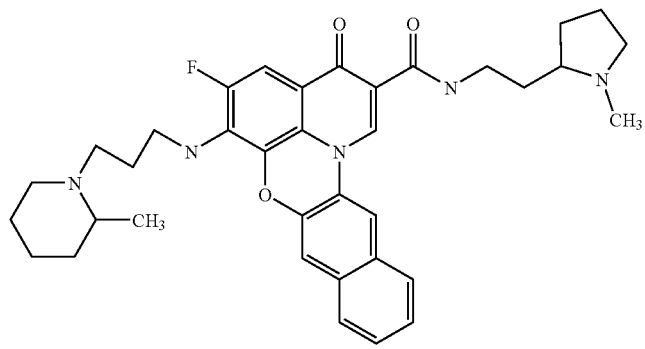 | 0.375 |
| 558 | 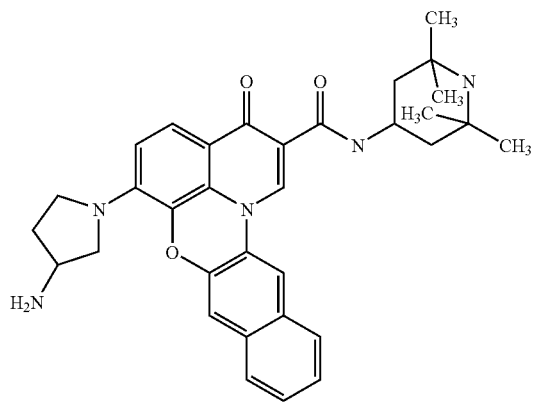 | 0.375 |
| 559 | 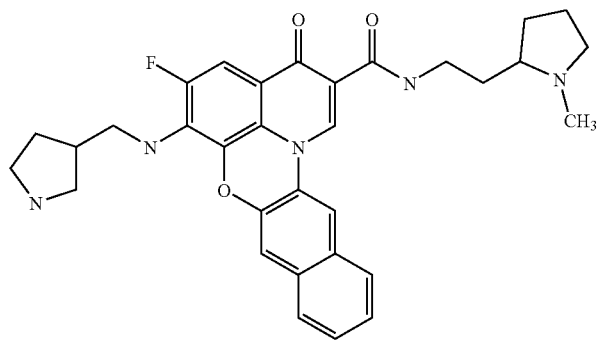 | 0.375 |

-continued
| | | 301 | | 302 | |
|---|---|---|---|---|---|
| 560 | 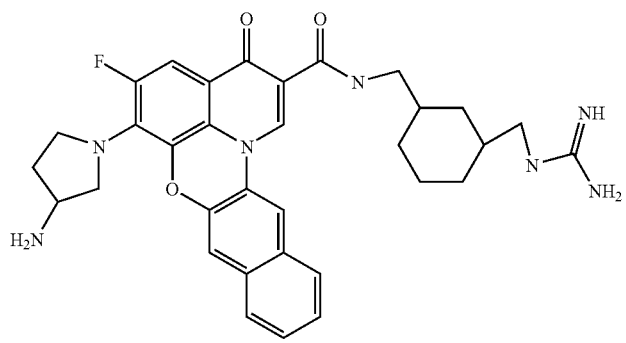 | | 0.37 | | |
| 561 | 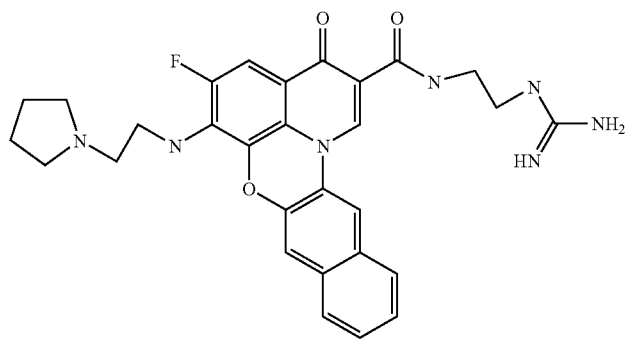 | | 0.34 | | |
| 562 | 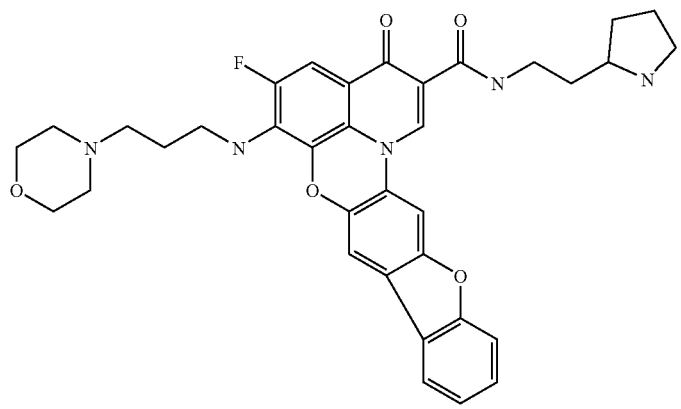 | | 0.32 | 0.85 | |
| 563 | 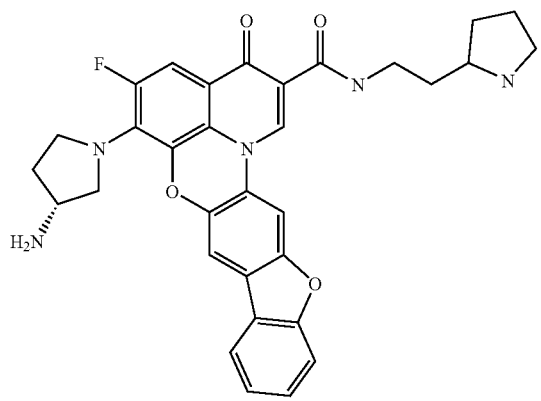 | | 0.25 | 0.31 | |

-continued
| | | | | |
|---|---|---|---|---|
| 564 | 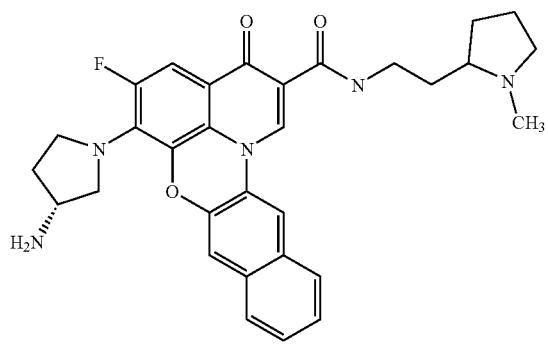 | Chiral | 0.25 | 0.29 |
| 565 | 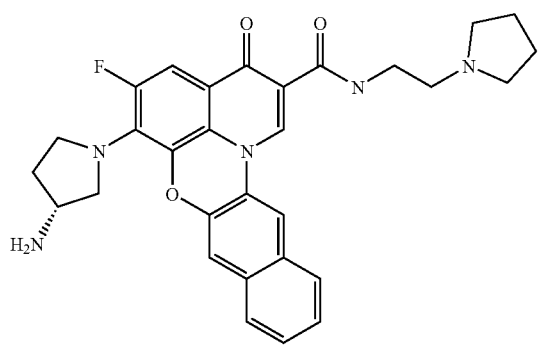 | | 0.25 | 0.20 |
| 566 | 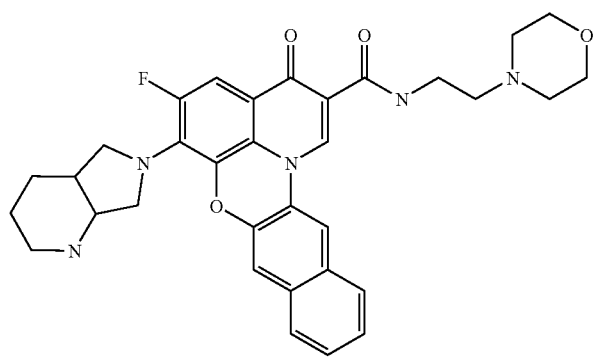 | | 0.25 | 0.03 |
| 567 | 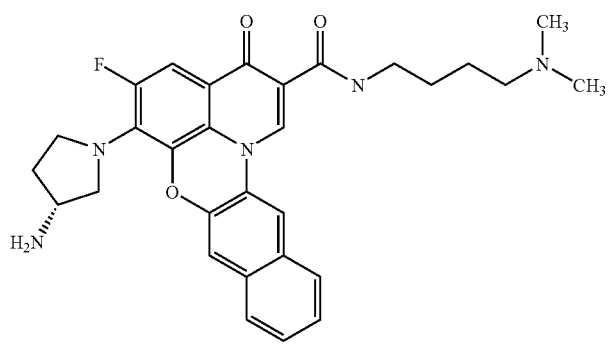 | | 0.25 | |

-continued
| | | | |
|---|---|---|---|
| 568 | 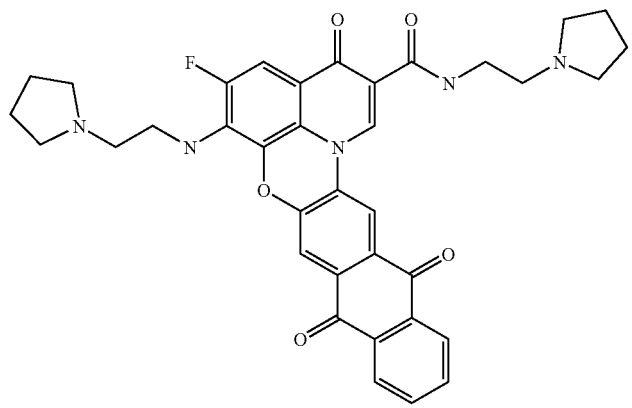 | 0.22 | 4.10 |
| 569 | 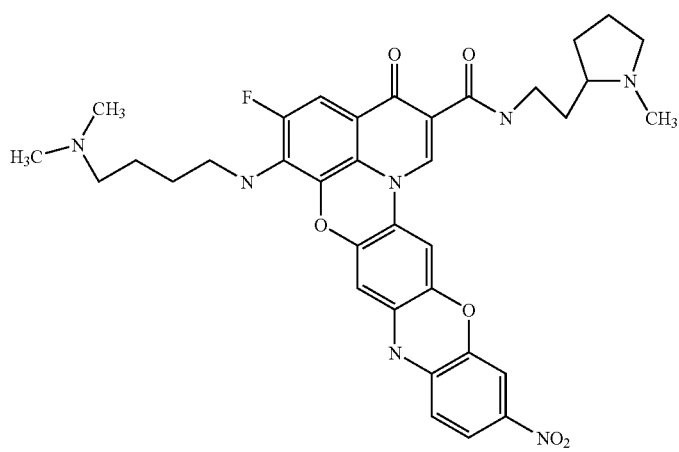 | 0.18 | 7.80 |
| 570 | 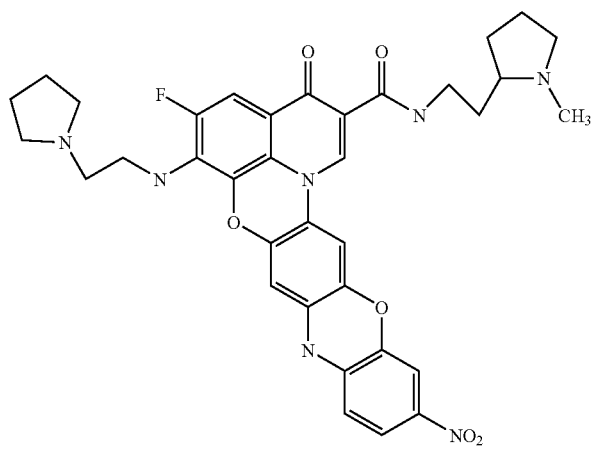 | 0.18 | 6.80 |

-continued
| | | | |
|---|---|---|---|
| 571 | 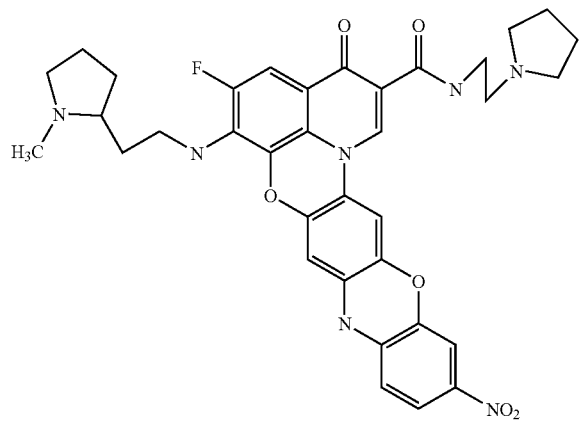 | | 0.18 4.80 |
| 572 | 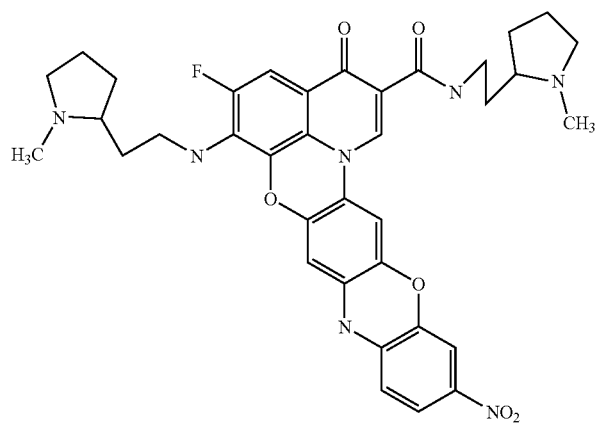 | | 0.18 4.80 |
| 573 | 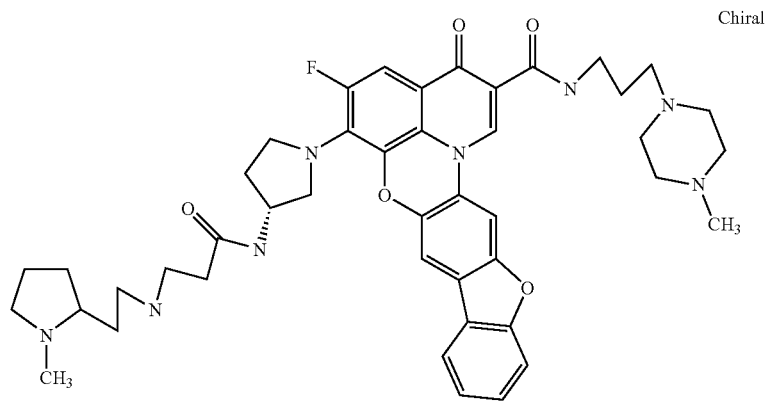 | Chiral | 0.18 4.50 |

-continued
| | | | |
|---|---|---|---|
| 574 | 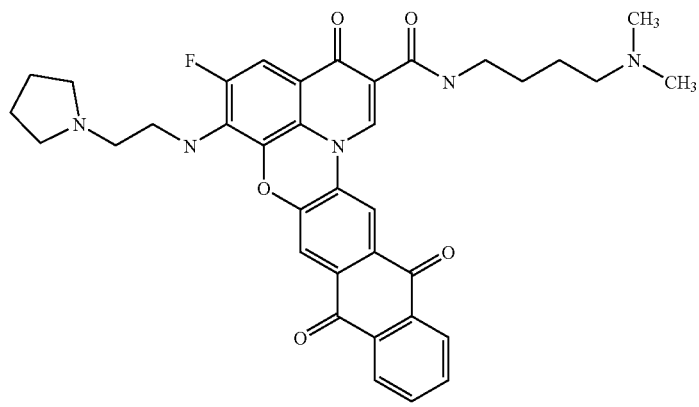 | 0.18 | 4.00 |
| 575 | 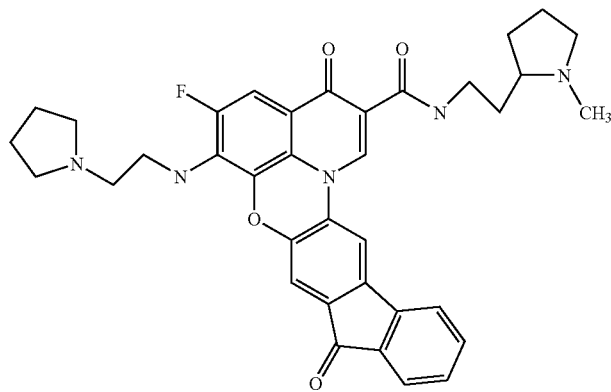 | 0.18 | 2.10 |
| 576 | 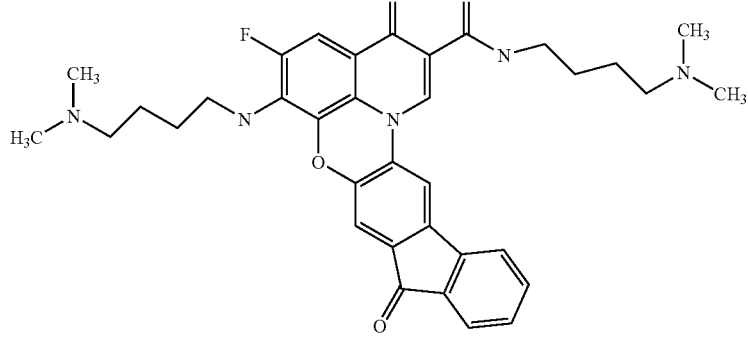 | 0.18 | 2.10 |
| 577 | 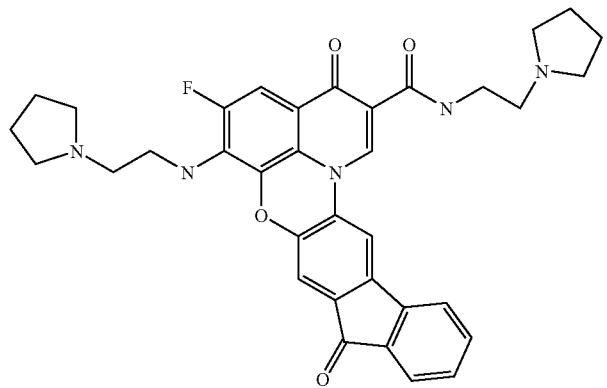 | 0.18 | 1.10 |

-continued
| | | | |
|---|---|---|---|
| 578 | 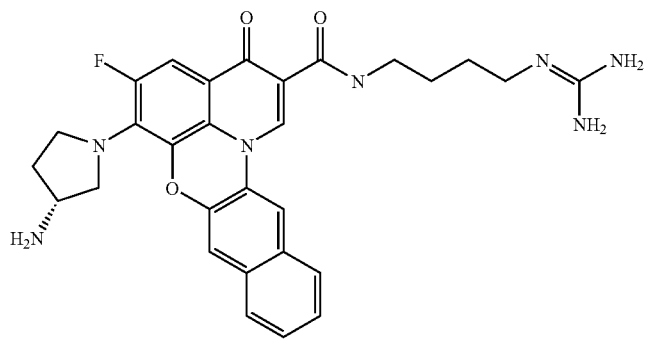 | 0.18 | 0.58 |
| 579 | 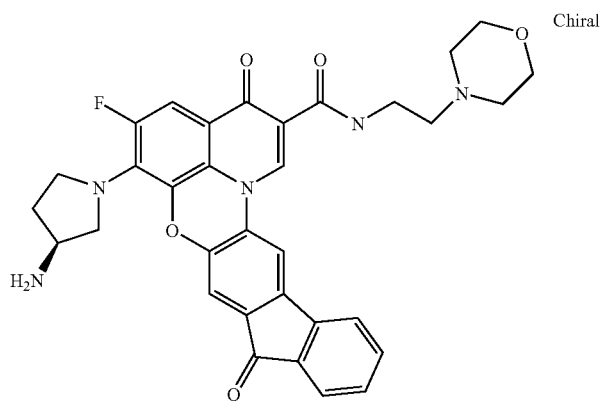 Chiral | 0.18 | 0.49 |
| 580 | 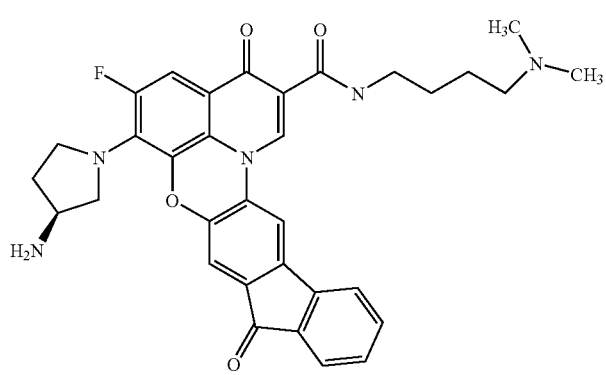 Chiral | 0.18 | 0.30 |
| 581 | 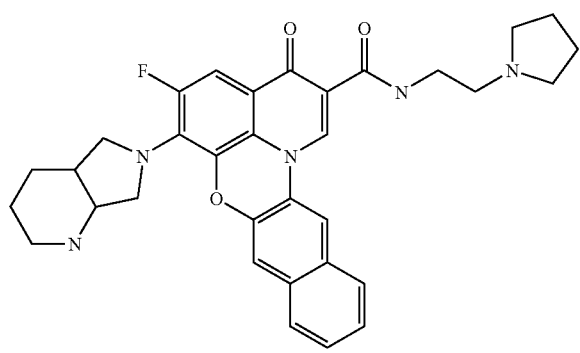 | 0.18 | 0.30 |

-continued
| | | | |
|---|---|---|---|
| 582 | 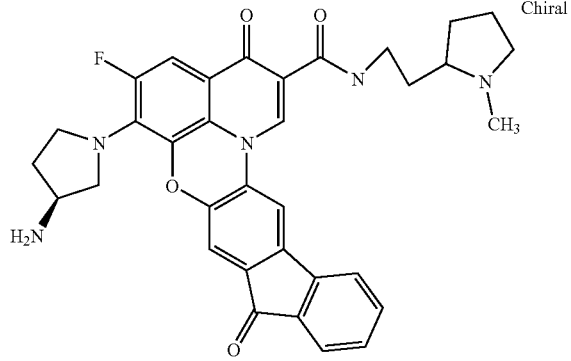 Chiral | 0.18 | 0.28 |
| 583 | 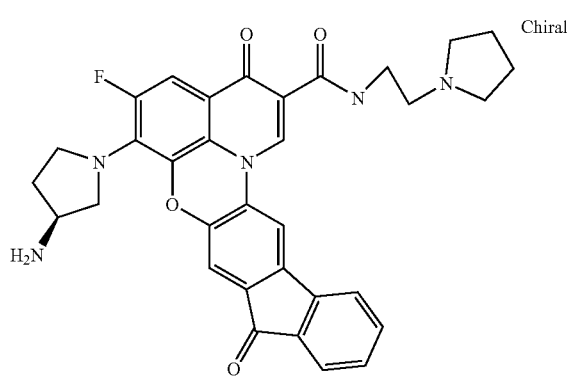 Chiral | 0.18 | 0.25 |
| 584 | 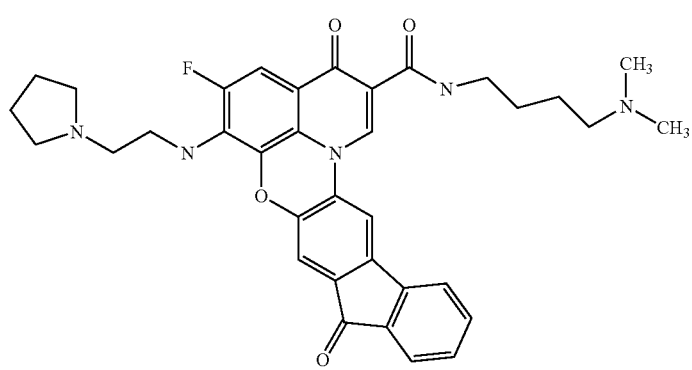 | 0.18 | 0.19 |
| 585 | 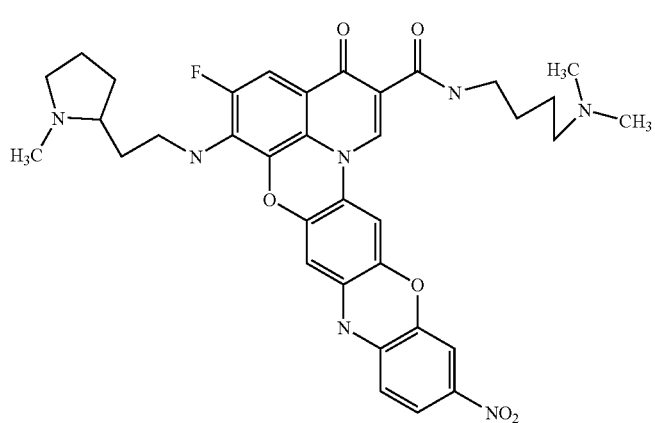 | 0.18 | |

-continued
| 586 | 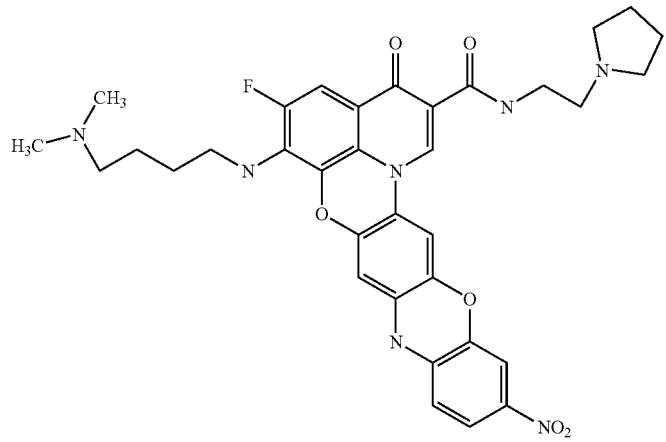 | 0.18 |
| 587 | 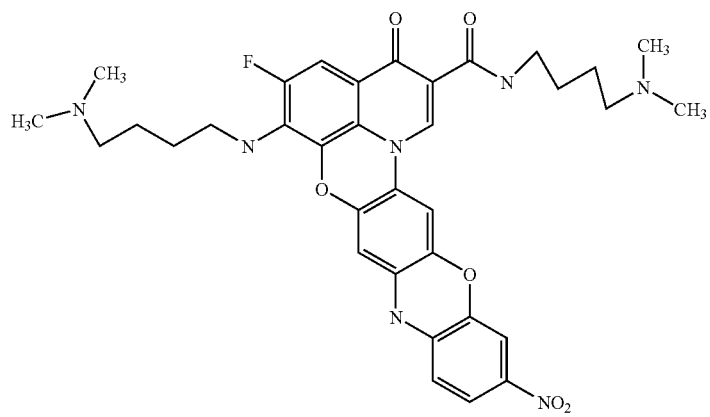 | 0.18 |
| 588 | 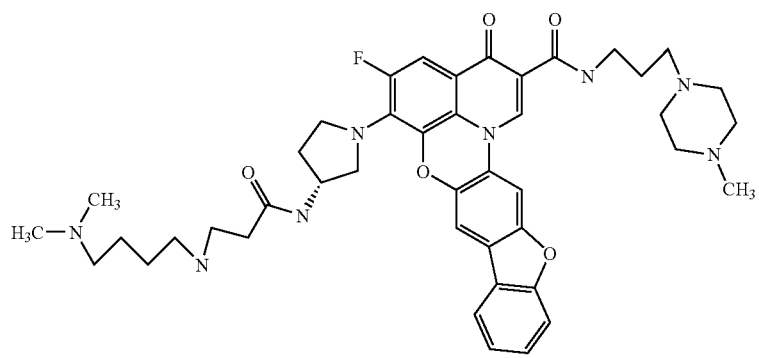 Chiral | 0.18 |
| 589 | 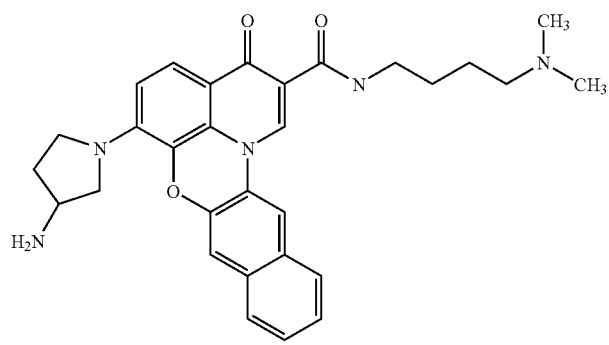 | 0.18 |

-continued
| | | | |
|---|---|---|---|
| 590 | 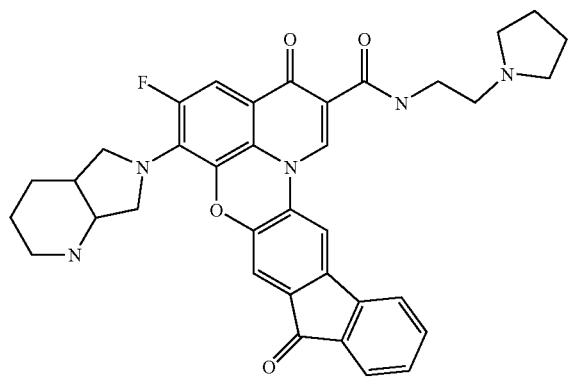 | 0.18 | |
| 591 | 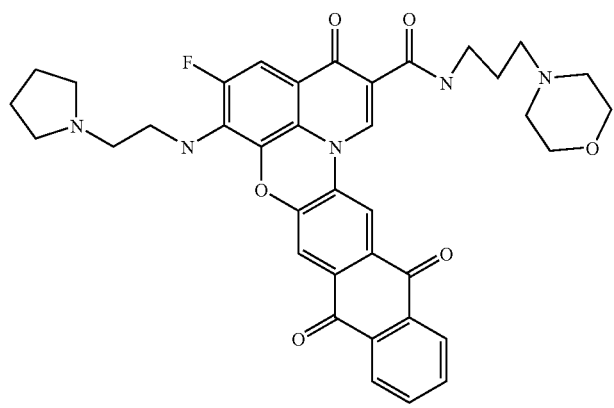 | 0.13 | 3.30 |
| 592 | 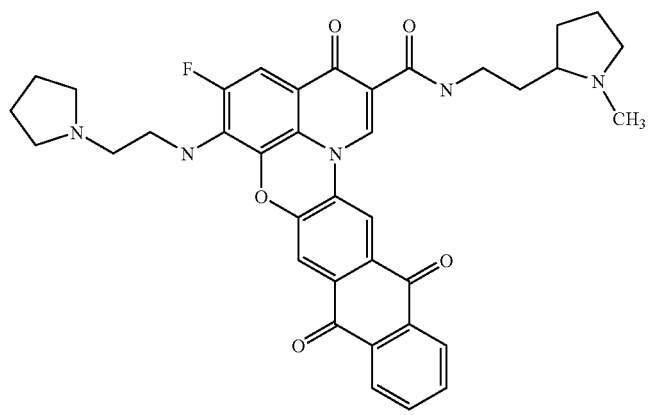 | 0.1 | 3.80 |
| 1467 | 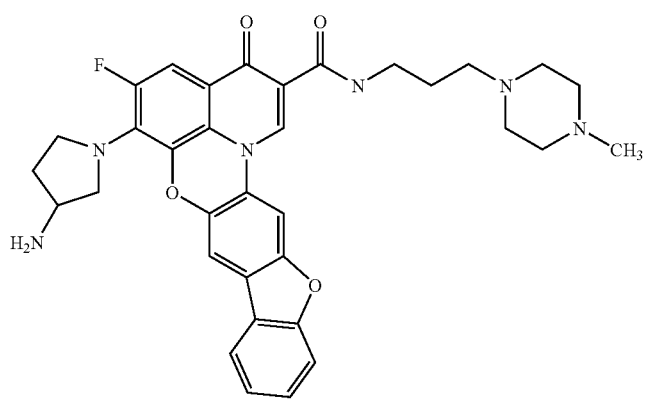 | 0.25 | 0.35 |

-continued
| | | | |
|---|---|---|---|
| 1468 | 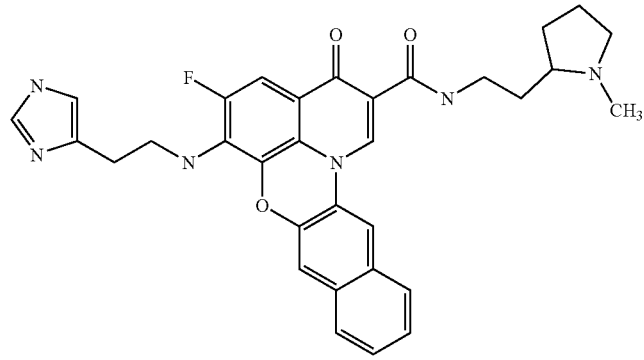 | 0.375 | 0.35 |
| 1469 | 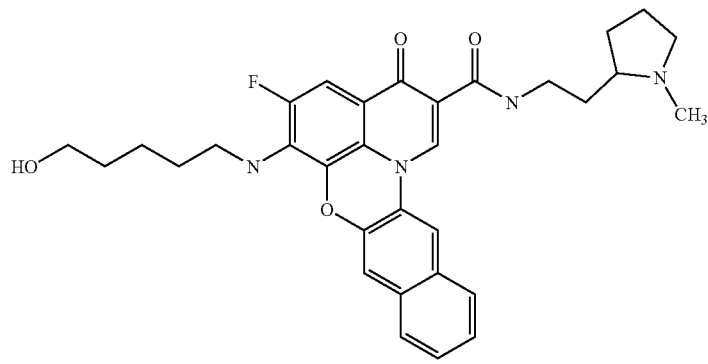 | 1.75 | |
| 1470 | 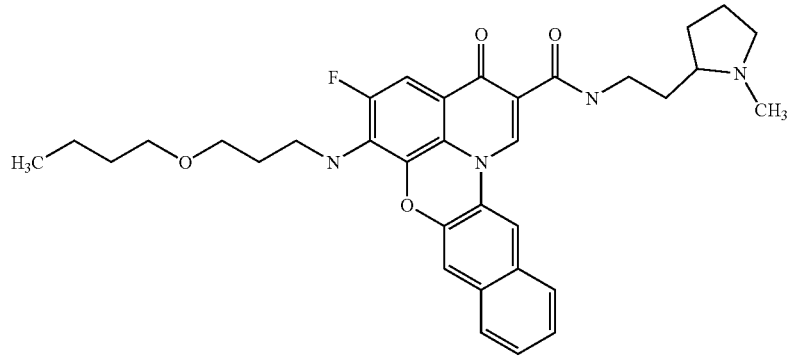 | 1.75 | |
| 1471 | 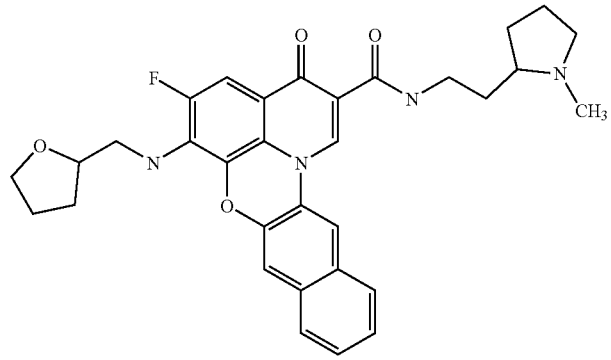 | 5 | |

Table 1C
1472
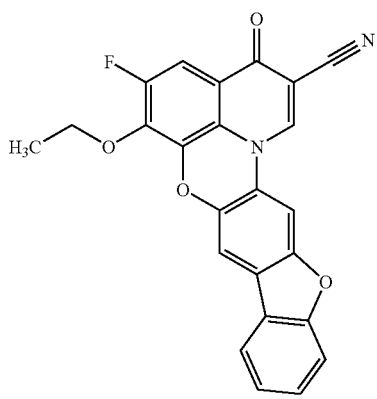
1473
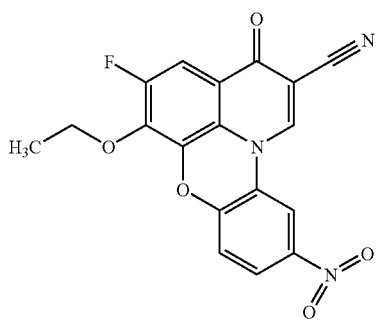
1474
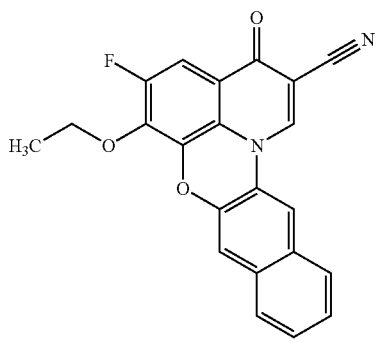
1475
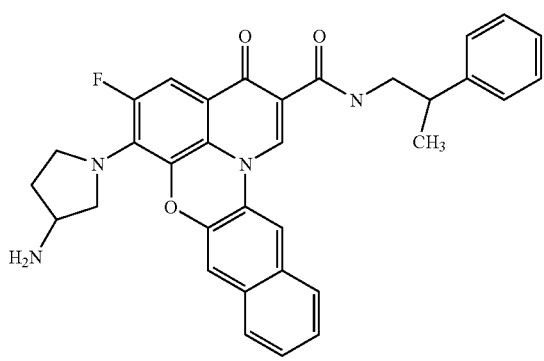

-continued
1476
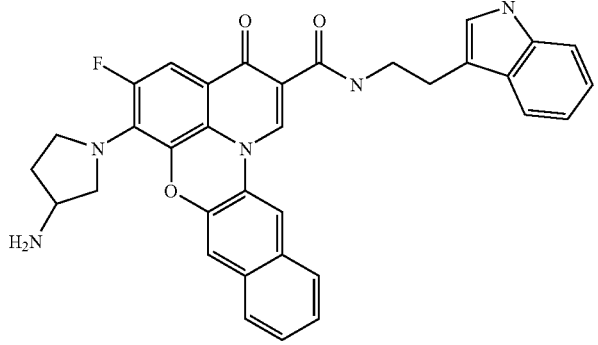
593
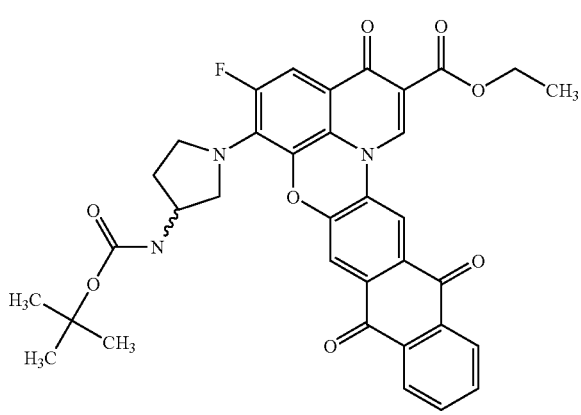
594
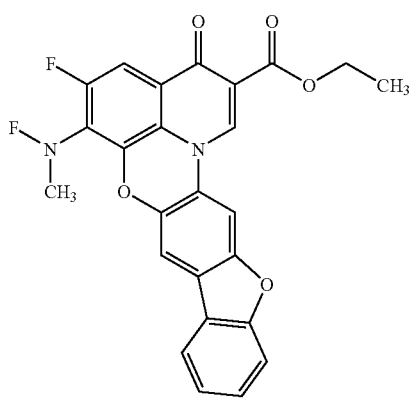
595
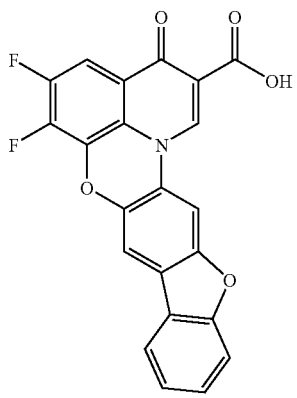

-continued
596
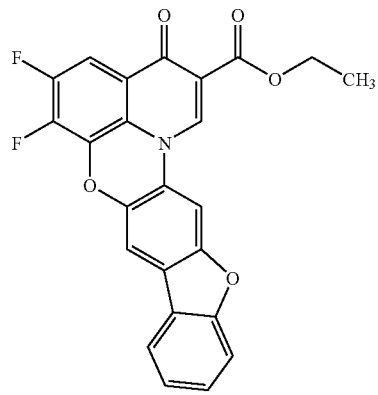
597
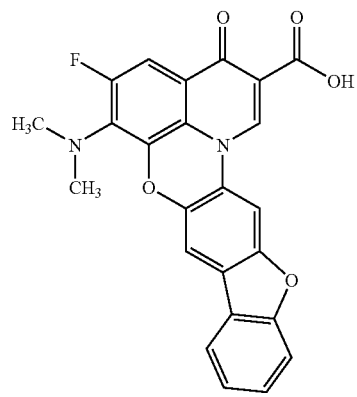
598
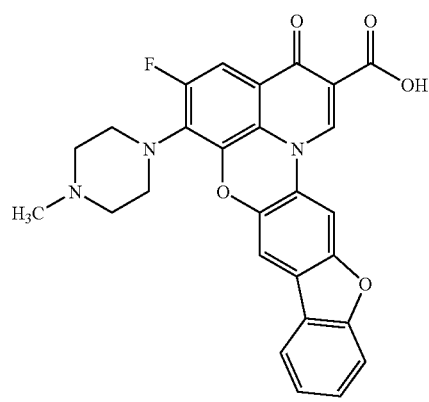
599
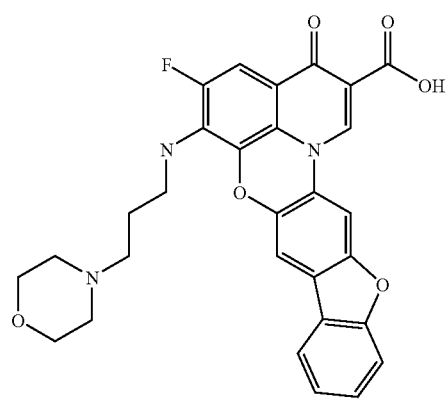

-continued
600
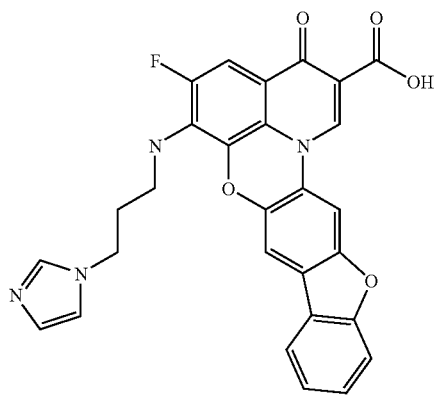
601
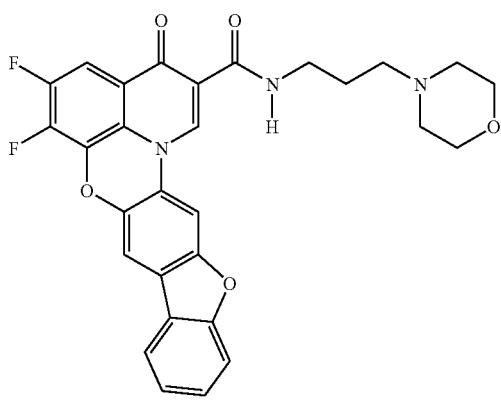
602
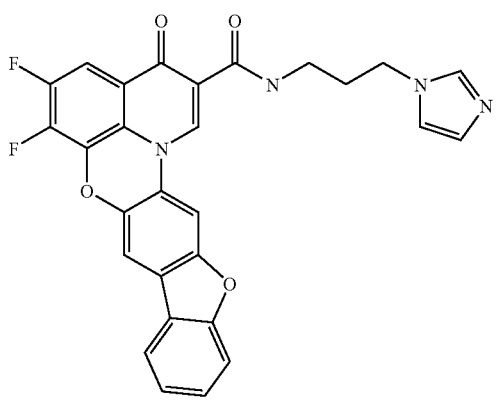
603
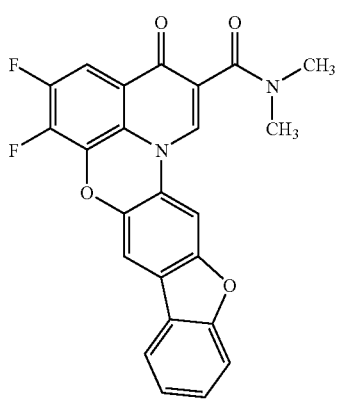

-continued
604
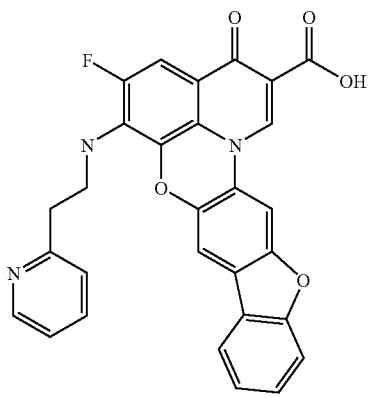
605
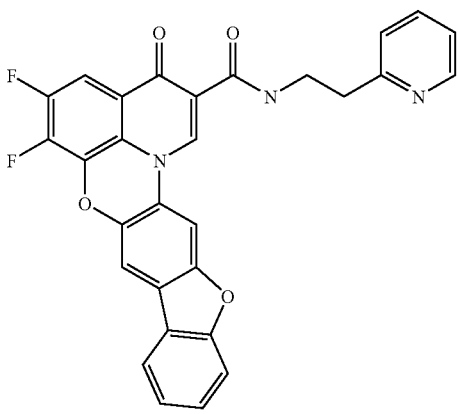
606
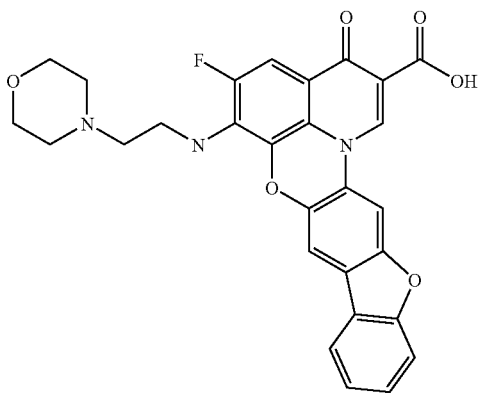
607
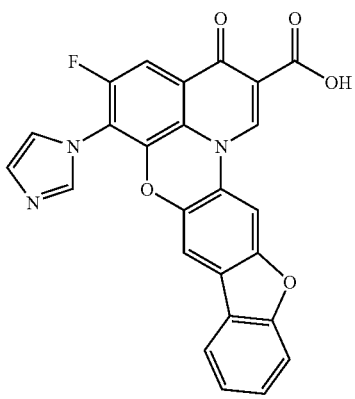

-continued
608
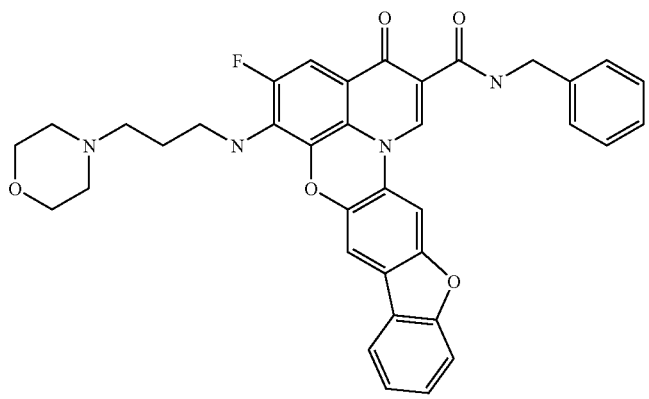
609
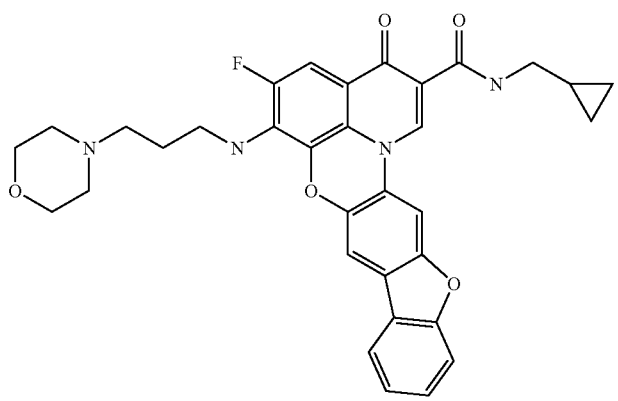
610
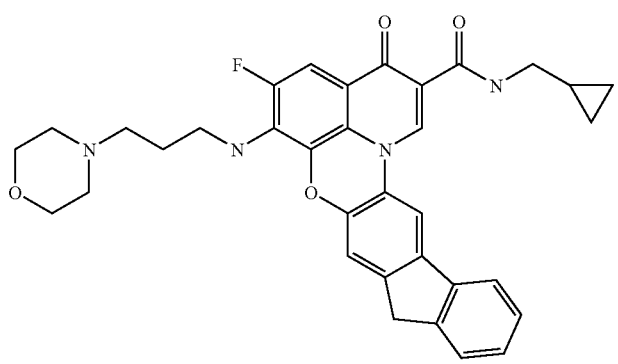
611
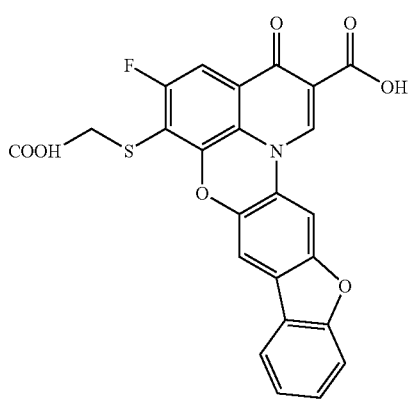

612
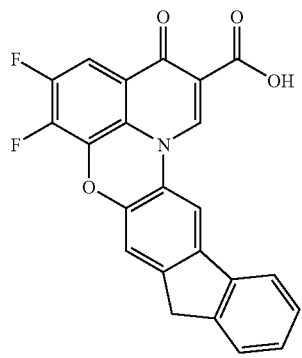
613
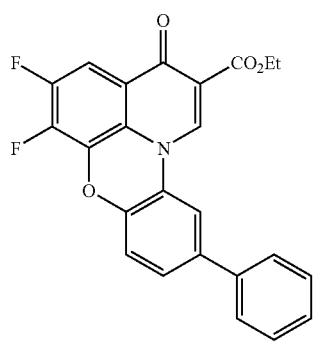
614
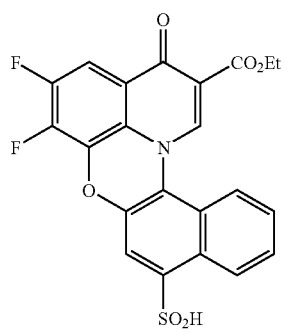
615
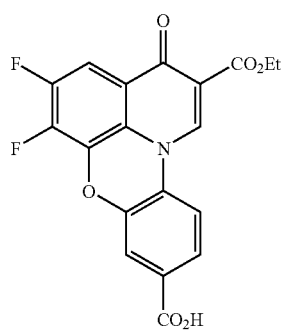

616
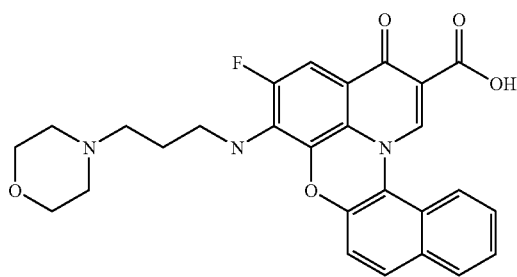
617
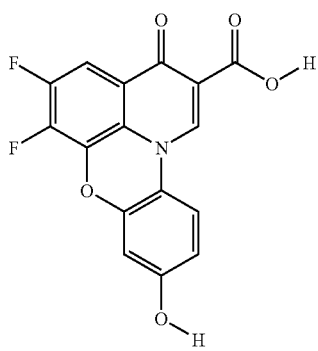
618
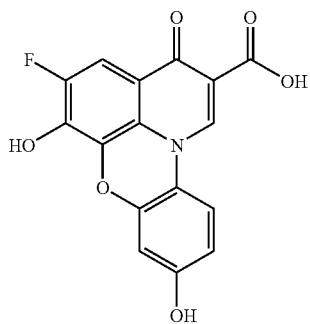
619
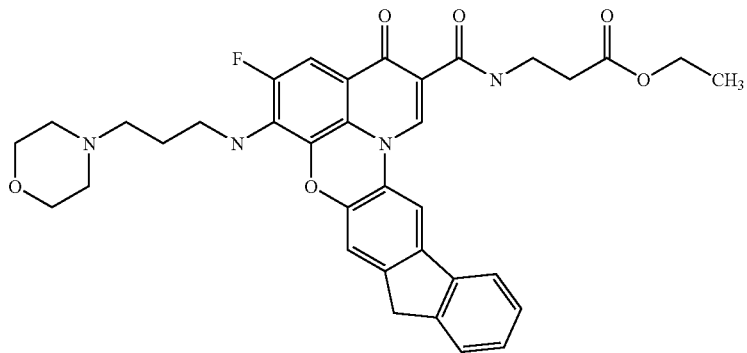

620
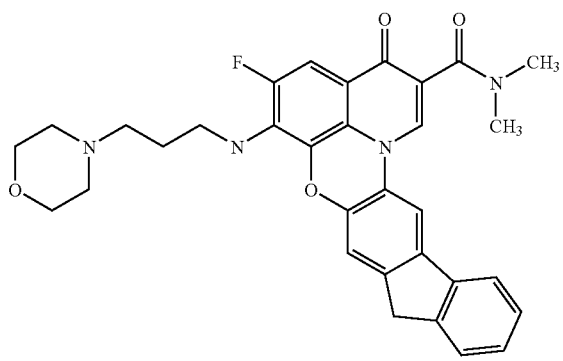
621
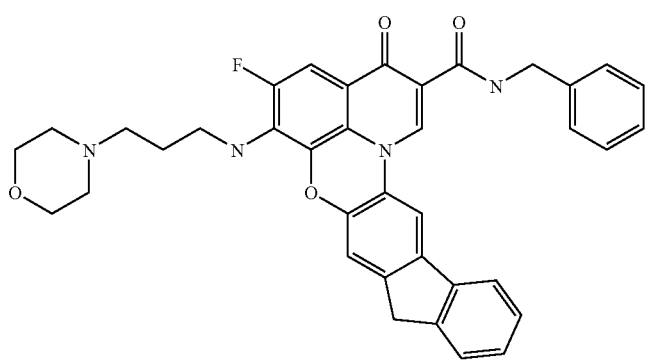
622
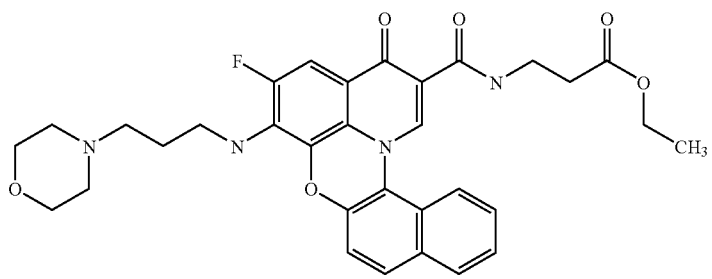
623
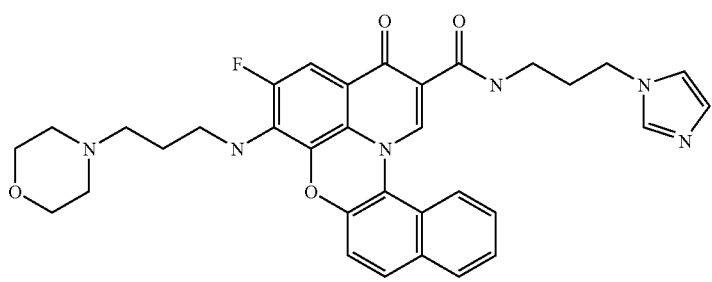
624
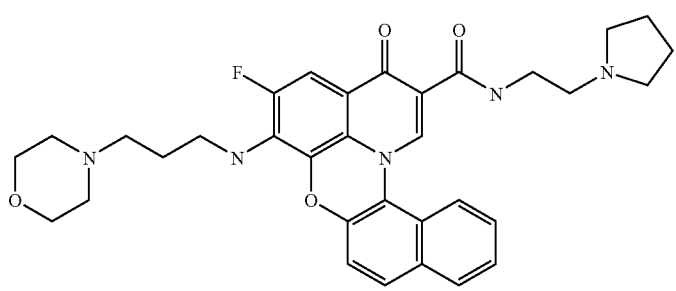

625 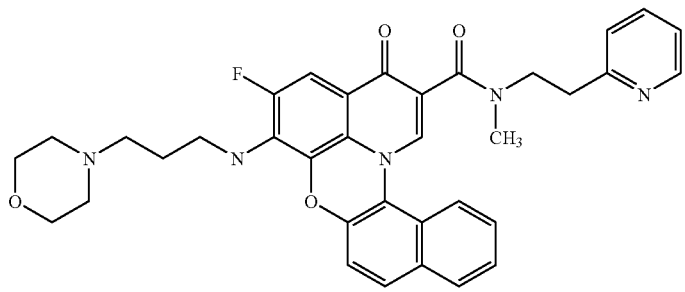
626 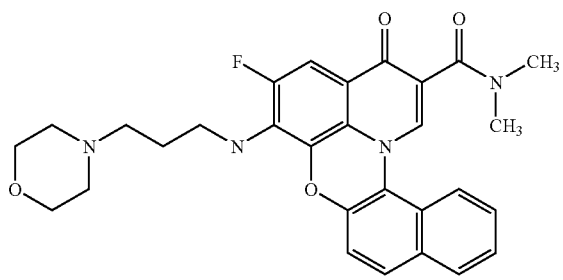
627 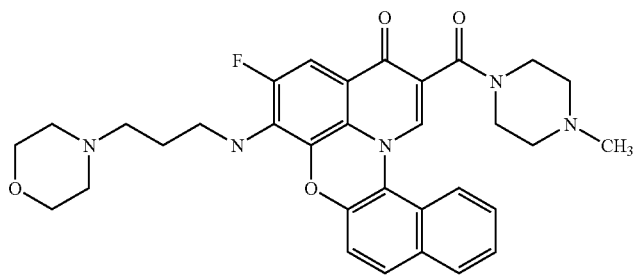
628 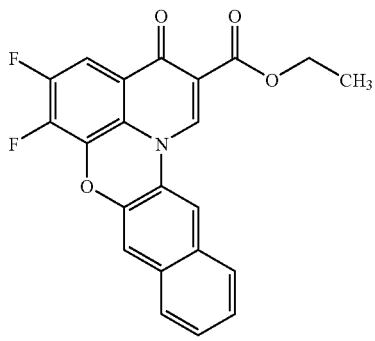
629 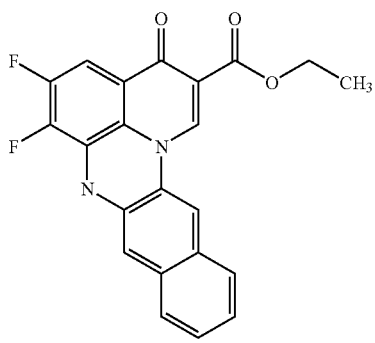

-continued
630
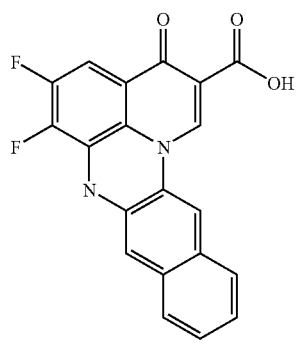
631
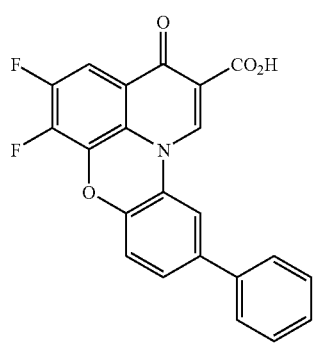
632
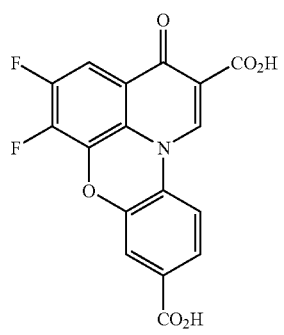
633
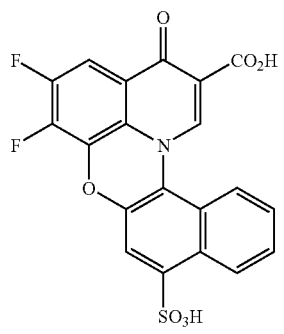

634
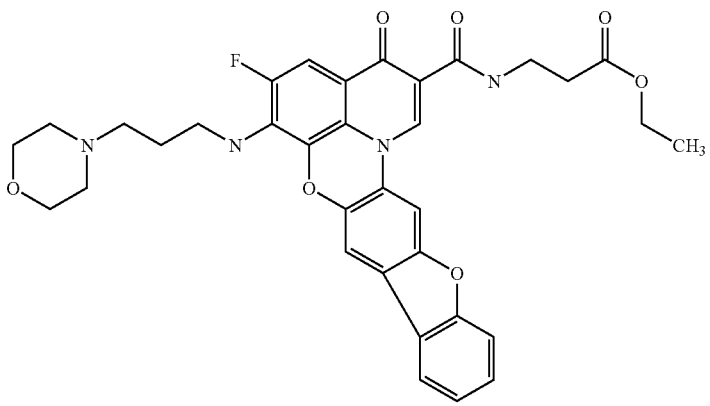
635
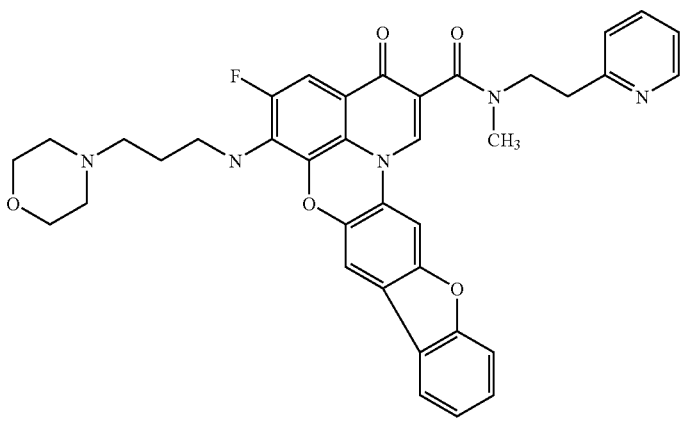
636
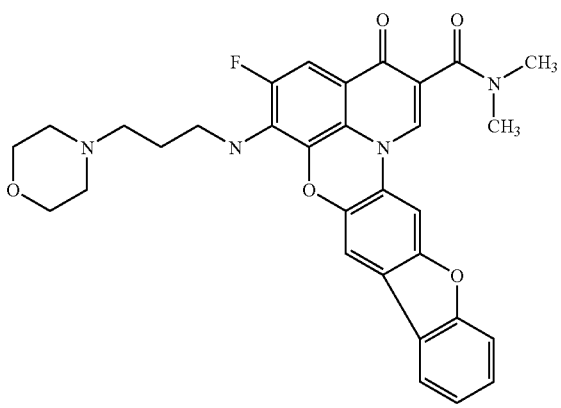

-continued
637
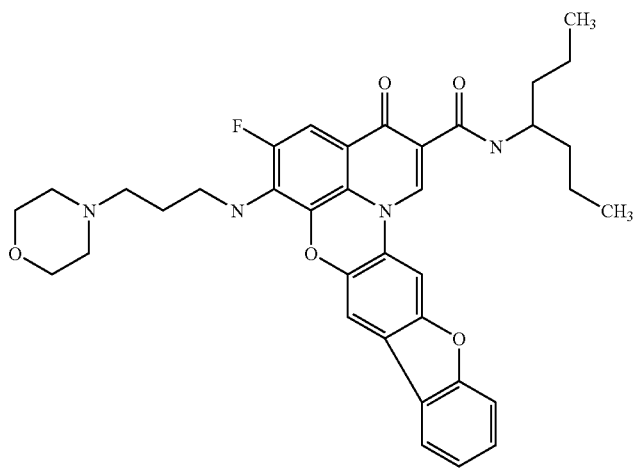
638
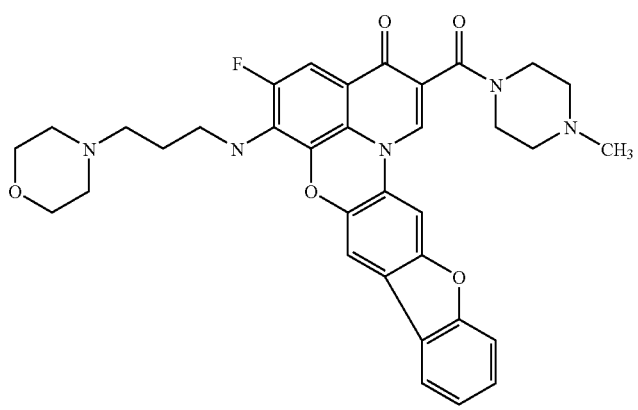
639
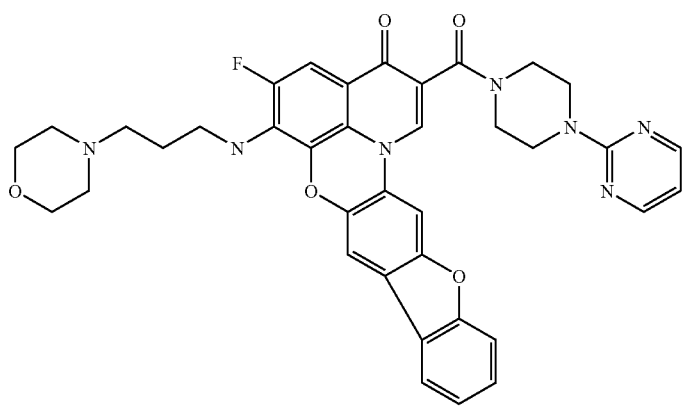

640 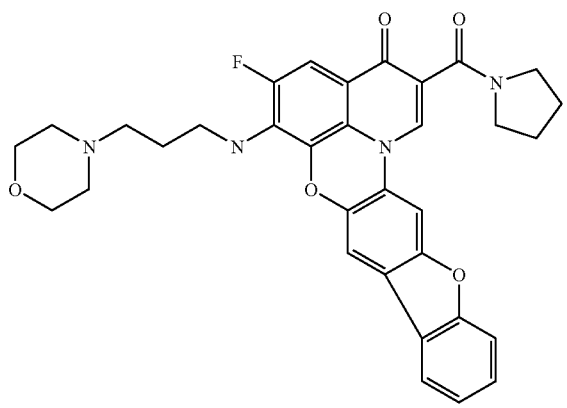
641 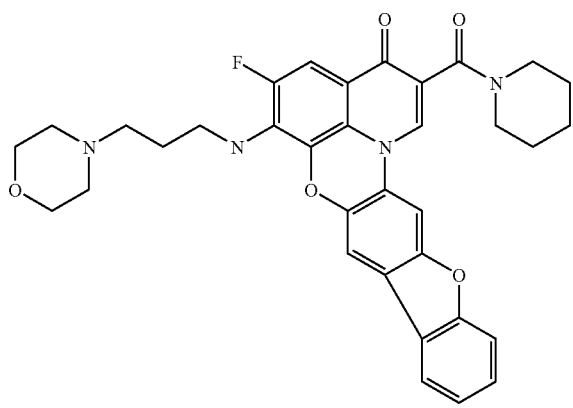
642 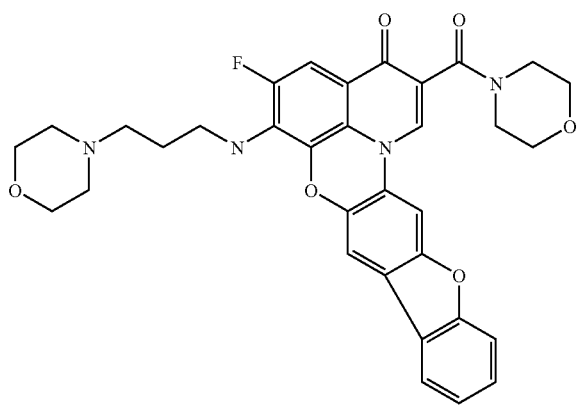
643 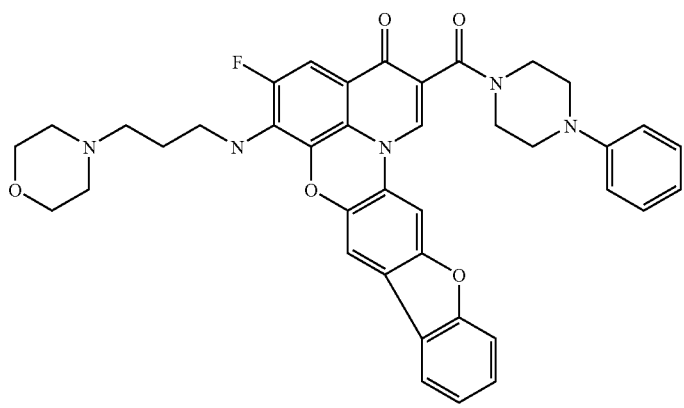

644
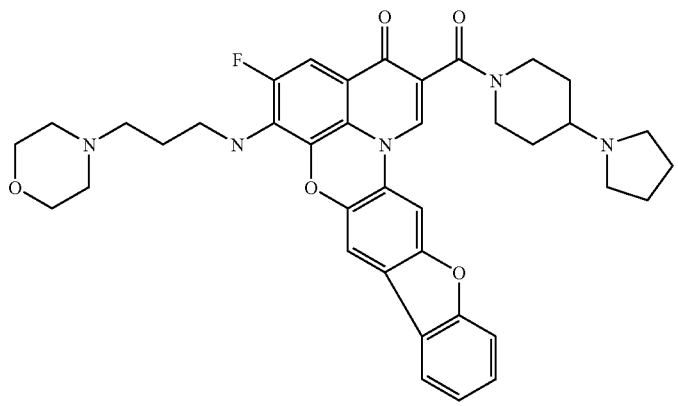
645
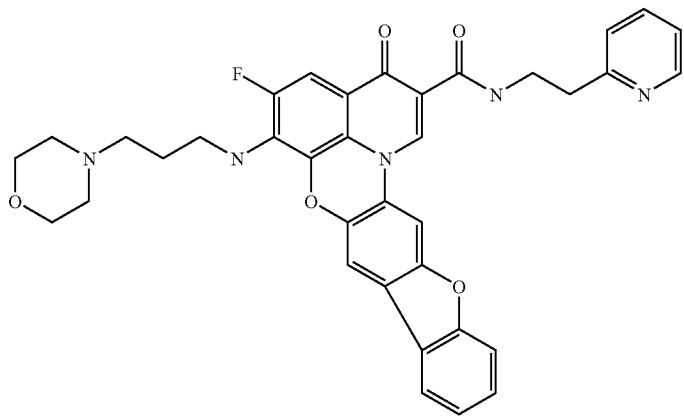
646
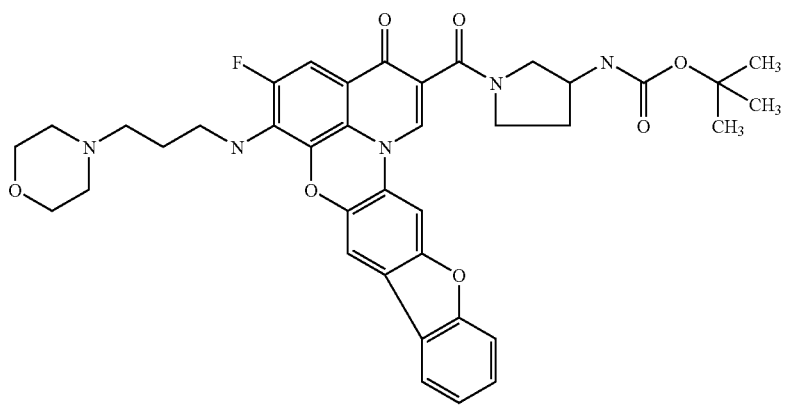
647
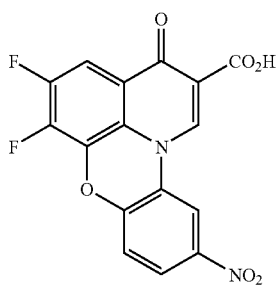

-continued
648
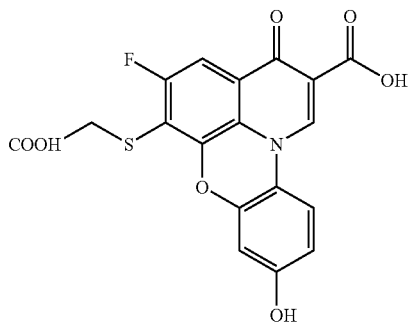
649
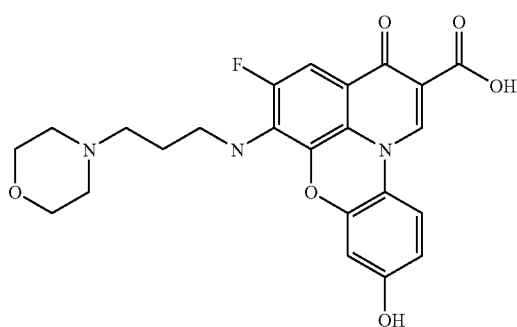
650
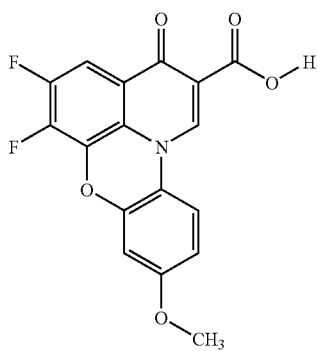
651
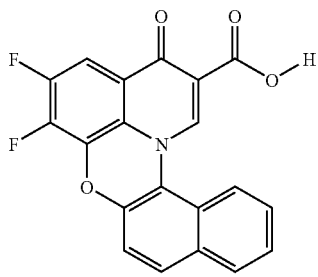
652
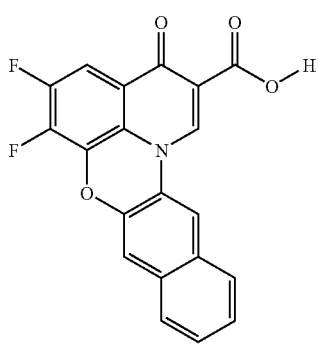

653 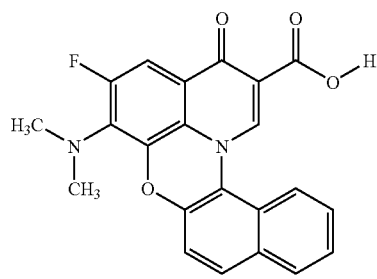
654 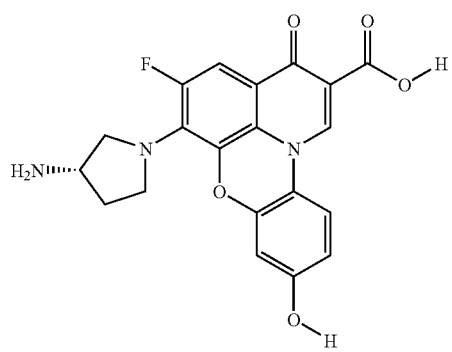
655 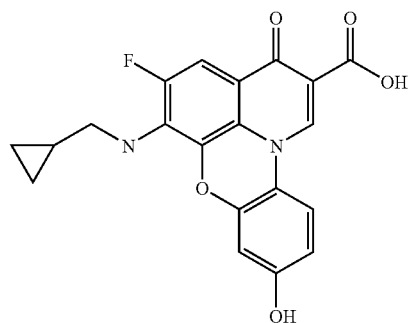
656 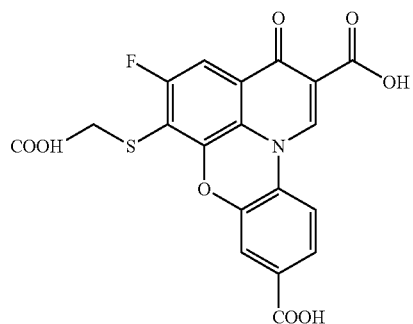

-continued
657
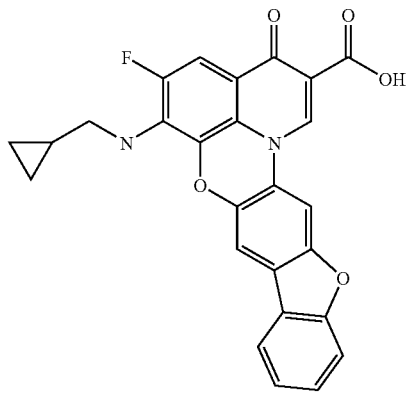
658
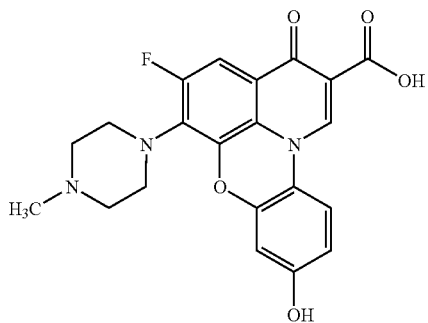
659
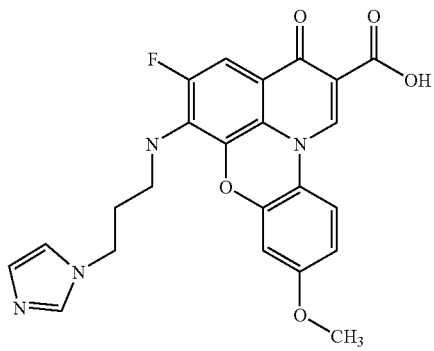
660
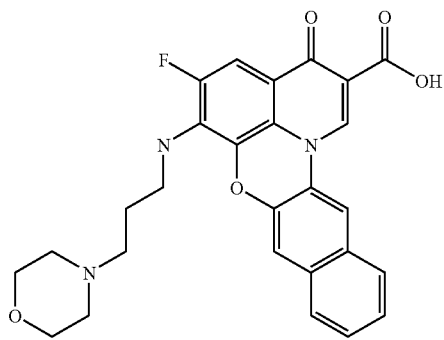

-continued
661
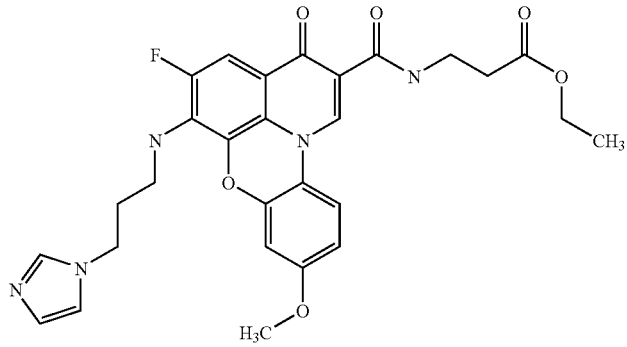
662
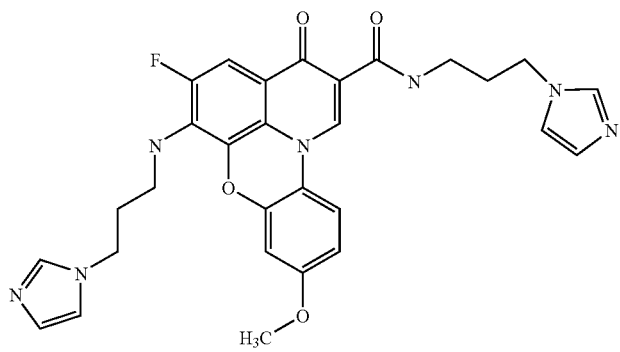
663
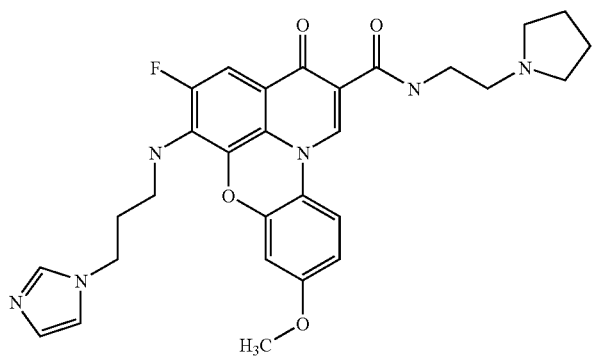
664
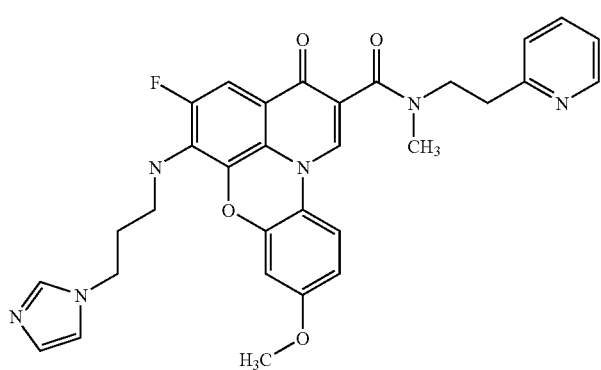

665 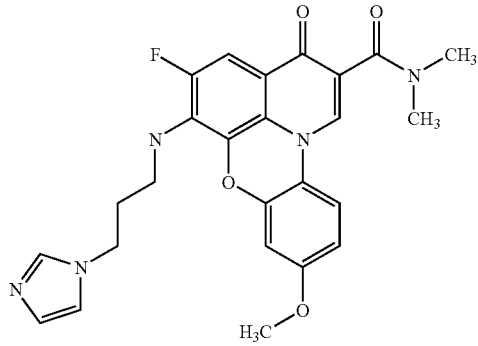
666 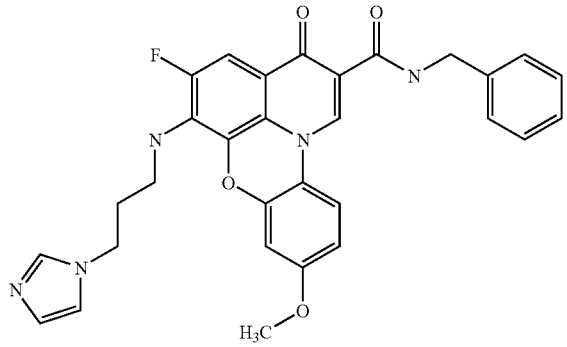
667 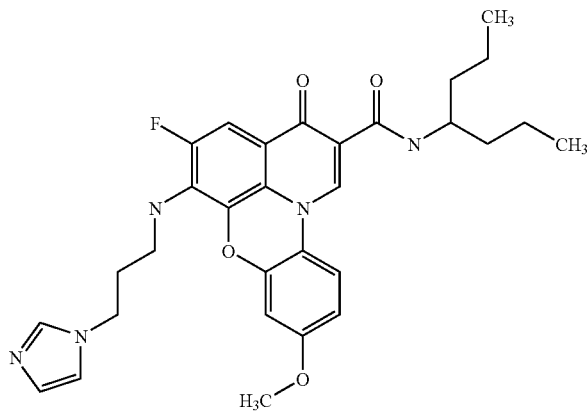
668 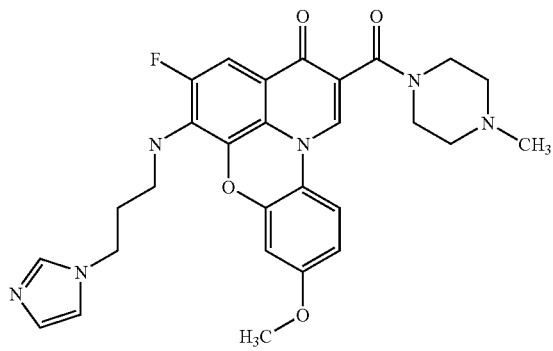

-continued
669 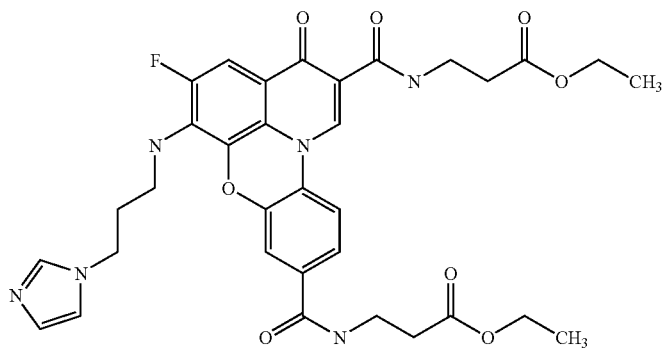
670 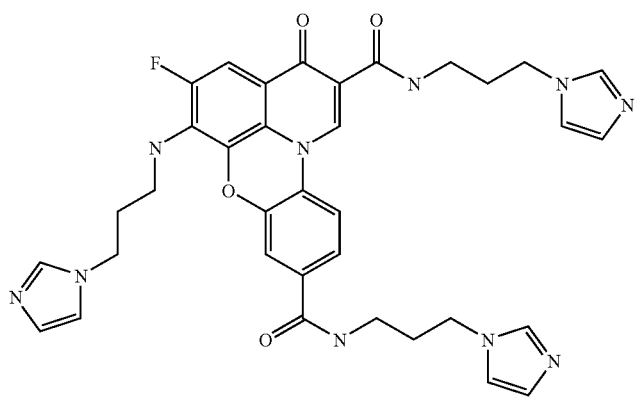
671 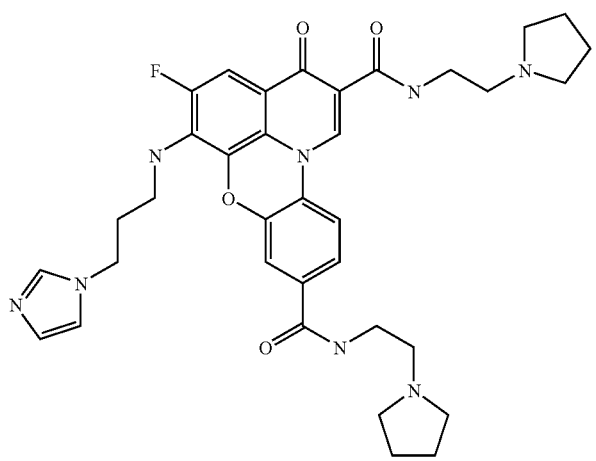
672 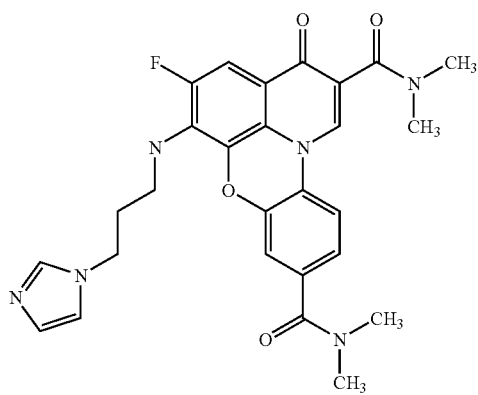

673 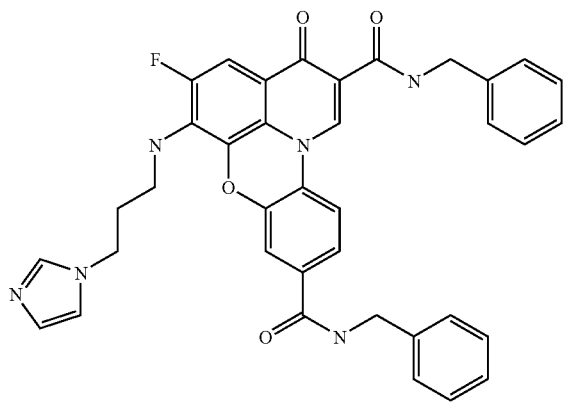
674 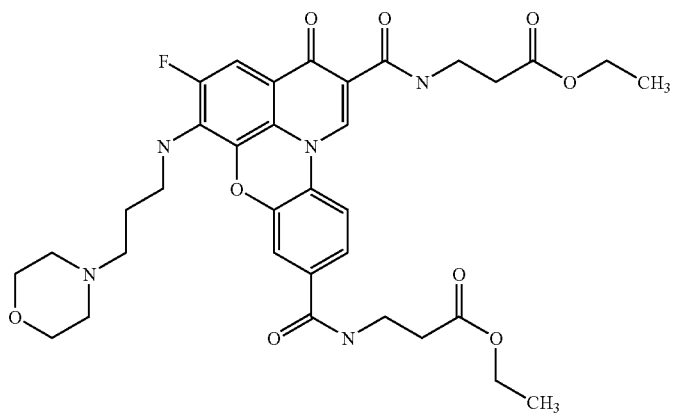
675 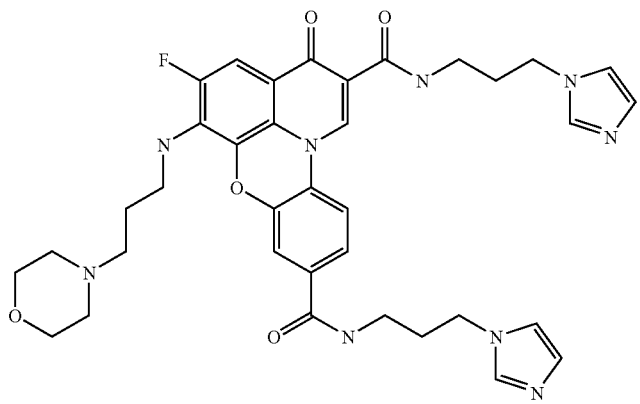
676 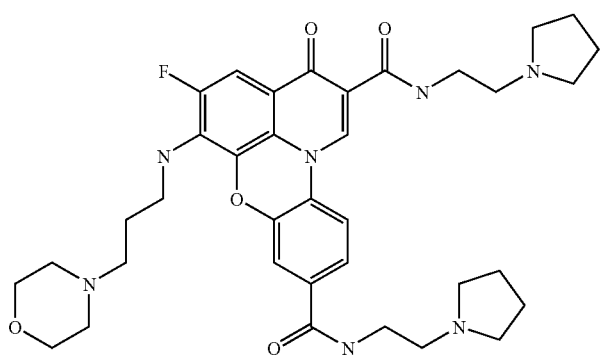

-continued
677
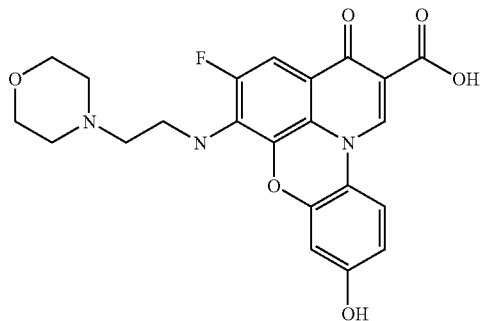
678
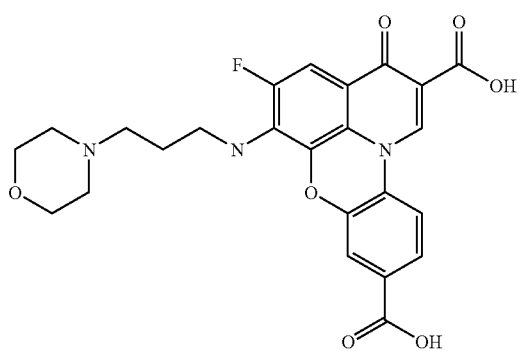
679
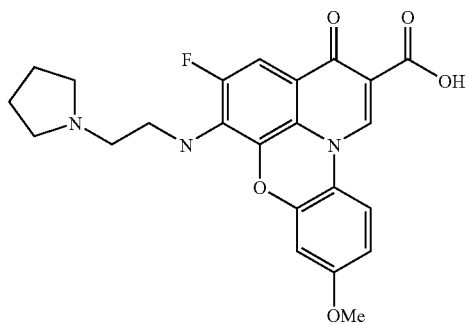
680
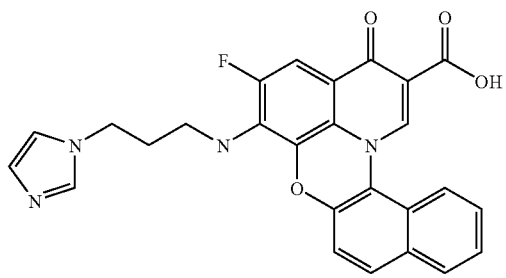
681
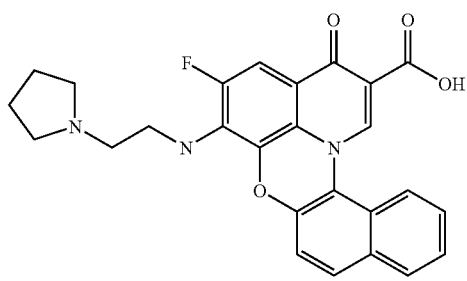

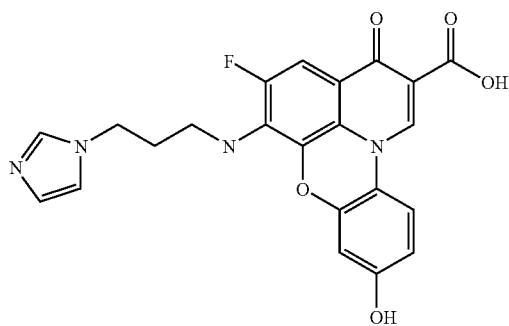
682
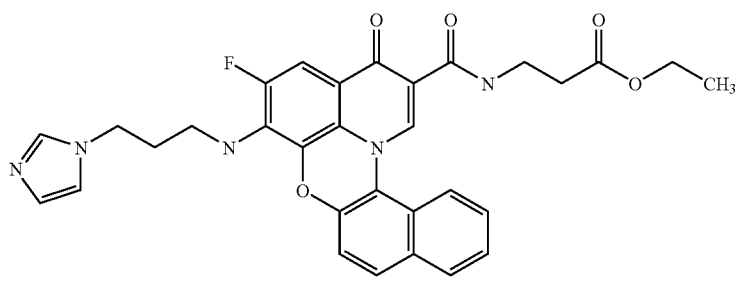
683
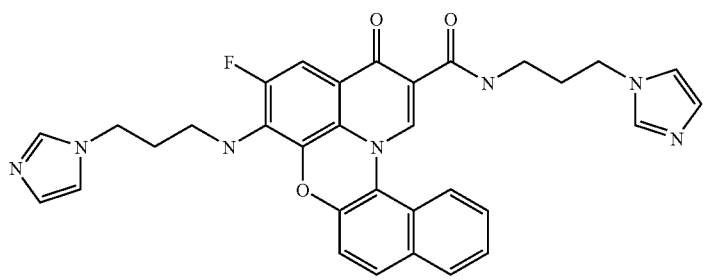
684
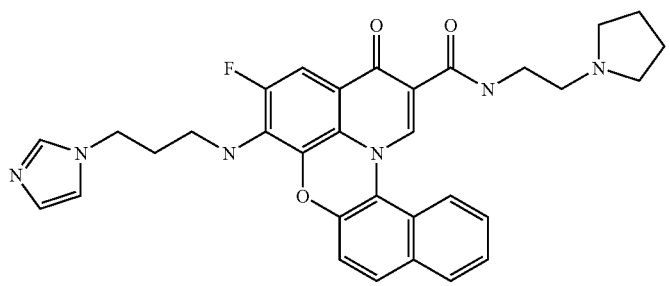
685
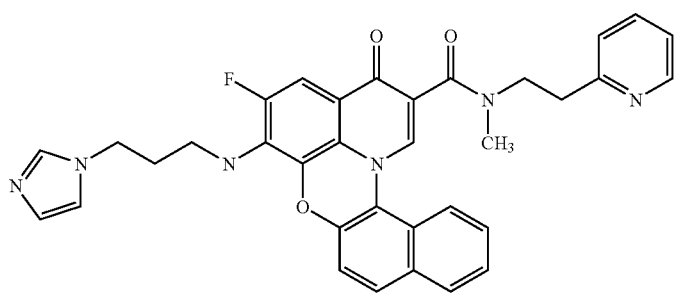
686

687 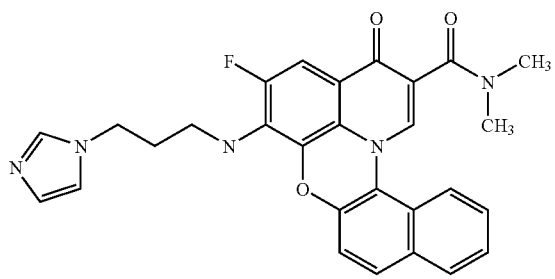
688 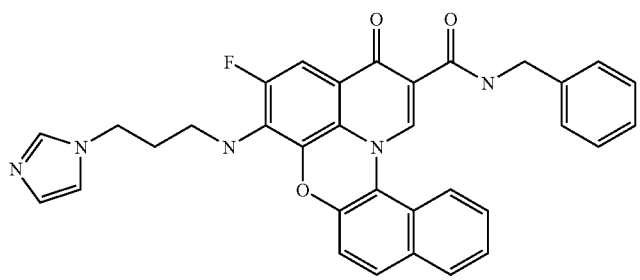
689 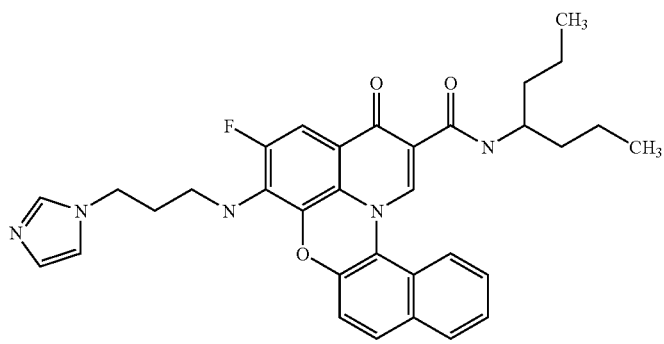
690 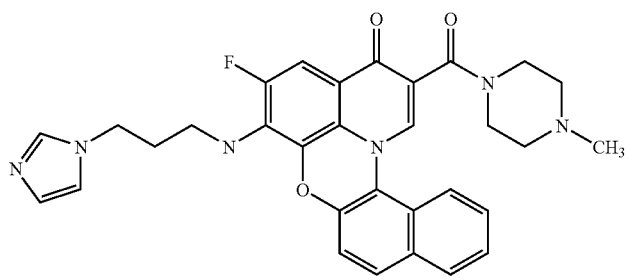
691 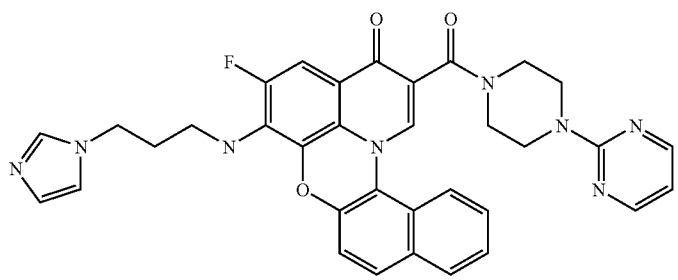

-continued
692
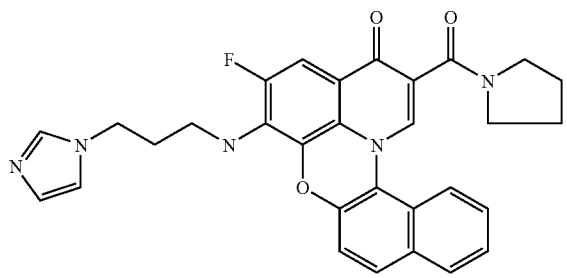
693
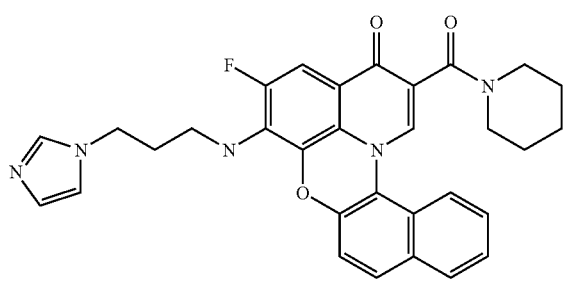
694
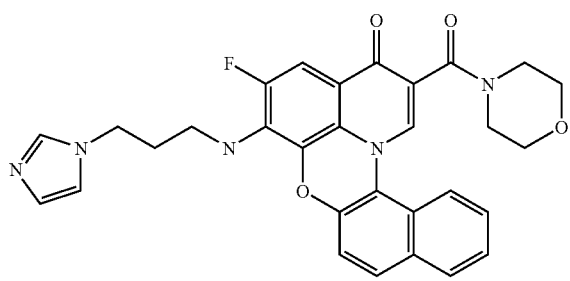
695
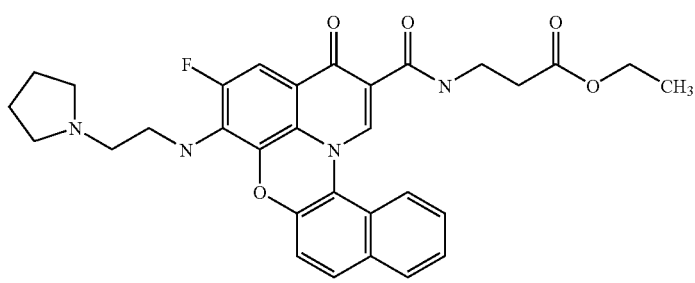
696
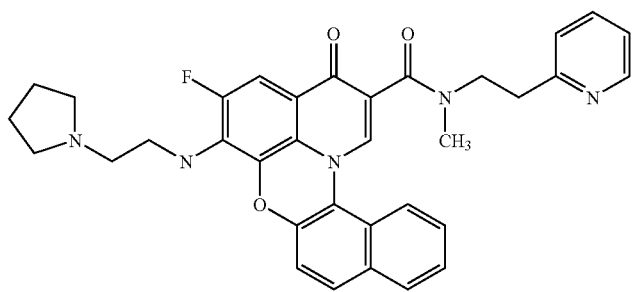

-continued
697
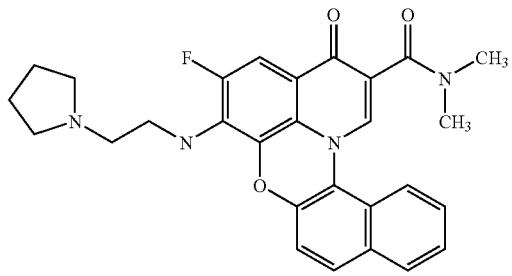
698
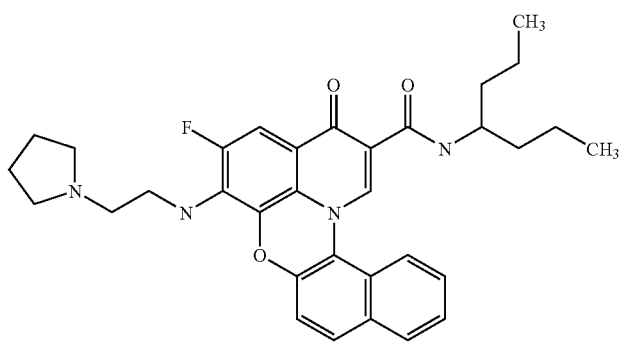
699
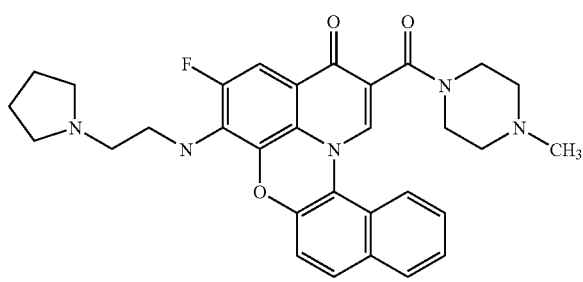
700
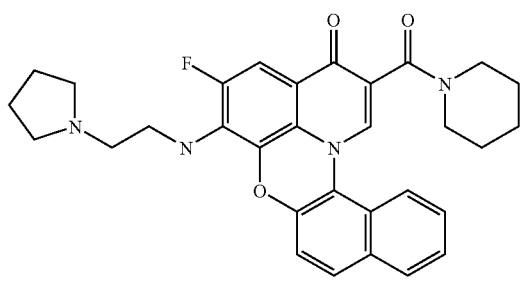
701
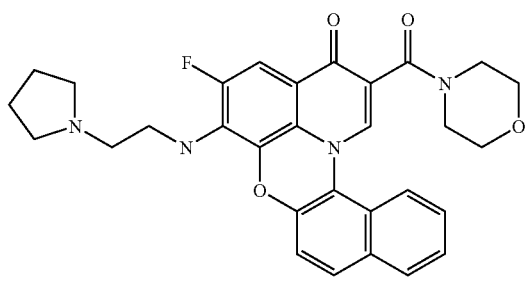

-continued
702
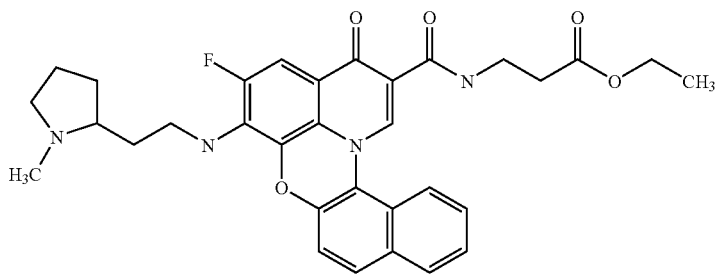
703
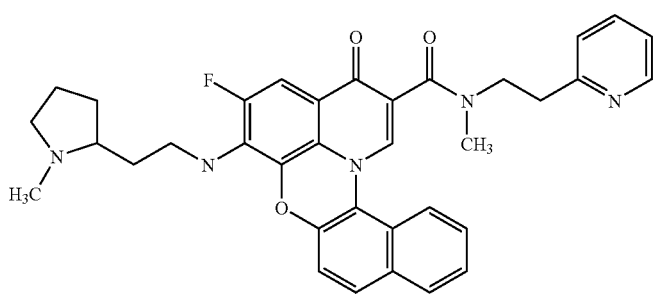
704
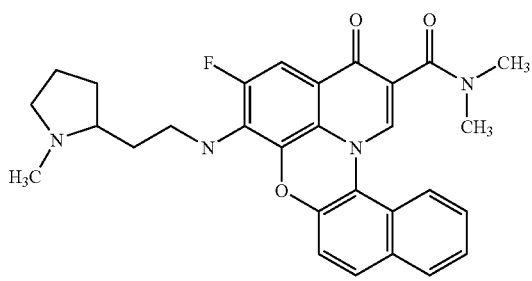
705
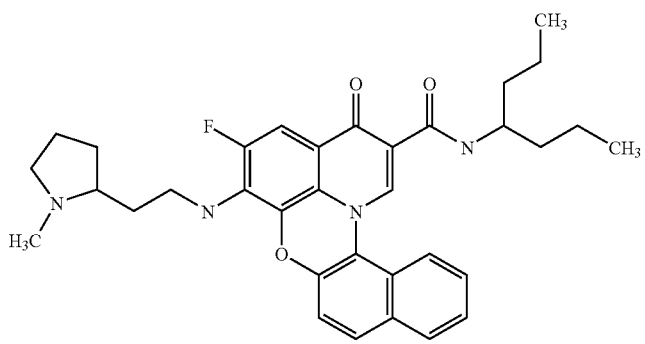
706
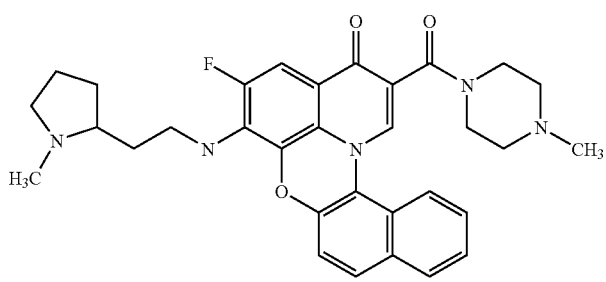

707 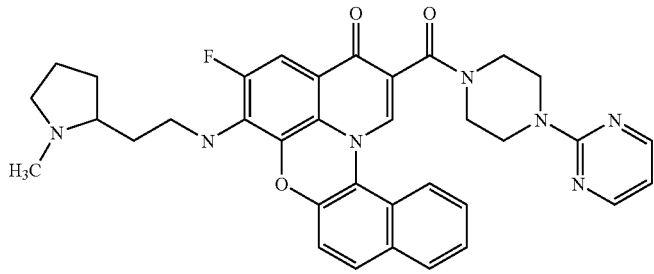
708 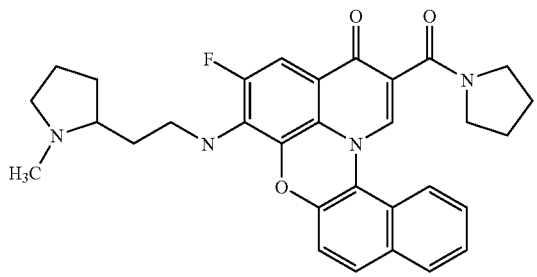
709 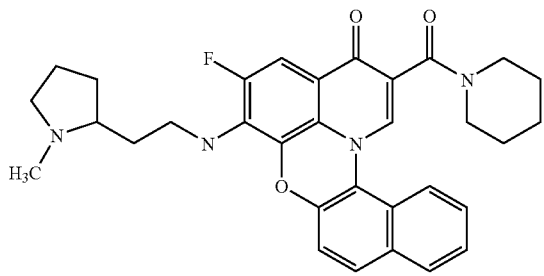
710 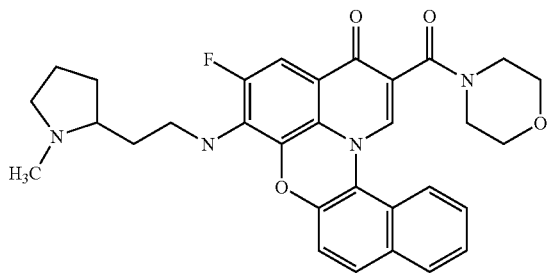
711 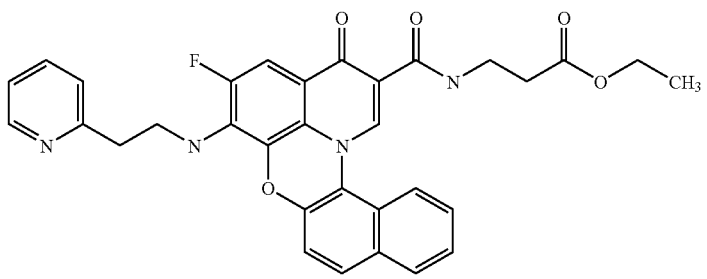

712 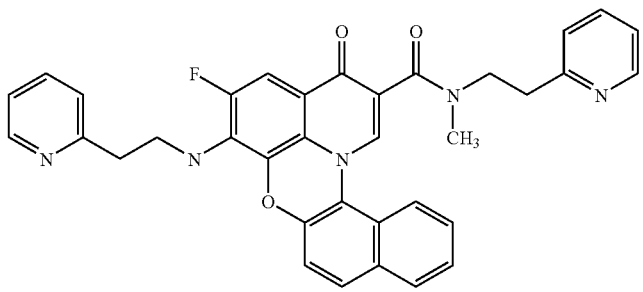
713 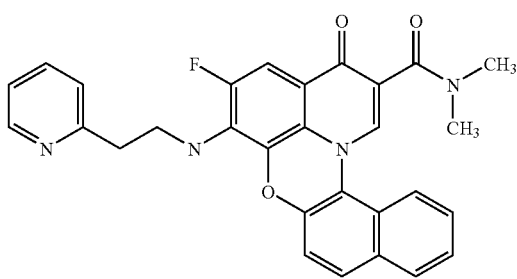
714 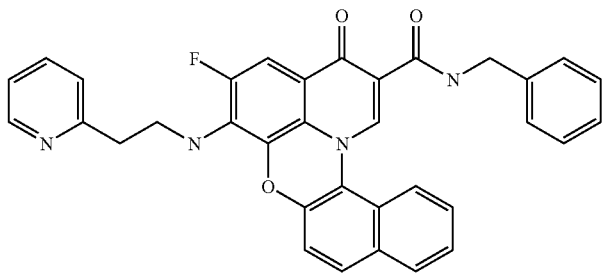
715 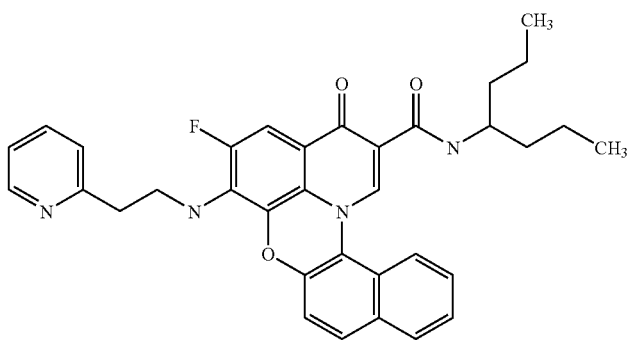
716 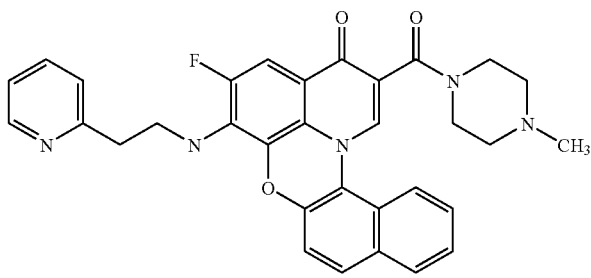

-continued
717 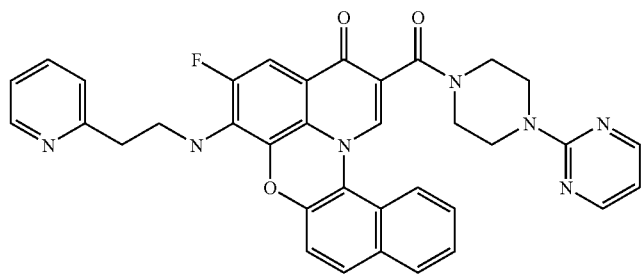
718 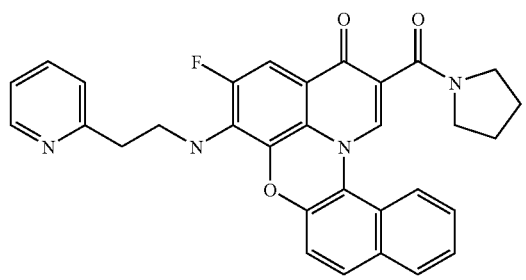
719 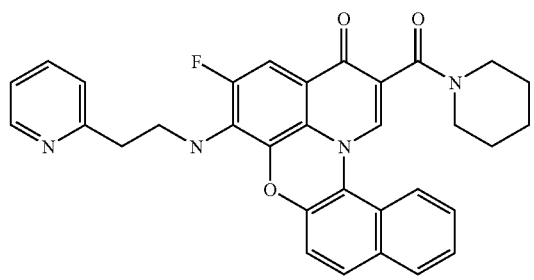
720 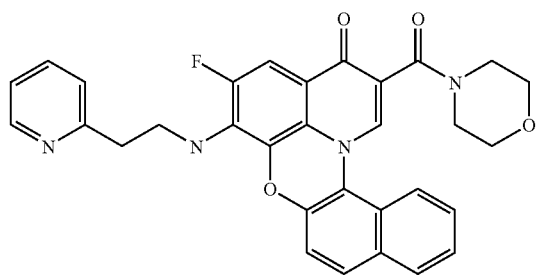
721 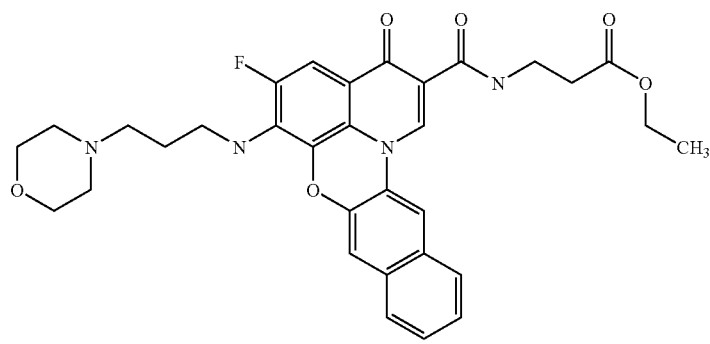

722 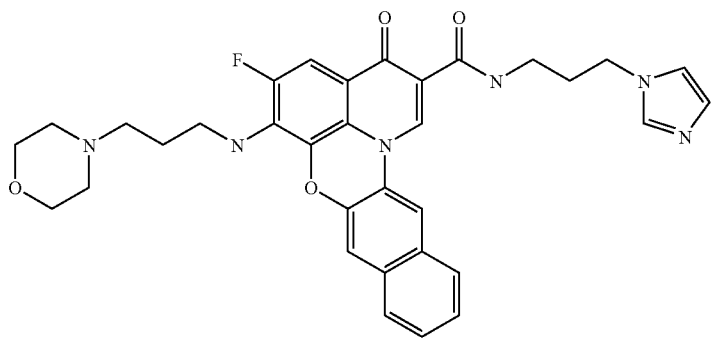
723 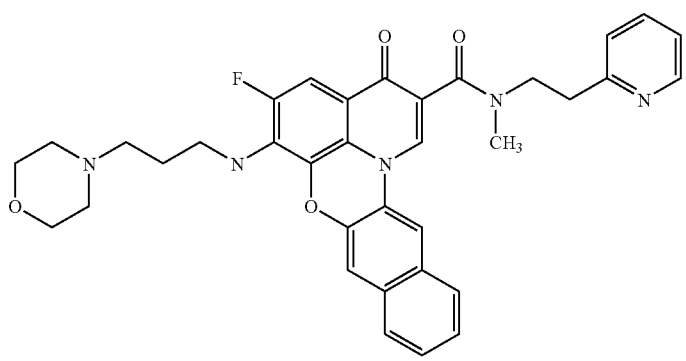
724 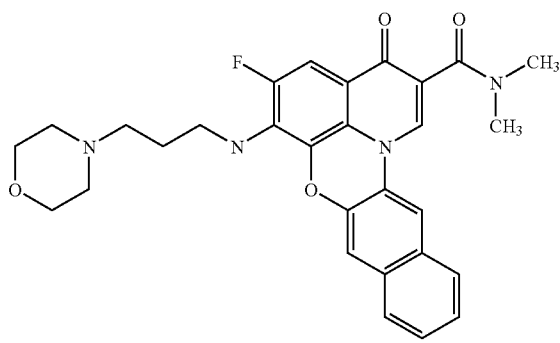
725 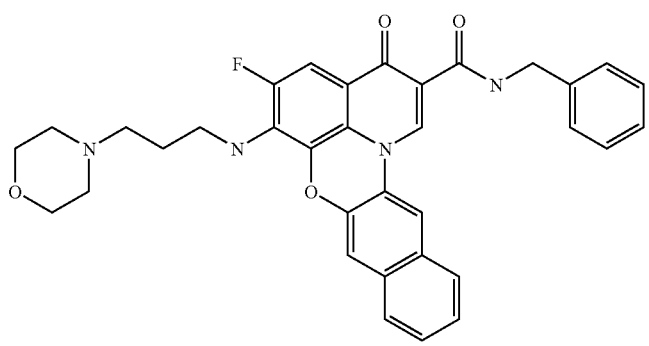

-continued
726
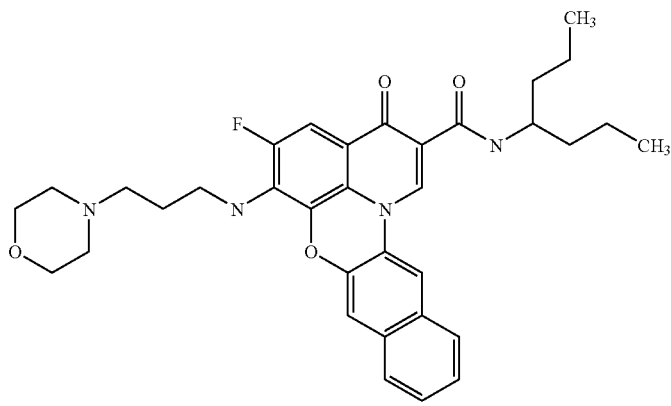
727
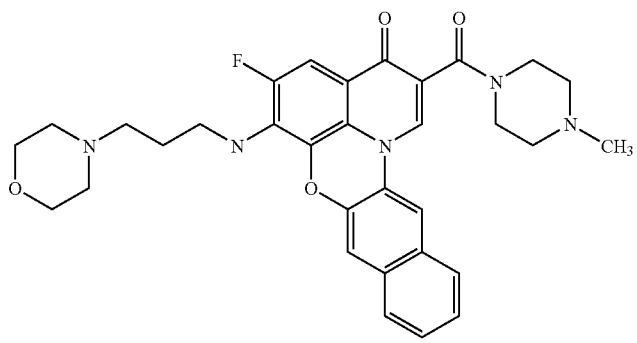
728
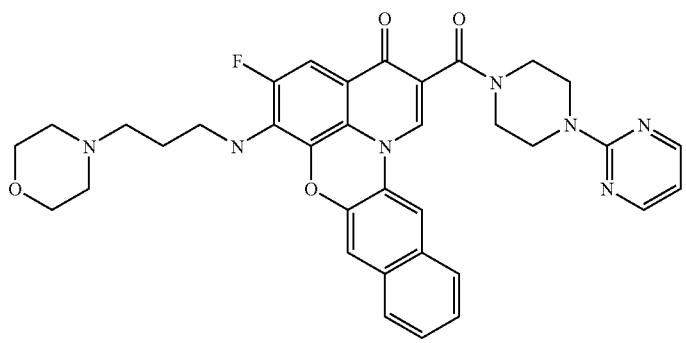
729
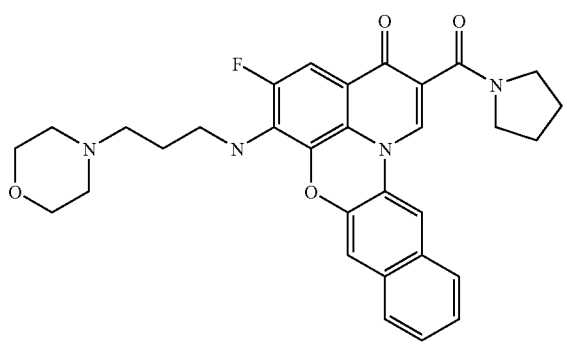

730 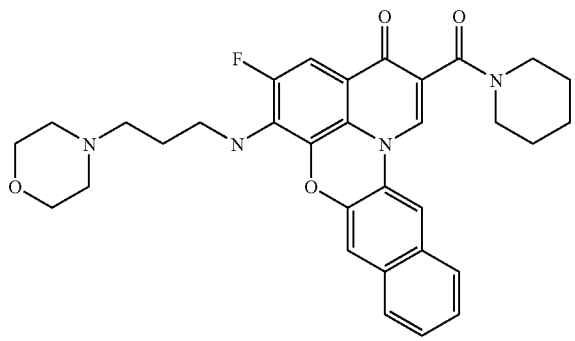
731 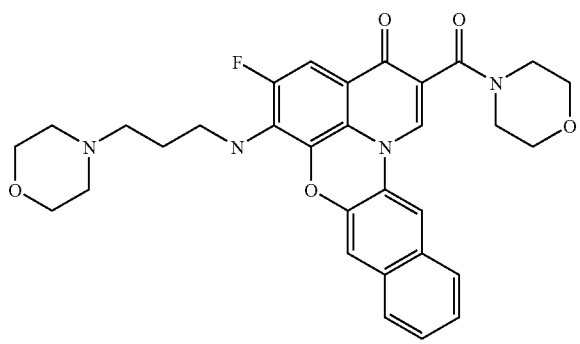
732 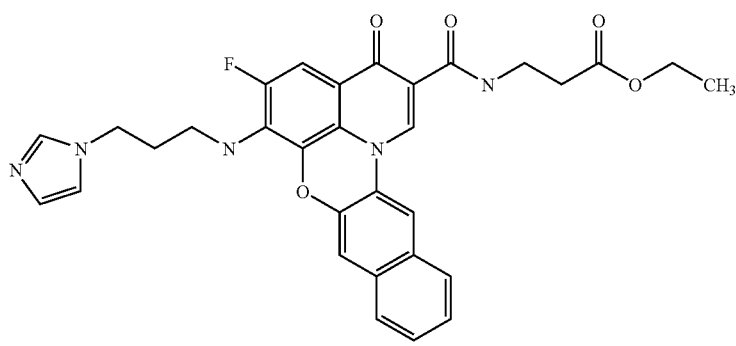
733 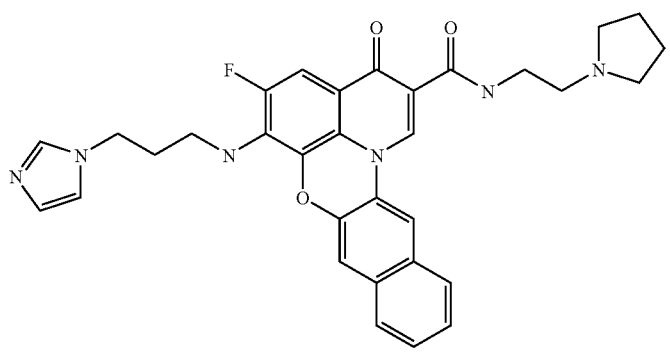

-continued
734
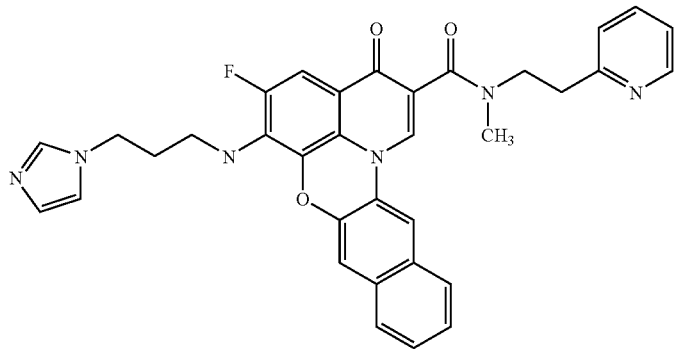
735
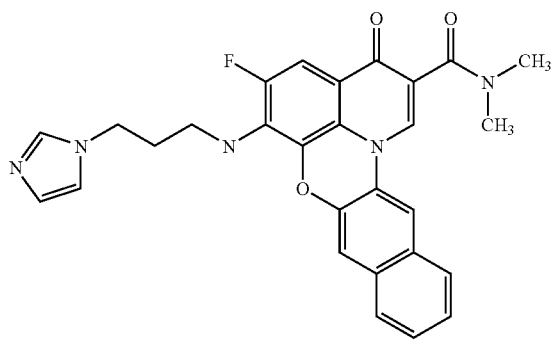
736
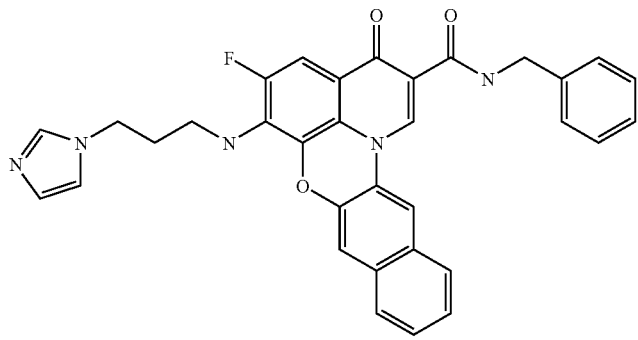
737
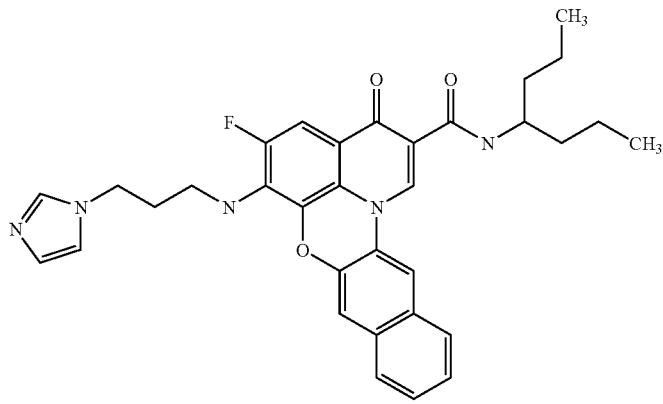

-continued
738
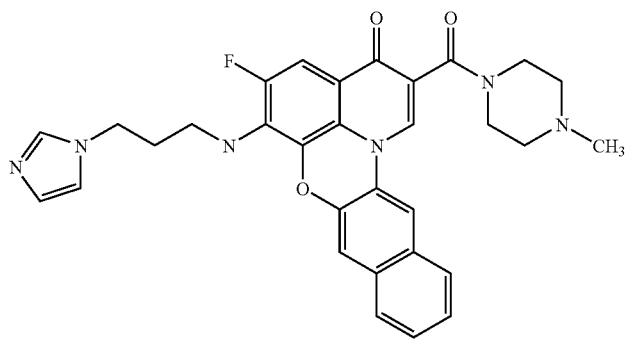
739
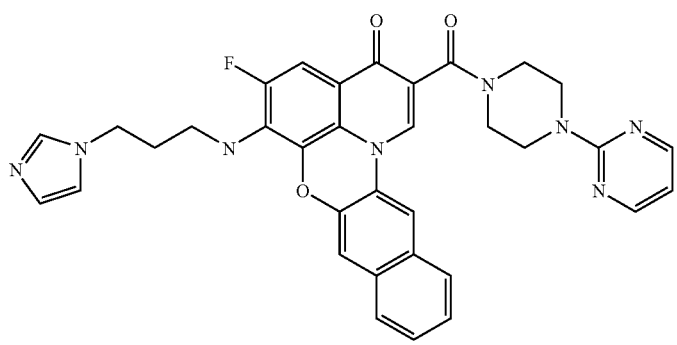
740
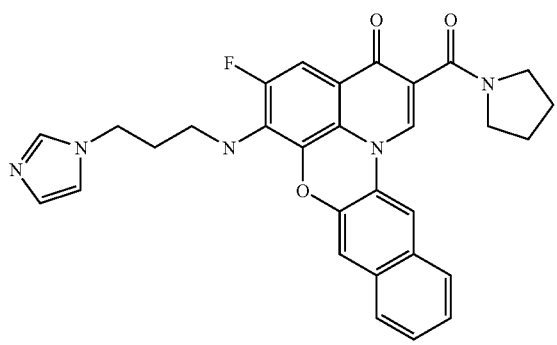
741
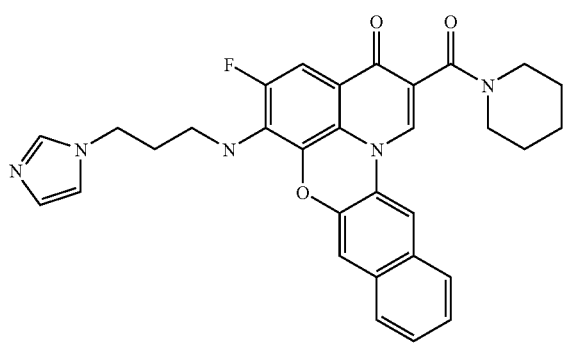

-continued
742
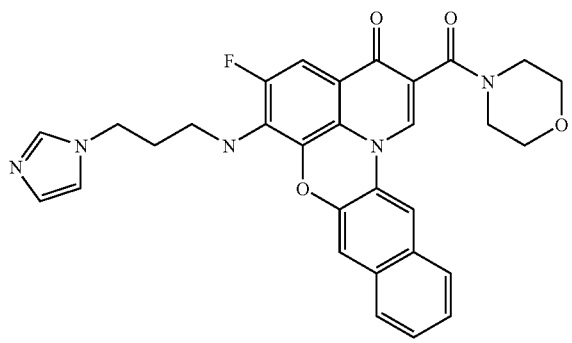
743
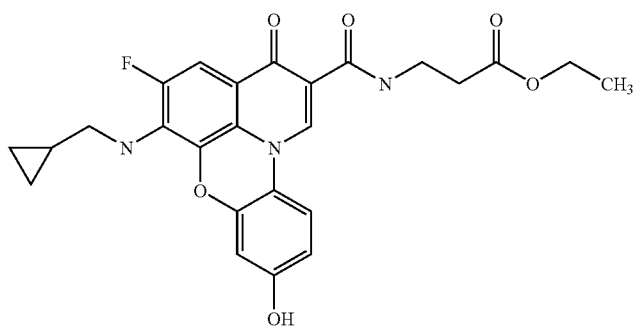
744
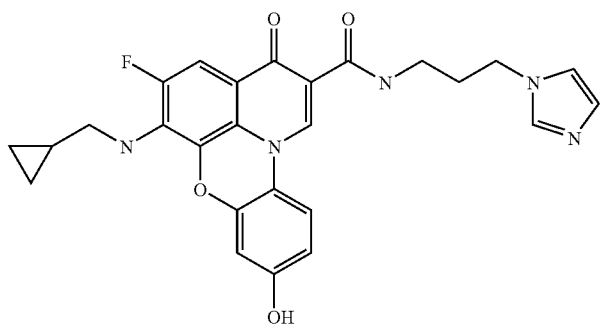
745
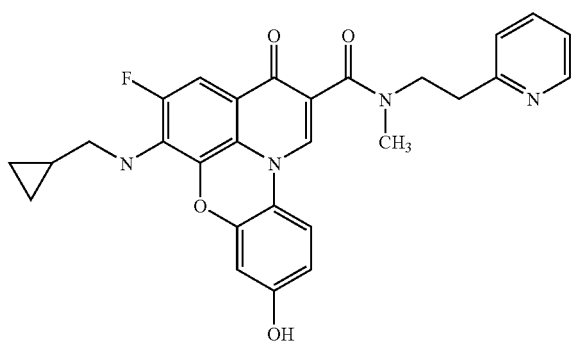

746 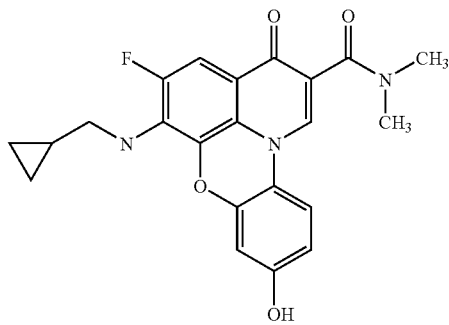
747 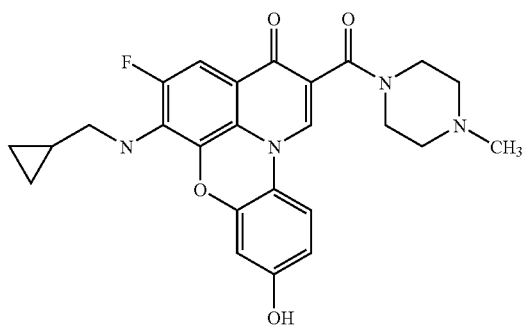
748 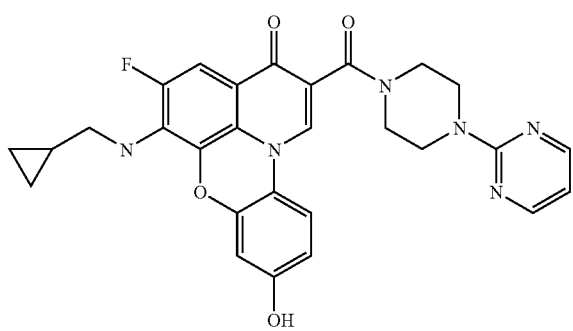
749 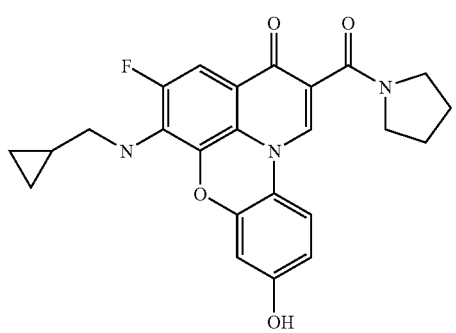

-continued
750
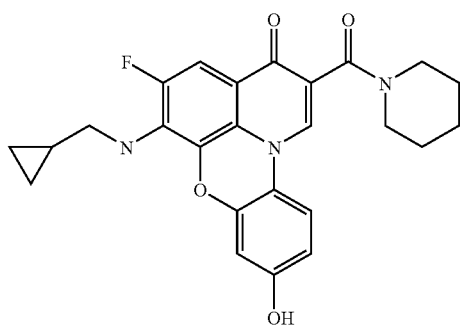
751
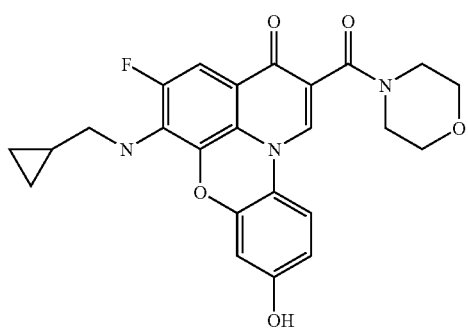
752
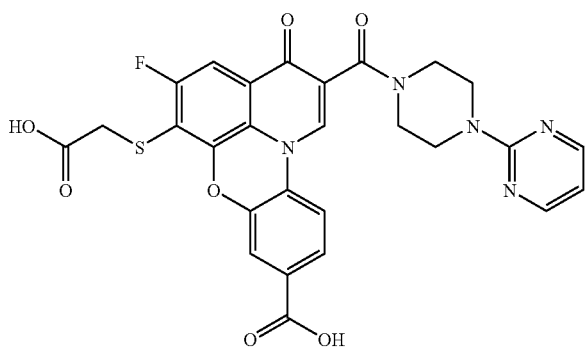
753
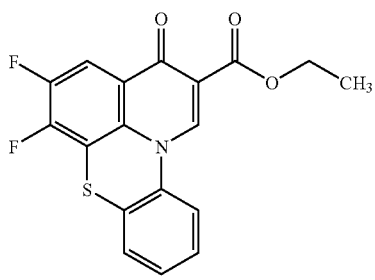
754
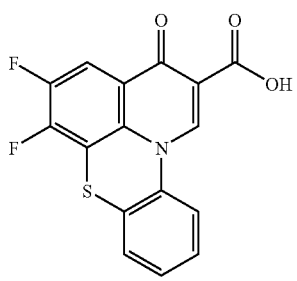

-continued
755
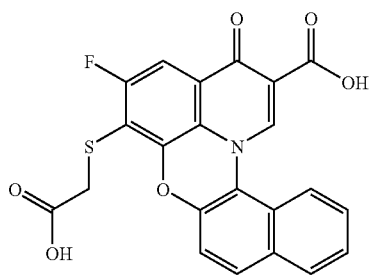
756
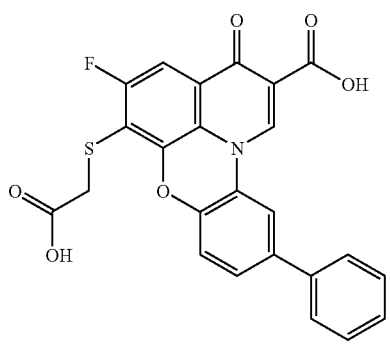
757
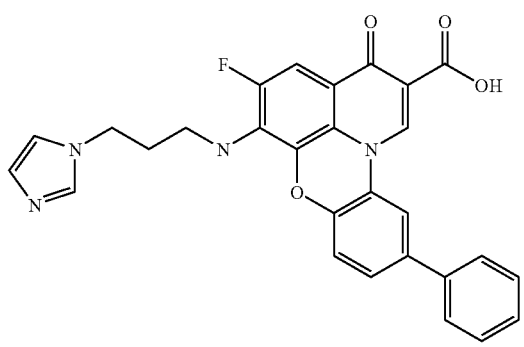
758
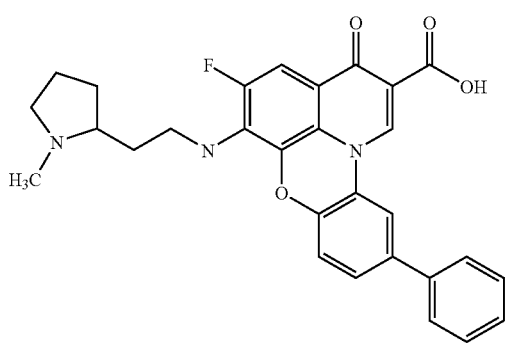
759
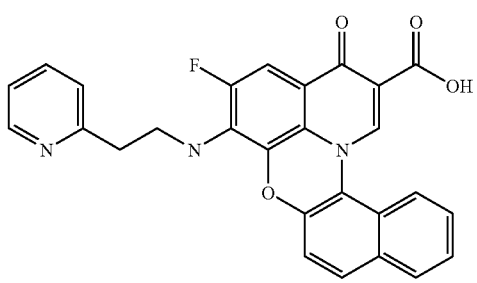

760 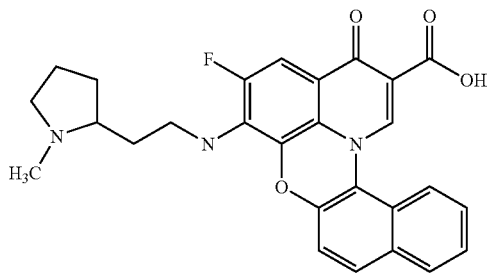
761 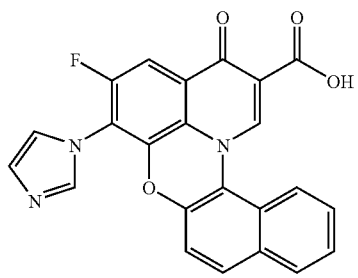
762 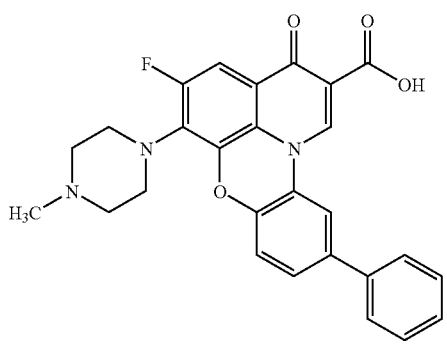
763 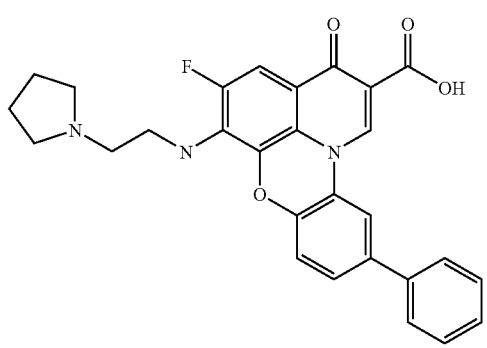
764 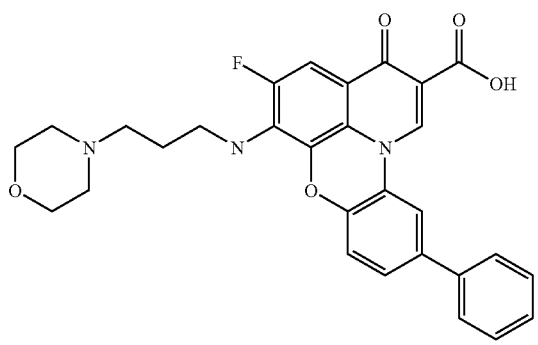

-continued
765 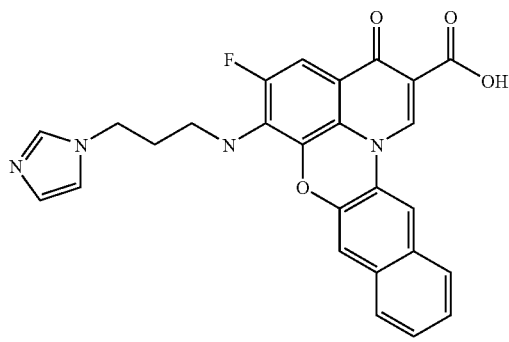
766 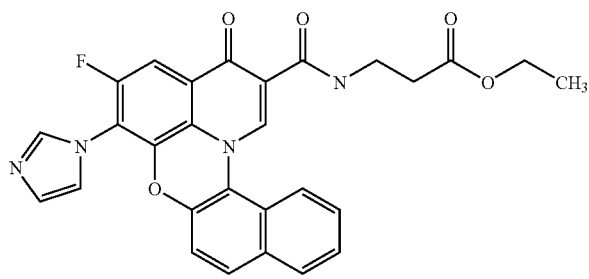
767 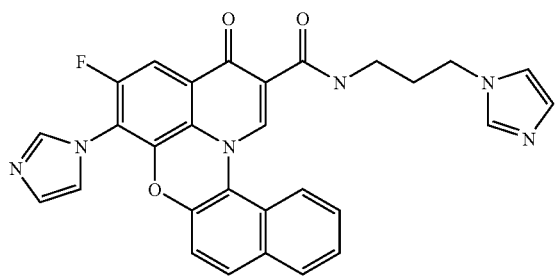
768 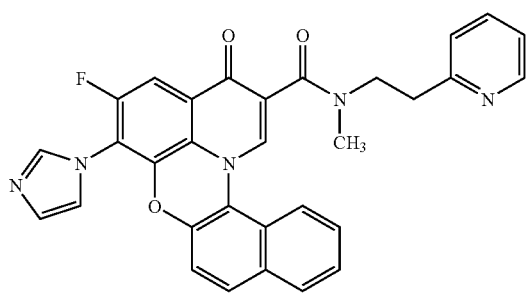
769 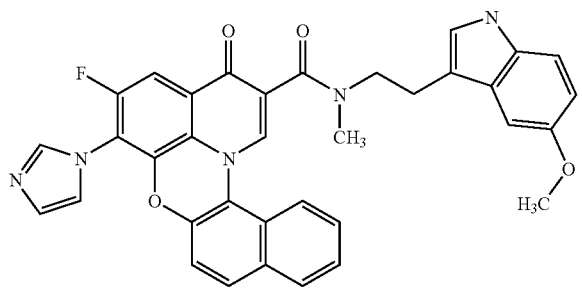

770 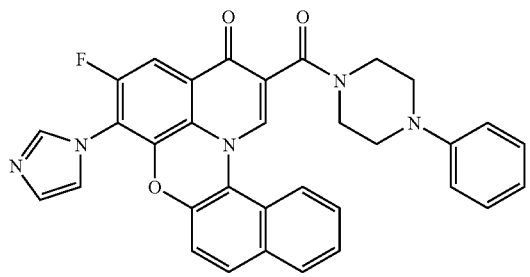
771 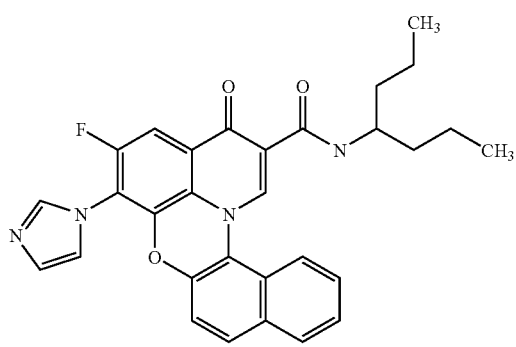
772 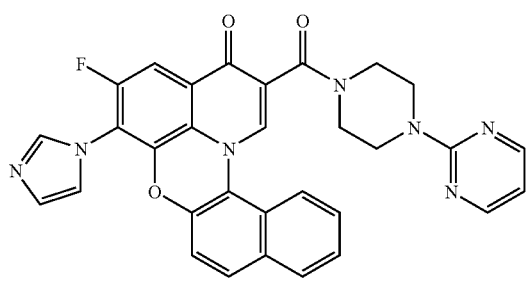
773 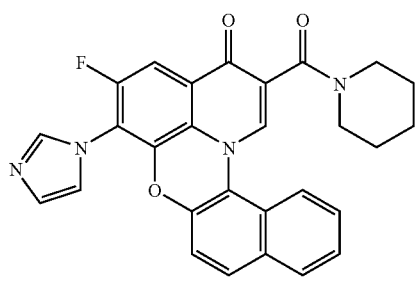
774 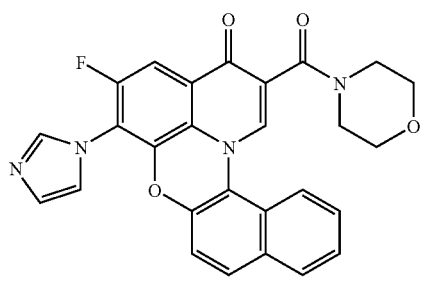

-continued
775
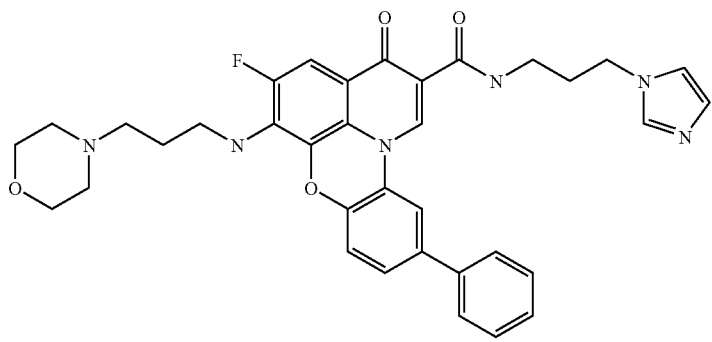
776
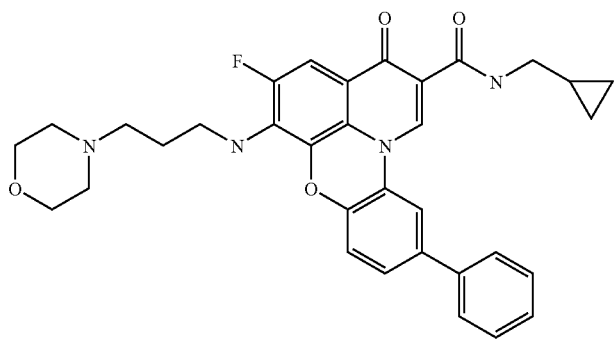
777
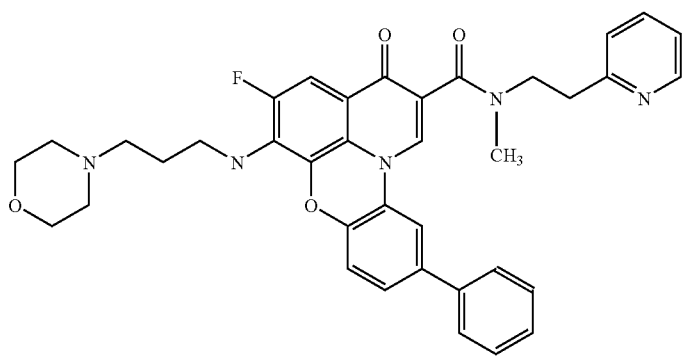
778
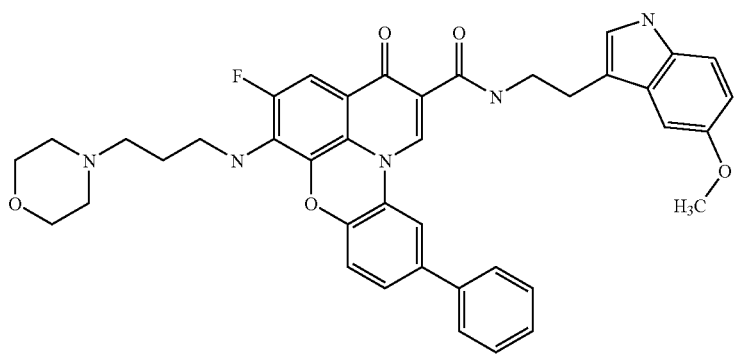

779 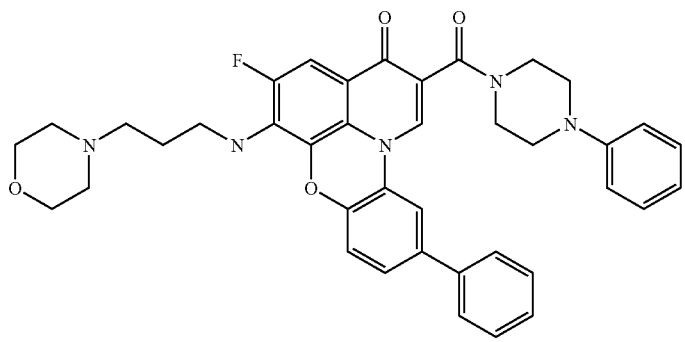
780 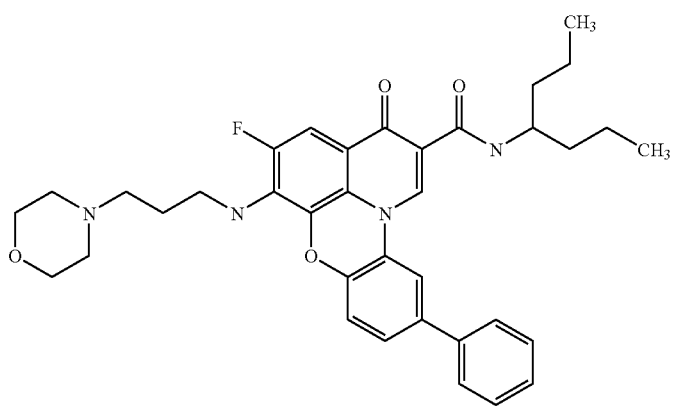
781 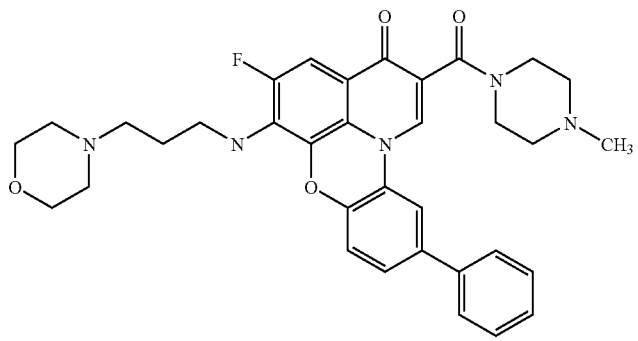
782 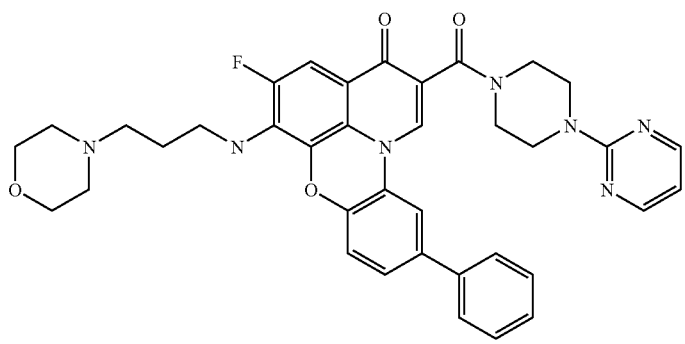

783
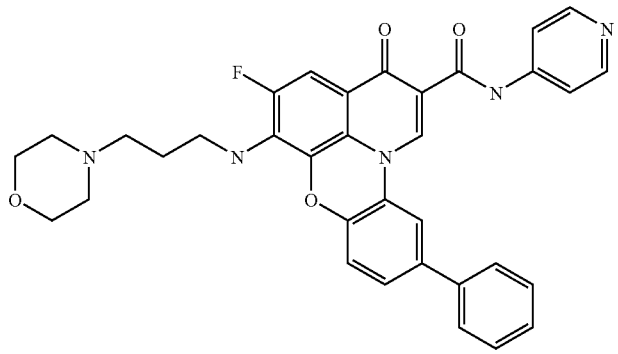
784
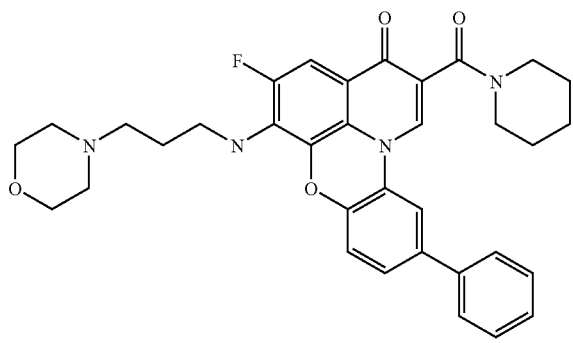
785
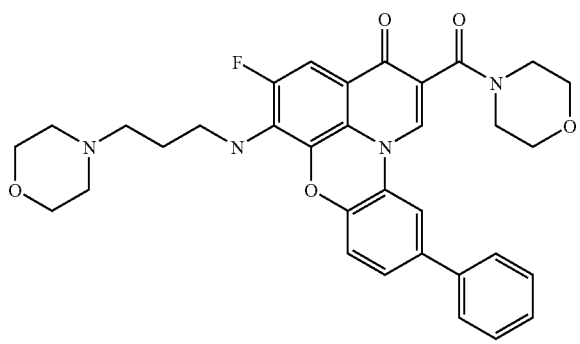
786
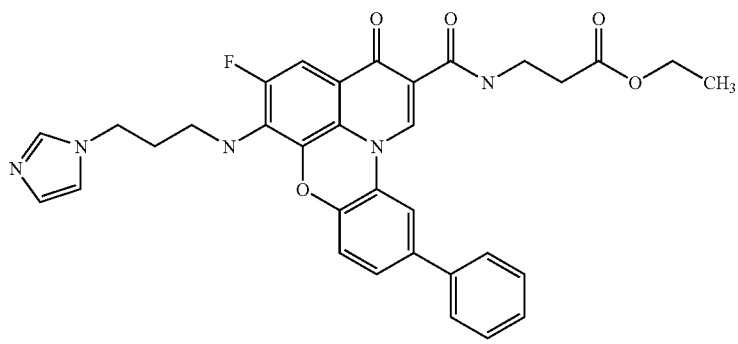

-continued
787
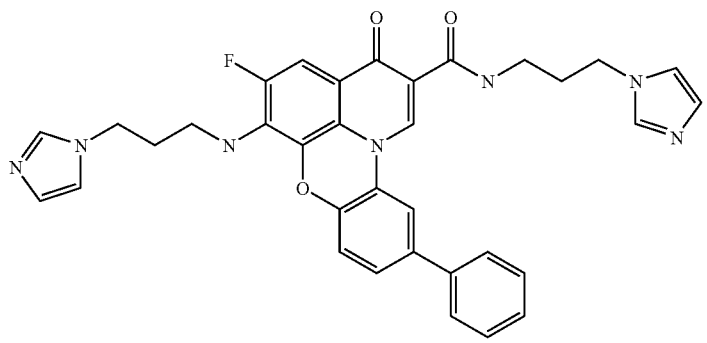
788
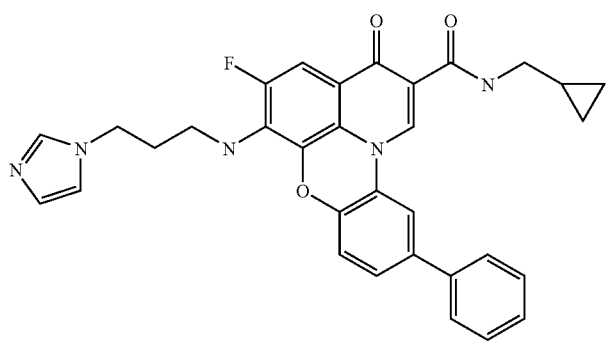
789
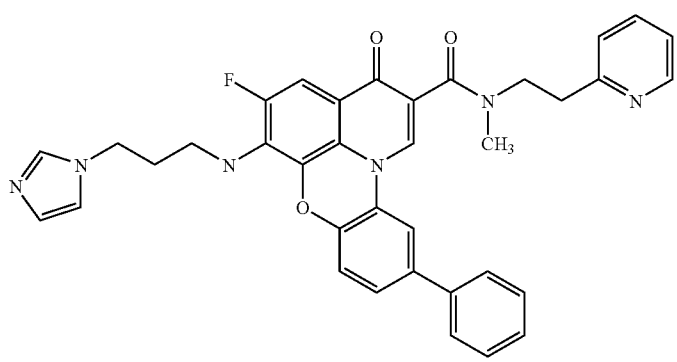
790
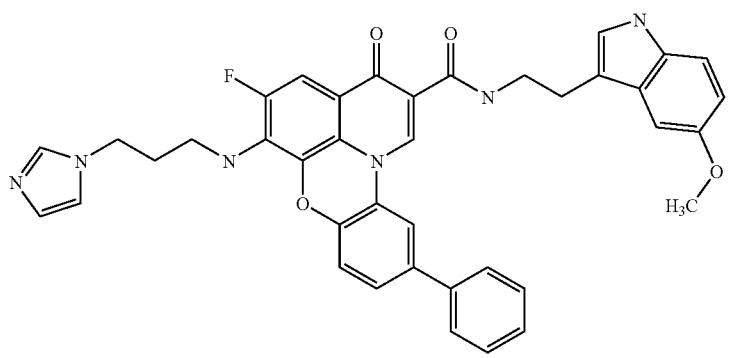

791 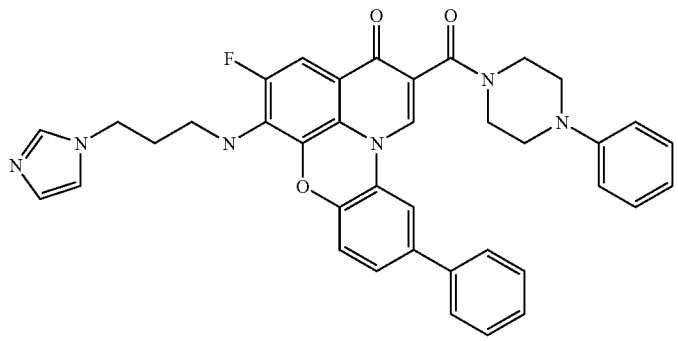
792 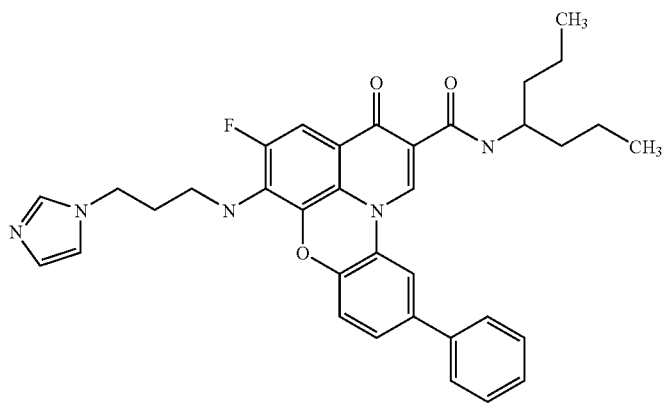
793 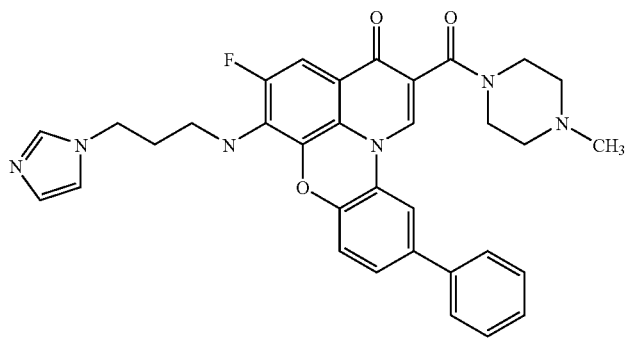
794 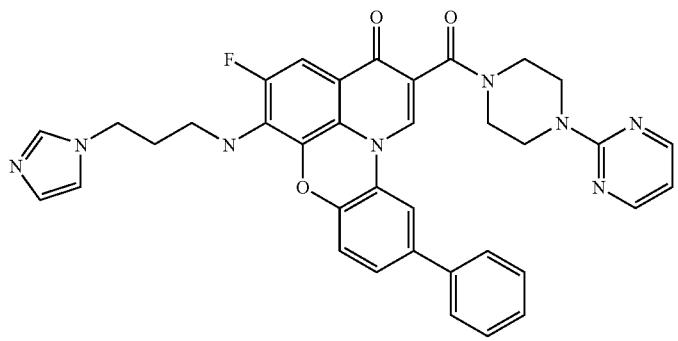

-continued
795
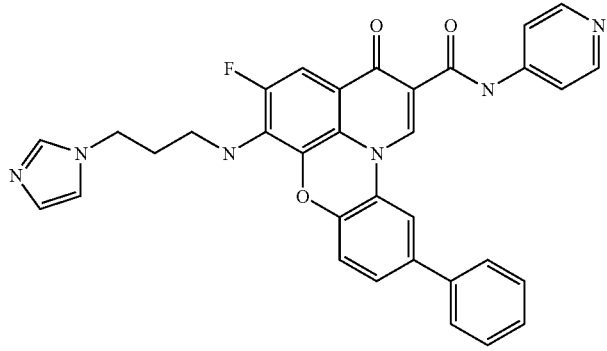
796
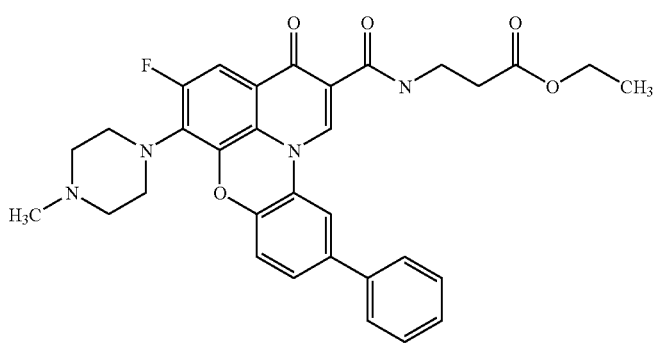
797
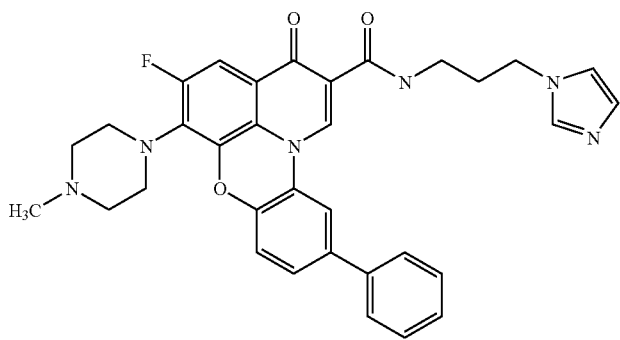
798
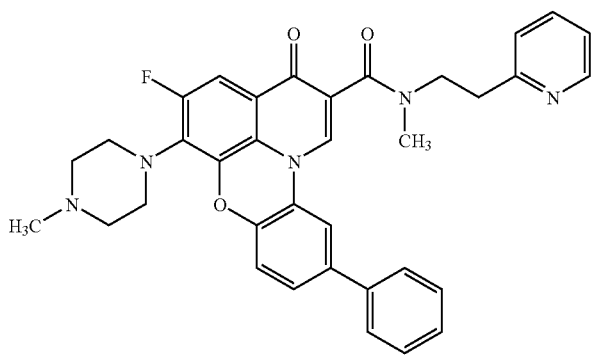

799 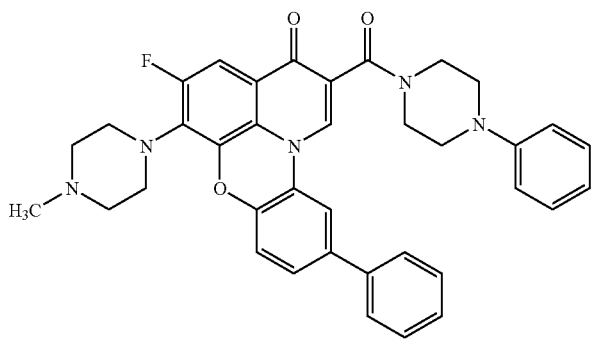
800 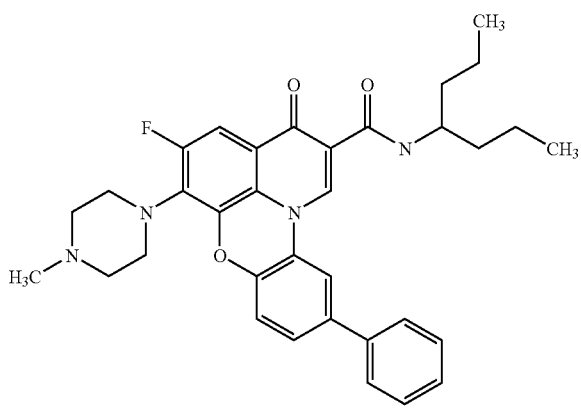
801 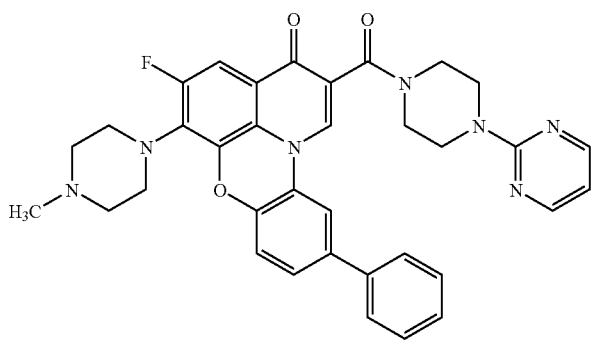
802 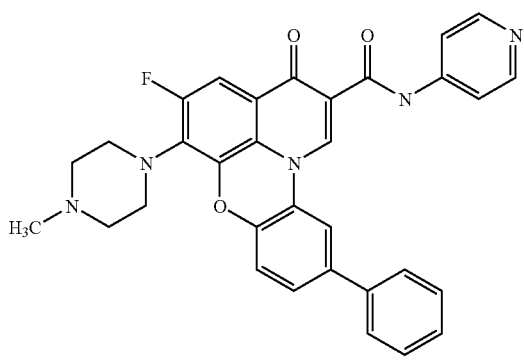

-continued
803
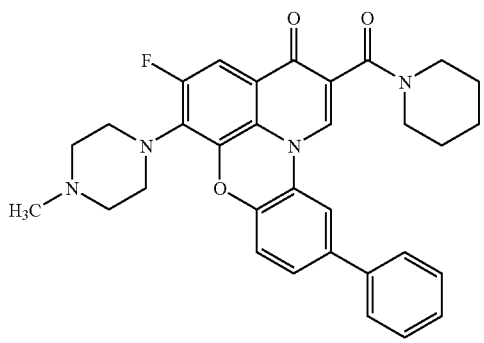
804
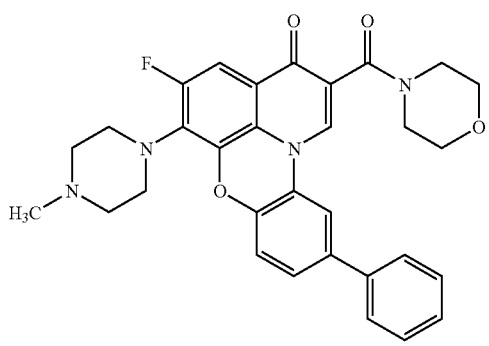
805
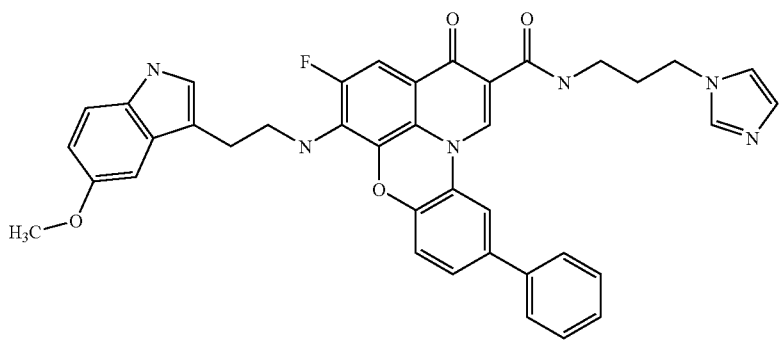
806
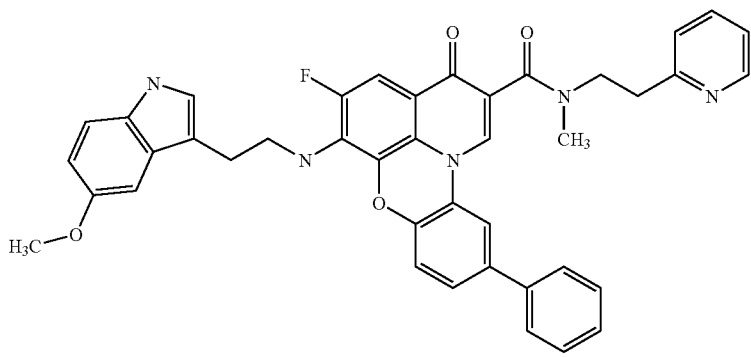

-continued
807
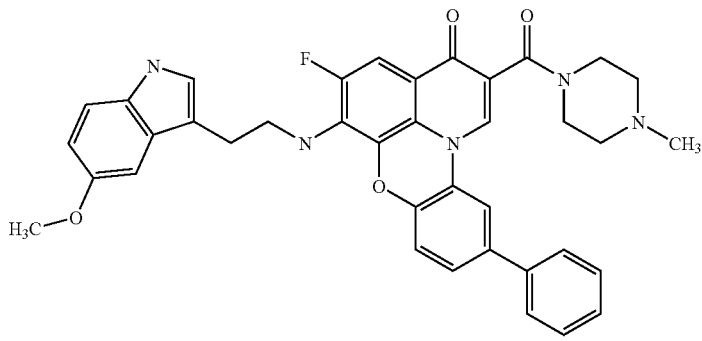
808
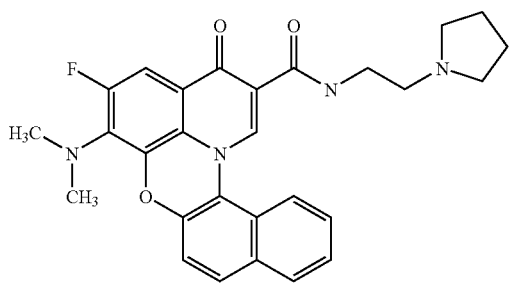
809
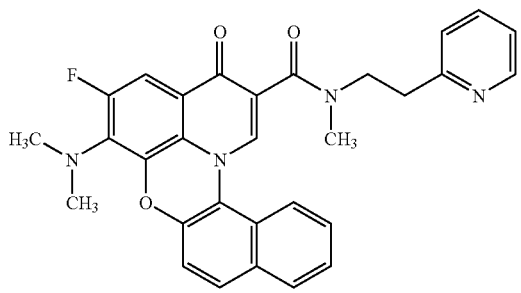
810
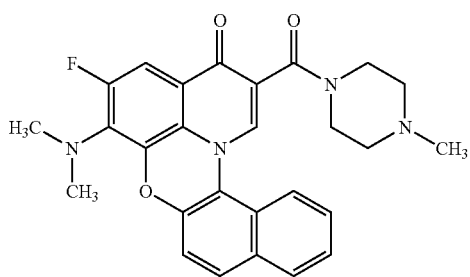
811
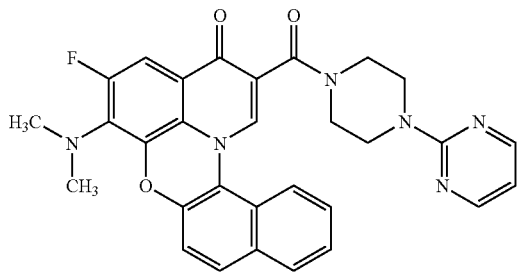

| | |
|---|---|
| 812 | 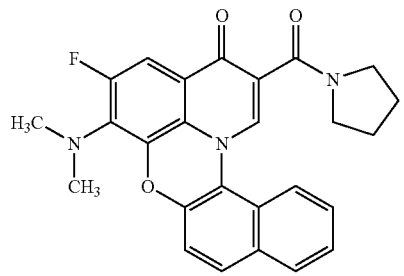 |
| 813 | 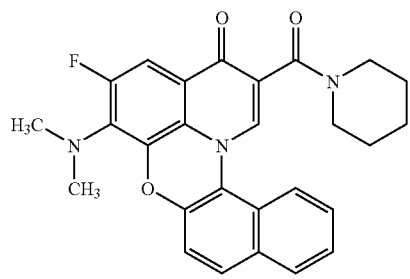 |
| 814 | 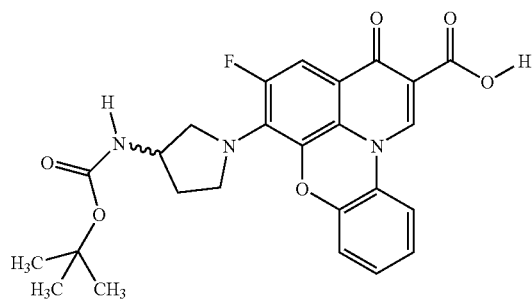 |
| 815 | 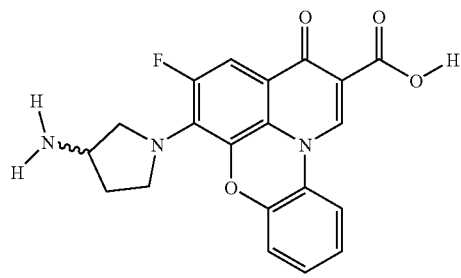 |
| 816 | 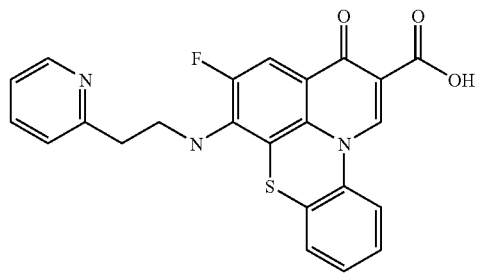 |

817 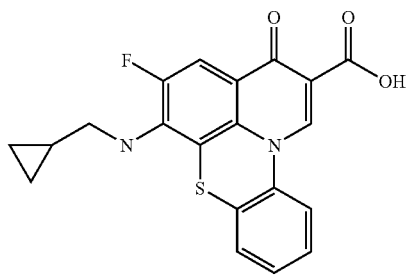
818 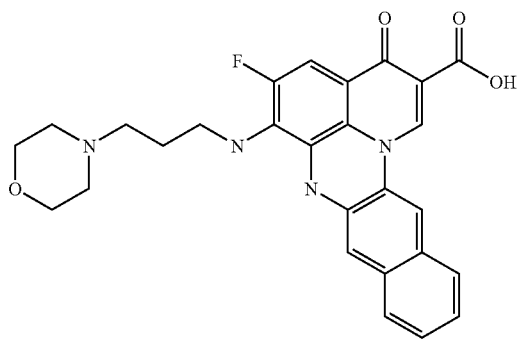
819 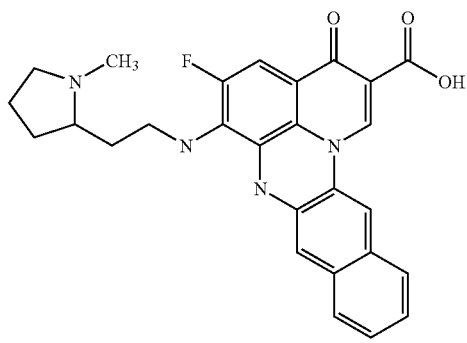
820 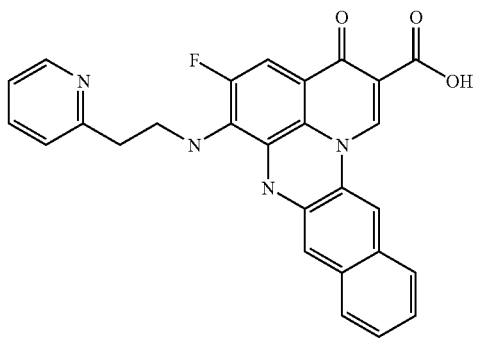

821 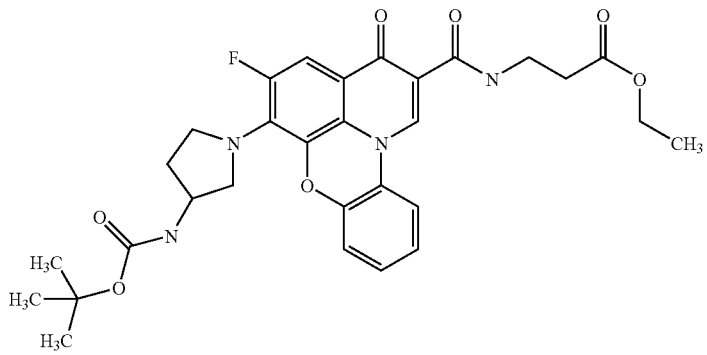
822 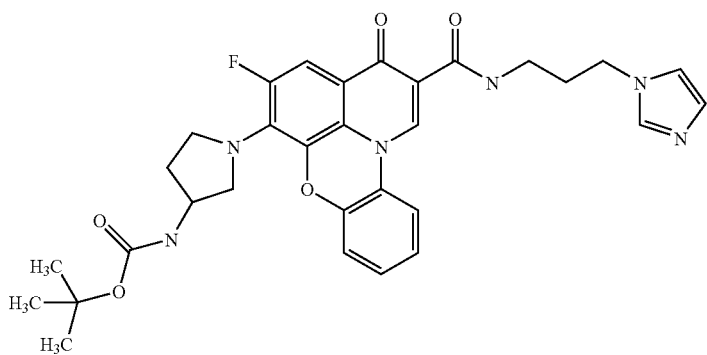
823 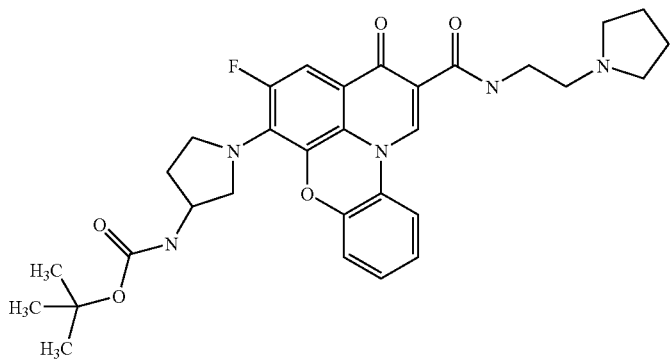
824 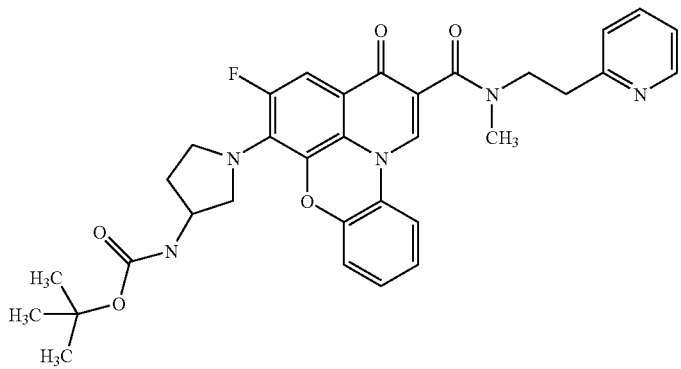

825 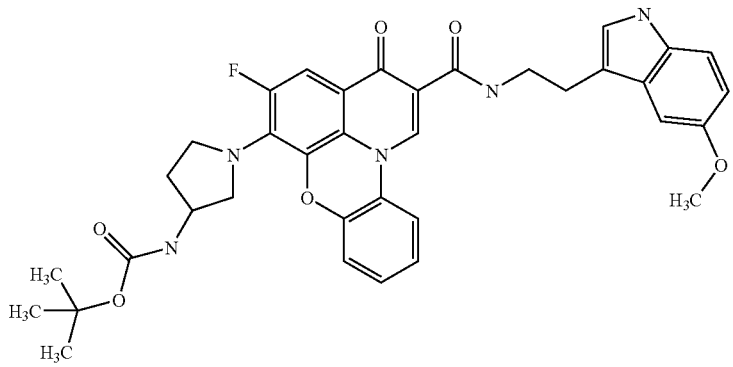
826 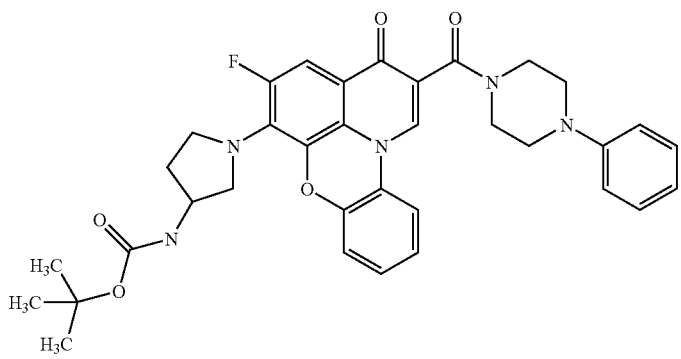
827 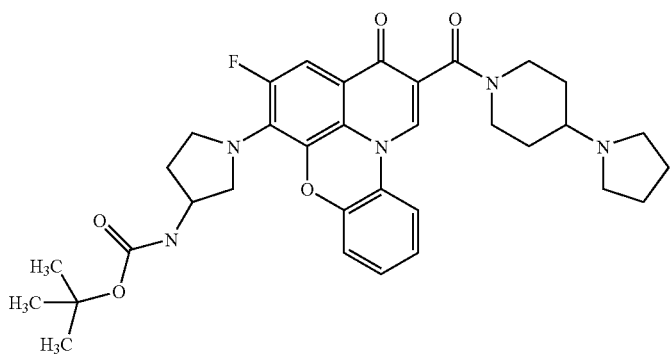
828 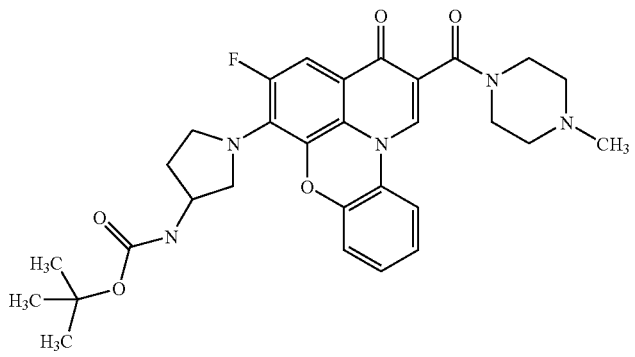

-continued
829
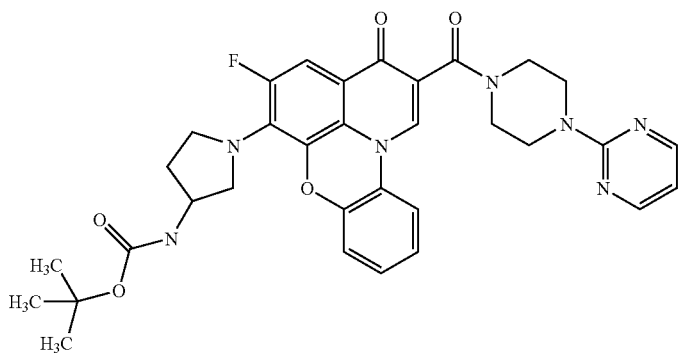
830
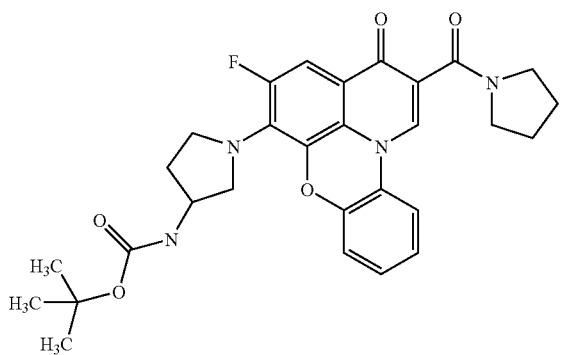
831
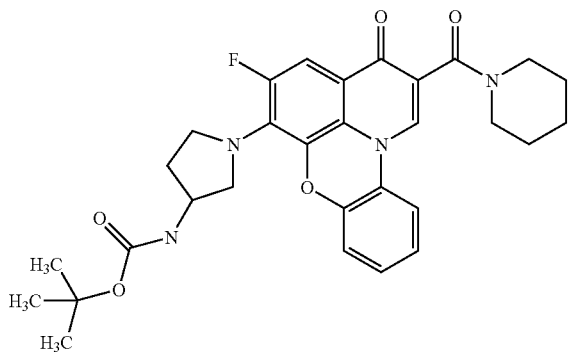
832
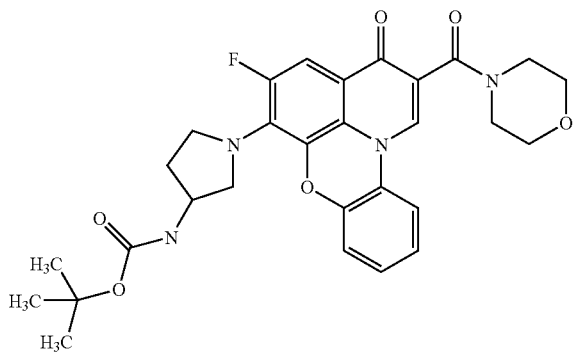

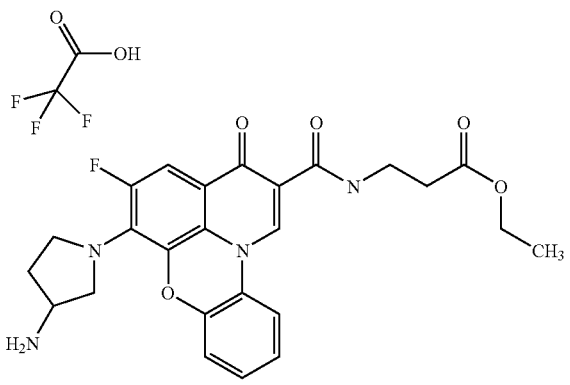
833
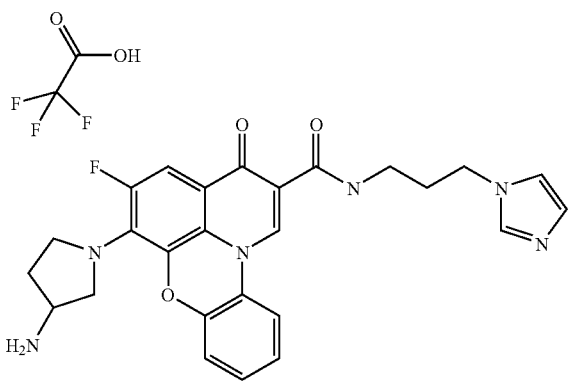
834
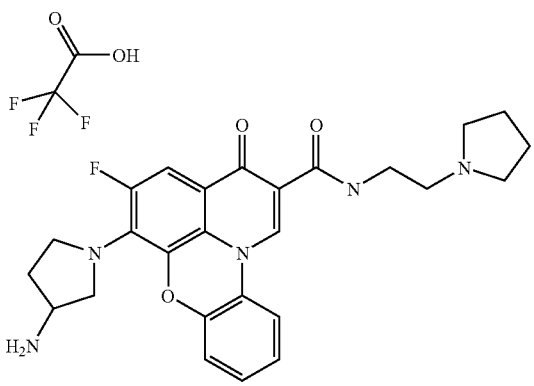
835
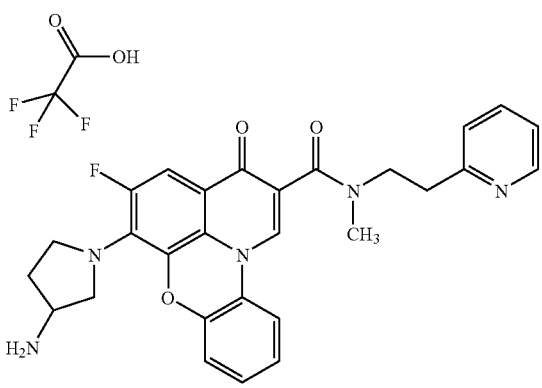
836

837 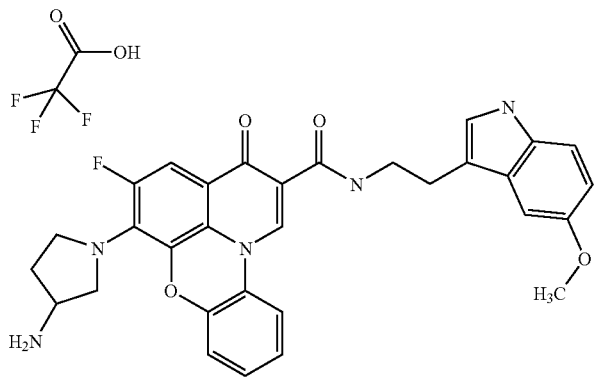
838 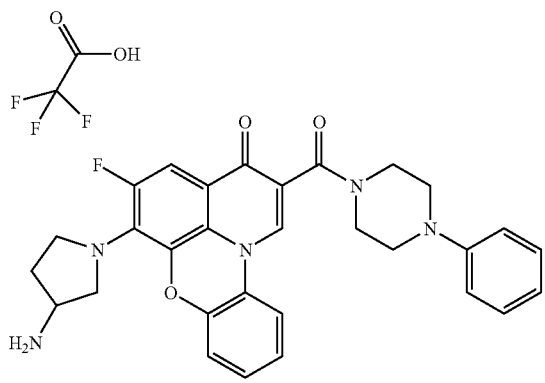
839 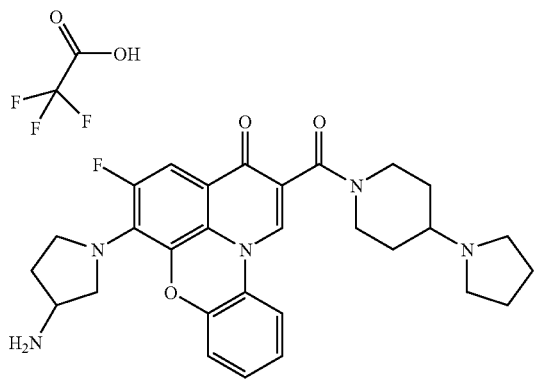
840 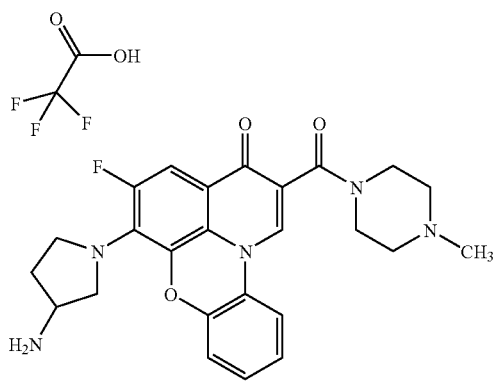

841 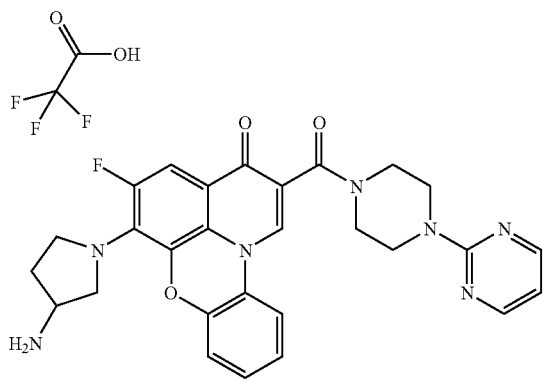
842 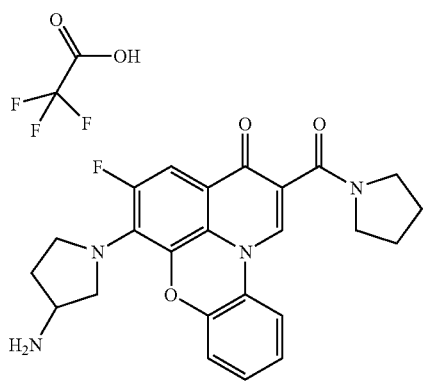
843 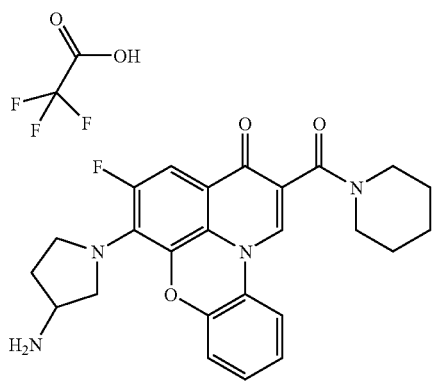
844 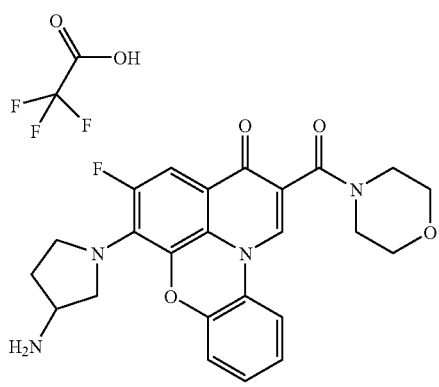

845 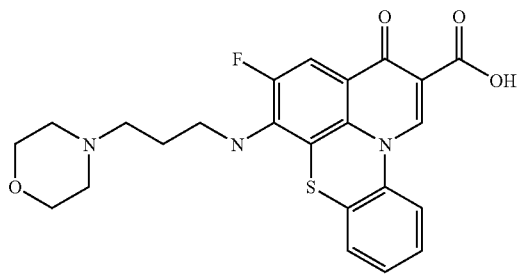
846 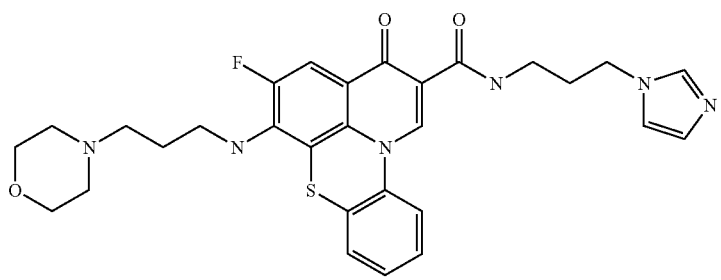
847 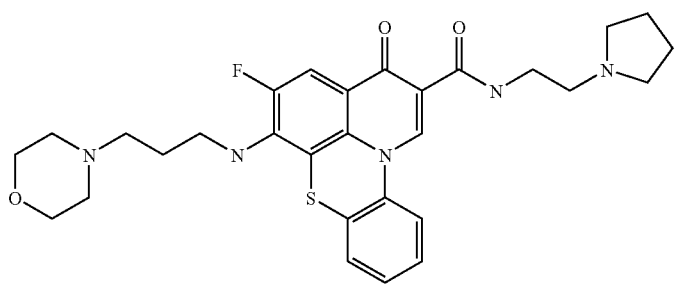
848 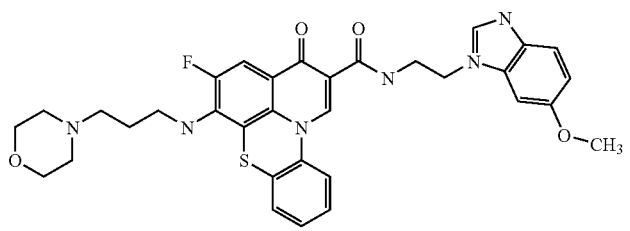
849 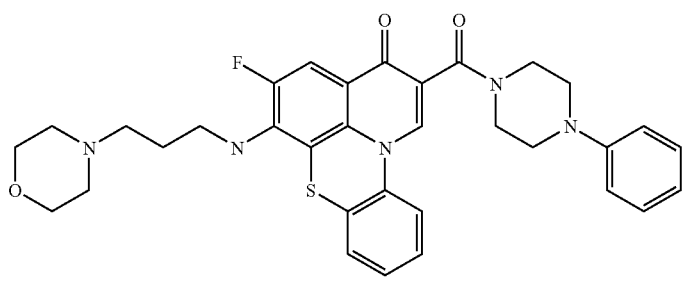

-continued
850 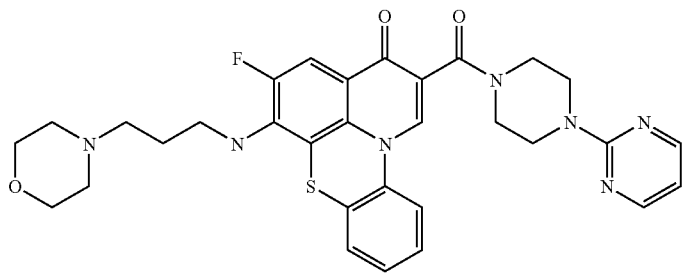
851 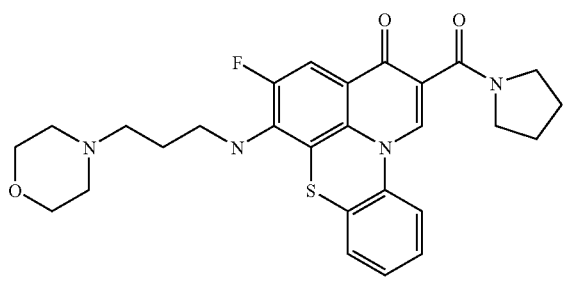
852 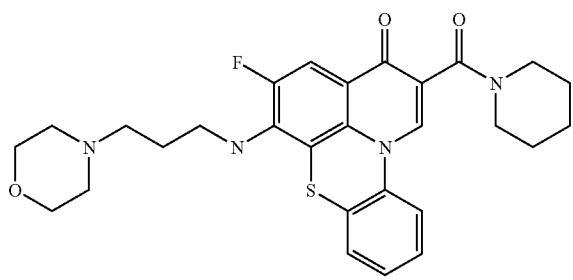
853 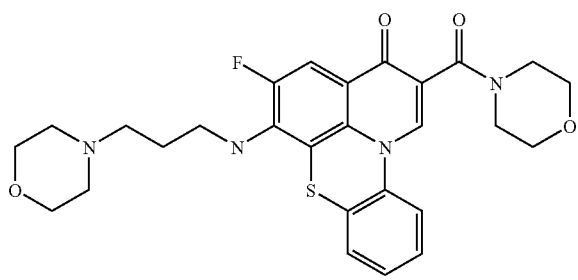
854 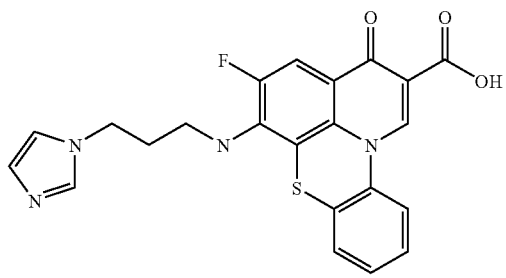

-continued
855
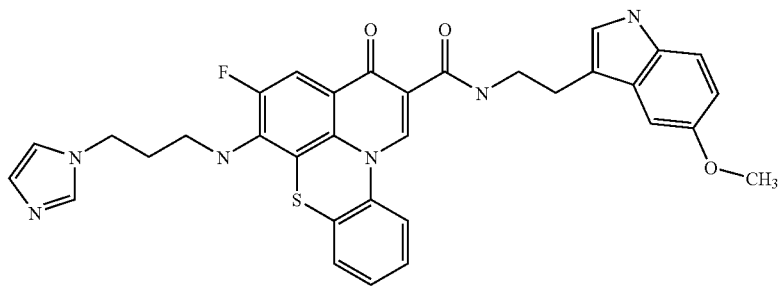
856
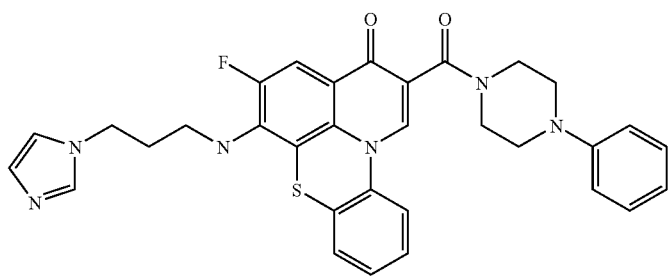
857
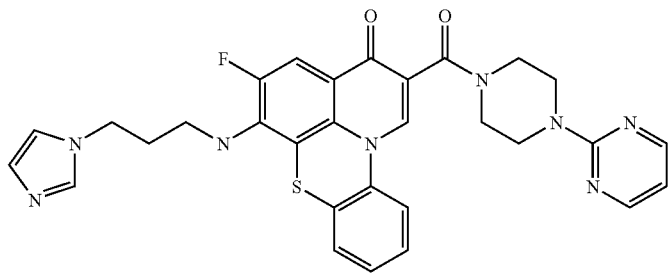
858
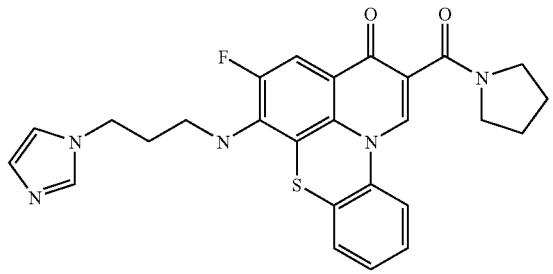
859
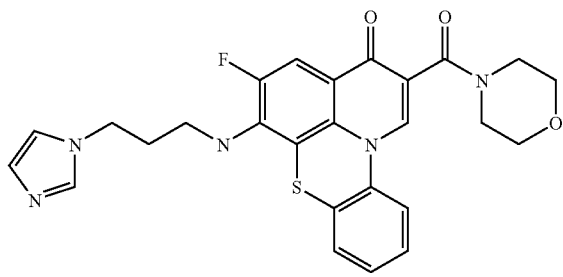

-continued
860
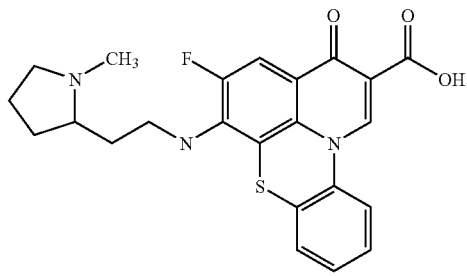
861
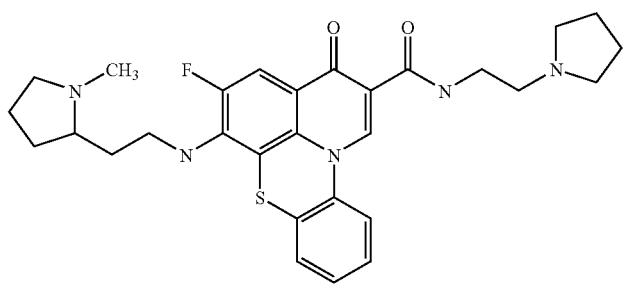
862
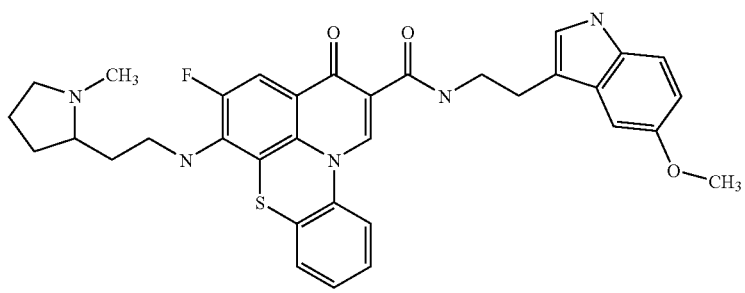
863
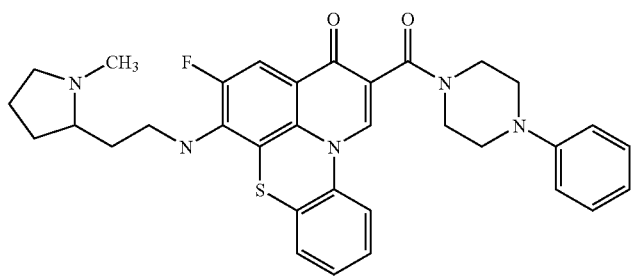
864
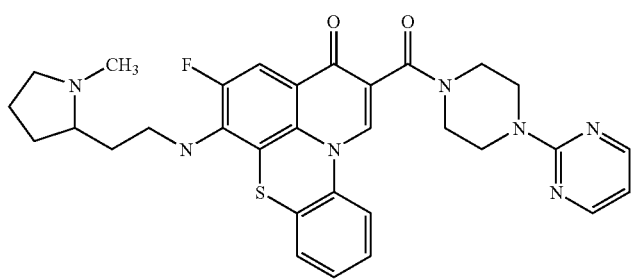

865
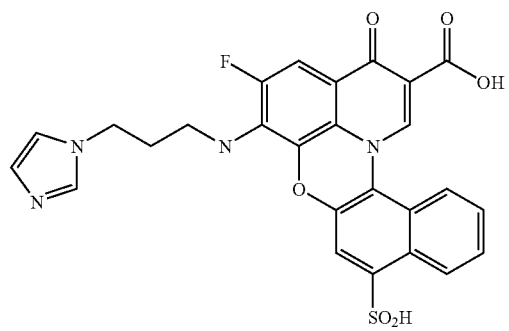
866
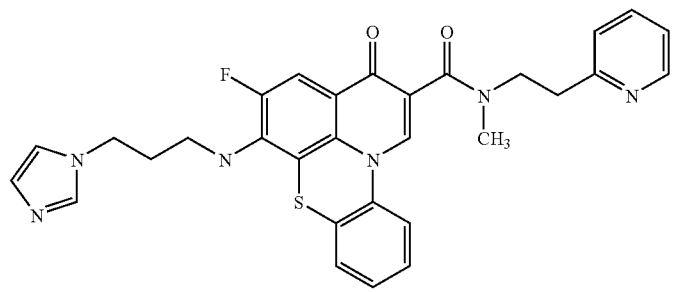
867
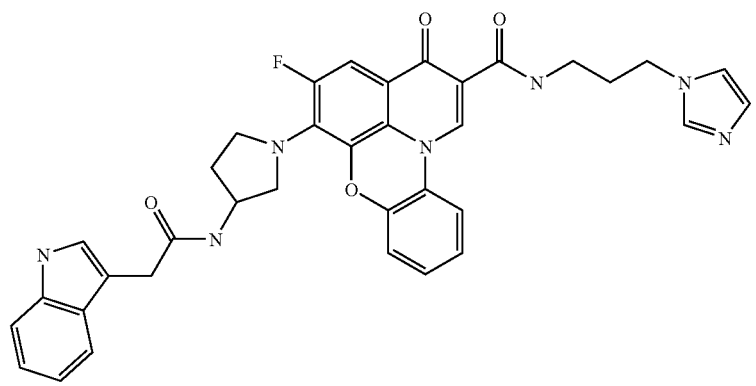
868
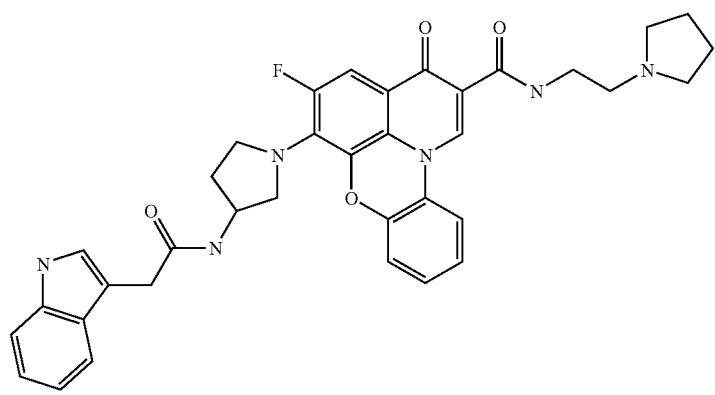

-continued
869
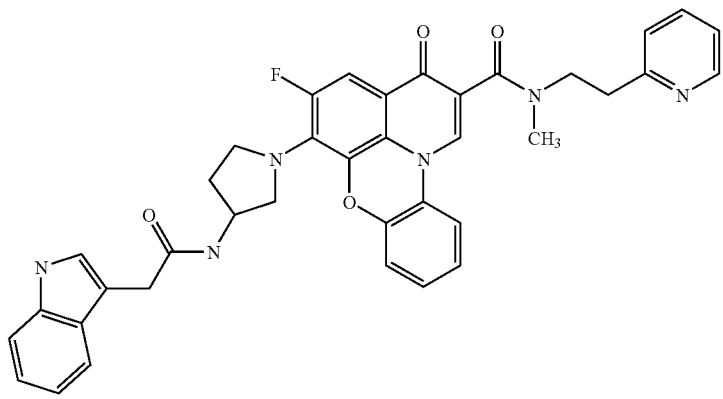
870
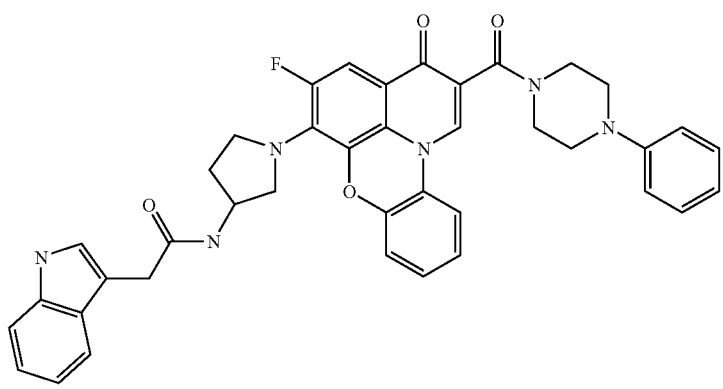
871
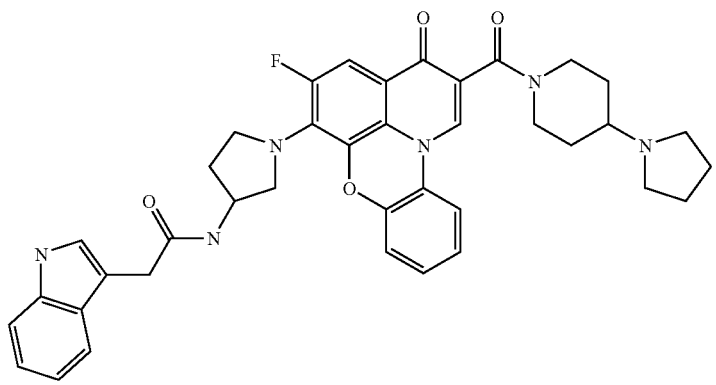
872
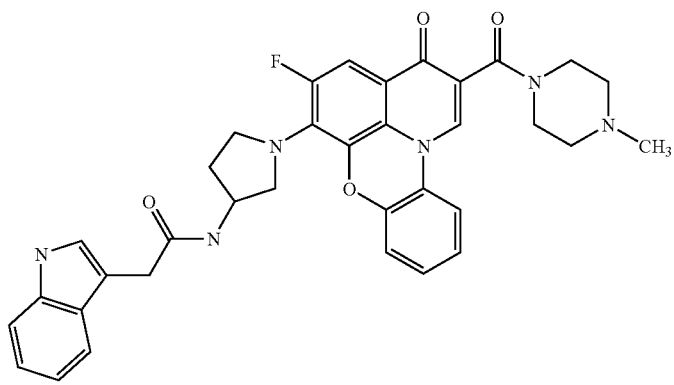

873 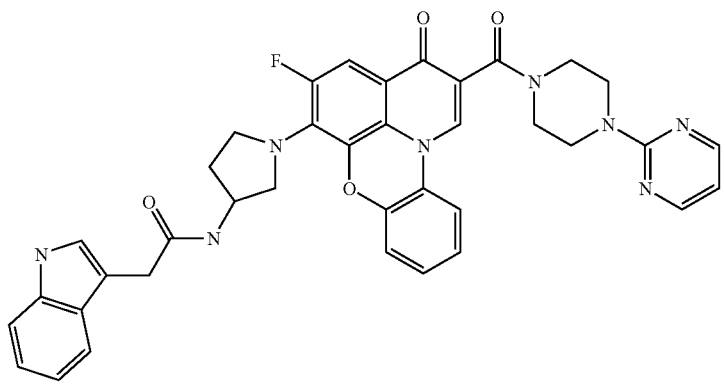
874 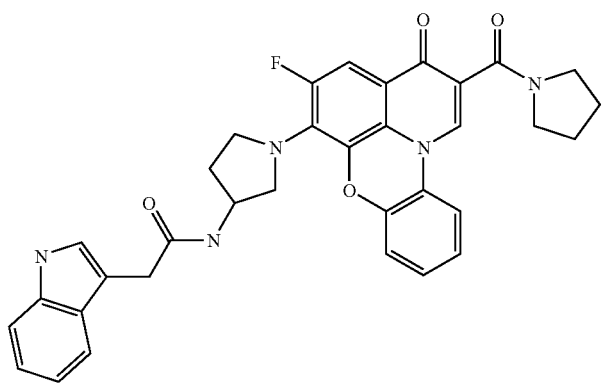
875 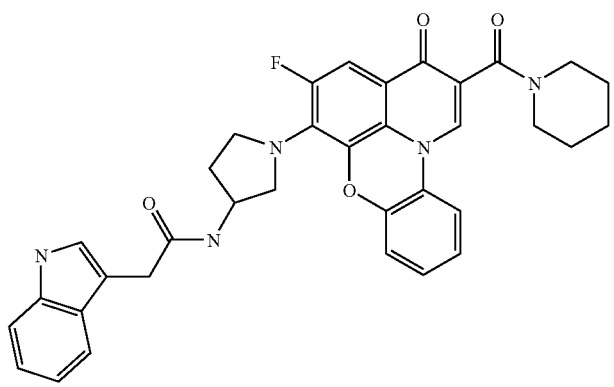
876 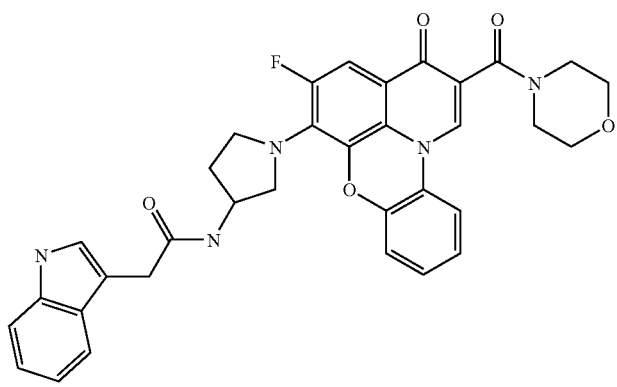

877 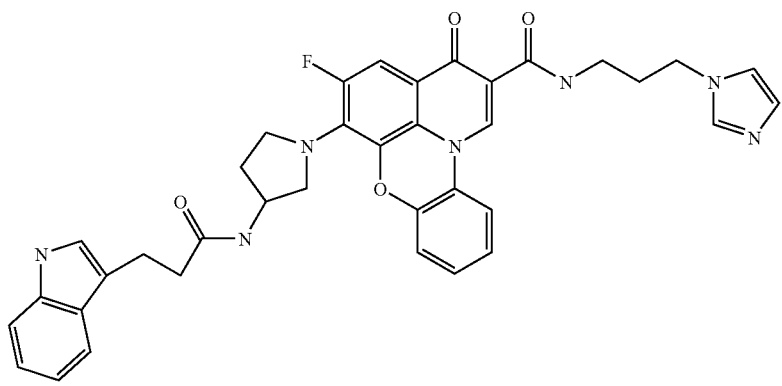
878 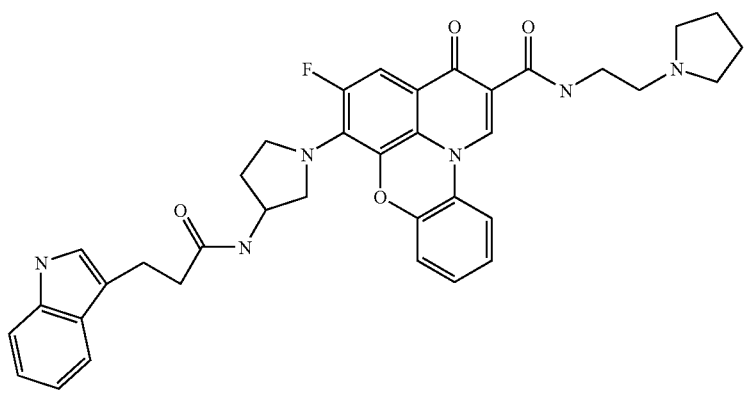
879 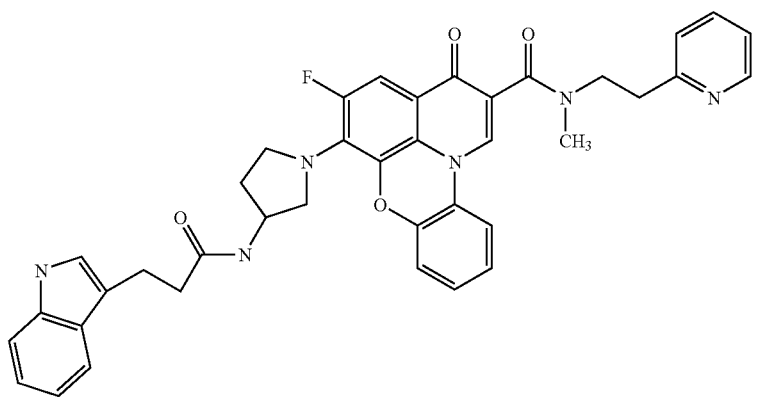
880 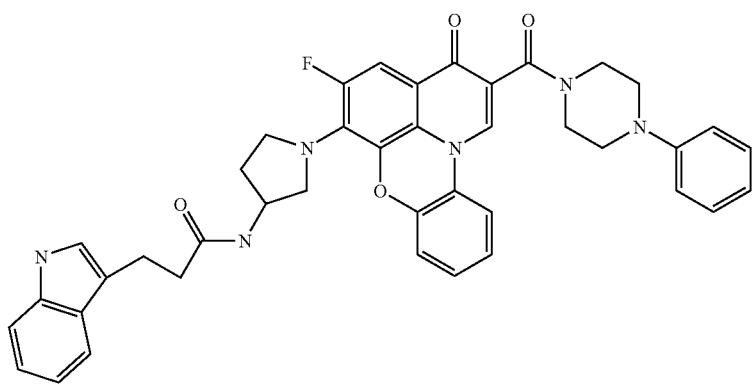

881
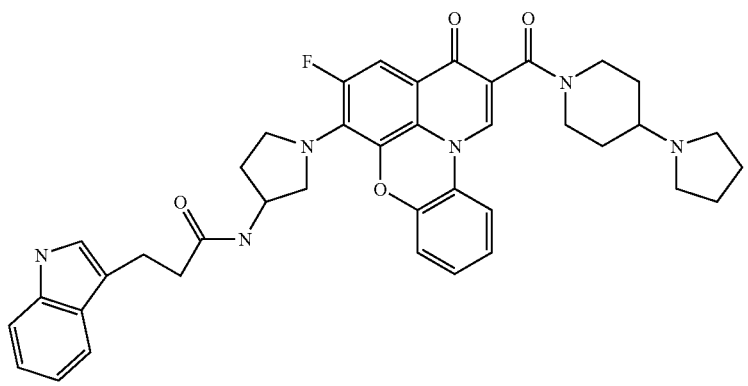
882
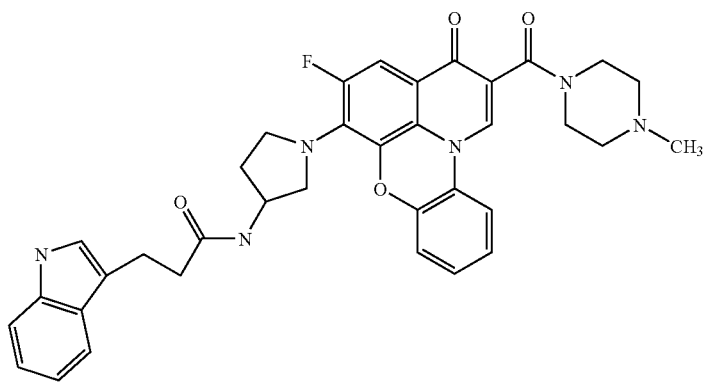
883
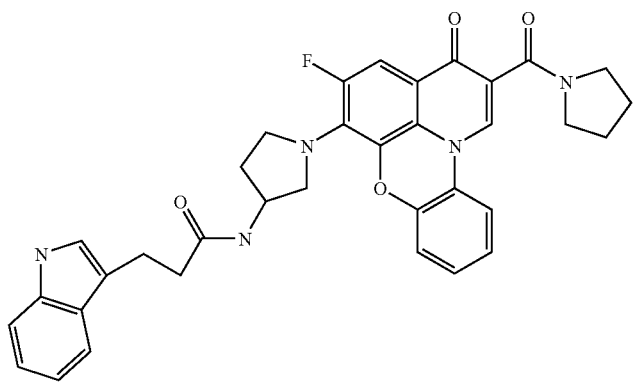
884
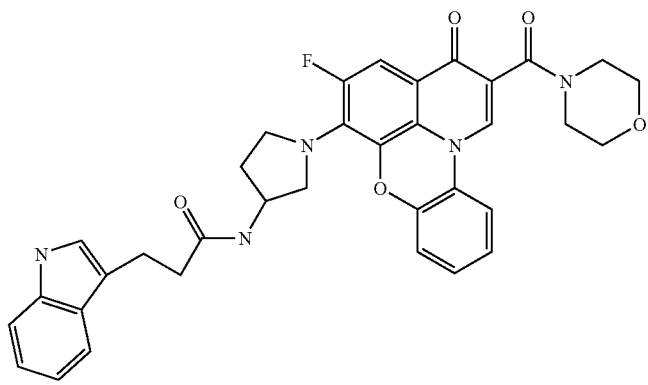

-continued
885
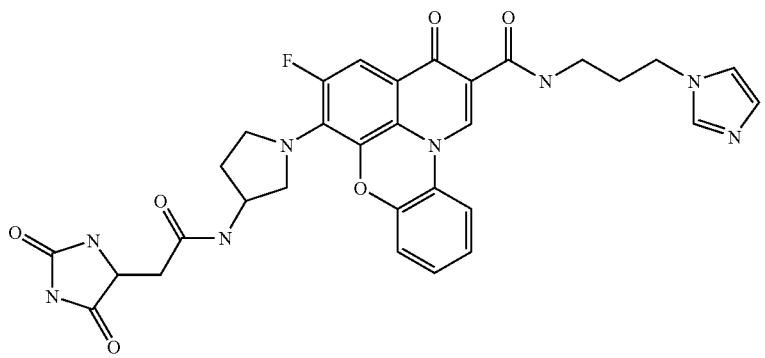
886
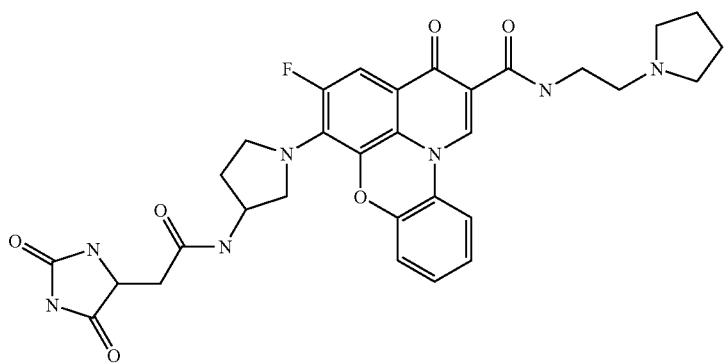
887
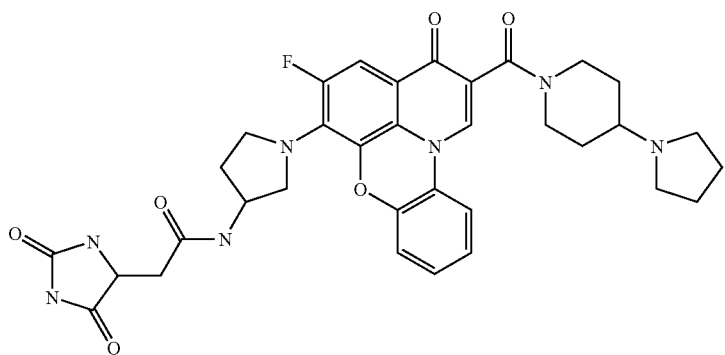
888
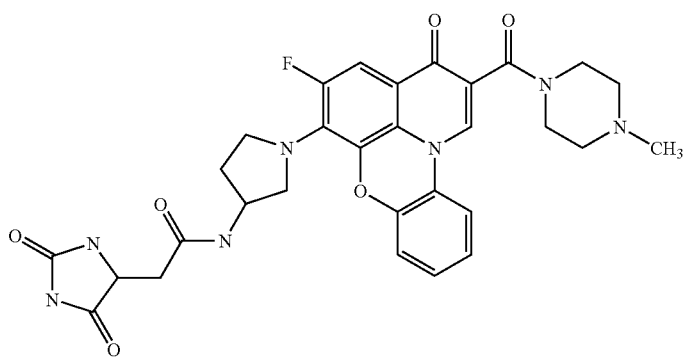

-continued
889
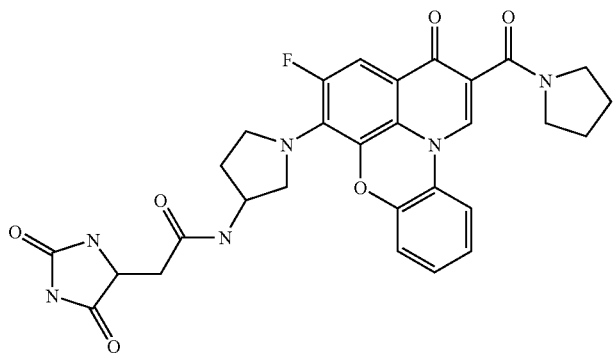
890
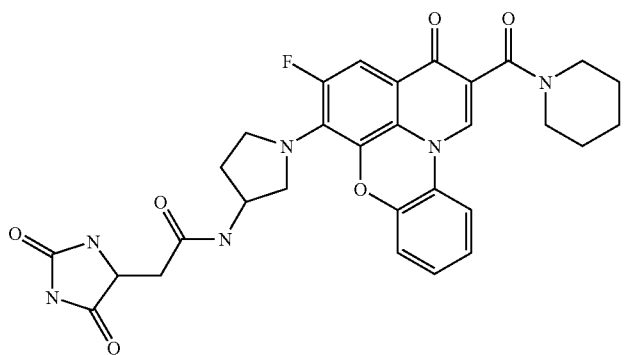
891
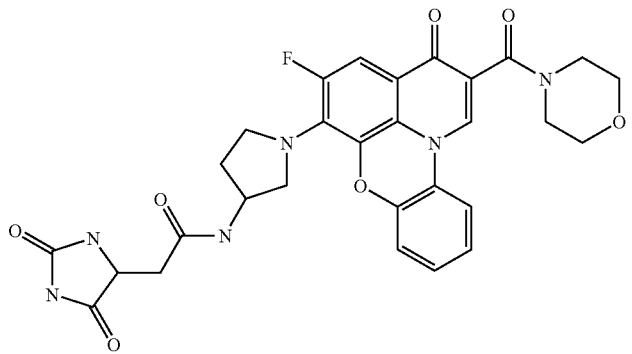
892
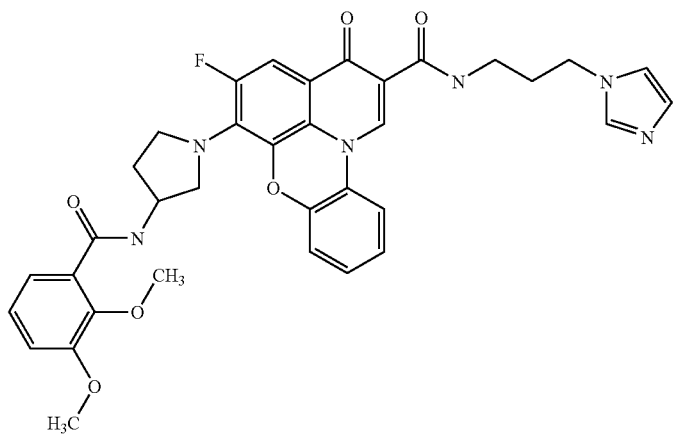

-continued
893
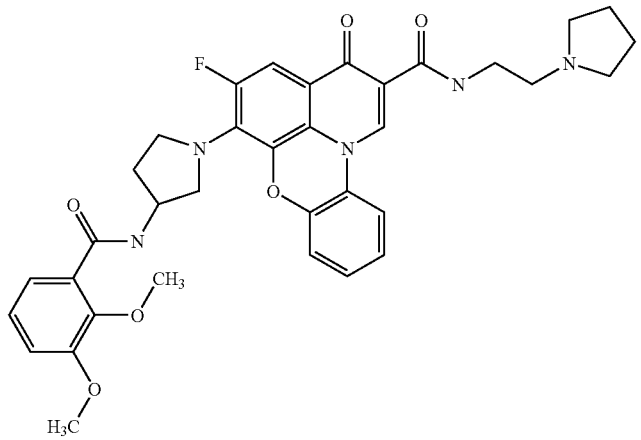
894
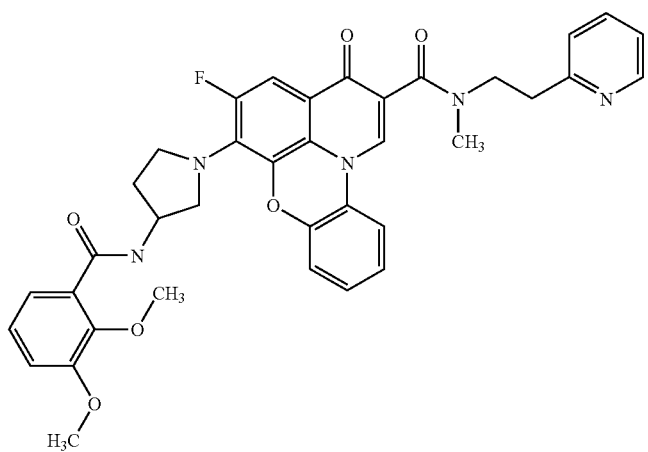
895
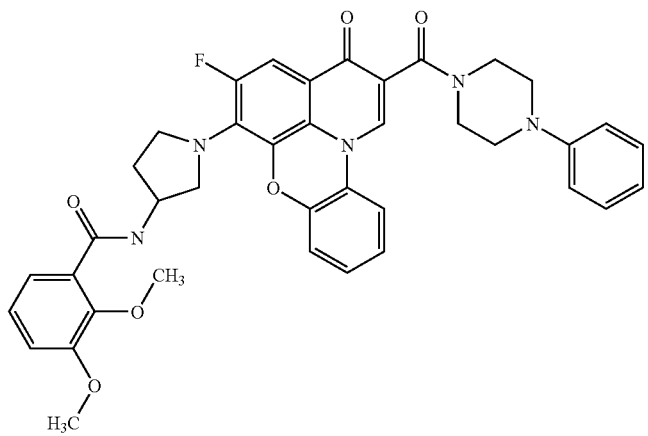

896 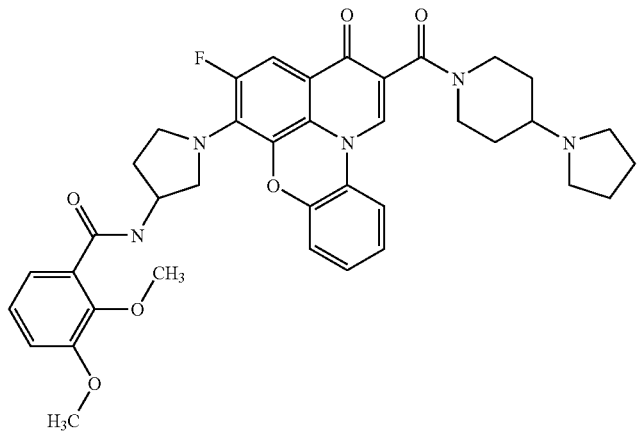
897 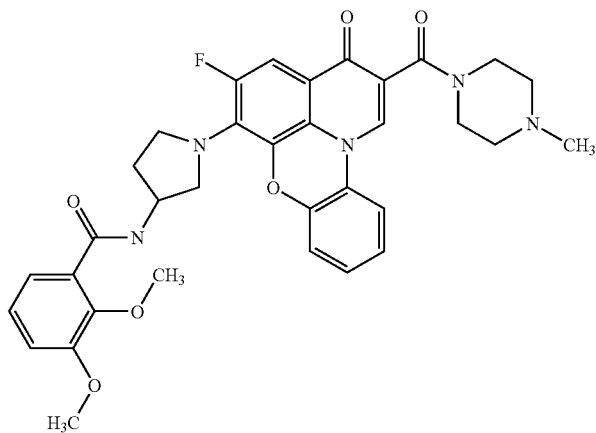
898 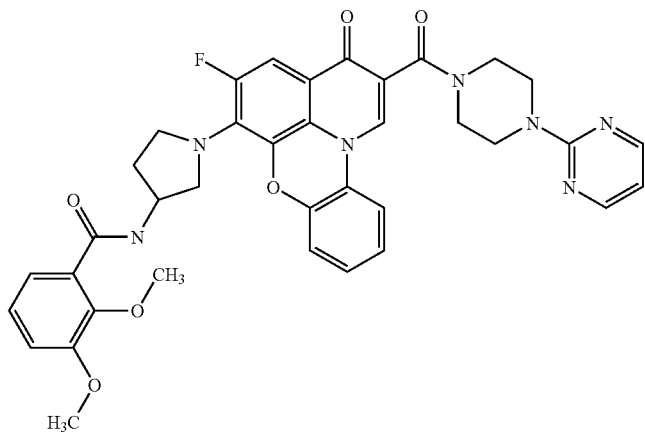

899
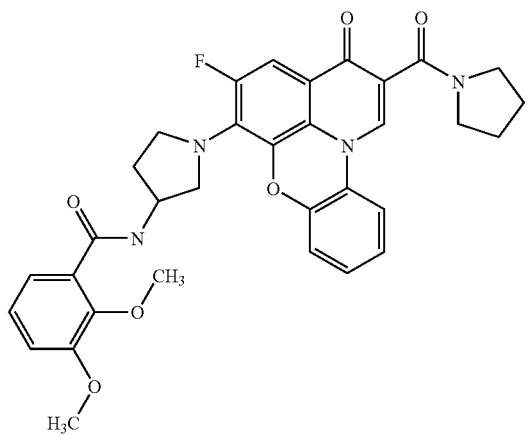
900
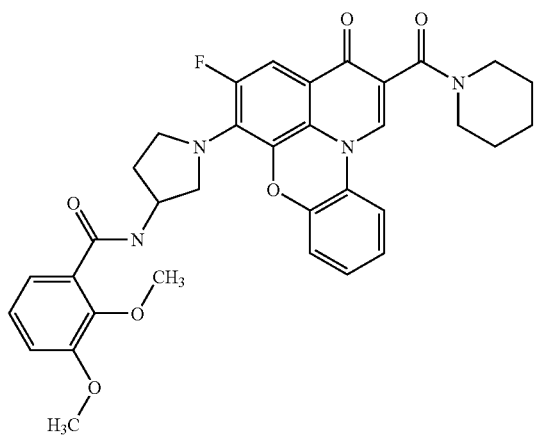
901
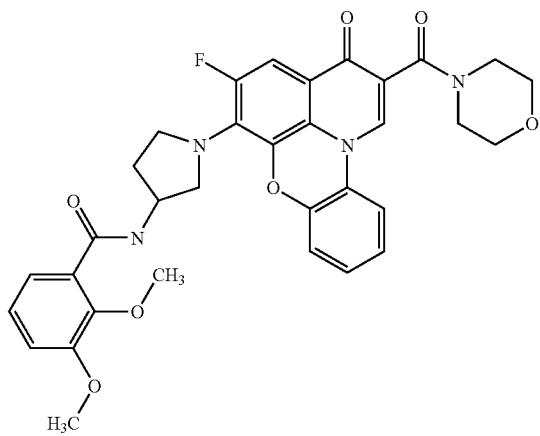

-continued
902
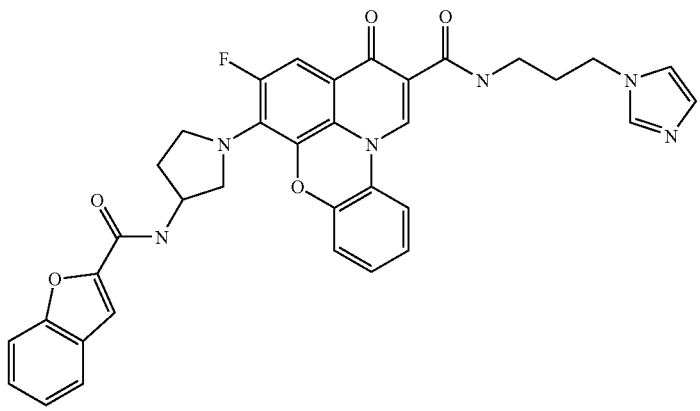
903
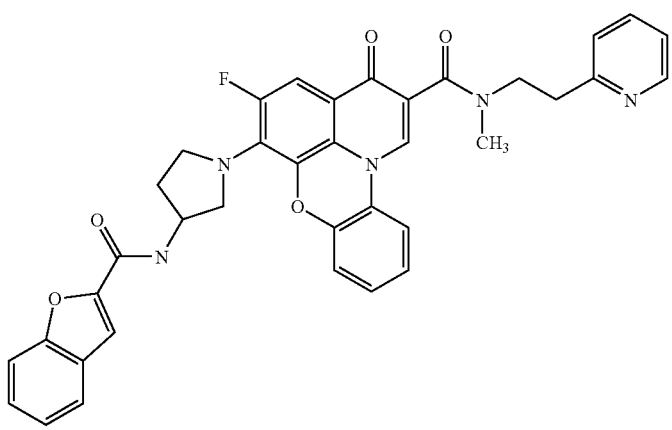
904
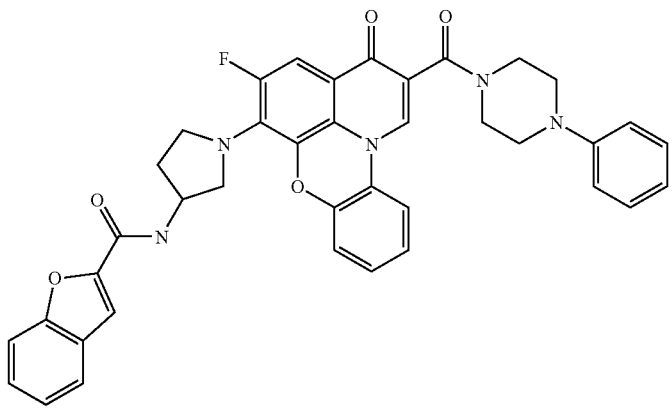

905 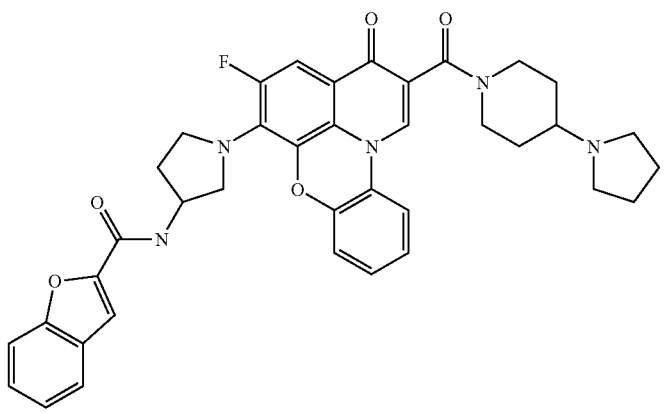
906 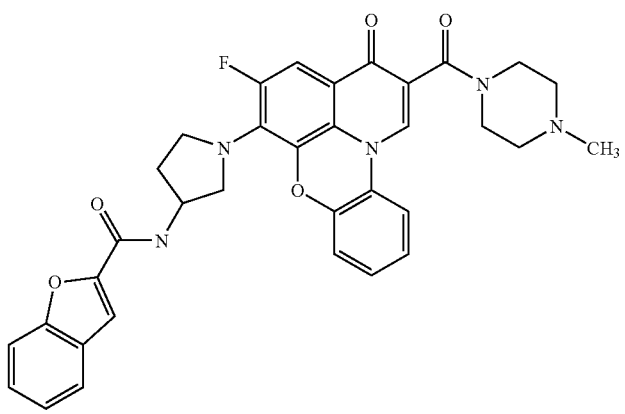
907 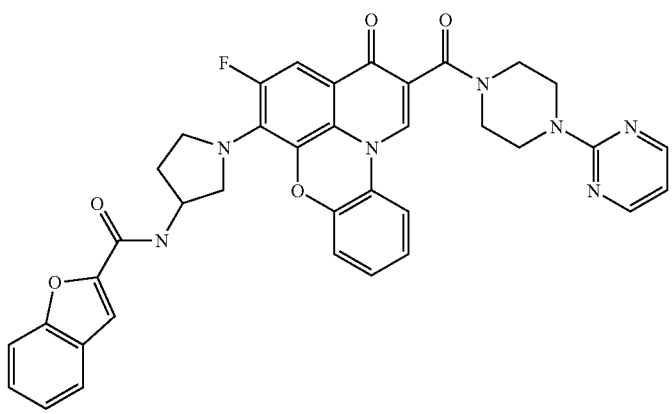
908 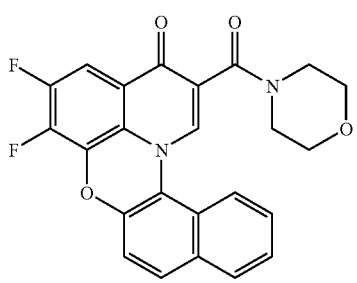

-continued
909
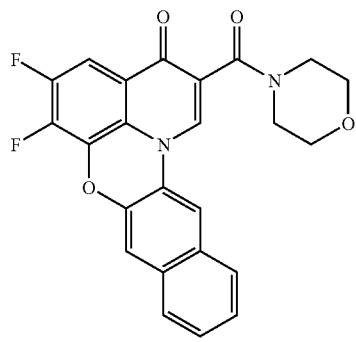
910
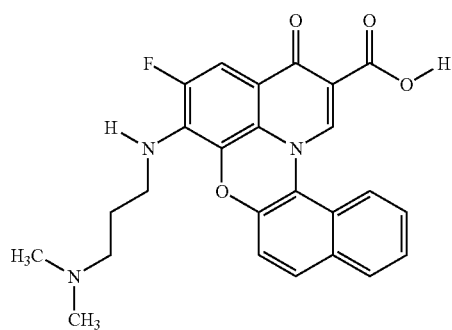
911
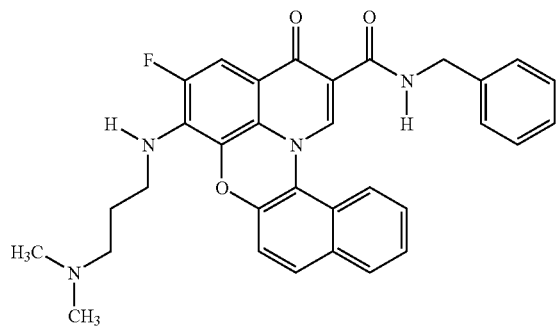
912
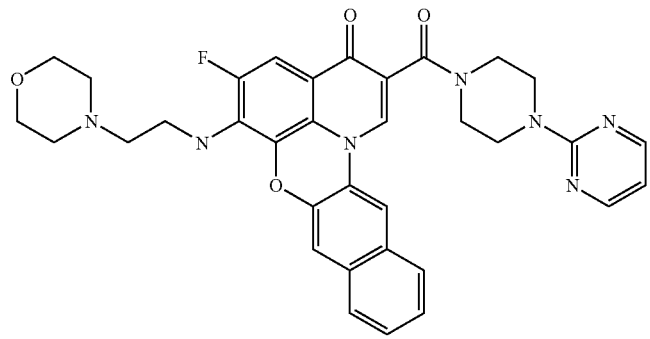

-continued
913
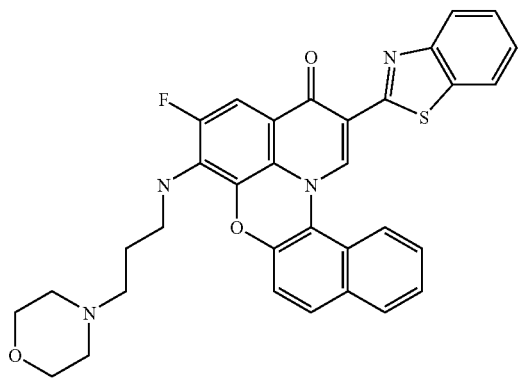
914
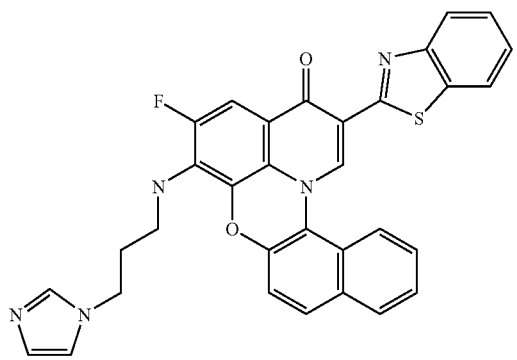
915
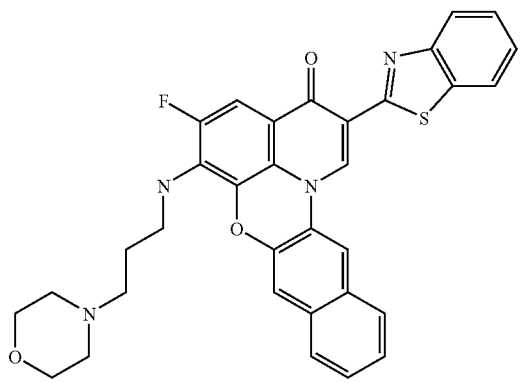
916
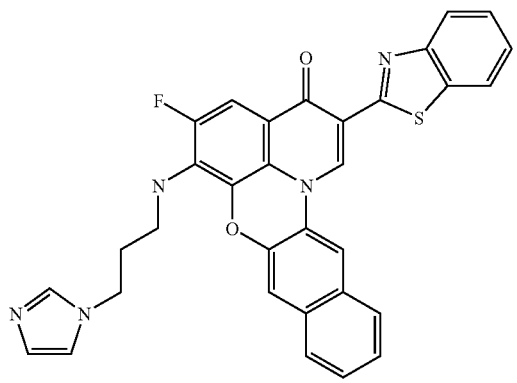

-continued
917
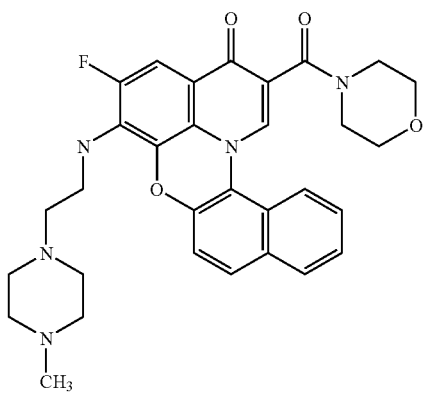
918
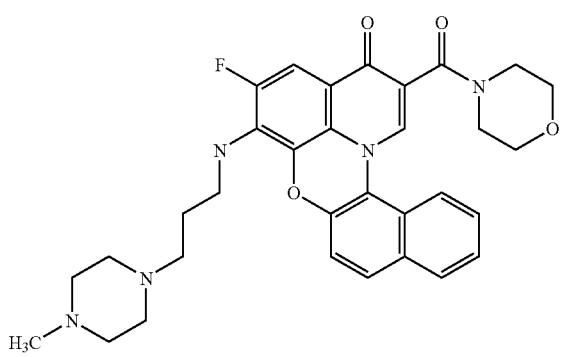
919
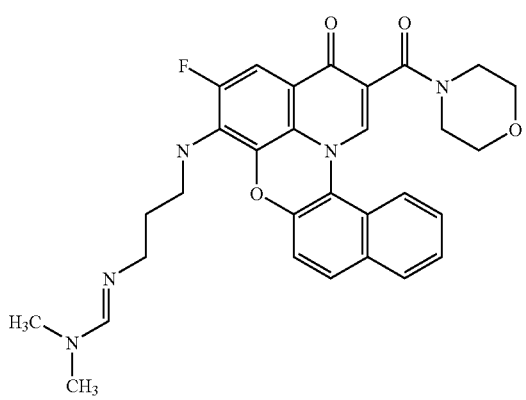
920
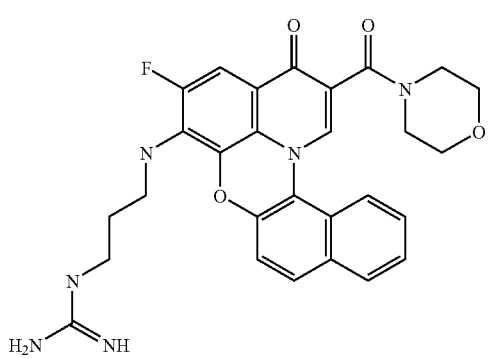

-continued
921
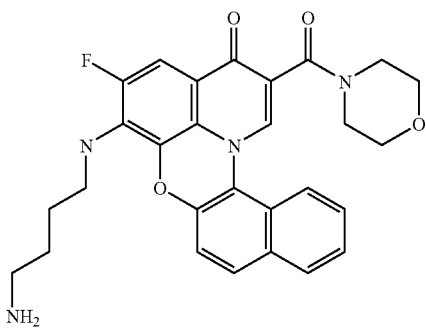
922
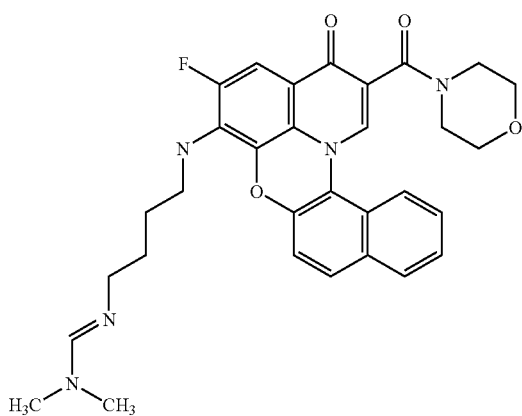
923
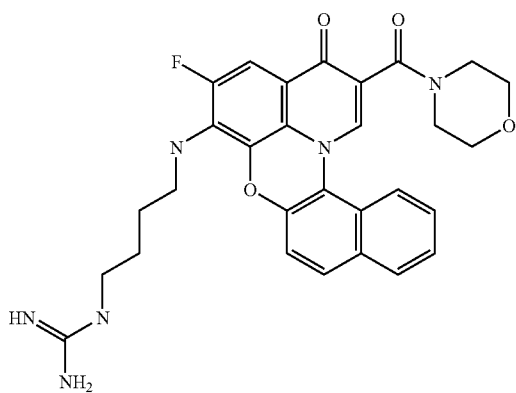
924
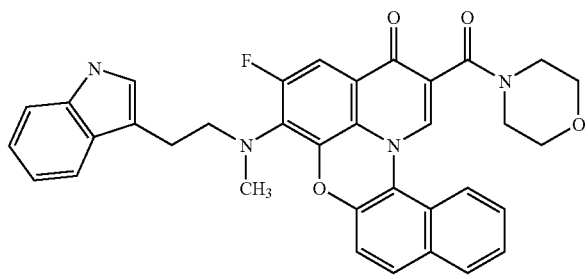

-continued
925
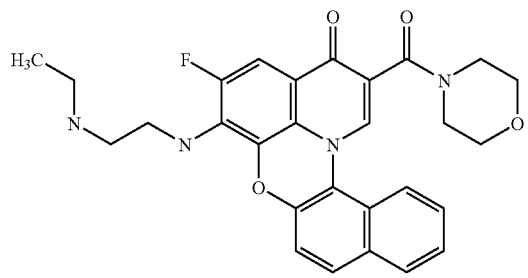
926
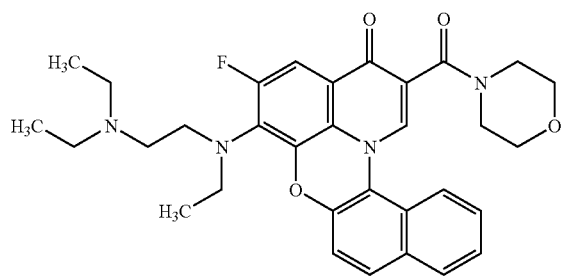
927
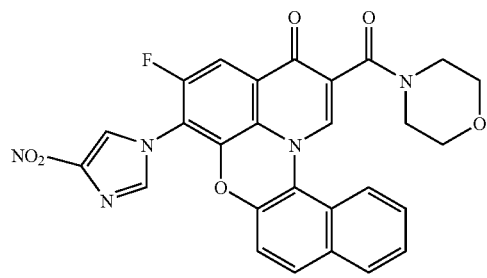
928
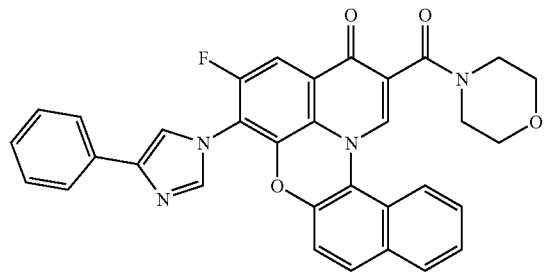
929
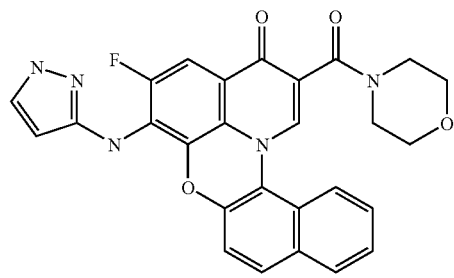

-continued
930
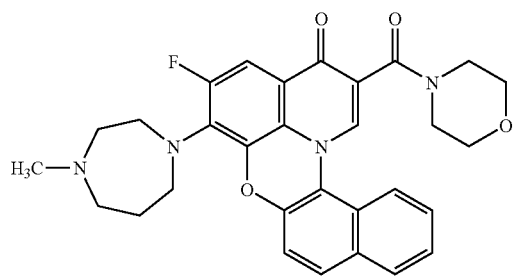
931
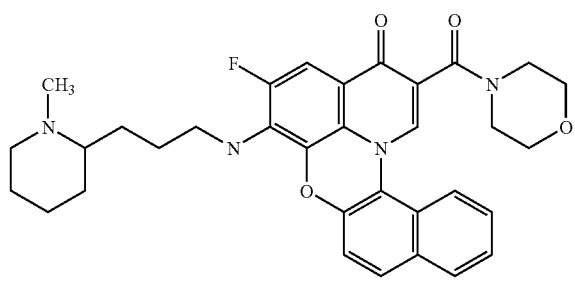
932
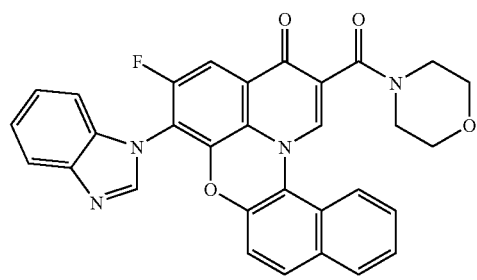
933
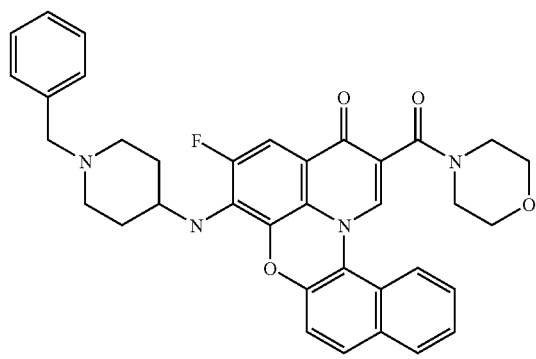
934
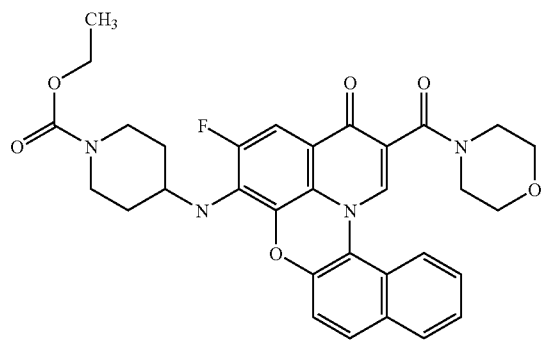

935 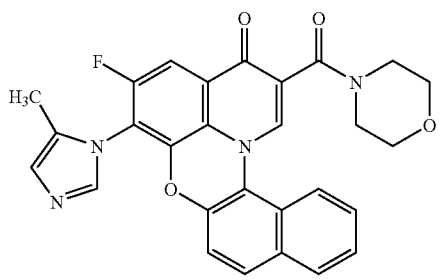
936 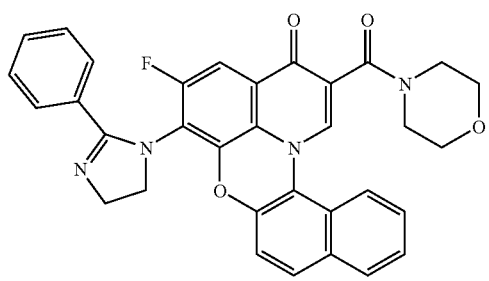
937 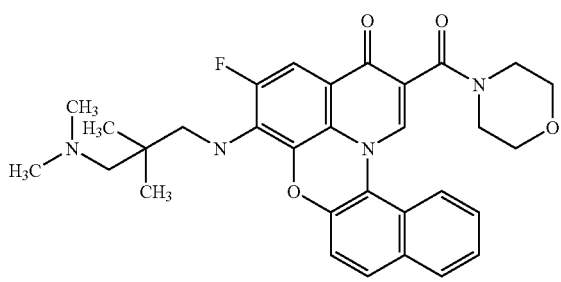
938 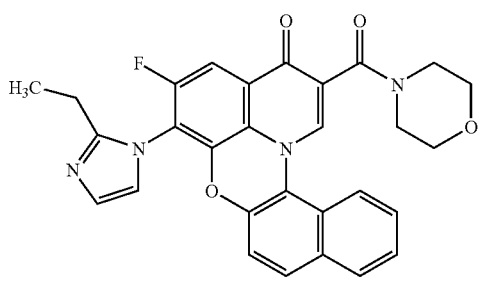
939 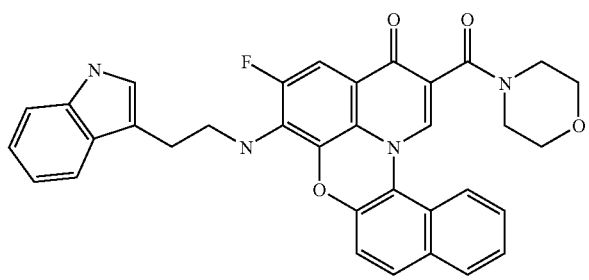

-continued
940
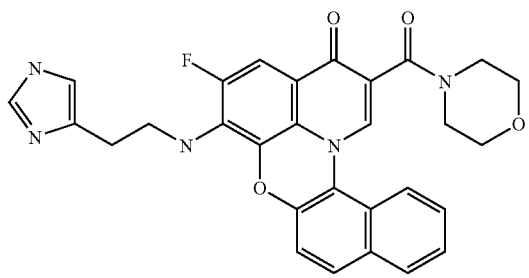
941
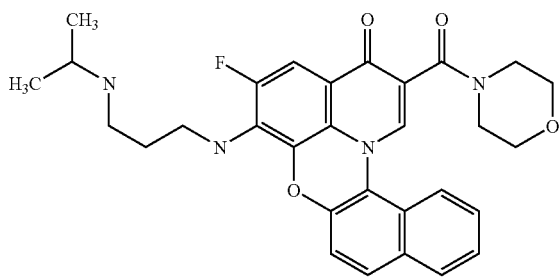
942
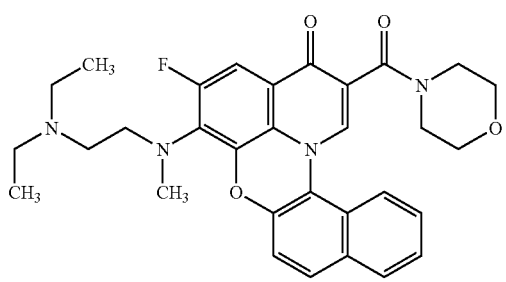
943
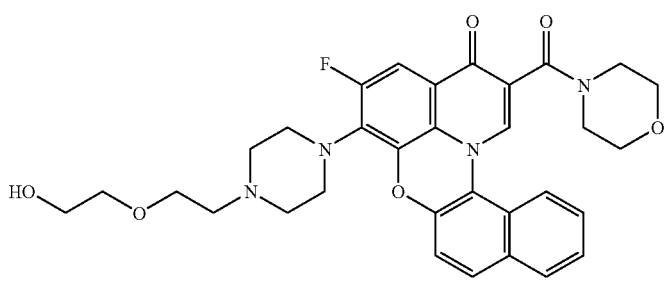
944
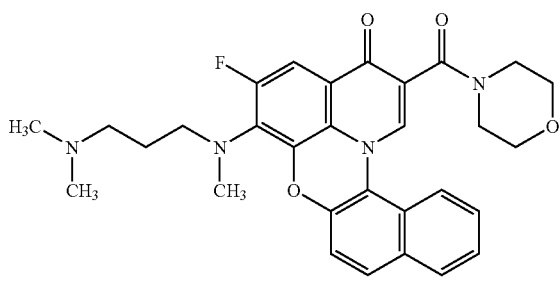

945 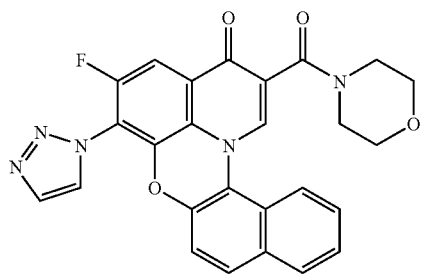
946 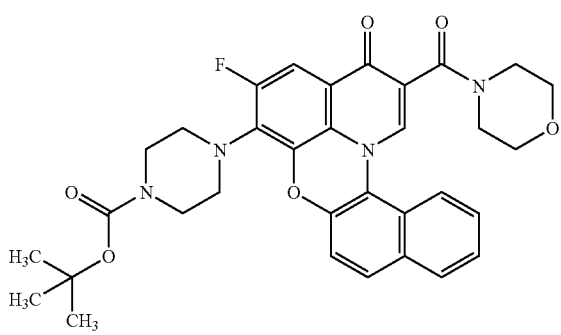
947 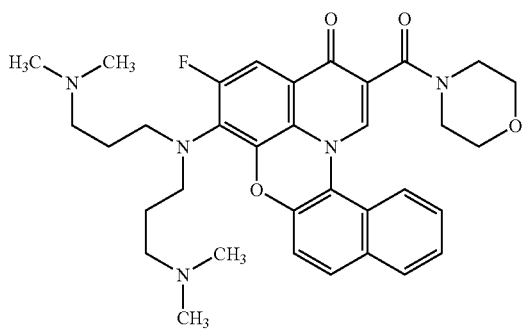
948 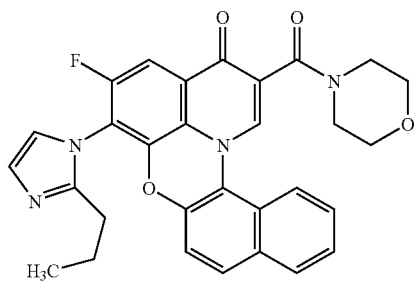
949 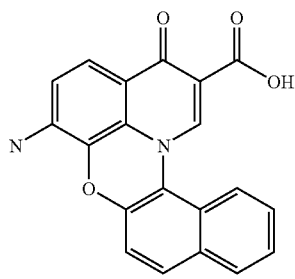

950 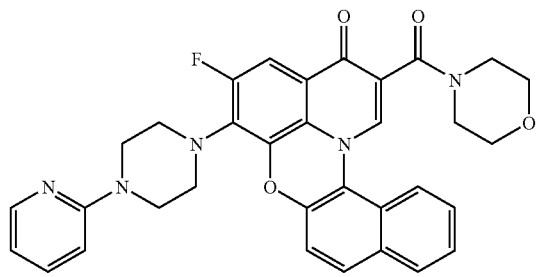
951 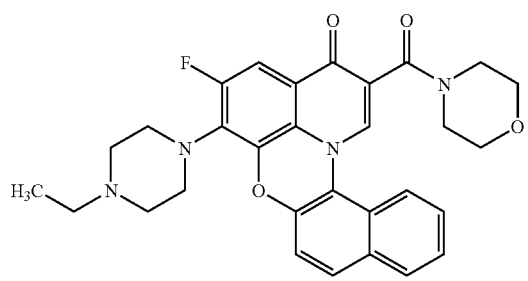
952 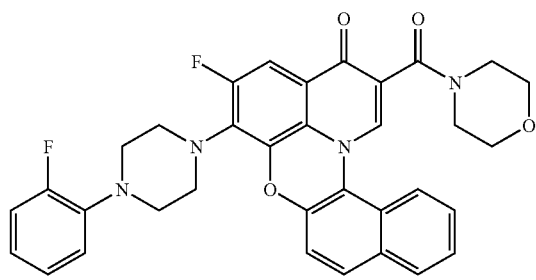
953 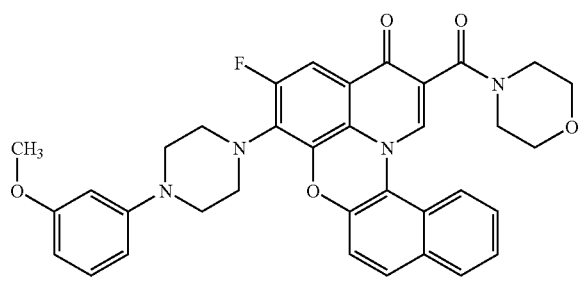
954 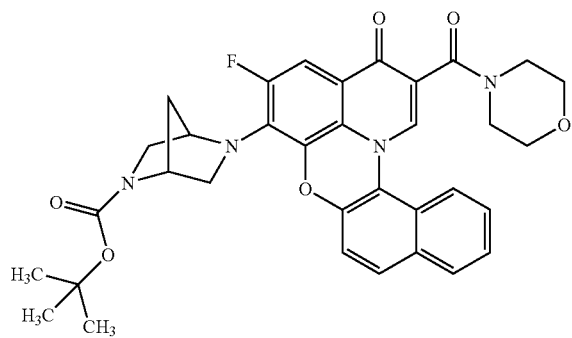

-continued
955
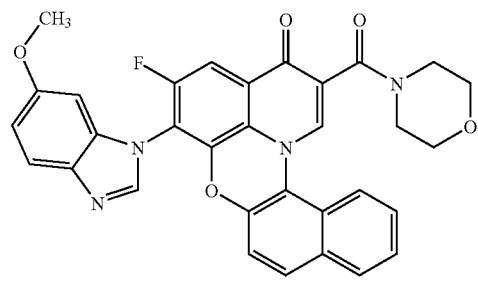
956
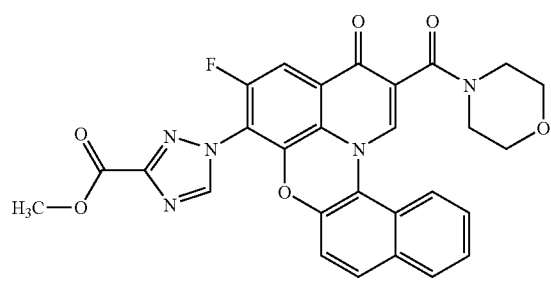
957
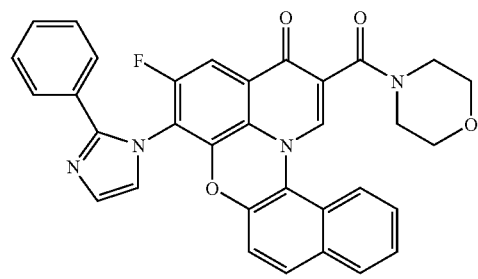
958
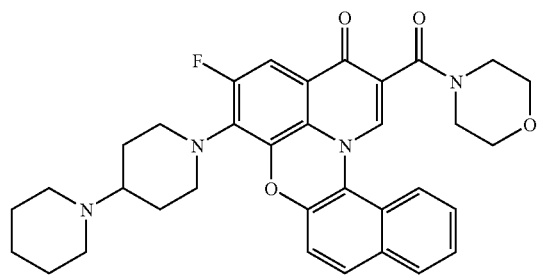
959 Chiral
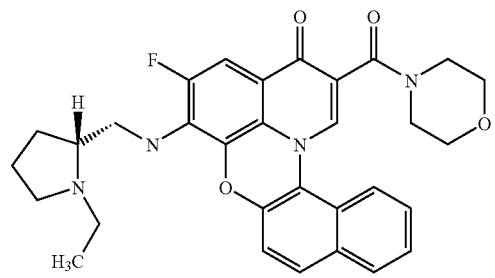

-continued
| | |
|---|---|
| 960 | 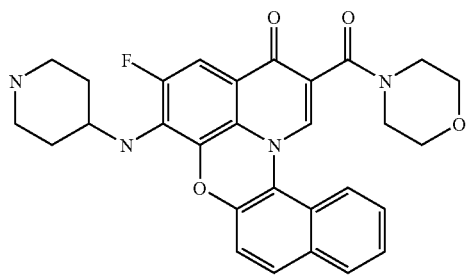 |
| 961 | 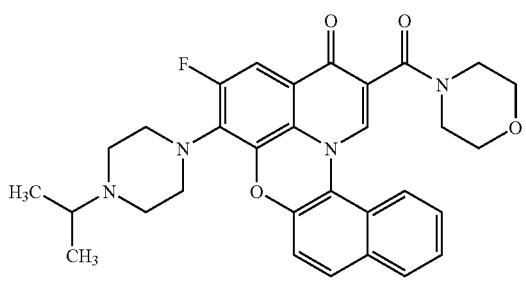 |
| 962 | 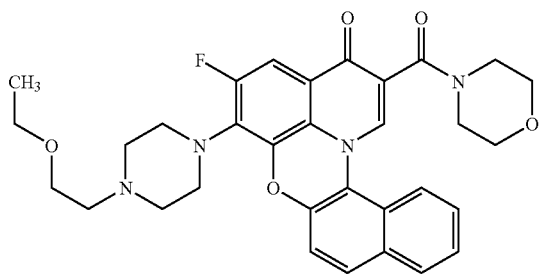 |
| 963 | 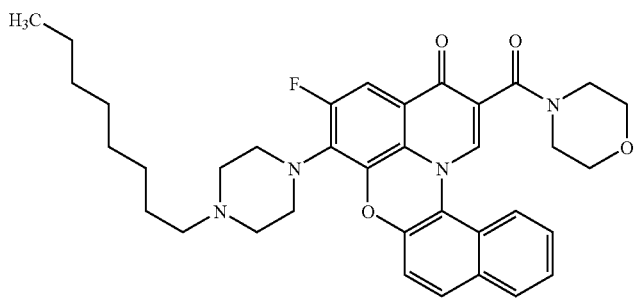 |
| 964 | 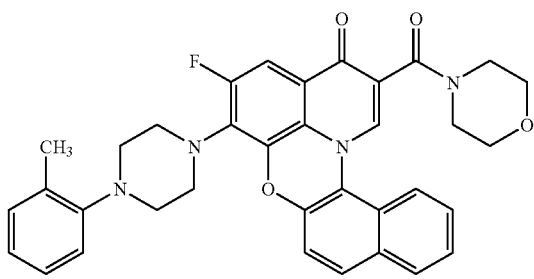 |

-continued
965
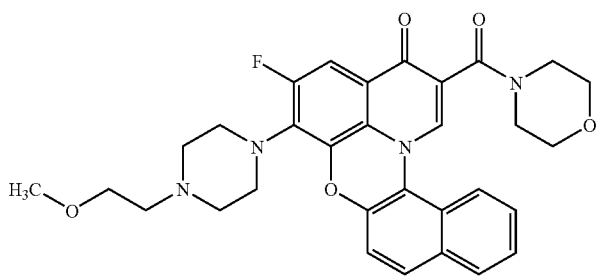
966
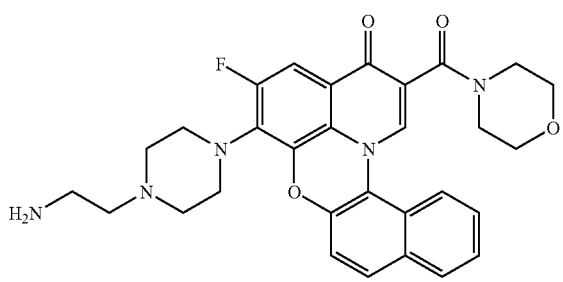
967
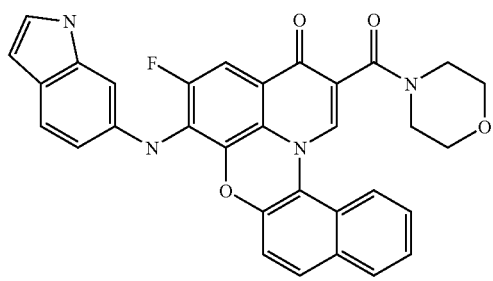
968
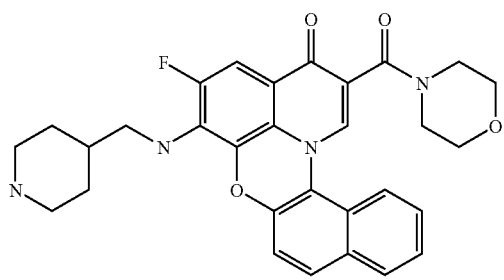
969
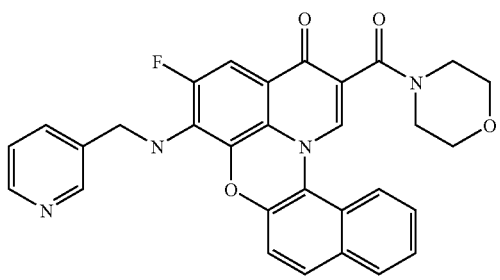

-continued
970
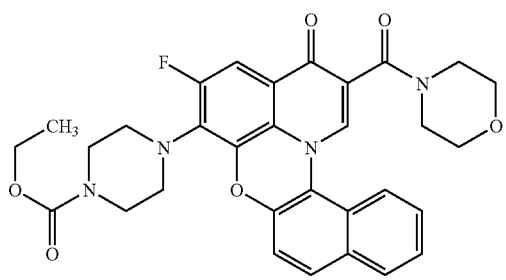
971
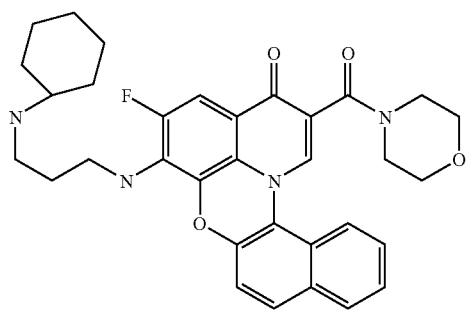
972
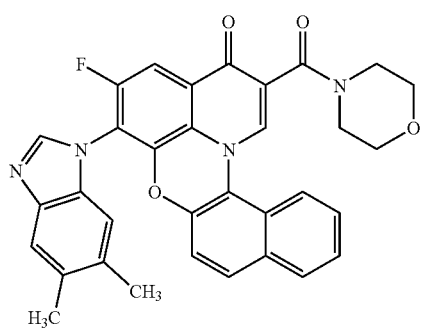
973
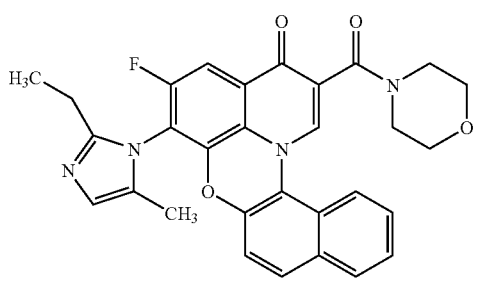
974
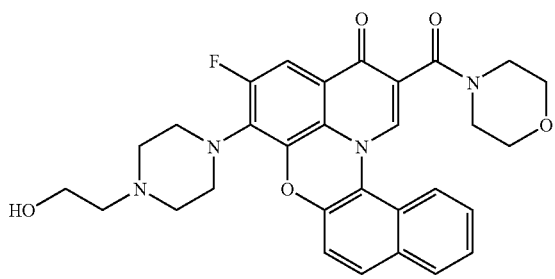

-continued
975
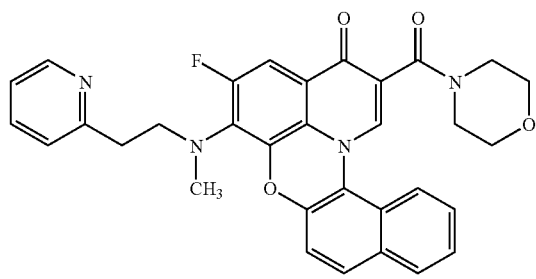
976
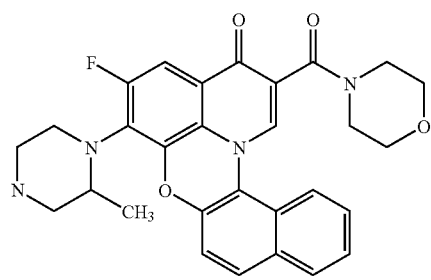
977
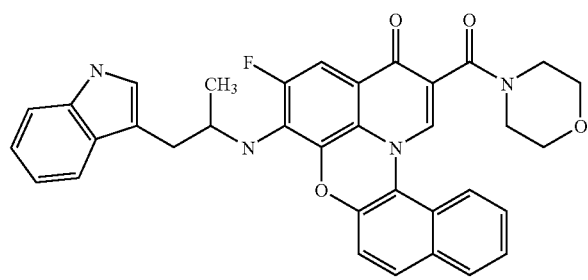
978
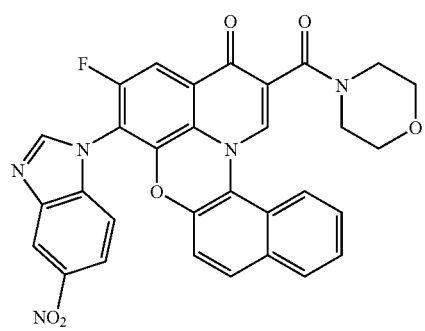
979
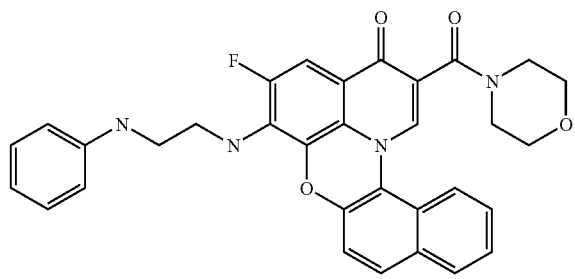

980 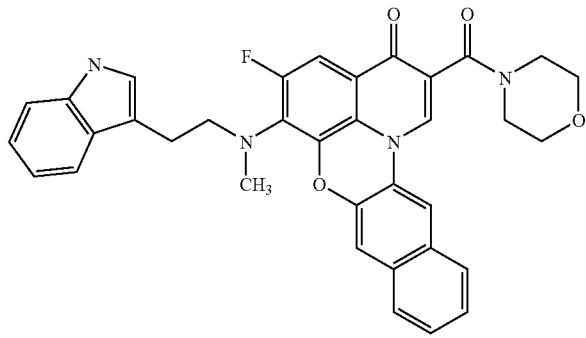
981 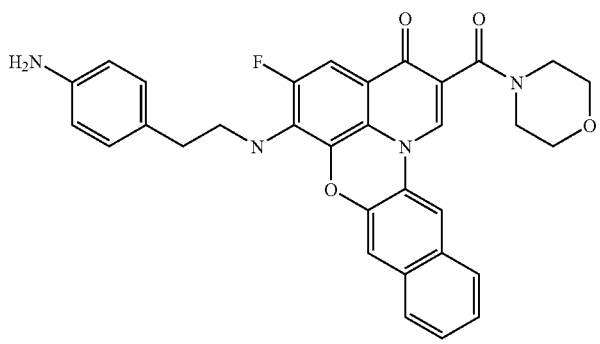
982 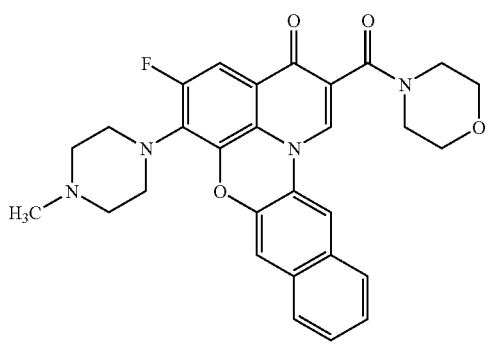
983 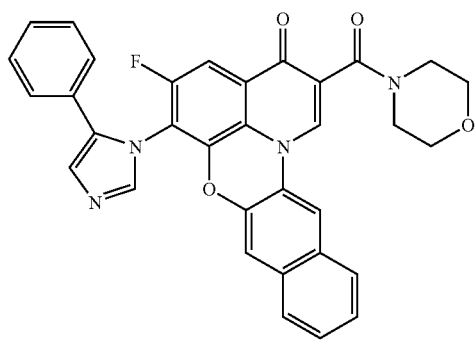

984 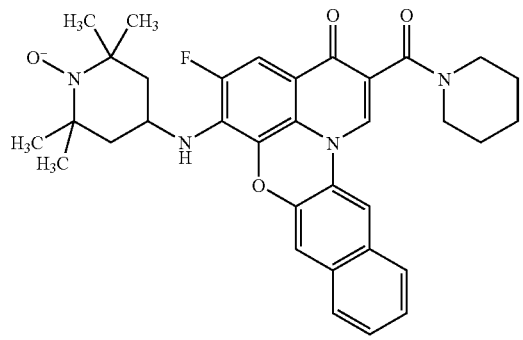
985 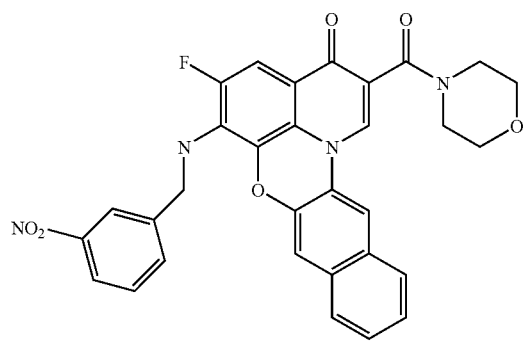
986 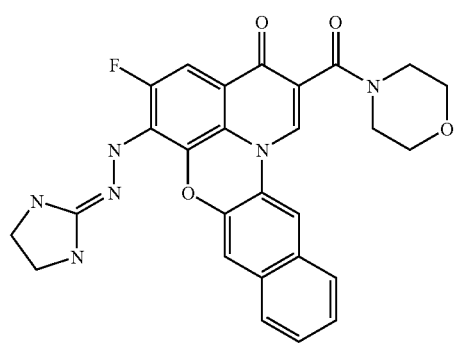
987 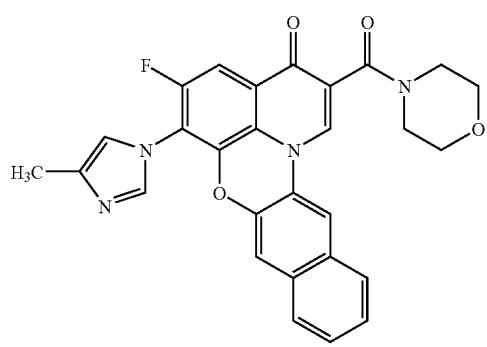

-continued
988
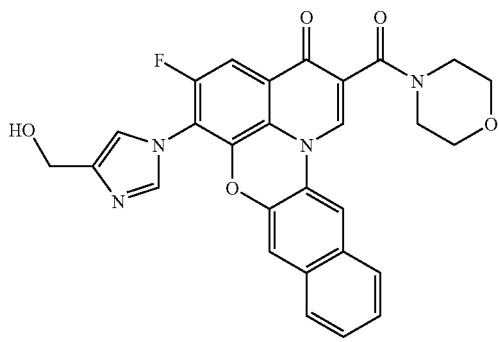
989
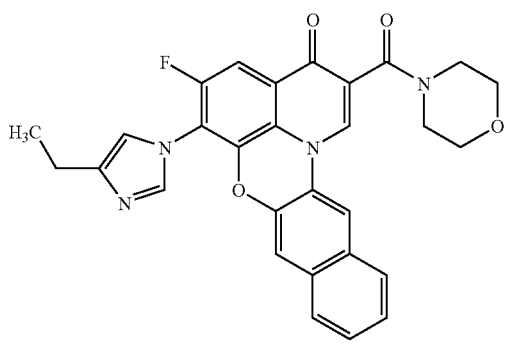
990
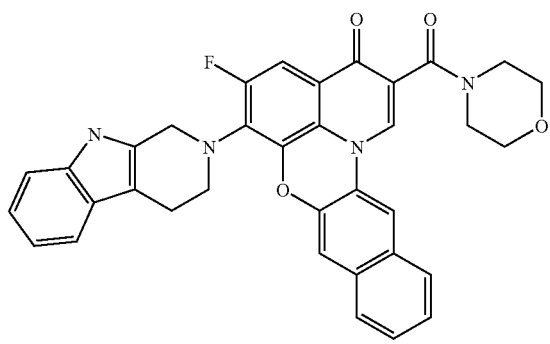
991
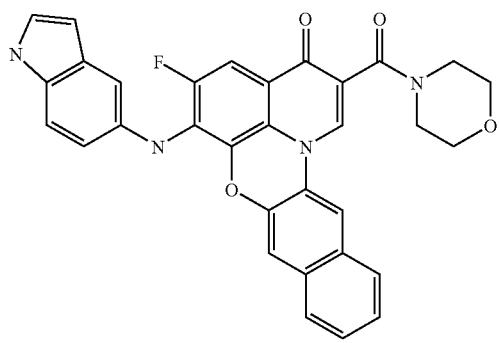

992 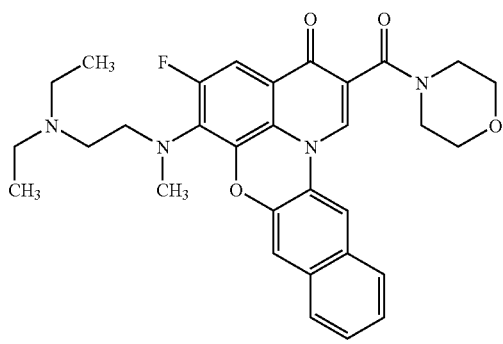
993 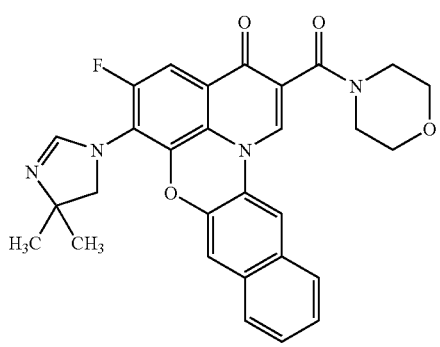
994 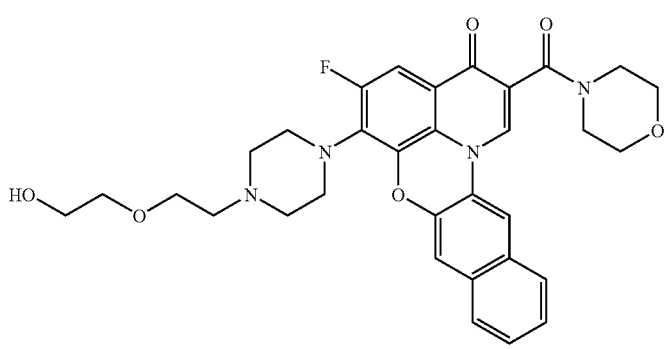
995 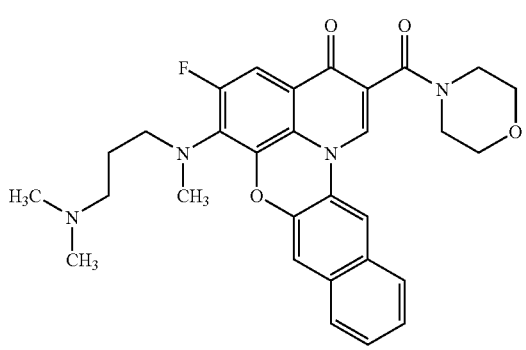

-continued
996
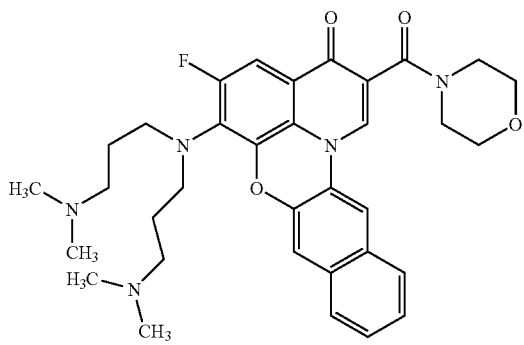
997
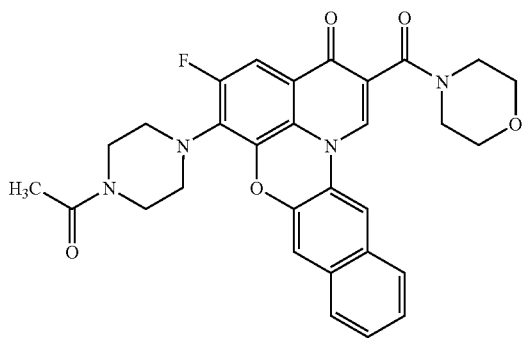
998 Chiral
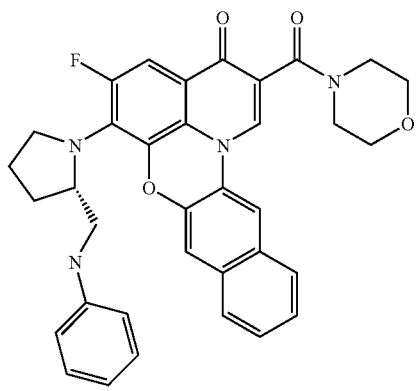
999
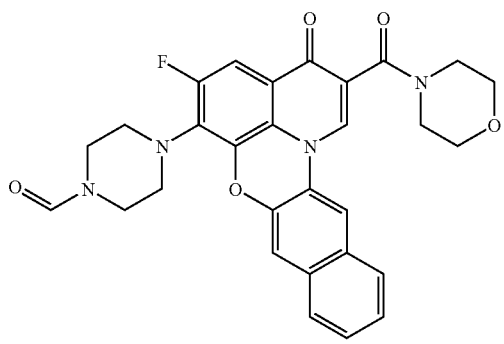

1000
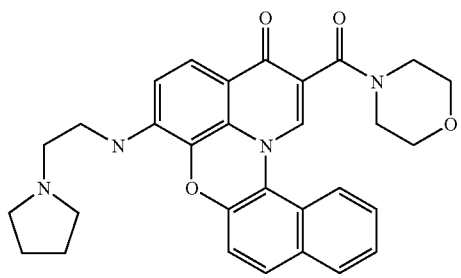
1001
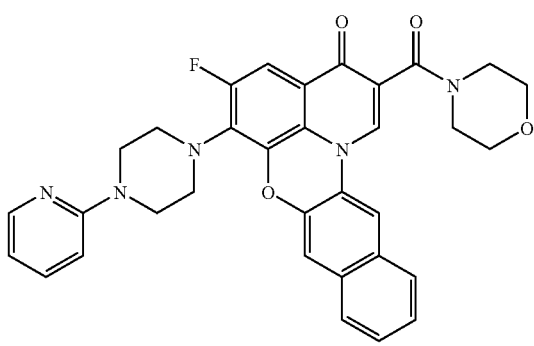
1002
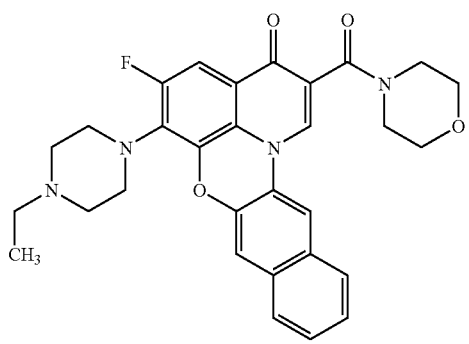
1003
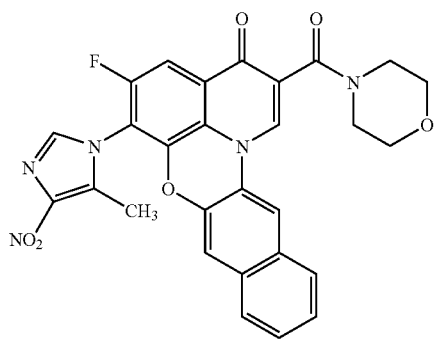

-continued
1004
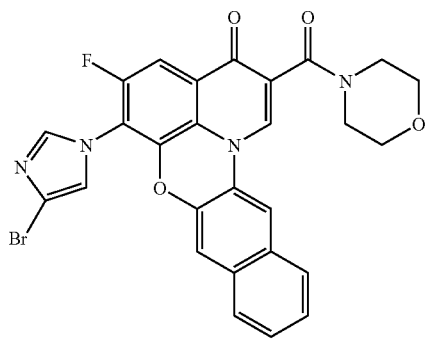
1005
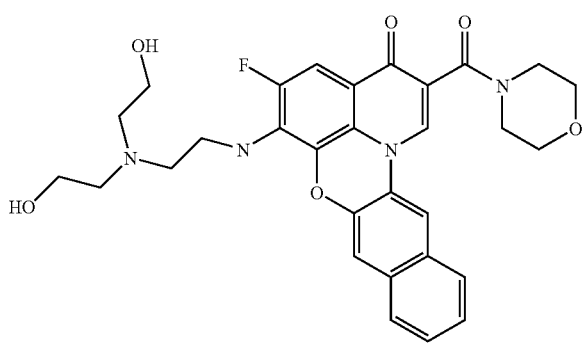
1006
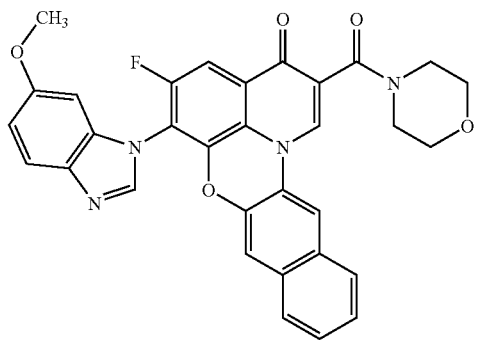
1007
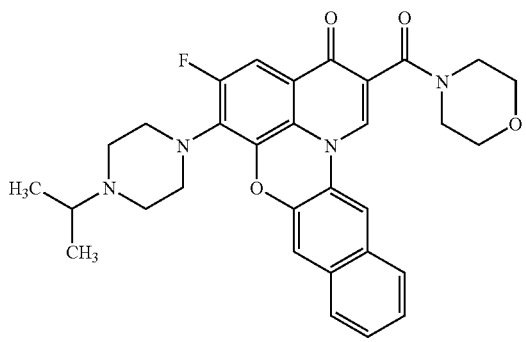

-continued
1008
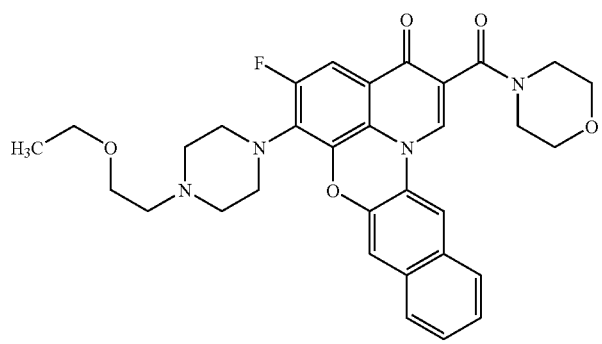
1009
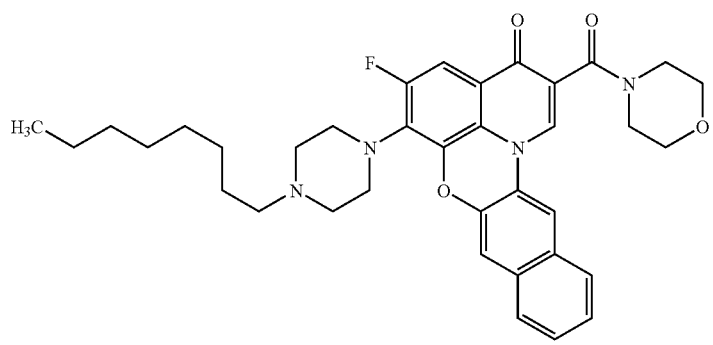
1010
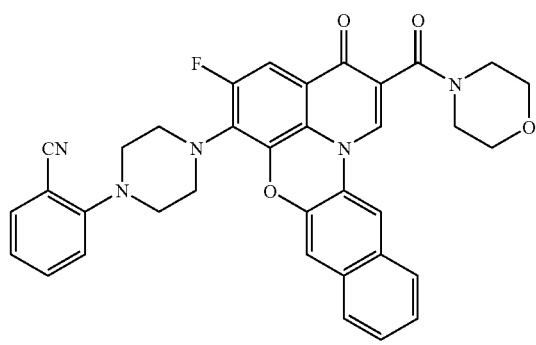
1011
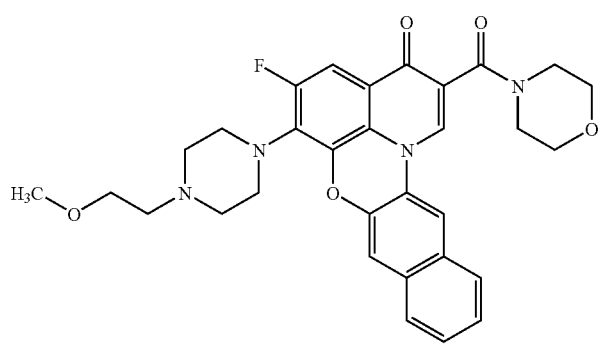

-continued
1012 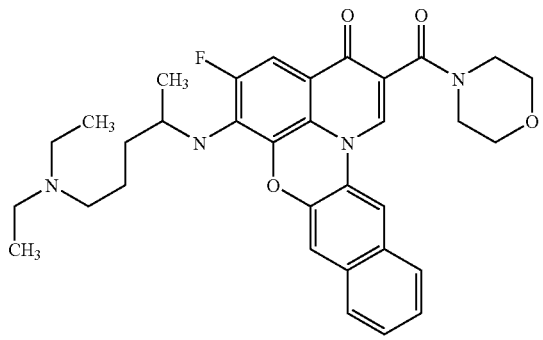
1013 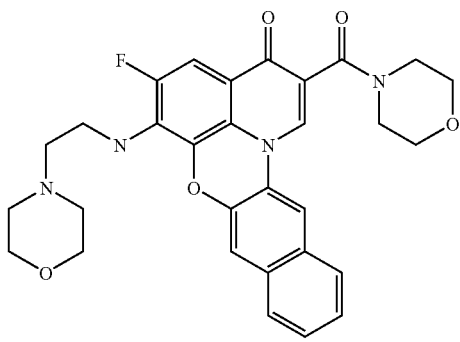
1014 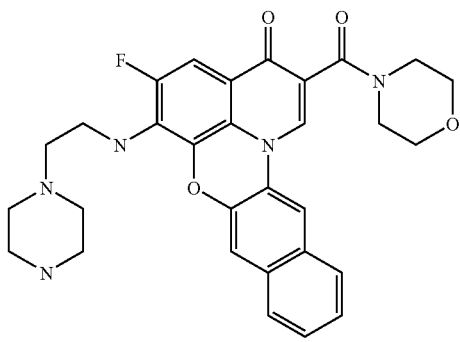
1015 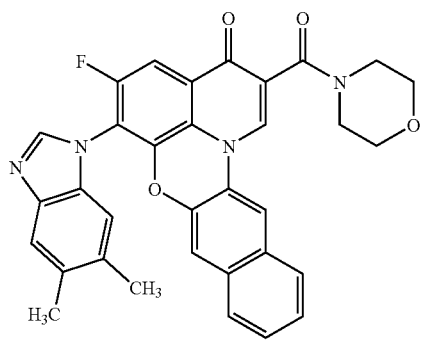

-continued
1016
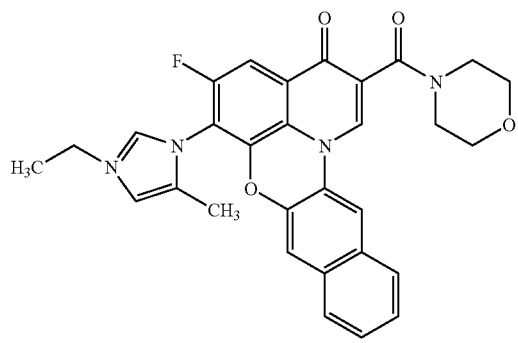
1017
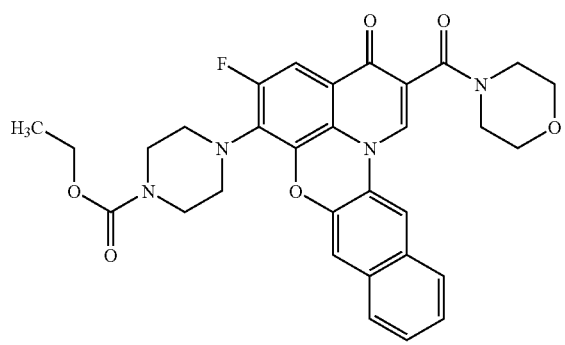
1018
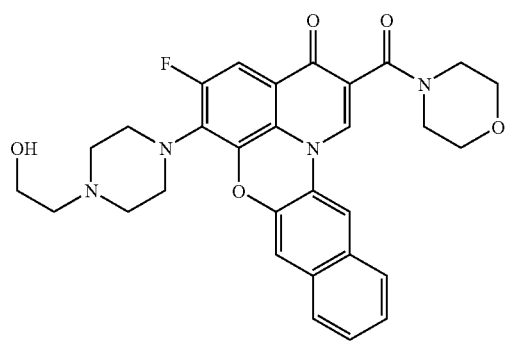
1019
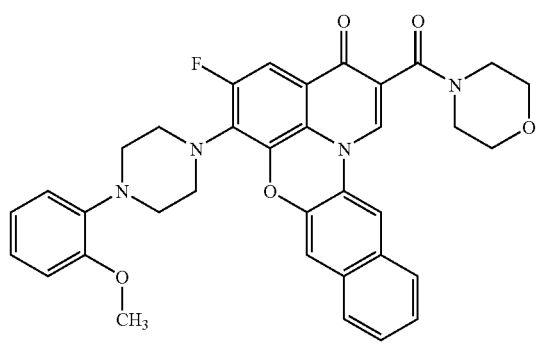

1020
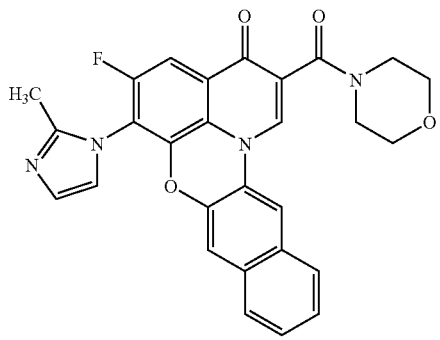
1021
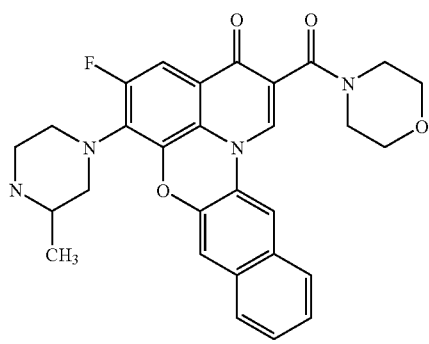
1022
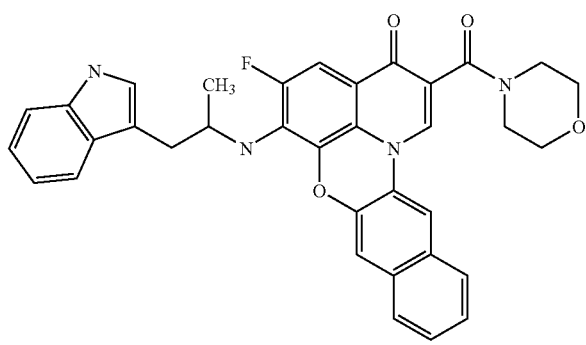
1023
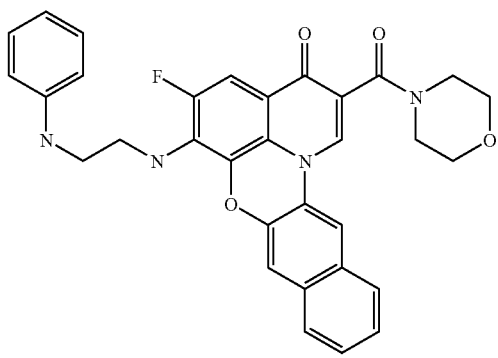

-continued
1024 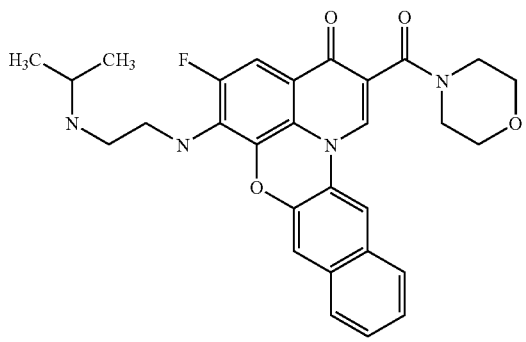
1025 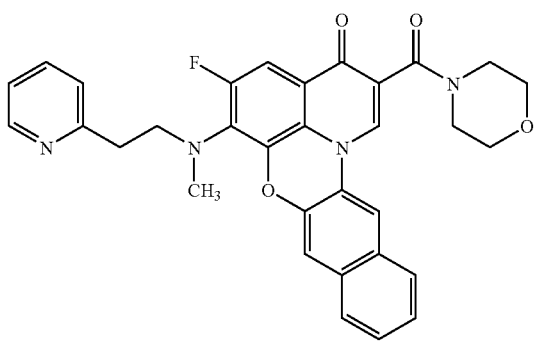
1026 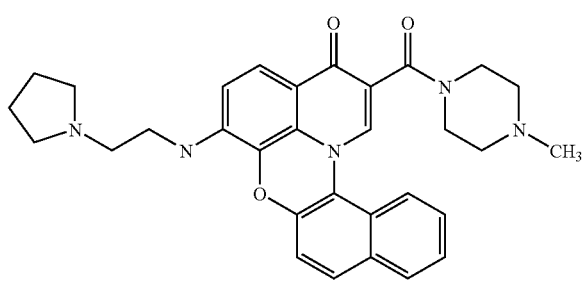
1027 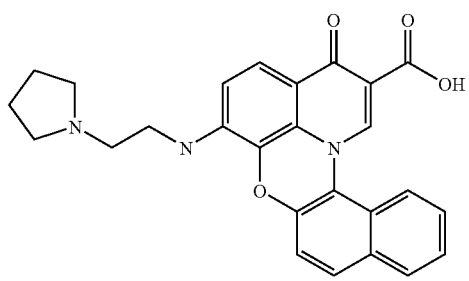
1028 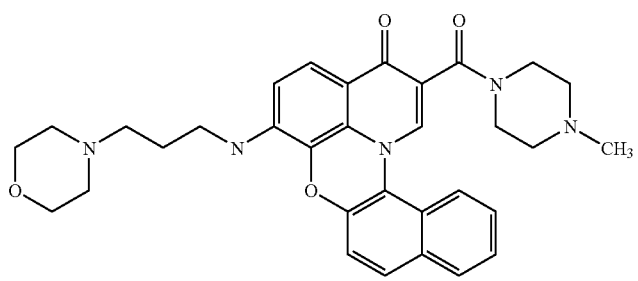

-continued
1029
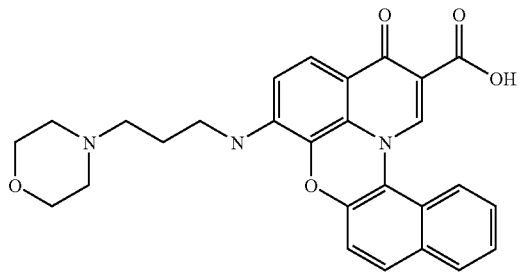
1030
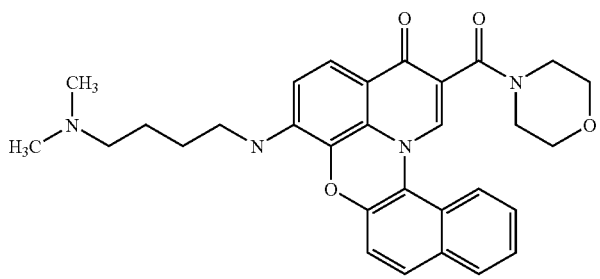
1031
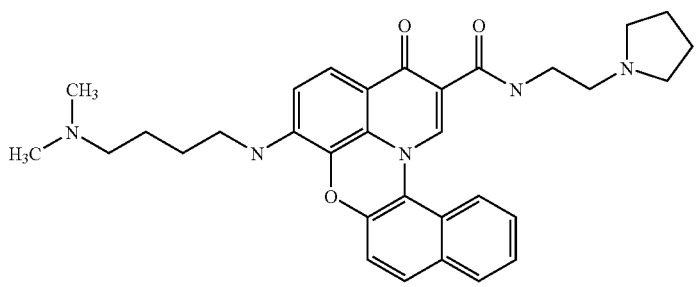
1032
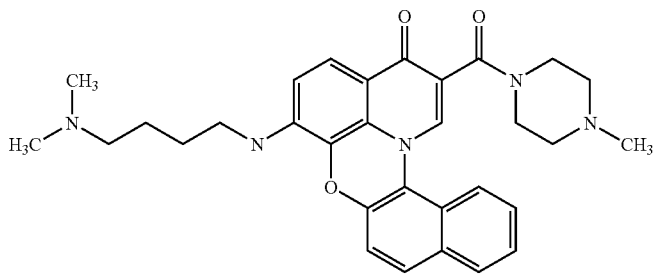
1033
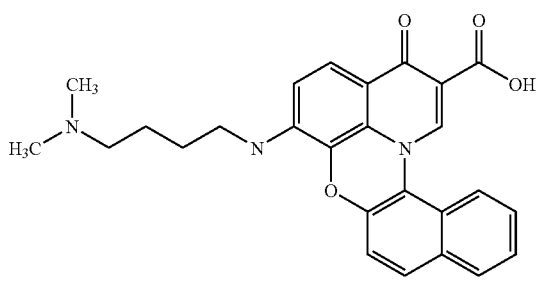

-continued
1034 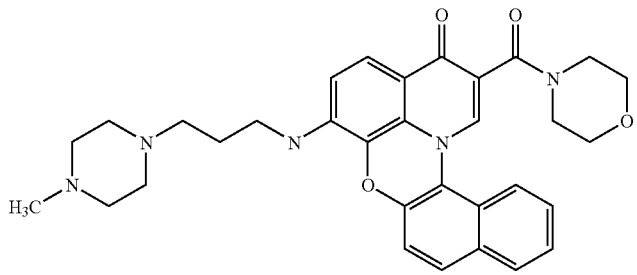
1035 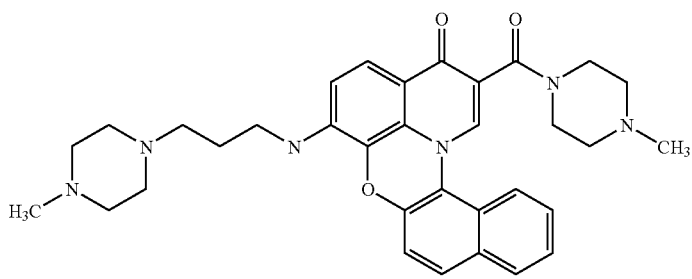
1036 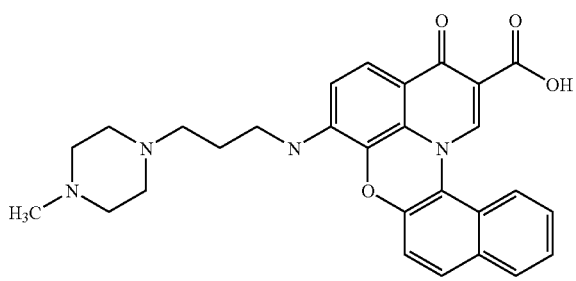
1037 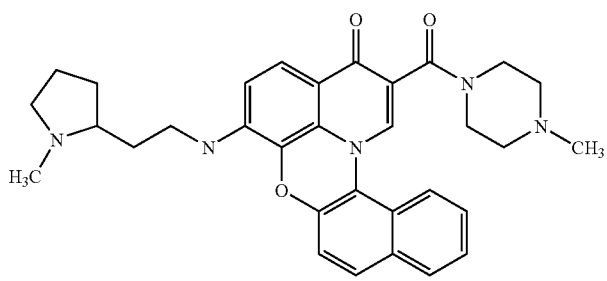
1038 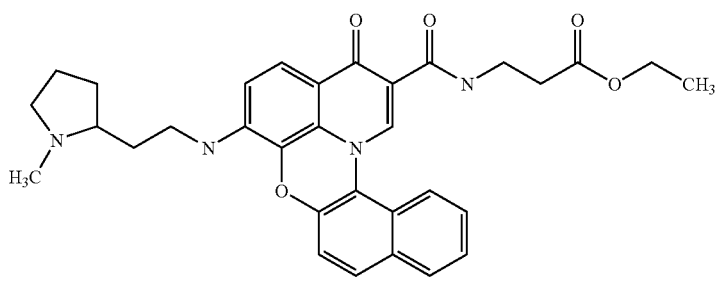

-continued
1039 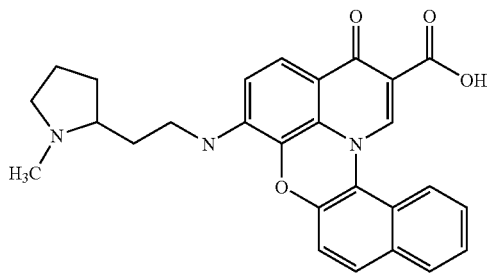
1040 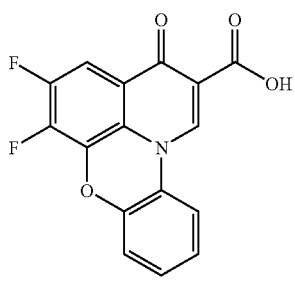
1041 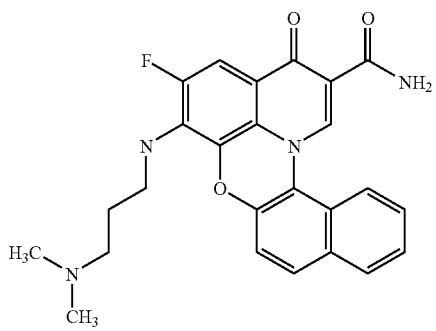
1042 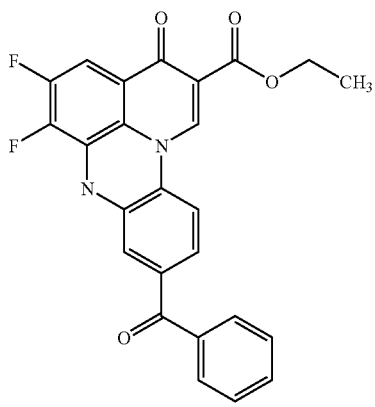
1043 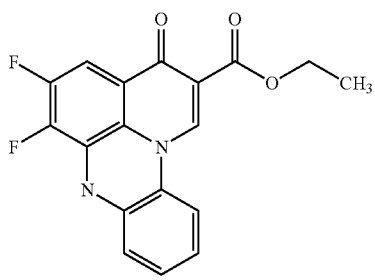

1044 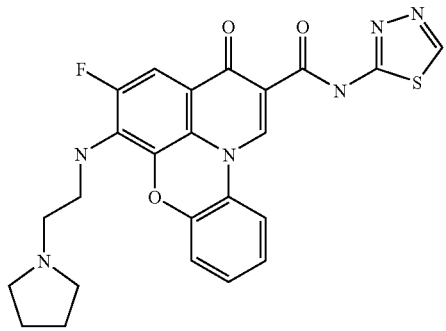
1045 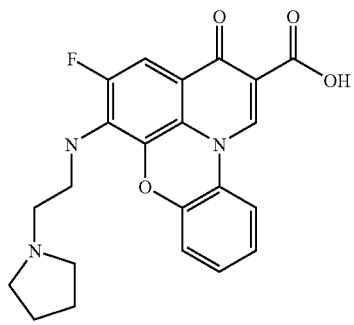
1046 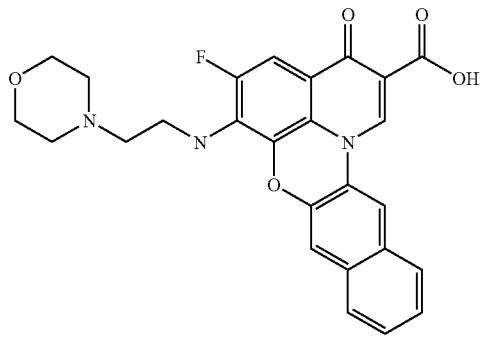
1047 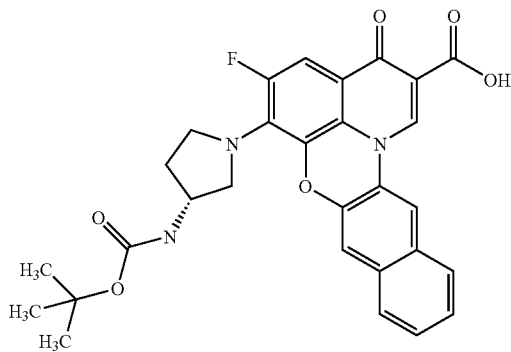

-continued
1048 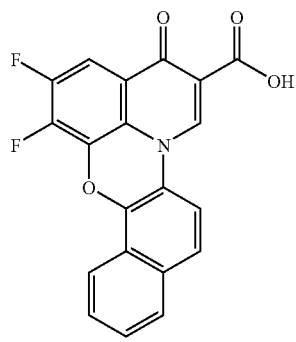
1049 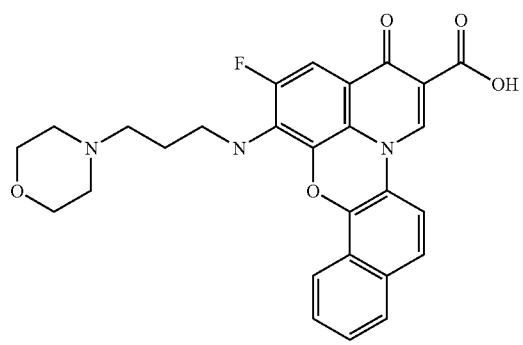
1050 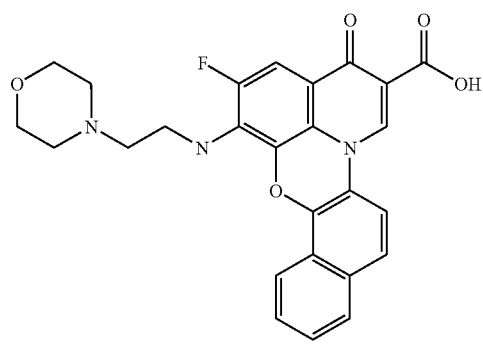
1051 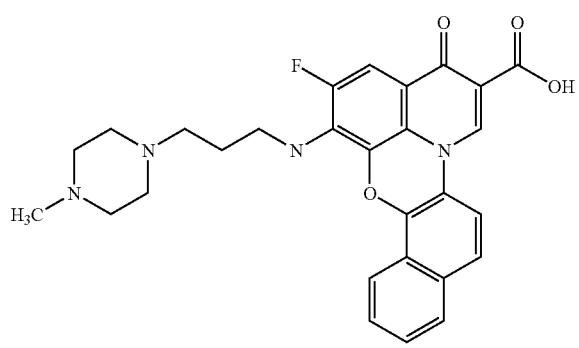

-continued
1052
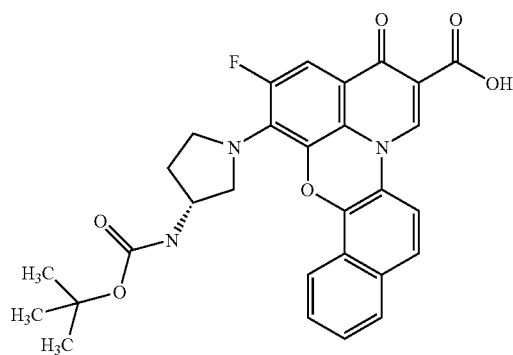
1053
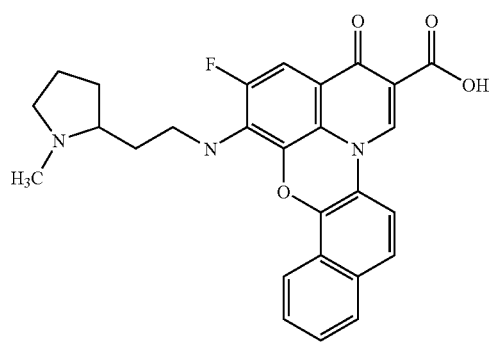
1054
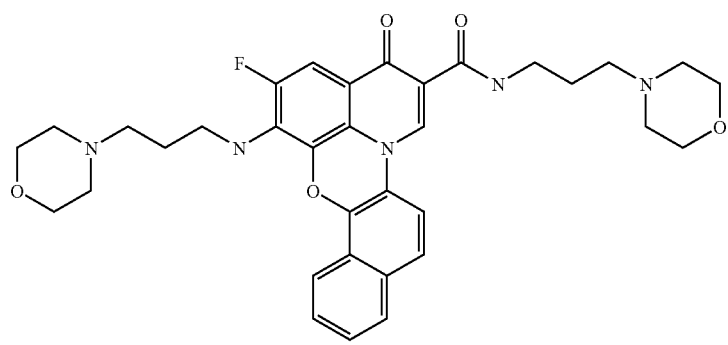
1055
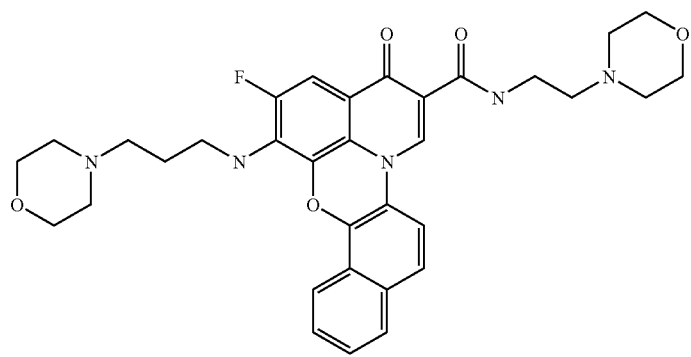

1056 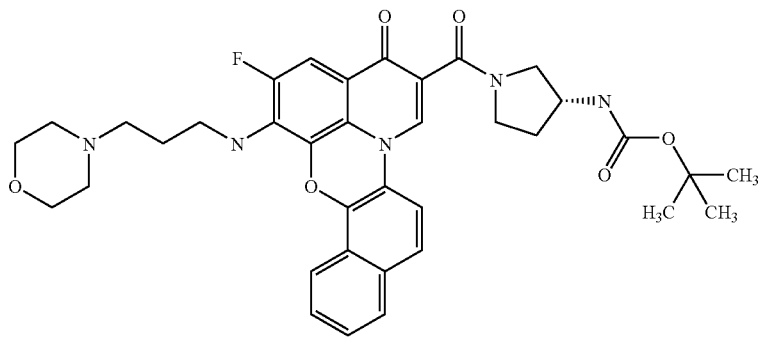
1057 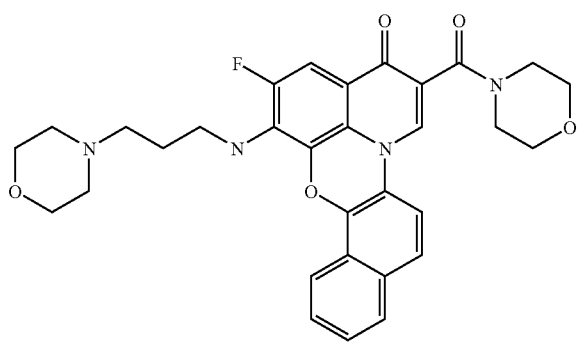
1058 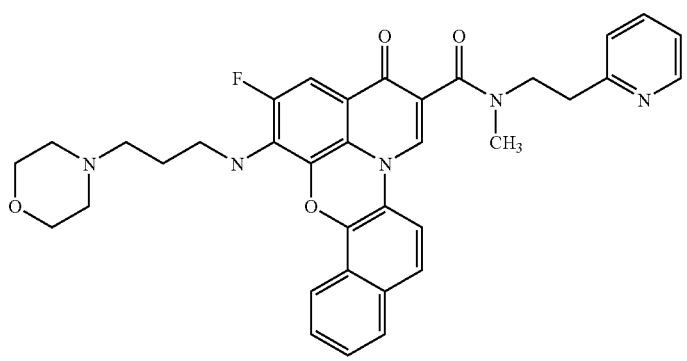
1059 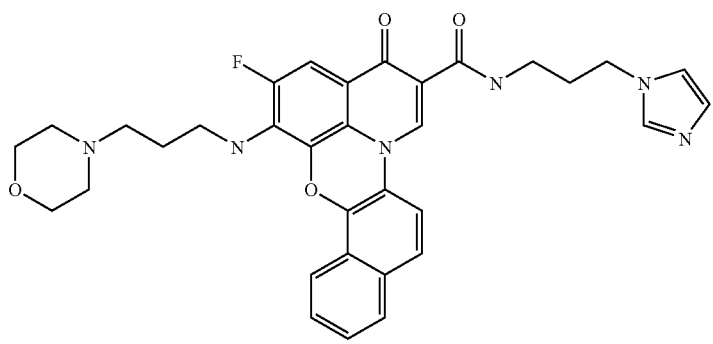

-continued
1060
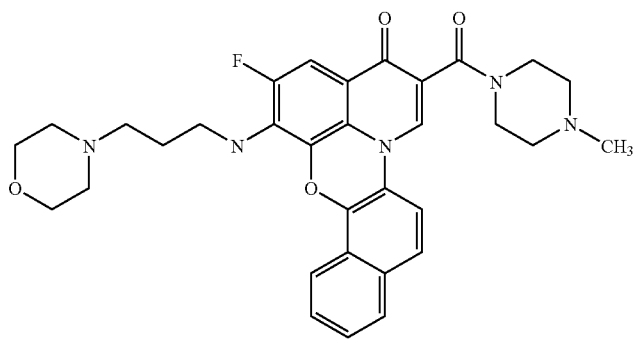
1061
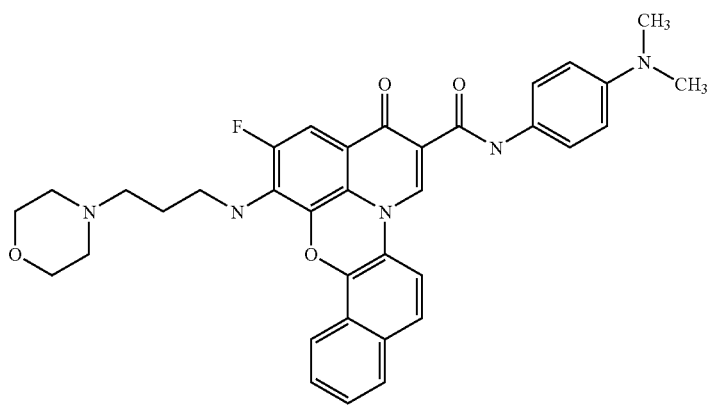
1062
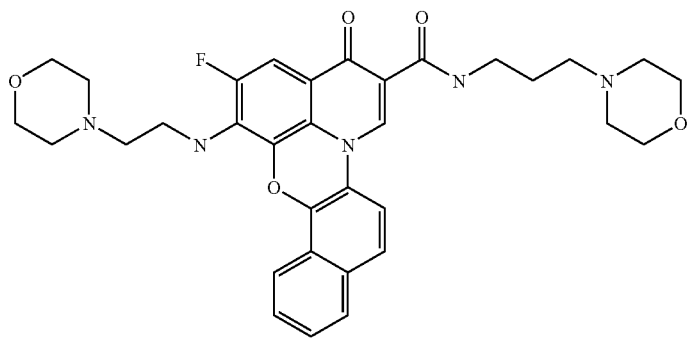
1063
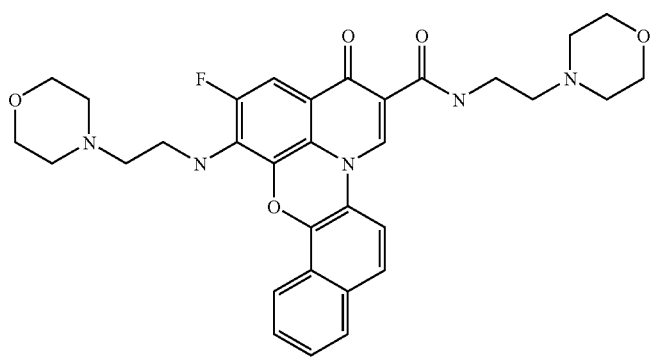

-continued
1064
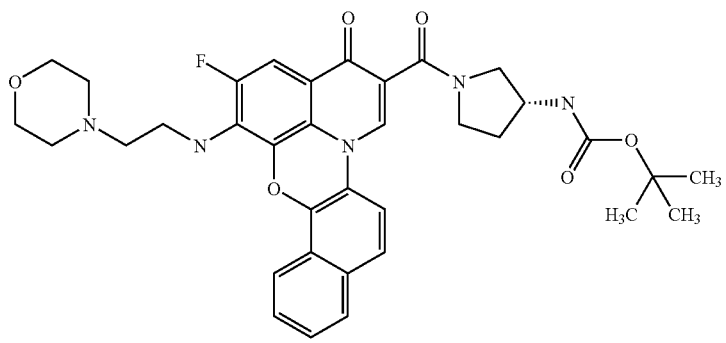
1065
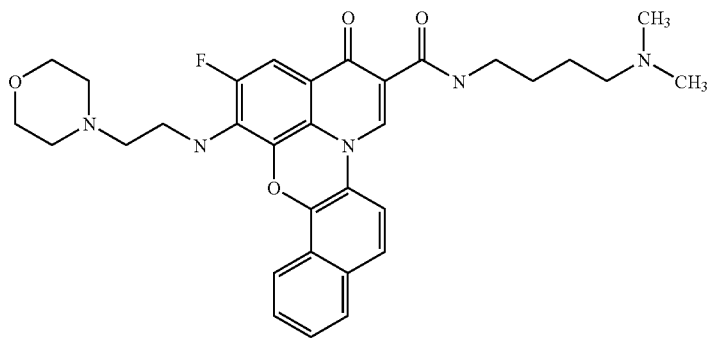
1066
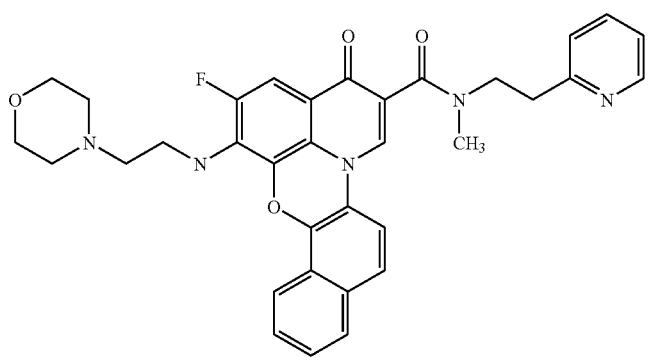
1067
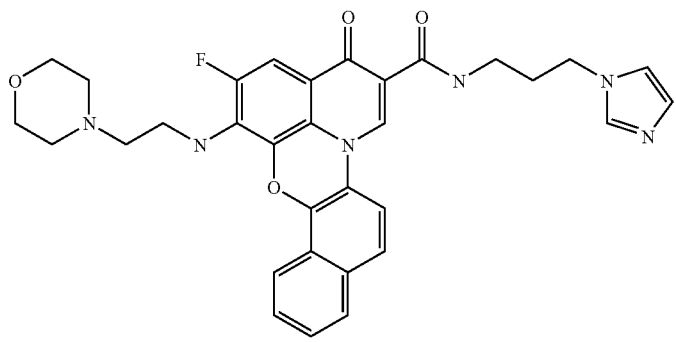

-continued
1068
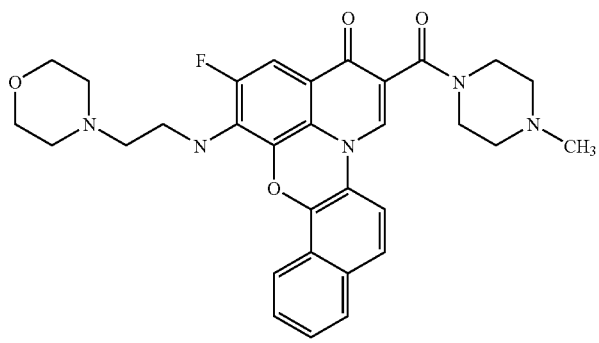
1069
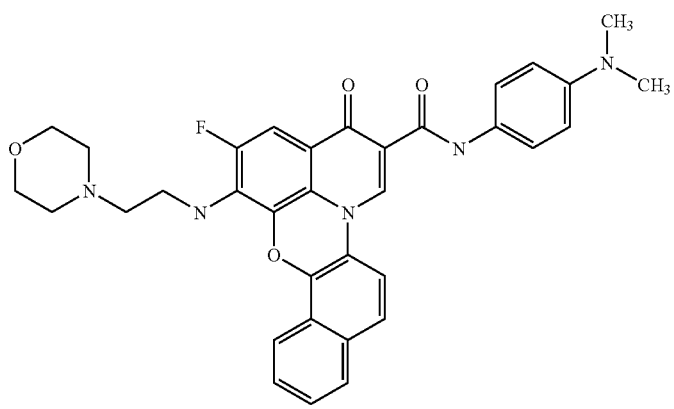
1070
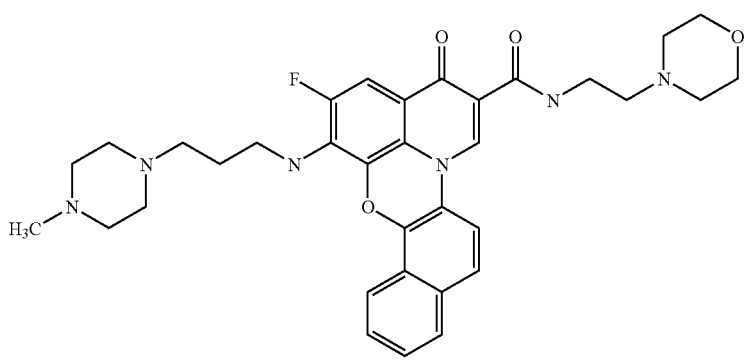
1071
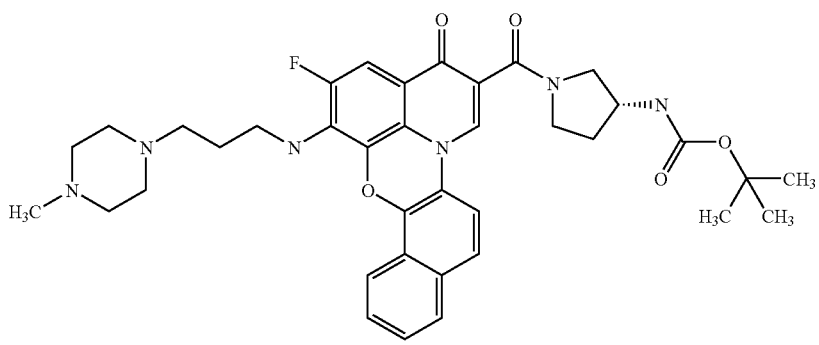

-continued
1072
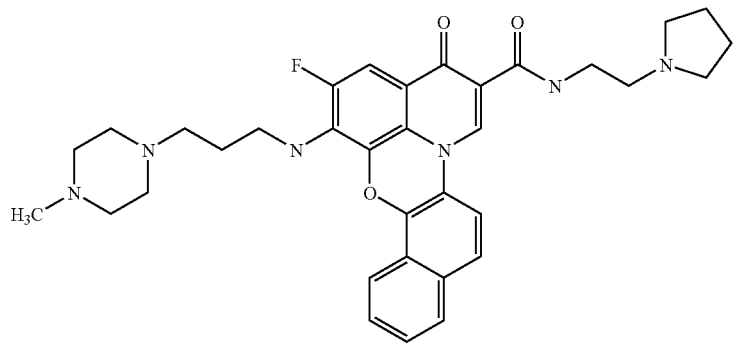
1073
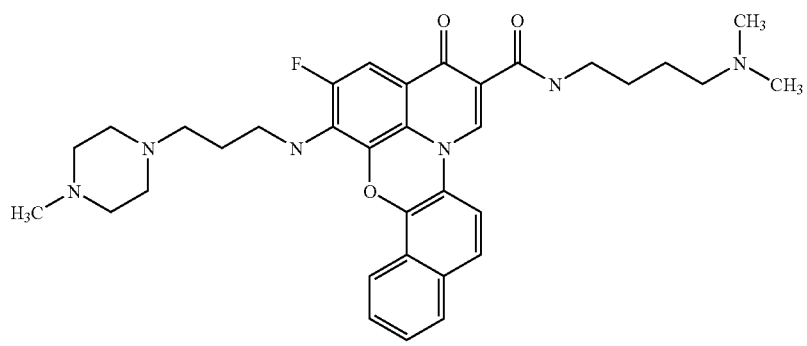
1074
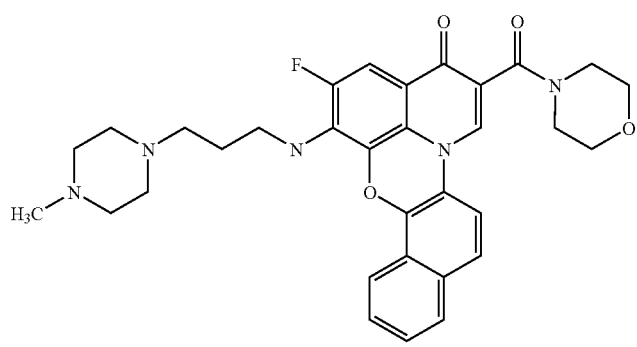
1075
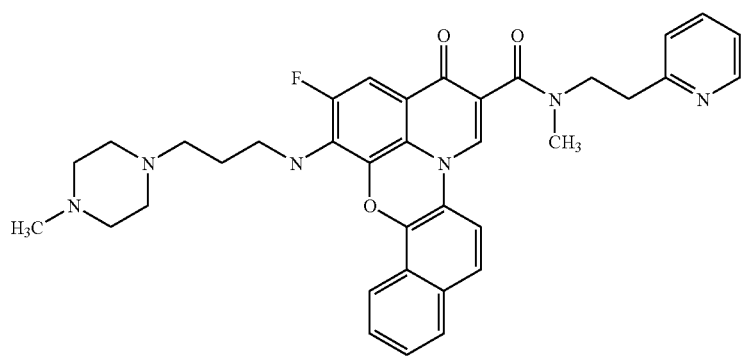

1076 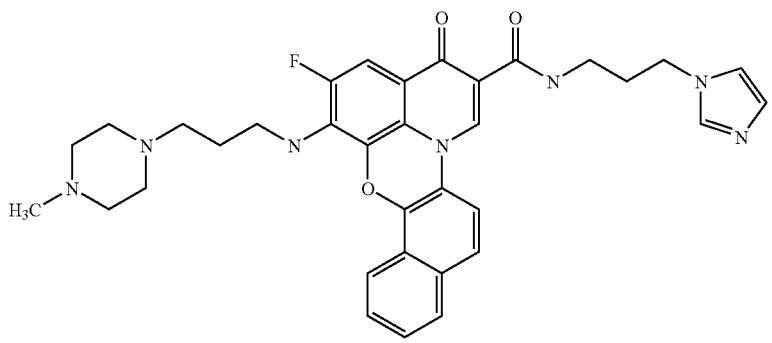
1077 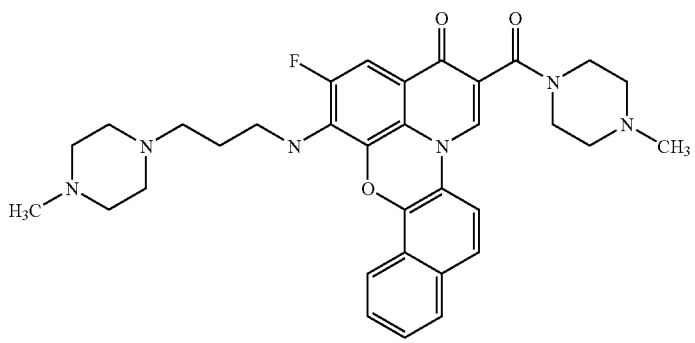
1078 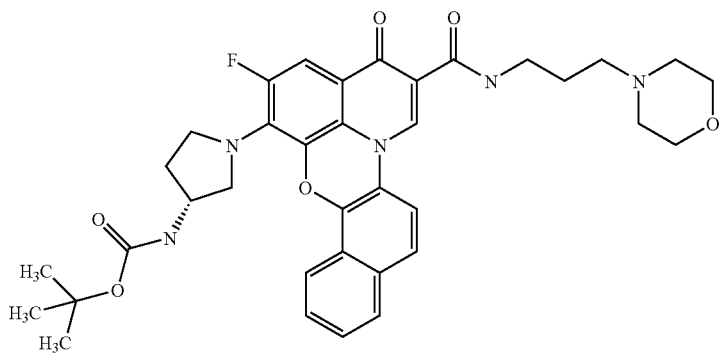
1079 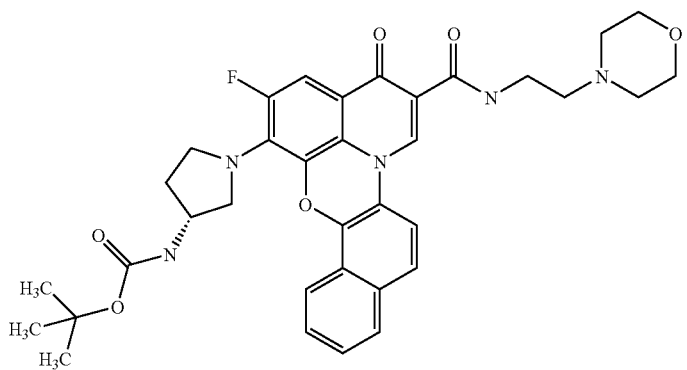

1080 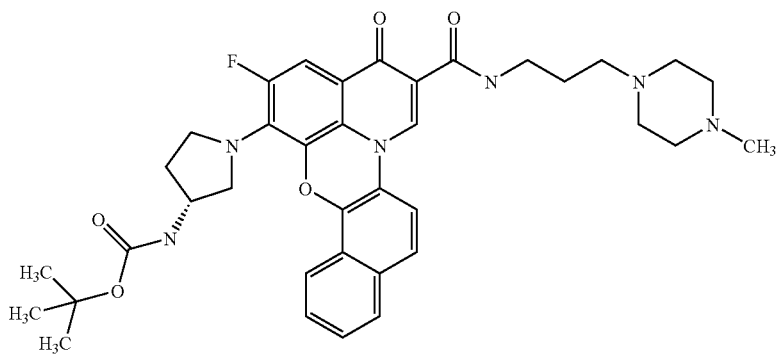
1081 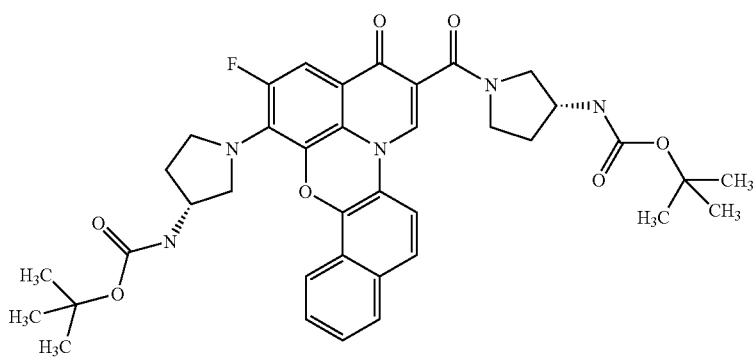
1082 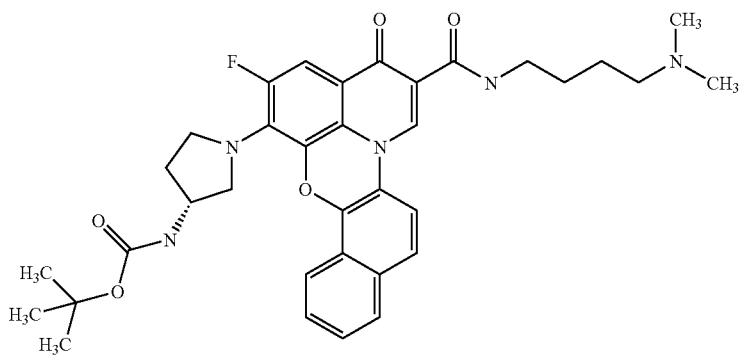
1083 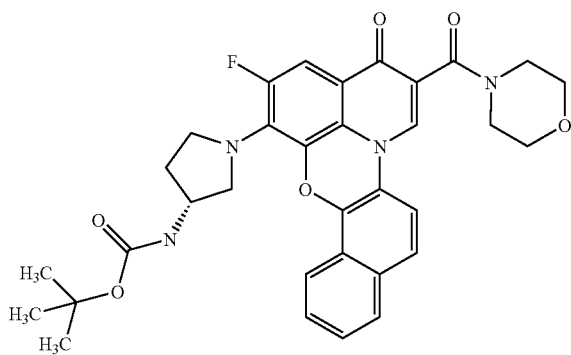

1084 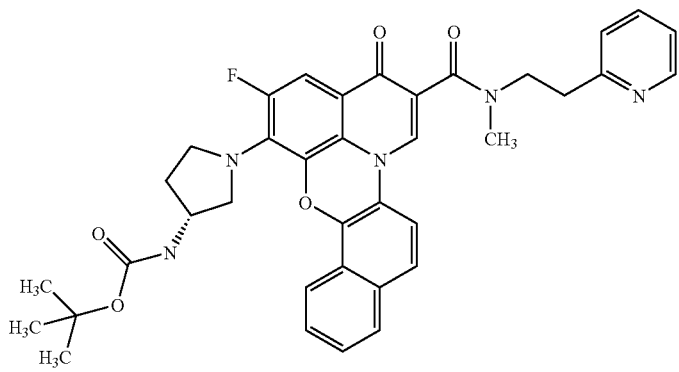
1085 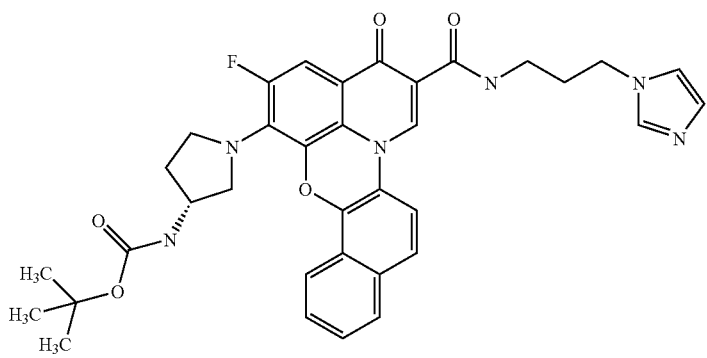
1086 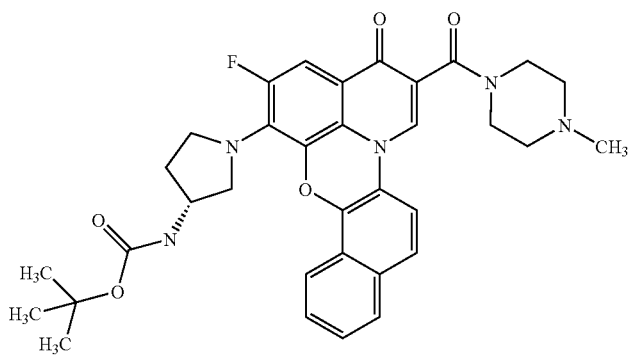
1087 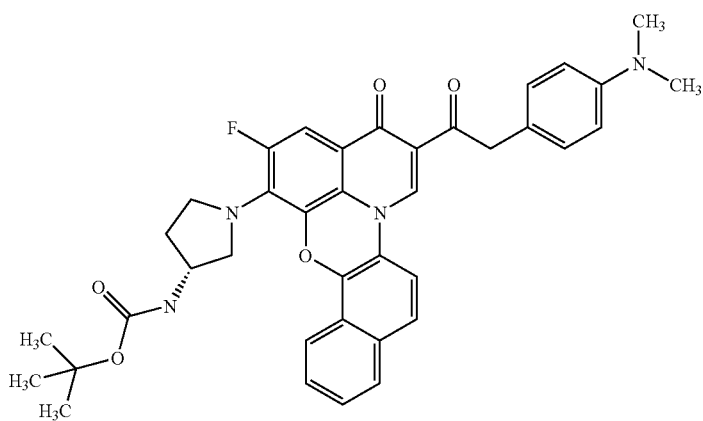

1088 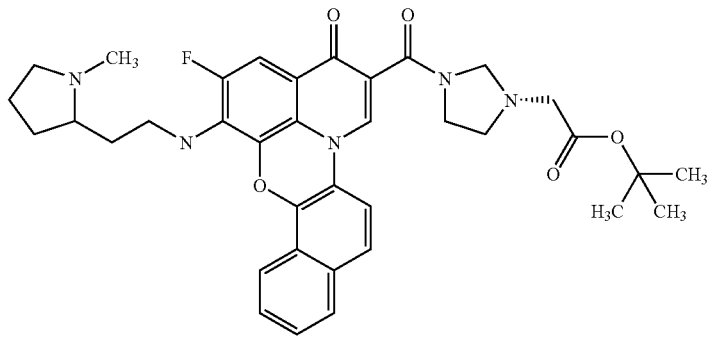
1089 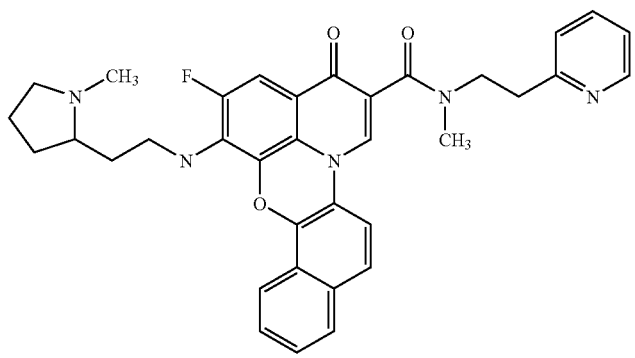
1090 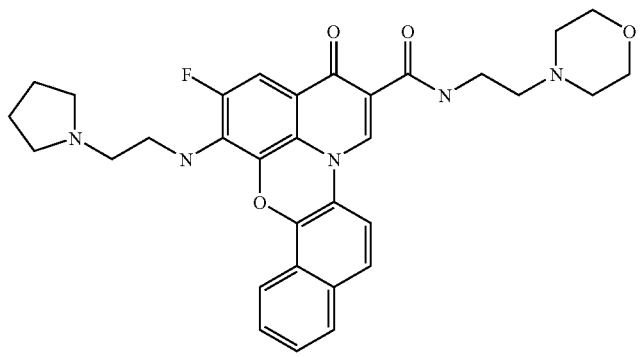
1091 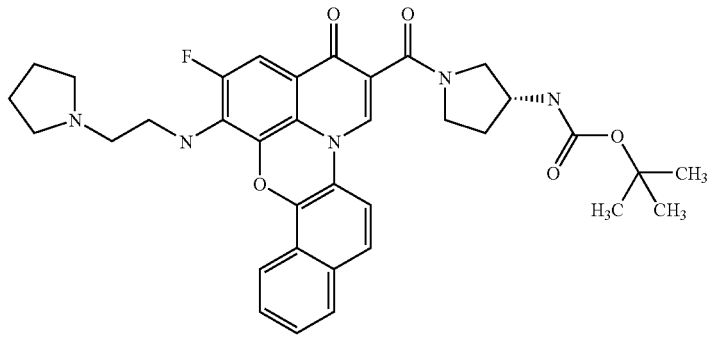

-continued
1092
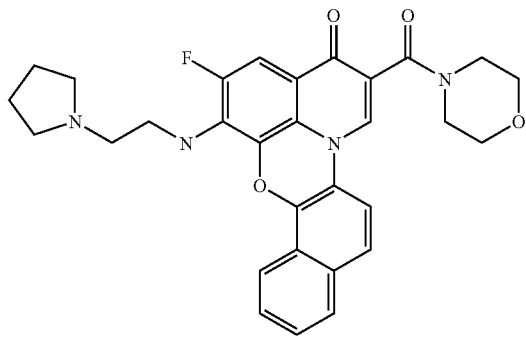
1093
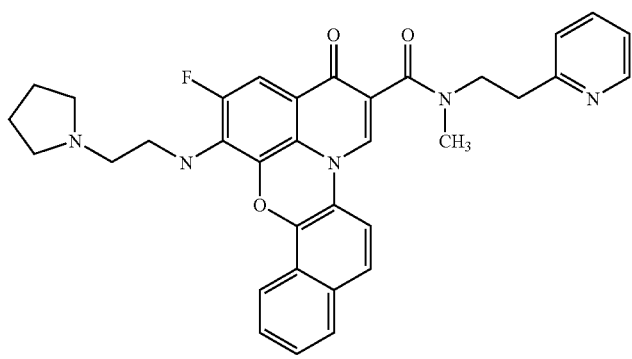
1094
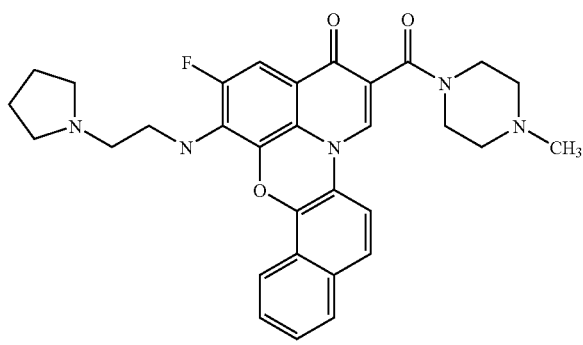
1095
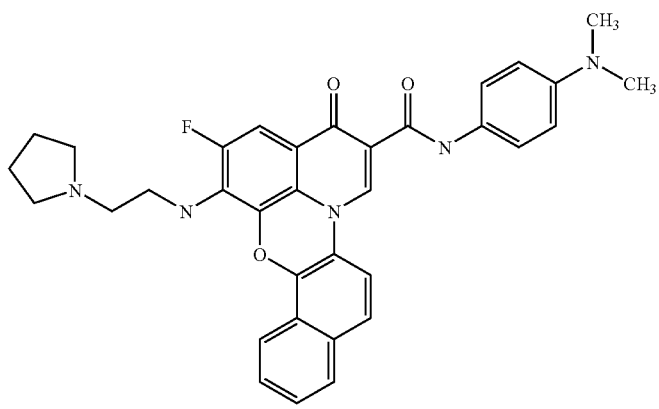

-continued
1096
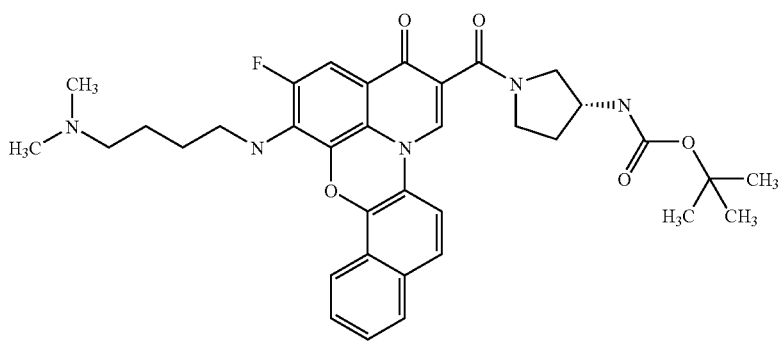
1097
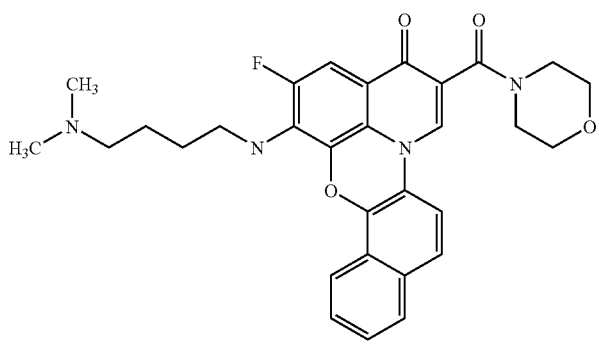
1098
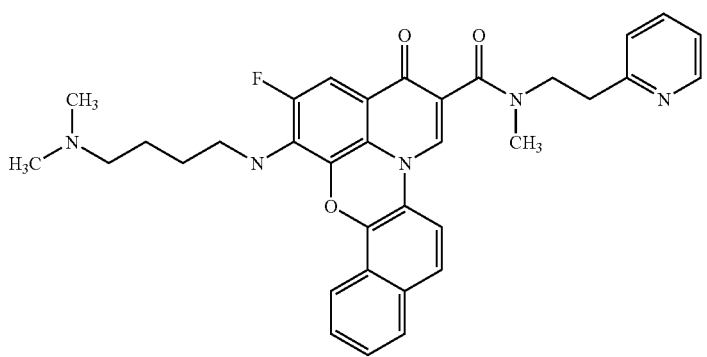
1099
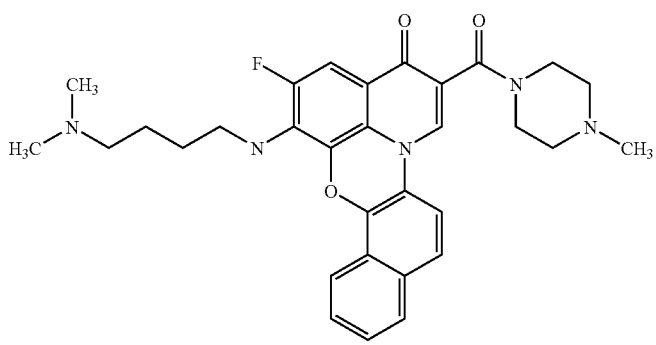

1100
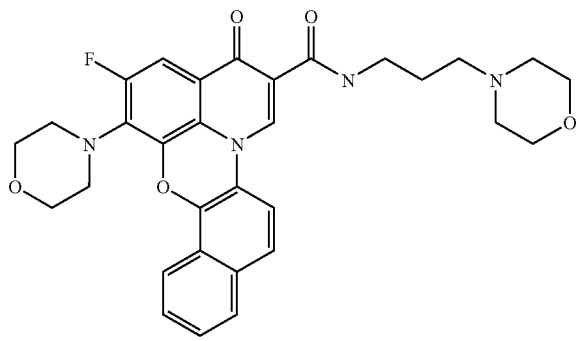
1101
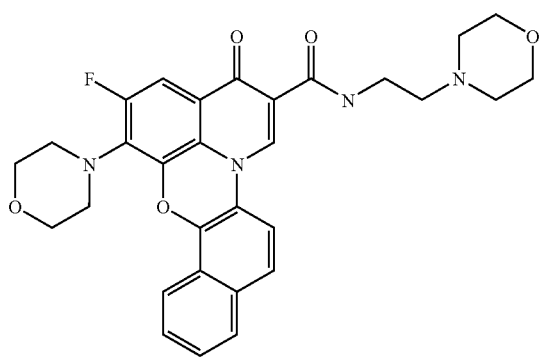
1102
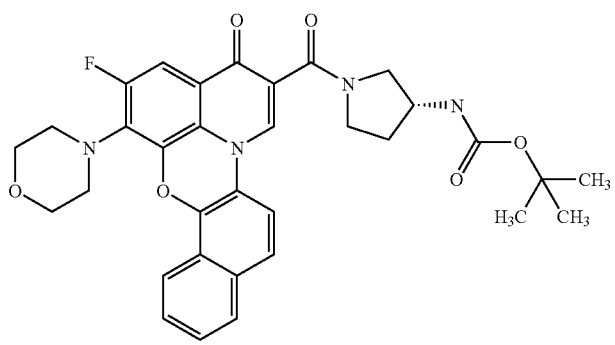
1103
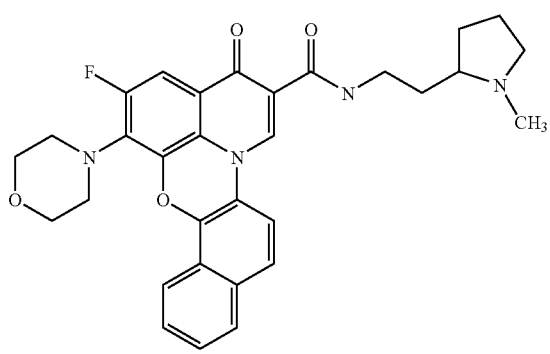

-continued
1104
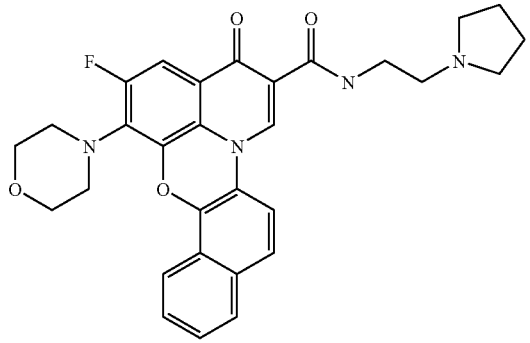
1105
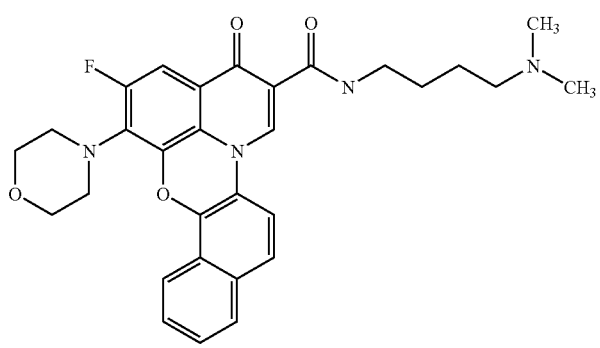
1106
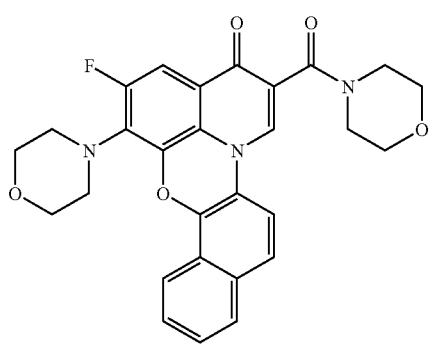
1107
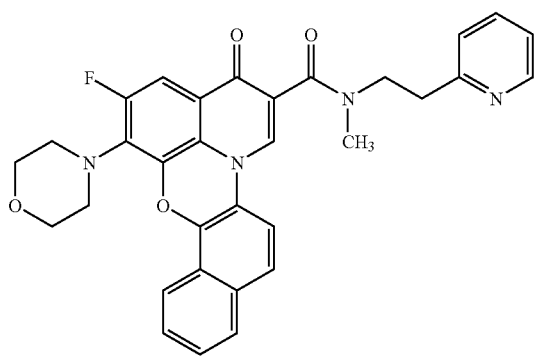

-continued
| 1108 | 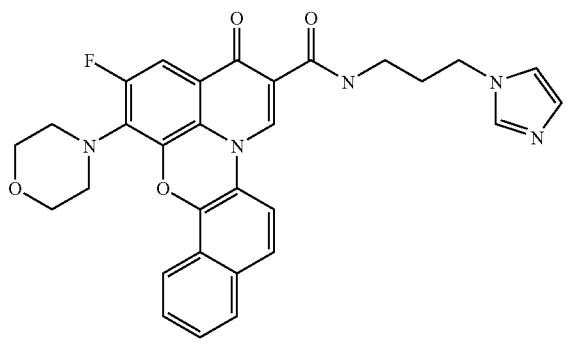 |
| 1109 | 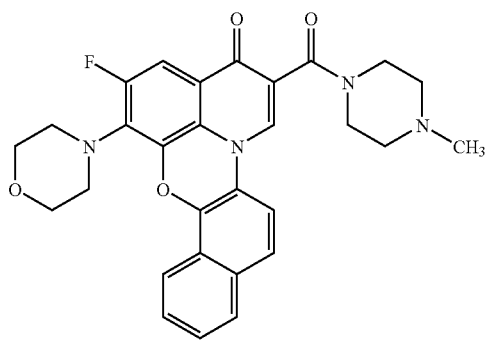 |
| 1110 | 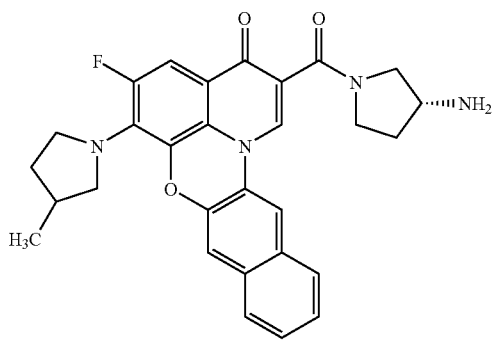 |
| 1111 | 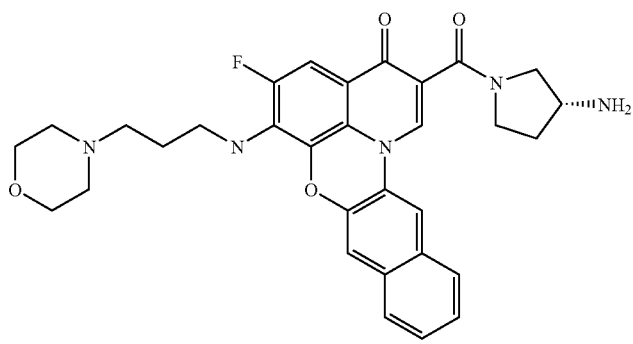 |

-continued
1112
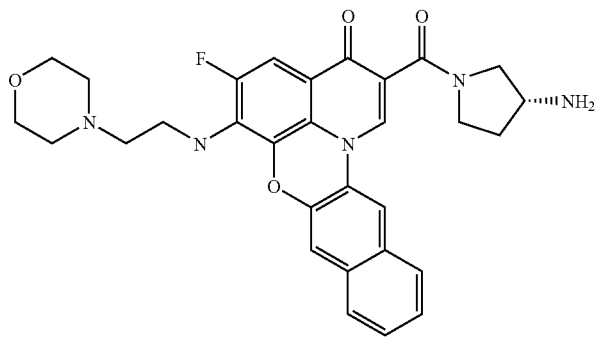
1113
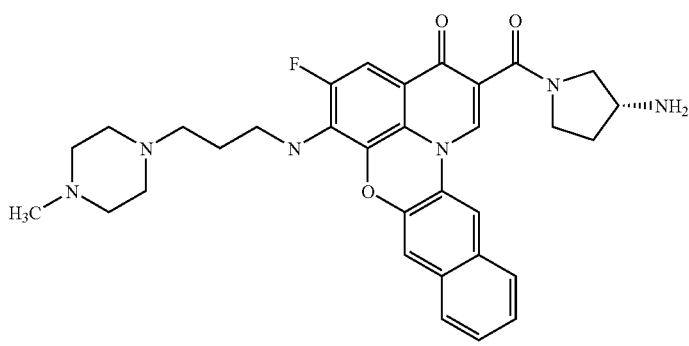
1114
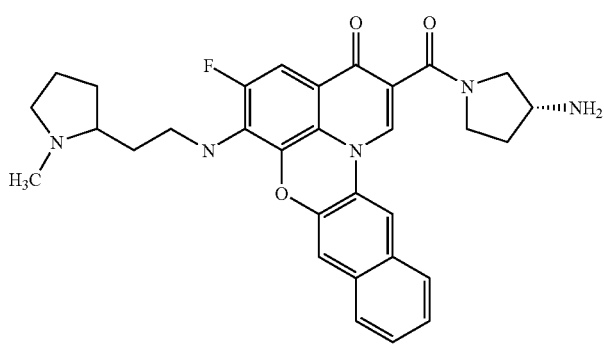
1115
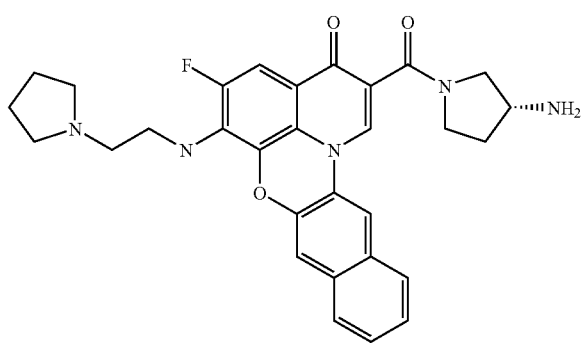

1116 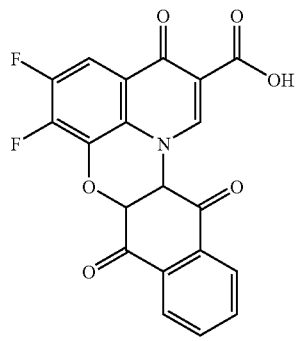
1117 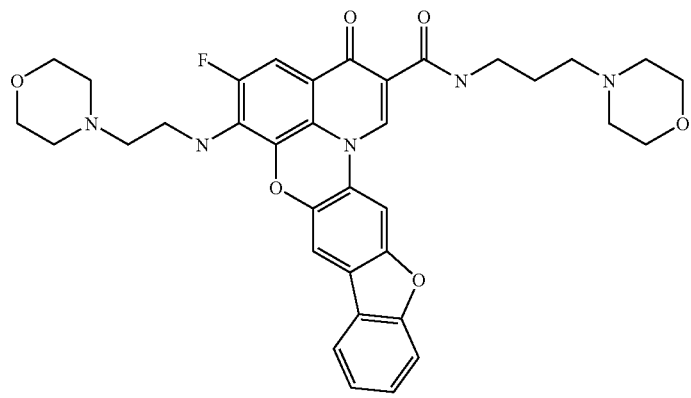
1118 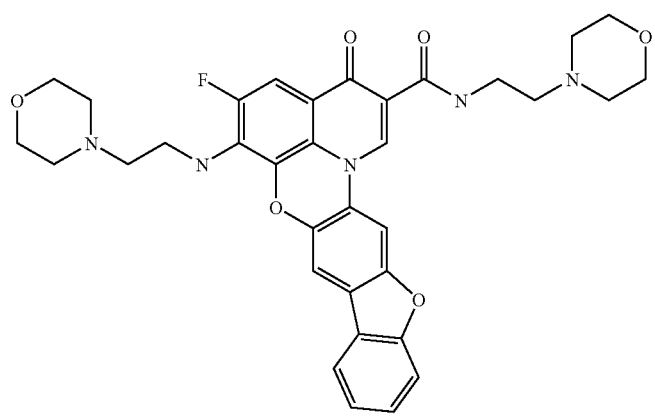
1119 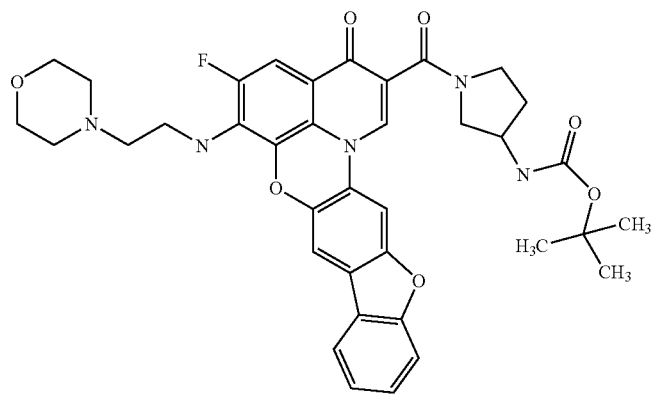

-continued
1120
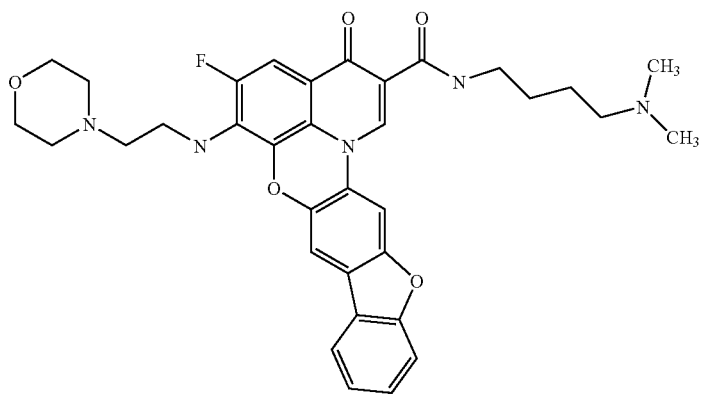
1121
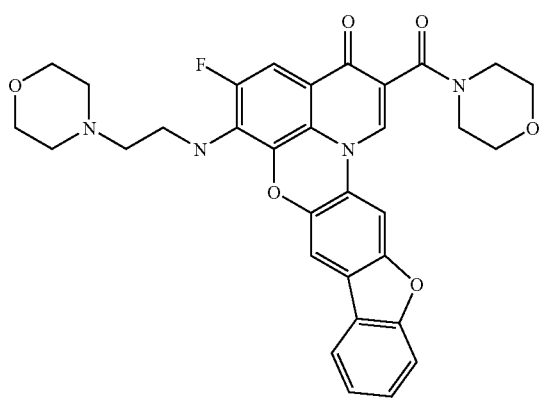
1122
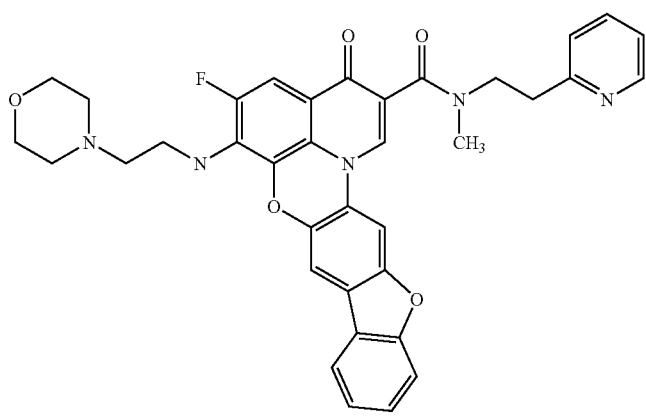
1123
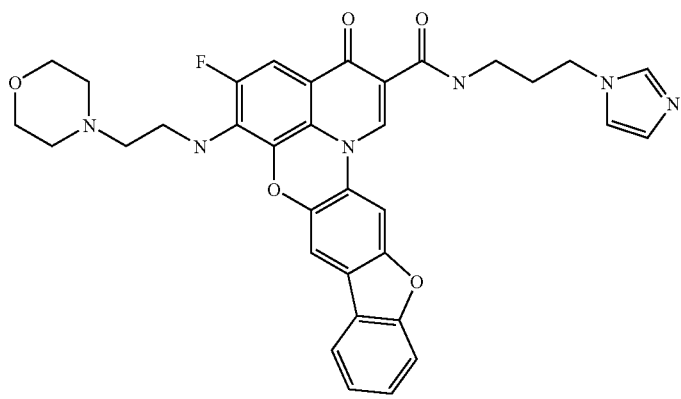

-continued
1124
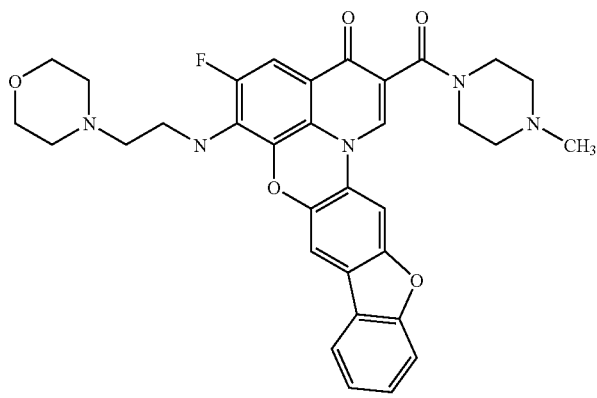
1125
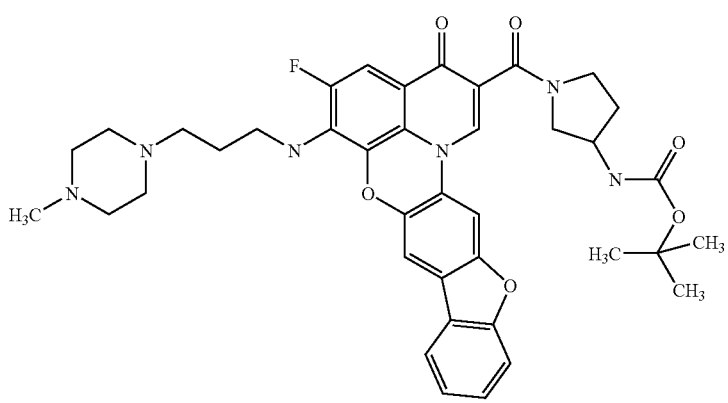
1126
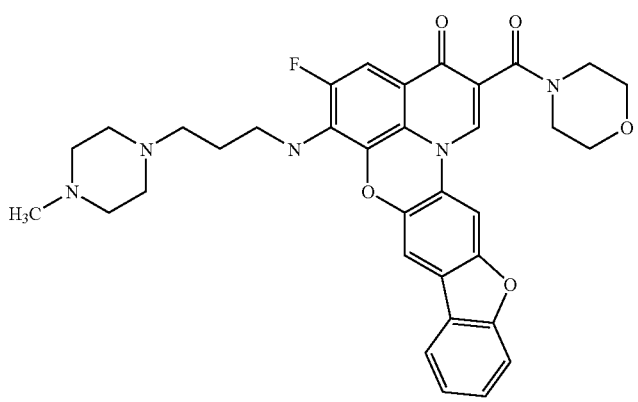
1127
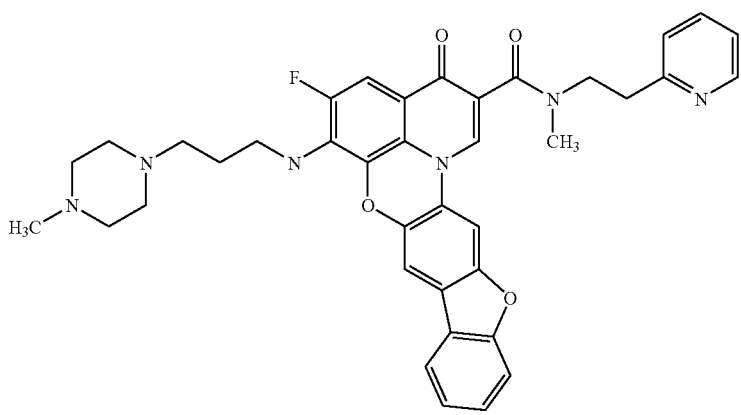

-continued
| | |
|---|---|
| 1128 | 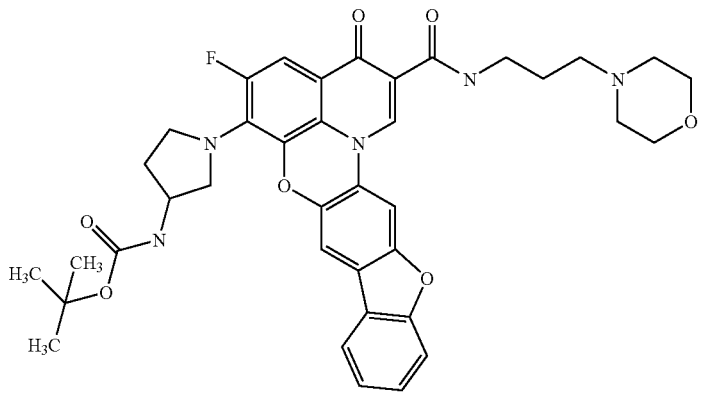 |
| 1129 | 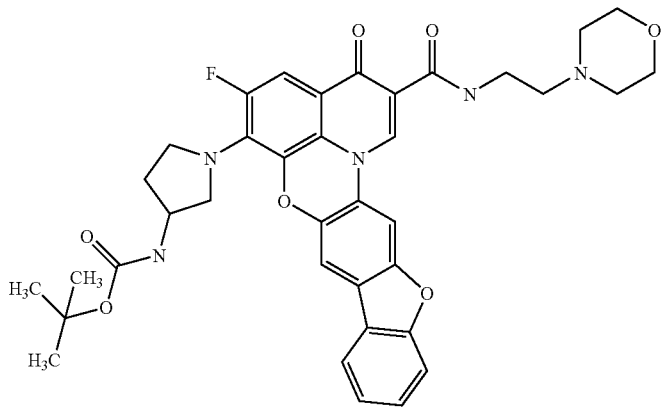 |
| 1130 | 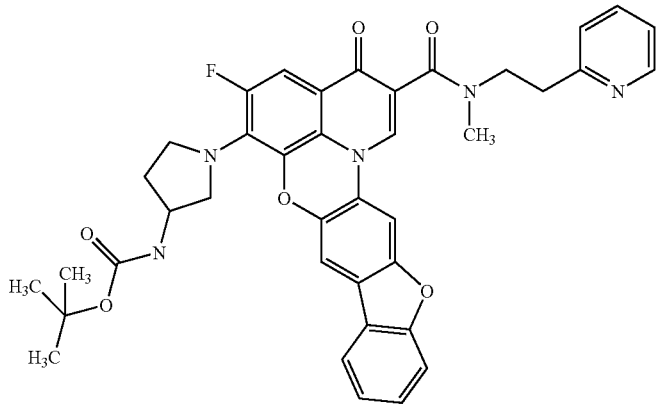 |
| 1131 | 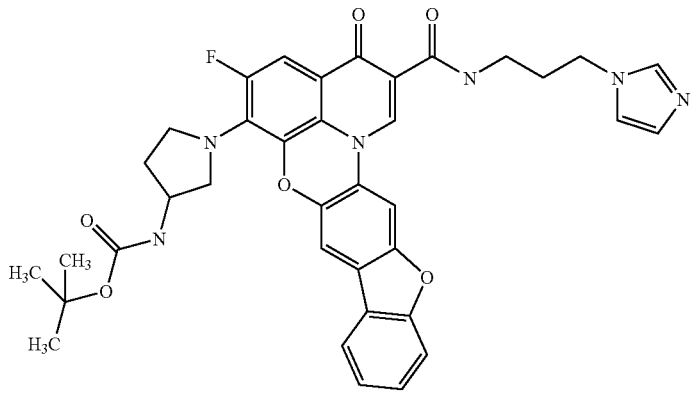 |

1132 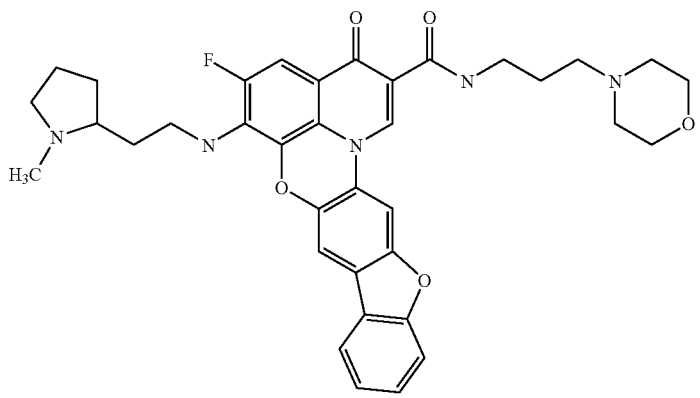
1133 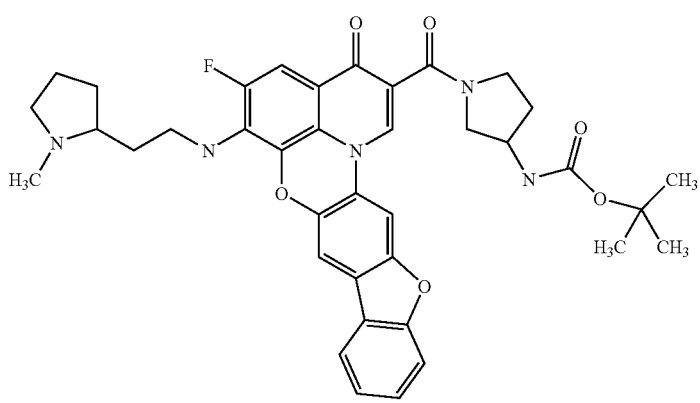
1134 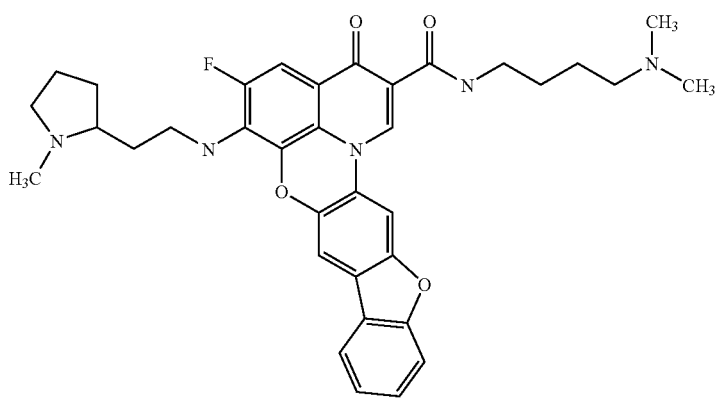
1135 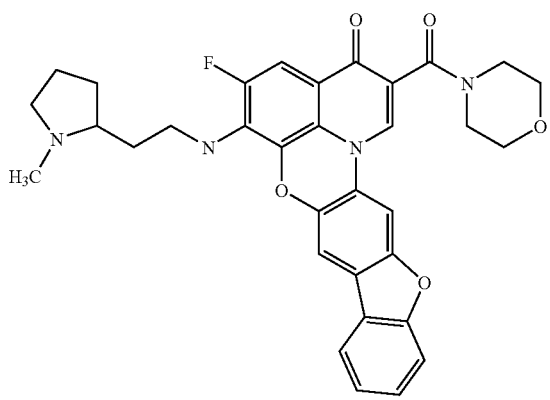

1136
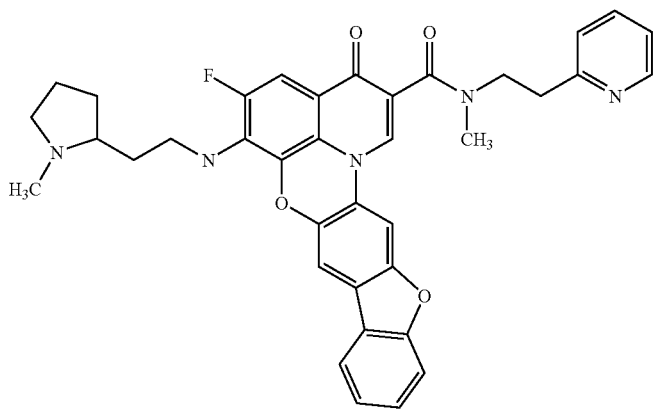
1137
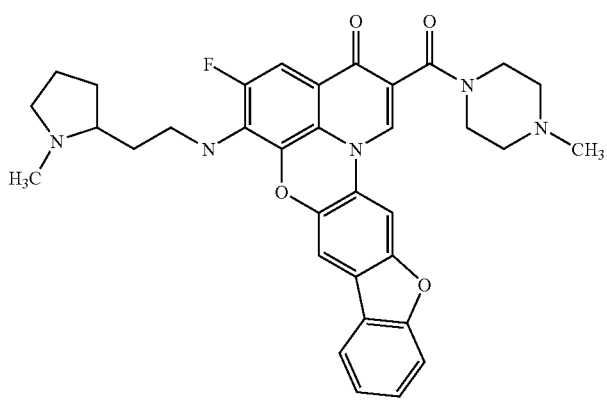
1138
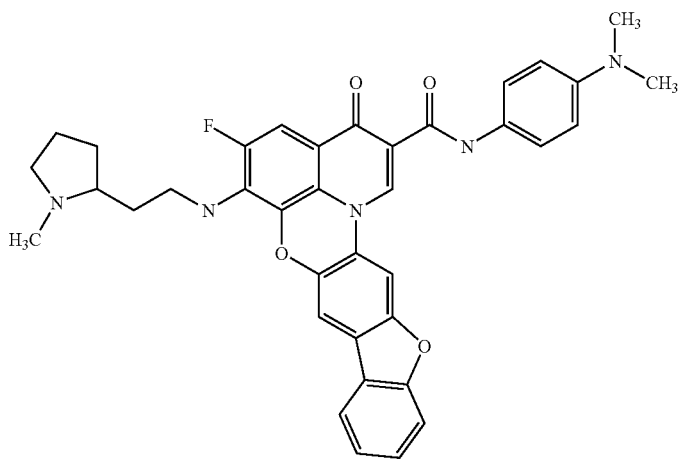

1139 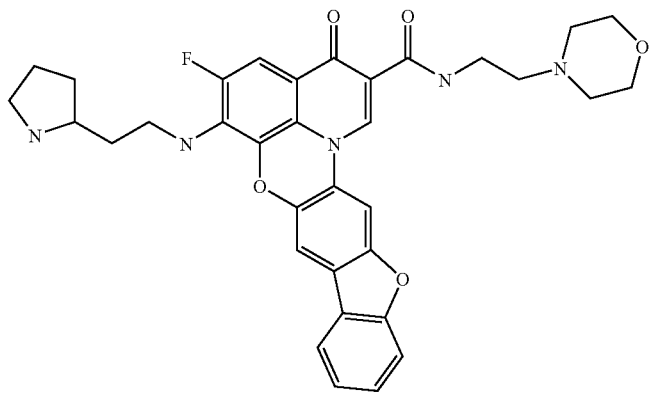
1140 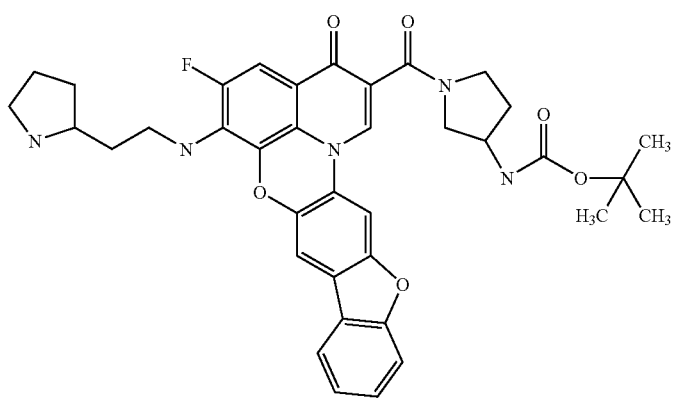
1141 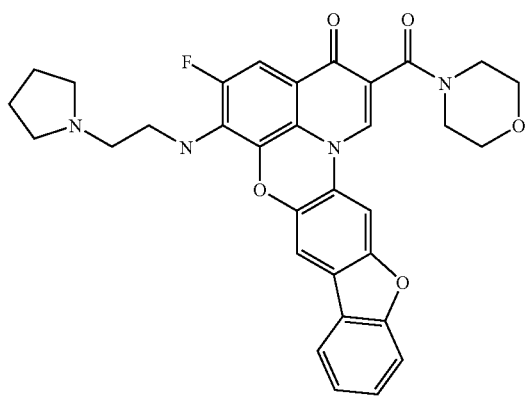
1142 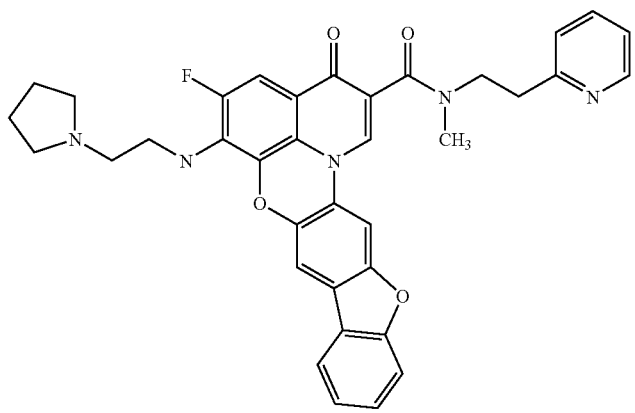

-continued
1143
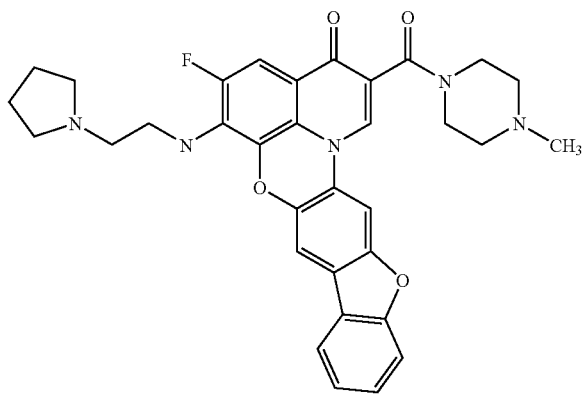
1144
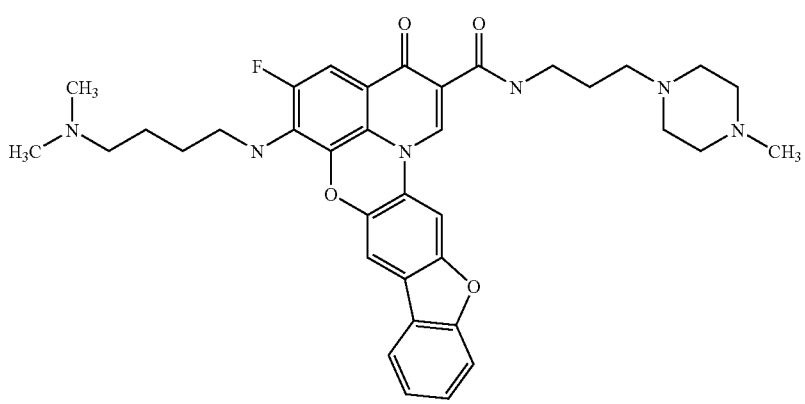
1145
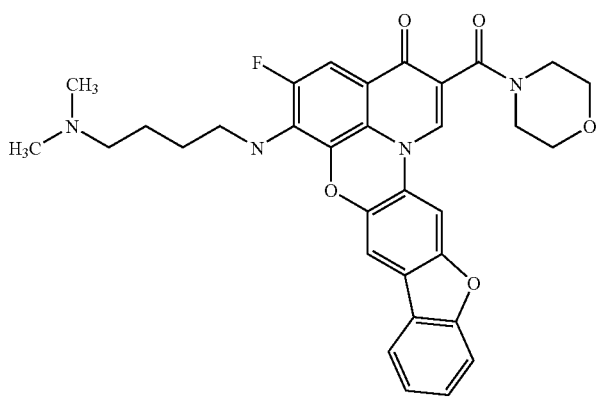
1146
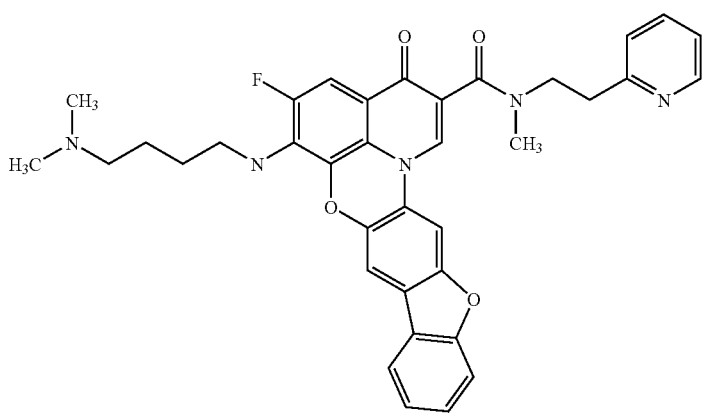

-continued
1147
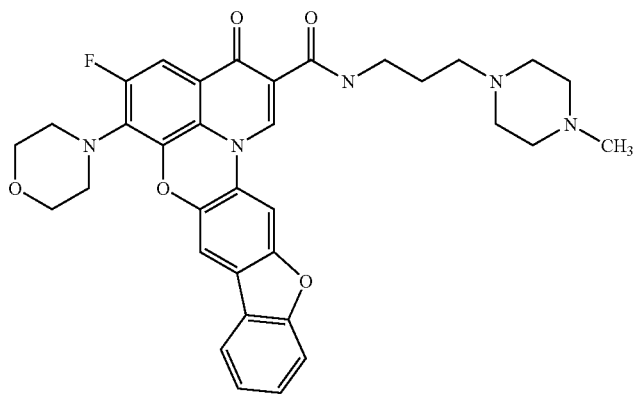
1148
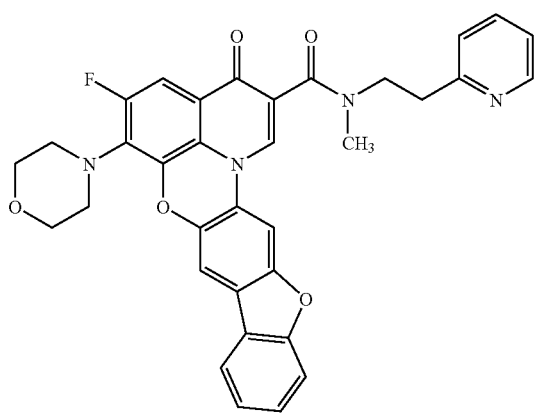
1149
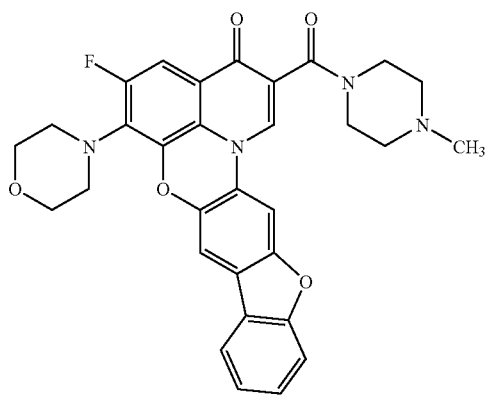
1150
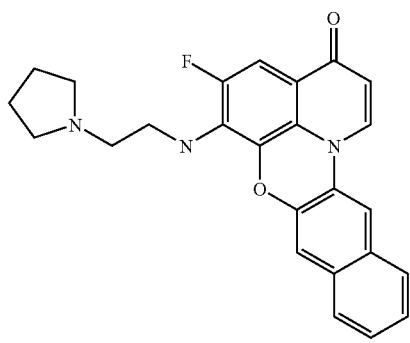

-continued
1151
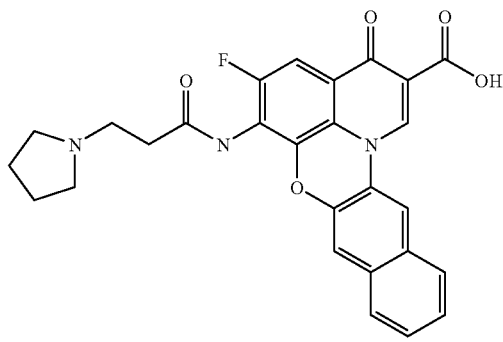
1152
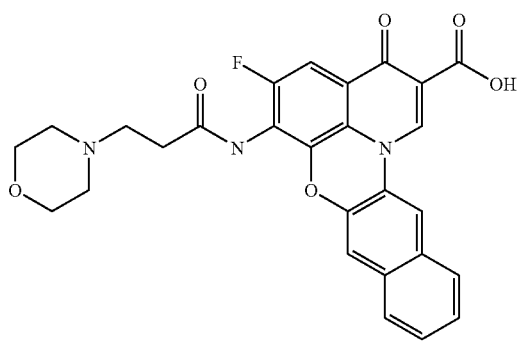
1153
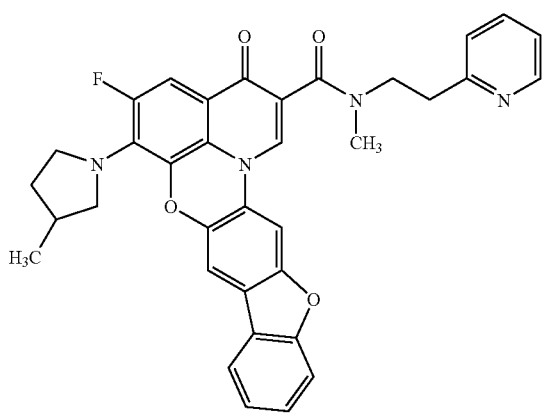
1154
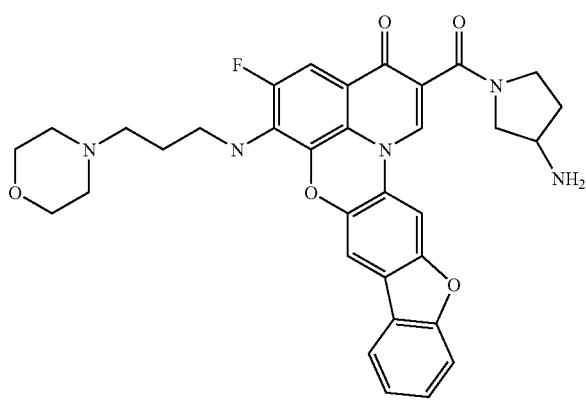

-continued
1155
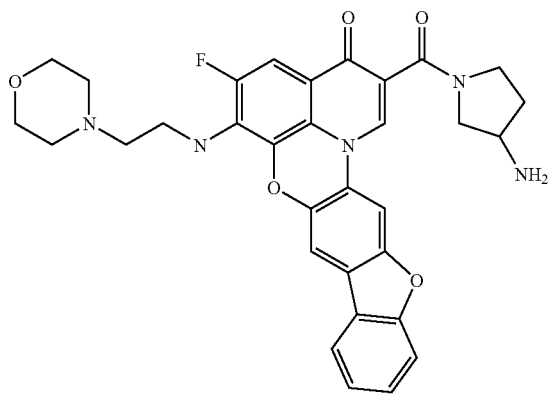
1156
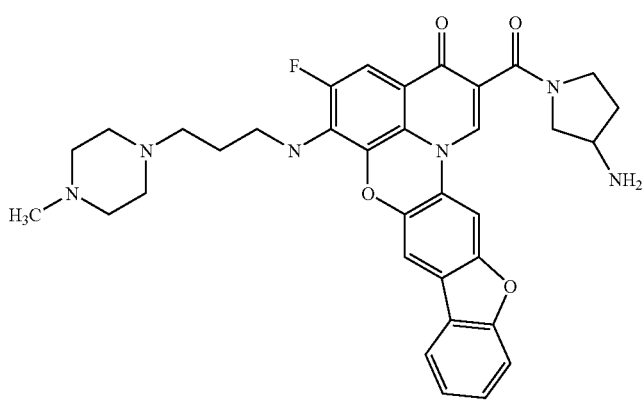
1157
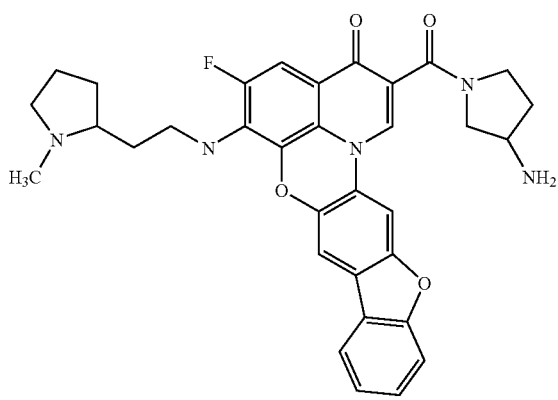
1158
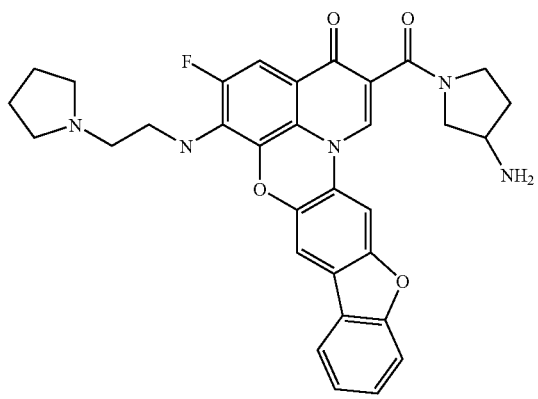

1159
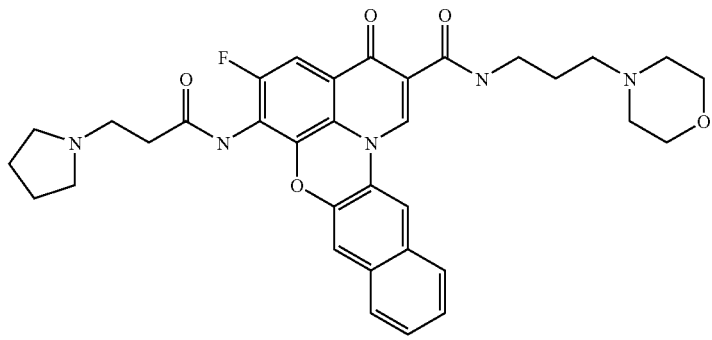
1160
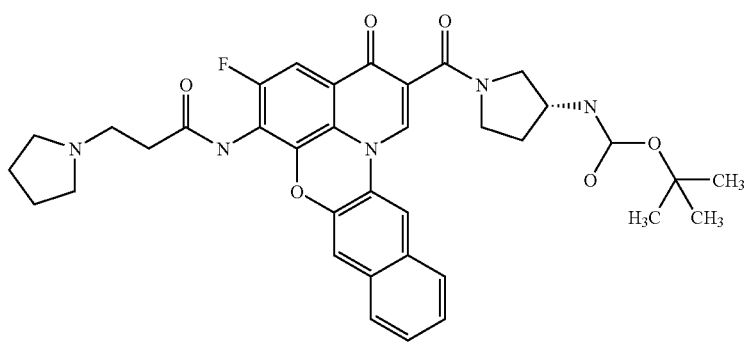
1161
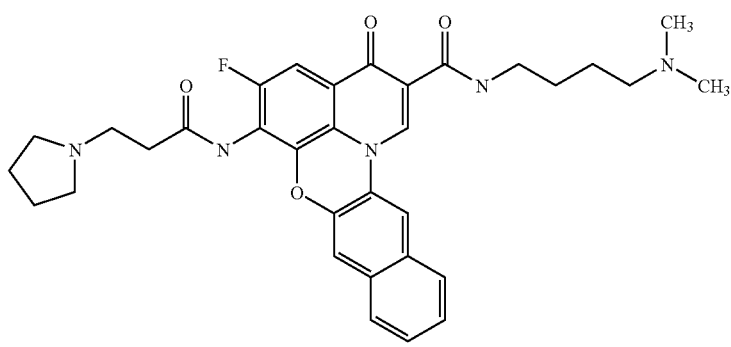
1162
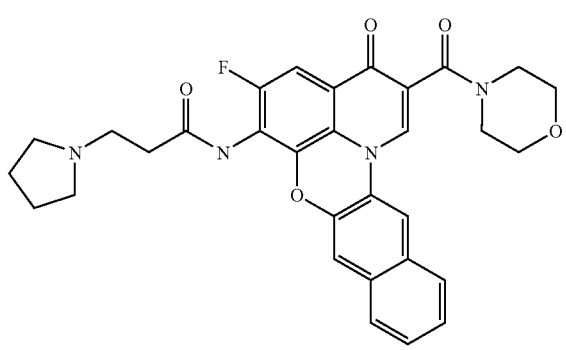

-continued
1163
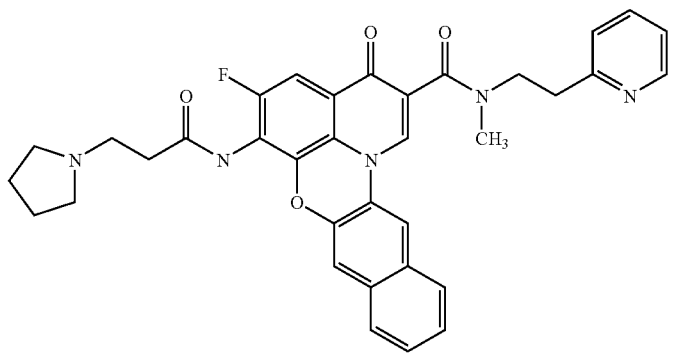
1164
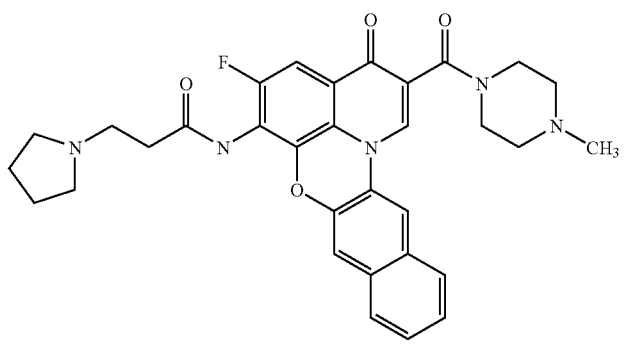
1165
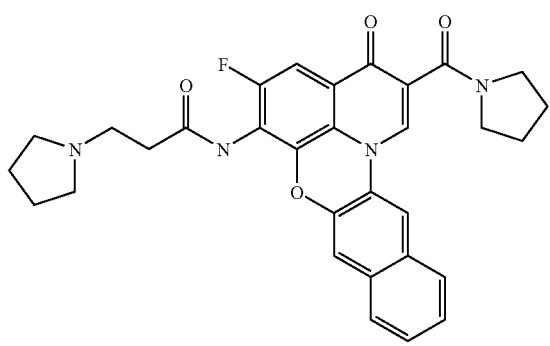
1166
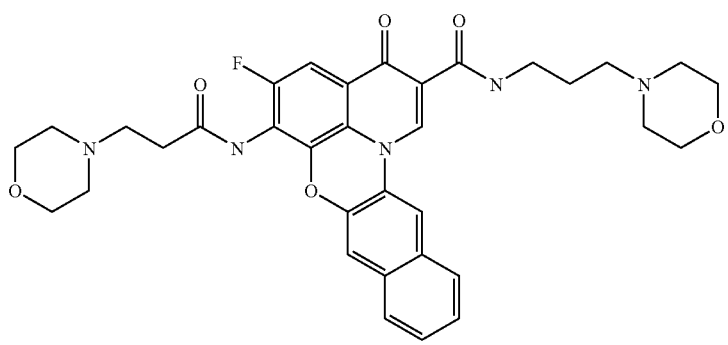

-continued
1167
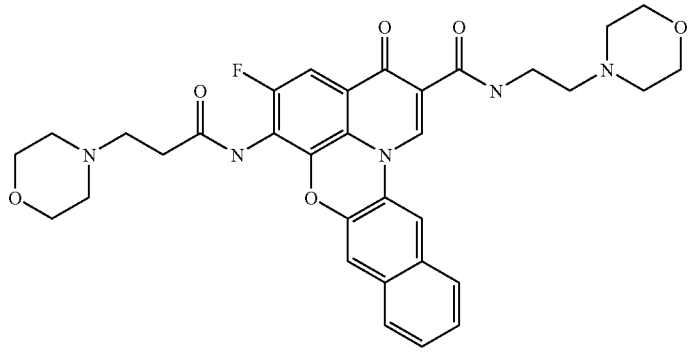
1168
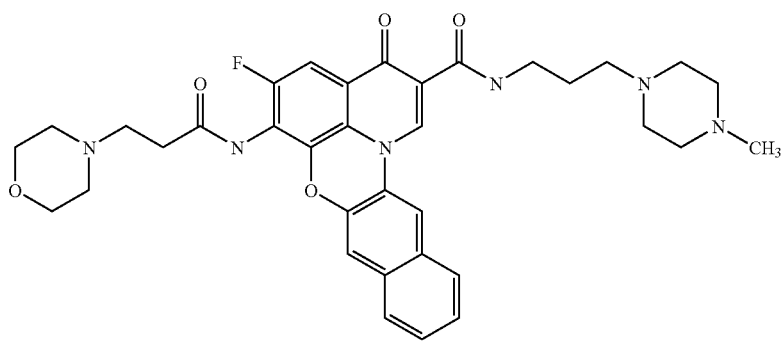
1169
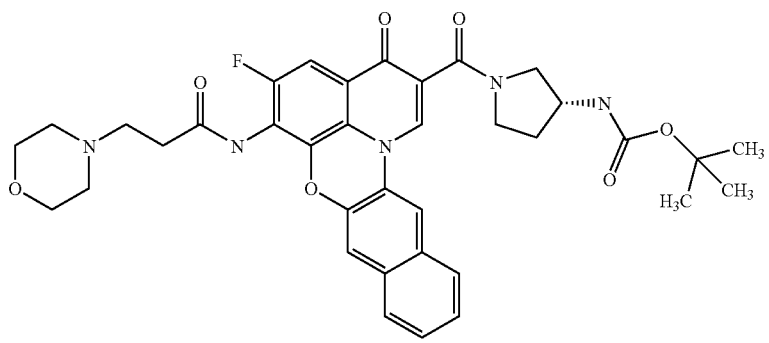
1170
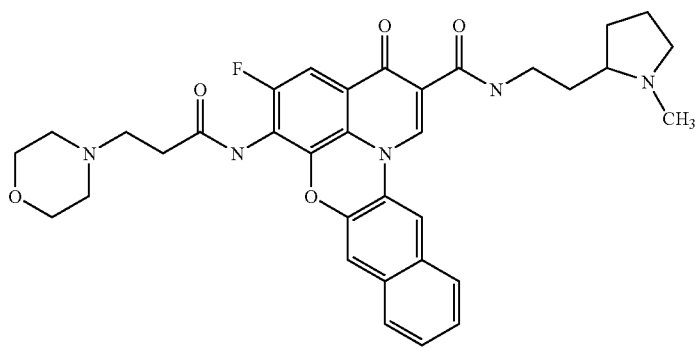

-continued
1171
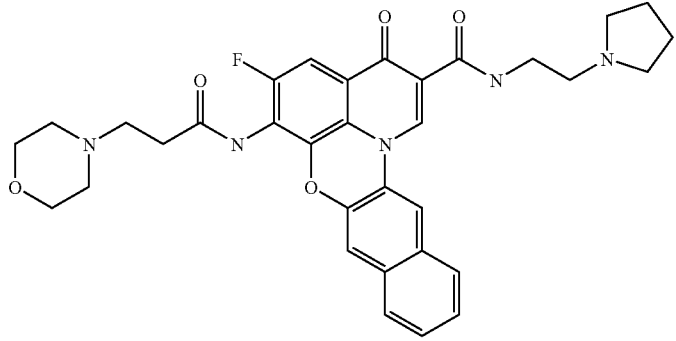
1172
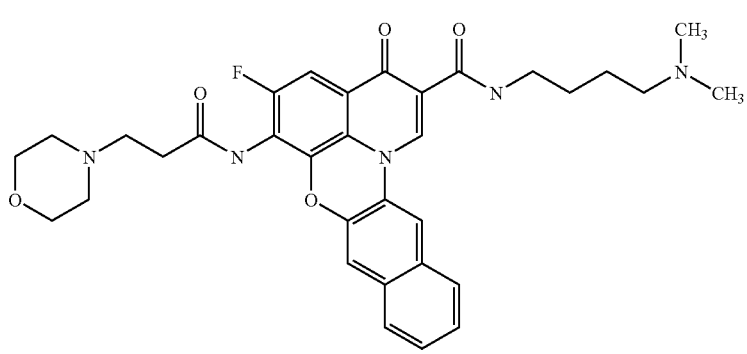
1173
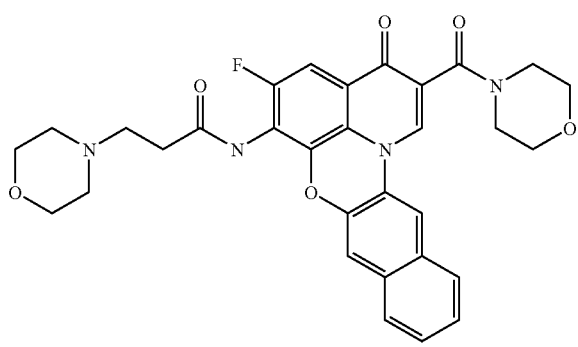
1174
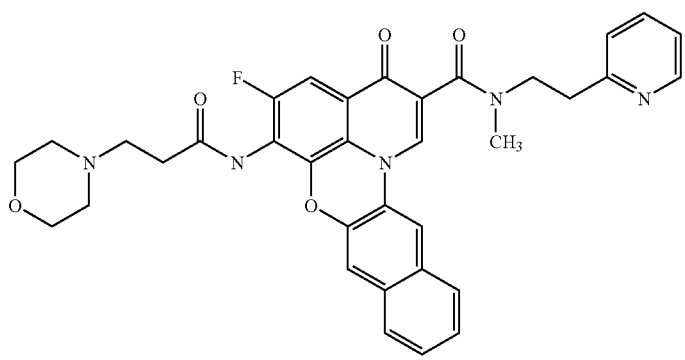

-continued
1175
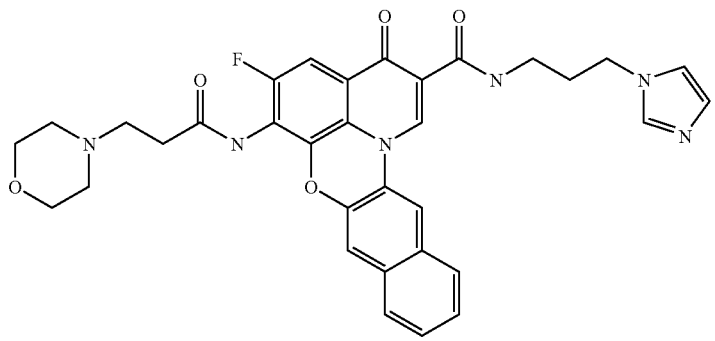
1176
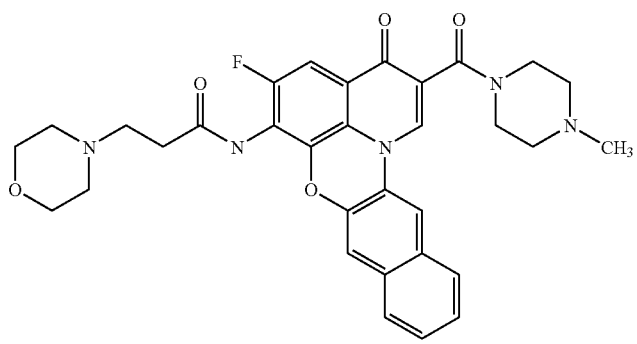
1177
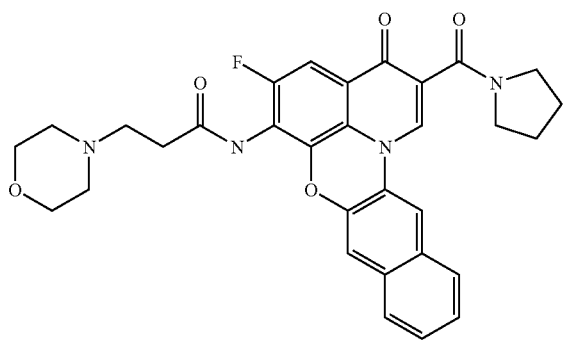
1178
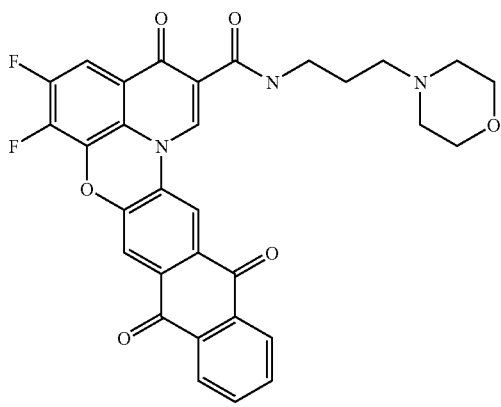

-continued
1179
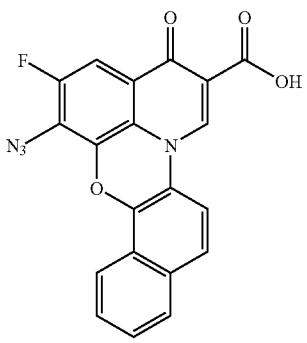
1180
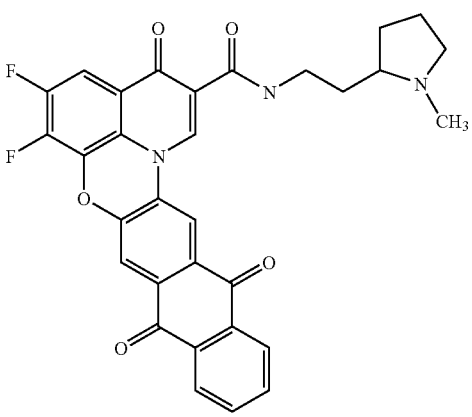
1181
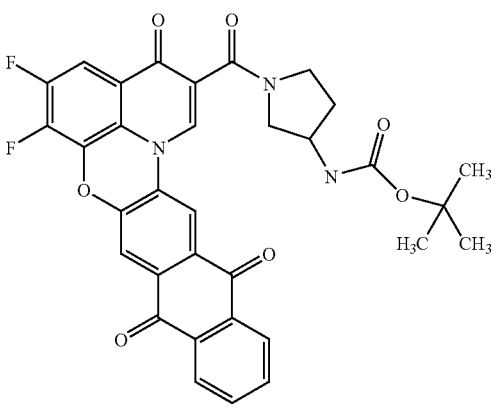
1182
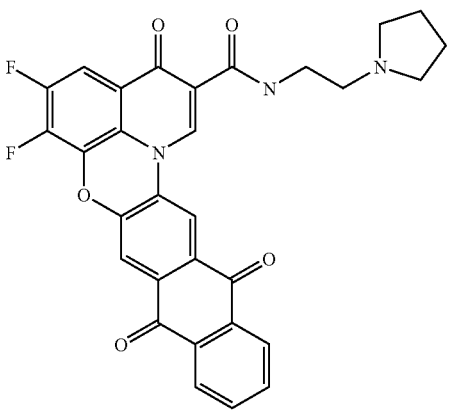

-continued
1183 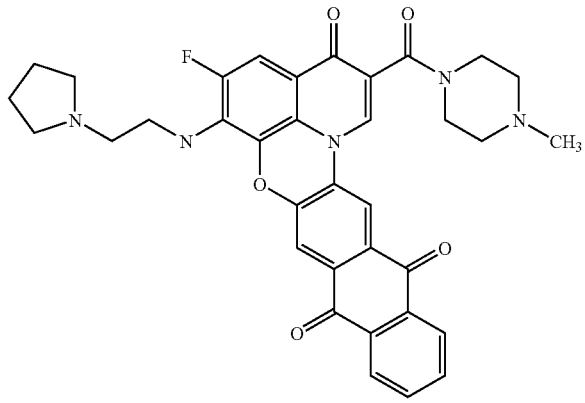
1184 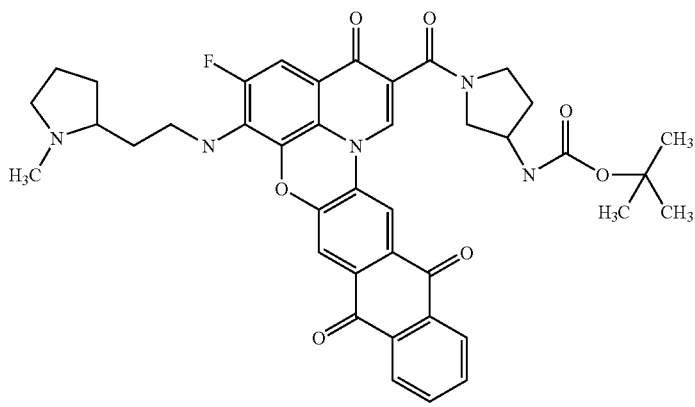
1185 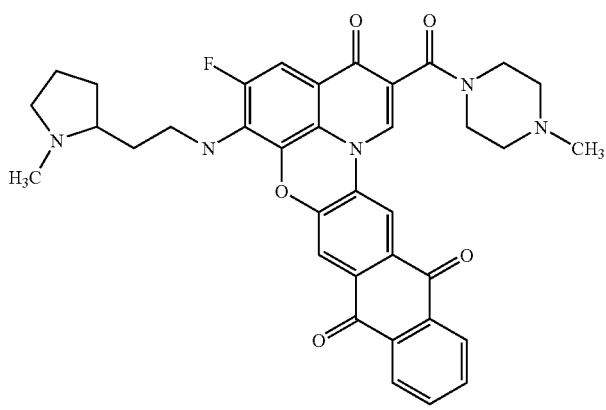
1186 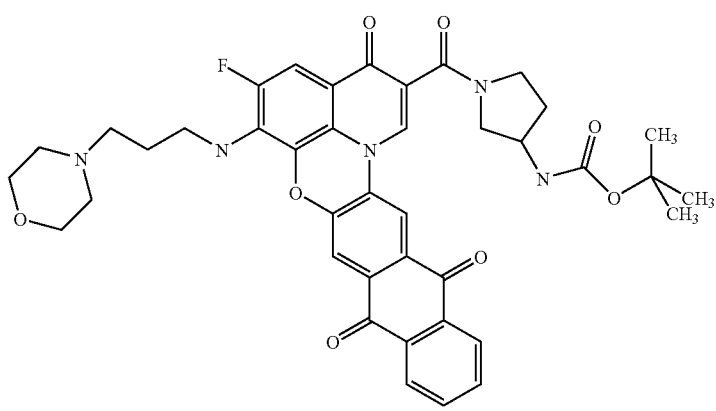

-continued
1187
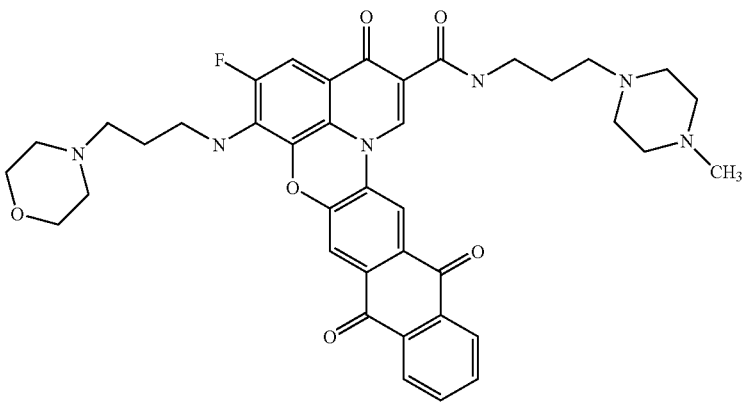
1188
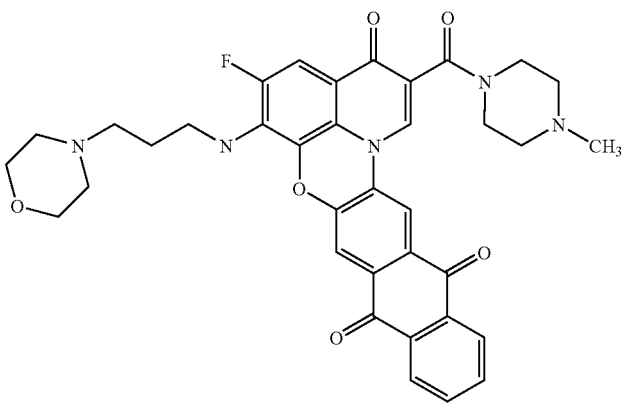
1189
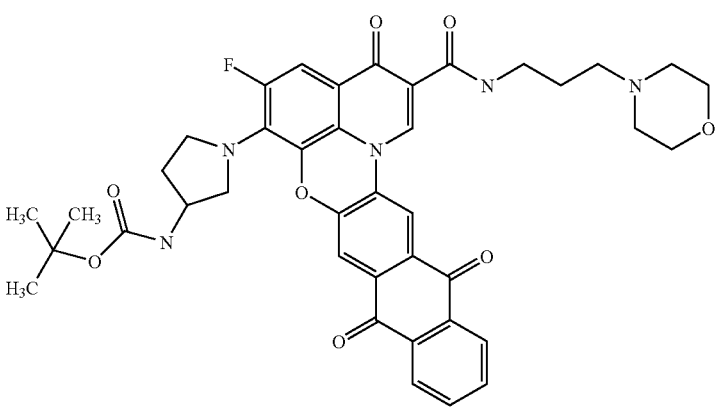
1190
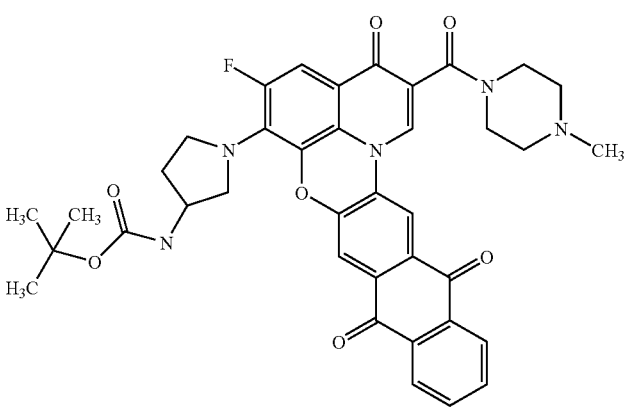

-continued
1191 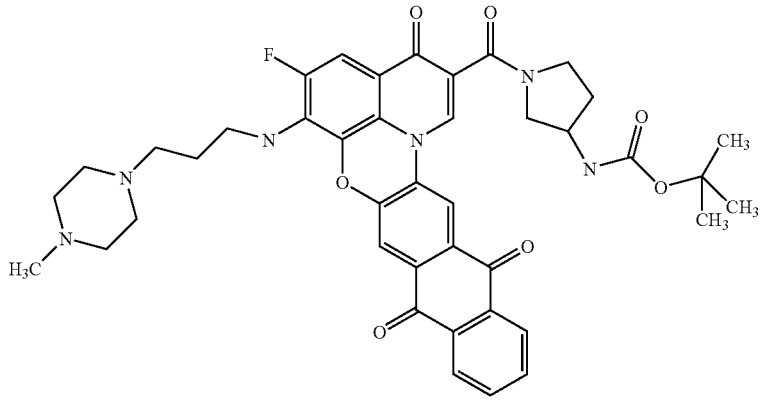
1192 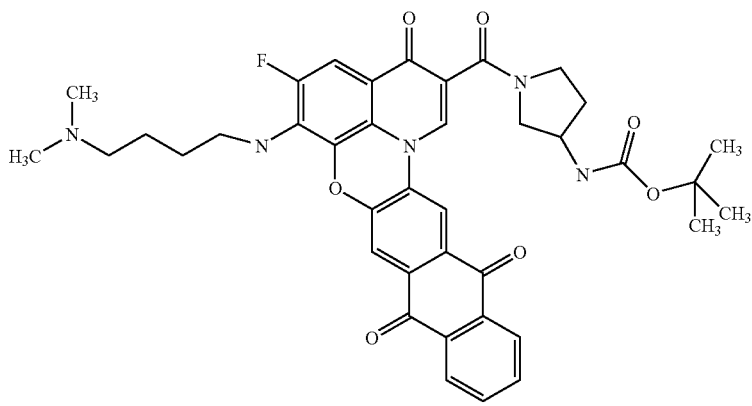
1193 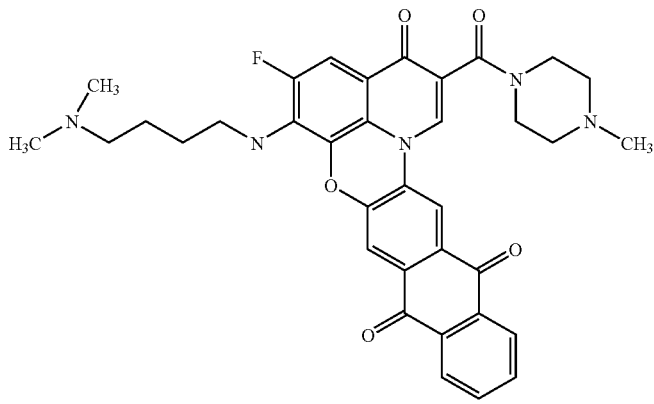
1194 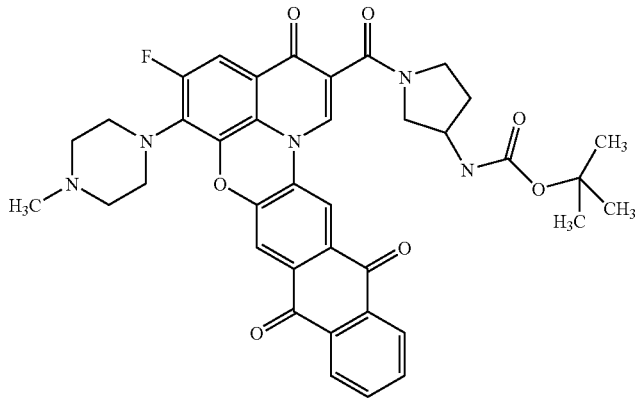

-continued
1195
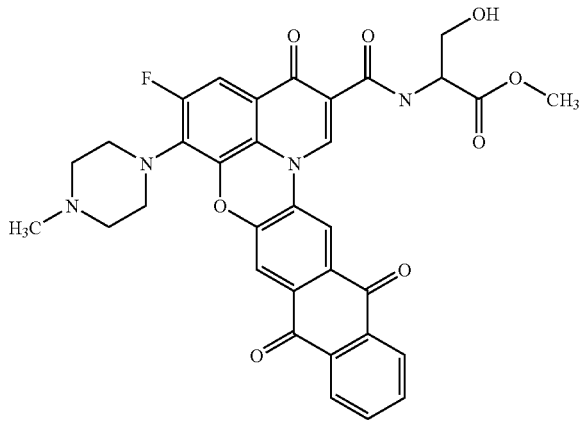
1196
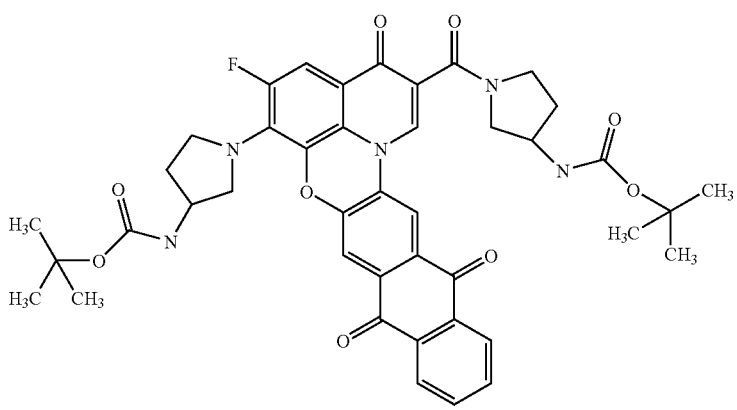
1197
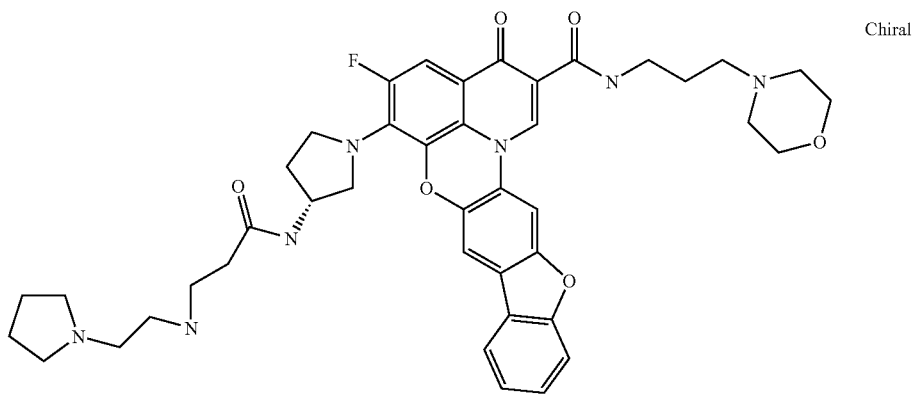
Chiral

| | |
|---|---|
| 1198 | 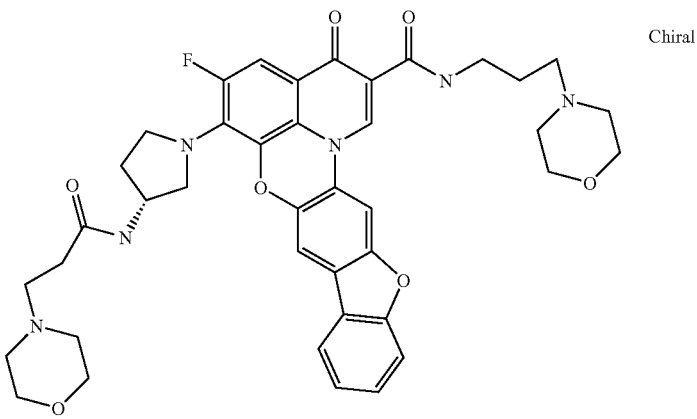 Chiral |
| 1199 | 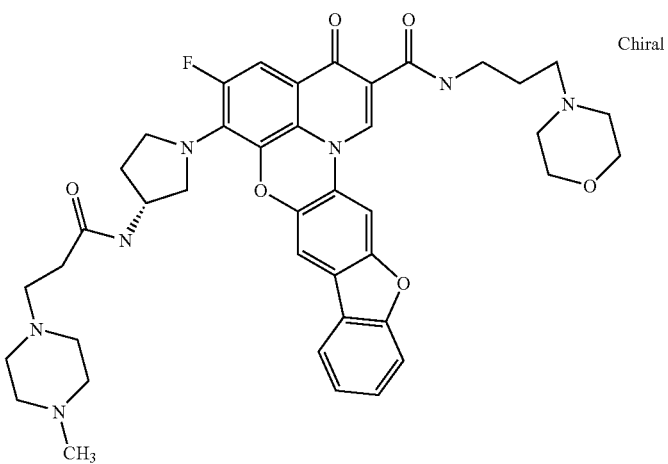 Chiral |
| 1200 | 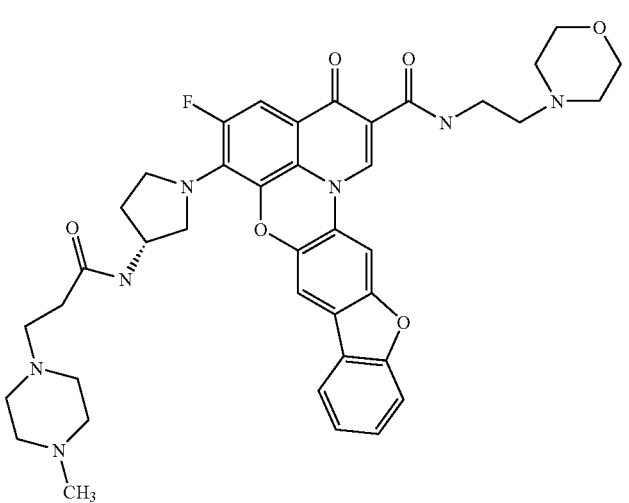 Chiral |

-continued
| | |
|---|---|
| 1201 | Chiral |
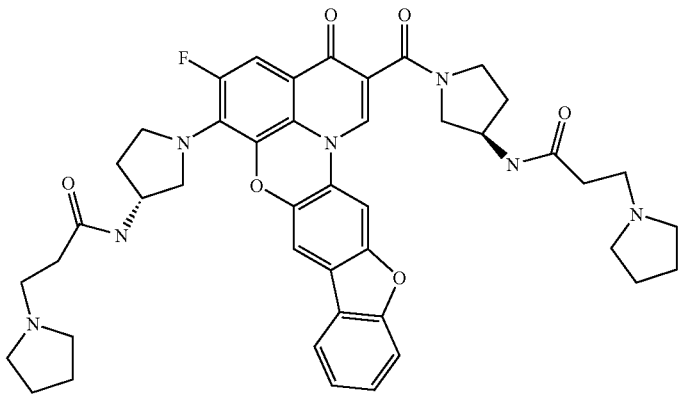
| | |
|---|---|
| 1202 | Chiral |
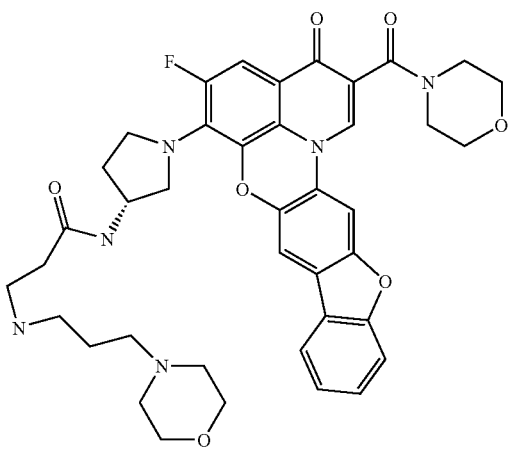
| | |
|---|---|
| 1203 | Chiral |
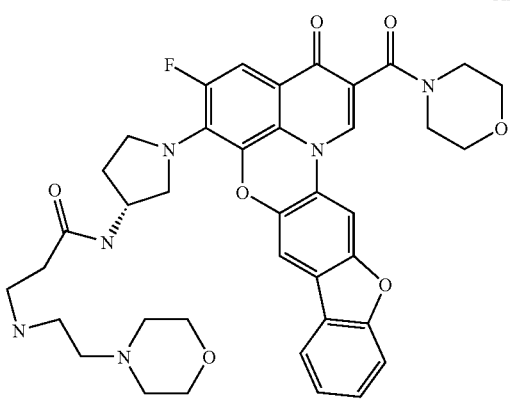

-continued
1204 Chiral
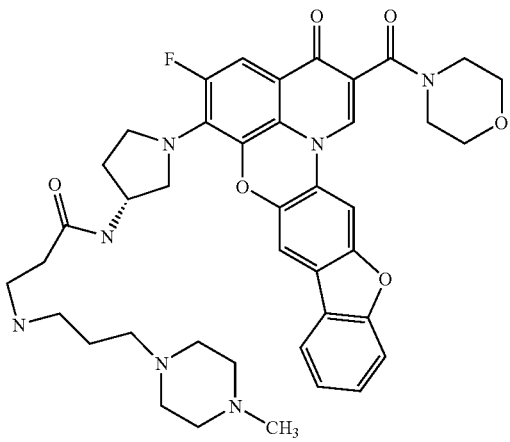
1205 Chiral
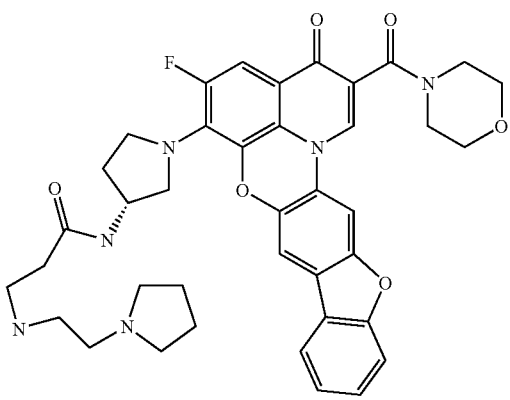
1206 Chiral
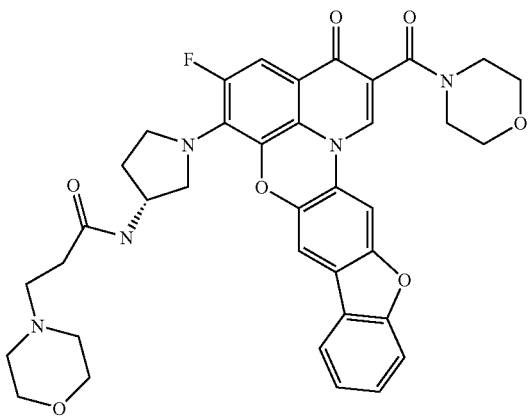

-continued
1207 Chiral
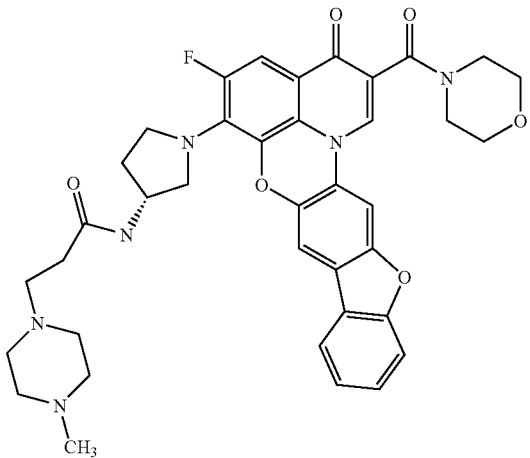
1208 Chiral
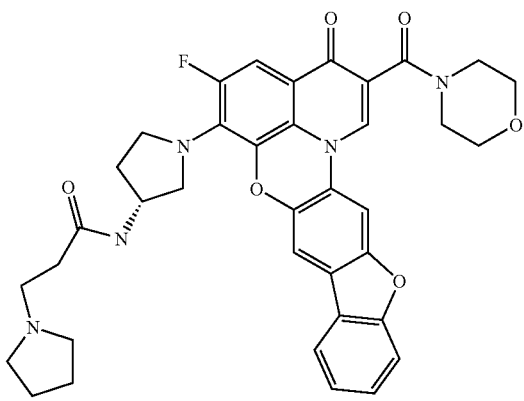
1209 Chiral
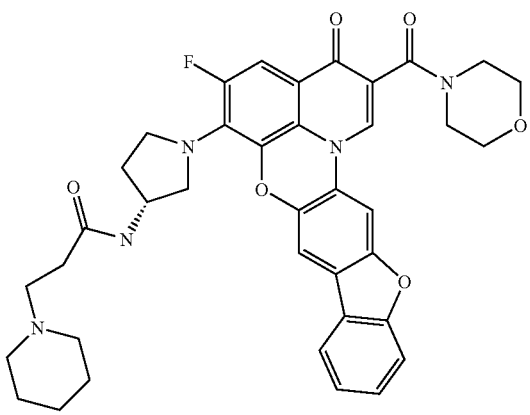

1210 Chiral
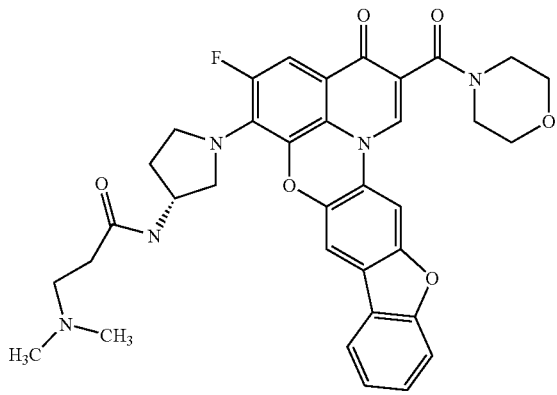
1211 Chiral
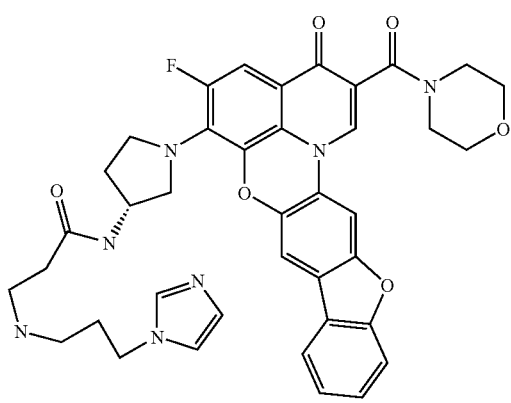
1212
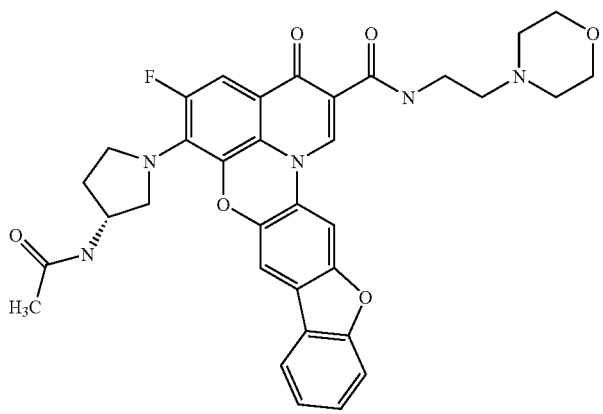

-continued
1213
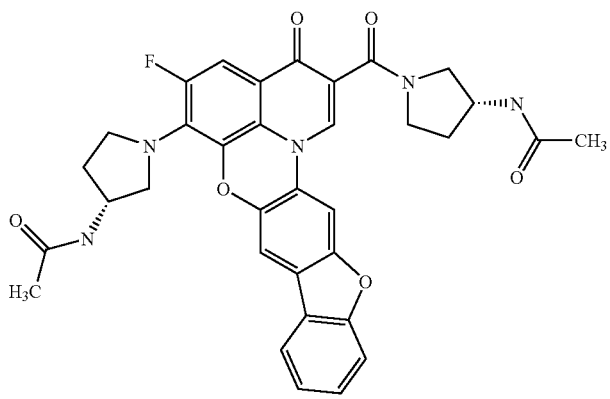
1214
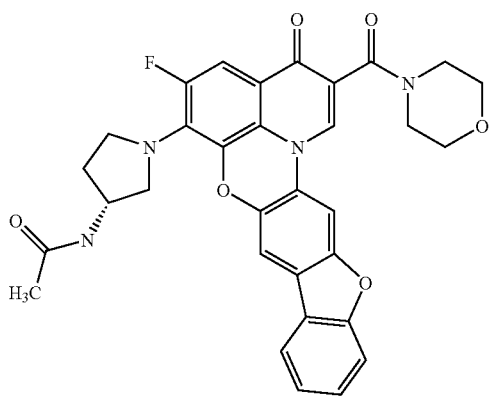
1215
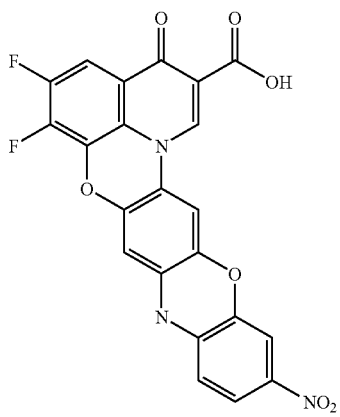
1216
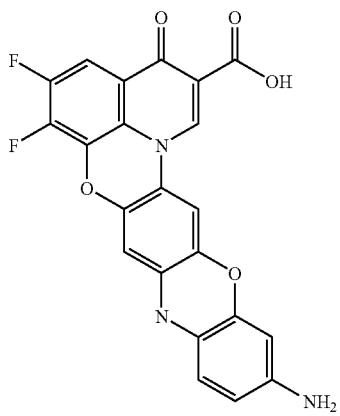

1217
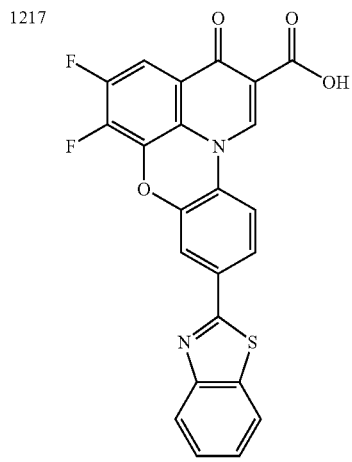
1218
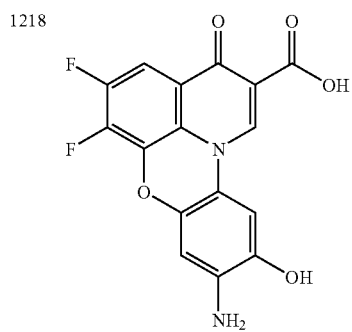
1219
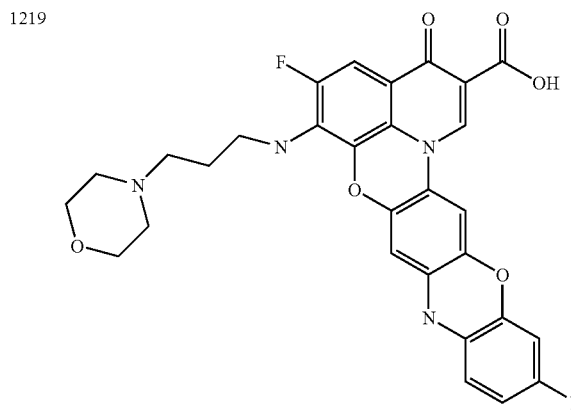
1220
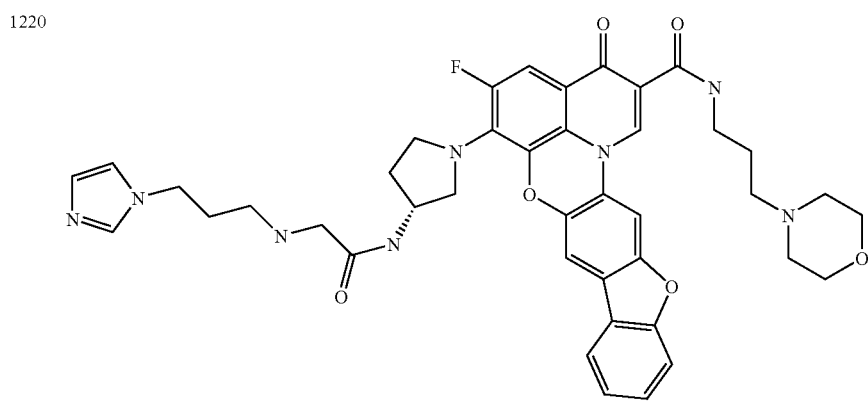

-continued
1221 Chiral
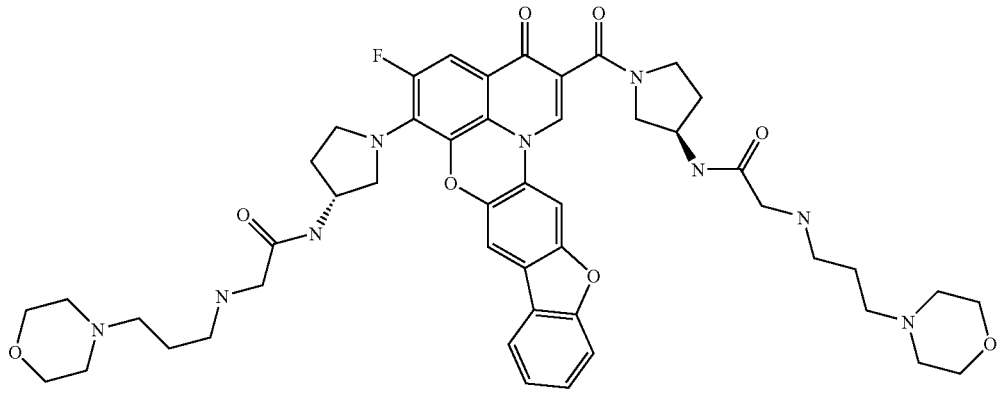
1222 Chiral
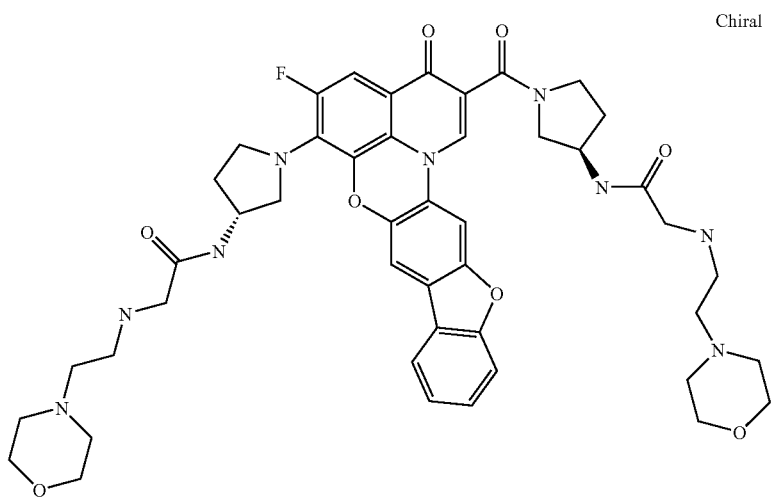
1223 Chiral
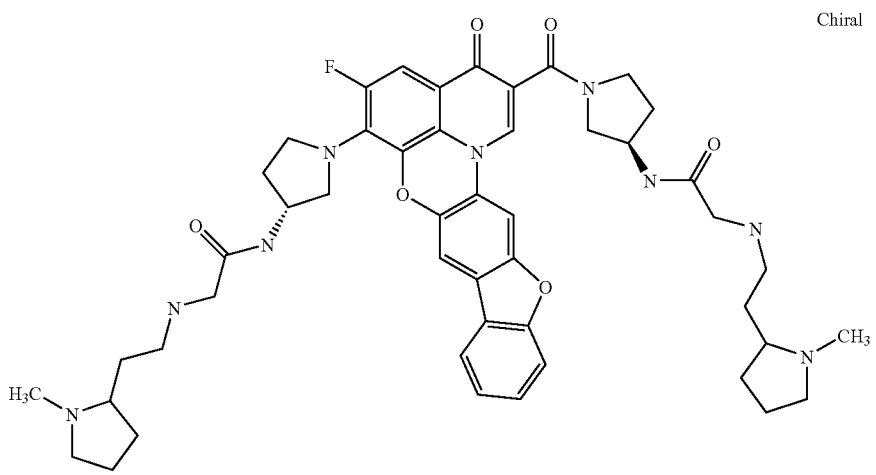

-continued
1224
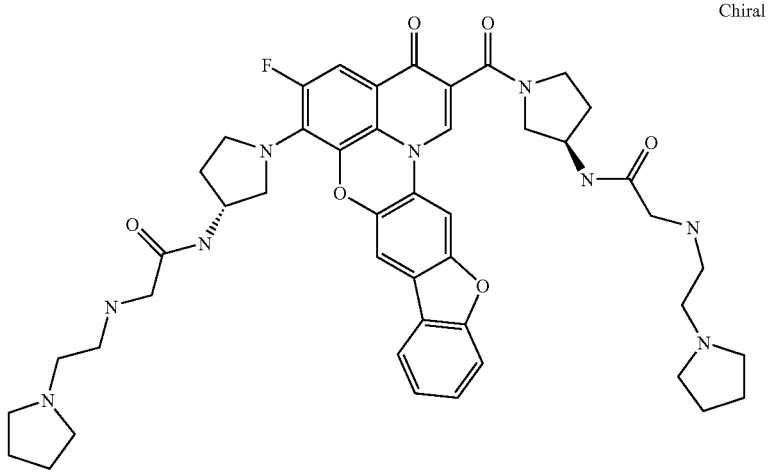
Chiral
1225
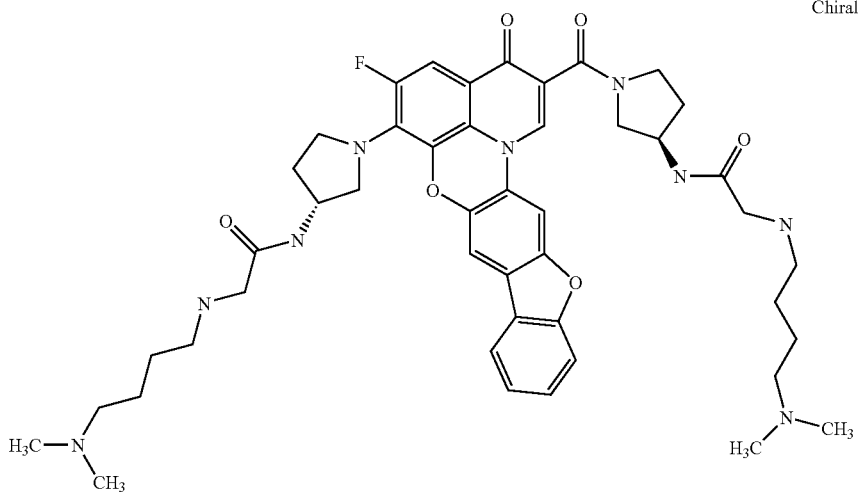
Chiral
1226
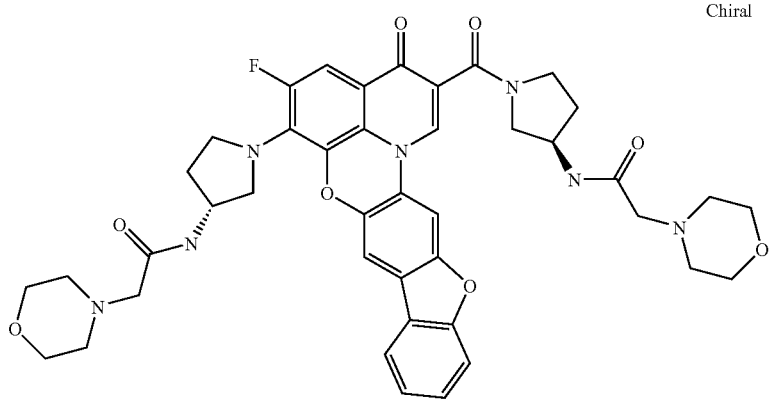
Chiral -continued
1227 Chiral
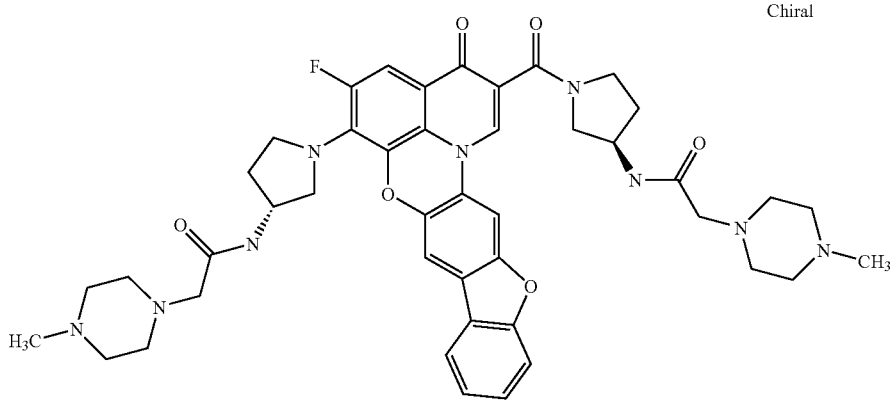
1228 Chiral
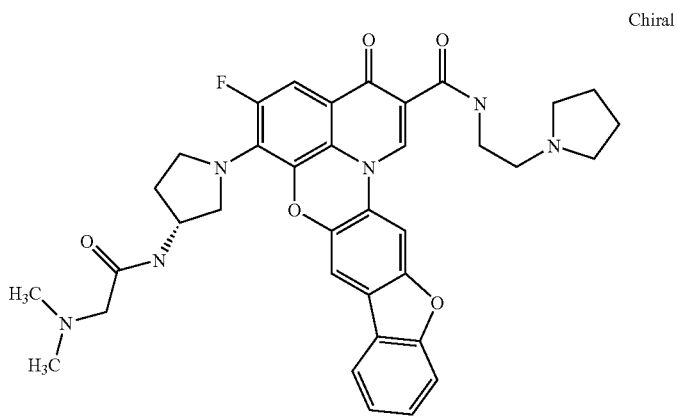
1229 Chiral
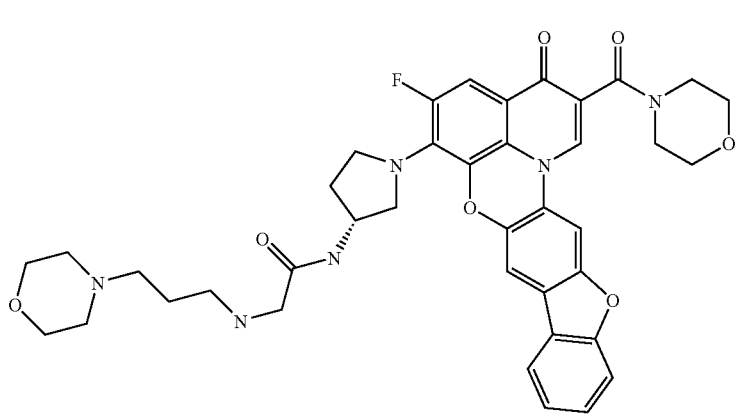

-continued
1230 Chiral
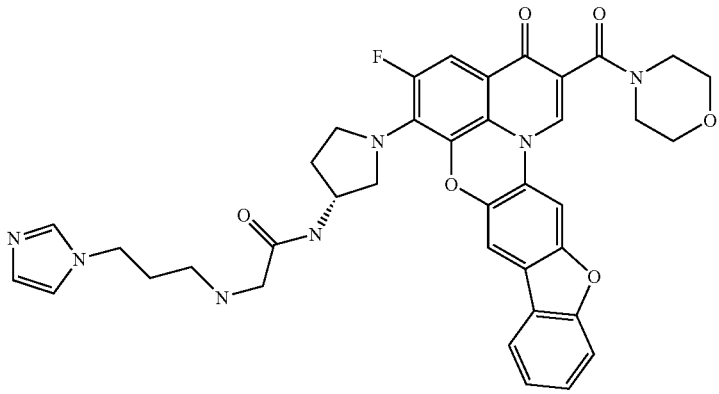
1231 Chiral
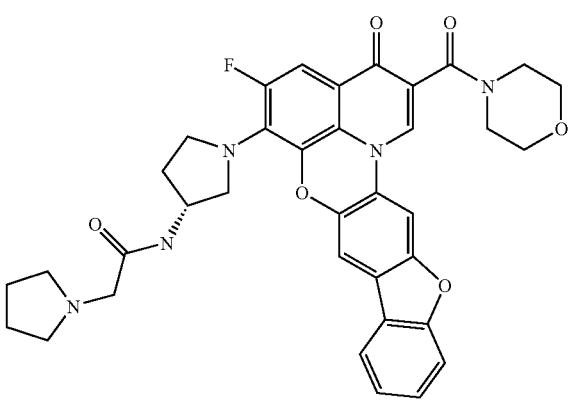
1232 Chiral
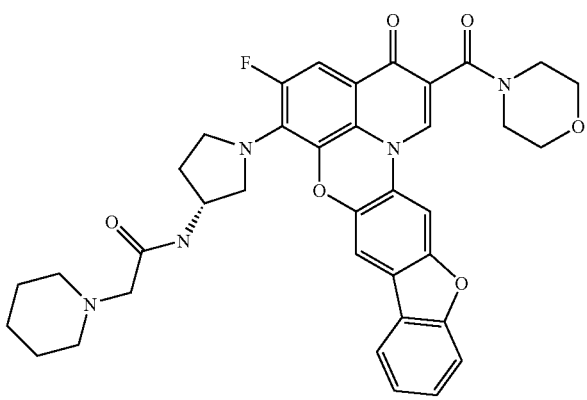

-continued
1233  Chiral
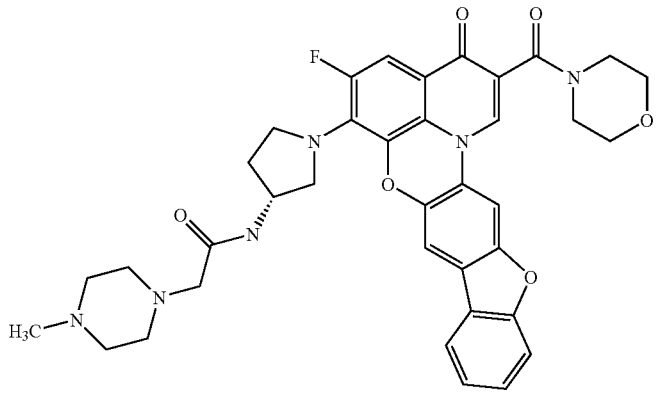
1234  Chiral
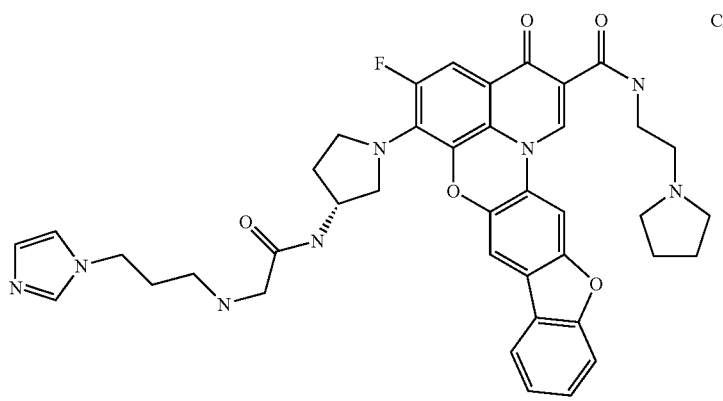
1235
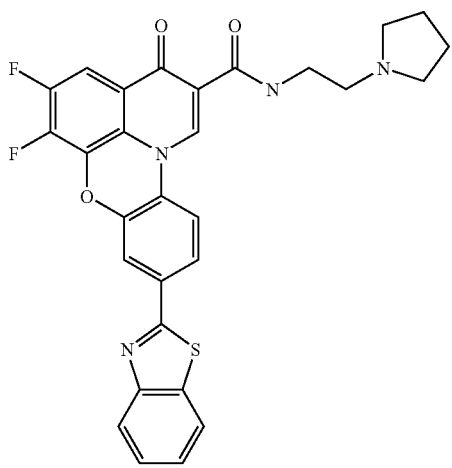

1236 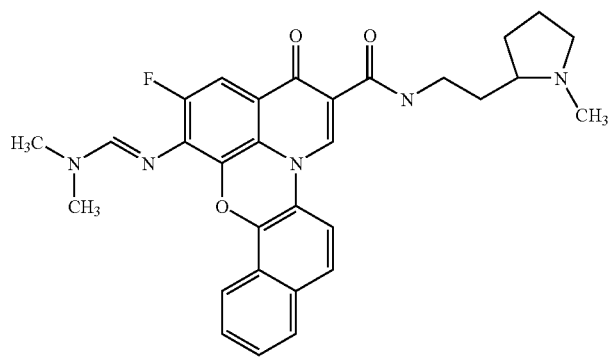
1237 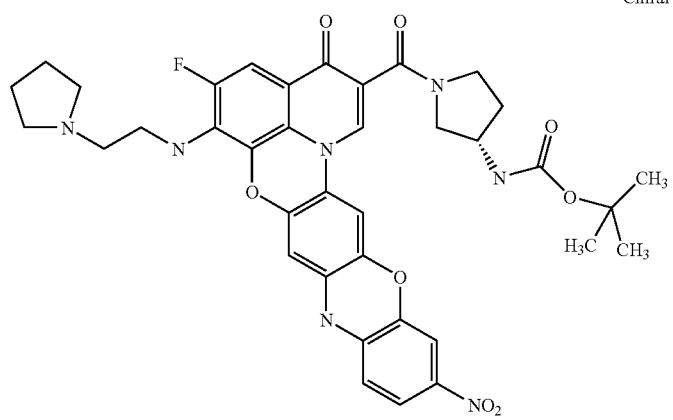
1238 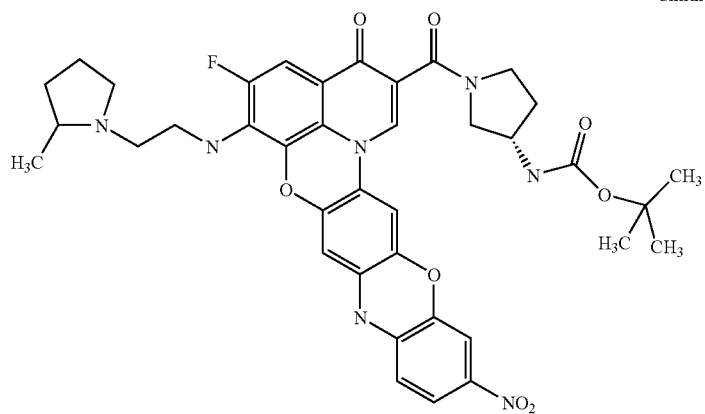

1239  Chiral
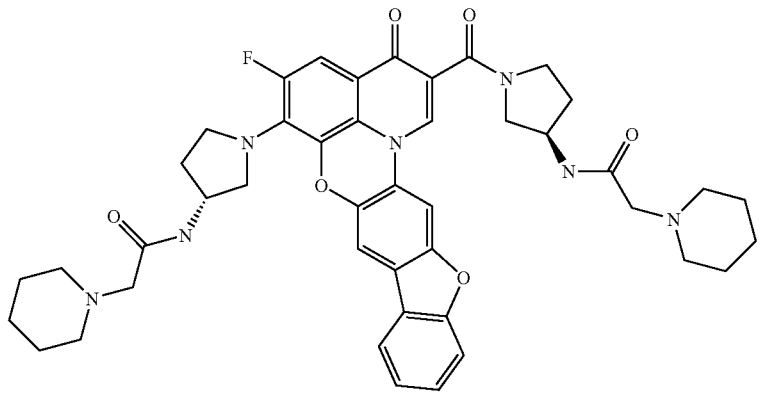
1240  Chiral
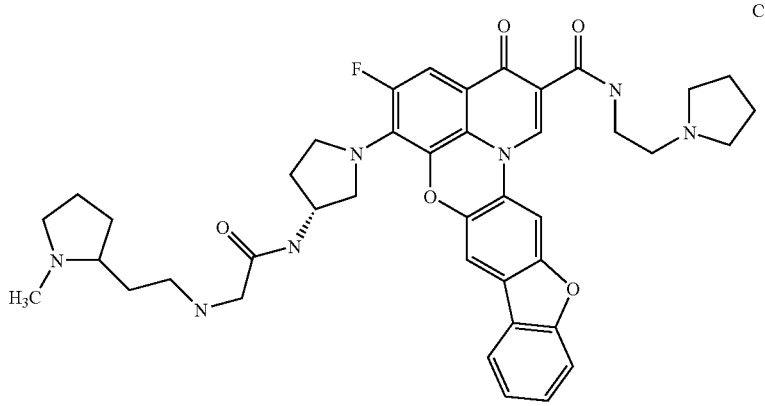
1241  Chiral
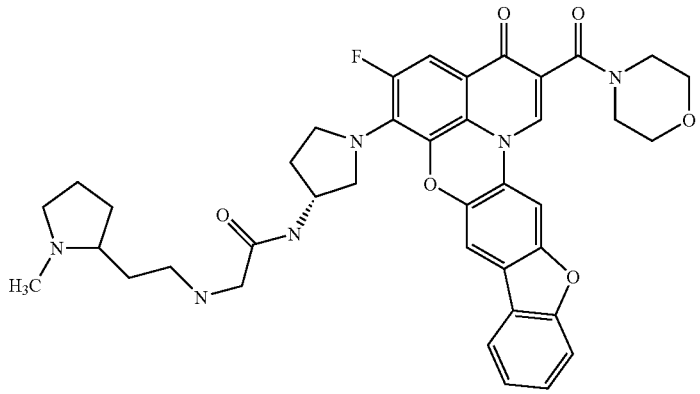

-continued
| 1242 | 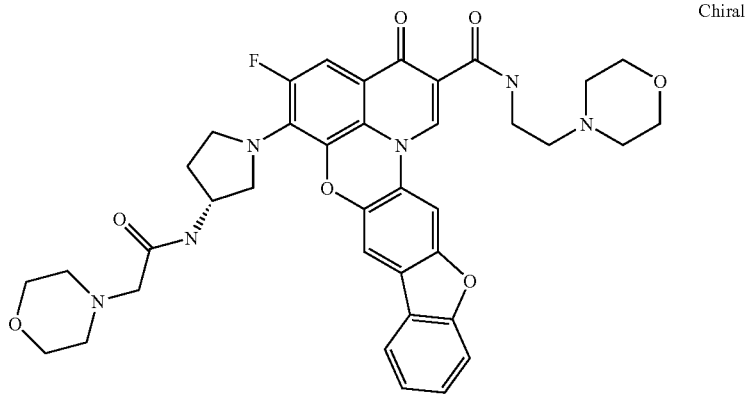 Chiral |
|---|---|
| 1243 | 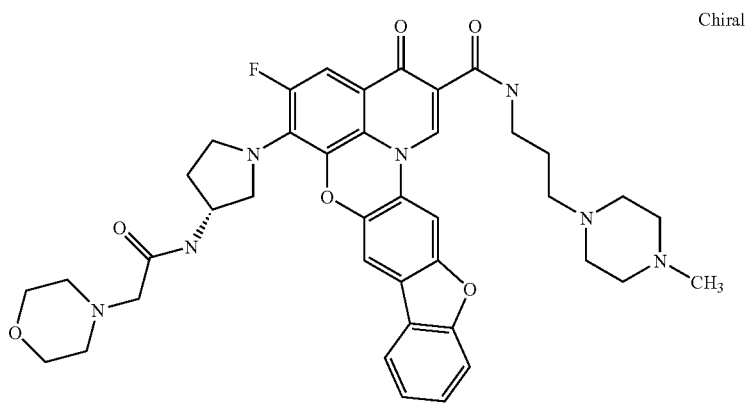 Chiral |
| 1244 | 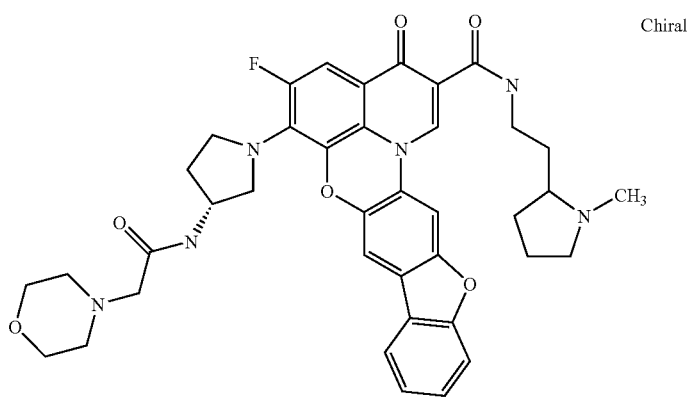 Chiral |
| 1245 | 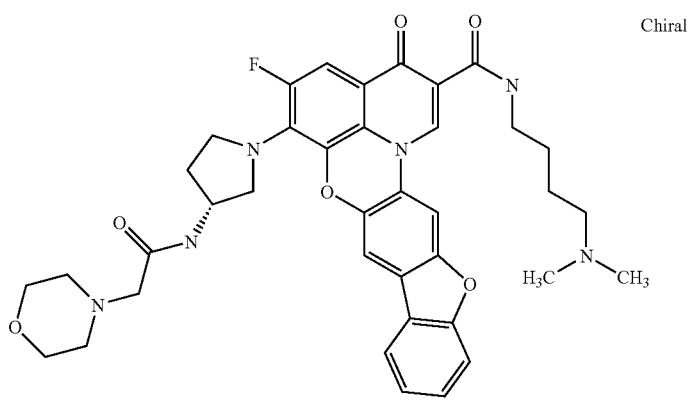 Chiral |

1246
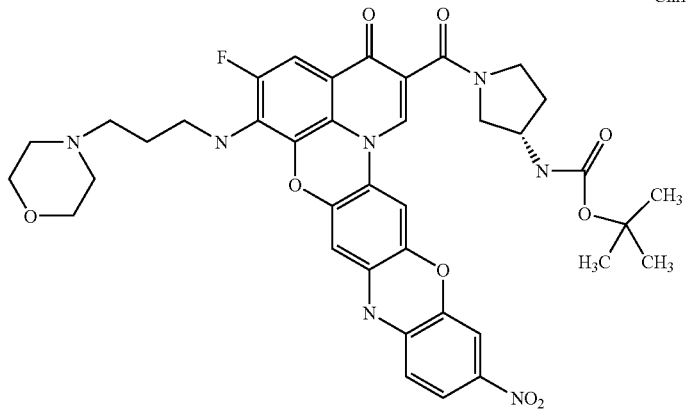
1247
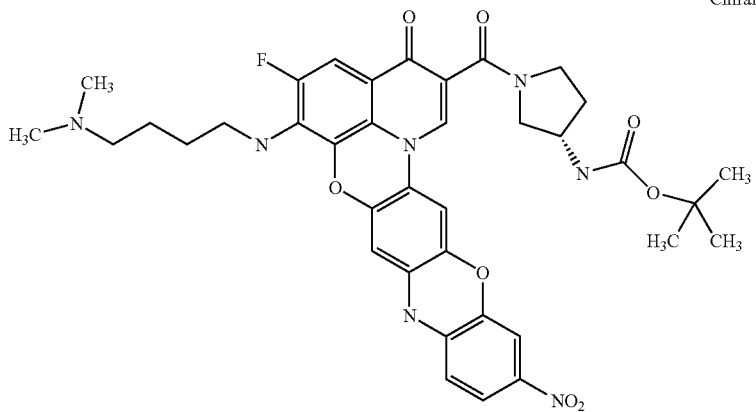
1248
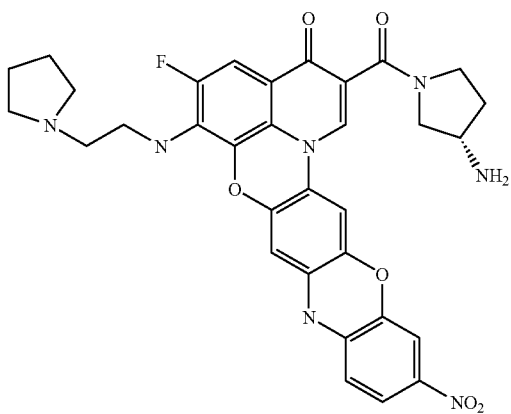

| | |
|---|---|
| 1249 | Chiral |
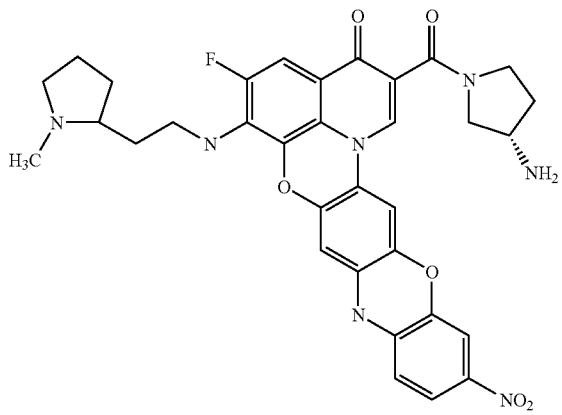
| | |
|---|---|
| 1250 | Chiral |
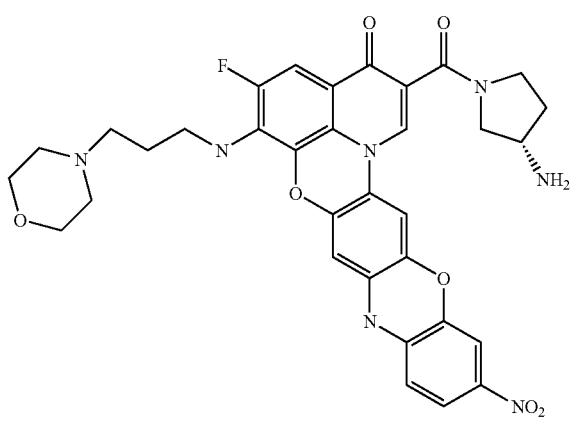
| | |
|---|---|
| 1251 | Chiral |
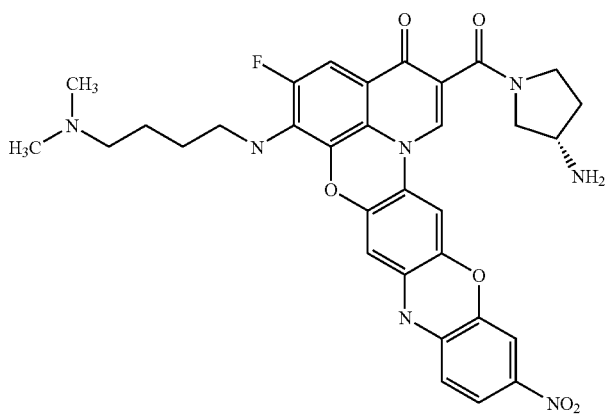

-continued
1252
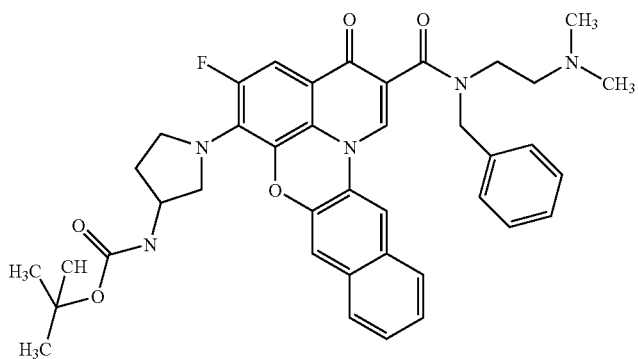
1253
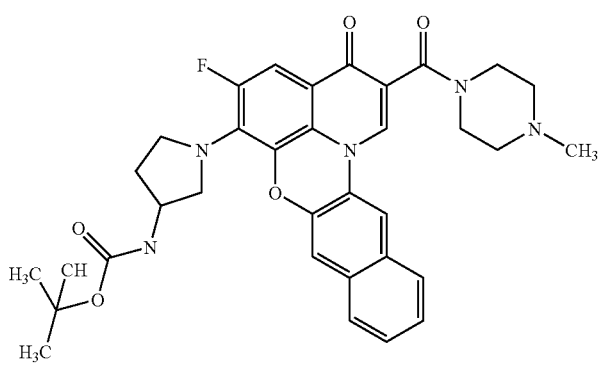
1254
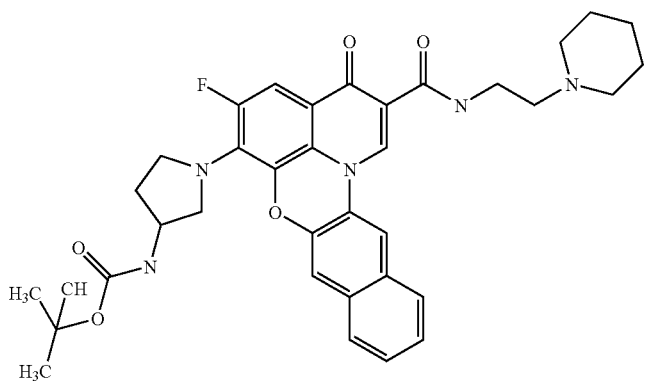
1255
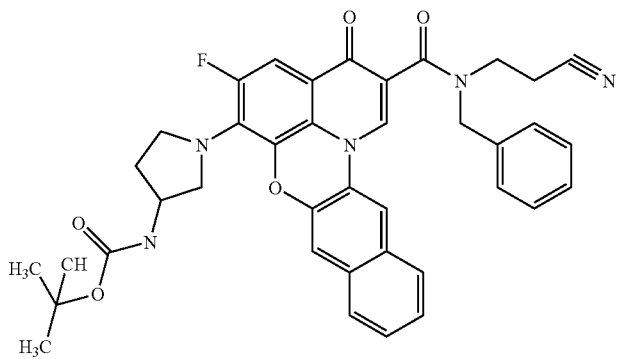

1256 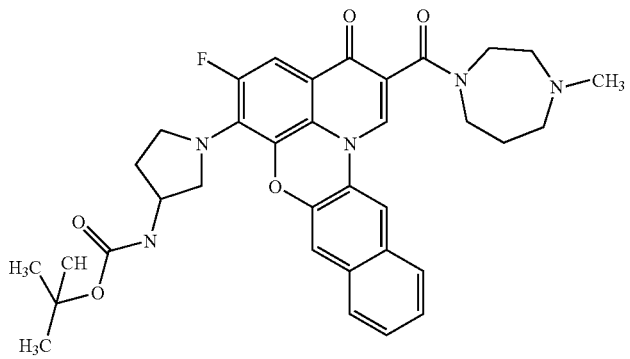
1257 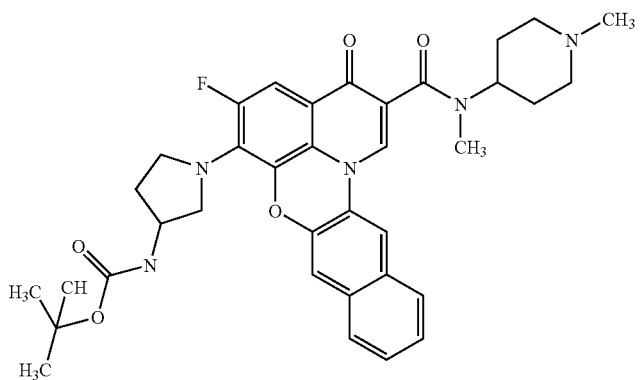
1258 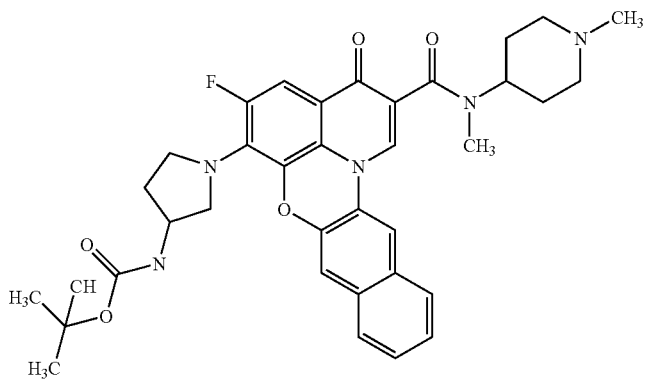
1259 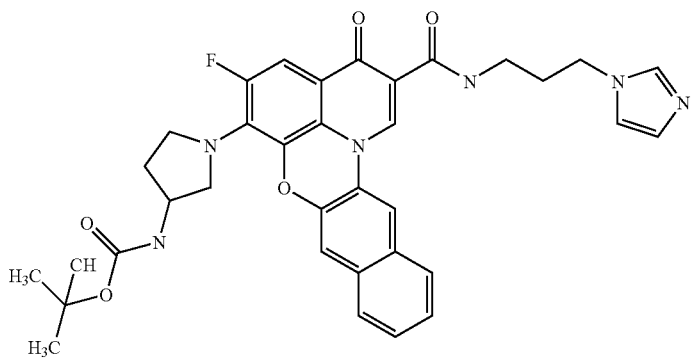

1260 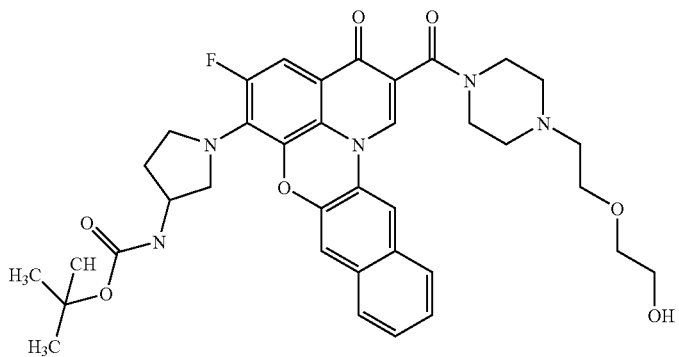
1261 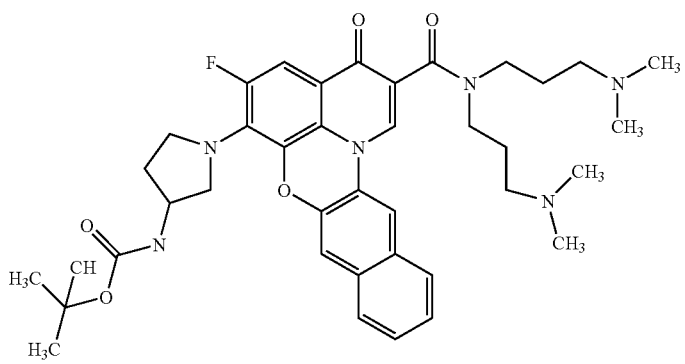
1262 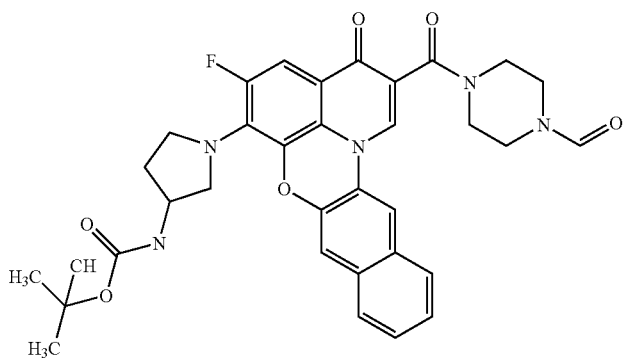
1263 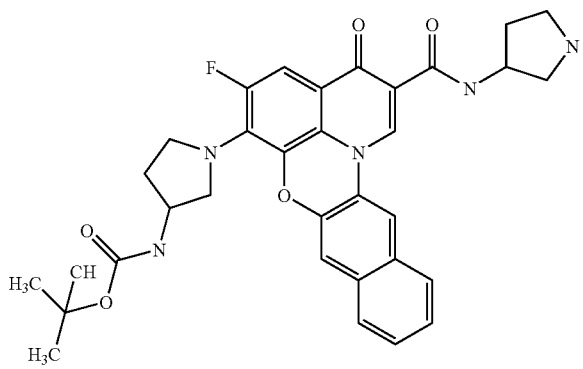

-continued
1264
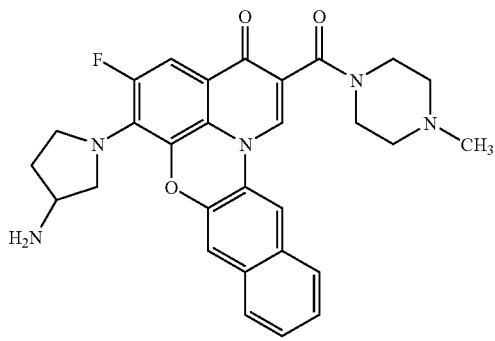
1265
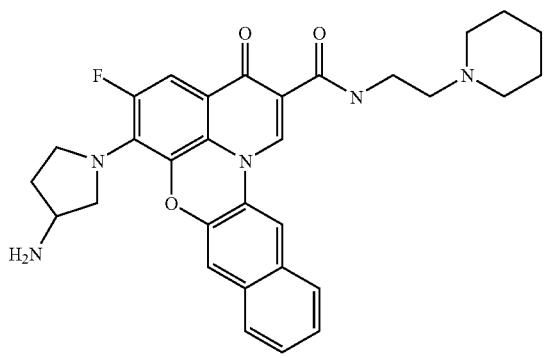
1266
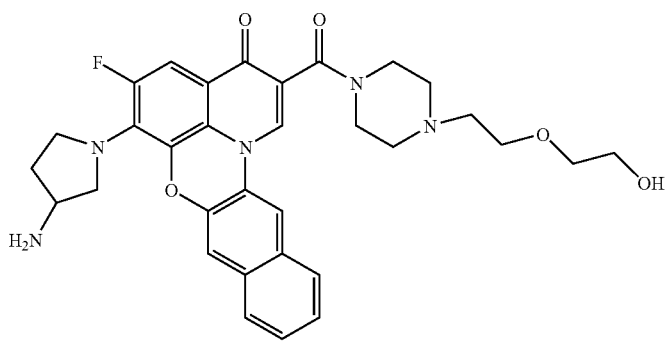
1267
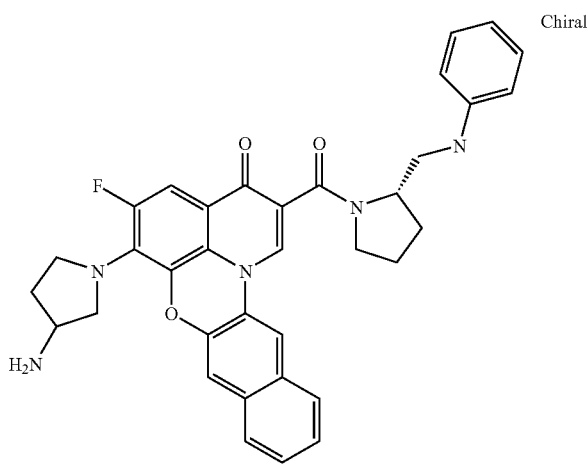

-continued
1268
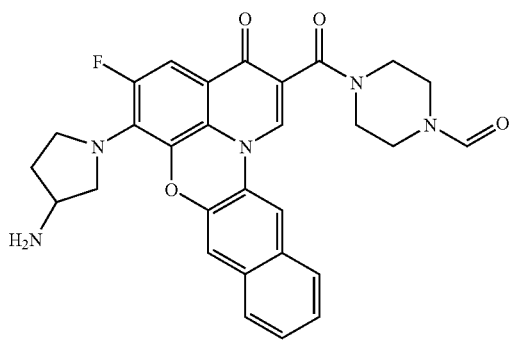
1269 Chiral
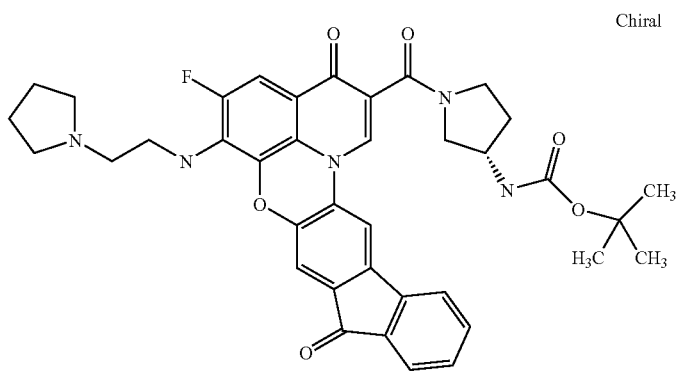
1270 Chiral
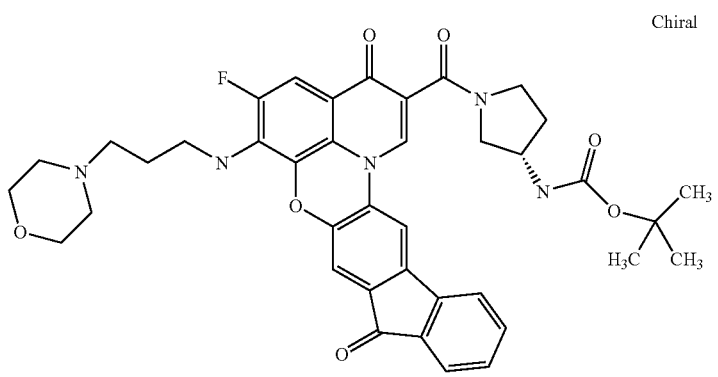
1271 Chiral
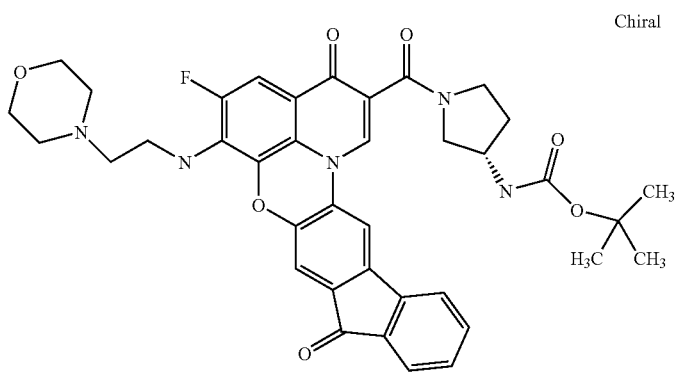

-continued
1272
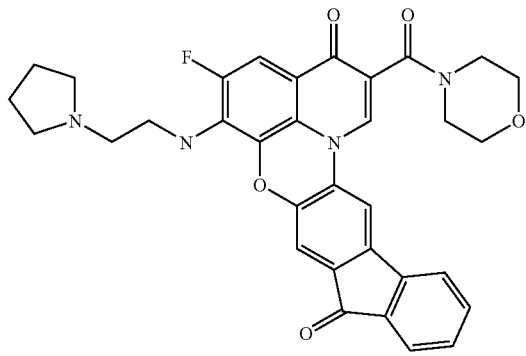
1273
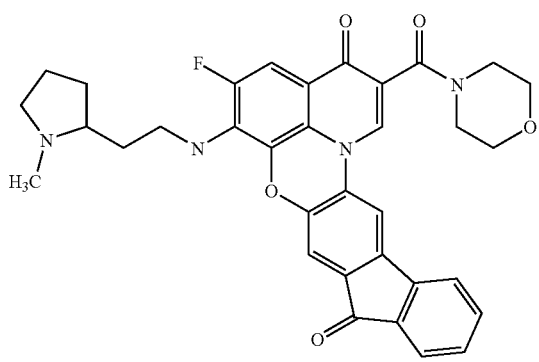
1274
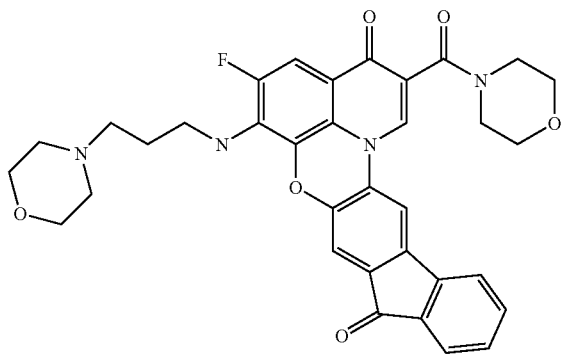
1275
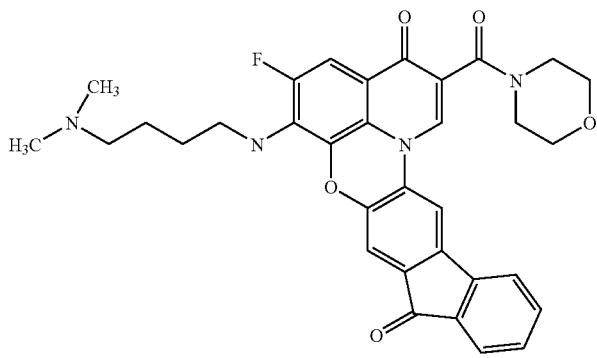

1276 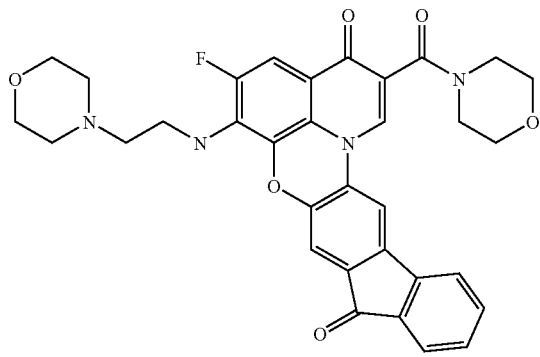
1277 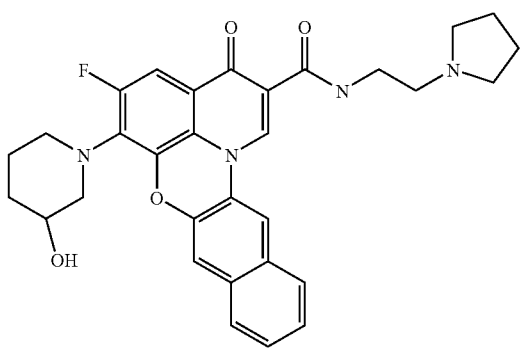
1278 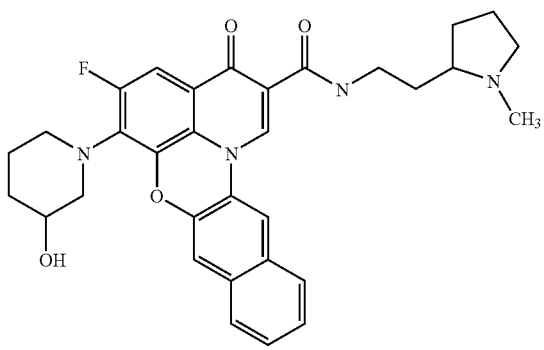
1279 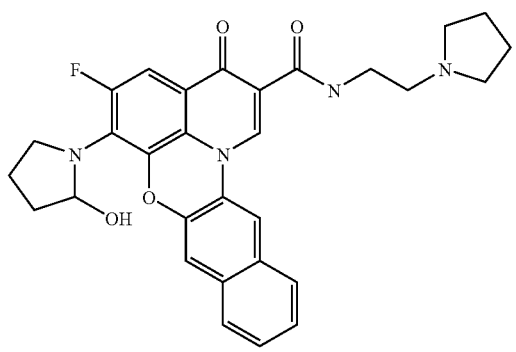

-continued
1280
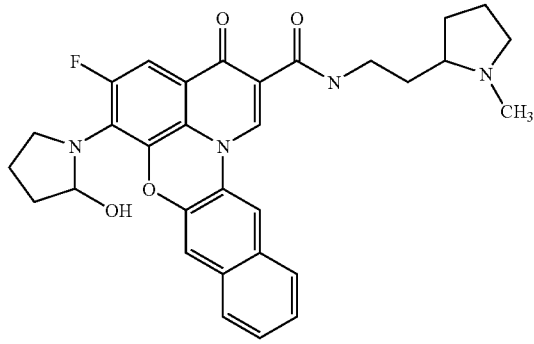
1281 Chiral
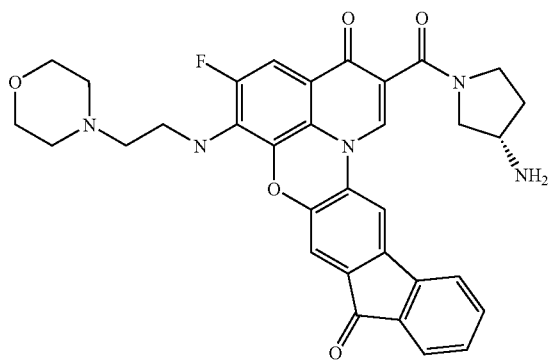
1282
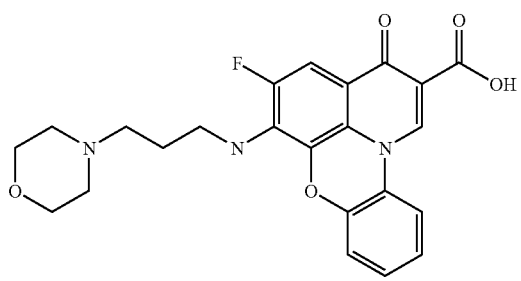
1283
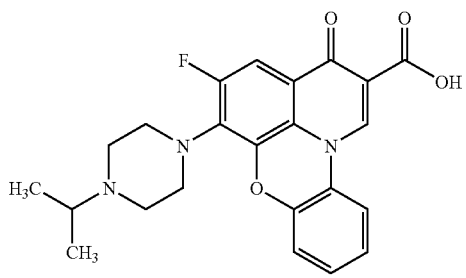
1284
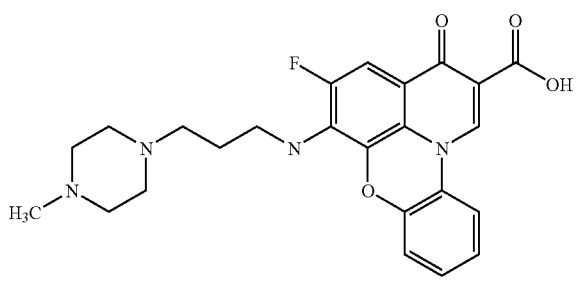

-continued
1285
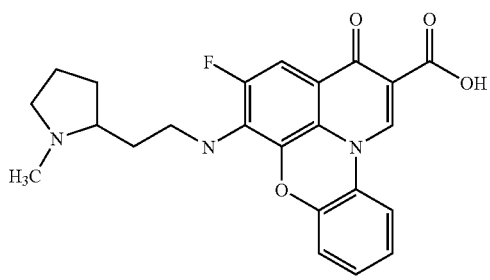
1286
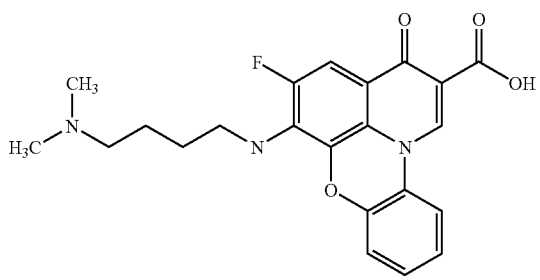
1287
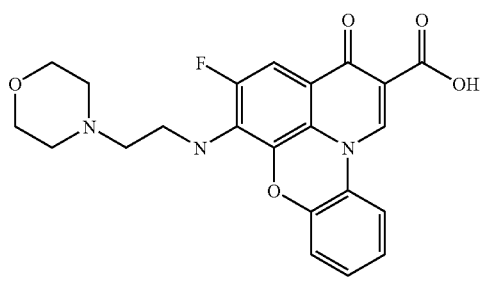
1288
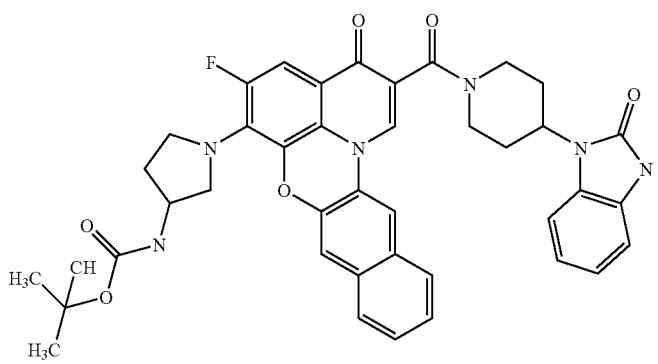
1289
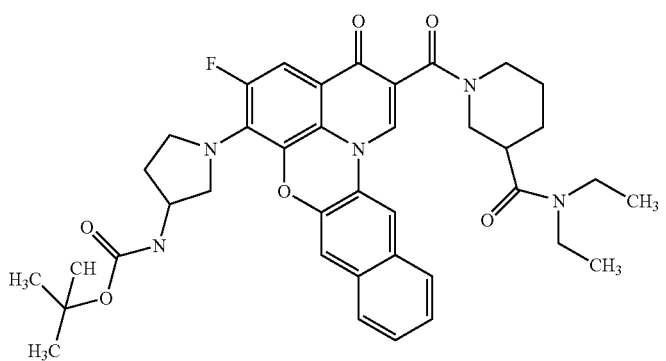

1290
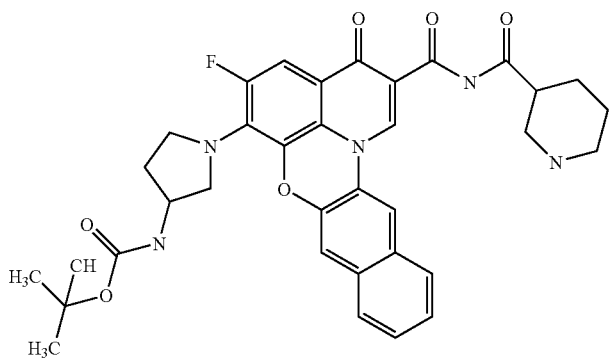
1291
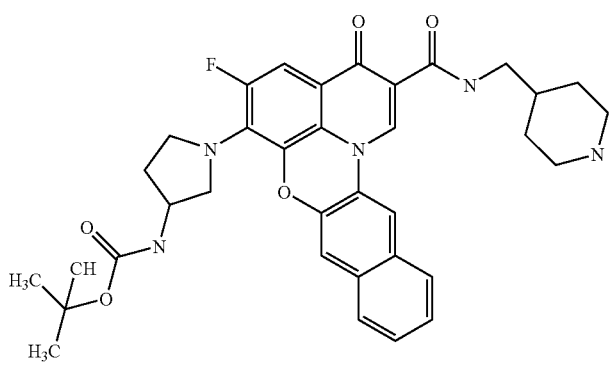
1292
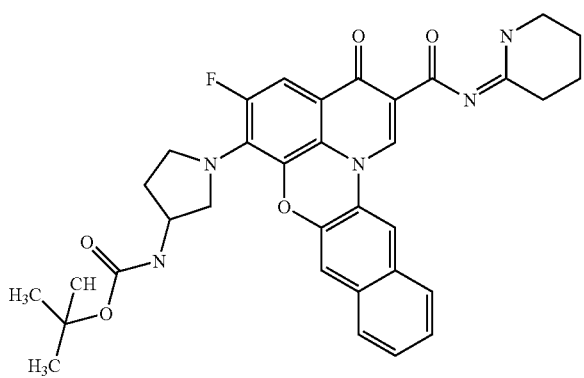
1293
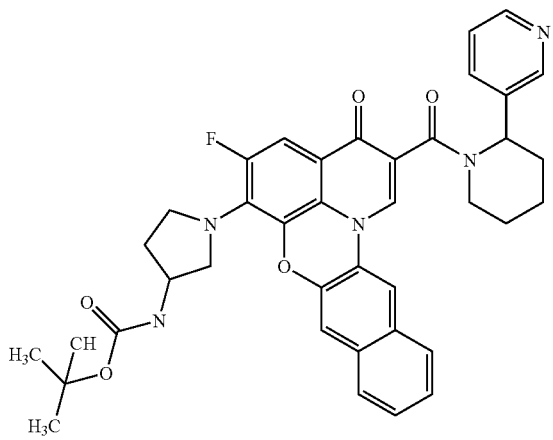

1294
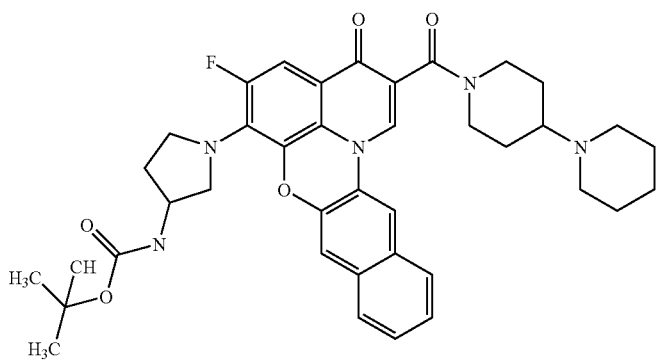
1295
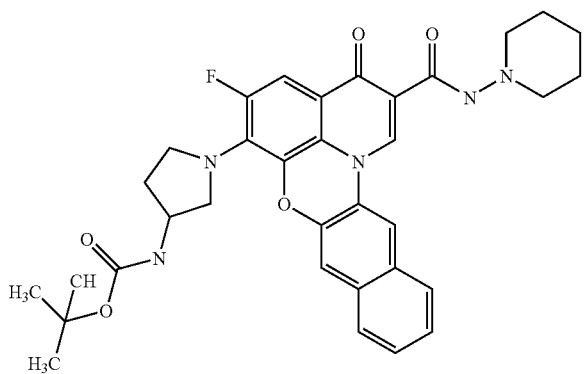
1296
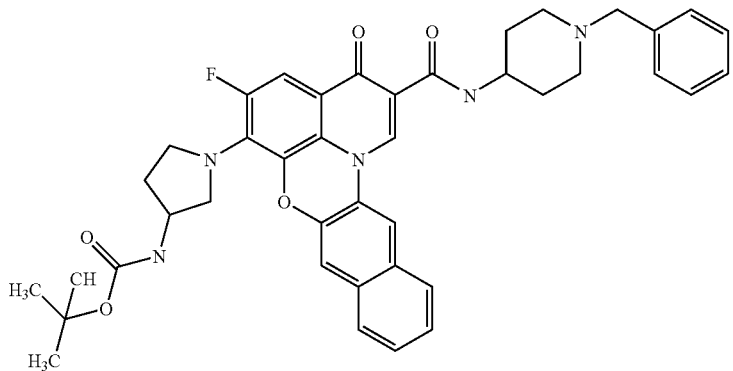
1297
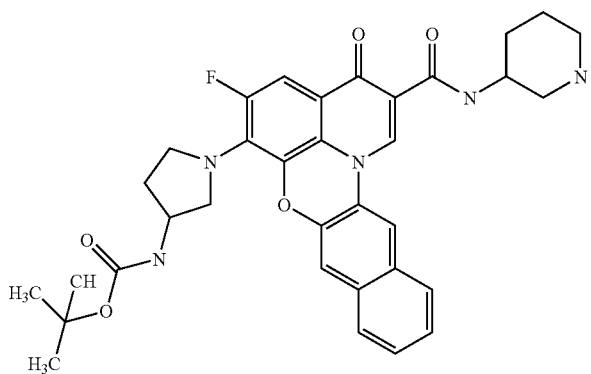

-continued
1298
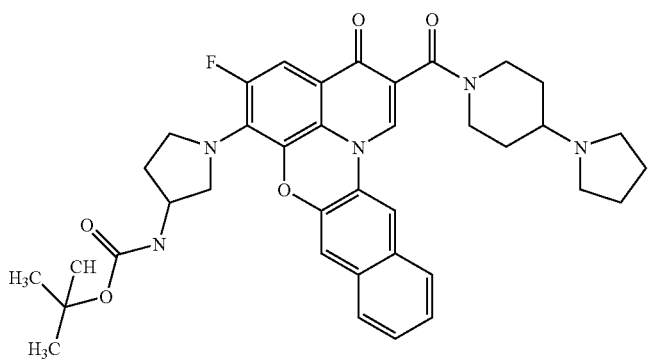
1299
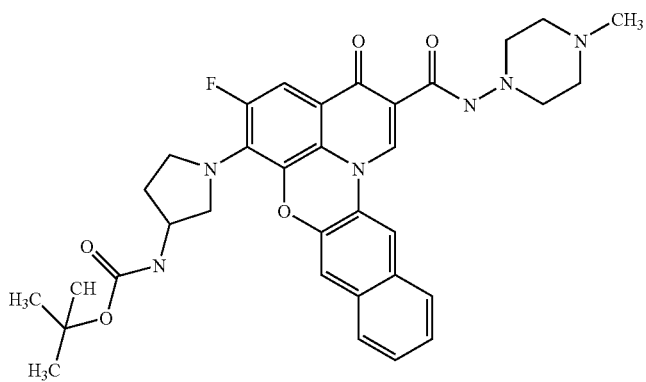
1300
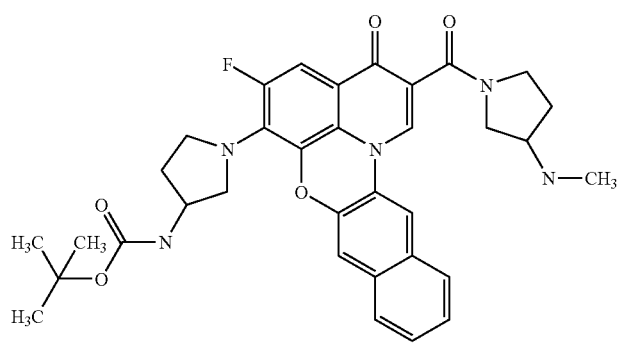
1301
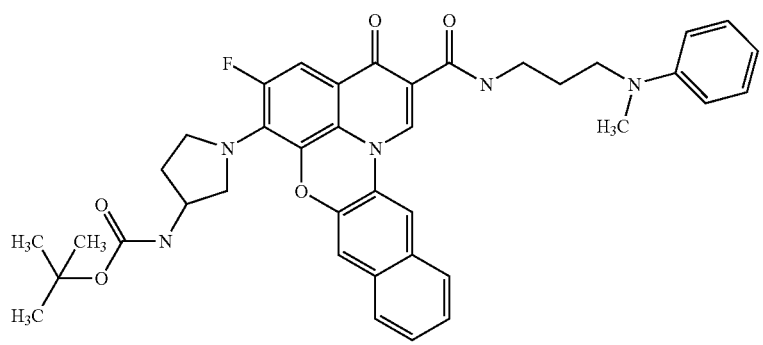

-continued
1302
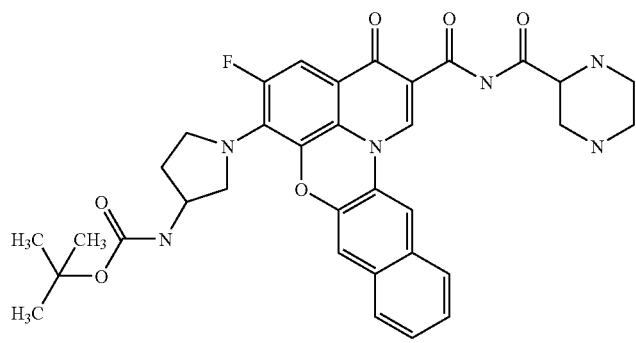
1303
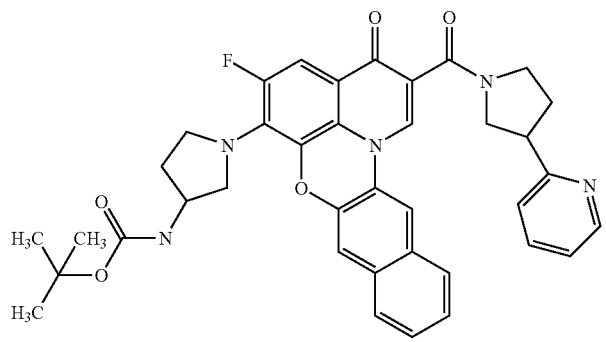
1304
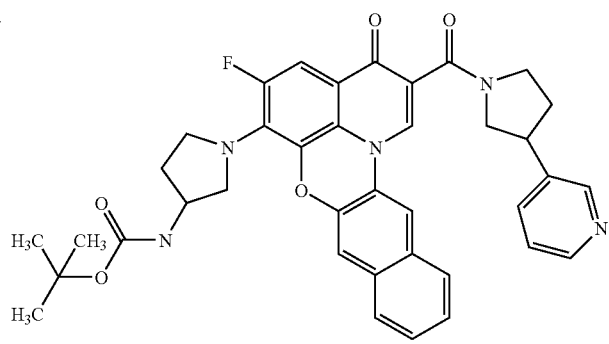
1305
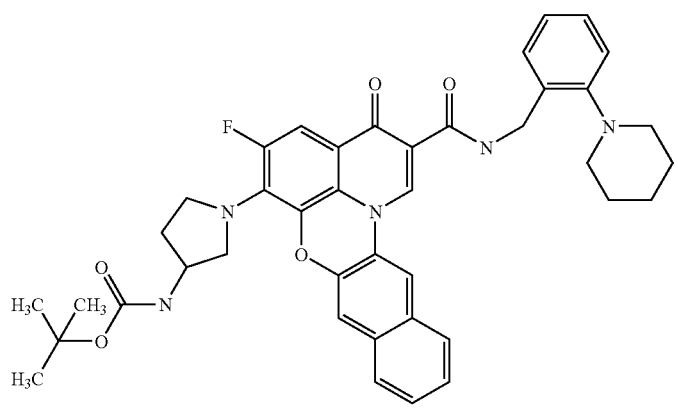

-continued
1306
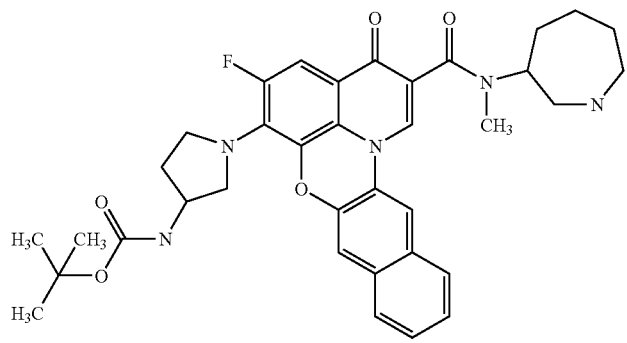
1307
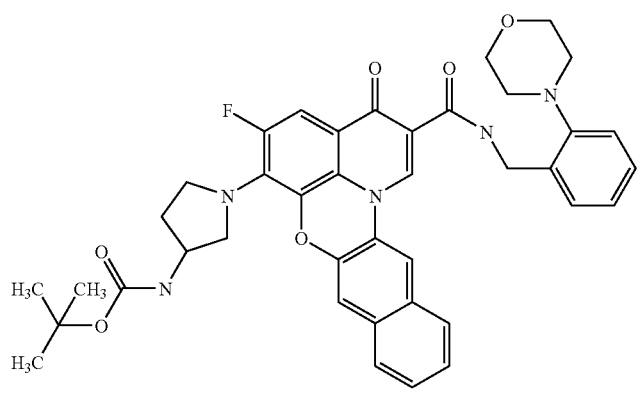
1308
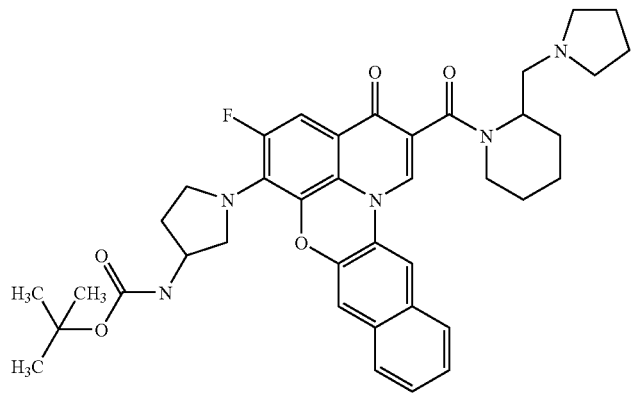
1309
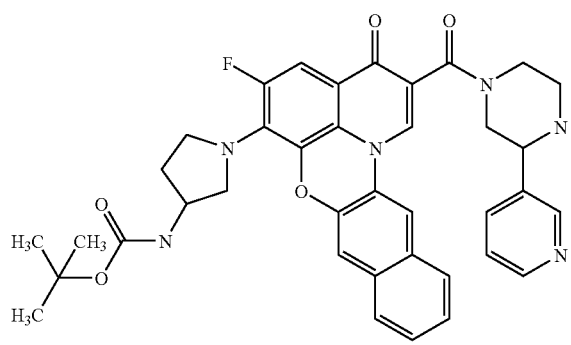

-continued
1310
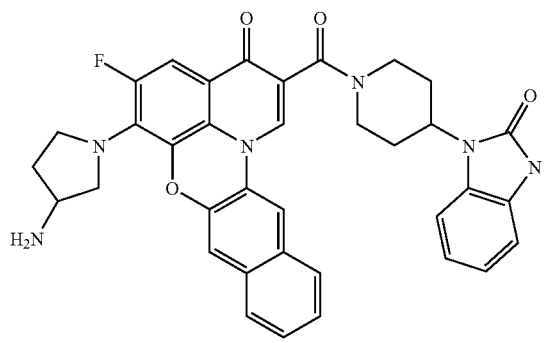
1311
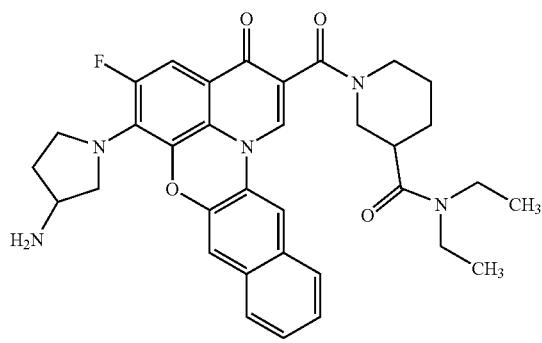
1312
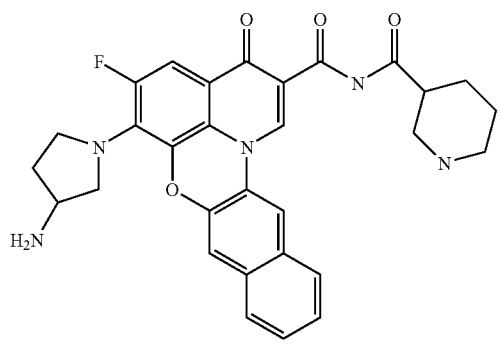
1313
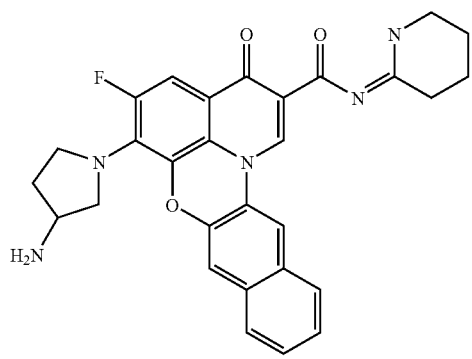

-continued
1314
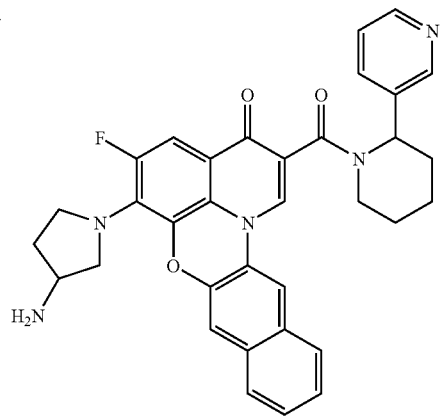
1315
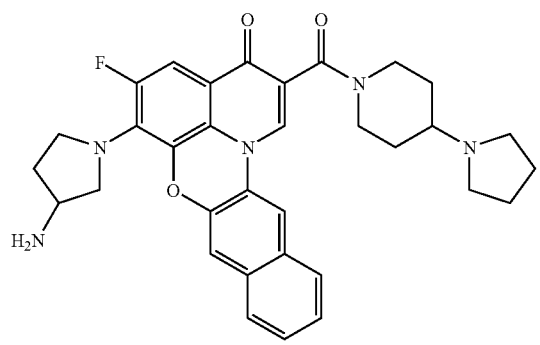
1316
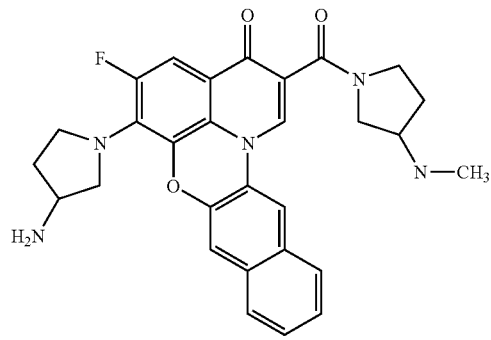
1317
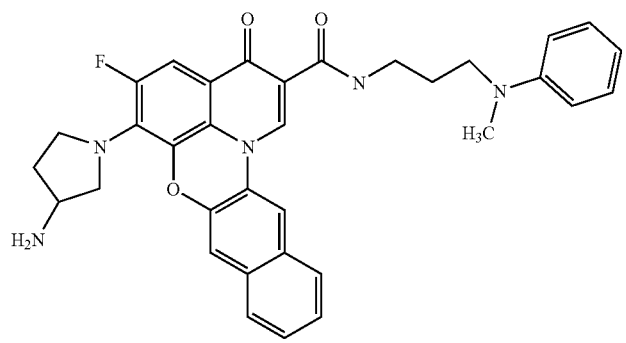

-continued
1318
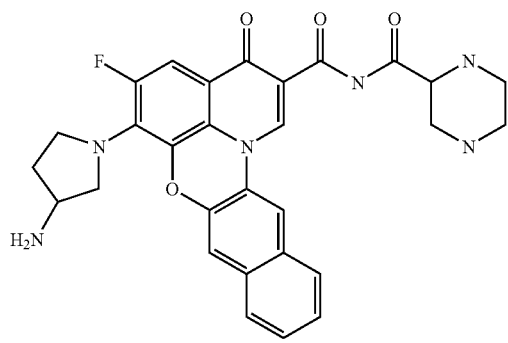
1319
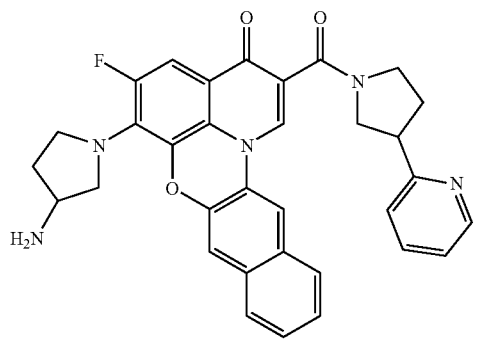
1320
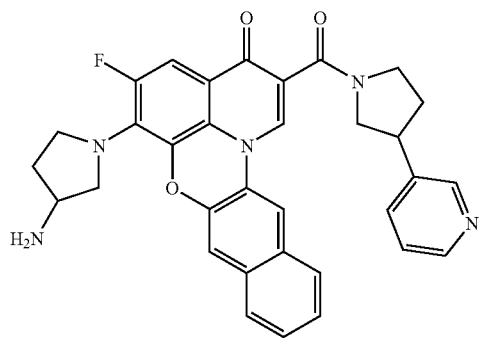
1321
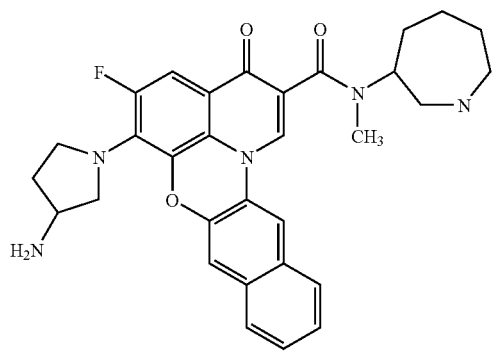

-continued
1322
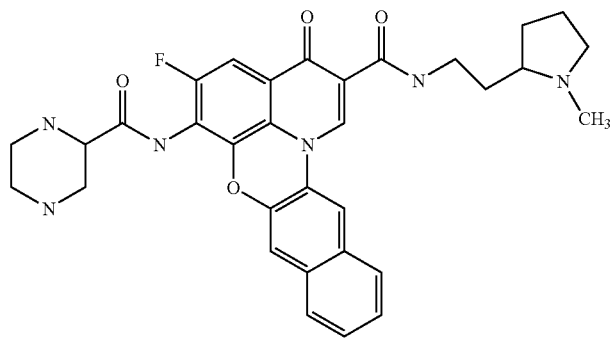
1323
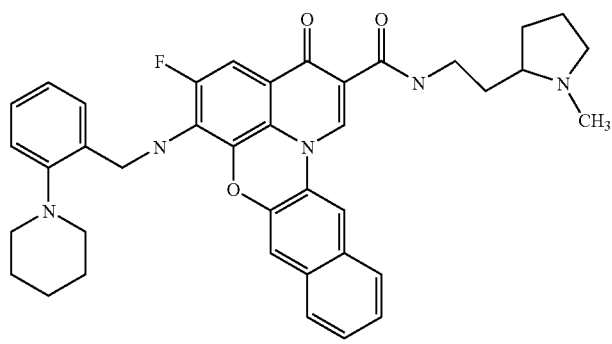
1324
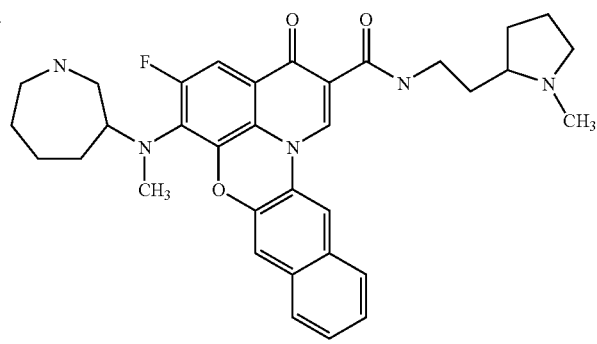
1325
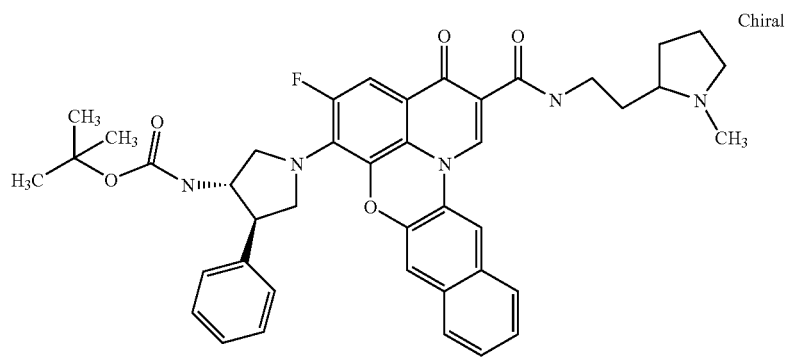

-continued
1326 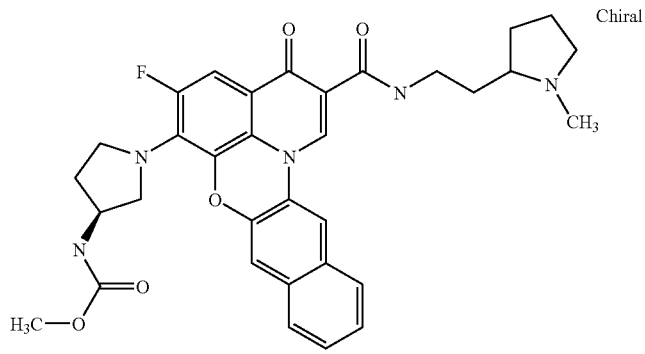
1327 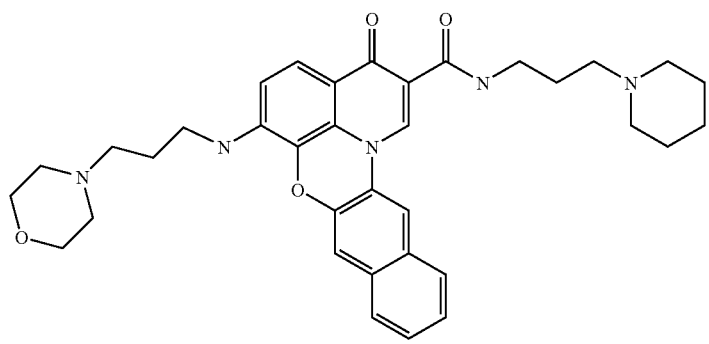
1328 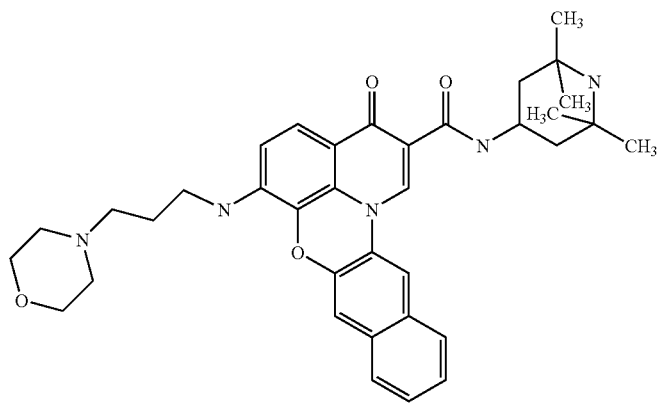
1329 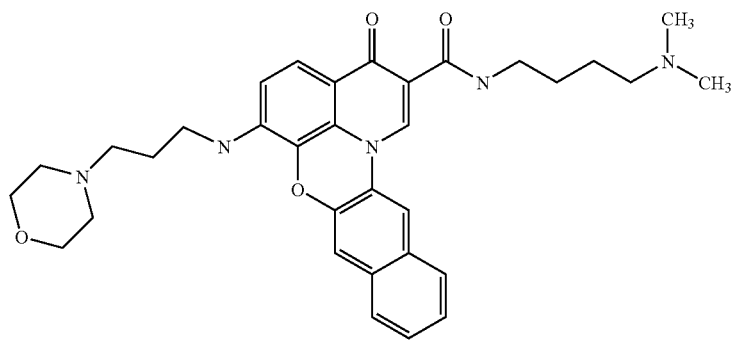

-continued
1330
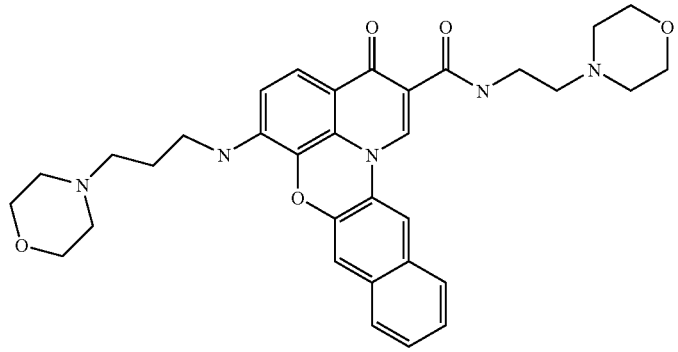
1331
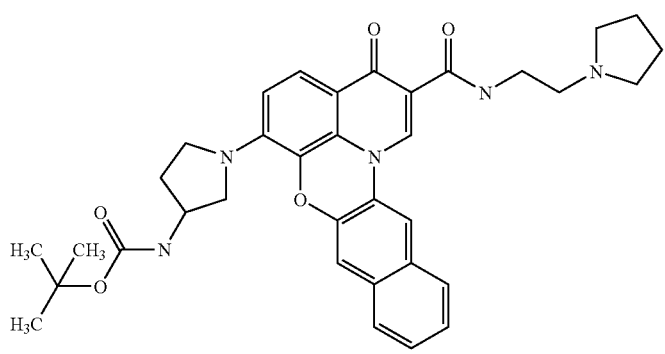
1332
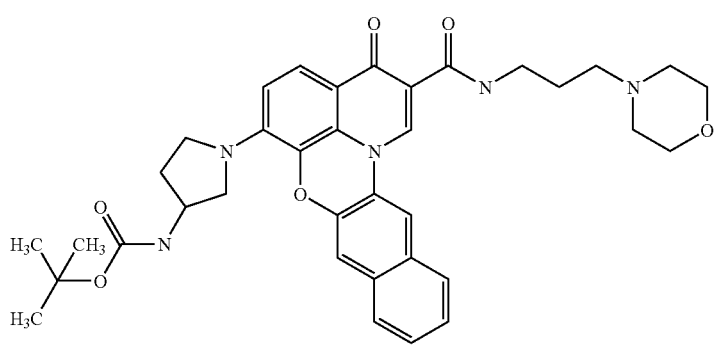
1333
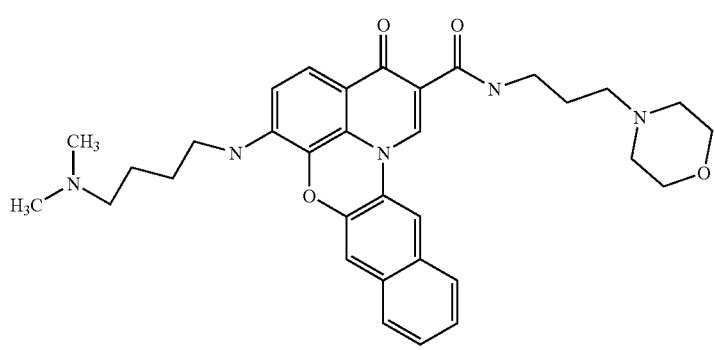

-continued
1334
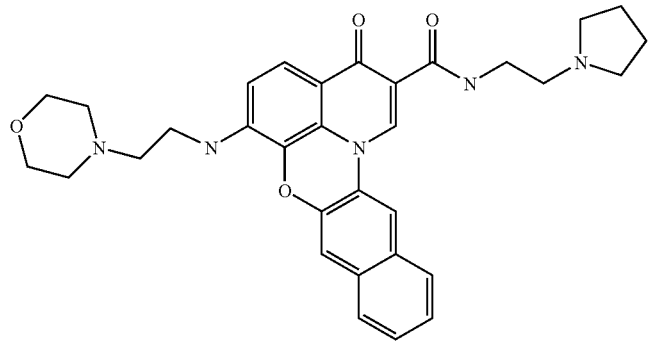
1335
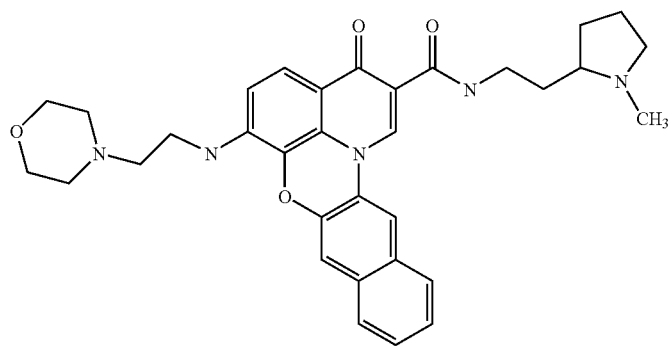
1336
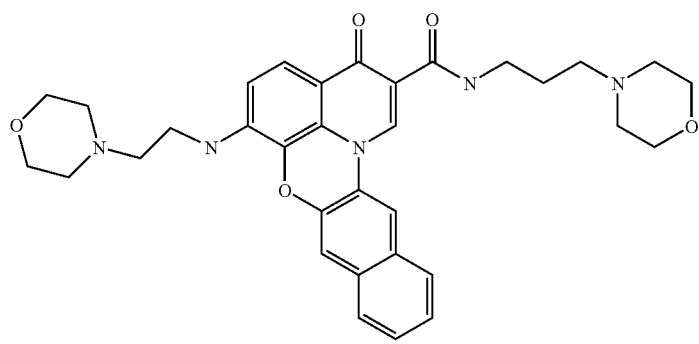
1337
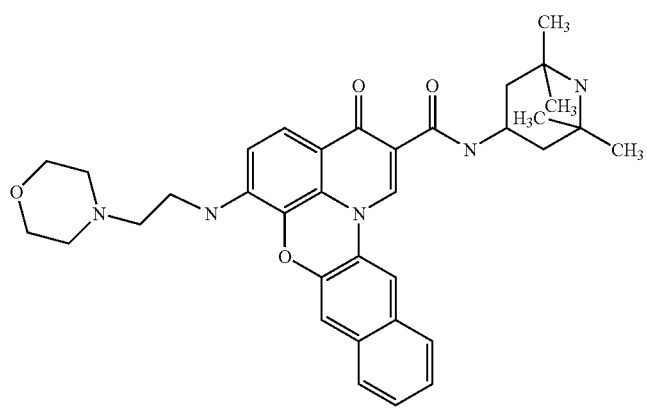

-continued
1338
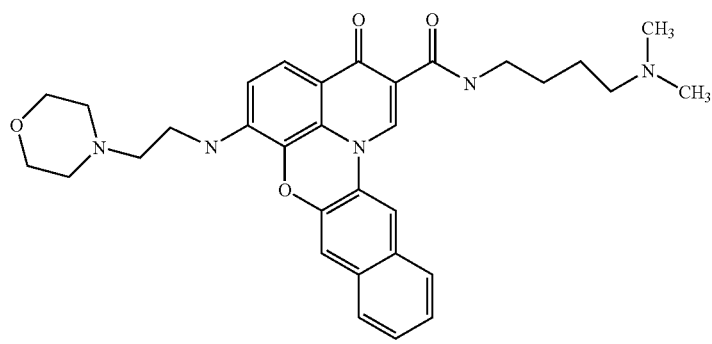
1339
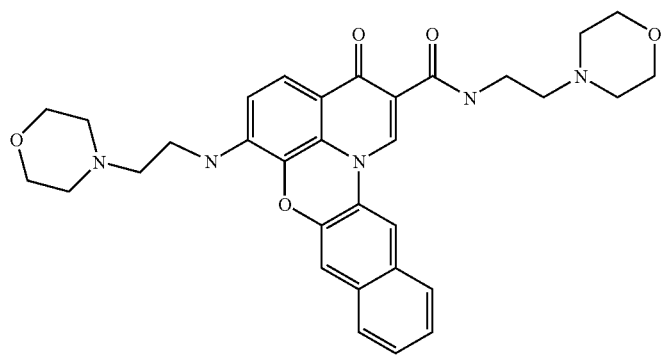
1340
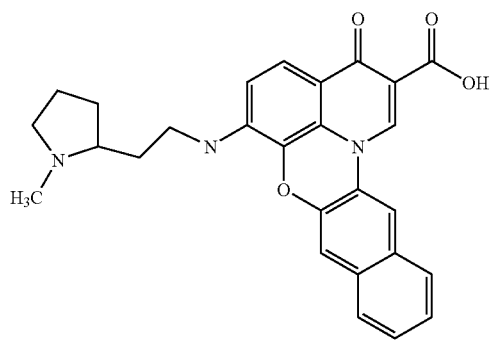
1341
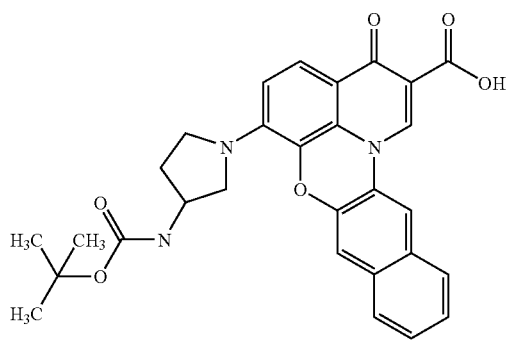

-continued
1342
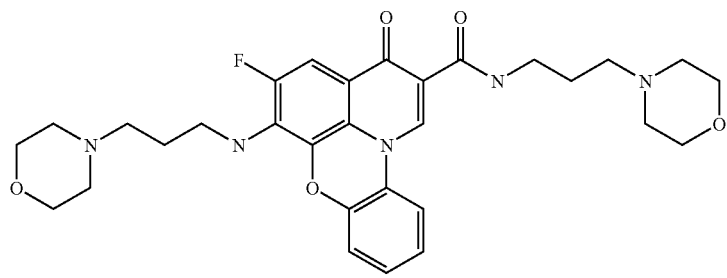
1343
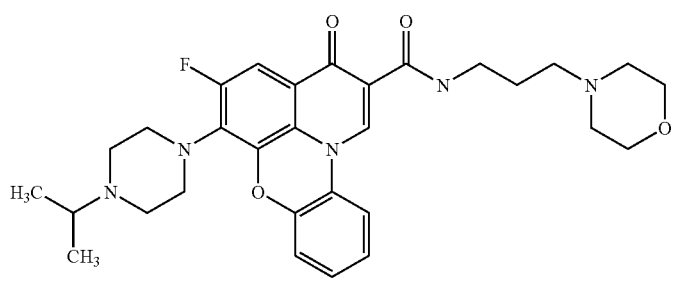
1344
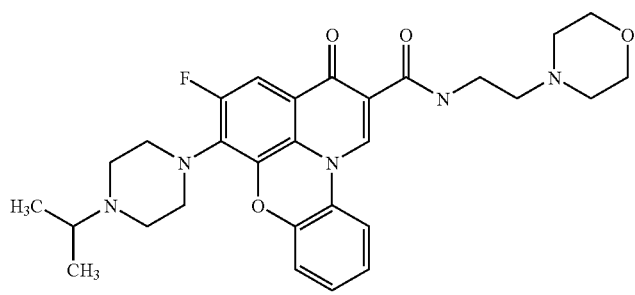
1345
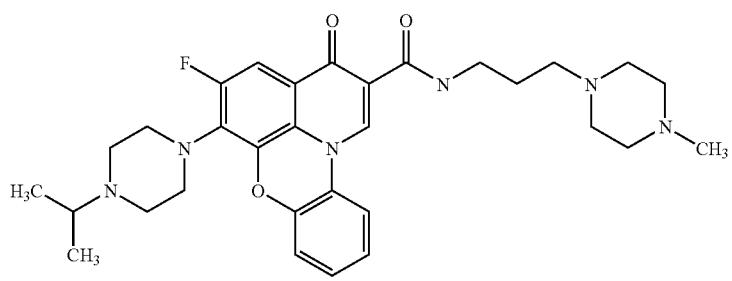
1346
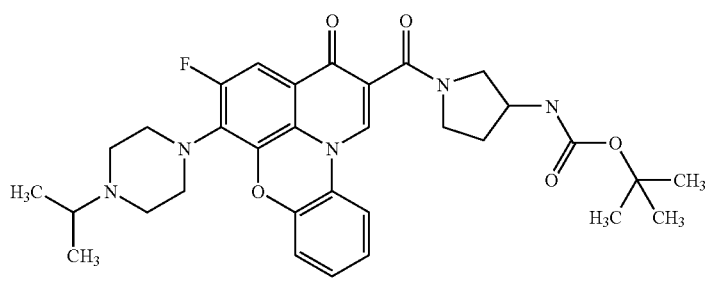

-continued
1347
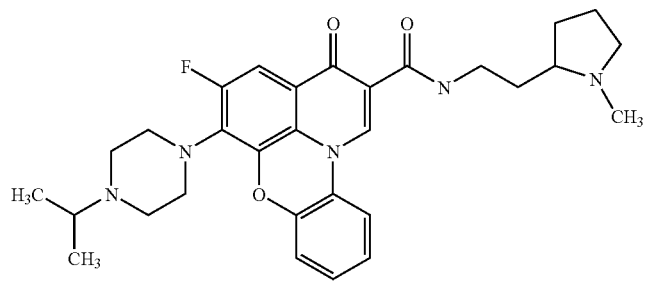
1348
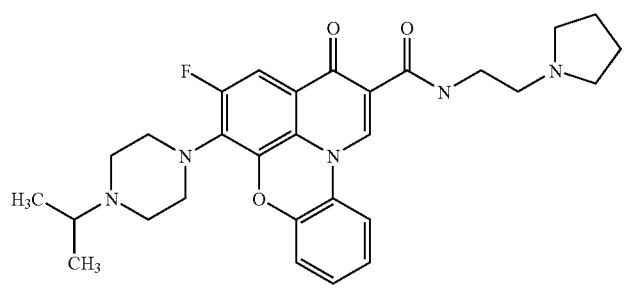
1349
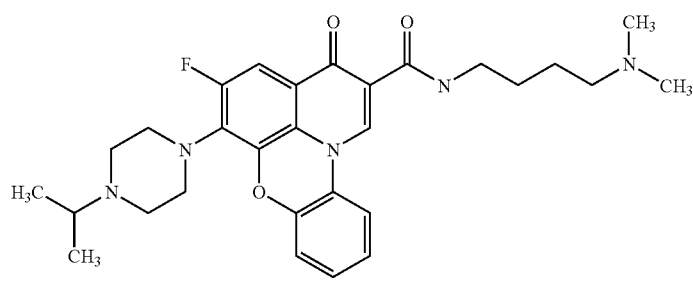
1350
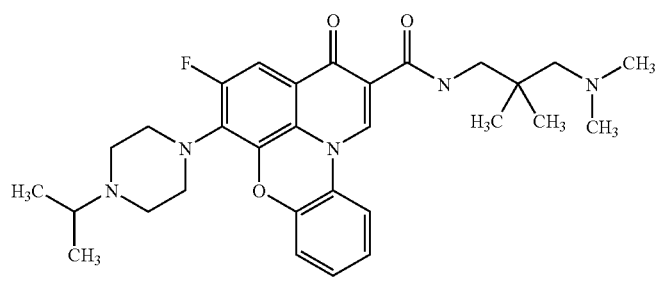
1351
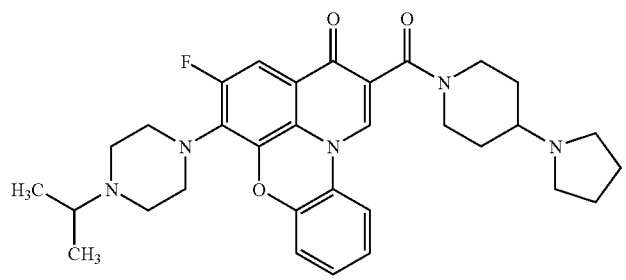

-continued
1352
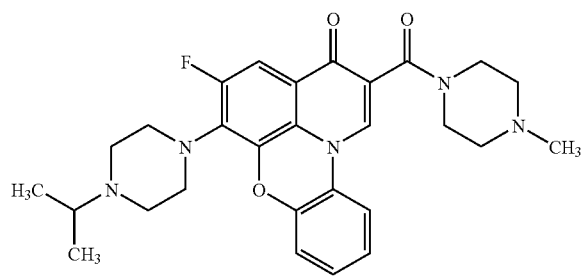
1353
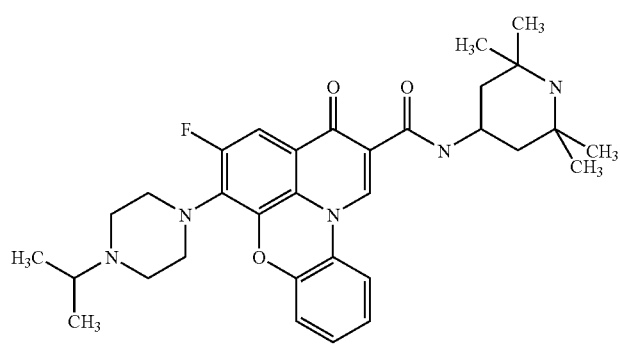
1354
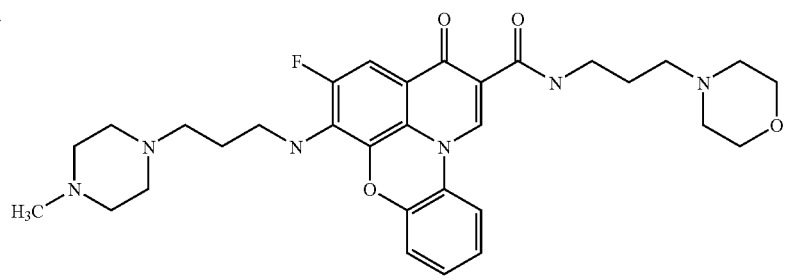
1355
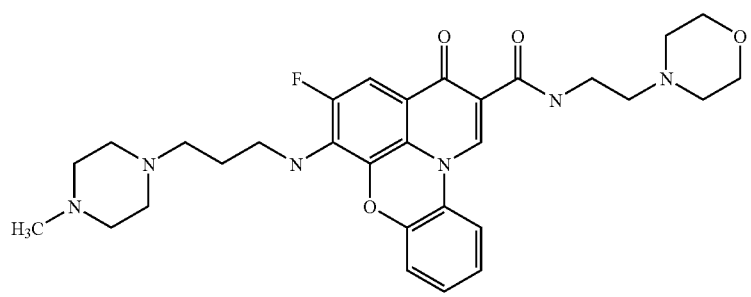
1356
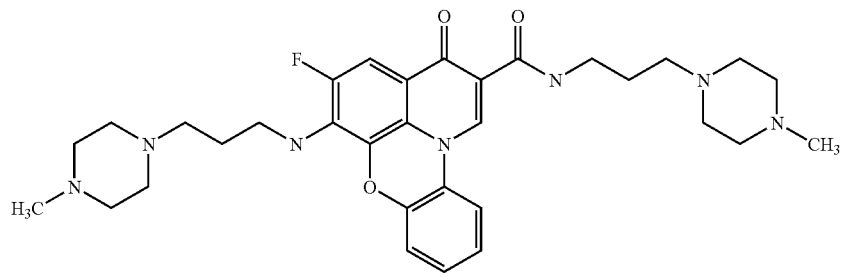

-continued
1357
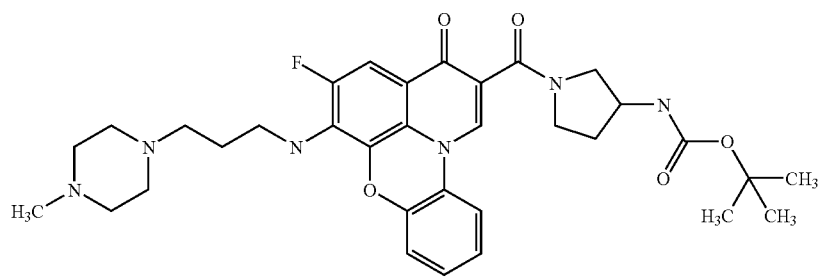
1358
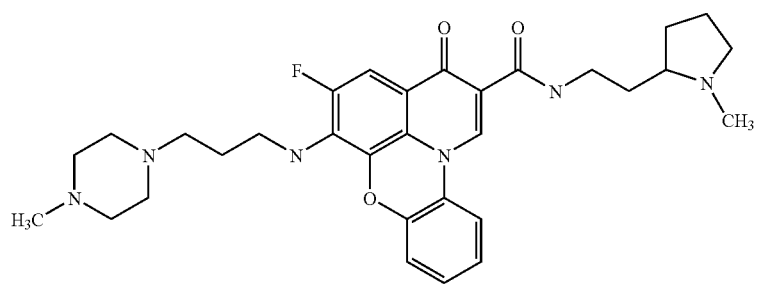
1359
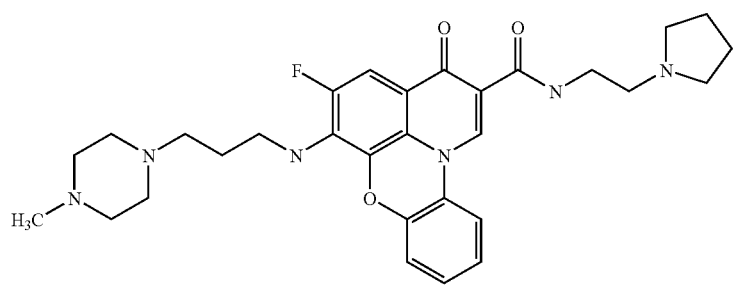
1360
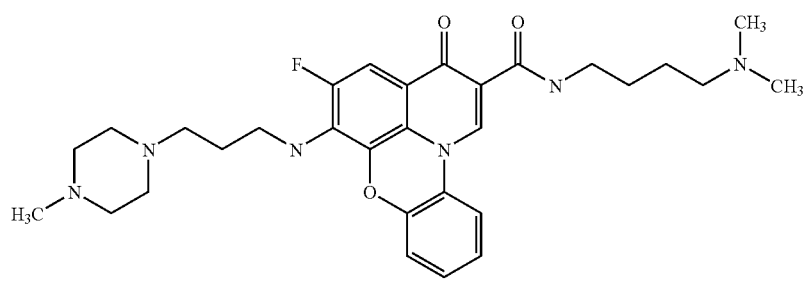
1361
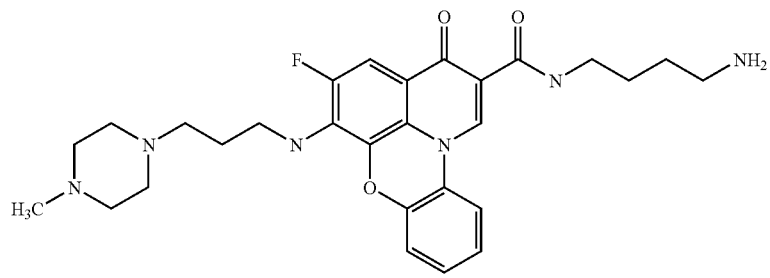

-continued
1362 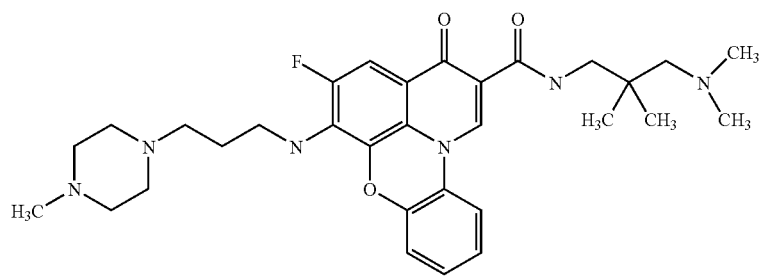
1363 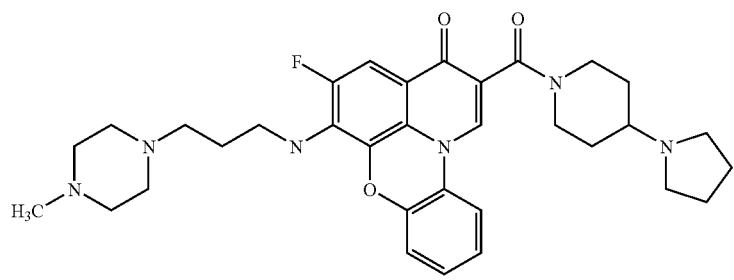
1364 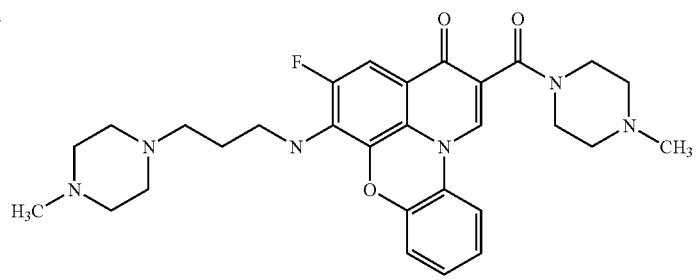
1365 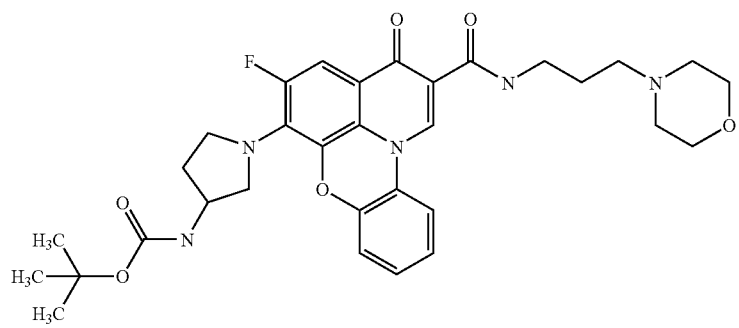
1366 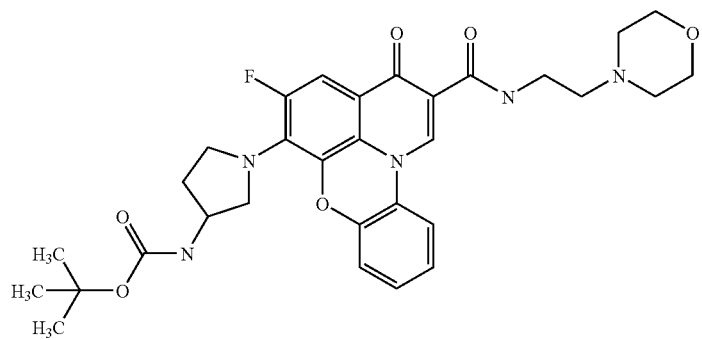

-continued
1367
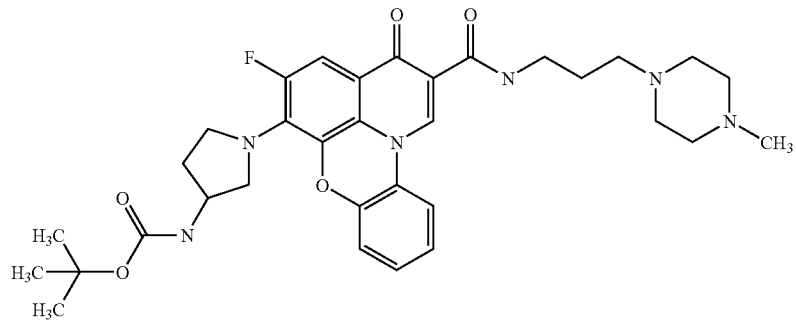
1368
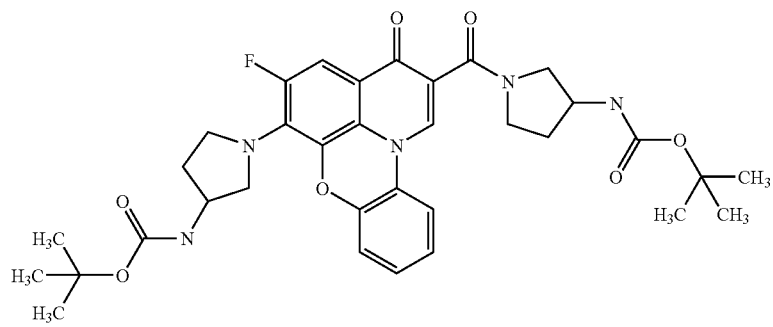
1369
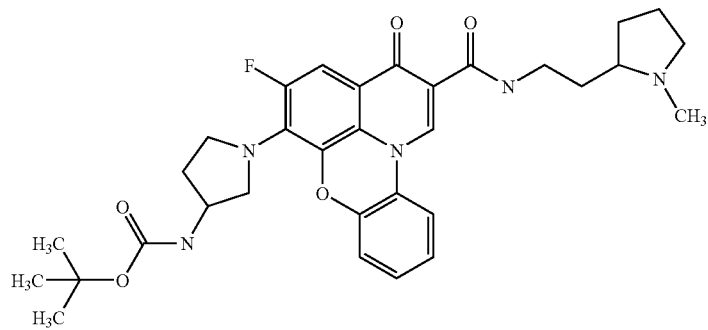
1370
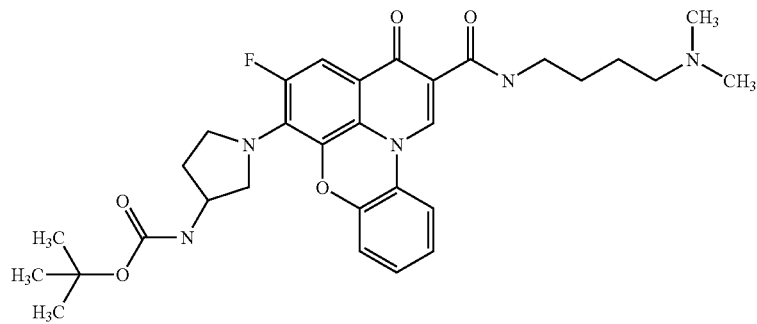

-continued
1371
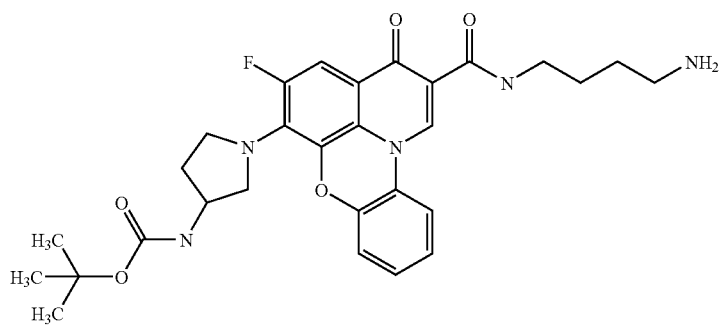
1372
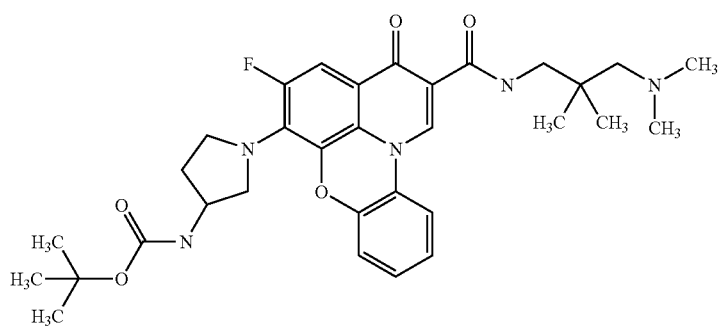
1373
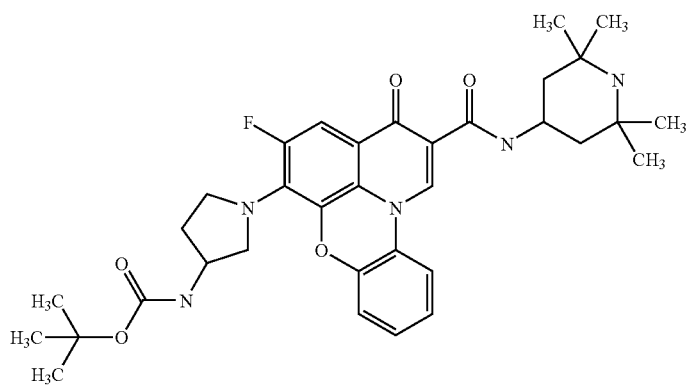
1374
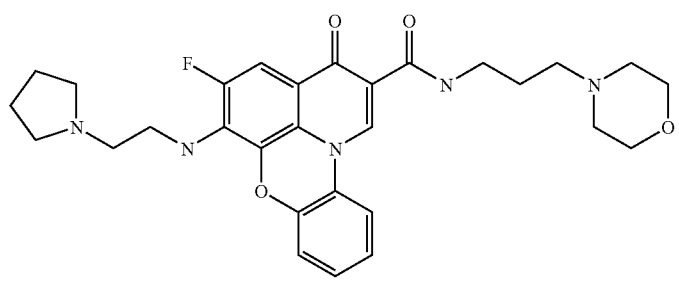
1375
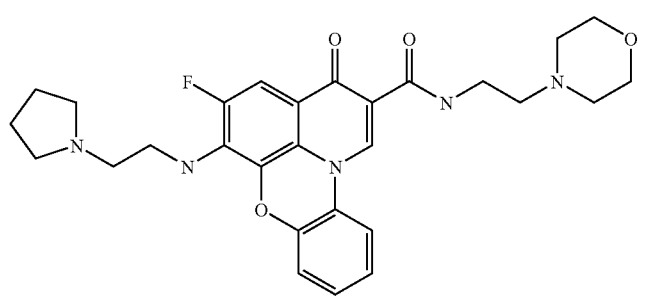

-continued
1376
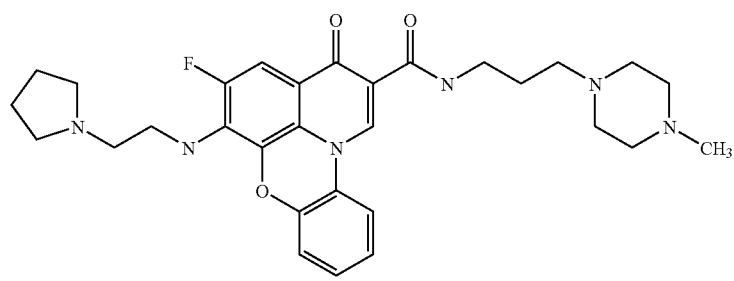
1377
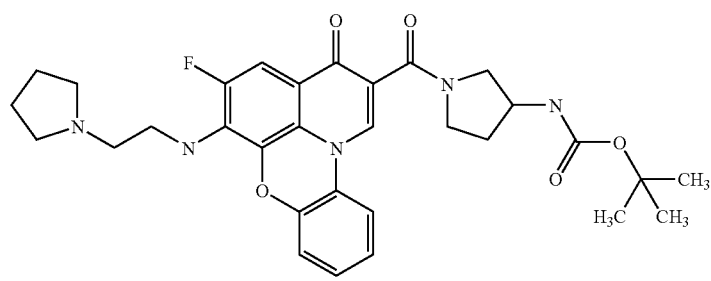
1378
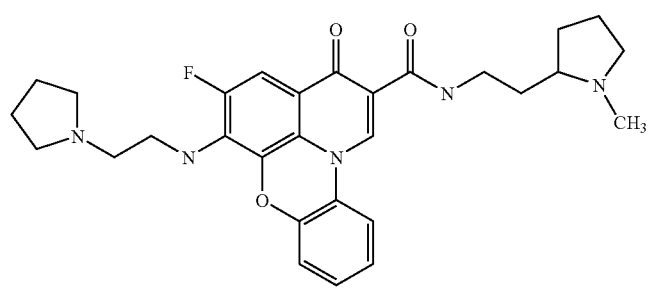
1379
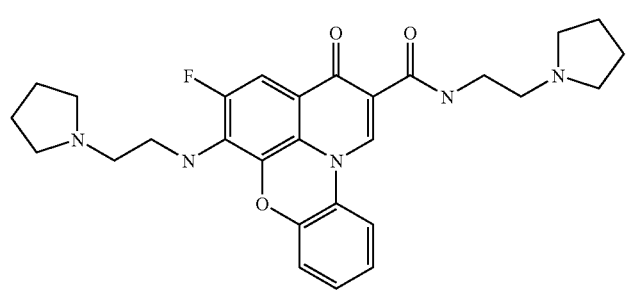
1380
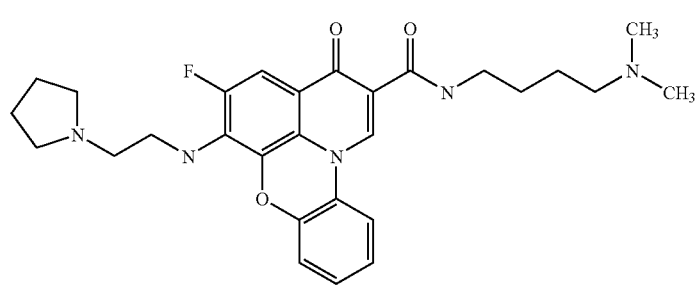

-continued
1381
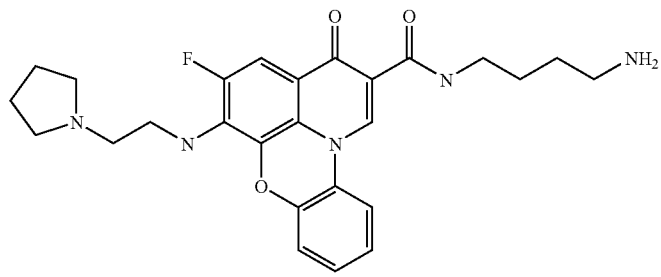
1382
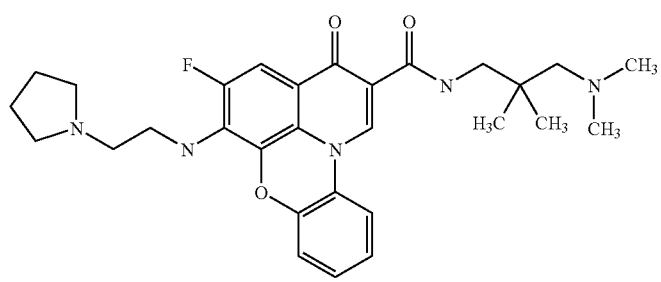
1383
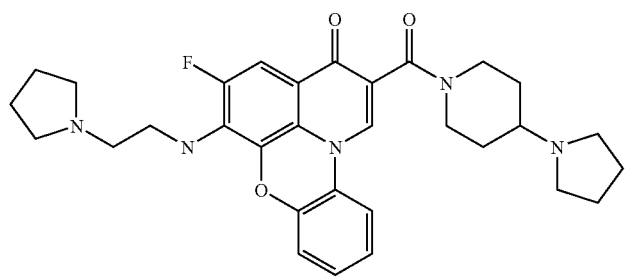
1384
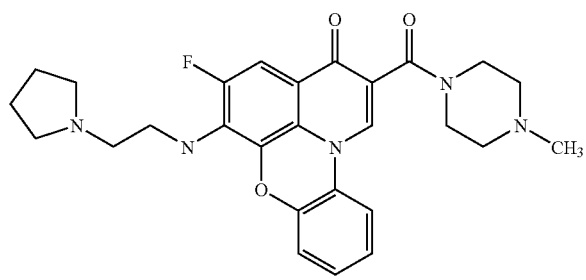
1385
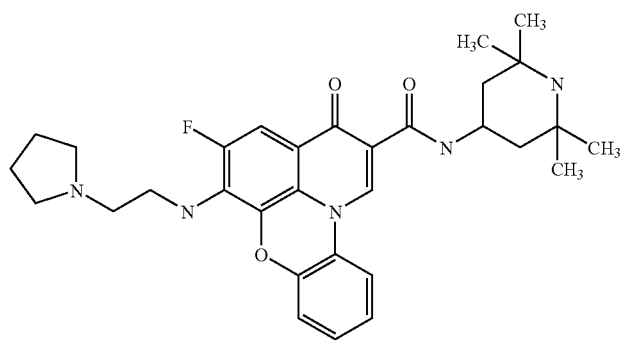

-continued
1386
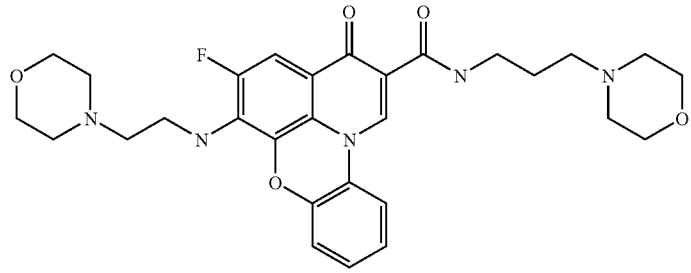
1387
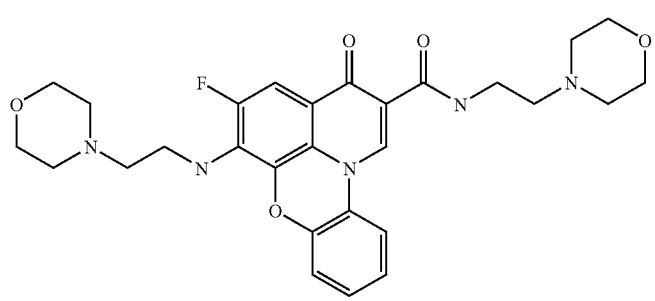
1388
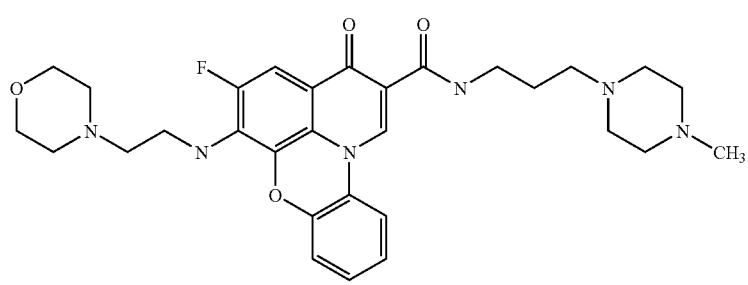
1389
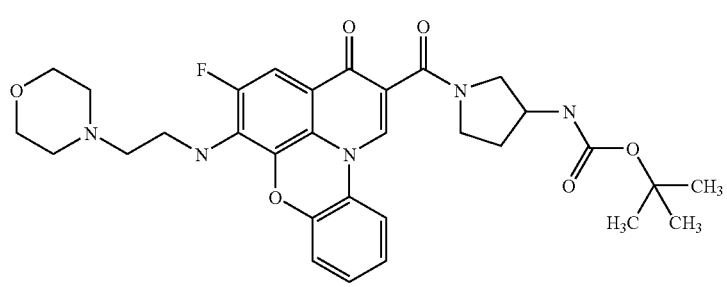
1390
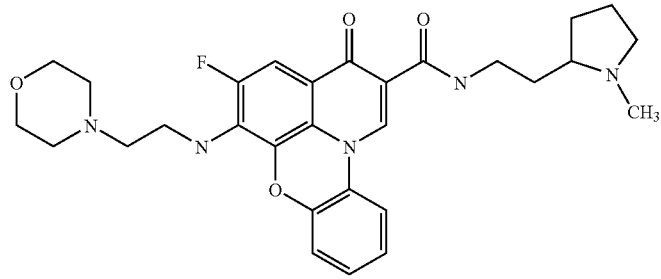

-continued
1391 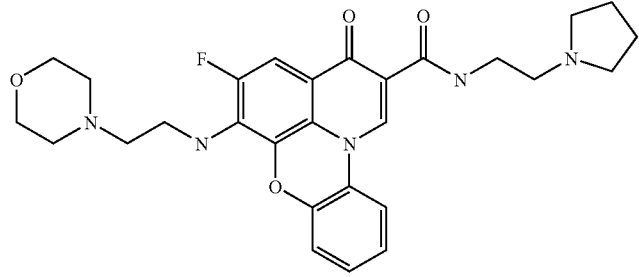
1392 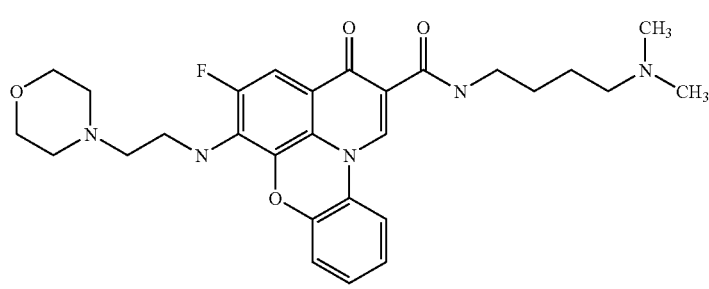
1393 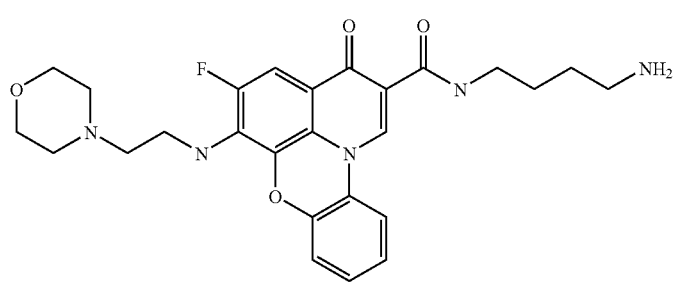
1394 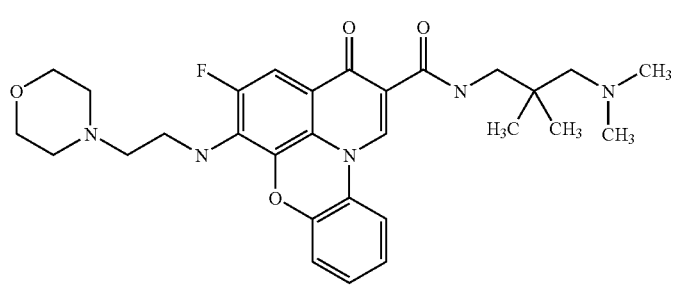
1395 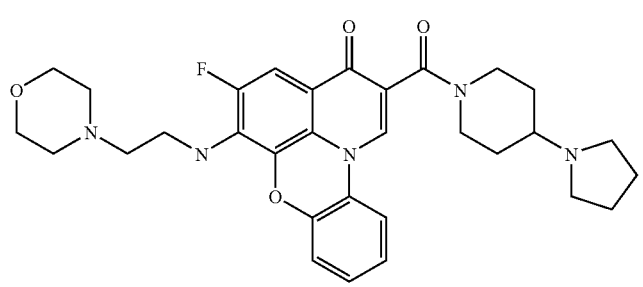

-continued
1396
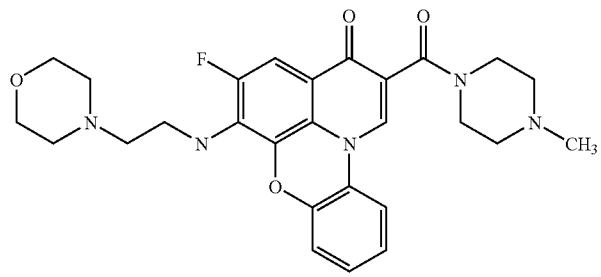
1397
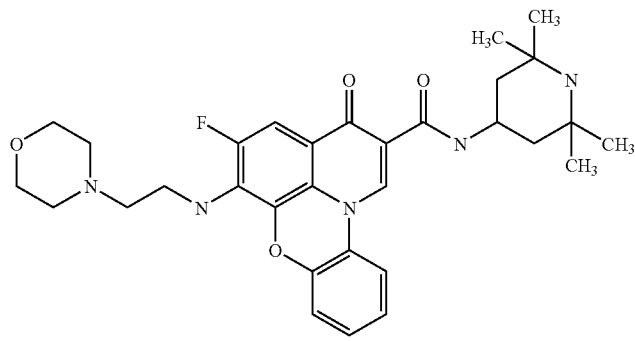
1398
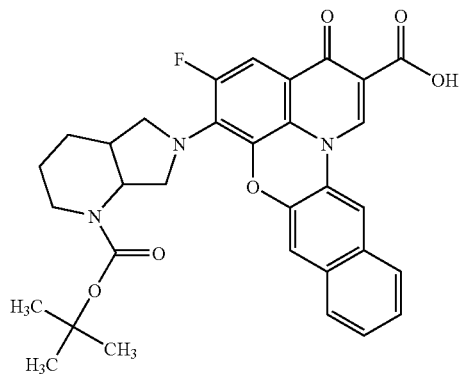
1399
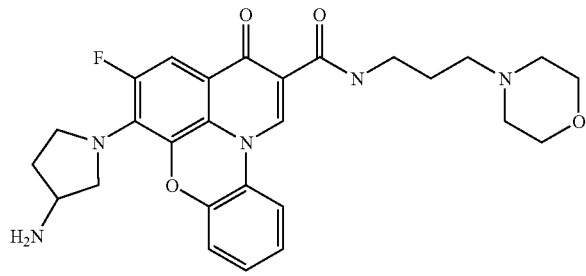
1400
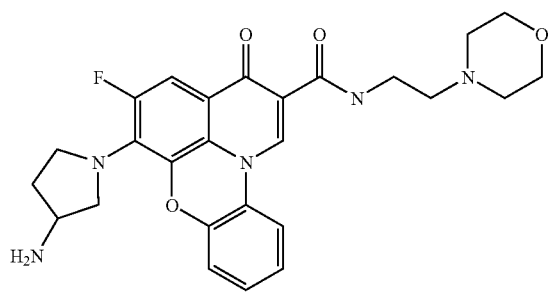

-continued
1401 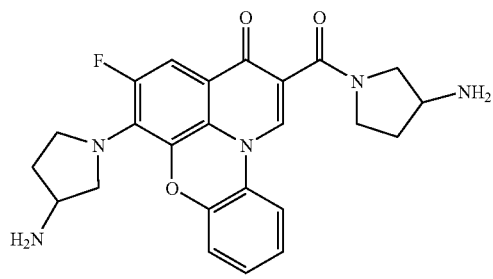
1402 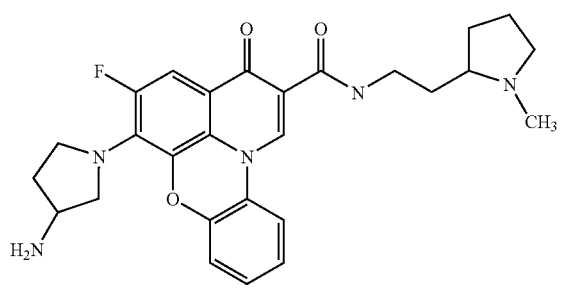
1403 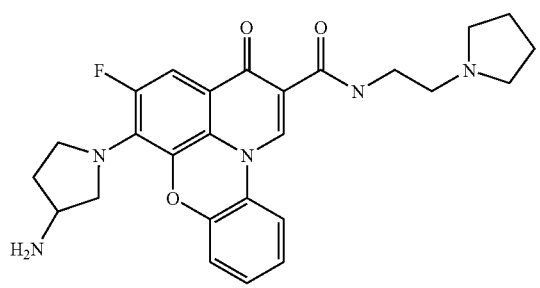
1404 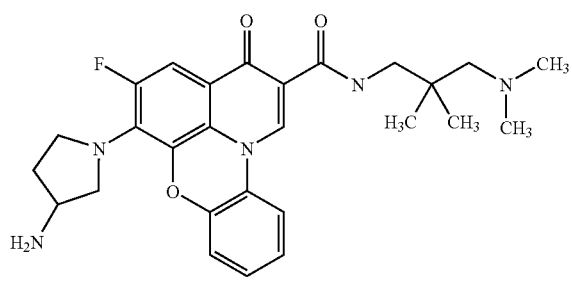
1405 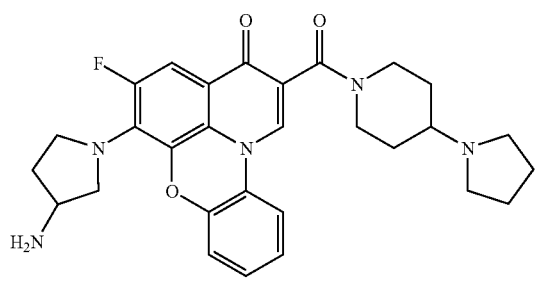

-continued
1406
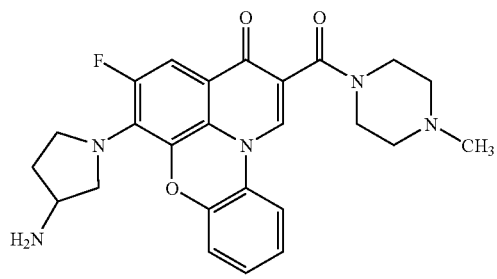
1407
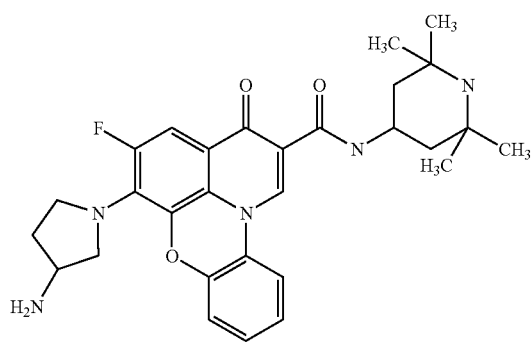
1408
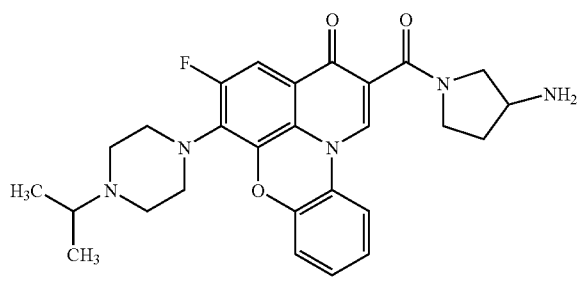
1409
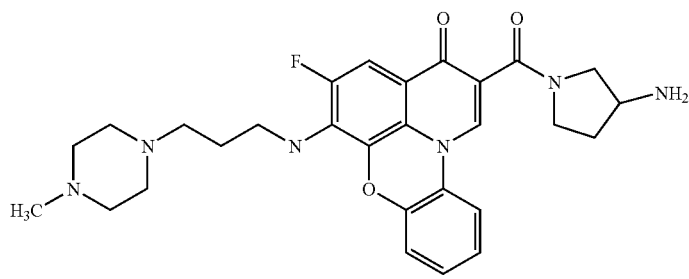
1410
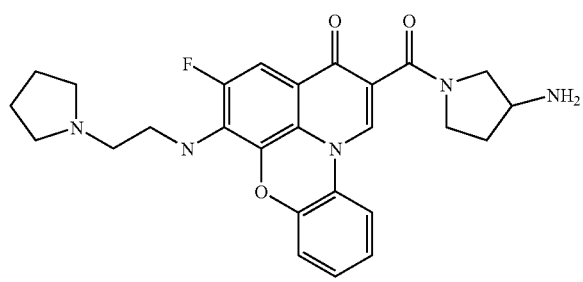

-continued
1411
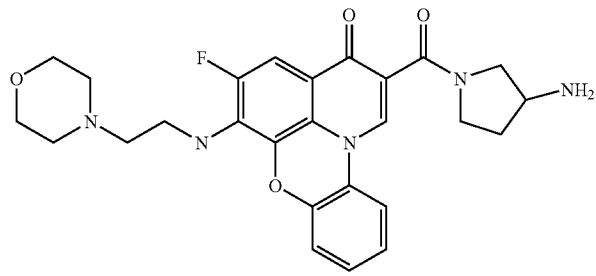
1412
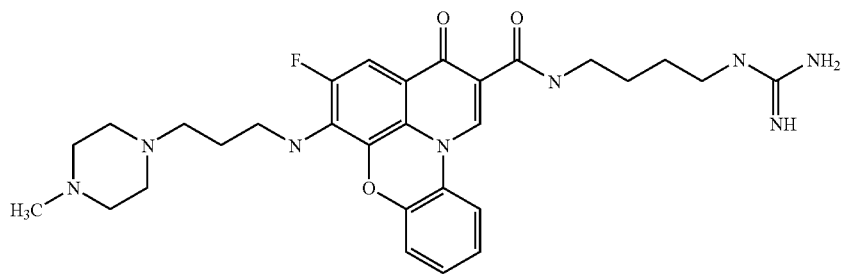
1413
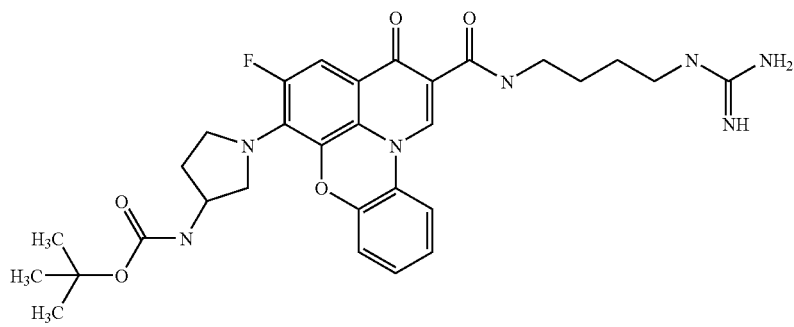
1414
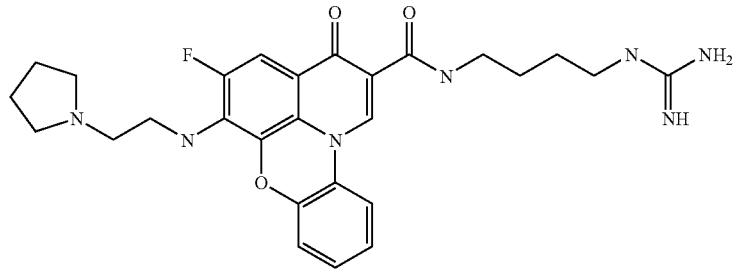
1415
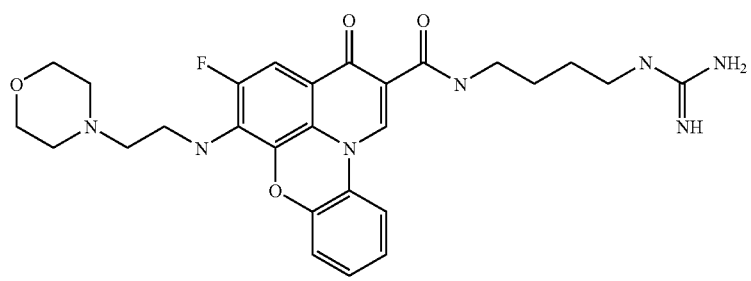

1416
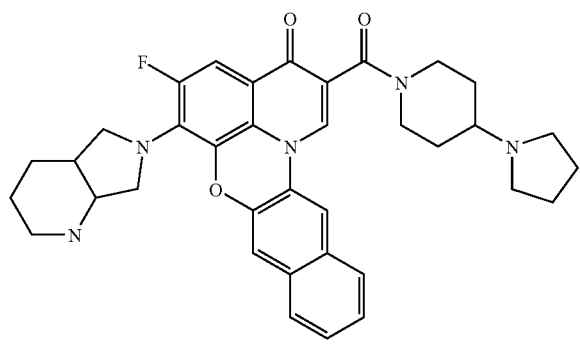
1417
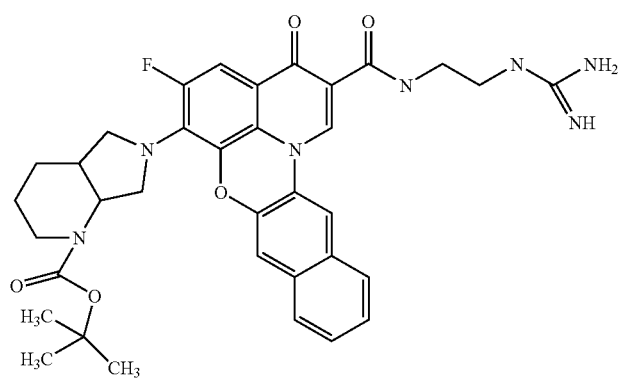
1418
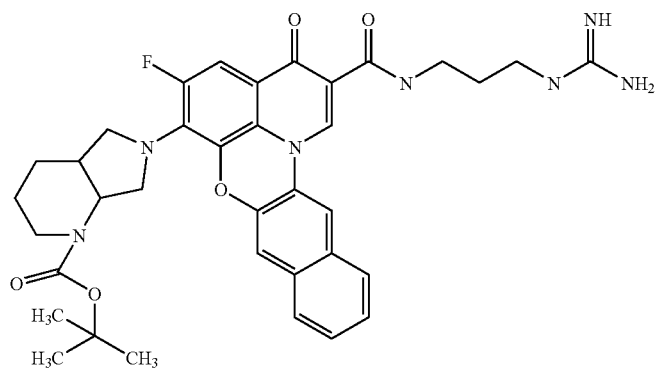
1419
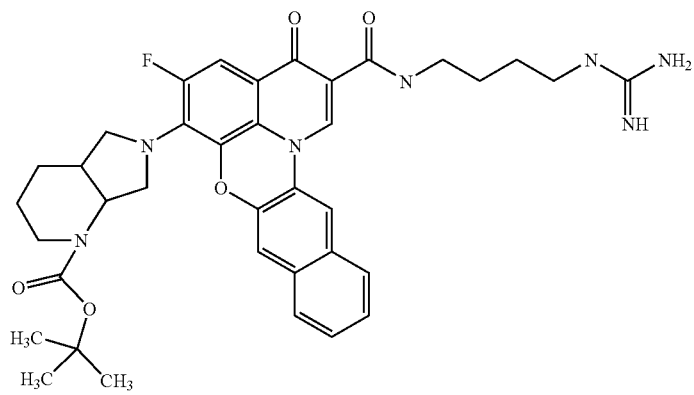

-continued
1420
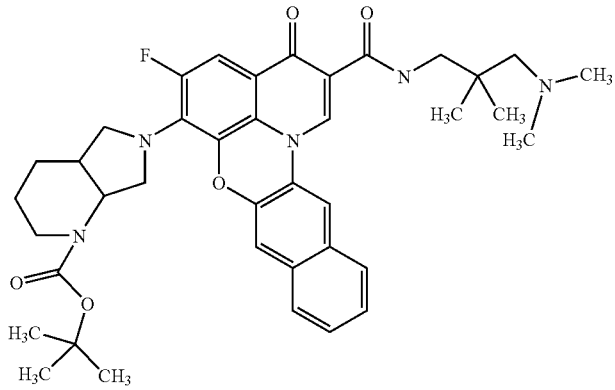
1421
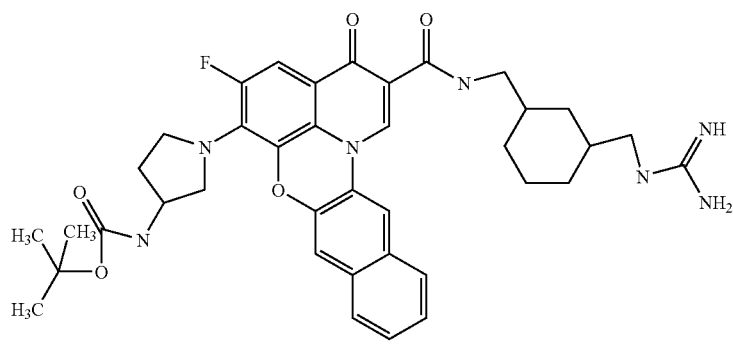
1422
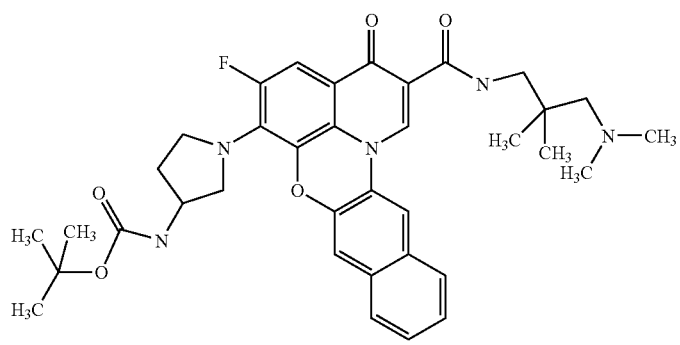
1423
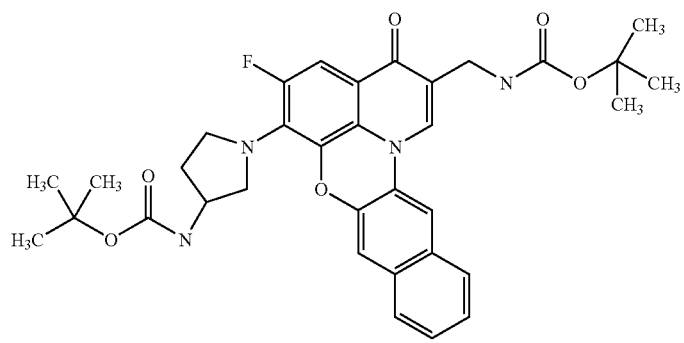

-continued
1424
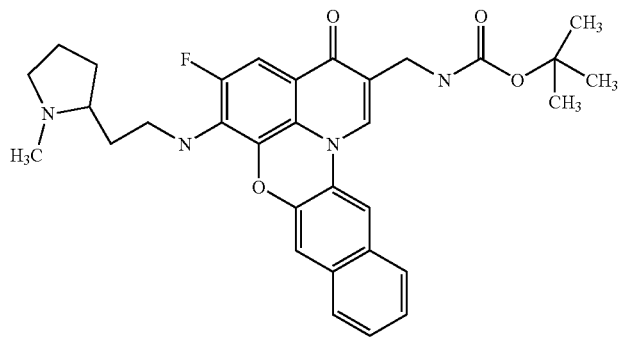
1425
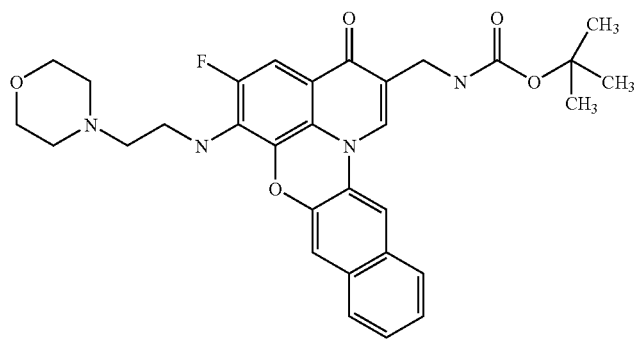
1426                                                                 Chiral
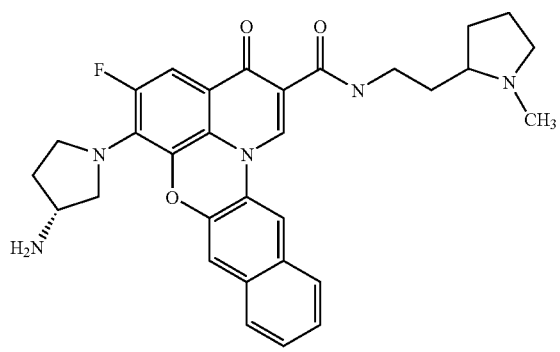
1427
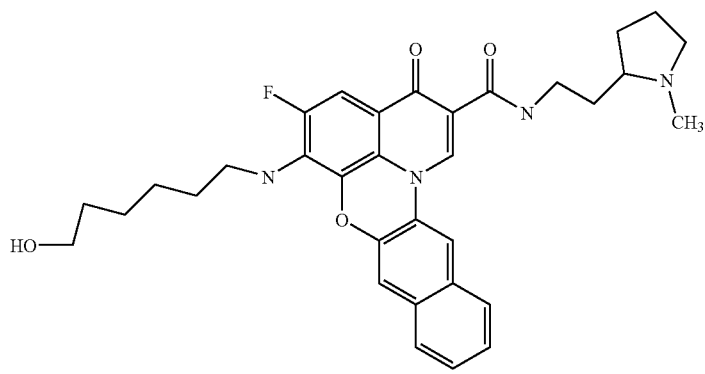

-continued
1428
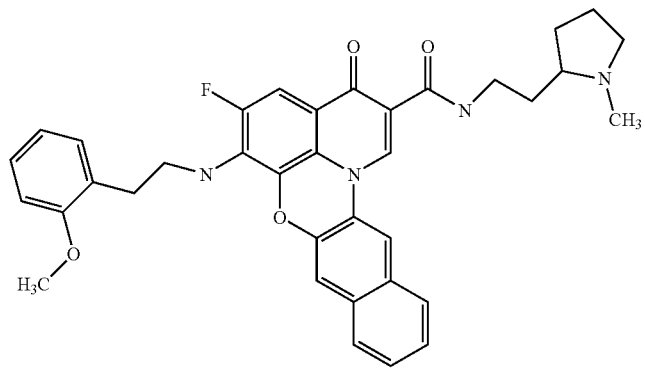
1429
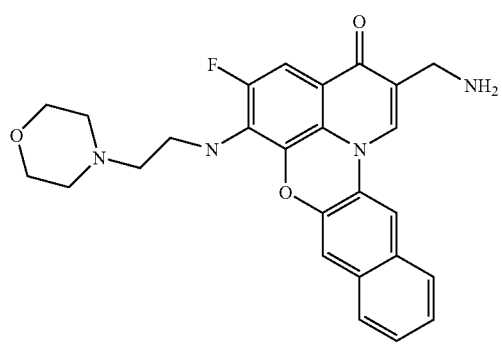
1430
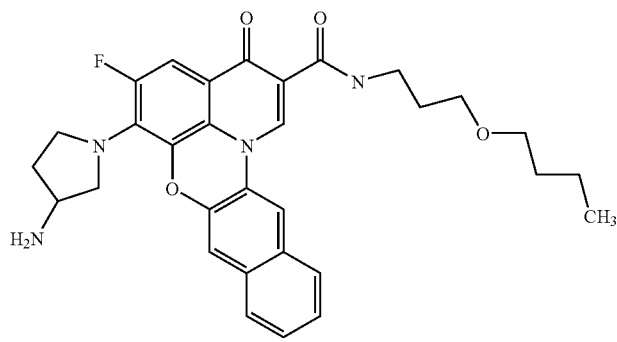
1431
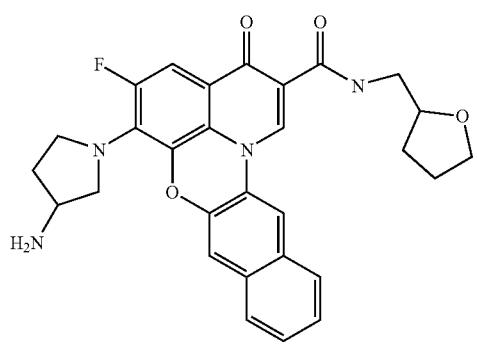

-continued
1432
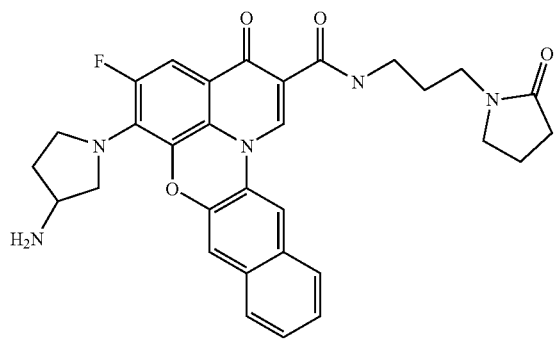
1433
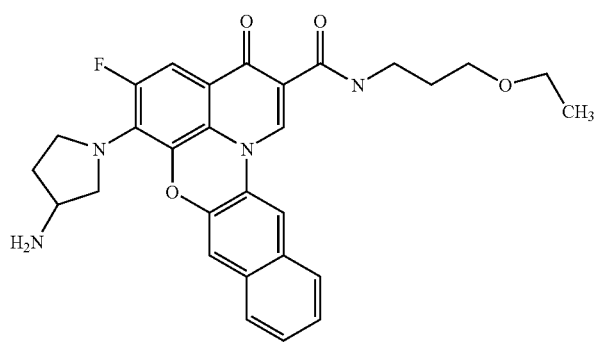
1434
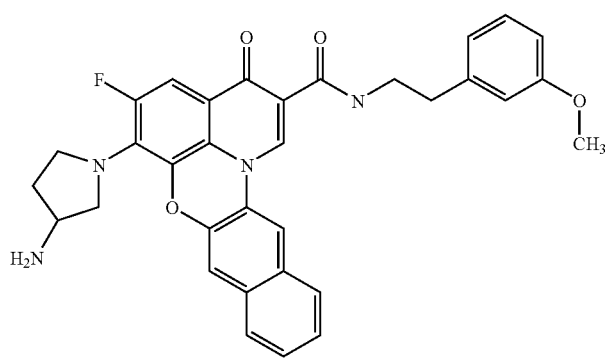
1435
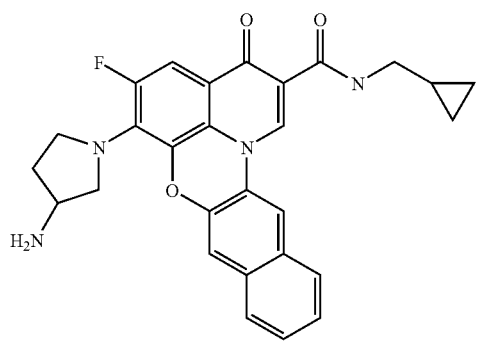

-continued
1436
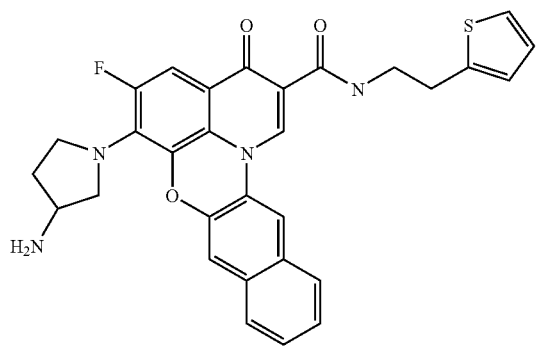
1437
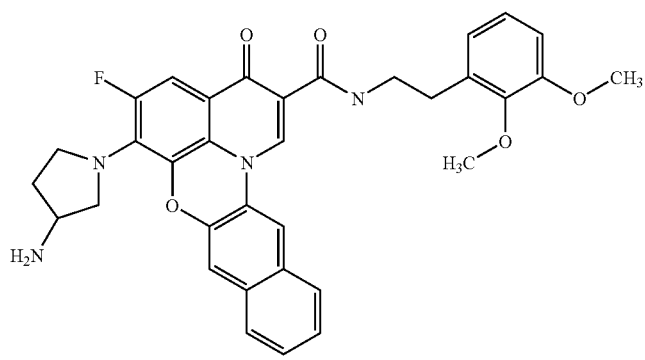
1438
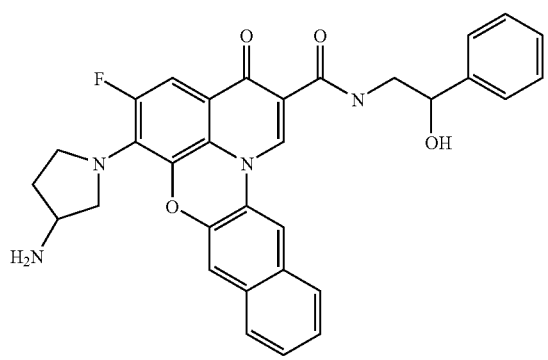
1439
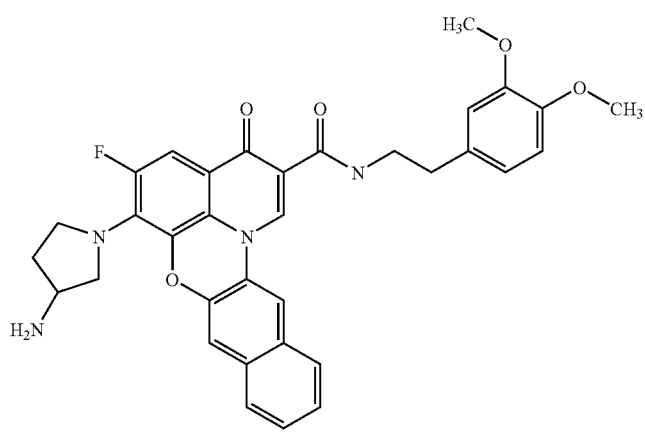

-continued
1440
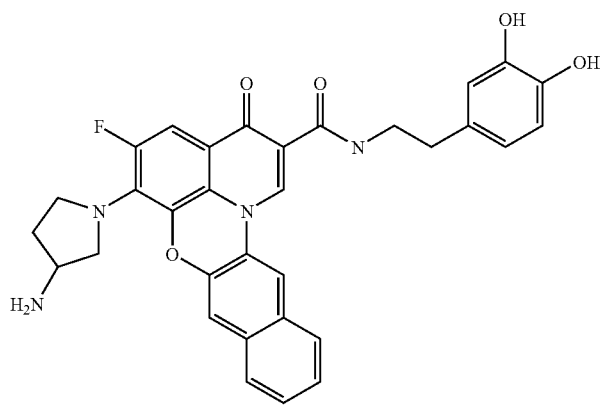
1441
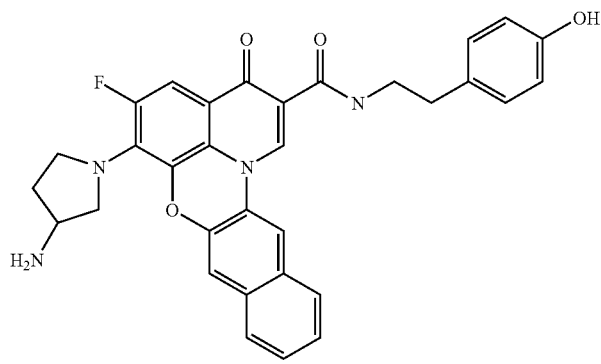
1442 Chiral
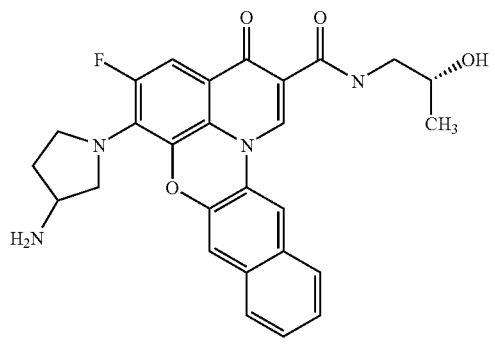
1443 Chiral
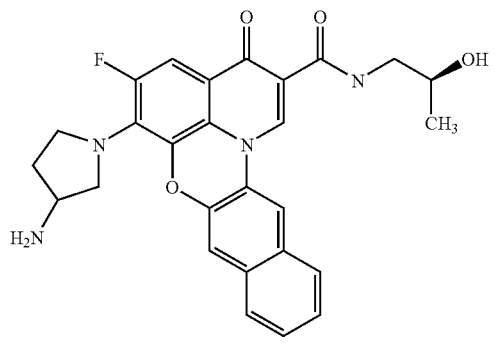

-continued
1444
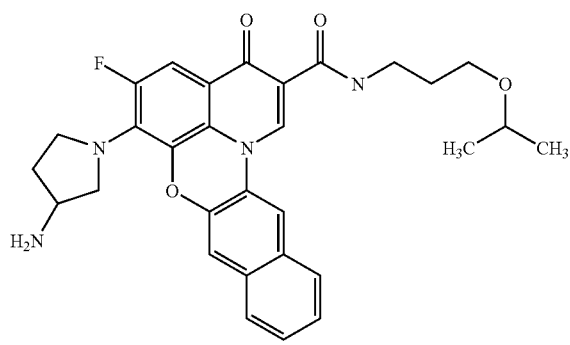
1445
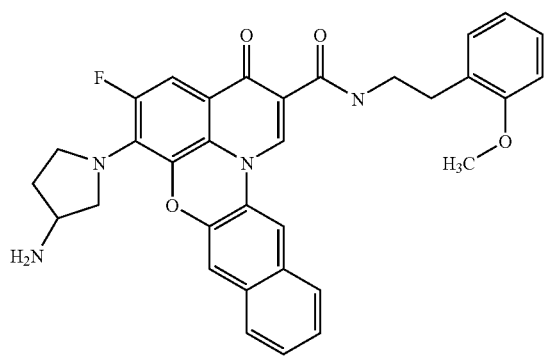
1446
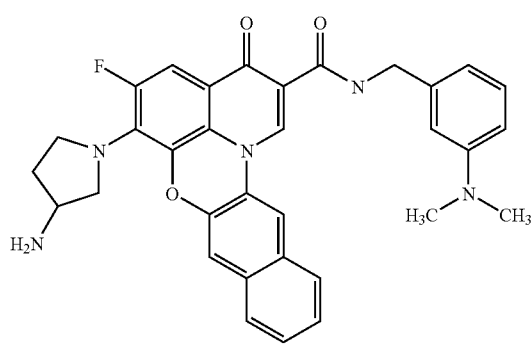
1447
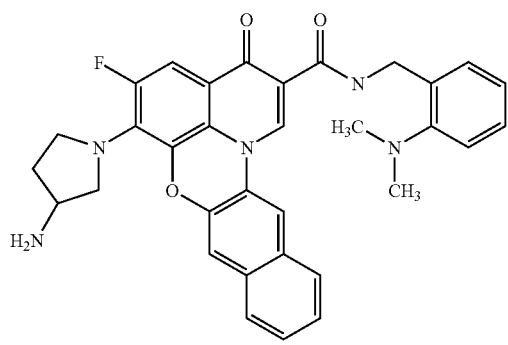

-continued
1448
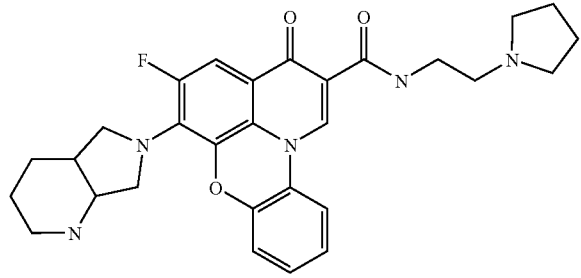
1449
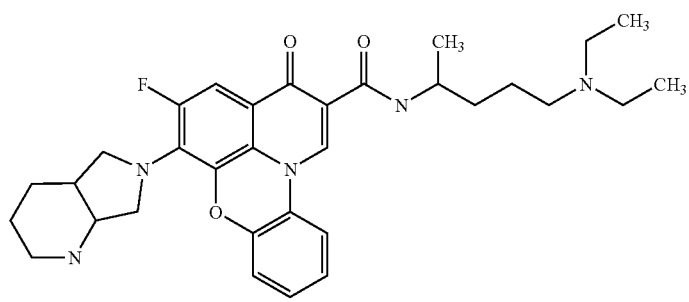
1450
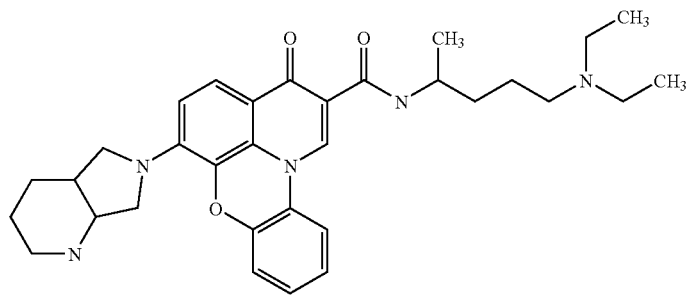
1451
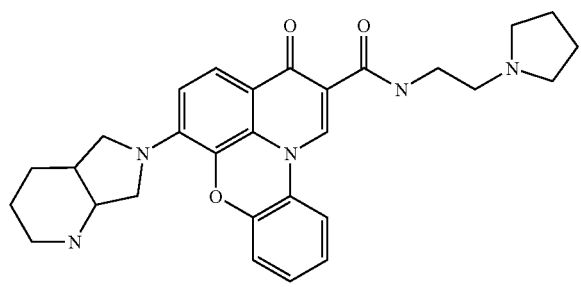
1452
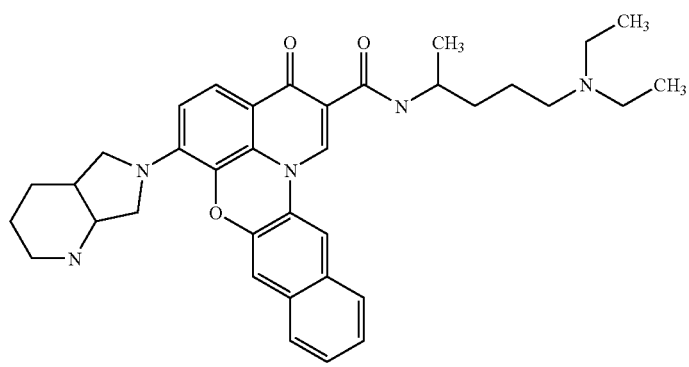

-continued
1453 Chiral
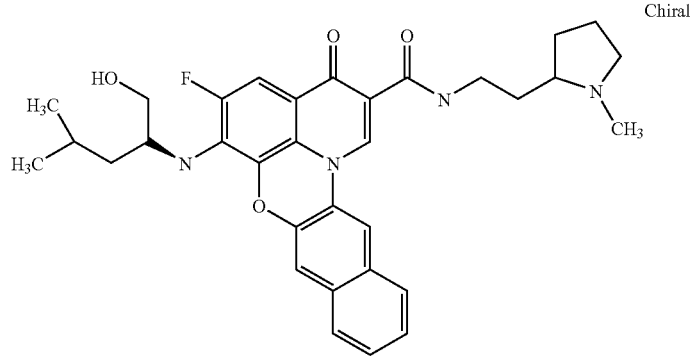
1454
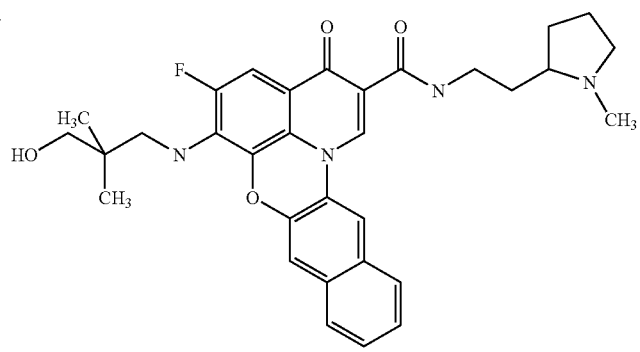
1455
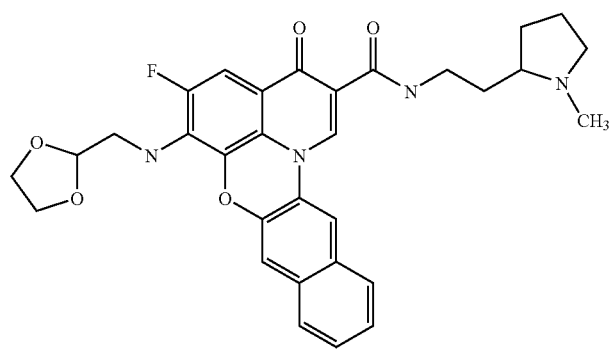
1456
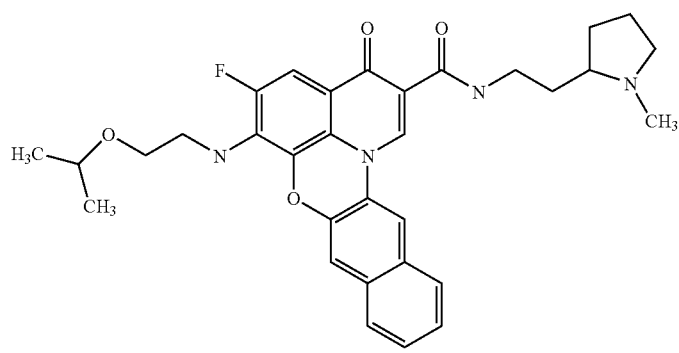

-continued
1457 Chiral
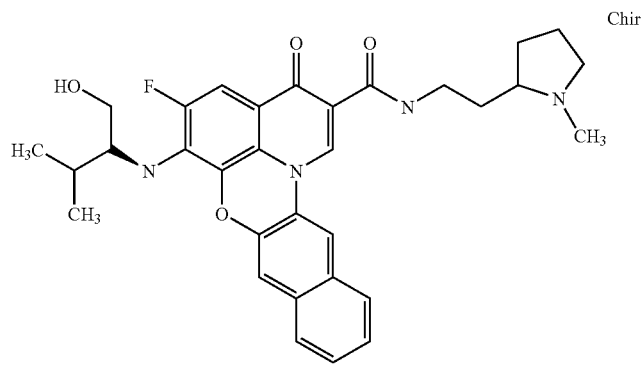
1458 Chiral
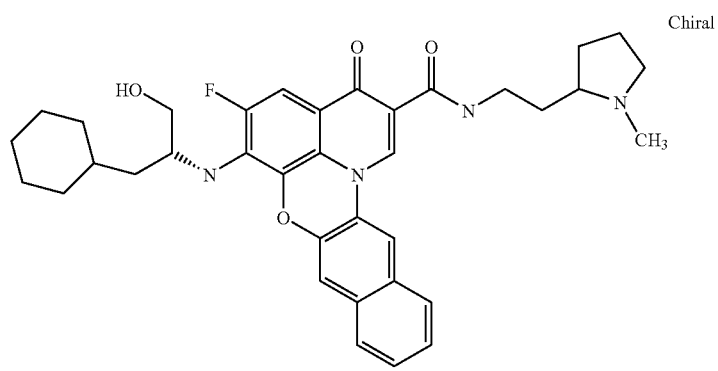
1459 Chiral
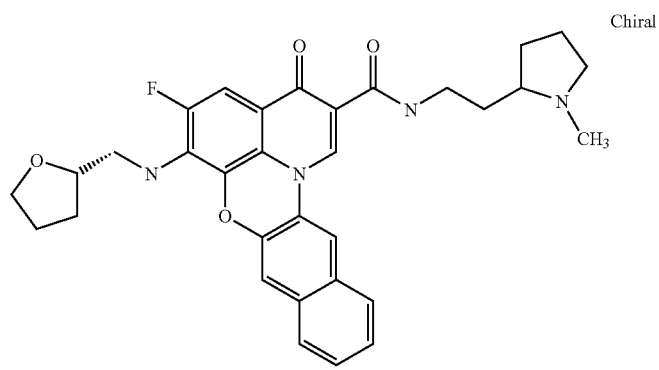
1460
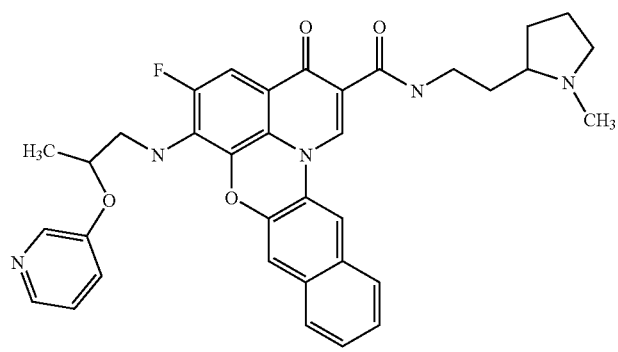

-continued
1461
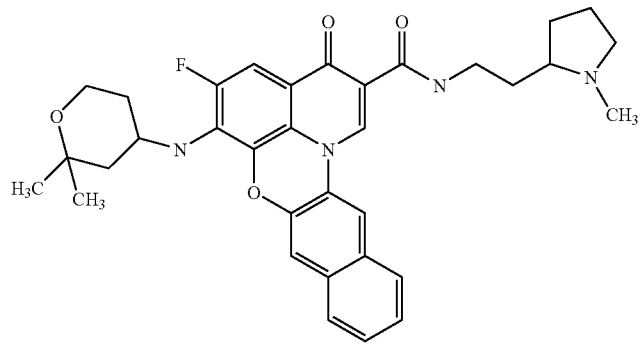
1462
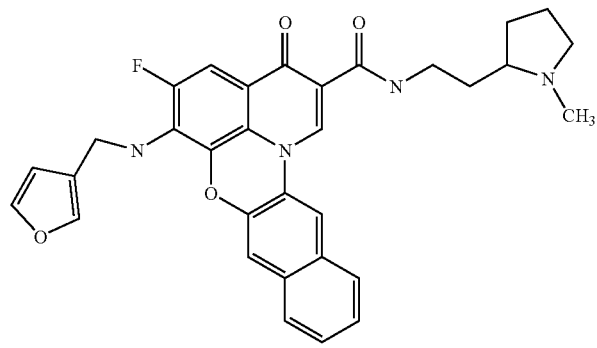
1463
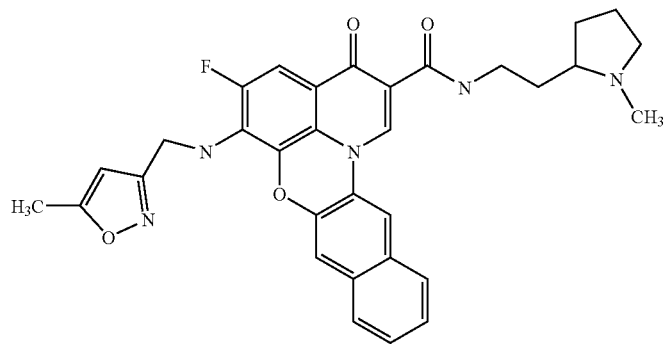
1464
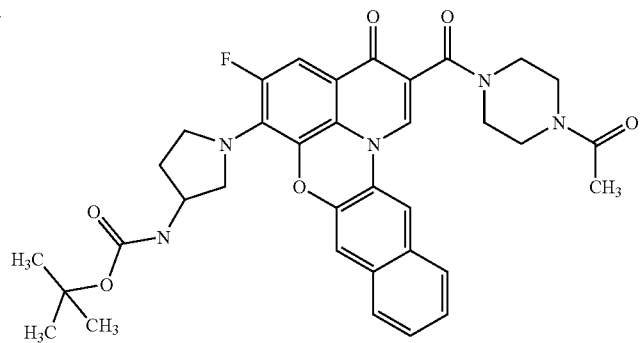

-continued
1465 Chiral
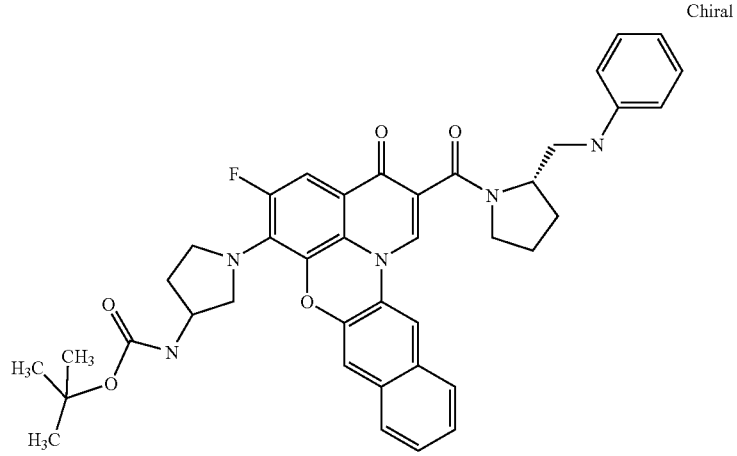
1466
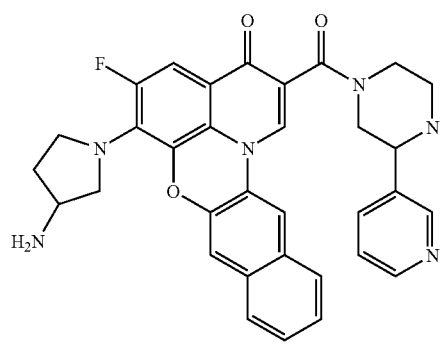
TABLE 1D
| Structure | S DATA μM | Hela MTS μM | HCT-116 |
|---|---|---|---|
| 1477 | | | 1 |

TABLE 1D-continued

| Structure | S DATA μM | Hela MTS μM | HCT-116 |
|---|---|---|---|
| 1478 | 1 | | |
| 1479 | 1.75 | | |
| 1480 | 1.75 | | |
| 1481 | 1.75 | | |

TABLE 1D-continued

| Structure | S DATA μM | Hela MTS μM | HCT-116 |
|---|---|---|---|
| 1482 | | 1.75 | |
| 1483 | | 1.75 | |
| 1484 | | 1.75 | |
| 1485 | | 1.75 | |

TABLE 1D-continued

| Structure | S DATA μM | Hela MTS μM | HCT-116 |
|---|---|---|---|
| 1486 | 1.75 | | |
| 1487 | 1.75 | | |
| 1488 | 0.75 | | |
| 1489 | 0.95 | | |

TABLE 1D-continued

| Structure | S DATA μM | Hela MTS μM | HCT-116 |
|---|---|---|---|
| 1490 | 0.75 | | |
| 1491 | 1.75 | | |
| 1492 | 0.75 | | |
| 1493 | 1.75 | | |

TABLE 1D-continued
| Structure | S DATA μM | Hela MTS μM | HCT-116 |
|---|---|---|---|
| 1494 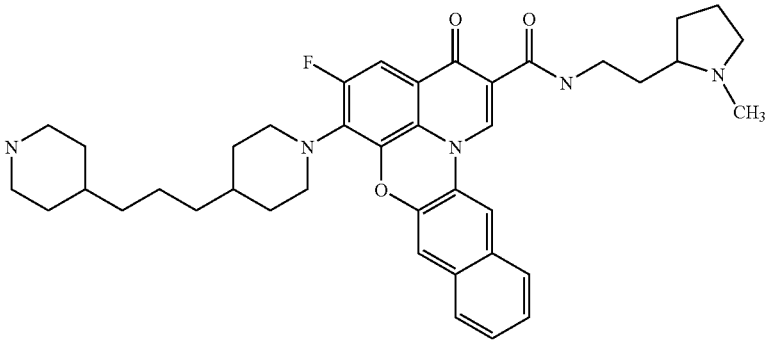 | 0.375 | 0.31 | |
| 1495 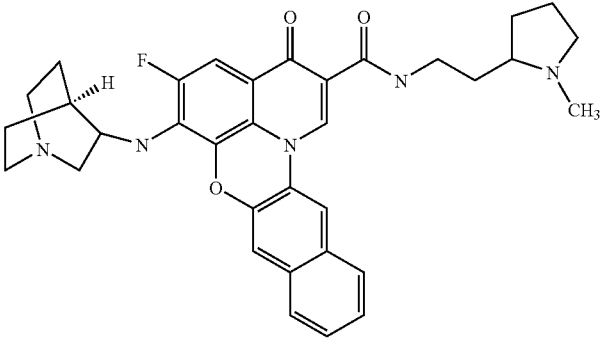 | 0.75 | | |
| 1496 Chiral 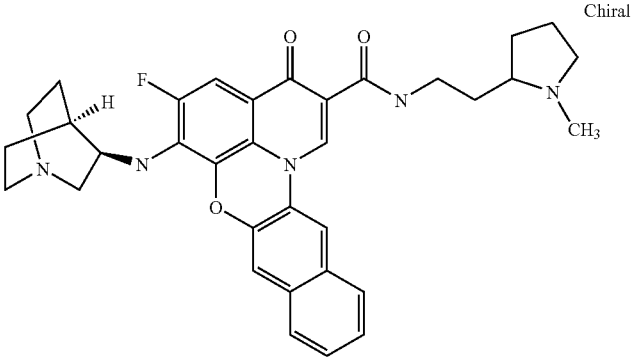 | 0.375 | 0.34 | |
| 1497 Chiral 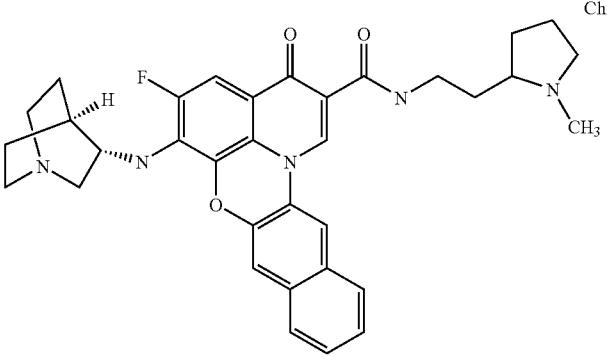 | 0.5 | 0.39 | |

TABLE 1D-continued
| Structure | S DATA μM | Hela MTS μM | HCT-116 |
|---|---|---|---|
| 1498 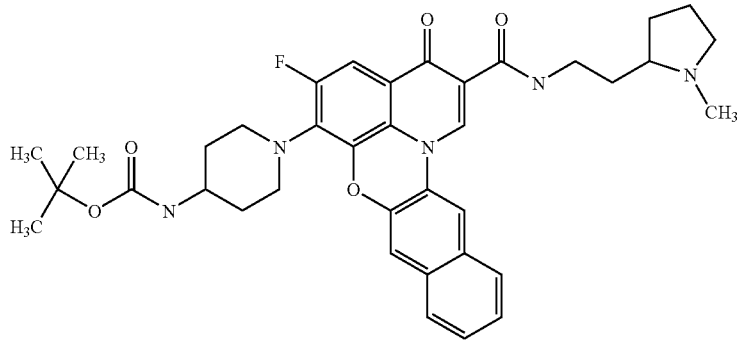 | | 1.75 | |
| 1499 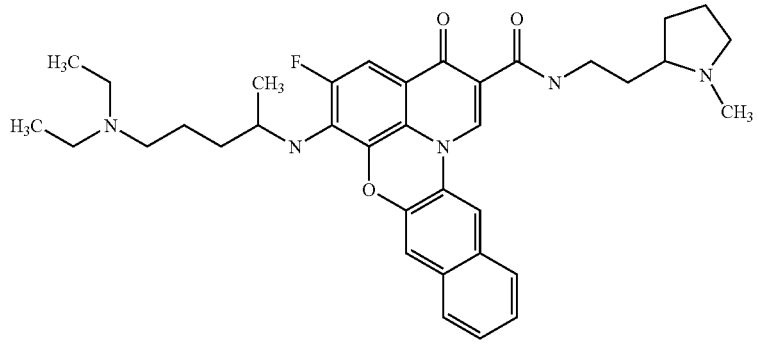 | | 0.75 | |
| 1500 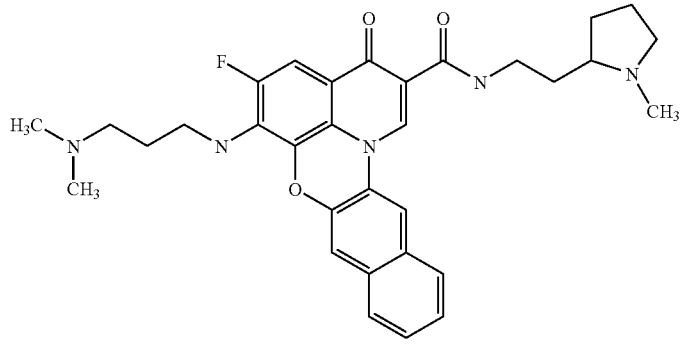 | | 0.75 | |
| 1501 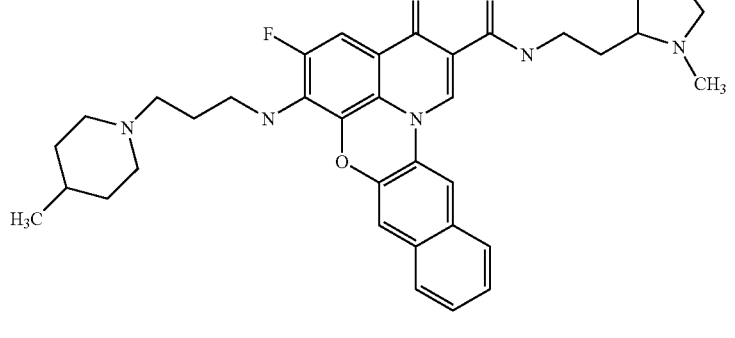 | | 0.75 | |

TABLE 1D-continued

| Structure | S DATA µM | Hela MTS µM | HCT-116 |
|---|---|---|---|
| 1502 | 0.75 | | |
| 1503 | 1.75 | | |
| 1504 | 0.75 | | |
| 1505 | >15 | | |

TABLE 1D-continued
| Structure | S DATA μM | Hela MTS μM | HCT-116 |
|---|---|---|---|
| 1506 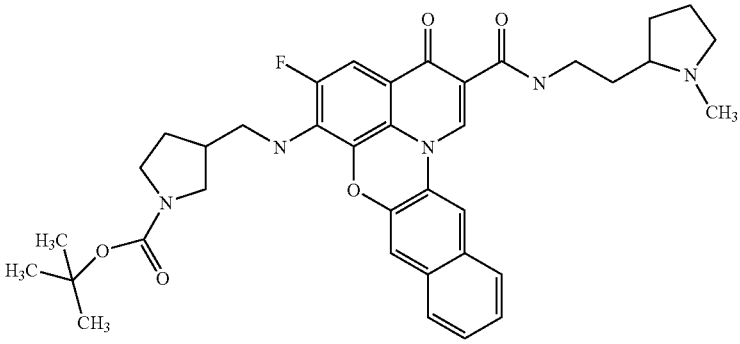 | | 0.75 | |
| 1507 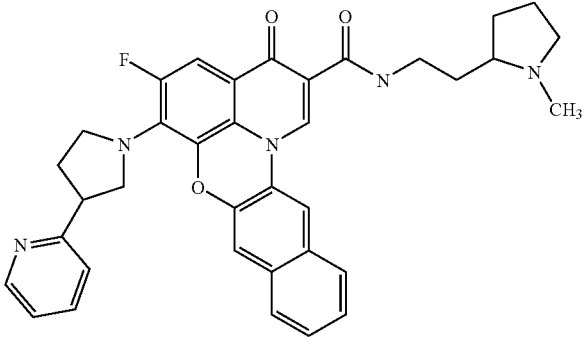 | | 0.75 | |
| 1508 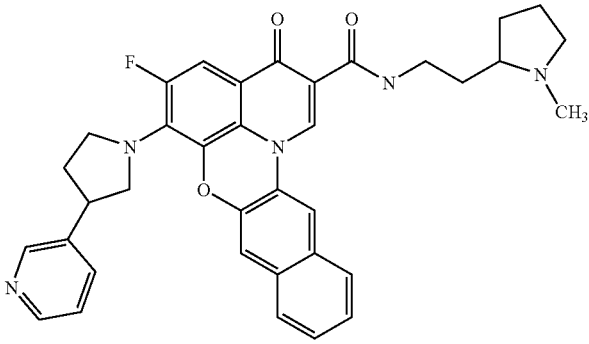 | | 0.75 | |
| 1509 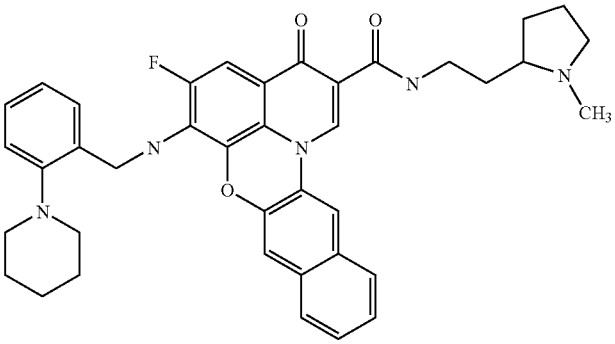 | | >15 | |

TABLE 1D-continued
| Structure | S DATA μM | Hela MTS μM | HCT-116 |
|---|---|---|---|
| 1510 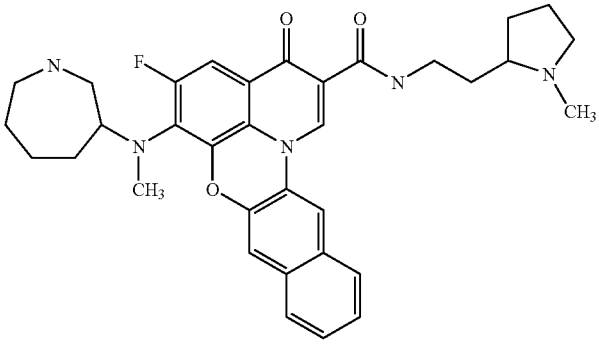 | >15 | | |
| 1511 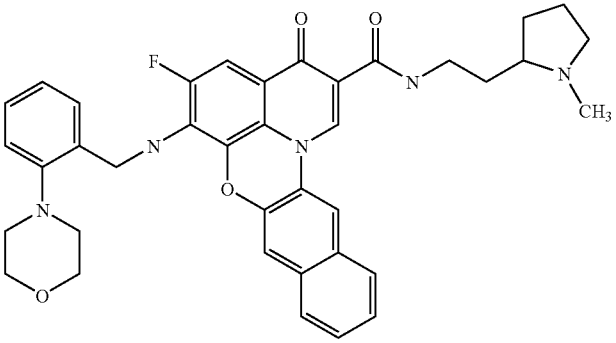 | 1.75 | | |
| 1512 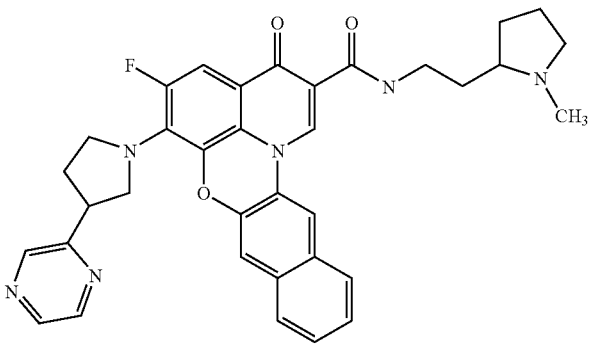 | 0.78 | 3.1 | |
| 1513 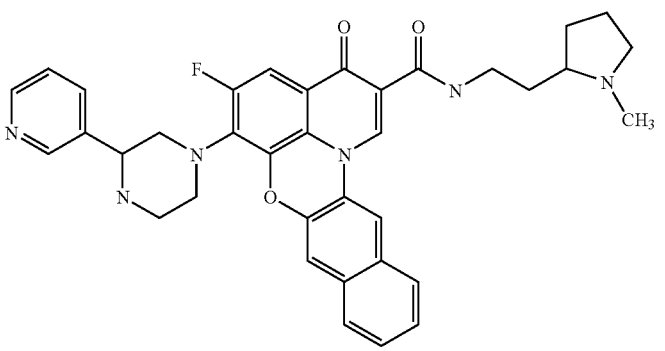 | 1.75 | | |

TABLE 1D-continued
| Structure | S DATA μM | Hela MTS μM | HCT-116 |
|---|---|---|---|
| 1514 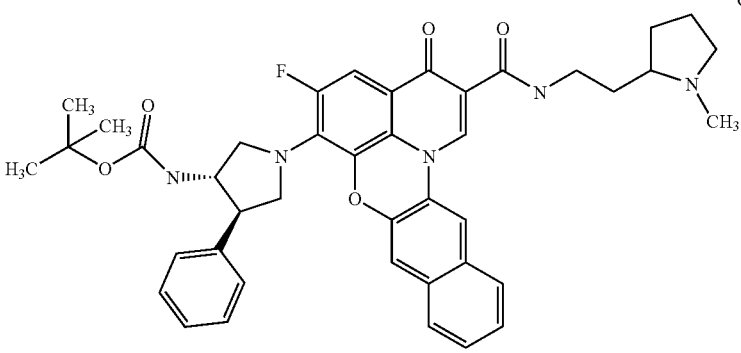 Chiral | >15 | | |
| 1515 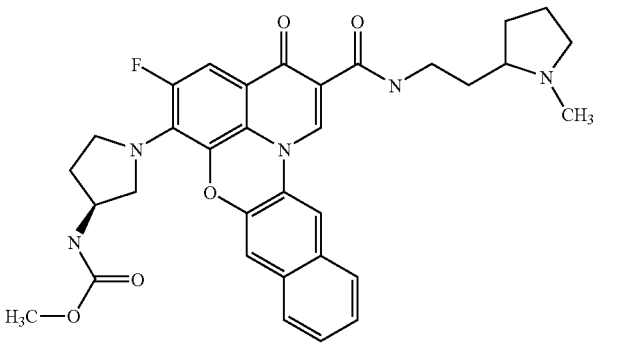 Chiral | >15 | | |
| 1516 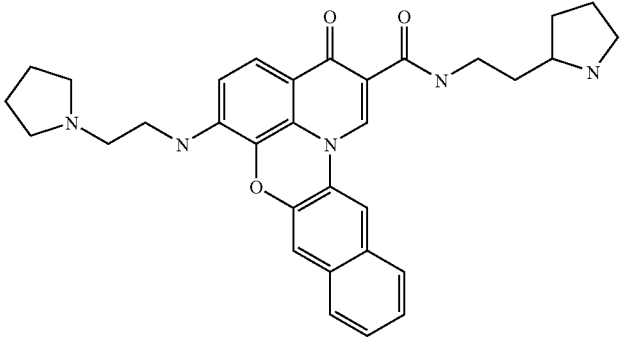 | | | 1.75 |
| 1517 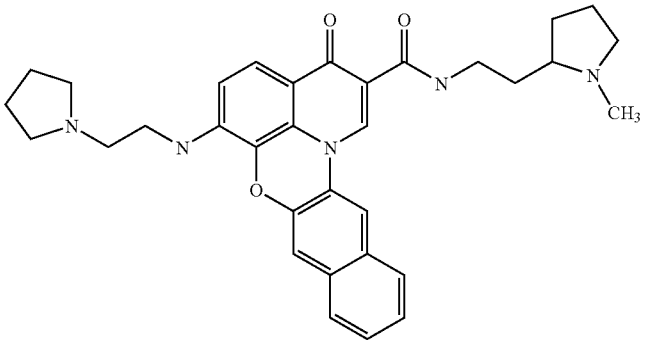 | | | 0.75 |

TABLE 1D-continued
| Structure | S DATA μM | Hela MTS μM | HCT-116 |
|---|---|---|---|
| 1518 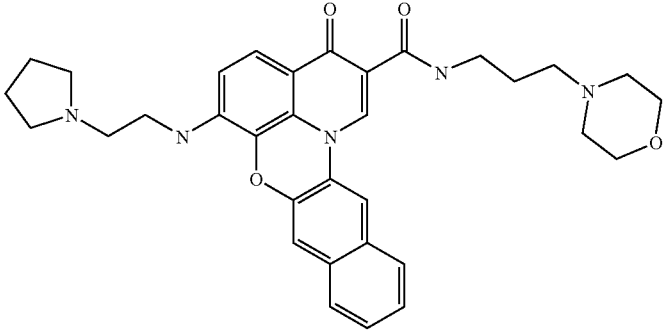 | 1.75 | | |
| 1519 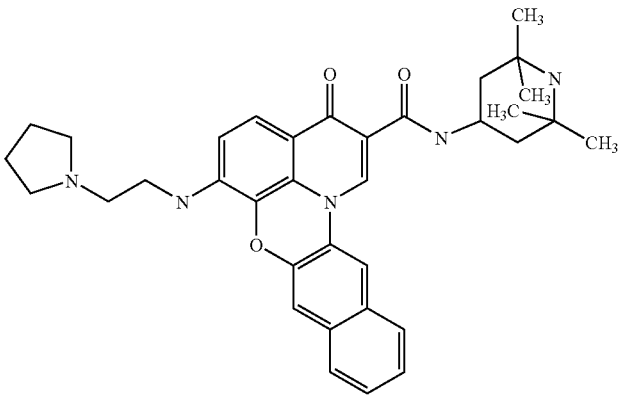 | 0.75 | | |
| 1520 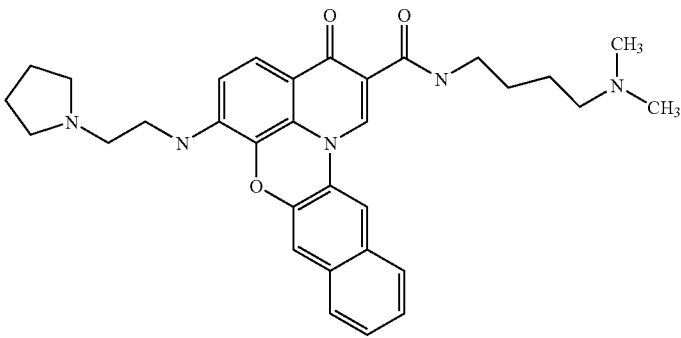 | 0.375 | 0.2 | |
| 1521 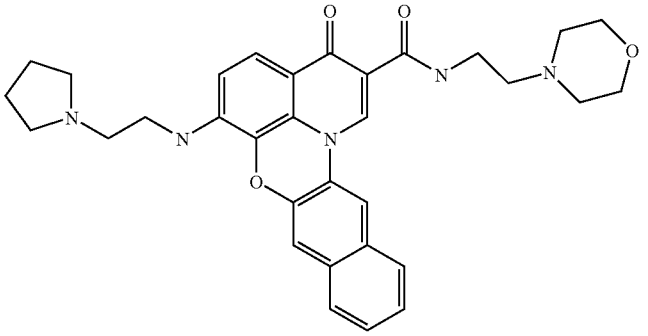 | 1.75 | | |

TABLE 1D-continued

| Structure | S DATA μM | Hela MTS μM | HCT-116 |
|---|---|---|---|
| 1522 | 0.75 | | |
| 1523 | 0.75 | | |
| 1524 | 1.75 | | |
| 1525 | 1.75 | | |

TABLE 1D-continued
| Structure | S DATA μM | Hela MTS μM | HCT-116 |
|---|---|---|---|
| 1526 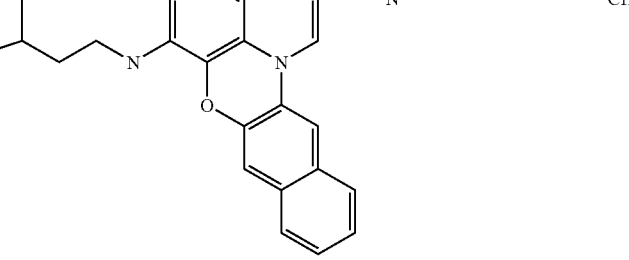 | 0.75 | | |
| 1527 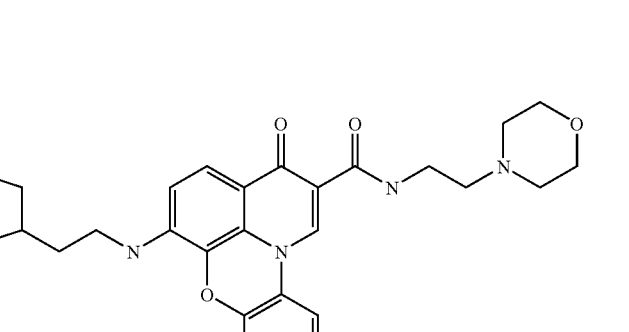 | 1.75 | | |
| 1528 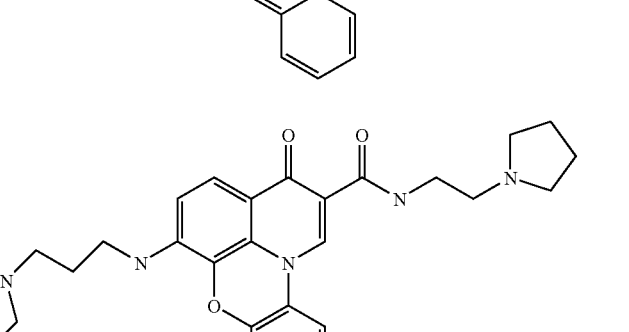 | 1.75 | | |
| 1529 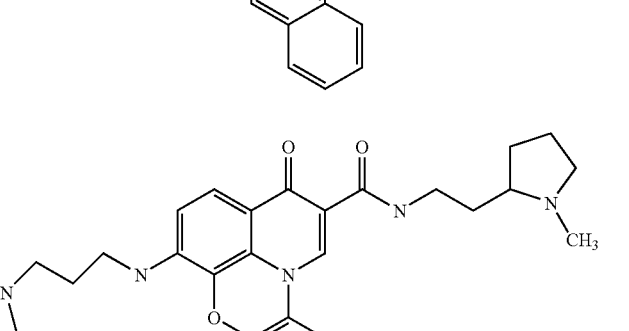 | 1.75 | | |

TABLE 1D-continued

| Structure | S DATA µM | Hela MTS µM | HCT-116 |
|---|---|---|---|
| 1530 | | >15 | |
| 1531 | | >15 | |
| 1532 | | >15 | |
| 1533 | | >15 | |

TABLE 1D-continued

| Structure | S DATA μM | Hela MTS μM | HCT-116 |
|---|---|---|---|
| 1534 | | >15 | |
| 1535 | | 0.75 | |
| 1536 | | >15 | |
| 1537 | | 1.75 | |

TABLE 1D-continued

| Structure | S DATA μM | Hela MTS μM | HCT-116 |
|---|---|---|---|
| 1538 | | | 1 |
| 1539 | | | 0.75 |
| 1540 | | | 1 |
| 1541 | | | 1.75 |

TABLE 1D-continued

| Structure | S DATA μM | Hela MTS μM | HCT-116 |
|---|---|---|---|
| 1542 | | | >15 |
| 1543 | | | 1.75 |
| 1544 | | | 1.75 |
| 1545 | | | 0.75 |

TABLE 1D-continued

| Structure | S DATA μM | Hela MTS μM | HCT-116 |
|---|---|---|---|
| 1546 | >15 | | |
| 1547 | >15 | | |
| 1548 | >15 | | |
| 1549 | >15 | | |

TABLE 1D-continued

| Structure | S DATA μM | Hela MTS μM | HCT-116 |
|---|---|---|---|
| 1550 | >15 | | |
| 1551 | >15 | | |
| 1552 | 0.75 | | |
| 1553 | 0.75 | | |

TABLE 1D-continued
| Structure | S DATA μM | Hela MTS μM | HCT-116 |
|---|---|---|---|
| 1554 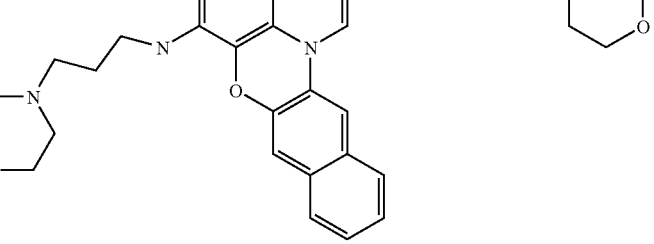 | 1.75 | | |
| 1555 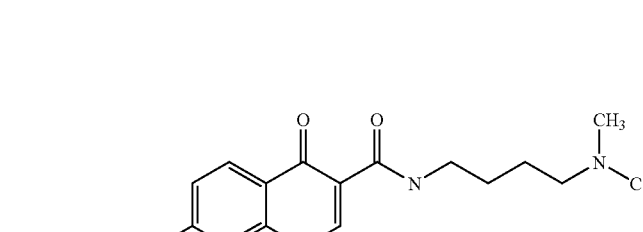 | 0.75 | | |
| 1556 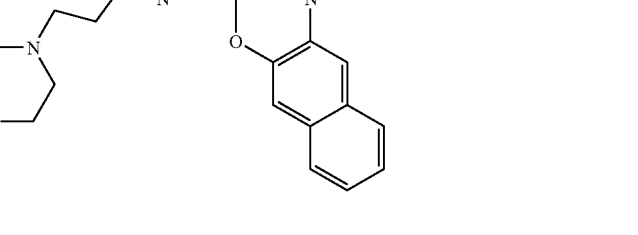 | 1.75 | | |
| 1557 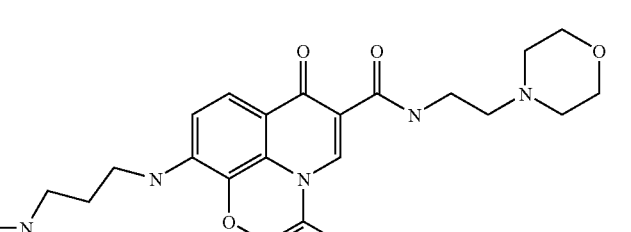 | 0.75 | 1.5 | |

TABLE 1D-continued

| Structure | S DATA μM | Hela MTS μM | HCT-116 |
|---|---|---|---|
| 1558 | 0.375 | 0.24 | |
| 1559 | 0.18 | 0.24 | |
| 1560 | >15 | | |
| 1561 | >15 | | |

TABLE 1D-continued

| Structure | S DATA μM | Hela MTS μM | HCT-116 |
|---|---|---|---|
| 1562 | >15 | | |
| 1563 | >15 | | |
| 1564 | >15 | | |
| 1565 | >15 | | |
| 1566 | >15 | | |

TABLE 1D-continued

| Structure | S DATA μM | Hela MTS μM | HCT-116 |
|---|---|---|---|
| 1567 | >15 | | |
| 1568 | >15 | | |
| 1569 | >15 | | |
| 1570 | >15 | | |
| 1571 | >15 | | |

TABLE 1D-continued

| Structure | S DATA μM | Hela MTS μM | HCT-116 |
|---|---|---|---|
| 1572 | | >15 | |
| 1573 | | >15 | |
| 1574 | | >15 | |
| 1575 | | >15 | |
| 1576 | | >15 | |

TABLE 1D-continued

| Structure | S DATA μM | Hela MTS μM | HCT-116 |
|---|---|---|---|
| 1577 | >15 | | |
| 1578 | >15 | | |
| 1579 | >15 | | |
| 1580 | >15 | | |
| 1581 | >15 | | |

TABLE 1D-continued

| Structure | S DATA µM | Hela MTS µM | HCT-116 |
|---|---|---|---|
| 1582 | >15 | | |
| 1583 | >15 | | |
| 1584 | >15 | | |
| 1585 | >15 | | |

TABLE 1D-continued

| Structure | S DATA μM | Hela MTS μM | HCT-116 |
|---|---|---|---|
| 1586 | >15 | | |
| 1587 | >15 | | |
| 1588 | >15 | | |
| 1589 | >15 | | |

TABLE 1D-continued

| Structure | S DATA μM | Hela MTS μM | HCT-116 |
|---|---|---|---|
| 1590 | >15 | | |
| 1591 | >15 | | |
| 1592 | >15 | | |
| 1593 | >15 | | |
| 1594 | >15 | | |

TABLE 1D-continued

| Structure | S DATA μM | Hela MTS μM | HCT-116 |
|---|---|---|---|
| 1595 | >15 | | |
| 1596 | >15 | | |
| 1597 | >15 | | |
| 1598 | >15 | | |
| 1599 | >15 | | |

TABLE 1D-continued

| Structure | S DATA μM | Hela MTS μM | HCT-116 |
|---|---|---|---|
| 1600 | >15 | | |
| 1601 | >15 | | |
| 1602 | >15 | | |
| 1603 | >15 | | |
| 1604 | >15 | | |

TABLE 1D-continued
| Structure | S DATA μM | Hela MTS μM | HCT-116 |
|---|---|---|---|
| 1605 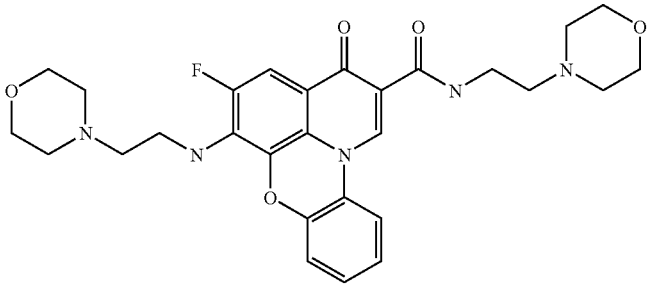 | >15 | | |
| 1606 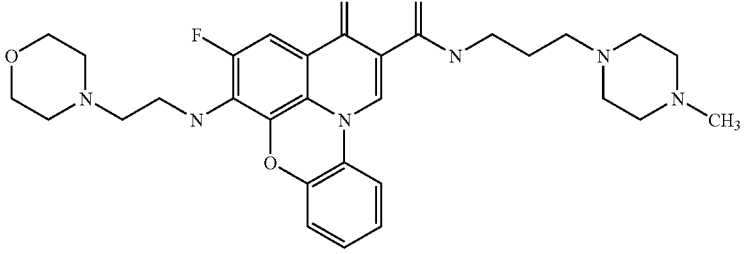 | >15 | | |
| 1607 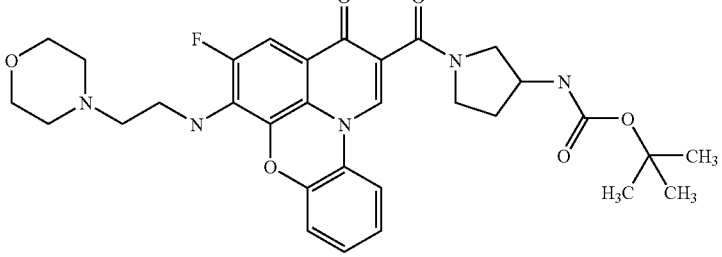 | >15 | | |
| 1608 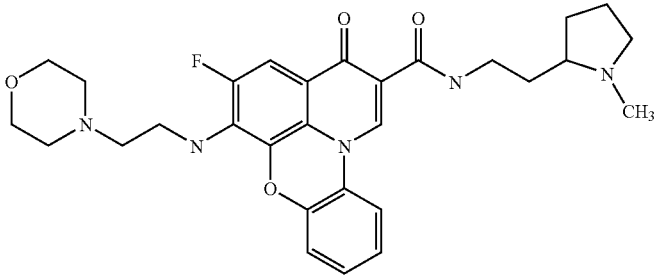 | >15 | | |
| 1609 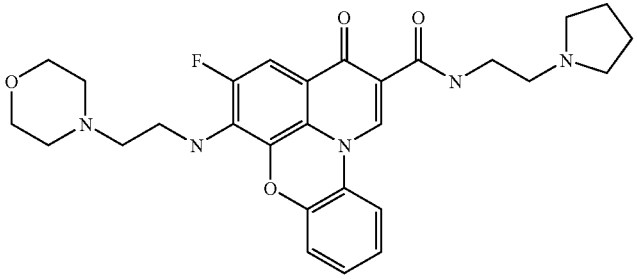 | >15 | | |

TABLE 1D-continued
| Structure | S DATA μM | Hela MTS μM | HCT-116 |
|---|---|---|---|
| 1610 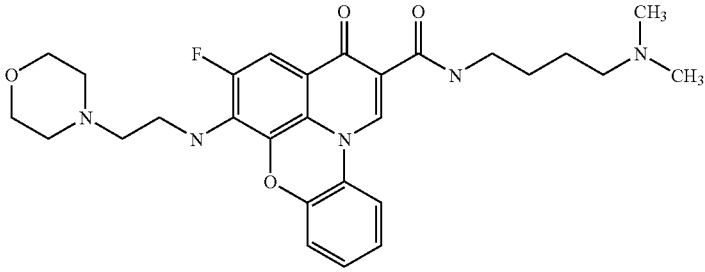 | >15 | | |
| 1611 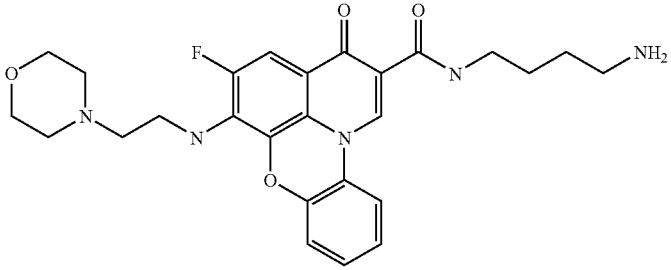 | >15 | | |
| 1612 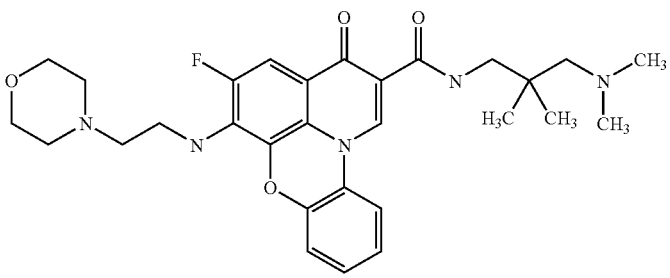 | >15 | | |
| 1613 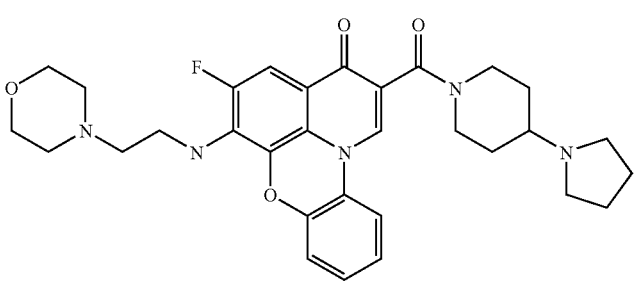 | >15 | | |
| 1614 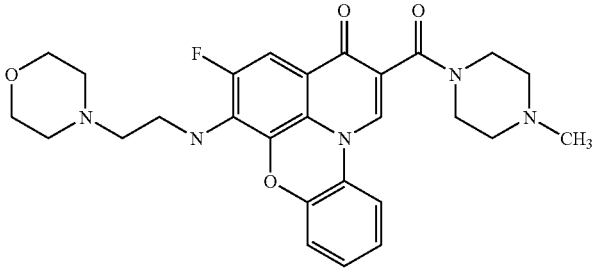 | >15 | | |

TABLE 1D-continued

| Structure | S DATA μM | Hela MTS μM | HCT-116 |
|---|---|---|---|
| 1615 | >15 | | |
| 1616 | 1.75 | | |
| 1617 | 0.375 | | |
| 1618 Chiral | 0.75 | | |

TABLE 1D-continued

| Structure | S DATA μM | Hela MTS μM | HCT-116 |
|---|---|---|---|
| 1619 | | >15 | |
| 1620 | | >15 | |
| 1621 | | 0.75 | |
| 1622 | | >15 | |
| 1623 | | >15 | |

TABLE 1D-continued

| Structure | S DATA μM | Hela MTS μM | HCT-116 |
|---|---|---|---|
| 1624 | 0.75 | | |
| 1625 | >15 | | |
| 1626 | >15 | | |
| 1627 | >15 | | |
| 1628 | >15 | | |

TABLE 1D-continued

| Structure | S DATA μM | Hela MTS μM | HCT-116 |
|---|---|---|---|
| 1629 | | >15 | |
| 1630 | | >15 | |
| 1631 | | >15 | |
| 1632 | | >15 | |
| 1633 | | >15 | |

TABLE 1D-continued
| Structure | S DATA μM | Hela MTS μM | HCT-116 |
|---|---|---|---|
| 1634 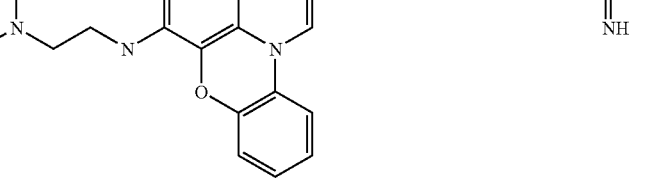 | >15 | | |
| 1635 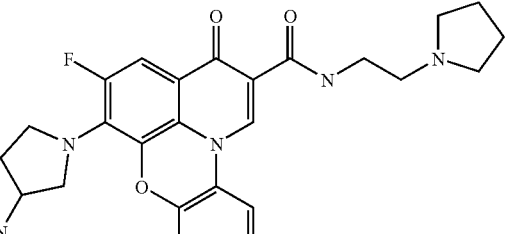 | 0.18 | 0.3 | |
| 1636 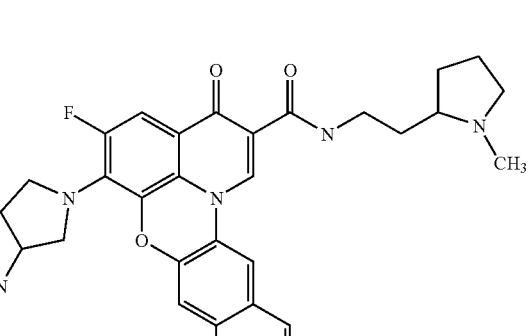 | 0.375 | 0.15 | |
| 1637 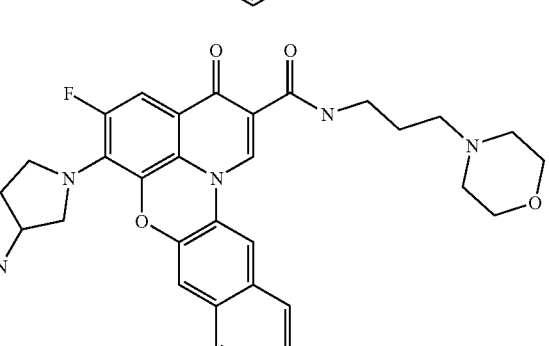 | 0.375 | 0.1 | |

TABLE 1D-continued

| Structure | S DATA μM | Hela MTS μM | HCT-116 |
|---|---|---|---|
| 1638 | 1.75 | | |
| 1639 | 0.375 | 0.1 | |
| 1640 | 0.25 | 0.03 | |
| 1641 | 0.75 | | |

TABLE 1D-continued

| Structure | S DATA μM | Hela MTS μM | HCT-116 |
|---|---|---|---|
| 1642 | 0.5 | 0.18 | |
| 1643 | >15 | | |
| 1644 | 0.375 | 0.65 | |
| 1645 | 0.62 | 3.3 | |

TABLE 1D-continued

| Structure | S DATA μM | Hela MTS μM | HCT-116 |
|---|---|---|---|
| 1646 | 0.64 | 0.4 | |
| 1647 | | 1 | |
| 1648 | | 1 | |
| 1649 | 0.37 | 2.2 | |

TABLE 1D-continued

| Structure | S DATA μM | Hela MTS μM | HCT-116 |
|---|---|---|---|
| 1650 | | | 1 |
| 1651 | | | 1 |
| 1652 | | | 1 |
| 1653 | | | 0.34 |

TABLE 1D-continued

| Structure | S DATA μM | Hela MTS μM | HCT-116 |
|---|---|---|---|
| 1654 | 1 | | |
| 1655 | 1 | | |
| 1656 | 1.75 | | |
| 1657 | 0.375 | 0.5 | |

TABLE 1D-continued

| Structure | S DATA μM | Hela MTS μM | HCT-116 |
|---|---|---|---|
| 1658 | 1.75 | | |
| 1659 | 1.75 | | |
| 1660 | 1.8 | | |
| 1661 | 1.75 | | |

TABLE 1D-continued
| Structure | S DATA μM | Hela MTS μM | HCT-116 |
|---|---|---|---|
| 1662 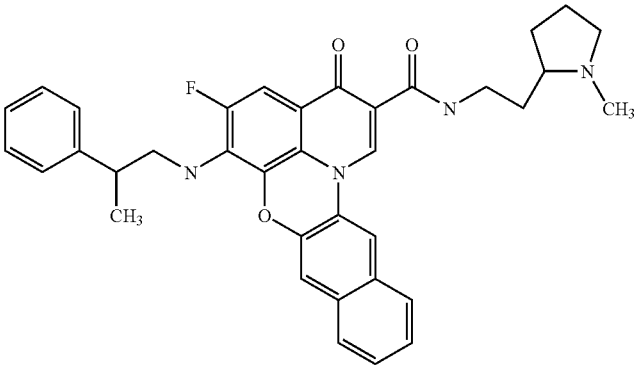 | 1.75 | | |
| 1663 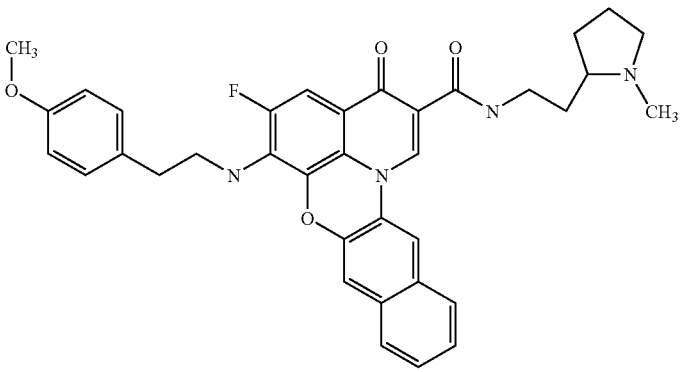 | 1.75 | | |
| 1664 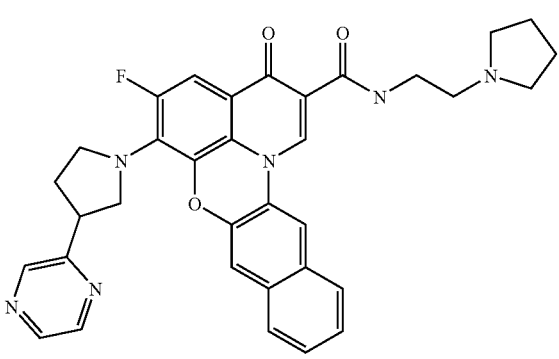 | 1.12 | | |
| 1665 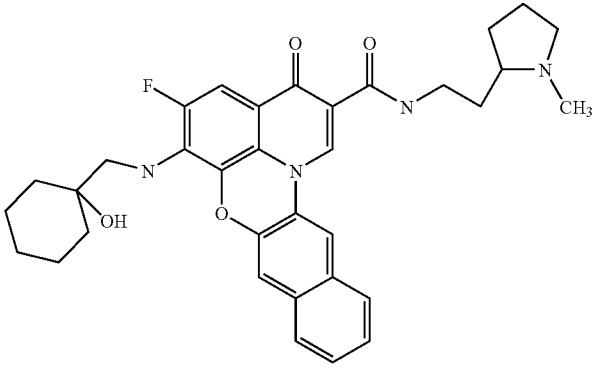 | 0.75 | 0.24 | |

TABLE 1D-continued
| Structure | S DATA μM | Hela MTS μM | HCT-116 |
|---|---|---|---|
| 1666 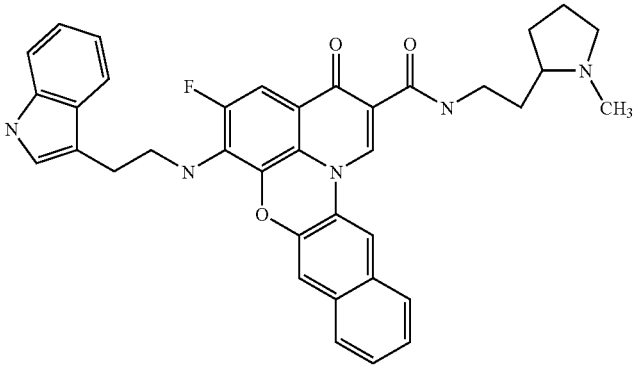 | 1.75 | | |
| 1667 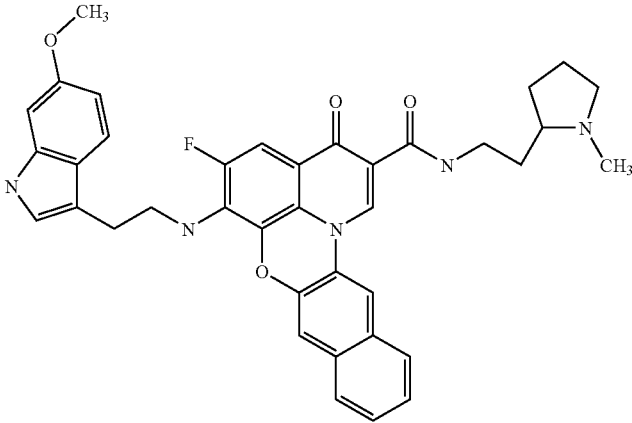 | 1.75 | | |
| 1668 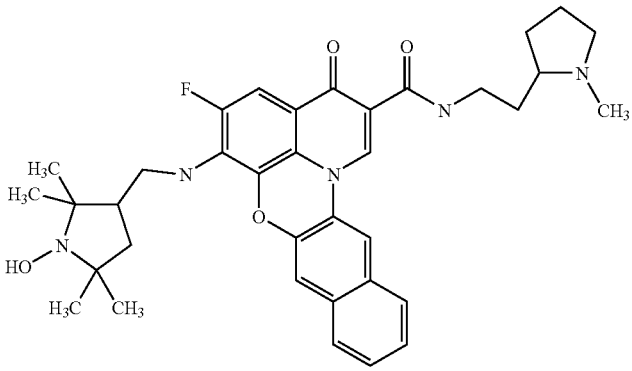 | 0.375 | | |
| 1669 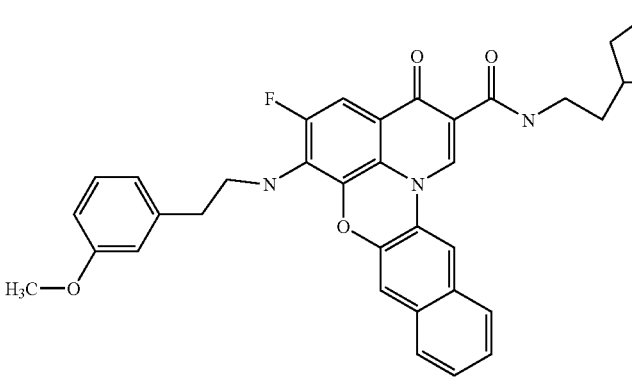 | 1.75 | | |

TABLE 1D-continued

| Structure | S DATA µM | Hela MTS µM | HCT-116 |
|---|---|---|---|
| 1670 | | | 1 |
| 1671 | | | 1.75 |
| 1672 | | | 1.75 |
| 1673 | | | 2.5 |

TABLE 1D-continued
| Structure | S DATA μM | Hela MTS μM | HCT-116 |
|---|---|---|---|
| 1674 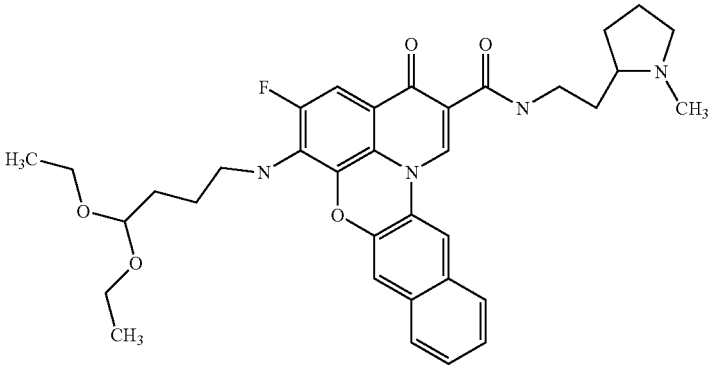 | 0.75 | | |
| 1675 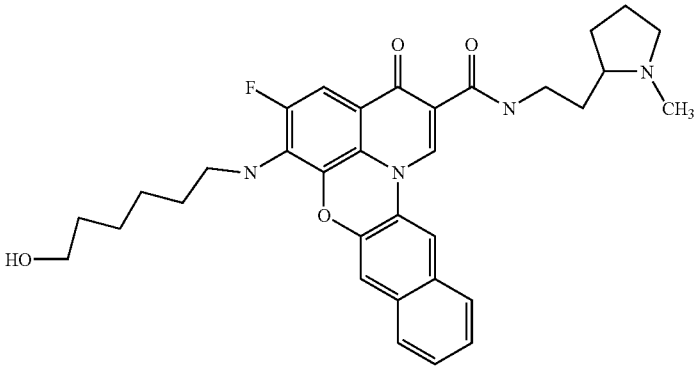 | >15 | | |
| 1676 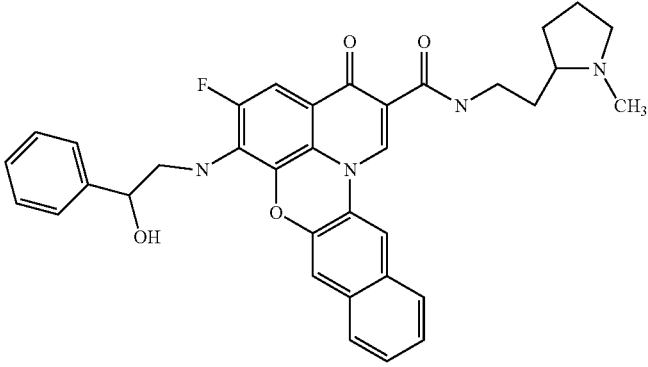 | 0.75 | 0.19 | |
| 1677 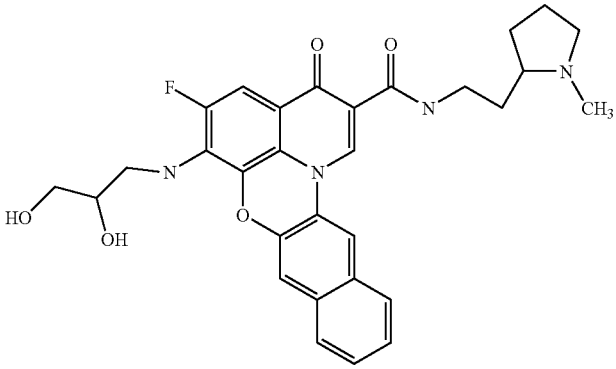 | 1.75 | | |

TABLE 1D-continued

| Structure | S DATA μM | Hela MTS μM | HCT-116 |
|---|---|---|---|
| 1678 | | 1.75 | |
| 1679 | | 0.69 | |
| 1680 | | 0.75 | 1.8 |
| 1681 | | 0.75 | 2.1 |

TABLE 1D-continued

| Structure | S DATA μM | Hela MTS μM | HCT-116 |
|---|---|---|---|
| 1682 Chiral | | 0.75 | |
| 1683 Chiral | | 1.75 | |
| 1684 | | >15 | |
| 1685 | | 1.75 | |

TABLE 1D-continued

| Structure | S DATA μM | Hela MTS μM | HCT-116 |
|---|---|---|---|
| 1686 | 0.375 | 0.4 | |
| 1687 | 1.75 | | |
| 1688 | 0.75 | 0.25 | |
| 1689 | 1.75 | | |

TABLE 1D-continued

| Structure | S DATA μM | Hela MTS μM | HCT-116 |
|---|---|---|---|
| 1690 | 0.75 | 0.31 | |
| 1691 | | 1 | |
| 1692 | >15 | | |
| 1693 | >15 | | |

TABLE 1D-continued

| Structure | S DATA μM | Hela MTS μM | HCT-116 |
|---|---|---|---|
| 1694 | | >15 | |
| 1695 | | >15 | |
| 1696 | | >15 | |
| 1697 | | >15 | |

TABLE 1D-continued

| Structure | S DATA μM | Hela MTS μM | HCT-116 |
|---|---|---|---|
| 1698 | >15 | | |
| 1699 | 1.75 | | |
| 1700 | >15 | | |
| 1701 | >15 | | |

TABLE 1D-continued
| Structure | S DATA μM | Hela MTS μM | HCT-116 |
|---|---|---|---|
| 1702 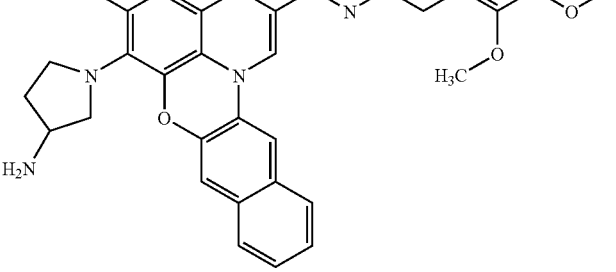 | | >15 | |
| 1703 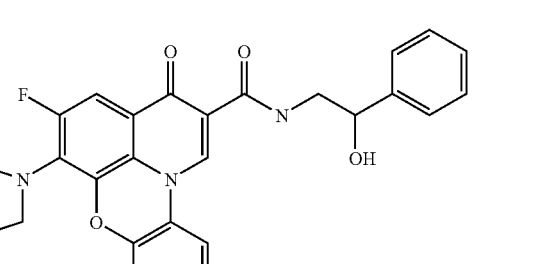 | | >15 | |
| 1704 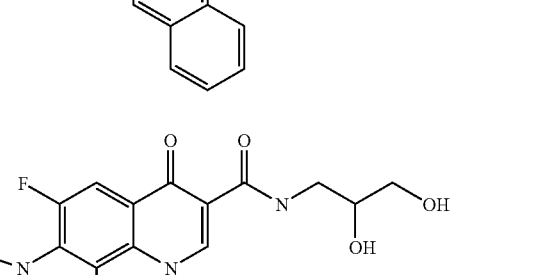 | | 1.75 | |
| 1705 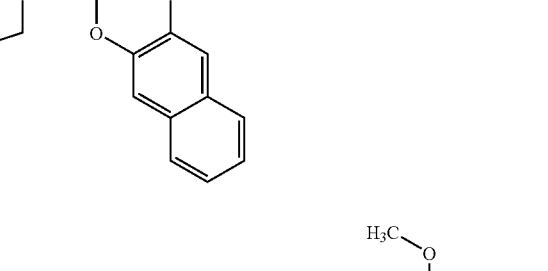 | | >15 | |

TABLE 1D-continued

| Structure | S DATA μM | Hela MTS μM | HCT-116 |
|---|---|---|---|
| 1706 | >15 | | |
| 1707 | >15 | | |
| 1708 Chiral | >15 | | |
| 1709 Chiral | >15 | | |

TABLE 1D-continued
| Structure | S DATA μM | Hela MTS μM | HCT-116 |
|---|---|---|---|
| 1710 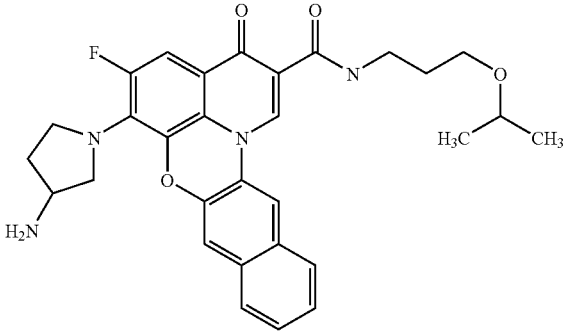 | | | >15 |
| 1711 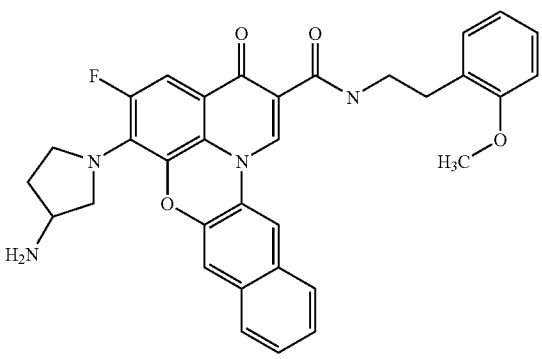 | | | >15 |
| 1712 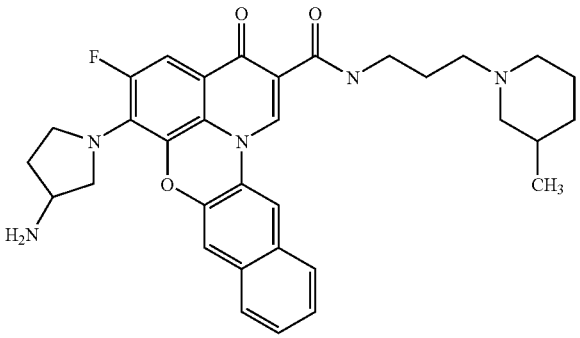 | | | >15 |
| 1713 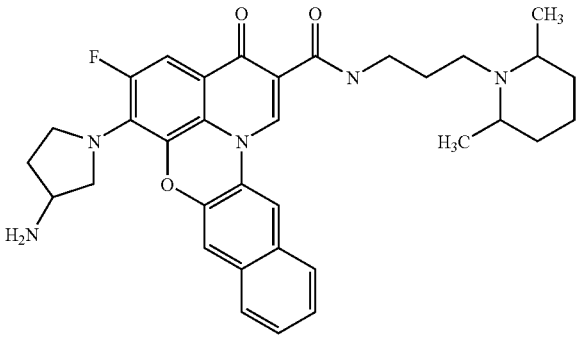 | | | 0.75 |

TABLE 1D-continued

| Structure | S DATA μM | Hela MTS μM | HCT-116 |
|---|---|---|---|
| 1714 | | >15 | |
| 1715 | | >15 | |
| 1716 | | 0.75 | |
| 1717 | | 0.75 | |

TABLE 1D-continued

| Structure | S DATA µM | Hela MTS µM | HCT-116 |
|---|---|---|---|
| 1718 | 1.75 | | |
| 1719 | 3 | | |
| 1720 | 1 | | |
| 1721 | 3 | | |

TABLE 1D-continued
| Structure | S DATA μM | Hela MTS μM | HCT-116 |
|---|---|---|---|
| 1722 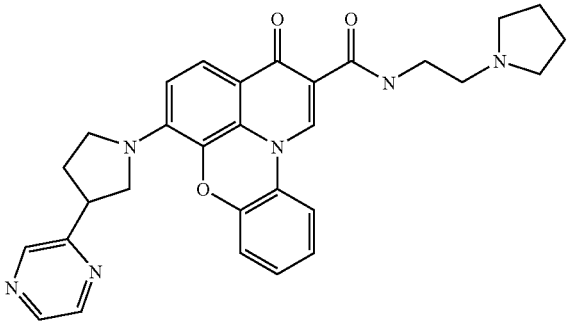 | | | 3 |
| 1723 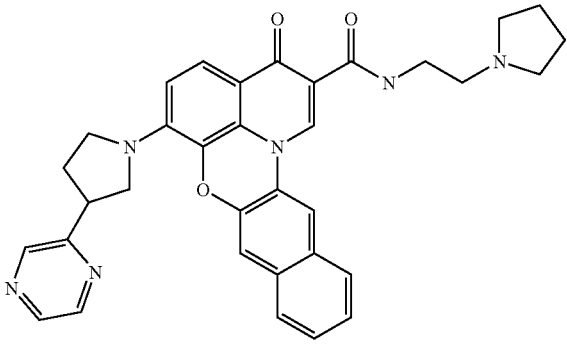 | | | 1.5 |
| 1724 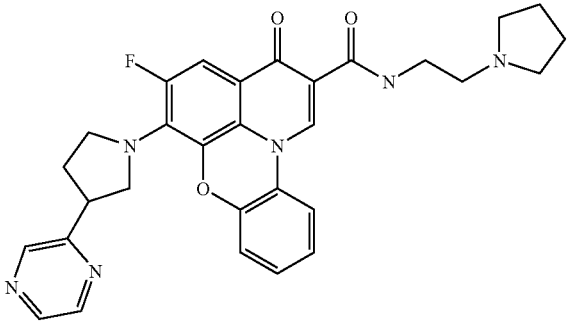 | | | 11 |
| 1725 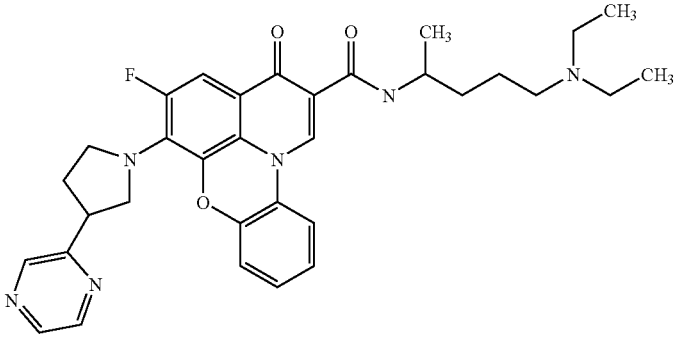 | | | 3 |

TABLE 1D-continued
| Structure | S DATA µM | Hela MTS µM | HCT-116 |
|---|---|---|---|
| 1726 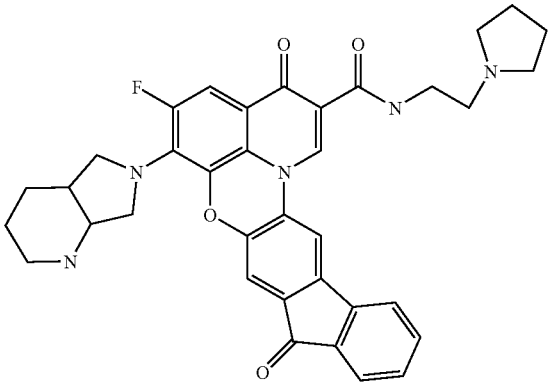 | 0.125 | 2.6 | |
| 1727 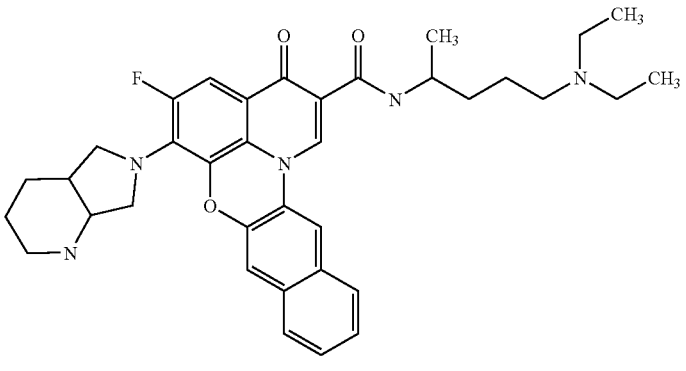 | 0.75 | 0.36 | |
| 1728 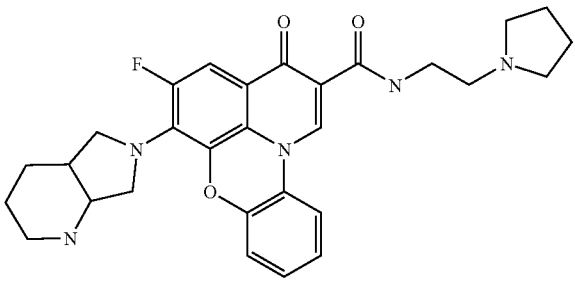 | >15 | | |
| 1729 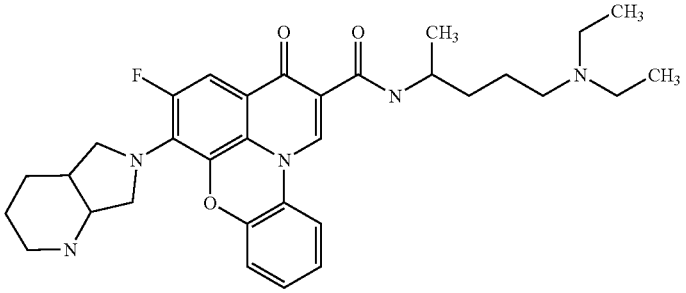 | >15 | | |

TABLE 1D-continued

| Structure | S DATA μM | Hela MTS μM | HCT-116 |
|---|---|---|---|
| 1730 | >15 | | |
| 1731 | >15 | | |
| 1732 | 0.375 | 0.2 | |
| 1733 | >15 | | |

TABLE 1D-continued

| Structure | S DATA µM | Hela MTS µM | HCT-116 |
|---|---|---|---|
| 1734 | | 3 | |
| 1735 Chiral | | 2.5 | |
| 1736 Chiral | | 3 | |
| 1737 Chiral | | 4 | |

TABLE 1D-continued

| Structure | S DATA μM | Hela MTS μM | HCT-116 |
|---|---|---|---|
| 1738 | 2.25 | | |
| 1739 | 3.3 | | |
| 1740 | 8.5 | | |
| 1741 Chiral | 0.74 | | |

TABLE 1D-continued
| Structure | | S DATA μM | Hela MTS μM | HCT-116 |
|---|---|---|---|---|
| 1742 | 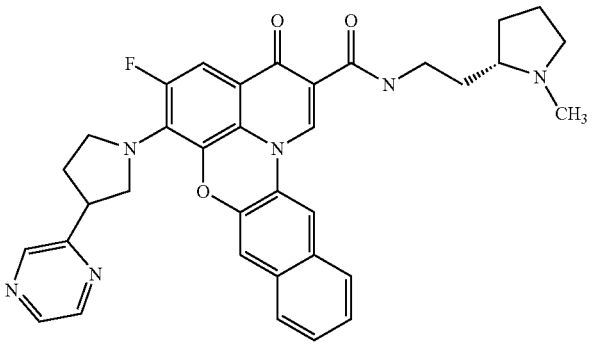 Chiral | 0.85 | 3.3 | |
| 1743 | 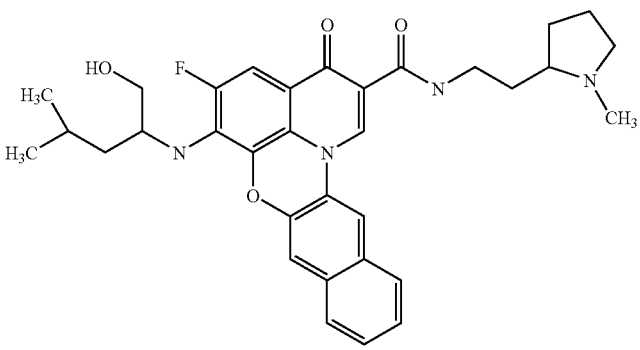 | | >15 | |
| 1744 | 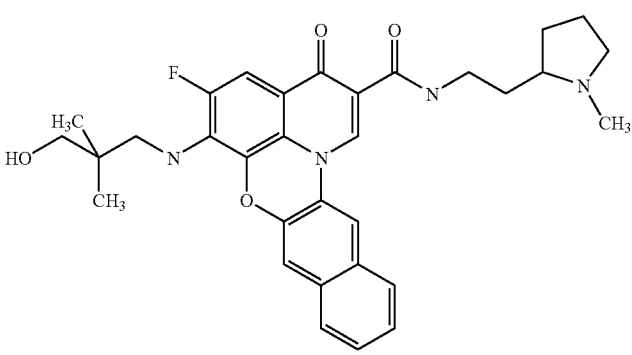 | | >15 | |
| 1745 | 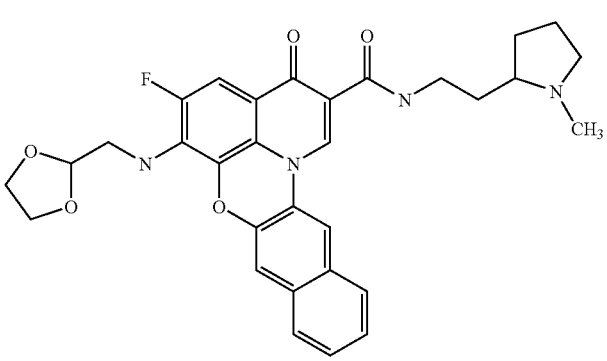 | | >15 | |

TABLE 1D-continued

| Structure | S DATA μM | Hela MTS μM | HCT-116 |
|---|---|---|---|
| 1746 | | >15 | |
| 1747 | | >15 | |
| 1748 | | >15 | |
| 1749 | | 1.95 | |

TABLE 1D-continued
| Structure | S DATA μM | Hela MTS μM | HCT-116 |
|---|---|---|---|
| 1750 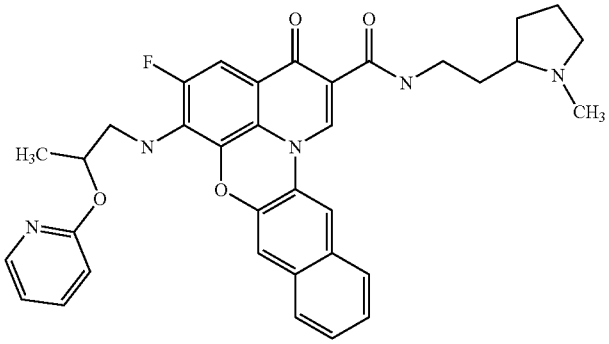 | 9.7 | | |
| 1751 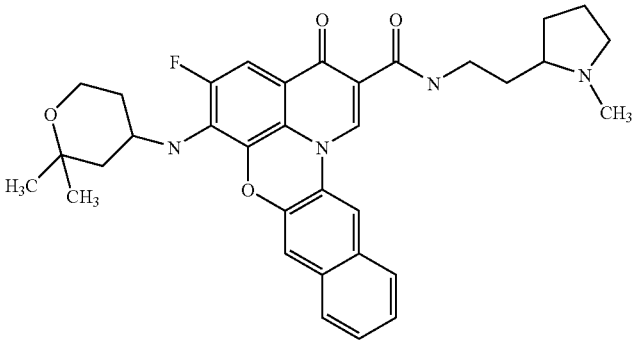 | >15 | | |
| 1752 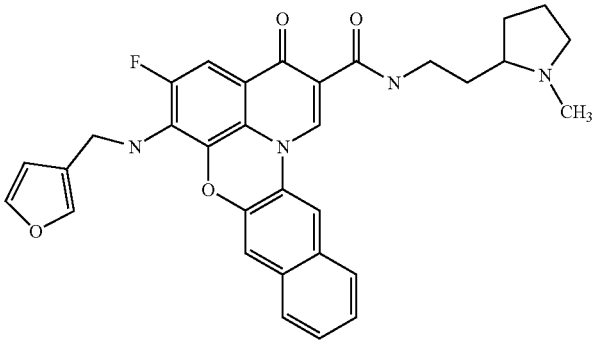 | >15 | | |
| 1753 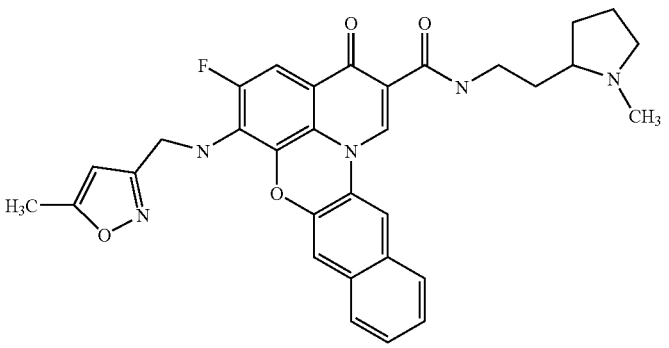 | >15 | | |

TABLE 1D-continued

| Structure | S DATA μM | Hela MTS μM | HCT-116 |
|---|---|---|---|
| 1754 | 5 | | |
| 1755 | 4.2 | | |
| 1756 | 1.81 | | |
| 1757 | 9.8 | | |

TABLE 1D-continued

| Structure | S DATA µM | Hela MTS µM | HCT-116 |
|---|---|---|---|
| 1758 | 9.4 | | |
| 1759 | 10 | | |
| 1760 | 1.85 | | |
| 1761 | 1.75 | | |

TABLE 1D-continued
| Structure | S DATA μM | Hela MTS μM | HCT-116 |
|---|---|---|---|
| 1762 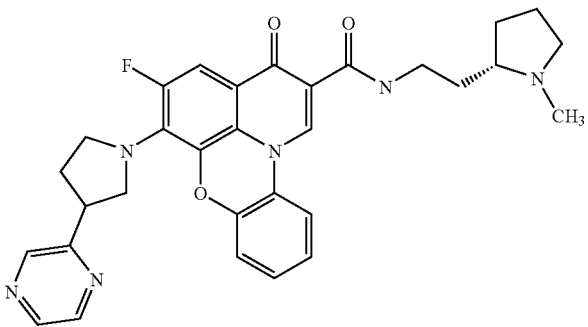 Chiral | 5.7 | | |
| 1763 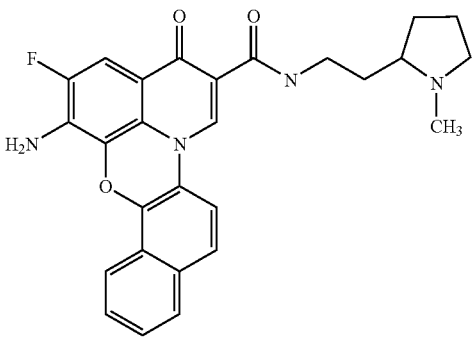 | 1.5 | 3.8 | |
| 1764 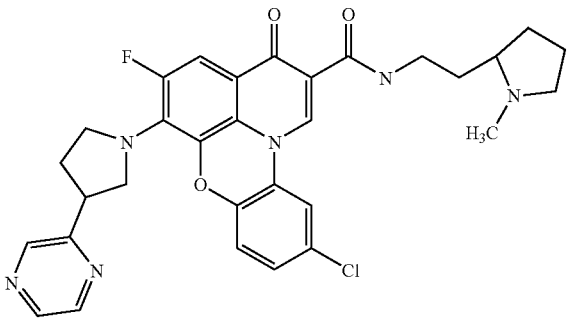 | 4.8 | | |
| 1765 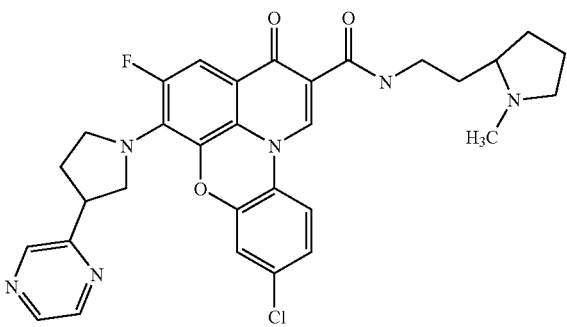 | 3.6 | | |

TABLE 1D-continued
| Structure | S DATA μM | Hela MTS μM | HCT-116 |
|---|---|---|---|
| 1766 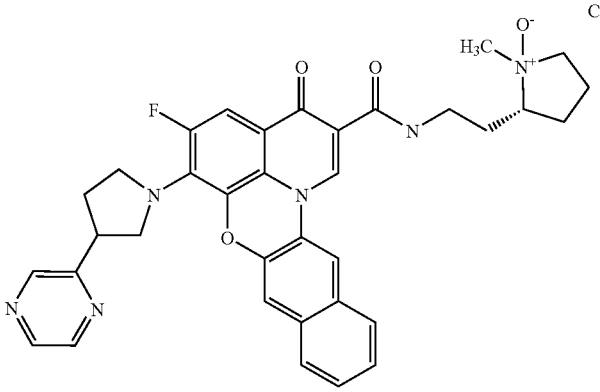 Chiral | 6.3 | | |
| 1767 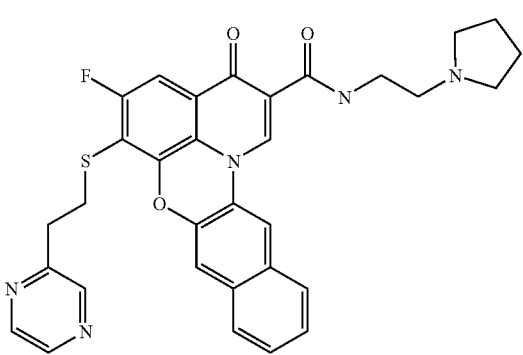 | 3.2 | | |
| 1768 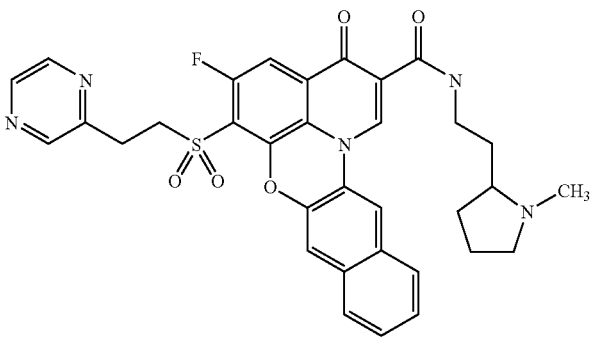 | 0.92 | | |
| 1769 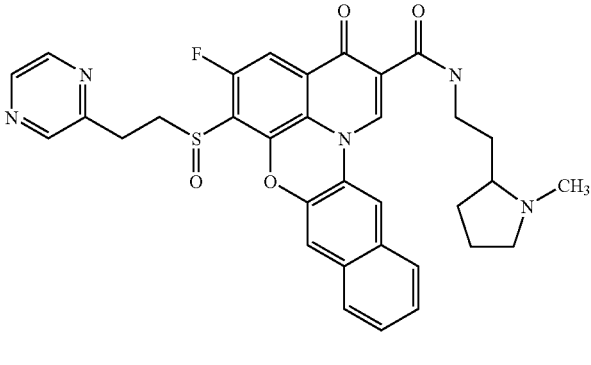 | 10 | | |

TABLE 1D-continued

| Structure | S DATA μM | Hela MTS μM | HCT-116 |
|---|---|---|---|
| 1770 | 4.7 | | |
| 1771 | 10 | | |
| 1772 | 14.1 | | |
| 1773 | 6.1 | | |

TABLE 1D-continued

| Structure | S DATA μM | Hela MTS μM | HCT-116 |
|---|---|---|---|
| 1774 | | 5.8 | |
| 1775 | | >15 | |
| 1776 | | 6.8 | |
| 1777 | | 6.8 | |

TABLE 1D-continued

| Structure | S DATA μM | Hela MTS μM | HCT-116 |
|---|---|---|---|
| 1778 | 2.9 | 0.21 | |
| 1779 | >15 | | |
| 1780 | 5.2 | | |
| 1781 | 5.5 | | |

TABLE 1D-continued

| Structure | S DATA μM | Hela MTS μM | HCT-116 |
|---|---|---|---|
| 1782 | 3.3 | 2.1 | |
| 1783 | >15 | | |
| 1784 | >15 | | |
| 1785 | >15 | | |
| 1786 | >15 | | |

TABLE 1D-continued

| Structure | S DATA μM | Hela MTS μM | HCT-116 |
|---|---|---|---|
| 1787 | >15 | | |
| 1788 | >15 | | |
| 1789 | >15 | | |
| 1790 | >15 | | |
| 1791 | >15 | | |

TABLE 1D-continued

| Structure | S DATA µM | Hela MTS µM | HCT-116 |
|---|---|---|---|
| 1792 | >15 | | |
| 1793 | 5.3 | | |
| 1794 | >15 | | |
| 1795 | 2.9 | 0.5 | |

TABLE 1D-continued

| Structure | S DATA μM | Hela MTS μM | HCT-116 |
|---|---|---|---|
| 1796 | >15 | | |
| 1797 | 8 | | |
| 1798 | 6.6 | | |
| 1799 | >15 | | |
| 1800 | 2.6 | 0.18 | |

TABLE 1D-continued

| Structure | S DATA μM | Hela MTS μM | HCT-116 |
|---|---|---|---|
| 1801 | | 8.2 | |
| 1802 | | 4 | |
| 1803 | | 3 | |
| 1804 | | >15 | |

TABLE 1D-continued
| Structure | S DATA µM | Hela MTS µM | HCT-116 |
|---|---|---|---|
| 1805 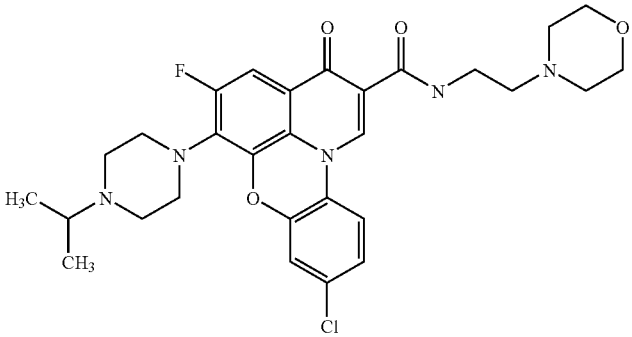 | >15 | | |
| 1806 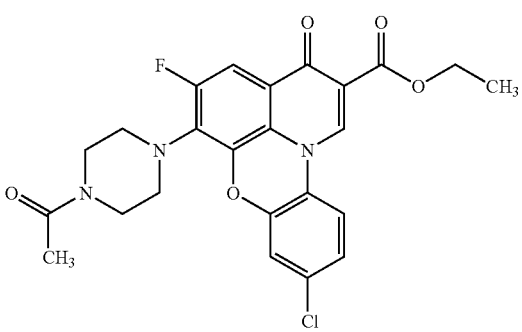 | >15 | | |
| 1807 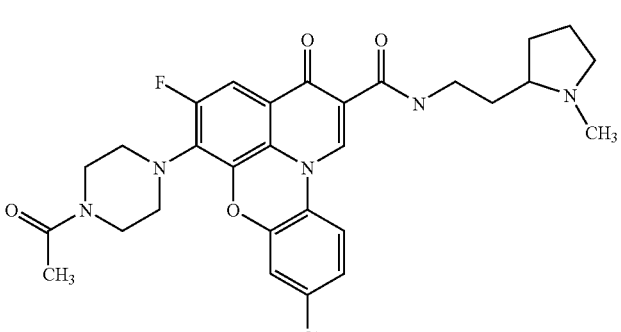 | >15 | | |
| 1808 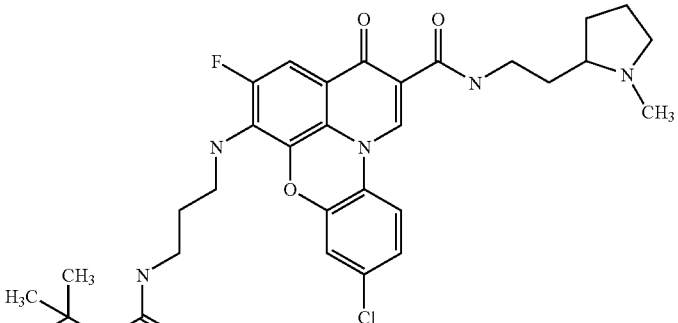 | >15 | | |

TABLE 1D-continued
| Structure | S DATA μM | Hela MTS μM | HCT-116 |
|---|---|---|---|
| 1809 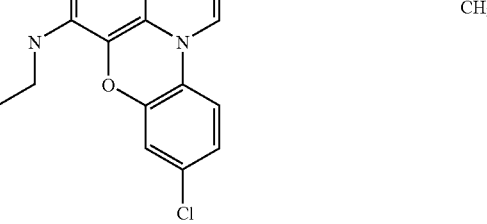 | >15 | | |
| 1810 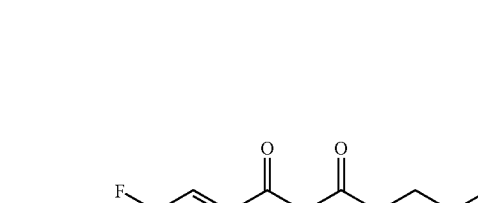 | 7.8 | | |
| 1811 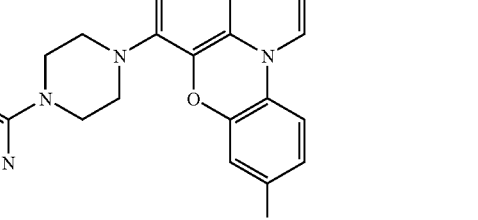 | 2.8 | 0.2 | |
| 1812 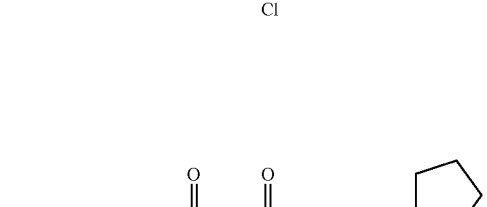 | 3.2 | | |

TABLE 1D-continued

| Structure | S DATA μM | Hela MTS μM | HCT-116 |
|---|---|---|---|
| 1813 | 5.1 | | |
| 1814 | 7.2 | | |
| 1815 | 10 | | |
| 1816 | 5.0 | | 0.03 |

TABLE 1D-continued
| Structure | S DATA µM | Hela MTS µM | HCT-116 |
|---|---|---|---|
| 1817 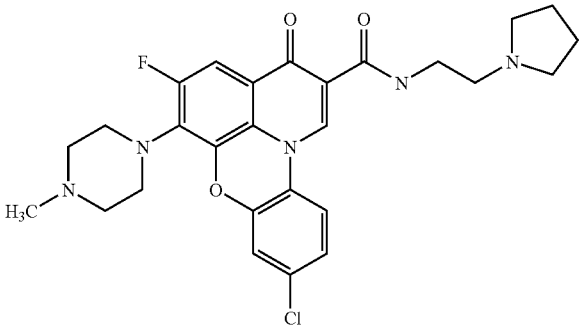 | 10 | | |
| 1818 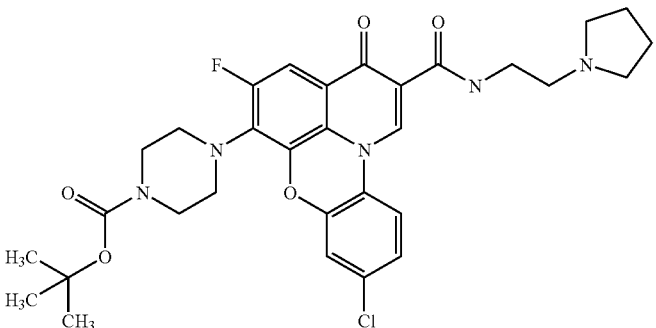 | 2.9 | 0.04 | |
| 1819 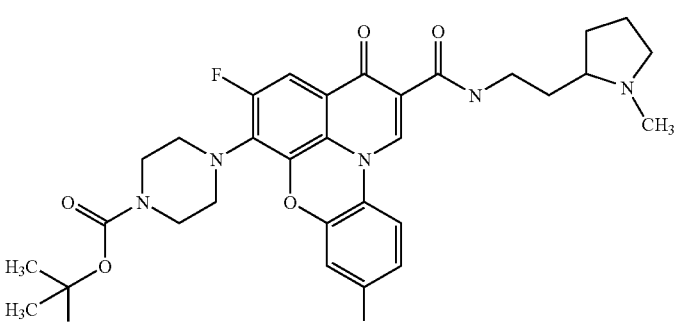 | 10 | | |
| 1820 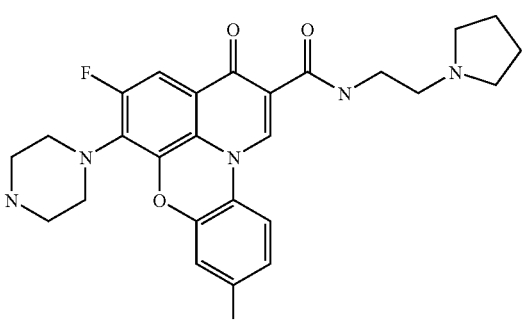 | 8.2 | 0.03 | |

TABLE 1D-continued

| Structure | S DATA μM | Hela MTS μM | HCT-116 |
|---|---|---|---|
| 1821 | 10 | | |
| 1822 | 10 | | |
| 1823 | 10 | | |
| 1824 | 9.4 | | |

TABLE 1D-continued
| Structure | S DATA μM | Hela MTS μM | HCT-116 |
|---|---|---|---|
| 1825 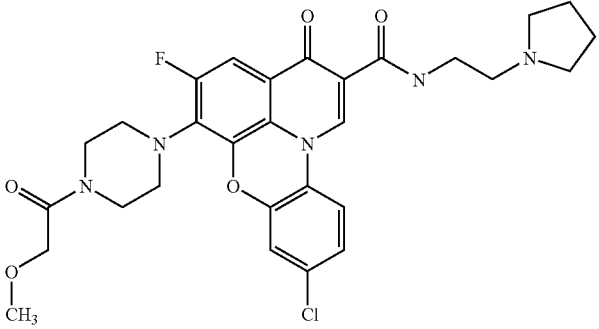 | 10 | | |
| 1826 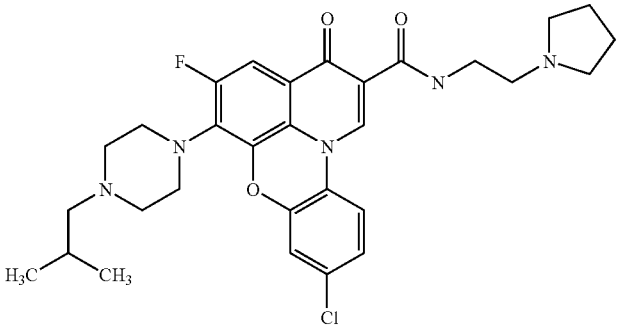 | 7.5 | | 0.03 |
| 1827 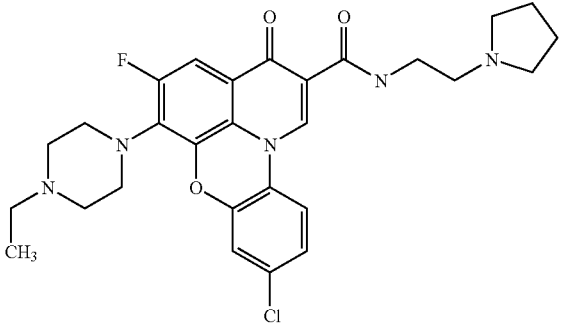 | 4.8 | | 0.01 |
| 1828 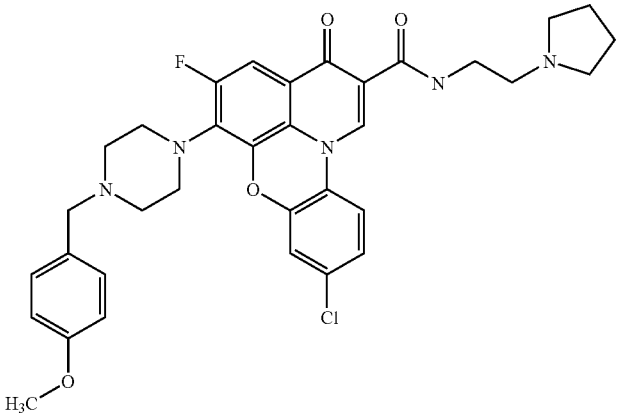 | 7.5 | | 0.1 |

TABLE 1D-continued

| Structure | S DATA μM | Hela MTS μM | HCT-116 |
|---|---|---|---|
| 1829 | | 10 | |
| 1830 | | 8.6 | |
| 1831 | | 9.8 | |
| 1832 | | 10 | |

TABLE 1D-continued

| Structure | S DATA µM | Hela MTS µM | HCT-116 |
|---|---|---|---|
| 1833 [fluoroquinolone-type structure with pyrrolidine, piperazine-pyrrole, chloro-phenoxazine] | | 10 | |

The compounds described herein may interact with regions of DNA that can form quadruplexes. Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders and quadruplex structures typically down-regulate oncogene expression. Examples of oncogenes include but are not limited to MYC, HIF, VEGF, ABL, TGF, PDGFA, MYB, SPARC, HER, VAV, RET, H-RAS, EGF, SRC, BCL1, BCL2, DHFR, HMGA, and other oncogenes known to one of skill in the art.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders.

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in Oncol./Hemotol. 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Compounds that interact with regions of DNA that can form quadruplexes also can be utilized to target cancer related processes and conditions, such as increased angiogenesis, by inhibiting angiogenesis in a subject.

The present invention provides a method for reducing cell proliferation or for treating or alleviating cell proliferative disorders, comprising contacting a system having a DNA capable of forming a quadruplex with a compound having formula 1, formula 1A, or formula 2. The system may be a group of cells or one or more tissues. In one embodiment, the system is a subject in need of a treatment of a cell proliferative disorder (e.g., a mammal such as a mouse, rat, monkey, or human).

The present invention also provides a method for treating or ameliorating a cancer associated with c-Myc overexpression, by administering a compound that interacts with a c-MYC quadruplex forming region to a subject in need thereof. Examples of cancers associated with c-Myc overexpression include but are not limited to colorectal cancer, prostate cancer, and pancreatic cancer. Furthermore, the present invention provides a method for inhibiting angiogenesis and optionally treating a cancer associated with angiogenesis, comprising administering a compound that interacts with a vascular endothelial growth factor (VEGF) quadruplex forming region to a subject in need thereof, thereby reducing angiogenesis and optionally treating a cancer associated with angiogenesis.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the +strand, occurring near the center of the viral duplex DNA, which is known to a play a role in the nuclear import of the PIC. Oligonucleotide mimics of the CDF have been shown to form intermolecular G-quadruplex structures in cell-free systems.

Thus, compounds that recognize quadruplex forming regions can be used to stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets, is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

The present invention provides a method for reducing a microbial titer in a system, comprising contacting a system having a native DNA quadruplex forming region with a compound having formula 1, formula 1A, or formula 2. The system may be one or more cells or tissues. Examples of microbial titers include but are not limited to viral, bacterial or fungal titers. In a particular embodiment, the system is a subject in need of a treatment for a viral infection (e.g., a mammal such as a mouse, rat, monkey, or human). Examples of viral infections include infections by a hepatitis virus (e.g., hepatitis B or C), human immunodeficiency virus (HIV), rhinovirus, herpes-zoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus. The present invention also provides a method for treating HIV infection by administering a compound having formula 1 to a subject in need thereof, thereby reducing the HIV infection.

Identifying Compounds that can Bind to Quadruplex Forming Regions of DNA

Compounds described herein are identified as compounds that can bind to quadruplex forming regions of DNA where a biological activity of this region, often expressed as a "signal," produced in a system containing the compound is different than the signal produced in a system not containing the compound. While background signals may be assessed each time a new molecule is probed by the assay, detecting the background signal is not required each time a new molecule is assayed.

Examples of quadruplex forming nucleic acid sequences are set forth in the following Table 2:

TABLE 2

| SEQUENCE | SEQ ID NO | ORIGIN |
| --- | --- | --- |
| $TG_4AG_3TG_4AG_3TG_4AAGG$ | 1 | CMYC |
| GGGGGGGGGGGGGCGGGGGCGGGGCGGGGGAGGGC | 2 | PDGFA |
| $G_8ACGCG_3AGCTG_5AG_3CTTG_4CCAG_3CG_4CGCTTAG_5$ | 3 | PDGFB/c-sis |
| AGGAAGGGGAGGGCCGGGGGGAGGTGGC | 4 | CABL |
| AGGGGCGGGGCGGGGCGGGGC | 5 | RET |
| GGGAGGAAGGGGCGGGAGCGGGGC | 6 | BCL-2 |
| GGGGGCGGGGCGGGCGCAGGGGAGGGGC | 7 | Cyclin D1/BCL-1 |
| CGGGGCGGGGCGGGGCGGGGC | 8 | H-RAS |

TABLE 2-continued

| SEQUENCE | SEQ ID NO | ORIGIN |
|---|---|---|
| AGAGGAGGAGGAGGTCACGGAGGAGGAGGAGAAGGAGGAGGAGGAA | 9 | CMYB |
| (GGA)$_4$ | 10 | VAV |
| AGAGAAGAGGGGAGGAGGAGGAGGAGAGGAGGAGGCGC | 11 | HMGA2 |
| GGAGGGGGAGGGG | 12 | CPIM |
| AGGAGAAGGAGGAGGTGGAGGAGGAGG | 13 | HER2/neu |
| AGGAGGAGGAGAATGCGAGGAGGAGGGAGGAGA | 14 | EGFR |
| GGGGCGGGCCGGGGCGGGGTCCCGGCGGGGCGGAG | 15 | VEGF |
| CGGGAGGAGGAGGAAGGAGGAAGCGCG | 16 | CSRC |

In addition to determining whether a test molecule or test nucleic acid gives rise to a different signal, the affinity of the interaction between the nucleic acid and the compound may be quantified. $IC_{50}$, $K_d$, or $K_i$ threshold values may be compared to the measured $IC_{50}$ or $K_d$ values for each interaction, and thereby identify a test molecule as a quadruplex interacting molecule or a test nucleic acid as a quadruplex forming nucleic acid. For example, $IC_{50}$ or $K_d$ threshold values of 10 µM or less, 1 µM or less, and 100 nM or less are often utilized. In another example, threshold values of 10 nM or less, 1 nM or less, 100 pM or less, and 10 pM or less may be utilized to identify quadruplex interacting molecules and quadruplex forming nucleic acids.

Many assays are available for identifying compounds that have affinity for quadruplex forming regions of DNA. In some of these assays, the biological activity is the quadruplex nucleic acid binding to a compound and binding is measured as a signal. In other assays, the biological activity is a polymerase arresting function of a quadruplex and the degree of arrest is measured as a decrease in a signal. In certain assays, the biological activity is transcription and transcription levels can be quantified as a signal. In another assay, the biological activity is cell death and the number of cells undergoing cell death is quantified. Another assay monitors proliferation rates of cancer cells. Examples of assays are fluorescence binding assays, gel mobility shift assays (see, e.g., Jin & Pike, *Mol. Endocrinol.* (1996) 10:196-205), polymerase arrest assays, transcription reporter assays, cancer cell proliferation assays, and apoptosis assays (see, e.g., Amersham Biosciences (Piscataway, N.J.)), and embodiments of such assays are described hereafter. Also, topoisomerase assays can be utilized to determine whether the quadruplex interacting molecules have a topoisomerase pathway activity (see, e.g., TopoGEN, Inc. (Columbus, Ohio)).

Gel Electrophoretic Mobility Shift Assay (EMSA)

An EMSA is useful for determining whether a nucleic acid forms a quadruplex and whether a nucleotide sequence is quadruplex-destabilizing. EMSA is conducted as described previously (Jin & Pike, *Mol. Endocrinol.* 10: 196-205 (1996)) with minor modifications. Generally, synthetic single-stranded oligonucleotides are labeled in the 5'-terminus with T4-kinase in the presence of [γ-$^{32}$P] ATP (1,000 mCi/mmol, Amersham Life Science) and purified through a sephadex column. $^{32}$P-labeled oligonucleotides (~30,000 cpm) are then incubated with or without various concentrations of a testing compound in 20 µl of a buffer containing 10 mM Tris pH 7.5, 100 mM KCl, 5 mM dithiothreitol, 0.1 mM EDTA, 5 mM $MgCl_2$, 10% glycerol, 0.05% Nonedit P-40, and 0.1 mg/ml of poly(dI-dC) (Pharmacia). After incubation for 20 minutes at room temperature, binding reactions are loaded on a 5% polyacrylamide gel in 0.25×Tris borate-EDTA buffer (0.25× TBE, 1×TBE is 89 mM Tris-borate, pH 8.0, 1 mM EDTA). The gel is dried and each band is quantified using a phosphoimager.

DMS Methylation Protection Assay

Chemical footprinting assays are useful for assessing quadruplex structure. Quadruplex structure is assessed by determining which nucleotides in a nucleic acid are protected or unprotected from chemical modification as a result of being inaccessible or accessible, respectively, to the modifying reagent. A DMS methylation assay is an example of a chemical footprinting assay. In such an assay, bands from EMSA are isolated and subjected to DMS-induced strand cleavage. Each band of interest is excised from an electrophoretic mobility shift gel and soaked in 100 mM KCl solution (300 µl) for 6 hours at 4° C. The solutions are filtered (microcentrifuge) and 30,000 cpm (per reaction) of DNA solution is diluted further with 100 mM KCl in 0.1×TE to a total volume of 70 µl (per reaction). Following the addition of 1 µl salmon sperm DNA (0.1 µg/µl), the reaction mixture is incubated with 1 µl DMS solution (DMS:ethanol; 4:1; v:v) for a period of time. Each reaction is quenched with 18 µl of stop buffer (b-mercaptoethanol:water:NaOAc (3 M); 1:6:7; v:v:v). Following ethanol precipitation (twice) and piperidine cleavage, the reactions are separated on a preparative gel (16%) and visualized on a phosphoimager.

Polymerase Arrest Assay

An arrest assay includes a template nucleic acid, which may comprise a quadruplex forming sequence, and a primer nucleic acid which hybridizes to the template nucleic acid 5' of the quadruplex-forming sequence. The primer is extended by a polymerase (e.g., Taq polymerase), which advances from the primer along the template nucleic acid. In this assay, a quadruplex structure can block or arrest the advance of the enzyme, leading to shorter transcription fragments. Also, the arrest assay may be conducted at a variety of temperatures, including 45° C. and 60° C., and at a variety of ion concentrations.

An example of the Taq polymerase stop assay is described in Han, et al., *Nucl. Acids Res.* (1999) 27:537-542, which is a modification of that used by Weitzmann, et al., *J. Biol. Chem.* (1996) 271:20958-20964. Briefly, a reaction mixture of template DNA (50 nM), Tris.HCl (50 mM), $MgCl_2$ (10 mM), DTT (0.5 mM), EDTA (0.1 mM), BSA (60 ng), and 5'-end-labeled quadruplex nucleic acid (~18 nM) is heated to 90° C. for 5 minutes and allowed to cool to ambient temperature over 30 minutes. Taq Polymerase (1 µl) is added to the reaction mixture, and the reaction is maintained at a constant temperature for 30 minutes. Following the addition of 10 µl stop buffer (formamide (20 ml), 1 M NaOH (200 µl), 0.5 M EDTA (400 µl), and 10 mg bromophenol blue), the reactions are separated on a preparative gel (12%) and visualized on a phosphoimager. Adenine sequencing (indicated by "A" at the top of the gel) is performed using double-stranded DNA Cycle Sequencing System from Life Technologies. The general sequence for the template strands is TCCAACTATG-TATAC (SEQ ID NO.19)-INSERT -TTAGCGACACG-CAATTGCTATAGTGAGTCGTATTA (SEQ ID NO.20), where "INSERT" refers to a nucleic acid sequence comprising a quadruplex forming sequence (See e.g., Table 2). Bands on the gel that exhibit slower mobility are indicative of quadruplex formation.

High Throughput Polymerase Arrest Assay

A high throughput polymerase arrest assay has been developed. The assay comprises contacting a template nucleic acid, often DNA, with a primer, which also is often DNA; contacting the primer/template complex with a compound described herein (also referred to as a "test compound"); contacting the primer/template complex with a polymerase; and separating reaction products. The assay often includes the step of denaturing the primer/template complex mixture and then renaturing the complex, which often is carried out before a test molecule is added to the system. Multiple assays often are carried out using varying concentrations of a test compound, such that an $IC_{50}$ value can be obtained, for example. The reaction products often include extended primers of different lengths. Where a test compound does not significantly interact with a quadruplex structure in the template, the primer often is extended to the end of the template.

Where a test compound significantly interacts with a quadruplex structure in the template, the primer often is extended only to the quadruplex structure in the template and no further. Thus, the reaction mixture often includes at least two reaction products when a test compound interacts with a quadruplex structure in the template, one having a completely extended primer and one having an incompletely extended primer, and these two reaction products are separated. The products may be separated using any convenient separation method, such as mass spectrometry and in one embodiment, capillary electrophoresis.

The reaction products often are identified by detecting a detectable label linked to the primer. The detectable label may be non-covalently linked to the 5' end of the primer (e.g., a biotin molecule covalently linked to the 5' end of the primer which is non-covalently linked to an avidin molecule joined to a detectable label). The detectable label may be joined to the primer at any stage of the assay, sometimes before the primer is added to the system, after the primer is extended, or after the products are separated. The detectable label often is covalently linked to the primer using a procedure selected based upon the nature of the chemical groups in the detectable label.

Many methods for covalently linking detectable labels to nucleic acids are available, such as chemically coupling an allylamine-derivatized nucleotide to a succinimidyl-ester derivative of a detectable label, and then generating a primer using the labeled nucleotide. (See, e.g., *Nature Biotech* (2000) 18:345-348 and http address info.med.yale.edu/genetics/ward/tavi/n-coupling.html). A spacer (often between 5-16 carbon atoms long) sometimes is incorporated between the detectable label and the nucleotide. Any convenient detectable label may be utilized, including but not limited to a radioactive isotope (e.g., $^{125}I$, $^{131}I$, $^{35}S$, $^{32}P$, $^{14}C$ or $^{3}H$); a light scattering label (e.g., a spherical gold or silver label; Genicon Sciences Corporation, San Diego, Calif. and U.S. Pat. No. 6,214,560); an enzymic or protein label (e.g., GFP or peroxidase); or another chromogenic label or dye sometimes is utilized. Often, a fluorescent label is utilized (e.g., aminomethyl coumarin (AMCA); diethyl aminomethyl coumarin (DEAC); cascade blue (CB); fluorescein isothiocyanate (FITC); Oregon green (OG); Alexa 488 (A488); rhodamine green (RGr); lanthanide chelate (e.g., europium), carboxyrhodamine 6G ($R^6G$); tetramethyl rhodamine (TAMRA); Texas Red (TxR); Cy3; Cy3.5; Cy5, Cy5.5 and carboxynaphtofluorescein (CNF), digoxigenin (DIG); and 2,4-dinitrophenyl (DNP)). Other fluorophores and attendant excitation and emission wavelengths are described in Anantha, et al., *Biochemistry* (1998) 37:2709-2714 and Qu & Chaires, *Methods Enzymol* (2000) 321:353-369).

In an embodiment, a primer oligonucleotide covalently linked to a fluorescent label is contacted with template DNA. The resulting complex is contacted with a test molecule and then contacted with a polymerase capable of extending the primer. The reaction products then are separated and detected by capillary electrophoresis. A longer primer sequence was used for practicing this embodiment as compared to embodiments where the primer includes no covalently-linked fluorophore or where capillary electrophoresis is not utilized for separation. Deoxynucleotides are added at any stage of the assay before the separation, often when the primer is contacted with the template DNA. The template DNA/primer complex often is denatured (e.g., by increasing the temperature of the system) and then renatured (e.g., by cooling the system) before a test compound is added).

Quadruplex Binding Assay

Generally, a 5'-fluorescent-labeled (FAM) primer (P45, 15 nM) was mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). In one example, the FAM-P45 primer (5'-6FAM-AGTCTGACTGACTGTACGTAGCTAATAC-GACTCACTATAG CAATT-3') (SEQ ID NO. 17) and the c-Myc template DNA (5'-TCCAACTATGTATACTGGGG AGGGTGGGGAGGGTGGGGAAGGTTAGC-GACACGCAATTGCTATAGTGAGTCGTATTAG CTACG-TACAGTCAGTCAGACT-3') (SEQ ID NO. 18) were synthesized and HPLC purified by Applied Biosystems. The mixture was denatured at 95° C. for 5 minutes and, after cooling down to room temperature, was incubated at 37° C. for 15 minutes.

After cooling down to room temperature, 1 mM KCl and the test compound (various concentrations) were added and the mixture incubated for 15 minutes at room temperature. The primer extension was performed by adding 10 mM KCl and Taq DNA Polymerase (2.5 U/reaction, Promega) and incubating at 70° C. for 30 minutes. The reaction was stopped by adding 1 µl of the reaction mixture to 10 µl Hi-Di Formamide mixed and 0.25 µl LIZ120 size standard. Hi-Di Formamide and LIZ120 size standard were purchased from Applied Biosystems. The method is repeated with the addition of various concentrations of competitor nucleic acids at the first step, along with the primer and template sequences. The G-quadruplex binding ligand is added at the concentration previously established to produce a 1:1 ratio of stop-product to full-length product. A CC50 for each nucleic acid competitor is defined as the concentration of competitor required to change the ratio of arrest product to full-length product from 1:1 to 1:2.

The partially extended quadruplex arrest product was between 61 or 62 bases long and the full-length extended product was 99 bases long. The products were separated and analyzed using capillary electrophoresis. Capillary electrophoresis was performed using an ABI PRISM 3100-Avant Genetic Analyzer. The assay was performed using compounds described above and results are shown in Table 1. µM concentrations reported in Table 1 are concentrations at which 50% of the DNA was arrested in the assay (i.e., the ratio of shorter partially extended DNA (arrested DNA) to full-length extended DNA is 1:1).

Transcription Reporter Assay

In a transcription reporter assay, test quadruplex DNA is coupled to a reporter system, such that a formation or stabilization of a quadruplex structure can modulate a reporter signal. An example of such a system is a reporter expression system in which a polypeptide, such as luciferase or green fluorescent protein (GFP), is expressed by a gene operably linked to the potential quadruplex forming nucleic acid and expression of the polypeptide can be detected. As used herein, the term "operably linked" refers to a nucleotide sequence which is regulated by a sequence comprising the potential quadruplex forming nucleic acid. A sequence may be operably linked when it is on the same nucleic acid as the quadruplex DNA, or on a different nucleic acid. An exemplary luciferase reporter system is described herein.

A luciferase promoter assay described in He, et al., *Science* (1998) 281:1509-1512 often is utilized for the study of quadruplex formation. Specifically, a vector utilized for the assay is set forth in reference 11 of the He, et al., document. In this assay, HeLa cells are transfected using the lipofectamin 2000-based system (Invitrogen) according to the manufacturer's protocol, using 0.1 µg of pRL-TK (*Renilla* luciferase reporter plasmid) and 0.9 µg of the quadruplex-forming plasmid. Firefly and *Renilla* luciferase activities are assayed using the Dual Luciferase Reporter Assay System (Promega) in a 96-well plate format according to the manufacturer's protocol.

Circular Dichroism Assay

Circular dichroism (CD) is utilized to determine whether another molecule interacts with a quadruplex nucleic acid. CD is particularly useful for determining whether a PNA or PNA-peptide conjugate hybridizes with a quadruplex nucleic acid in vitro. PNA probes are added to quadruplex DNA (5 µM each) in a buffer containing 10 mM potassium phosphate (pH 7.2) and 10 or 250 mM KCl at 37° C. and then allowed to stand for 5 minutes at the same temperature before recording spectra. CD spectra are recorded on a Jasco J-715 spectropolarimeter equipped with a thermoelectrically controlled single cell holder. CD intensity normally is detected between 220 nm and 320 nm and comparative spectra for quadruplex DNA alone, PNA alone, and quadruplex DNA with PNA are generated to determine the presence or absence of an inter-action (see, e.g., Datta, et al., *JACS* (2001) 123: 9612-9619). Spectra are arranged to represent the average of eight scans recorded at 100 nm/min.

Fluorescence Binding Assay

An example of a fluorescence binding assay is a system that includes a quadruplex nucleic acid, a signal molecule, and a test molecule. The signal molecule generates a fluorescent signal when bound to the quadruplex nucleic acid (e.g., N-methylmesoporphyrin IX (NMM)), and the signal is altered when a test compound competes with the signal molecule for binding to the quadruplex nucleic acid. An alteration in the signal when test molecule is present as compared to when test compound is not present identifies the test compound as a quadruplex interacting compound.

50 µl of quadruplex nucleic acid or a nucleic acid not capable of forming a quadruplex is added in 96-well plate. A test compound also is added in varying concentrations: A typical assay is carried out in 100 µl of 20 mM HEPES buffer, pH 7.0, 140 mM NaCl, and 100 mM KCl. 50 µl of the signal molecule NMM then is added for a final concentration of 3 µM. NMM is obtained from Frontier Scientific Inc, Logan, Utah. Fluorescence is measured at an excitation wavelength of 420 nm and an emission wavelength of 660 nm using a FluroStar 2000 fluorometer (BMG Labtechnologies, Durham, N.C.). Fluorescence often is plotted as a function of concentration of the test compound or quadruplex-targeted nucleic acid and maximum fluorescent signals for NMM are assessed in the absence of these molecules.

Cell Proliferation Assay

In a cancer cell proliferation assay, cell proliferation rates are assessed as a function of different concentrations of test compounds added to the cell culture medium. Any cancer cell type can be utilized in the assay. In one embodiment, colon cancer cells are cultured in vitro and test compounds are added to the culture medium at varying concentrations. A useful colon cancer cell line is colo320, which is a colon adenocarcinoma cell line deposited with the National Institutes of Health as accession number JCRB0225. Parameters for using such cells are available at the http address cell-bank.nihs.go.jp/cell/data/jcrb0225.htm.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Gerge, S. M., et al., "Pharmaceutical Salts," *J. Pharm. Sci.* (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to a mammalian host in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

Table 3 shows various formulations for use with compounds described herein. For example, the compound CX-3543 may be formulated having dosages from 10 mg/mL to 20 mg/mL solution, using the formulations herein. In Table 3, the designation "D5W" refers to deionized water with 5% dextrose. Each component in each formulation may be varied without affecting the activity of the compound. In one example, the compound is formulated in a solution comprising polyethylene glycol and propylene glycol in a buffer solution such as a phosphate buffer. The concentration of polyethylene glycol may be between 5% (w/w) and 10% (w/w); and the concentration of propylene glycol may be in between 6% (w/w) and 12% (w/w).

TABLE 3

| Formulations | % (w/w) | Compound (mL) + Placebo solution (mL) | pH of the Placebo solution | pH of the formulated solution (10 mg/mL) |
|---|---|---|---|---|
| 1. Mannitol | 4 | 35 ml + 35 mL | 6.1 | 6.1 |
| Sucrose | 0.5 | | | |
| 5% D5W solution | 95.5 | | | |
| 2. Mannitol | 4 | 35 ml + 35 mL | 6 | 5.8 |
| 50 mM PO$_4$ buffer, pH = 6.0 | 96 | | | |
| 3. Mannitol | 4 | 35 ml + 35 mL | 5 | 5 |
| 50 mM Citrate buffer, pH = 5.0 | 96 | | | |
| 4. Mannitol | 4 | 35 ml + 35 mL | 6 | 6 |
| 5% D5W | 96 | | | |
| 5. CX3543 (20 mg/mL) | 1 | 35 ml + 35 mL | 6.4 | 6.1 |
| 5% D5W | 99 | | | |
| 6. PEG 300 | 7 | 5 ml + 5 mL | N/A | 5.80 |
| Propylene glycol | 9 | | | |
| 5% D5W | 84 | | | |
| 7. PEG 300 | 7 | 5 ml + 5 mL | N/A | 5.8 |
| Propylene glycol | 9 | | | |
| 50 mM PO$_4$ buffer, pH = 6.0 | 84 | | | |
| 8. Mannitol | 4 | 5 ml + 5 mL | N/A | 5.7 |
| PEG 300 | 20 | | | |
| 50 mM PO$_4$ buffer, pH = 6.0 | 76 | | | |
| 9. Mannitol | 4 | 5 ml + 5 mL | N/A | 5.8 |
| Propylene glycol | 10 | | | |
| 50 mM PO$_4$ buffer, pH = 6.0 | 86 | | | |

The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

Dosages

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938, 949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e. the concentration of the test compound which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (199.4) 2:166-173). Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., *Analytical Chemistry* (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Antitumor Activity

In one embodiment, the compounds of the present invention utilizes a fluoroquinolone core having DNA recognition properties for targeting G-quadruplex DNA motif in the promoter regions of many well-characterized oncogenes. The compounds may be modified with various drug-like moieties to achieve desirable molecular recognition and ADMET properties, and to remove undesired activity against bacterial and eukaryotic enzymes.

In one example, a compound having formula 1A was designed to bind to a parallel-type quadruplex with significant molecular selectivity relative to other types of quadruplex conformations or other forms of DNA. CX-3543 selectively binds to the quadruplex structures that form in the promoter regions of several major oncogenes including VEGF, pDGF-A, HIF-1α, H-Ras, c-MYC and others. CX-3543 displays no significant inhibition of liver CYP450 enzymes, demonstrates metabolic stability with human hepatocytes, and is non-mutagenic in the Ames genotoxicity test. Moreover, CX-3543 displays favorable pharmacokinetic properties in mice, rats and dogs, and is well tolerated in murine xenograft models at doses substantially above those needed to demonstrate an antitumor effect. In in vivo tests, CX-3543 inhibits tumor growth in pancreatic cancer (MiaPaCa), refractory prostate cancer (PC-3), and colorectal cancer (HCT-116) xenograft models. Using protocols for p53, Caspase-3, Annexin and cell-cycle experiments, CX-3543 was also shown to induce apoptosis. Thus, the compounds described herein may be used against cancers, specifically in tumors driven by relevant oncogenes, including certain lymphomas and colorectal, renal, lung, prostate, ovarian, pancreatic and breast cancers.

The following examples are offered to illustrate but not to limit the invention.

EXAMPLES

The following are exemplary procedures for synthesizing substituted quinobenzoxazines analogs.

Example 1

Preparation of Substituted Quinobenzoxazine Analogs

The general synthetic scheme for the preparation of substituted quinobenzoxazines analogs is shown in Scheme 1.

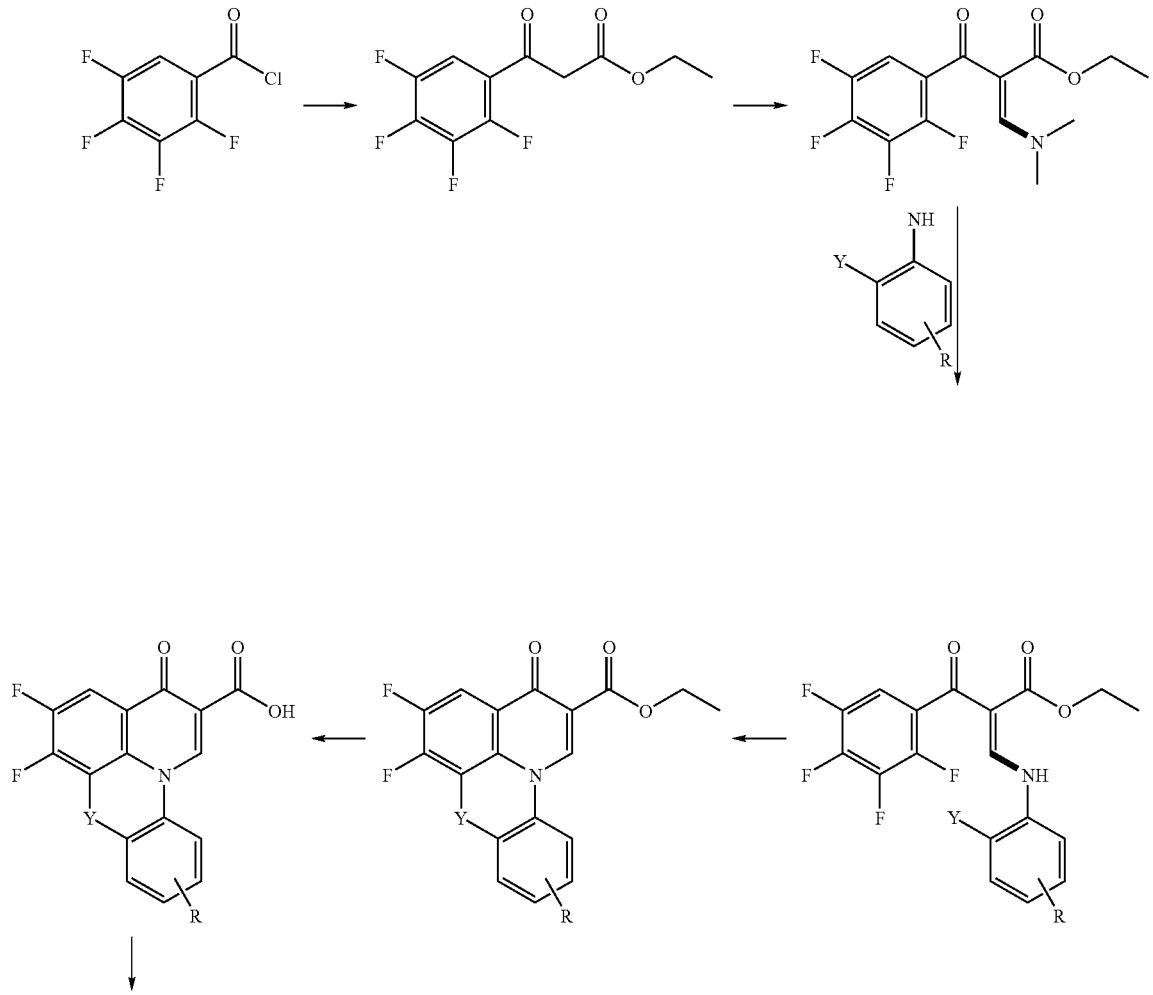

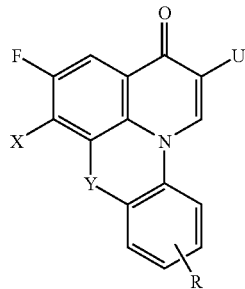

Ethyl-(2',3',4',5'-tetrafluorobenzoyl)-ethanoate

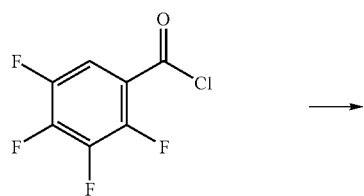

Potassium ethyl malonate (3.66 g, 21.5 mmol), MgCl$_2$ (2.44 g, 25.7 mmol) and TEA (2.05 g, 20.3 mmol) were mixed in acetonitrile (70 ml) at 10-15° C. for 2.5 hr. 2,3,4,5-tetrafluorobenzoyl chloride (2.00 g, 10.3 mmol) in acetonitrile (10 ml) was added at 0° C. over 15 min followed by a second addition of TEA (0.23 g, 2.3 mmol). After allowing to warm to RT, the mixture was stirred for 16 hr. After removal of volatiles in vacuo Toluene (30 ml) was added and removed in vacuo. Following the addition of toluene (60 ml), HCl 1.5 M (40 ml) was added cautiously, ensuring the temperature did not exceed 25° C. The organic fraction was washed with HCl 1.5 M (2×25 ml) and water (2×25 ml), dried over MgSO$_4$ and reduced to a light orange oil in vacuo ([M+1]$^+$ 265, 98%).

Ethyl-2-(2',3',4',5'-tetrafluorobenzoyl-)-3-(dimethylamino)-prop-2-enoate

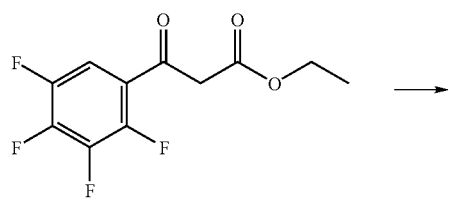

Dimethyl acetal dimethyl formamide (0.61 g, 5.1 mmol) was added dropwise to ethyl-(2',3',4',5'-tetrafluorobenzoyl)-ethanoate (0.9 g, 3.41 mmol) dissolved in acetic anhydride (2 ml), under argon. After 30 min solvent was removed in vacuo to leave the product as an orange oil in a quantitative yield ([M+1$^+$] 320).

Ethyl 1,2-Difluoro-4-oxo-4H-pyrido[3,2,1-kl]-8-phenyl-phenoxazine-5-carboxylate

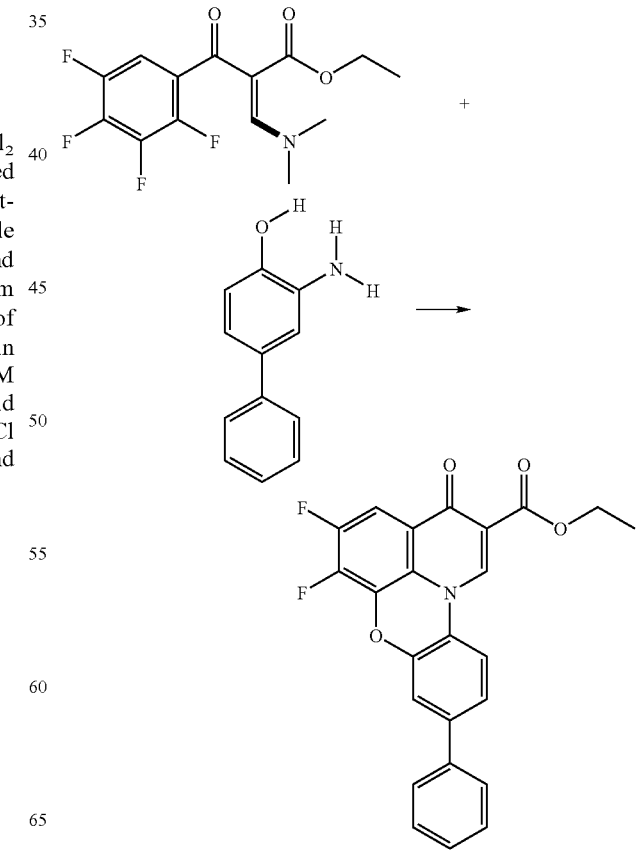

Ethyl-2-(2',3',4',5'-tetrafluorobenzoyl-)-3-(dimethylamino)-prop-2-enoate (3.4 g, 8.0 mmol) and 2-amino-4-phenyl-phenol (1.5 g, 8.0 mmol) in 20 DMSO (20 ml) was stirred under vacuum at 60° C. for 30 min. K2CO3 (5 g) and MeCN (20 ml) was added and the suspension was heated at 80° C. for 1 hr. After cooling to RT, the mixture was poured into a slight excess of dilute sulfuric acid and filtered. The product was recovered as a yellow-brown solid ([M+1]$^+$ 420, 65%).

Example 2

Preparation of 1,2-Difluoro-4-oxo-4H-pyrido[3,2,1-kl]-8-phenyl-phenoxazine-5-carboxylic acid

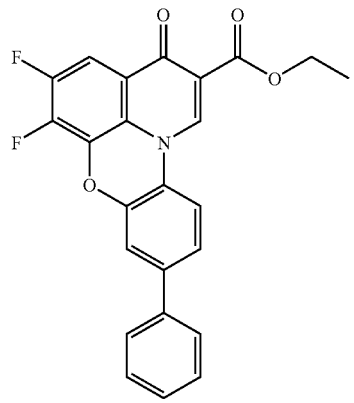

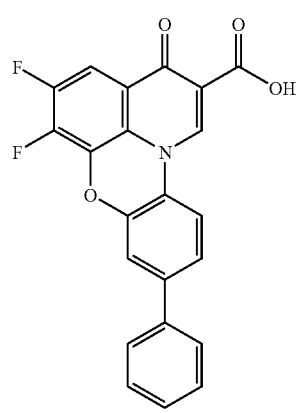

Ethyl 1,2-Difluoro-4-oxo-4H-pyrido[3,2,1-kl]-8-phenyl-phenoxazine-5-carboxylate (2.2 g, 5.3 mmol) was refluxed in a mixture of conc. HCl and acetic acid (20 ml each) for 2 hr. After cooling to room temperature cold water (40 ml) was added to the reaction mixture and the resulting precipitate filtered and washed with ether to afford the product as a yellow-brown solid 90% ([M+1]$^+$ 392).

Example 3

Preparation of Ethyl-2-(2',3',4',5'-tetrafluorobenzoyl-)-3-(napthyl-2'',3''-diamino)-prop-2-enoate

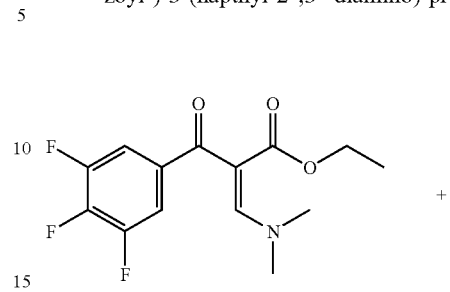

Ethyl-2-(2',3',4',5'-tetrafluorobenzoyl-)-3-(dimethylamino)-prop-2-enoate (10.53 g, 33 mmol) in acetonitrile (50 ml) was added to a solution of 2,3-diaminonapthalene (5.22 g, 33 mmol) in acetonitrile (150 ml), maintained at 50° C. under argon. After 3 hours, volatiles were removed in vacuo and the residue was subjected to chromatography over silica (15% EtOAc/Hexane) to yield the product as a yellow solid ([M+1]$^+$ 433) (55%).

Example 4

Preparation of Ethyl 1,2-Difluoro-4-oxo-4H-pyrido[3,2,1-kl]benzo[g]-phendiazine-5-carboxylate

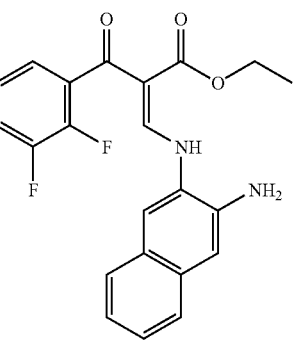

-continued

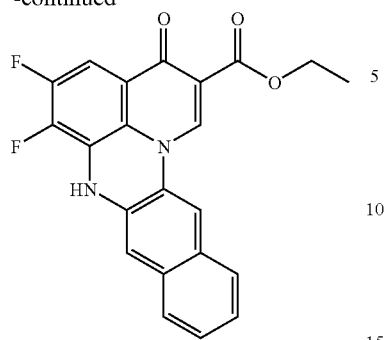

Ethyl-2-(2',3',4',5'-tetrafluorobenzoyl-)-3-(napthyl-2'', 3''diamino)-prop-2-enoate (600 mg 1.4 mmol) was dissolved in a slurry of K$_2$CO$_3$ in DMF (500 ml), The mixture was stirred vigorously at 100° C. for 1 hour, then allowed to cool to RT. The K$_2$CO$_3$ was removed by filtration and the DMF removed in vacuo to leave a yellow-brown solid in quantitative yield. ([M+1]$^+$ 393).

Example 5

Preparation of 1,2-Difluoro-4-oxo-4H-pyrido[3,2,1-kl]benzo[g]-phendiazine-5-carboxylic acid

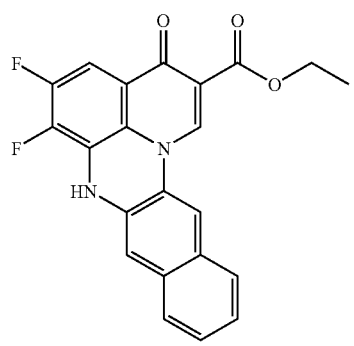

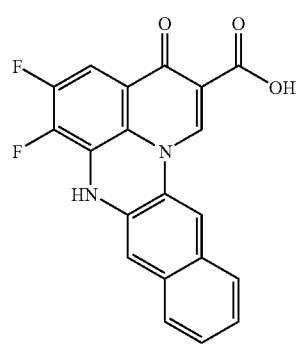

KOH solution (1N, 2.54 ml, 2.56 mmol) was added to a solution of ethyl 1,2-difluoro-4-oxo-4H-pyrido[3,2,1-kl]benzo[g]-phendiazine-5-carboxylate (500 mg, 1.28 mmol) in ethanol (400 ml), heated under reflux. After 2 hours the reaction mixture was allowed to cool to RT, then neutralized with HCl solution (1N). The product was collected by filtration as a yellow solid, 89%. ([M+1]+ 365).

Example 6

Preparation of Ethyl 1,2-Difluoro-4-oxo-4H-pyrido [3,2,1-kl]-phenthiazine-5-carboxylate Ethyl-2-(2',3',4',5'-tetrafluorobenzoyl-)-3-(N-aminobenzyldisulfide)-prop-2-enoate

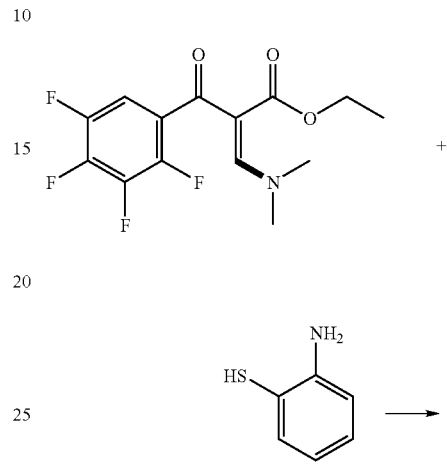

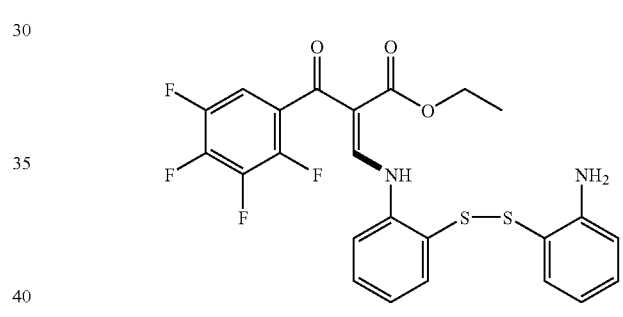

Ethyl-2-(2',3',4',5'-tetrafluorobenzoyl-)-3-(dimethylamino)-prop-2-enoate (17.7 g, 55.3 mmol) in acetonitrile (10 ml) was added to a solution of 1,2-aminothiophenol dimer (5.22 g, 33 mmol) in acetonitrile (100 ml). After 3 hours, volatiles were removed in vacuo and the residue was subjected to chromatography over silica (1% MeOH/DCM) to yield the product as a yellow solid ([M+1]+ 523) (50%).

Ethyl 1,2-Difluoro-4-oxo-4H-pyrido[3,2,1-kl]-phenthiazine-5-carboxylate

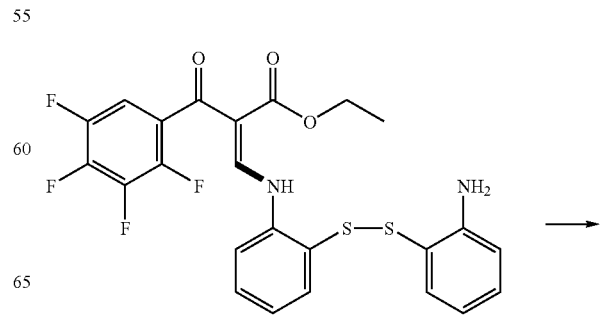

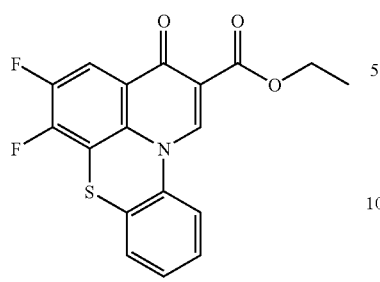

Ethyl-2-(2',3',4',5'-tetrafluorobenzoyl-)-3-(N-aminobenzyldisulfide)-prop-2-enoate (2.5 g 3.2 mmol) was dissolved in DMF (120 ml) and heated under reflux for six hours. Removal of DMF in vacuo gave the product as a yellow solid 90% ([M+1]+ 360).

Example 7

Preparation of 1,2-Difluoro-4-oxo-4H-pyrido[3,2,1-kl]-phenthiazine-5-carboxylic acid

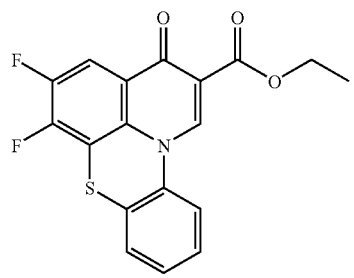

KOH solution (1N, 3.0, 3.0 mmol) was added to a solution of ethyl 1,2-difluoro-4-oxo-4H-pyrido[3,2,1-kl]-phenthiazine-5-carboxylate (1000 mg, 2.5 mmol) in ethanol (400 ml), heated under reflux. After 2 hours the reaction mixture was allowed to cool to RT, then neutralized with HCl solution (1N). The product was collected by filtration as a yellow solid, ([M+1]+ 332, 95%)

Example 8

Preparation of 5,6-Difluoro-9-hydroxy-3-oxo-3H-pyrido[3,2,1-kl]pyrimido[g]phenoxazine-2-carboxylic acid 7-nitroquinazoline-4,6-diol

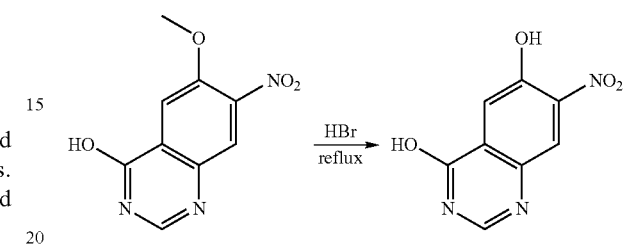

To a solution containing 20 ml of 48% aqueous HBr and 20 ml of AcOH was added 6-methoxy-7-nitro-3,4-dihydroquinazolin-4-one (1.4 g, 6.3 mmol) and the mixture was refluxed overnight. The resulting solution was evaporated to afford the crude phenol as a residue and was used without further purification (1.2 g, 5.8 mmol) (M+1, 208).

7-aminoquinazoline-4,6-diol

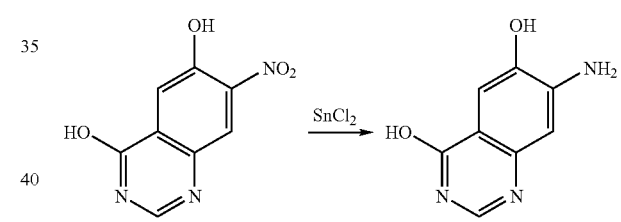

The crude product from above (1.0 g, 5.8 mmol) was diluted with 40 ml water and 3 g of Tin II chloride dihydrate was added and the reaction was stirred at room temperature. After 1 h the reaction was neutralized with K2CO3, and extracted with EtOAc (3×50 mL). The combined organic extracts were dried over sodium sulfate and the solvent was removed in vacuo to afford the crude amino alcohol (1.0 g, 5.6 mmol) (M+1, 178).

Ethyl; 5,6-difluoro-9-hydroxy-3-oxo-3H-pyrido[3,2,1-kl]pyrimido[g]phenoxazine-2-carboxylate

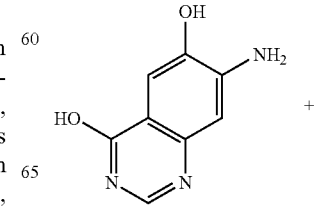 +

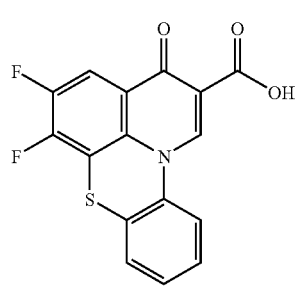

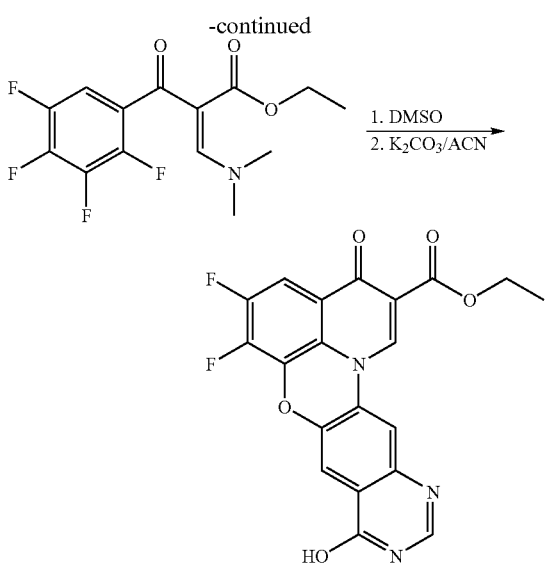

To a solution of the tetrafluoroenamine (2.2 g, 6.9 mmol) in DMSO (3 mL) was added the aminophenol (1.0 g, 5.6 mmol) and the reaction mixture was stirred under vacuum (rotary evaporator) at 60° C. for 20 minutes. The reaction mixture was allowed to cool to room temperature and was diluted with acetonitrile (200 mL) and potassium carbonate was added. The mixture was heated to reflux for 5 hours and poured into dilute HOAc/water. The solid product was collected by vacuum filtration and dried to afford the difluoroester as a tan solid (1.3 g, 3.2 mmol) (M+1, 412).

5,6-Difluoro-9-hydroxy-3-oxo-3H-pyrido[3,2,1-kl]pyrimido[g]phenoxazine-2-carboxylic acid

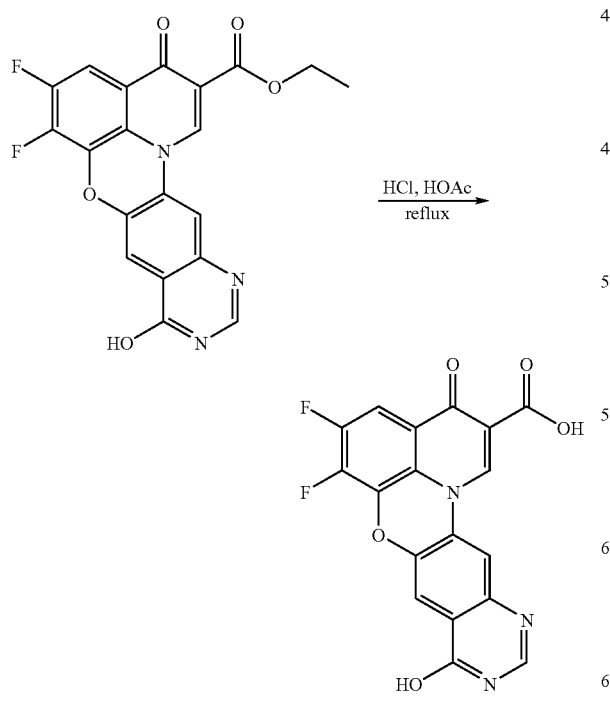

The difluoroester (1.3 g, 3.2 mmol) was dissolved in a 1:1 mixture of glacial acetic acid and 12 M HCl (20 mL) and refluxed for 30 min. The mixture was then cooled to room temperature and poured into water. The solid product was then collected by vacuum filtration and dried to afford the difluoroacid as a tan solid (0.98 g, 2.5 mmol) ([M+1]+ 392).

Example 9

Preparation of 2-(2-(Ethoxycarbonyl)-5,6-difluoro-3-oxo-3H-pyrido[3,2,1-kl]phenoxazin-9-yloxy)acetic acid Ethyl 5,6-difluoro-9-hydroxy-3-oxo-3H-pyrido[3,2,1-kl]phenoxazine-2-carboxylate

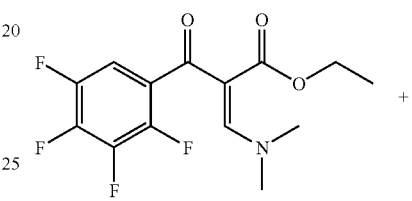

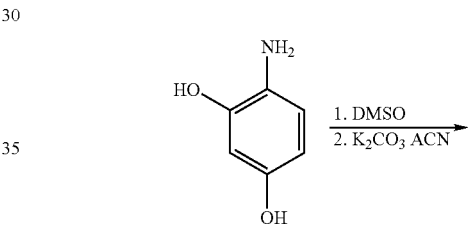

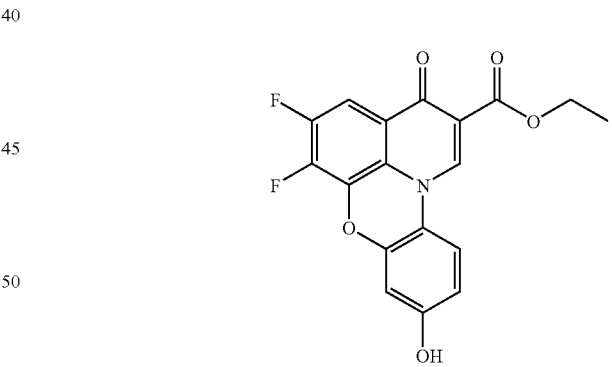

To a solution of the tetrafluoroenamine (5.8 g, 18.2 mmol), dissolved in DMSO (12 mL), was added 2,4-dihydroxyaniline hydrochloride (2.5 g, 15.5 mmol) and the mixture was heated to 60° C. under vacuum (rotary evaporator) for 20 minutes. The reaction mixture was then diluted with acetonitrile (100 mL) and potassium carbonate (3 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (5.0 g, 13.9 mmol) (M+1, 360).

941

2-(2-(Ethoxycarbonyl)-5,6-difluoro-3-oxo-3H-pyrido[3,2,1-kl]phenoxazin-9-yloxy)acetic acid

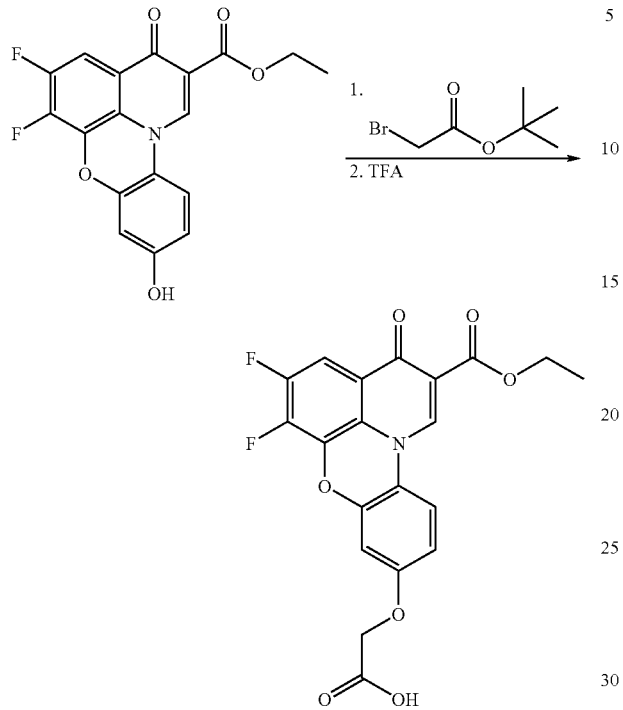

To a solution of the difluoroester (2.1 g, 5.8 mmol) and tert-butylbromoacetate (2.0 g, 10.3 mmol) in DMF (30 mL) was added potassium carbonate (2.0 g) and the mixture was heated to 60° C. for 1 hour. The reaction was allowed to cool and poured into water (500 mL) and extracted with ethyl acetate (3×100 mL),washed with brine, dried over magnesium sulfate and filtered over a pad of silica gel (30×50 mm), eluting with ethyl acetate. The solvent was removed in vacuo and the resulting material was triturated with hexanes and dried to afford the tert-butyl ester as a tan solid (2.8 g, 5.8 mmol). This material was dissolved in trifluoroacetic acid (40 mL) and stirred at room temperature for 30 minutes. The solvent was removed in vacuo to afford the acid as a tan solid (2.4 g, 5.7 mmol) (M+1, 418).

Example 10
Preparation of 9-(Carboxymethoxy)-5,6-difluoro-3-oxo-3H-pyrido[3,2,1-kl]phenoxazine-2-carboxylic acid

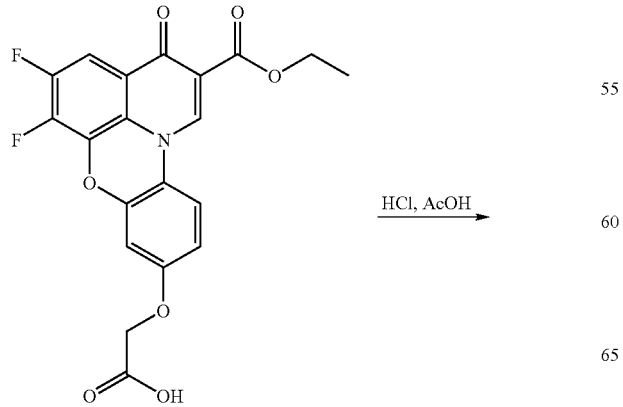

942

-continued

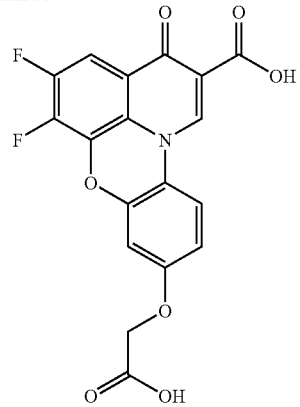

The difluoroester (2.4 g, 5.7 mmol) was dissolved in a 1:1 mixture of glacial acetic acid and 12 M HCl (40 mL) and refluxed for 1 hour. The mixture was then cooled to room temperature and poured into water. The solid product was then collected by vacuum filtration and dried to afford the difluoroacid as a tan solid (2.0 g, 5.1 mmol) (M+1, 390).

Example 11

Preparation of Ethyl 1,2,3-trifluoro-4-oxo-4H-pyrido[3,2,1-kl]benzo[g]-phenoxazine-5-carboxylate

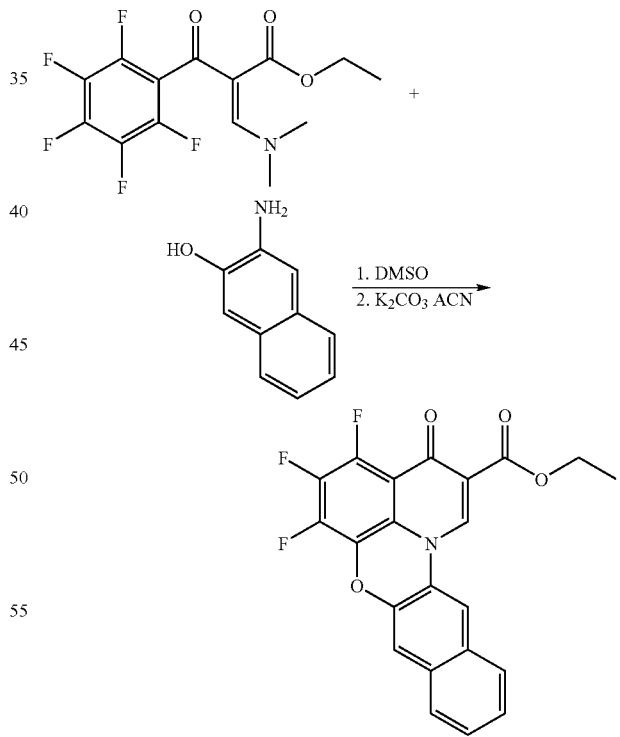

To a solution of pentafluoroenamine (8 g, 23.7 mmol), prepared by a similar procedure as for the tetrafluoroenamine dissolved in DMSO (12 mL) was added 3-amino-2-naphthol (3.5 g, 21.9 mmol) and the mixture was heated to 60° C. under vacuum (rotary evaporator) for 2 hours. The reaction mixture was then diluted with acetonitrile (200 mL) and potassium carbonate (8.0 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (1.3 g, 3.2 mmol) (M+1, 412).

Example 12

Preparation of 1,2,3-Trifluoro-4-oxo-4H-pyrido[3,2,1-kl]benzo[g]-phenoxazine-5-carboxylic acid

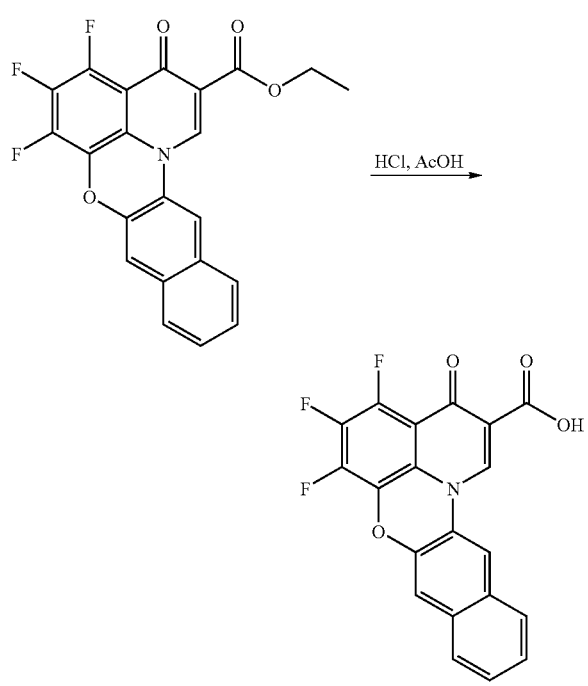

The trifluoroester (1.3 g, 3.2 mmol) was dissolved in acetic acid (5 mL) and 12 M HCl was added (5 mL) and the reaction mixture was heated to reflux for 2 hours. The mixture was then cooled to room temperature, poured into water and the solid product was collected by vacuum filtration and dried to afford the trifluoroacid as a pale solid (1.0 g, 2.6 mmol) (M+1, 384).

Example 13

Preparation of Ethyl 1,2-difluoro-4-oxo-4H-pyrido[3,2,1-kl]benzo[g]-phenoxazine-5-carboxylate

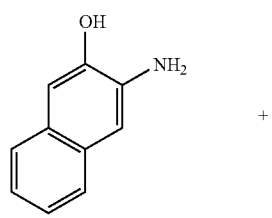

+

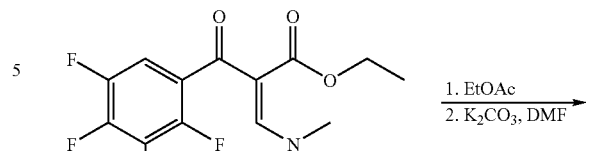

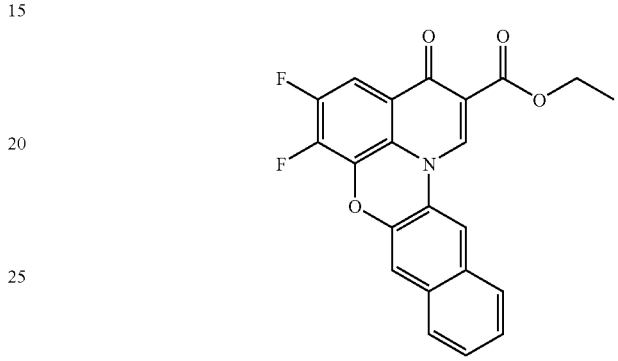

To a solution of the enamine (30 g, 94 mmol) in ethyl acetate (100 mL) was added 3-amino-2-naphthol (10 g, 63 mmol) at room temperature and the mixture was immediately placed on a rotary evaporator and the solvent was removed over 2 hours at a temperature below 0° C. (ice formed on the flask) to produce a yellow solid. To this solid was added ether (200 mL) and the slurry was filtered to afford a yellow solid. This solid was then dissolved in DMF (200 mL) and potassium carbonate was added (16.5 g, 120 mmol) and the mixture was heated to 90° C. for 1 hour. The mixture was allowed to cool to room temperature and water was added (500 mL) and the resulting solid was filtered, washed with water and dried to afford the difluoroester as a tan solid (12.2 g, 30.8 mmol) (M+1, 394).

Example 14

Preparation of 1,2-Difluoro-4-oxo-4H-pyrido[3,2,1-kl]benzo[g]-phenoxazine-5-carboxylic acid

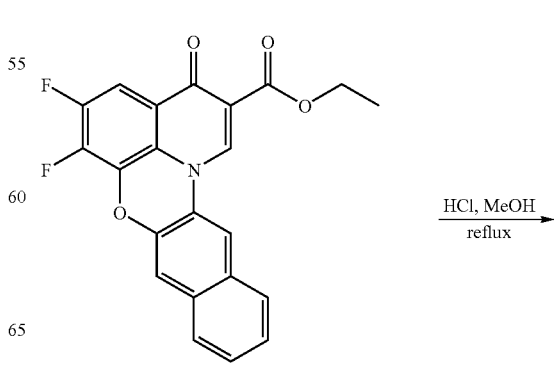

-continued

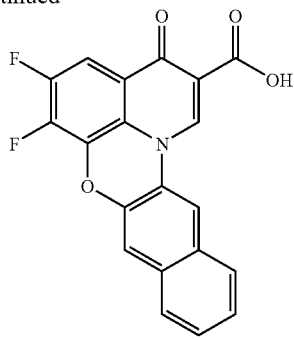

The difluoroester (5 g, 12.7 mmol) was dissolved in methanol (50 mL) and conc HCl was added (20 mL) and the mixture was refluxed for 12 hours. The mixture was allowed to cool to room temperature and the solid was collected by vacuum filtration, washing with methanol to afford the difluoroacid as a light tan powder (3.6 g, 9.9 mmol) (M+1, 366).

Example 15

Preparation of Ethyl 1-fluoro-4-oxo-4H-pyrido[3,2,1-kl]benzo[g]-phenoxazine-5-carboxylate

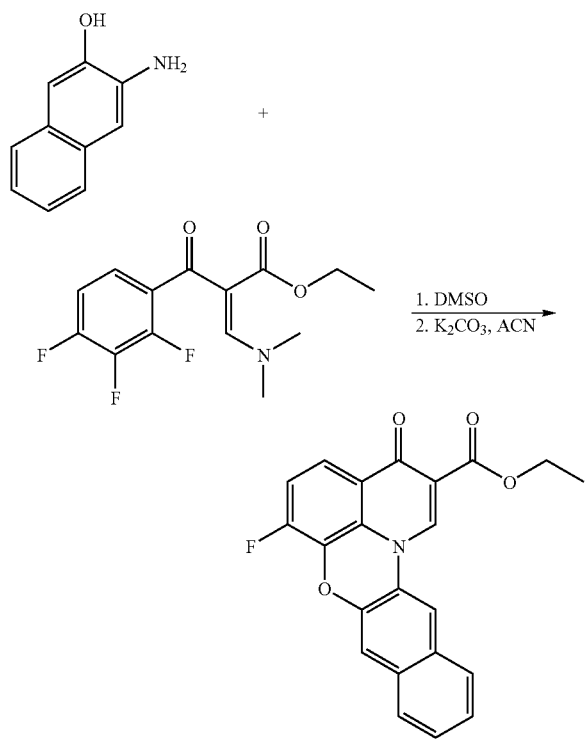

To a solution of the enamine, similarly prepared as the tetrafluoroenamine (14 g, 46.3 mmol) in ethyl acetate (100 mL) was added 3-Amino-2-naphthol (5.0 g, 31.2 mmol) at room temperature and the mixture was immediately placed on a rotary evaporator and the solvent was removed over 2 hours at a temperature below 0° C. (ice formed on the flask) to produce a yellow solid. To this solid was added methanol (200 mL) and the slurry was filtered to afford a yellow solid. This solid was then dissolved in acetonitrile (200 mL) and potassium carbonate was added (10.0 g, 72.5 mmol) and the mixture was heated to 80° C. for 1 hour. The mixture was allowed to cool to room temperature and water was added (500 mL) and the resulting solid was filtered, washed with water and dried to afford the fluoroester as a tan solid (6.0 g, 16.0 mmol) (M+1, 376).

Example 16

Preparation of 1-Fluoro-4-oxo-4H-pyrido[3,2,1-kl]benzo[g]-phenoxazine-5-carboxylic acid

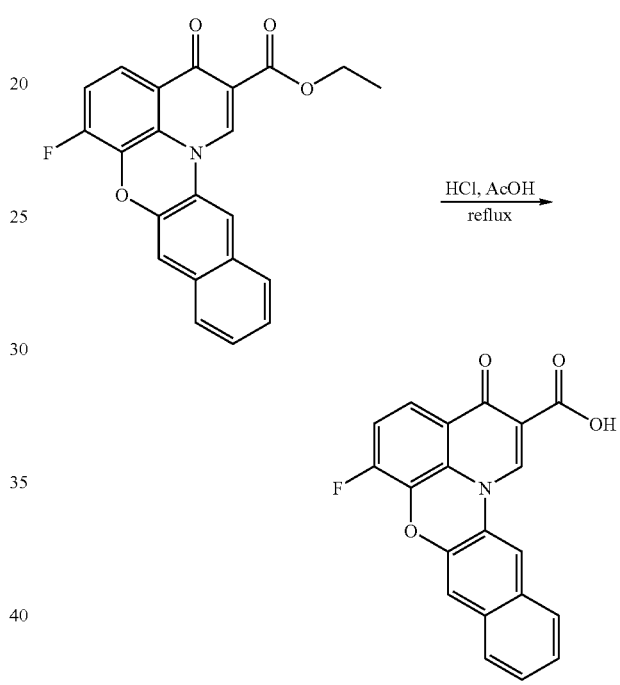

The fluoroester (6.0 g, 16.0 mmol) was dissolved in acetic acid (10 mL) and 12 M HCl was added (10 mL) and the reaction mixture was heated to reflux for 2 hours. The mixture was then cooled to room temperature, poured into water and the solid product was collected by vacuum filtration and dried to afford the fluoroacid as a pale solid (4.8 g, 13.8 mmol) (M+1, 348).

Example 17

Preparation of Ethyl 9-chloro-5,6-difluoro-3-oxo-3H-pyrido[3,2,1-kl]phenoxazine-2-carboxylate

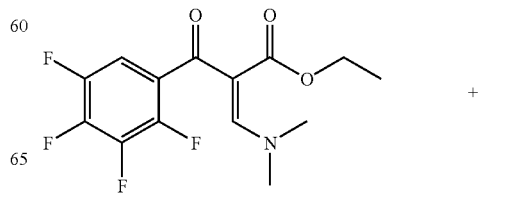

-continued

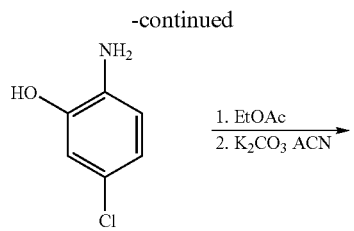

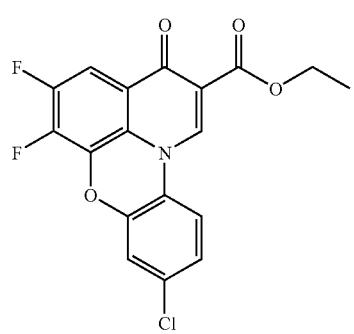

To a solution of the enamine (14.4 g, 45.3 mmol) in ethyl acetate (200 mL) was added 5-chloro-2-aminophenol (5.0 g, 34.8 mmol) and the solvent was removed in vacuo with a rotary evaporator over 2 hours without heating. Methanol was added and the resulting phenolic enamine was isolated by vacuum filtration. The resulting solid (7.0 g) was dissolved in acetonitrile and potassium carbonate was added and the resulting mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 378).

Example 18

Preparation of 9-Chloro-5,6-difluoro-3-oxo-3H-pyrido[3,2,1-kl]phenoxazine-2-carboxylic acid

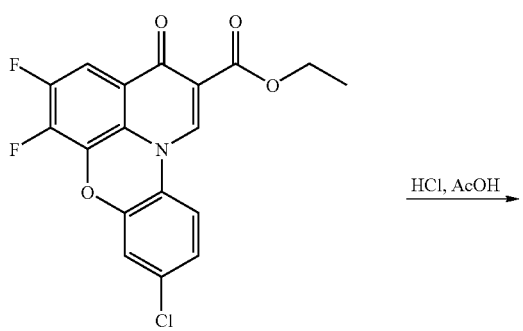

-continued

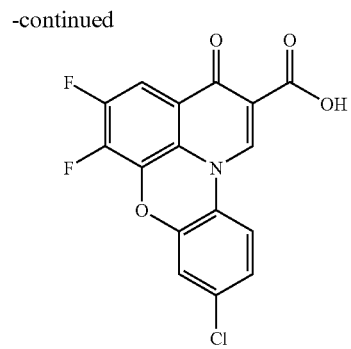

The difluoroester (5.0 g, 13.3 mmol) was dissolved in acetic acid (45 mL) and 12 M HCl was added (30 mL) and the reaction mixture was heated to reflux for 2 hours. The mixture was then cooled to room temperature, poured into water and the solid product was collected by vacuum filtration and dried to afford the difluoroacid as a pale solid (4.0 g, 10.6 mmol) (M+1, 350).

Example 19

Preparation of Ethyl 10-chloro-5,6-difluoro-3-oxo-3H-pyrido[3,2,1-kl]phenoxazine-2-carboxylate

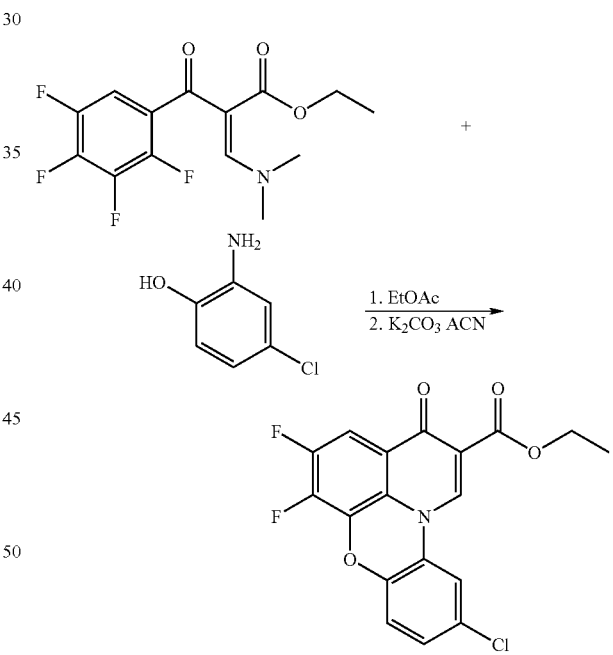

To a solution of the enamine (14.4 g, 45.3 mmol) in ethyl acetate (200 mL) was added 4-chloro-2-aminophenol (5.0 g, 34.8 mmol) and the solvent was removed in vacuo with a rotary evaporator over 2 hours without heating. Methanol was added and the resulting phenolic enamine was isolated by vacuum filtration. The resulting solid (7.5 g) was dissolved in acetonitrile and potassium carbonate was added and the resulting mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 378).

Example 20

Preparation of 10-Chloro-5,6-difluoro-3-oxo-3H-pyrido[3,2,1-kl]phenoxazine-2-carboxylic acid

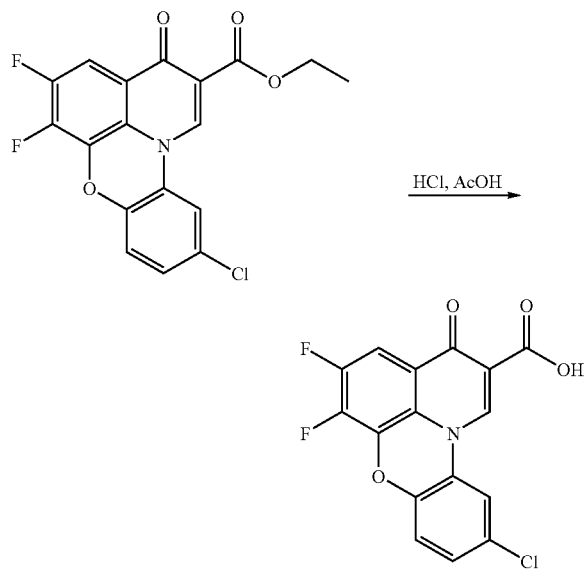

The difluoroester (2.5 g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (2.0 g, 5.3 mmol) (M+1, 350).

Example 21

Preparation of Ethyl 5,6-Difluoro-3-oxo-3H-pyrido[3,2,1-kl]phenoxazine-2-carboxylate

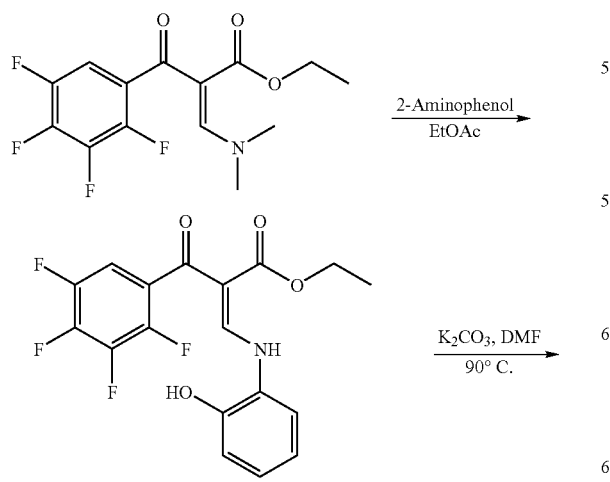

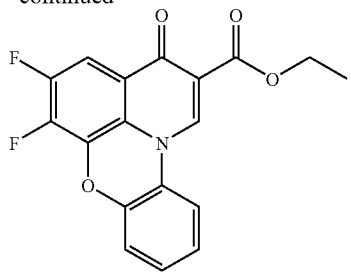

To a solution of the enamine (5.7 g, 17.9 mmol) in ethyl acetate (50 mL) was added 2-aminophenol (1.9 g, 17.43 mmol) at room temperature and the mixture was immediately placed on a rotary evaporator and the solvent was removed over 2 hours at a temperature below 0° C. (ice formed on the flask) to produce a yellow solid. To this solid was added ether (25 mL) and the slurry was filtered to afford a yellow solid. This solid was then dissolved in DMF (20 mL) and potassium carbonate was added (2.9 g, 21 mmol) and the mixture was heated to 90° C. for 1 hour. The mixture was allowed to cool to room temperature and water was added (200 mL) and the resulting solid was filtered, washed with water and dried to afford the phenoxazine as a tan solid (2.9 g, 8.45 mmol) (M+1, 344).

Example 22

Preparation of 5,6-Difluoro-3-oxo-3H-pyrido[3,2,1-kl]phenoxazine-2-carboxylic acid

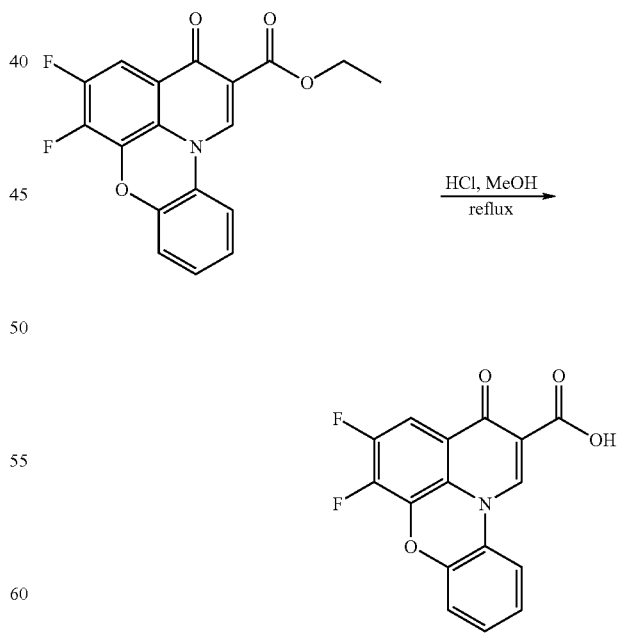

The difluoroester (5.0 g, 14 mmol) was dissolved in methanol (50 mL) and conc HCl was added (20 mL) and the mixture was refluxed for 2 hours. The mixture was allowed to cool to room temperature and the solid was collected by vacuum filtration, washing with methanol to afford the difluoroacid as a light tan powder (4.2 g, 13.3 mmol, 91%) (M+1,316).

Example 23

Preparation of Ethyl 1,2-Difluoro-4-oxo-4H-pyrido[3,2,1-kl]benzo[h]-phenoxazine-5-carboxylate

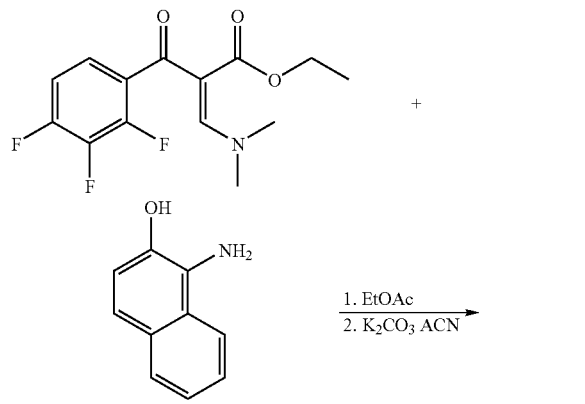

To a solution of the enamine (14.0 g, 45.3 mmol) in ethyl acetate (200 mL) was added 1-amino-2-naphthol (5.0 g, 31.3 mmol) and the solvent was removed in vacuo with a rotary evaporator over 2 hours without heating. Methanol was added and the resulting phenolic enamine was isolated by vacuum filtration. The solid was dissolved in acetonitrile and potassium carbonate (10 g) was added and the mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 376).

Example 24

Preparation of 1,2-Difluoro-4-oxo-4H-pyrido[3,2,1-kl]benzo[h]-phenoxazine-5-carboxylic acid

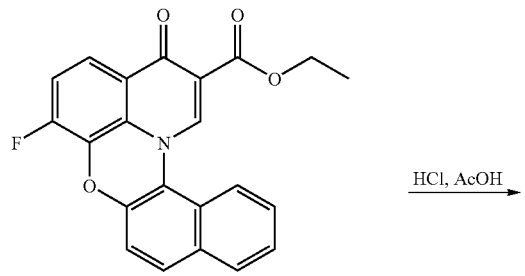

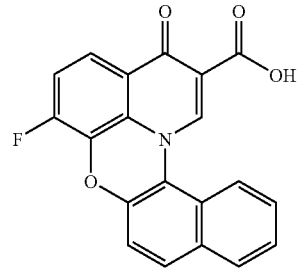

The difluoroester (5.5 g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (5.0 g, 14.4 mmol) (M+1, 348).

Example 25

Preparation of Ethyl 1,2-Difluoro-4-oxo-4H-pyrido[3,2,1-kl]benzo[f]-phenoxazine-5-carboxylate

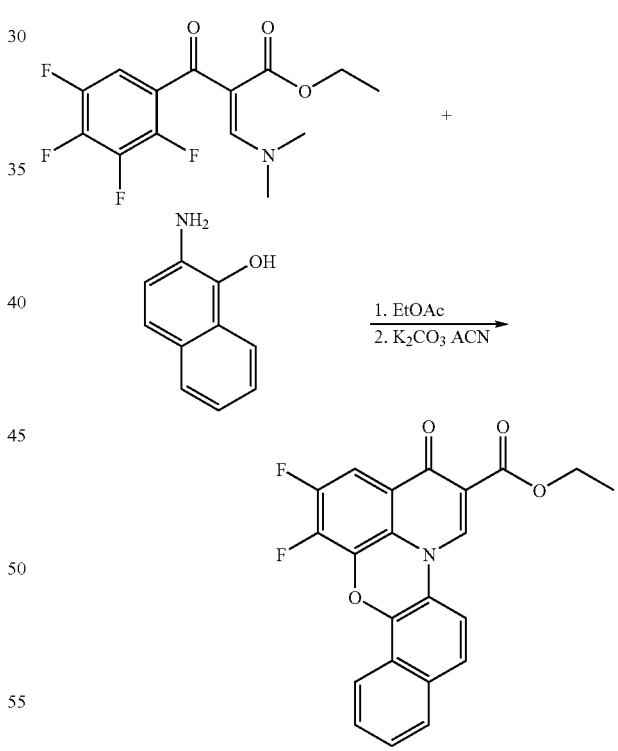

To a solution of the enamine (45 g, 141 mmol) in ethyl acetate (500 mL) was added 2-amino-1-naphthol (15.0 g, 93.8 mmol) and the solvent was removed in vacuo with a rotary evaporator over 2 hours without heating. Methanol was added and the phenolic enamine was isolated by vacuum filtration. The resulting solid was dissolved in acetonitrile (400 mL) and potassium carbonate (25 g) was added and the mixture was heated to reflux for 2.5 hours. The mixture was then allowed to cool to room temperature and poured into

Example 26

Preparation of 1,2-Difluoro-4-oxo-4H-pyrido[3,2,1-kl]benzo[f]-phenoxazine-5-carboxylic acid

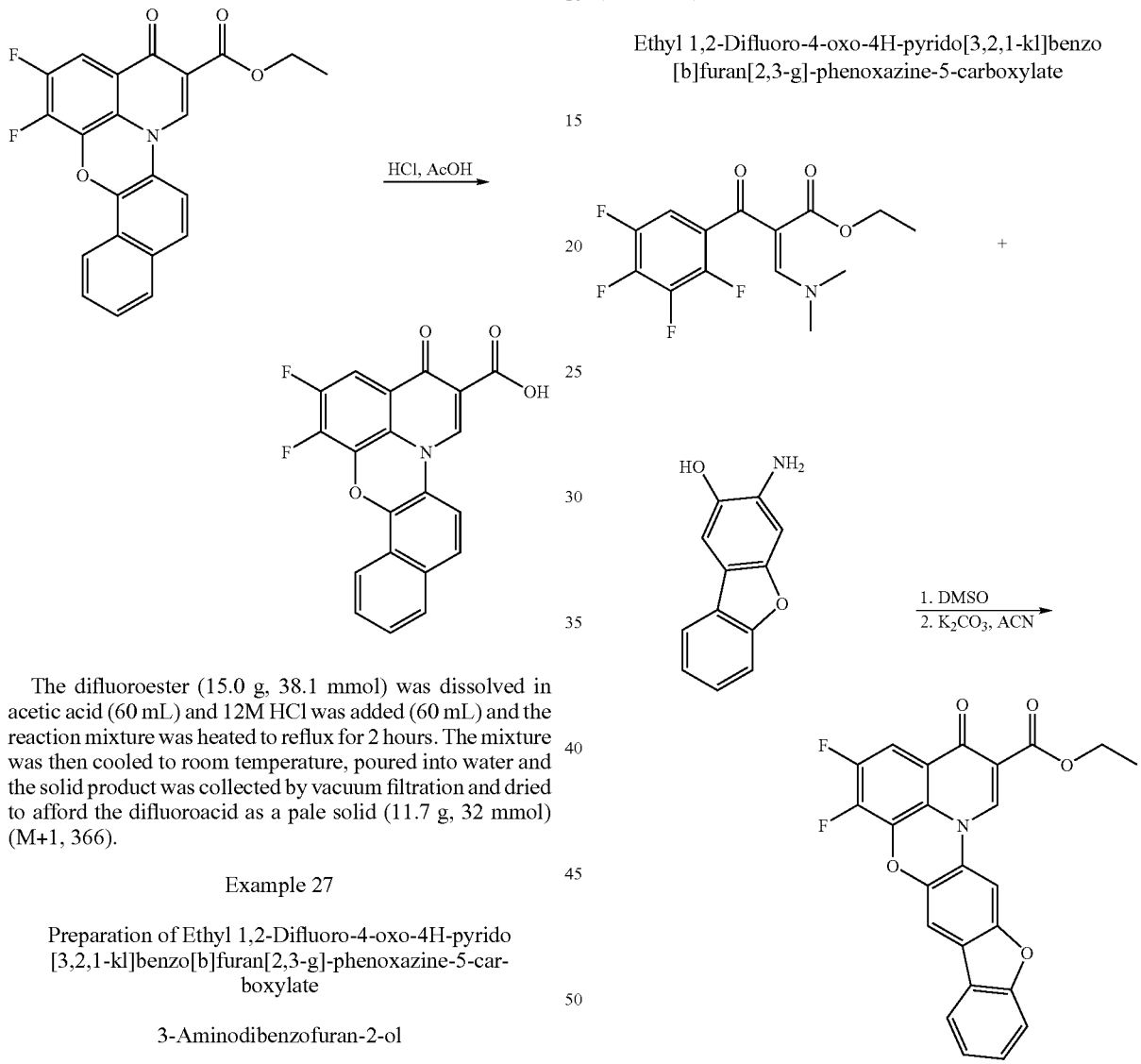

The difluoroester (15.0 g, 38.1 mmol) was dissolved in acetic acid (60 mL) and 12M HCl was added (60 mL) and the reaction mixture was heated to reflux for 2 hours. The mixture was then cooled to room temperature, poured into water and the solid product was collected by vacuum filtration and dried to afford the difluoroacid as a pale solid (11.7 g, 32 mmol) (M+1, 366).

Example 27

Preparation of Ethyl 1,2-Difluoro-4-oxo-4H-pyrido[3,2,1-kl]benzo[b]furan[2,3-g]-phenoxazine-5-carboxylate 3-Aminodibenzofuran-2-ol

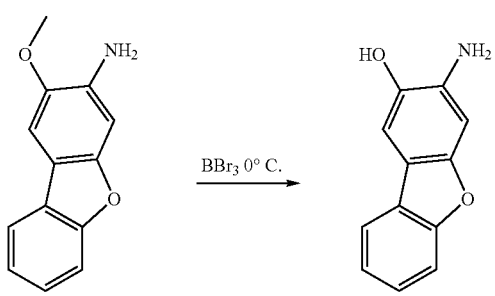

Dilute HCl. The resulting solid was collected by vacuum filtration and dried to afford the difluoroester as a pale yellow solid (19.69 g, 50.1 mmol) (M+1, 394).

To a solution of the dibenzofuran (15 g, 70.4 mmol) dissolved in methylene chloride (500 mL) at 0° C. was added BBr$_3$ (200 mL, 1 M in CH$_2$Cl$_2$) via addition funnel. After the addition was complete, the mixture was allowed to come to room temperature over 1 hour and then quenched with water followed by potassium carbonate (40 g). The resulting solid was recovered by vacuum filtration and dried to afford the hydroxyldibenzofuran as a white solid (13.2 g, 199 mmol) (M+1, 200).

Ethyl 1,2-Difluoro-4-oxo-4H-pyrido[3,2,1-kl]benzo[b]furan[2,3-g]-phenoxazine-5-carboxylate To a solution of the tetrafluoroenamine (15.0 g, 47 mmol) dissolved in DMSO (30 mL) was added the hydroxyl dibenzofuran (12.0 g, 60 mmol) and the mixture was heated to 60° C. under vacuum (rotary evaporator) for 20 minutes. The reaction mixture was then diluted with acetonitrile (200 mL) and potassium carbonate (17 g) was added and the mixture was refluxed for 2.5 hours. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (15.0 g, 34.6 mmol) (M+1, 434).

Example 28

Preparation of 1,2-Difluoro-4-oxo-4H-pyrido[3,2,1-kl]benzo[b]furan[2,3-g]-phenoxazine-5-carboxylic acid

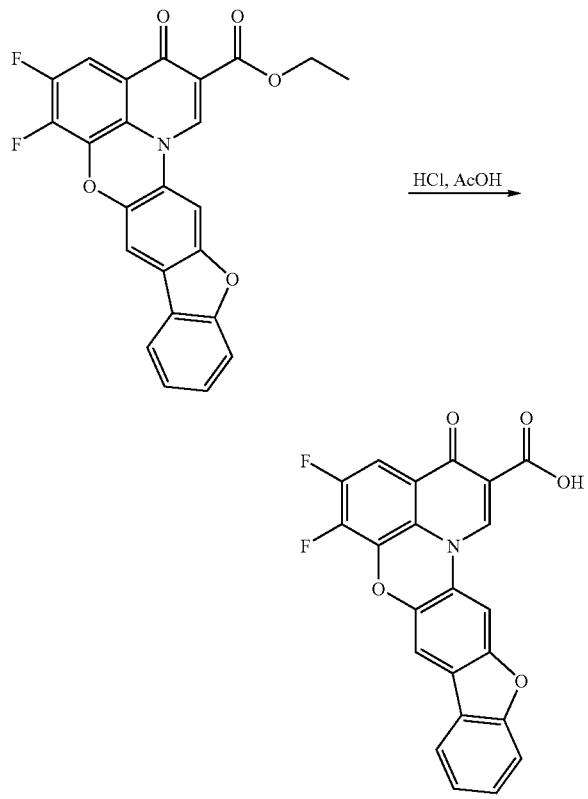

The difluoroester (15.0 g, 34.6 mmol) was dissolved in acetic acid (60 mL) and 12 M HCl was added (60 mL) and the reaction mixture was heated to reflux for 2 hours. The mixture was then cooled to room temperature, poured into water and the solid product was collected by vacuum filtration and dried to afford the difluoroacid as a pale solid (13.7 g, 34 mmol) (M+1, 406).

Example 29

Preparation of Ethyl 2-(ethoxycarbonyl)-5,6-difluoro-3-oxo-3H-pyrido[3,2,1-kl]phenoxazine-10-carboxylate

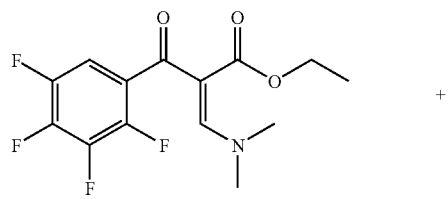

+

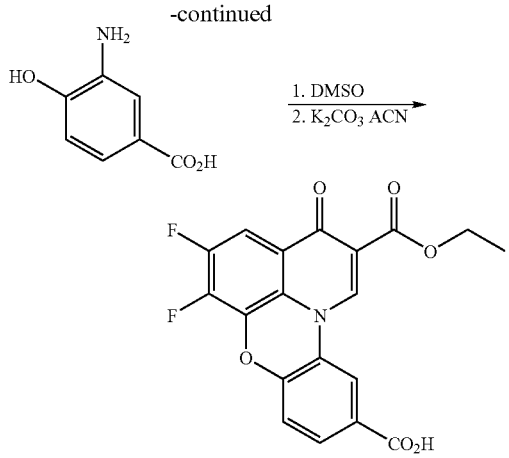

To a solution of the tetrafluoroenamine (7.0 g, 21.9 mmol) dissolved in DMSO (25 mL) was added 4-hydroxy-3-amino benzoic acid (3.0 g, 19.6 mmol) and the mixture was heated to 60° C. under vacuum (rotary evaporator) for 2 hours. The reaction mixture was then diluted with acetonitrile (200 mL) and potassium carbonate (8.0 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (6.2 g, 16.0 mmol) (M+1, 388).

Example 30

Preparation of 2-(Ethoxycarbonyl)-5,6-difluoro-3-oxo-3H-pyrido[3,2,1-kl]phenoxazine-10-carboxylic acid

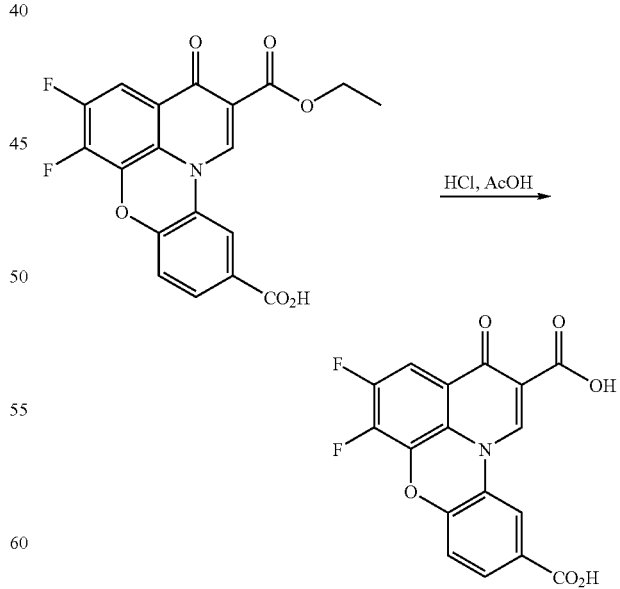

The difluoroester (6.2, 16.0 mmol g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluorodi-acid as a pale solid (5.3 g, 14.8 mmol) (M+1, 360).

Example 31

Preparation of Ethyl 5.6-difluoro-10-nitro-3-oxo-3H-pyrido[3,2,1-kl]phenoxazine-2-carboxylate

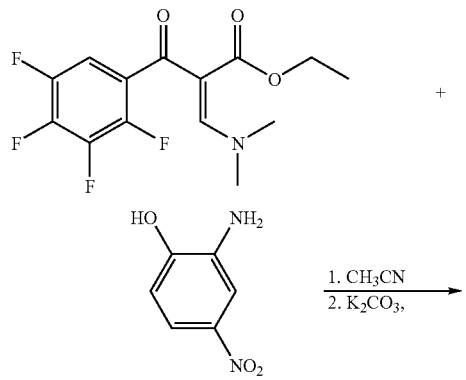

A solution of the enamine (6.0 g, 18.7 mmol) and 2-amino-4-nitrophenol (3.5 g, 23.3 mmol) in acetonitrile was heated to 80° C. for 15 minutes. Potassium carbonate was then added (8.0 g) and the mixture was heated to reflux overnight. The reaction mixture was then filtered hot and the solvent was removed in vacuo to afford the crude nitroester (5.0 g, 12.8 mmol) (M+1, 389).

Example 32

Preparation of 5,6-Difluoro-10-nitro-3-oxo-3H-pyrido[3,2,1-kl]phenoxazine-2-carboxylic acid

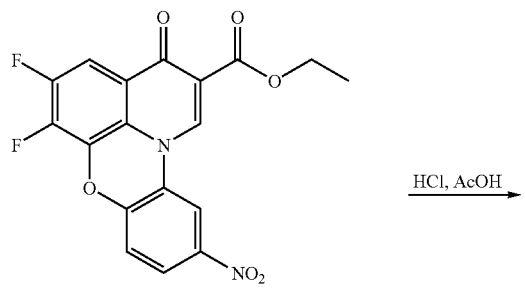

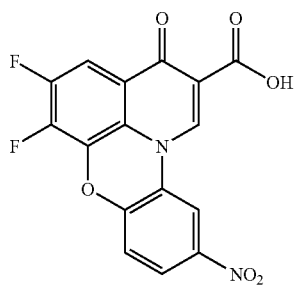

The crude difluoroester (5.0 g, 12.8 mmol) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (2.0 g, 5.5 mmol) (M+1, 361).

Example 33

Preparation of Ethyl 5,6-difluoro-3-oxo-10-phenyl-3H-pyrido[3,2,1-kl]phenoxazine-2-carboxylate

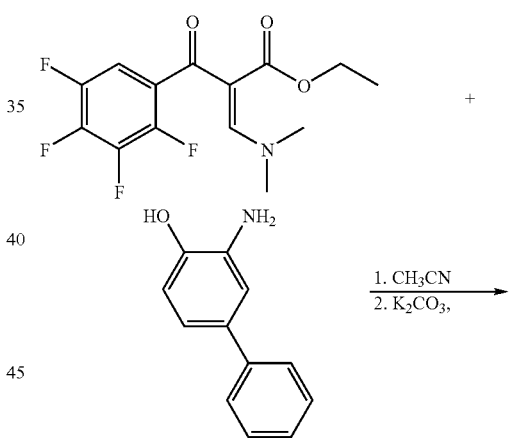

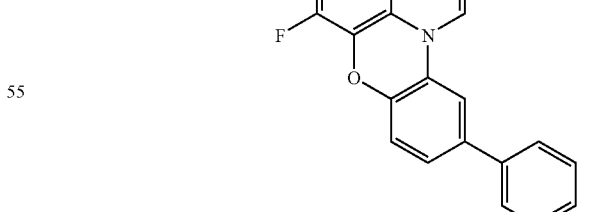

A solution of the enamine (5.4 g, 16.9 mmol) and 3-amino-4-hydroxybiphenyl (3.5 g, 18.9 mmol) in acetonitrile was heated to 80° C. for 90 minutes. Potassium carbonate was then added (8.0 g) and the mixture was heated to reflux overnight. The reaction mixture was then filtered hot and the

Example 34

Preparation of 5,6-Difluoro-3-oxo-10-phenyl-3H-pyrido[3,2,1-kl]phenoxazine-2-carboxylic acid

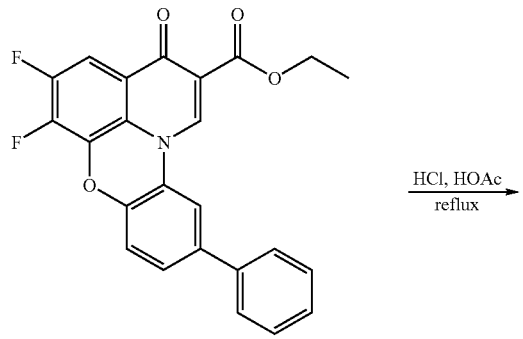

The crude difluoroester (3.6 g, 8.6 mmol) was dissolved in acetic acid (10 mL) and 12 M HCl was added (10 mL) and the reaction mixture was heated to reflux for 2 hours. The mixture was then cooled to room temperature, poured into water and the solid product was collected by vacuum filtration and dried to afford the difluoroacid as a pale solid (2.6 g, 6.6 mmol) (M+1, 392).

Example 35

Preparation of Ethyl 1,2-Difluoro-4-oxo-4H-11-sulfonic-acid-pyrido[3,2,1-kl]benzo[h]-phenoxazine-5-carboxylate

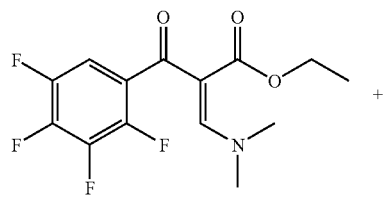

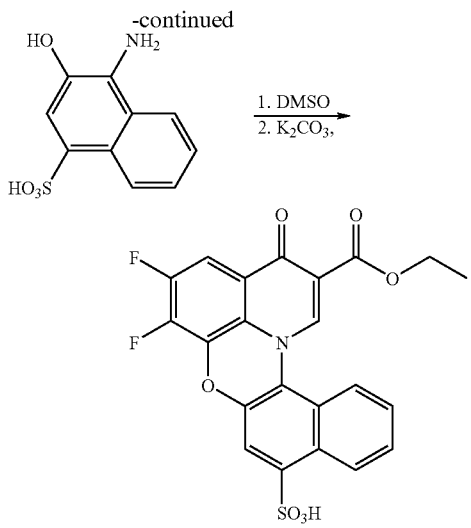

To a solution of the tetrafluoroenamine (5.4 g, 16.9 mmol) dissolved in DMSO (30 mL) was added 1-amino-2-hydroxy-4-naphthalenesulfonic acid (4.8 g, 20 mmol) and the mixture was heated to 60° C. under vacuum (rotary evaporator) for 2 hours. To the reaction mixture was added potassium carbonate (10.0 g) and the mixture was heated to 60° C. for 1 hour. The mixture was allowed to cool to room temperature and a slight excess of 2 M HCl was added to rapidly dissolve the carbonate. The aqueous layer was decanted and the remaining organic residue was dissolved in methanol (100 mL) and precipitated with ethyl acetate (200 mL) and the solid precipitate was filtered and dried to afford the sulfonic acid as a brown solid (3.1 g, 6.5 mmol) (M+1, 474).

Example 36

Preparation of 1,2-Difluoro-4-oxo-4H-11-sulfonic-pyrido[3,2,1-kl]benzo[h]-phenoxazine-5-carboxylic acids

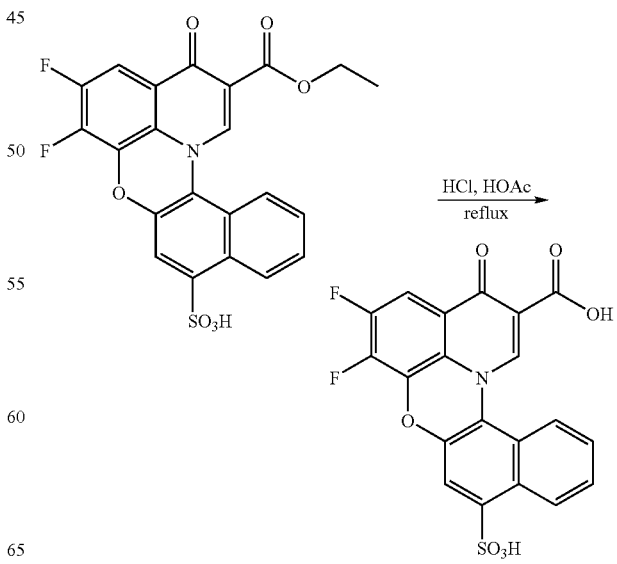

(solvent was removed in vacuo to afford the crude difluoroester (3.9 g, 9.3 mmol) (M+1, 420).)

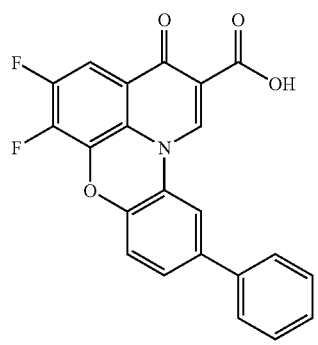

The crude difluoroester (1.5 g, 3.2 mmol) was dissolved in acetic acid (10 mL) and 12 M HCl was added (10 mL) and the reaction mixture was heated to reflux for 30 minutes. The solvent was removed in vacuo to afford the sulfonic acid as a brown solid (1.1 g, 2.5 mmol) (M+1, 446)

Example 37

Preparation of 2-(Ethoxycarbonyl)-5,6-difluoro-3-oxo-3H-pyrido[3,2,1-kl]phenoxazine-9-carboxylic acid

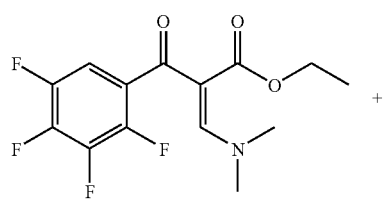

+

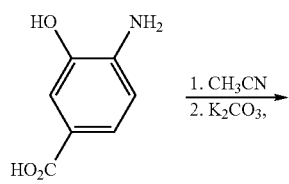

1. CH₃CN
2. K₂CO₃,

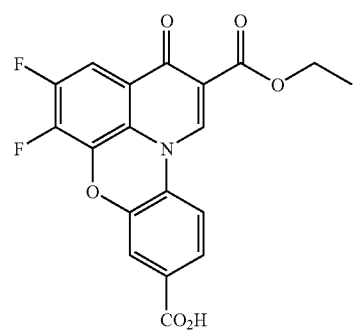

A solution of the difluoroenamine (5.2 g, 16.3 mmol) and 4-amino-3-hydroxybenzoic acid (4.0 g, 26.1 mmol) in DMSO was stirred at room temperature for 1.5 hours. Potassium carbonate (8 g) was then added and the reaction mixture was stirred under vacuum (rotary evaporator) for 1 hour. The mixture was then heated to 100° C. for 1 hour and then allowed to cool to room temperature. The reaction mixture was then poured into 1 M H₂SO₄ (500 mL) and the solids were recovered by vacuum filtration. The resulting solid was dried to afford the crude difluoroacid as a tan solid (5.0 g, 12.9 mmol) (M+1, 388).

Example 38

Preparation of 5,6-Difluoro-3-oxo-3H-pyrido[3,2,1-kl]phenoxazine-2,9-dicarboxylic acid

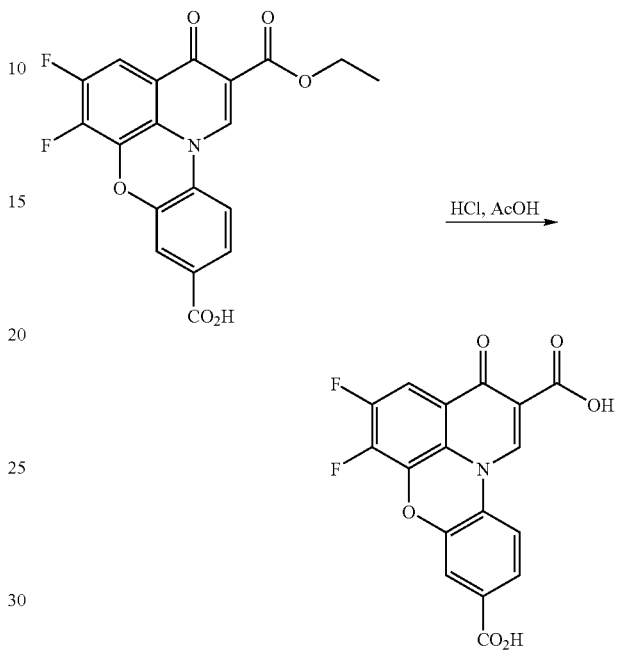

The crude difluoroester (5.0 g, 12.9 mmol) was dissolved in acetic acid (20 mL) and 12 M HCl was added (20 mL) and the reaction mixture was heated to reflux for 1 hour. The reaction was allowed to cool to room temperature and water was added. The resulting solid was collected by vacuum filtration and dried overnight to afford the di-acid as a tan solid (1.9 g, 5.3 mmol) (M+1, 360).

Example 39

Preparation of Ethyl 1,2-Difluoro-4-oxo-4H-pyrido [3,2,1-kl]-8-fluorenone-5-carboxylate 3-Nitro-2-hydroxyfluorenone

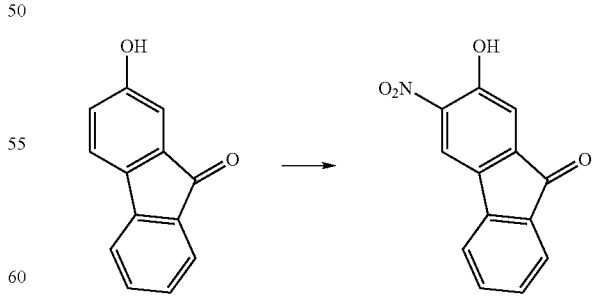

A solution of NO₂BF₄ (3.52 g, 25.5 mmol) in acetonitrile (100 ml) was added dropwise to a solution of 2-hydroxyfluorenone (5 g, 25.5 mmol) in acetonitrile (400 ml) at ambient temperature. The reaction mixture was then cooled to 0° C. and water (100 ml) was added to precipitate impurities. After filtration, water (200 ml) was added and the precipitate filtered off as a red solid (68%) (M+1, 242).

3-amino-2-hydroxyfluorenone

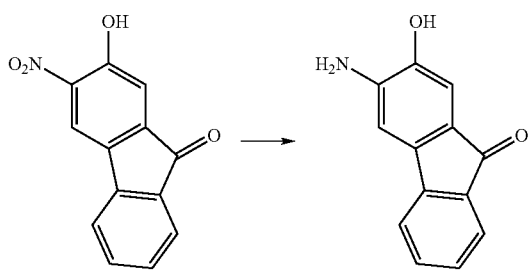

A mixture of 3-nitro-2-hydroxyfluorenone (1.6 g, 6.6 mmol) and SnCl$_2$ (3 g, 6.6 mmol) was refluxed in 100 ml acetic acid:conc. HCl (1:1) for 1 hour. The mixture was allowed to cool to room temperature and neutralized with ammonium hydroxide. After extracting with EtOAc (3×100 ml), combined organic fractions were dried over magnesium sulfate and evaporated to leave the product as a brown solid (65%) (M+1, 212).

Ethyl 1,2-Difluoro-4-oxo-4H-pyrido[3,2,1-kl]-8-fluorenone-5-carboxylate

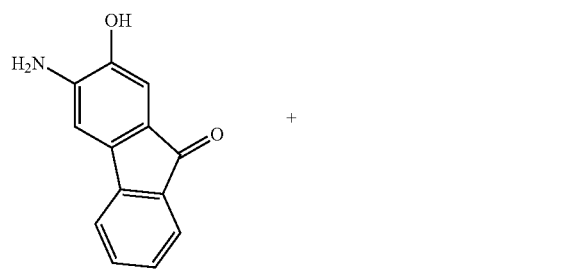

+

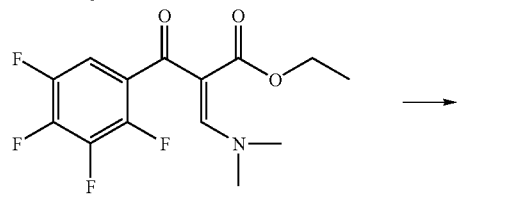

→

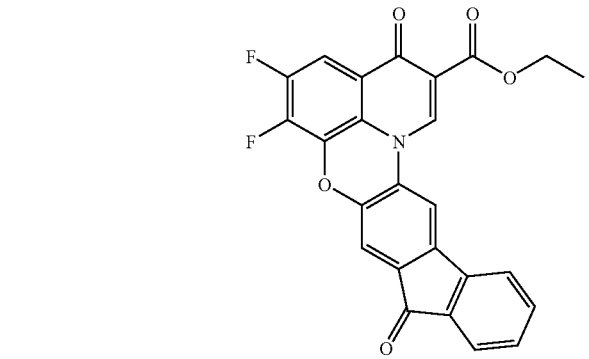

A mixture of 3-amino-2-hydroxyfluorenone (0.9 g, 4.26 mmol) and ethyl-2-(2',3',4',5'-tetrafluorobenzoyl-)-3-(dimethylamino)-prop-2-enoate (1.36 g, 4.26 mmol) were heated in DMSO (50 ml) under vacuum for 18 hr. The product was extracted using EtOAc/Brine and the organic layers combined and dried to give the product as a red solid. The solid was dissolved in DMSO (40 ml) containing a large excess of K$_2$CO$_3$ and heated at 100° C. for 30 min. After cooling to room temperature, brine (30 ml) was added and the precipitated product collected as a yellow solid (60% over two steps) (M+1, 446).

Example 40

Preparation of 1,2-Difluoro-4-oxo-4H-pyrido[3,2,1-kl]-8-fluorenone-5-carboxylic acid

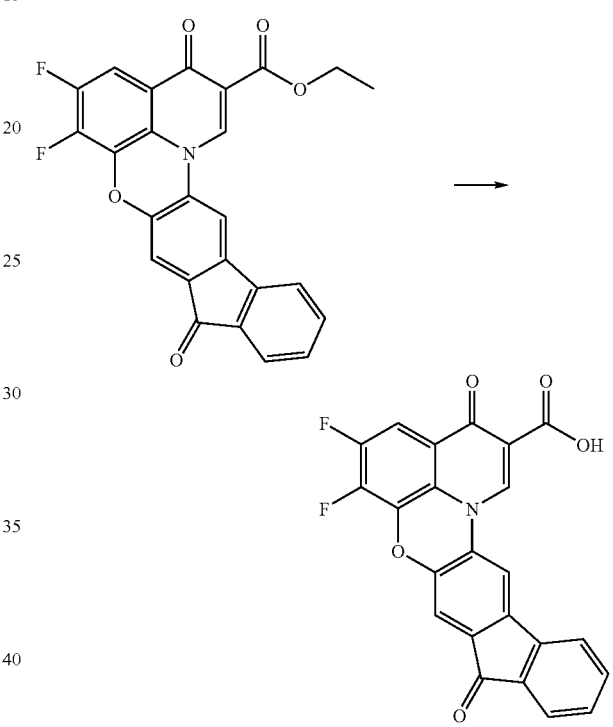

A mixture of ethyl 1,2-difluoro-4-oxo-4H-pyrido[3,2,1-kl]-8-fluorenone-5-carboxylate in acetic acid:conc. HCl (1:1) (50 ml each) was heated at reflux for 2 hr. After cooling to room temperature, water (50 ml) was added and the product collected as yellow solid (94%) (M+1, 418).

Example 41

Preparation of Ethyl 1,2-Difluoro-4-oxo-4H-pyrido [3,2,1-kl]-8-anthraquinone-5-carboxylate

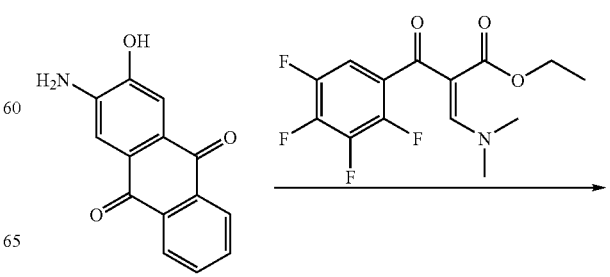

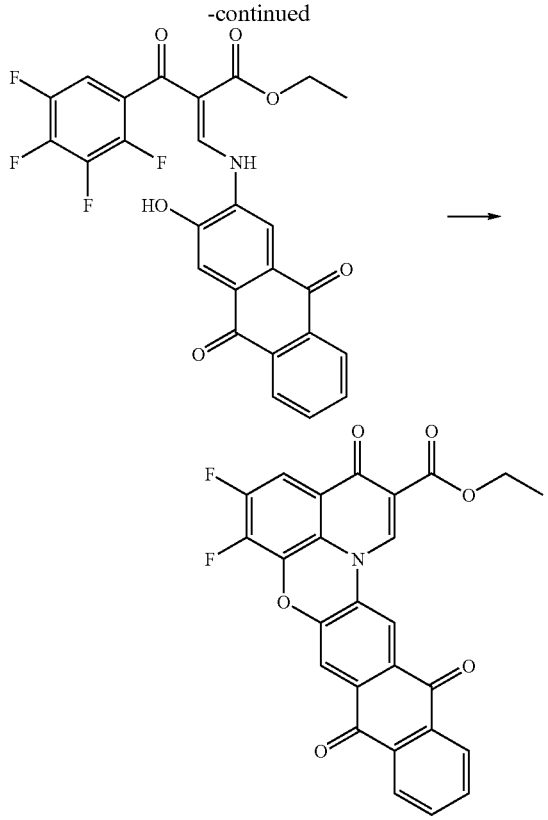

A mixture of 3-amino-2-hydroxyanthraquinone (5.54 g, 23.2 mmol) and ethyl-2-(2',3',4',5'-tetrafluorobenzoyl-)-3-(dimethylamino)-prop-2-enoate (8.7 g, 34.8 mmol) were heated in a minimum of DMSO (~10 ml) under vacuum for 24 hr. The product was precipitated by the addition of water (50 ml). The solid was dried overnight in a vacuum oven and dissolved in DMSO (40 ml) containing a large excess of K₂CO₃ and heated at 100° C. for 30 min. After cooling to room temperature, brine (30 ml) was added and the precipitated product collected as a yellow solid (60% over two steps) (M+1, 474).

Example 42

Preparation of 1,2-Difluoro-4-oxo-4H-pyrido[3,2,1-kl]-8-anthraquinone-5-carboxylic acid

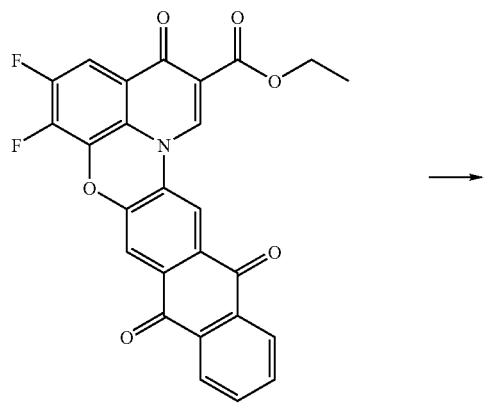

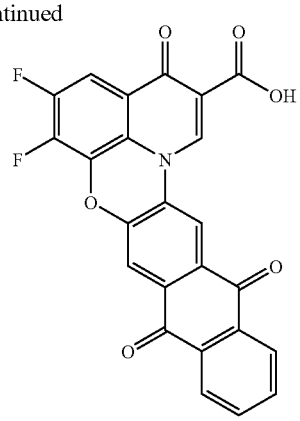

A mixture of ethyl 1,2-difluoro-4-oxo-4H-pyrido[3,2,1-kl]-8-anthraquinonenone-5-carboxylate (3.5 g, 6.8 mmol) in acetic acid:conc. HCl (1:1) (50 ml each) was heated at reflux for 2 hr. After cooling to room temperature, water (50 ml) was added and the product collected as yellow solid (94%) (M+1, 446).

Example 43

Preparation of Ethyl 1,2-Difluoro-4-oxo-4H-pyrido[3,2,1-kl]-8-phenyl-phenoxazole-5-carboxylate
2-amino(t-butoxy carbonyl)-5-amino hydroquinone

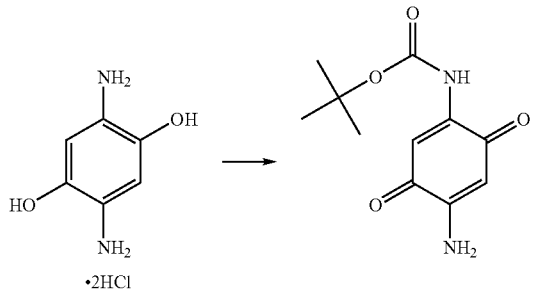

A solution of Boc anhydride (7.17 g, 33 mmol) and DIEA (17 ml, 99 mmol) in DMSO (20 ml) was added dropwise at room temperature to stirred solution of 1,4-dihydroxy-2,5-diaminobenzene (7 g, 33 mmol). After stirring for 18 hr, the product was separated between EtOAc and brine and the organic layers combined and dried over MgSO₄. After removal of solvent the residue was subjected to column chromatography on silica eluting with 25-50% EtOAc in hexane to give pure product (45%) (M+1,239).

4-hydroxy-3-amino(t-butoxy carbonyl)-phenoxazole

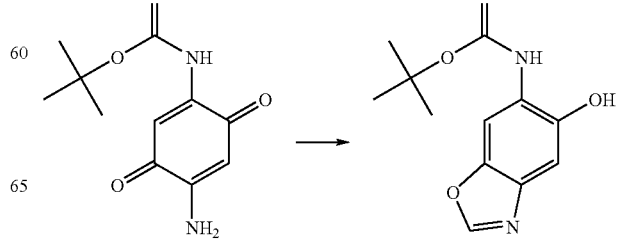

To solution of 2-amino(t-butoxy carbonyl)-5-amino hydroquinone (4.69 g, 23.3 mmol) dissolved in acetonitrile/water (1:1; 20 ml) was added Na hydrosulfite (large excess) and the mixture stirred at room temp. for 15 min. The acetonitrile was removed in vacuo and the aqueous mixture extracted with EtOAc (3×20 ml). Combined organic layers were dried over MgSO$_4$ and solvent removed in vacuo. The residue was taken up in neat triethyl orthoformate (100 ml), left to stir for 16 hr then heated to reflux for 10 min. The product was precipitated following cooling to room temp. by the addition of water (83%)(M+1, 251).

4-hydroxy-2-amino phenoxazole

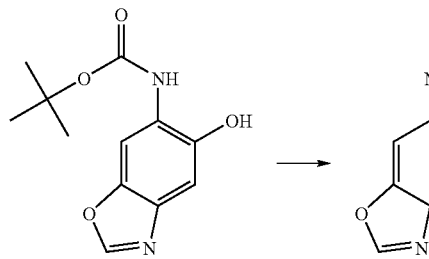

4-Hydroxy-3-amino(t-butoxy carbonyl)-phenoxazole (3 g, 12 mmol) was dissolved in neat TFA (100 ml) and allowed to stir at room temperature for 1 hour. TFA was removed in vacuo to leave the final product as a TFA salt (quant.) (M−1, 149)

Ethyl-2-(2',3',4',5'-tetrafluorobenzoyl-)-3-(N-(4-hydroxy-2-amino phenoxazole))-prop-2-enoate

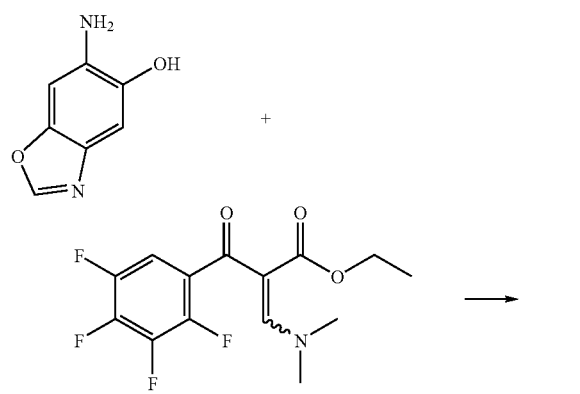

A solution of ethyl-2-(2',3',4',5'-tetrafluorobenzoyl-)-3-(dimethylamino)-prop-2-enoate (7.34 g, 23 mmol) and 2-amino-4-phenyl-phenol (3.45 g, 23 mmol) in EtOAc (20 ml) containing triethylamine (10 ml) was stirred under vacuum on the rotary evaporator for 3 hours. The EtOAc was removed in vacuo and the residue subjected to column chromatography on silica eluting with 50% EtOAc in hexane to give pure product (72%) (M+1, 425).

Ethyl 1,2-Difluoro-4-oxo-4H-pyrido[3,2,1-k]-8-phenyl-phenoxazole-5-carboxylate

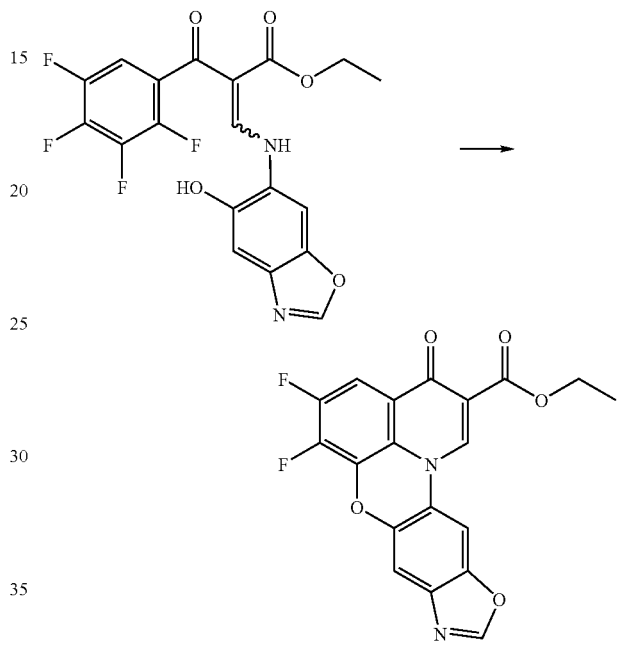

A solution of ethyl-2-(2',3',4',5'-tetrafluorobenzoyl-)-3-(N-(4-hydroxy-2-amino phenoxazole))-prop-2-enoate (3.5 g, 8.25 mmol) in DMSO (50 m) containing K$_2$CO$_3$ (large excess) was heated at 80° C. for 10 min. After cooling to room temperature, water was added to precipitate the product as a yellow sold (82%) (M+1, 385).

Example 44

Preparation of 1,2-Difluoro-4-oxo-4H-pyrido[3,2,1-kl]-8-(3'-hydroxy-4'-amino phenyl)-5-carboxylic acid

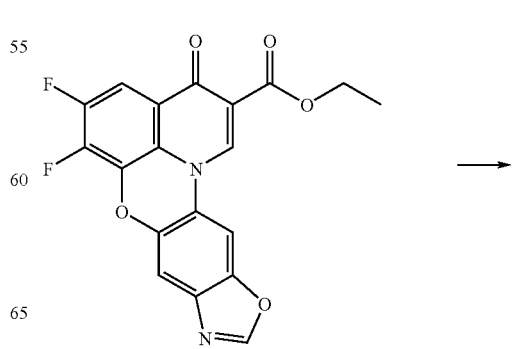

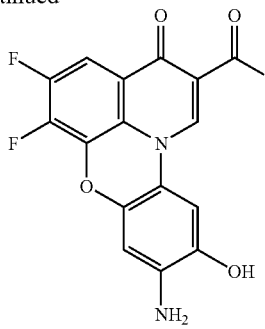

A mixture of ethyl 1,2-difluoro-4-oxo-4H-pyrido[3,2,1-kl]-8-phenyl-phenoxazole-5-carboxylate (2.3 g, 6 mmol) in acetic acid:conc. HCl (1:1; 100 ml) was heated to reflux for 30 min. After cooling to room temp., volatiles were removed in vacuo to leave the product as a brown solid (82%) (M+1, 347).

Example 45

Preparation of 1,2-Difluoro-4-oxo-4H-pyrido[3,2,1-kl]-8-(nitro-phenoxazine)-5-carboxylic acid 1,2-Difluoro-4-oxo-4H-pyrido[3,2,1-kl]-8-(3'-hydroxy-4'-amino-(N-2''-fluoro-4''-nitro phenyl)-phenyl))-5-carboxylic acid

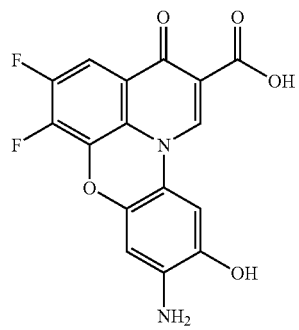

A solution of 1,2-difluoro-4-oxo-4H-pyrido[3,2,1-kl]-8-(3'-hydroxy-4'-amino phenyl)-5-carboxylic acid (0.5 g, 1.44 mmol), 3,4-difluoro-nitro benzene (0.5 ml, 4.3 mmol) and DIEA (1 ml) was heated to 90° C. in NMP (50 ml) for 30 min. After cooling to room temp. the product was precipitated by the addition of water and filtered (63%) (M+1, 486).

1,2-Difluoro-4-oxo-4H-pyrido[3,2,1-kl]-8-(nitro-phenoxazine)-5-carboxylic acid

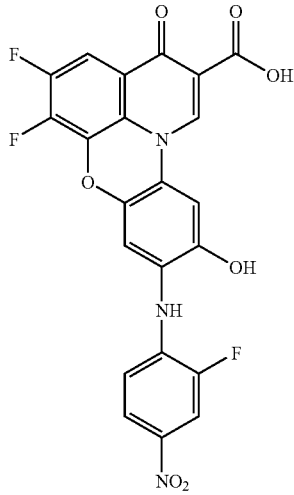

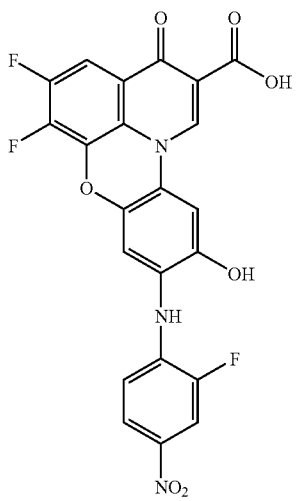

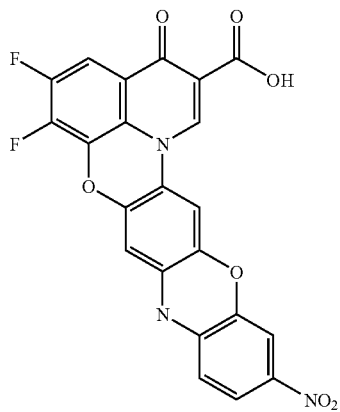

A solution of 2-difluoro-4-oxo-4H-pyrido[3,2,1-kl]-8-(3'-hydroxy-4'-amino phenyl)-5-carboxylic acid (0.3 g, 0.6 mmol) in DMSO (50 ml) containing an excess of $K_2CO_3$ was stirred and heated to 110° C. for 1 hr. After cooling to room temp. the product was precipitated by the addition of 3M HCl and filtered (71%) (M+1, 465).

Example 46

Preparation of 1,2-Difluoro-4-oxo-4H-pyrido[3,2,1-kl]-8-(amino-phenoxazine)-5-carboxylic acid

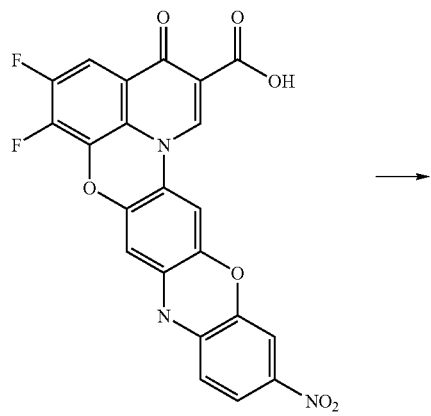

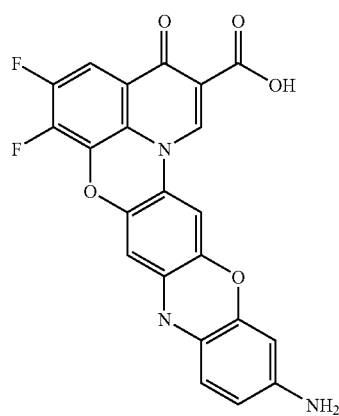

A mixture of 1,2-difluoro-4-oxo-4H-pyrido[3,2,1-kl]-8-(nitro-phenoxazine)-5-carboxylic acid (0.1 g, 0.2 mmol) and Tin (II) chloride (0.15 g, 0.6 mmol) in acetic acid:conc. HCl (1:1; 50 ml) was heated to reflux for four hr. After cooling to room temp. the product was precipitated by the addition of water and filtered (72%) (M+1,435).

Example 47

Preparation of Preparation of amide derivatives of substituted quinobenzoxazine analogs

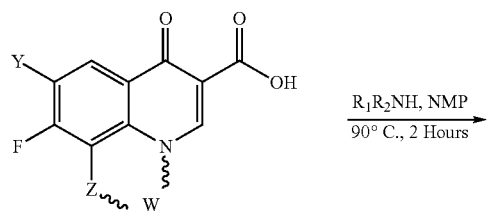

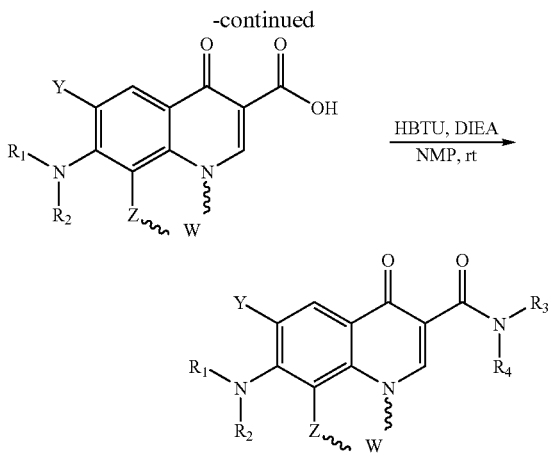

To a series of solutions of the fluoroacid (0.5 mmol) in NMP (3.6 mL) was added the amines $NHR_1R_2$ (0.5-2.0 mmol) at room temperature. The vessels were sealed and heated on a 90° C. hotplate with constant stirring for 1-2 hours until the reactions were determined to be complete by HPLC/MS analysis. The reaction mixtures were allowed to cool to room temperature and water was added (20 mL). The resulting precipitates were collected by vacuum filtration and dried under vacuum. In cases where 1.0 equivalent of amine was used, the resulting reaction mixtures were used in the next step "as is." The resulting solids or solutions were treated with HBTU (2.5 eq.) and DIEA in 3.6 mL NMP and allowed to stir for 30 minutes at room temperature under an inert atmosphere. These solutions were added to a series of amines $NHR_3R^4$ (2.5 equivalents) in a 96 well format (Whatman Uniplate, 2 mL) and allowed to react for 2 hours. Methanol was then added (50-100 µL) and the plate was filtered (Whatman Unifilter Polypropylene). The resulting liquids were directly chromatographed on reverse HPLC (Waters Xterra 19×50 mm) with mass directed collection (Micromass ZQ, Waters FCII). The fractions were analyzed for purity (MS TIC, UV) and dried by vacuum evaporation (Savant) with an average yield of 5-10 mg). Examples of substituted quinobenzoxazines analogs are described in Table 1.

Example 48

Synthesis of CX-3092 and CX-3543

One method for synthesizing CX-3543 is shown below. As shown in Scheme 2, CX-3543 is synthesized in a convergent manner, assembling the substructures 1, 1A and 2A in the final two synthetic steps (Scheme 2), to form CX-3543 having a 50:50 ratio of RS and SS isomers. CX-3092 may be synthesized in a similar manner using a non-chiral form of 1A.

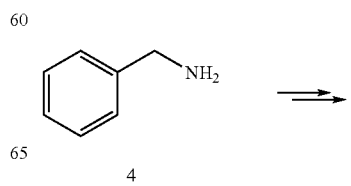

-continued

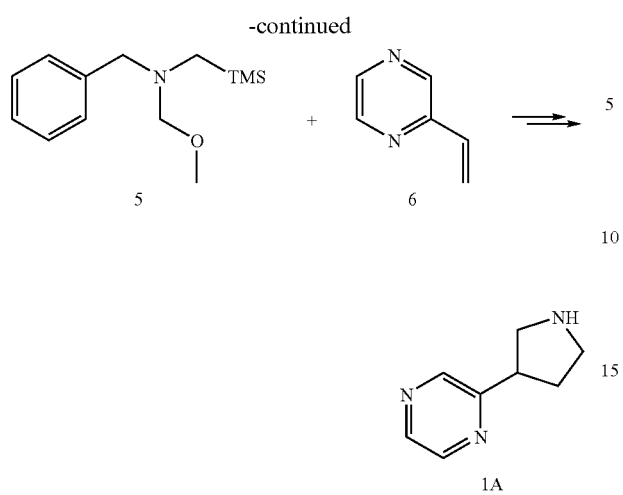

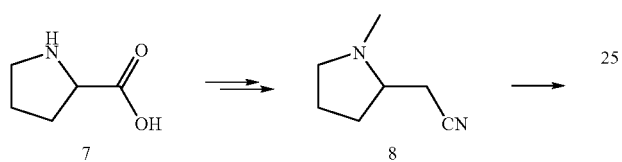

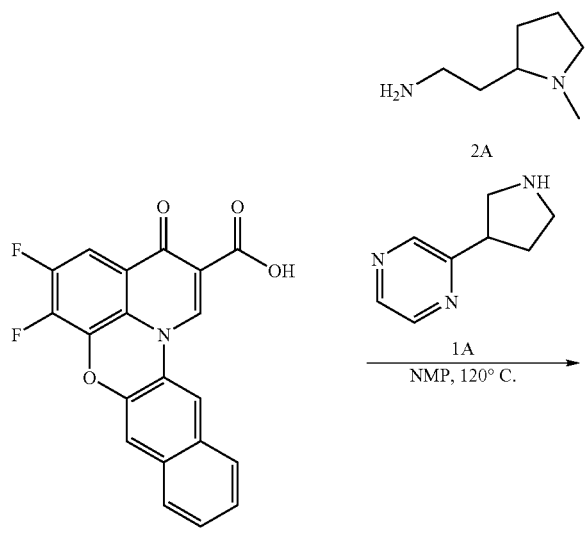

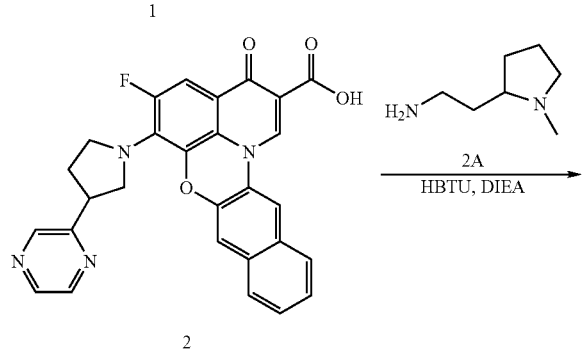

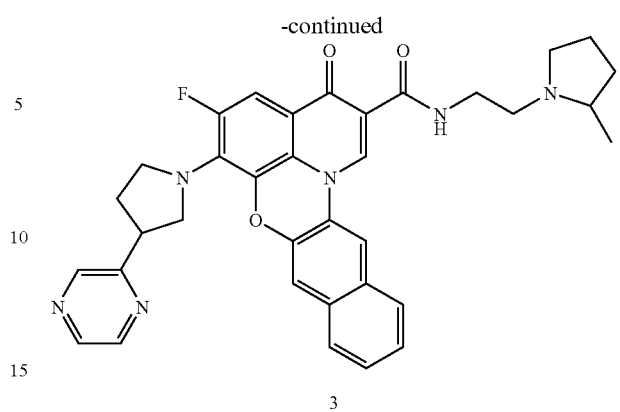

In more detail, pyrazinopyrrolidine 1A is synthesized via a [3+2] cycloaddition chemistry. Conversion of L-proline 7 to cyano-1-aminopyrrolidine 8 without loss of stereochemistry, followed by reduction provides the chiral 2-aminoethyl-1-methylpyrrolidine 2A in high yield. CX-3543 was found to have a formulated solubility of approximately 20 mg/mL.

Example 49

Cell Proliferation and/or Cytotoxicity Assay

Cell culture. Human cervical epithelial cells (HeLa cells) were obtained from American Type Culture Collection (Manassas, Va.). Cells were grown in Eagle's minimum essential medium (MEM, Hyclone, Utah) supplemented with 2 mM Glutamine, 0.1 mM nonessential amino acid, 1 mM Na Pyruvate, 1.5 g/L $NaHCO_3$, 50 mg/L gentamicin, and 10% fetal bovine serum (Hyclone, USA) in a humidified atmosphere of 5% $CO_2$ at 37° C.

MTS assays. Antiproliferative effects of the compounds were tested by the CellTiter 96 $AQ_{ueous}$ assay (Promega, WI), which is a calorimetric assay for determining the number of viable cells. (See, e.g., Wang, L., et al., *Methods Cell Sci* (1996) 18:249-255). In one example, cells (4,500 cells/well) were seeded on 96 well flat bottom plates (Corning, N.Y.) in 100 µl of culture medium without any anticancer drug on day 0, and the culture medium was exchanged for that //contained anticancer drugs at various concentrations on day 1. After incubation for 3 days under normal growth conditions (on day 4), the monolayers were washed once in PBS, and the medium was switched to 100 µl of PBS in each of the 96 well plate. After mixing MTS and PMS at the ratio of 20:1, 20 µl of MTS/PMS solution was added to each of the 96 well plate and incubated for 4 hours in a humidified atmosphere of 5% $CO_2$ at 37° C. The absorbance was read at 490 nm using FLUOstar Galaxy 96 well plate reader (BMG Labtechnologies, Germany). µM concentrations (MTS data) reported in Table 1 are concentrations at which 50% of antiproliferative cell response is seen. Compounds whose $IC_{50}$ values were greater than 5 µM were not reported.

Example 50

Measurement of mRNA Values in Cell Assays

Real-time quantitative PCR (QPCR) method was used to detect the changes of the target c-myc and the endogenous reference GAPDH gene copies in the same tube. Cells (15,000 cells/well) were seed on 96 well flat bottom plates (Corning, NY) and incubated under normal growth conditions for overnight. The next day, the culture medium was exchanged for that contained anticancer drugs at various concentrations and incubate for 4 hrs in a humidified atmosphere of 5% $CO_2$ at 37° C. Total RNA (tRNA) was extracted using the RNeasy 96 Kit (QIAGEN, CA). The concentration of the tRNA was determined using the RiboGreen RNA Quantitation Reagent (Molecular Probes, OR).

Reverse-transcription (RT) reaction was occurred using 50 ng of tRNA from each well in a 25 μl reaction containing 1×TaqMan RT buffer, 2.5 uM random hexamers, 5.5 mM $MgCl_2$, 0.5 mM each deoxynucleoside triphosphate (dNTP), 30 U MultiScribe Reverse Transcriptase, and 10 U RNase inhibitor. RT reactions were incubated for 10 min at 25° C., reverse-transcribed for 30 min at 48° C., inactivated for 5 min at 95° C., and placed at 4° C. All RT reagents were purchased from Applied Biosystems, CA.

Real-Time QPCR reaction was performed in a 50 μl reaction containing the 5 μl of cDNA, 1×Universal PCR Master Mix, 1×c-myc Pre-Developed Primers and Probe set, and 0.8×GAPDH Pre-Developed Primers and Probe set. Because of the relative abundance of GAPDH gene in Hela, GAPDH primers and probe concentration were adjusted to get accurate threshold cycles ($C_T$) for both genes in the same tube. The threshold cycle ($C_T$) indicates the fractional cycle number at which the amount of amplified target reaches a fixed threshold. By doing so, the GAPDH amplification was stopped before it can limit the common reactants available for amplification of the c-myc, resulted in a reduction in ΔRn value of GAPDH, but no effect on its $C_T$ value, and equal amplification efficiency for both genes. The ΔRn value represents the normalized reporter signal minus the baseline signal. ΔRn increases during PCR as amplicon copy number increases until the reaction approaches a plateau.

The c-myc probe was labeled with 6FAM™ dye-MGB and the GAPDH probe was labeled with VIC™ dye-MGB. Preincubation was performed for 2 min at 50° C. to activate AmpErase UNG enzyme and then for 10 min at 95° C. to activate AmpliTaq DNA Polymerase. DNA was amplified for 40 cycles of 15 sec at 95° C. and 1 min at 60° C. Human c-myc and GAPDH cDNA were amplified, detected, and quantitated in real time using the ABI Prism 7000 Sequence Detection system (Applied Biosystems, CA), which was set to detect both 6-FAM and VIC reporter dyes simultaneously.

The data was analyzed by using the ABI PRISM Sequence Detection System and Microsoft Excel. Relative quantitation was done using the standard curve and comparative $C_T$ method at the same time, and both methods gave equivalent results. The cycle at which the amplification plot crosses the $C_T$ is known to accurately reflect relative mRNA values. (See, Heid, et al., *Genome Res.* (1996) 6:986-994; Gibson, et al., *Genome Res.* (1996) 6:995-1001). QPCR reactions were set up in triplicate at each cDNA sample and the triplicate $C_T$ values were averaged. All reagents including Pre-Developed Primers and probe set were purchased from Applied Biosystems, CA. μM concentrations (STOP data) reported in Table 1 are concentrations at which 50% inhibition of c-myc mRNA levels are seen. Compounds whose $IC_{50}$ values were greater than 5 μM were not reported.

Example 51

In Vitro Characterization

Various methods were used for in vitro characterization of the compounds of the present invention, including but not limited to i) stop assays; ii) quadruplex/duplex competition assay; iii) quadrome footprints; and iv) direct assay in the absence of a competitor molecule.

Stop Assays. FIG. 1 represents a stop assay, a high throughput, first-pass screen for detecting drugs that bind to and stabilize the target G-quadruplex. As shown in FIG. 1, DNA template oligonucleotide is created, which contains the nucleotide sequence of the "target" quadruplex against which drug screening is desired. A fluorescently labeled primer DNA is then annealed to the 3' end of the template DNA. A DNA polymerase such as Taq polymerase is then introduced to synthesize a complementary strand of DNA by extending from the fluorescently labeled primer. When the progress of the Taq polymerase is unhindered, it synthesizes a full-length copy of the template. Addition of a test drug that merely binds to duplex DNA but does not bind selectively the quadruplex region results in a decrease in synthesis of full length product and a concomitant increase in variable-length DNA copies. If, however, the test drug selectively binds to and stabilizes the quadruplex, the progress of polymerase arrests only at the quadruplex, and a characteristic "Stop Product" is synthesized.

In one aspect, the present invention provides compounds that will selectively target oncogenes regulated by the propeller/chair type of quadruplex, such as c-myc. Compounds are initially screened at a single concentration, and "hits" are re-assayed over a range of doses to determine an $IC_{50}$ value (i.e., the concentration of drug required to produce an arrest product/full-length product ratio of 1:1). These products are visualized by capillary electrophoresis.

Figure 2:
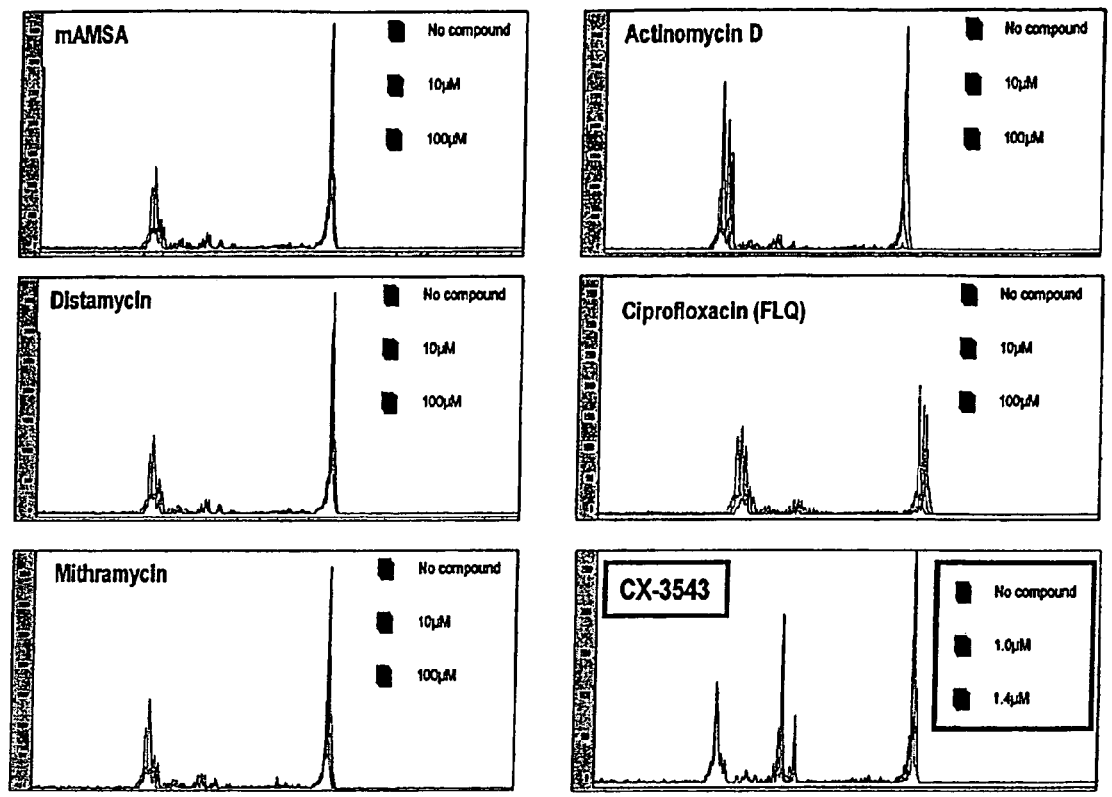
FIG. 2 shows the electrophoretogram for CX-3543, mAMSA, distamycins, mithramycin, actinomycin D, and ciprofloxacin.

FIG. 2 shows the electrophoretogram for CX-3543 as well as for other types of drugs, including DNA interactive drugs such as the topo-II poison m-AMSA; the antibiotics distamycin, actinomycin D (a non-specific transcription inhibitor), and mithramycin; and the antibiotic fluoroquinolone ciprofloxacin. CX-3543 demonstrated an $IC_{50}$ value of 1.0 μM in the stop assay, while none of the other DNA interactive drugs bound to the quadruplex at concentrations up to 100 μM. Thus, the first pass screen effectively identified agents having at least a 100-fold selectivity for the propeller/chair type quadruplex.

Quadruplex/Duplex Competitor Assay. The selectivity of compounds for the target quadruplex sequence relative to duplex DNA may be measured using a competition assay (i.e., "selectivity screen"). This selectivity screen uses the stop assay as a reporter system to measure the relative ability of an externally added DNA sequence to compete with the target quadruplex structure formed in the DNA template for binding of the drug. For example, the competitors are the c-myc quadruplex sequence, which is identical to the quadruplex sequence present in the template DNA; or a plasmid DNA which mimics complex genomic duplex DNA. The degree to which each competitor successfully "soaks up" drug in solution is reflected by the quantitative decrease in synthesis of the stop product. In this manner, the relative binding affinities of drug to both the target quadruplex and duplex DNA are determined.

Figure 3:
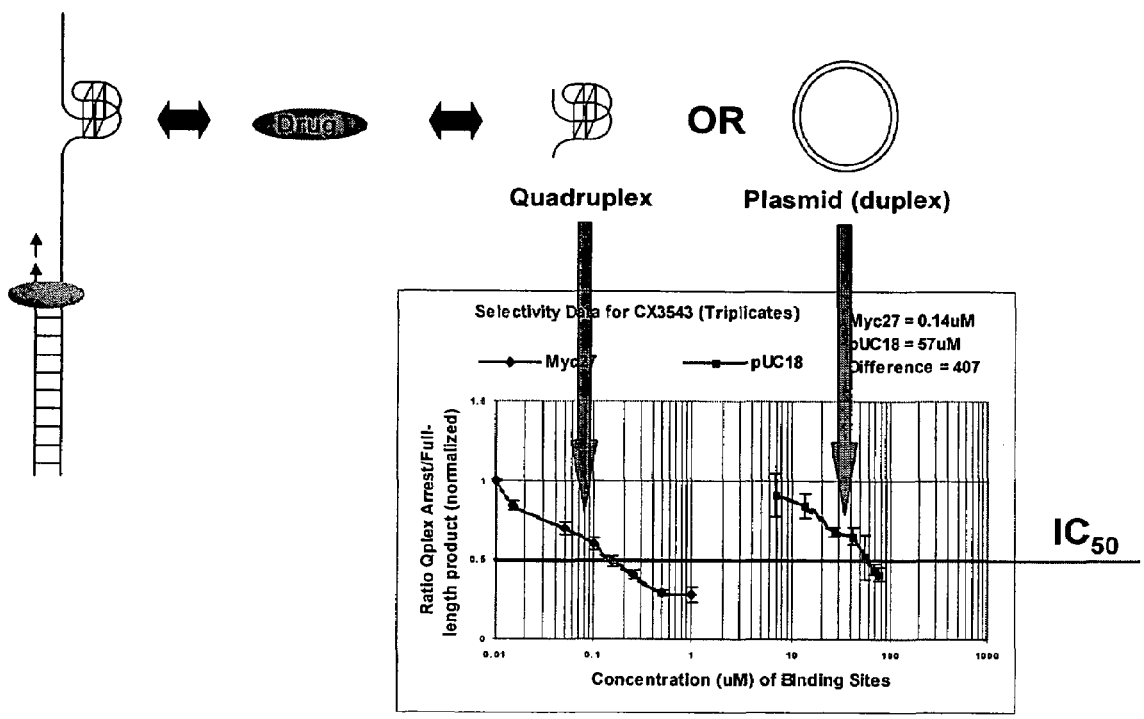
FIG. 3 shows the binding selectivity of CX-3543.

FIG. 3 is a selectivity assay showing quadruplex vs. duplex DNA binding selectivity of CX-3543. The ratio of the competitor $IC_{50}$ values indicates relative binding affinities of the compound for the quadruplex or duplex DNA. As shown in FIG. 3, CX-3543 exhibits approximately 400× selectivity for the c-myc quadruplex relative to pUC 18 plasmid DNA.

Figure 4A:
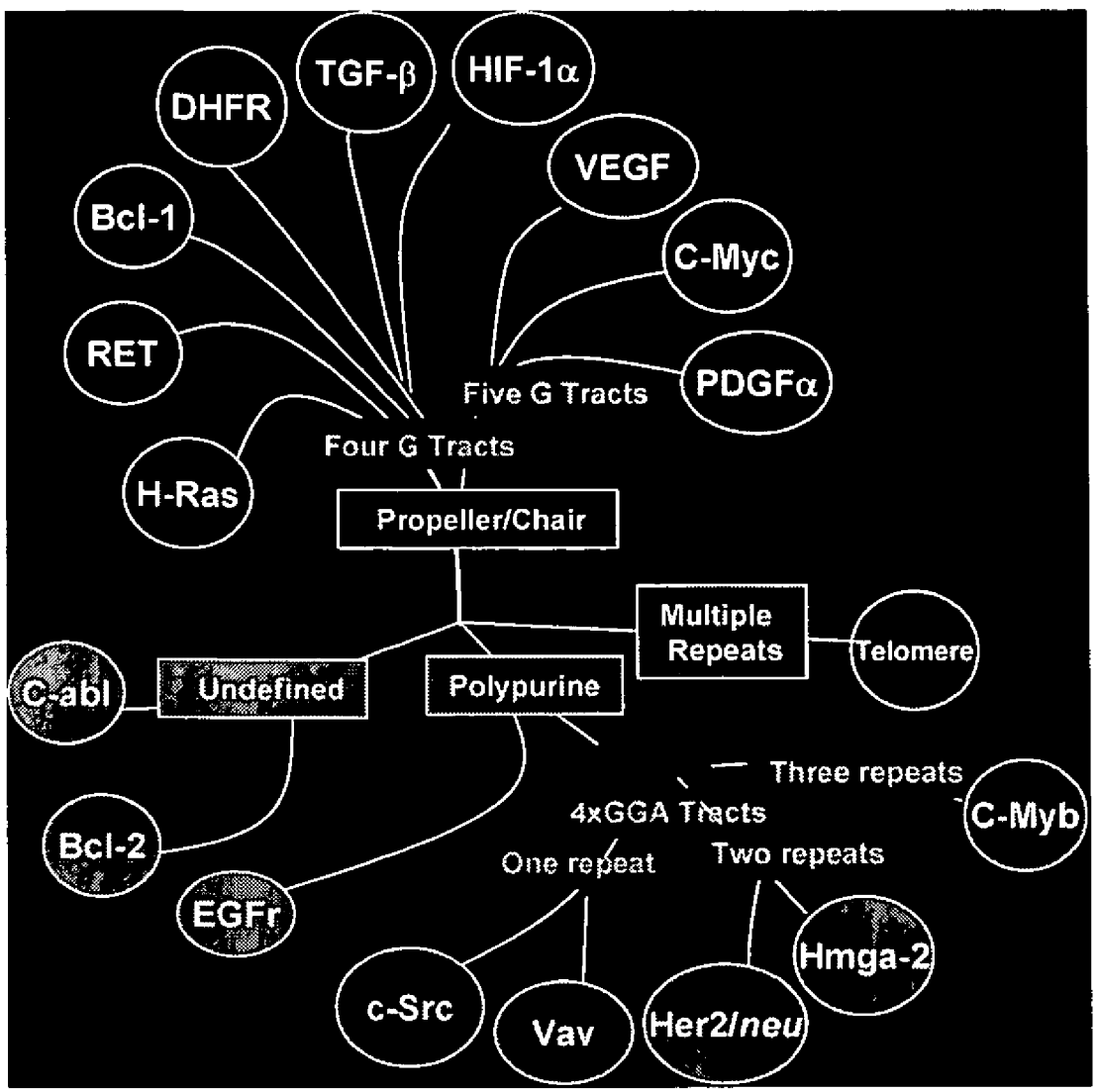
FIG. 4 shows a selectivity footprint (top panel, right) and stop assay (bottom panel, right) for CX-3543 by oncogene.
Figure 4B:
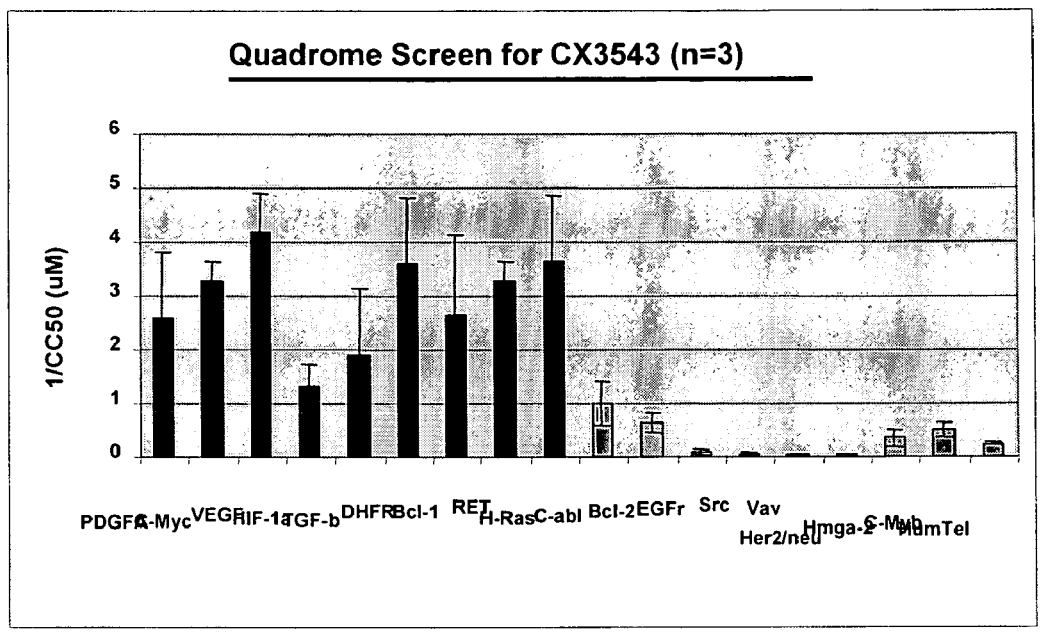
Figure 4B:
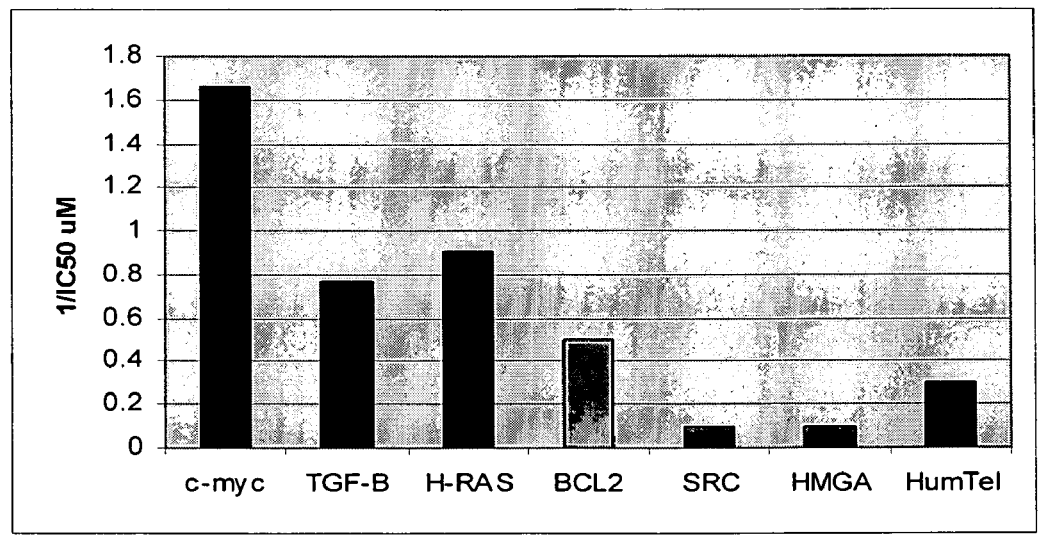

Quadrome Footprints. Compounds may be evaluated for their ability to bind to other native quadruplex structures of biological relevance, including quadruplex control elements that regulate a range of different oncogenes. FIG. 4 shows a selectivity footprint (top panel, right) and stop assay (bottom panel, right) for CX-3543 by oncogene. As shown in FIG. 4, CX-3543 selectively binds to those quadruplexes that are capable of adopting the chair/propeller conformation.

Direct Interaction Assay. Compounds may be evaluated for their ability to interact directly with nucleic acids capable of forming a quadruplex structure, wherein the nucleic acid is not a telomeric nucleic acid. The assay may be performed in the same or different vessels. For example, a compound may be contacted with each nucleic acid in the same vessel. Alternatively, a compound may be separately contacted with each of the nucleic acids tested in a different vessel. A telomeric nucleic acid as used herein represents a region of highly repetitive nucleic acid at the end of a chromosome. As used herein, a direct interaction is measured without the presence of a competitor nucleic acid.

An interaction between the compound and the nucleic acid may be determined for example, by measuring $IC_{50}$ values, which are indicative of the binding and/or quadruplex stabilization. The selectivity of interactions may be determined, for example, by comparing measured $IC_{50}$ values. For example, the-lowest $IC_{50}$ values may be used to indicate a strong interaction between the compound and the nucleic acid, while highest $IC_{50}$ values show a poor interaction; thus, showing selectivity of interaction. The reaction products were characterized by capillary electrophoresis.

Example 52

Direct Interaction Assay

Using a direct interaction assay, CX-3543 was screened for its ability to bind to and/or stabilize different types of quadruplexes. In this example, a 5'-fluorescent-labeled (FAM) primer (P45, 15 nM) is mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). The mixture is denatured at 95° C. for 5 minutes and, after cooling down to room temperature, is incubated at 37° C. for 15 minutes. After cooling down to room temperature, 1 mM KCl and the test compound at various concentrations are added, and the mixture incubated for 15 minutes at room temperature. The primer extension is performed by adding 13 mM KCl and Taq DNA Polymerase (2.5 U/reaction, Promega), and incubating at 70° C. for 20 minutes. The nucleic acid sequences of quadruplexes tested are set forth in Table 4.

TABLE 4

(STOP TEMPLATES)

TGFB3-81
TATACGGGGTGGGGGAGGGAGGGATTAGCGACACGCAATTGCTATAGTGA
GTCGTATTAGCTACGTACAGTCAGTCAGACT (SEQ ID NO.21)

HRAS-85
TATACCGGGCGGGGCGGGGCGGGGCTTAGCGACACGCAATTGCTATA
GTGAGTCGTATTAGCTACGTACAGTCAGTCAGACT (SEQ ID NO.22)

BCL2-97(full)
TAGGGGCGGGCGCGGGAGGAAGGGGCGGGAGCGGGGCTGTTAGCGACAC
GCAATTGCTATAGTGAGTCGTATTAGCTACGTACAGTCAGTCAGACT
(SEQ ID NO.23)

TABLE 4-continued (STOP TEMPLATES)

HMGA-97
TTAGAGAAGAGGGGAGGAGGAGGAGGAGAGGAGGAGGCGCTTAGCGACAC
GCAATTGCTATAGTGAGTCGTATTAGCTACGTACAGTCAGTCAGACT
(SEQ ID NO.24)

MYC99
TCCAACTATGTATACTGGGGAGGGTGGGGAGGGTGGGGAAGGTTAGCGAC
ACGCAATTGCTATAGTGAGTCGTATTAGCTACGTACAGTCAGTCAGACT
(SEQ ID NO.25)

IMOTIF99
TCCAACTATGTATACCCTTCCCCACCCTCCCCACCCTCCCCATTAGCGAC
ACGCAATTGCTATAGTGAGTCGTATTAGCTACGTACAGTCAGTCAGACT
(SEQ ID NO.26)

Humtel-95
TCATATATGACTACTTAGGGTTAGGGTTAGGGTTAGGGTTACTGCCACGC
AATTGCTATAGTGAGTCGTATTAGCTACGTACAGTCAGTCAGACT
(SEQ ID NO.27)

SRC89
ATGATCACCGGGAGGAGGAGGAAGGAGGAAGCGCGCTGCCACGCAATTGC
TATAGTGAGTCGTATTAGCTACGTACAGTCAGTCAGACT
(SEQ ID NO.28)

Primer:
(45 MER)
AGTCTGACTGACTGTACGTAGCTAATACGACTCACTATAGCAATT
(SEQ ID NO.29)

$IC_{50}$ values for CX-3543 shown in Table 5 indicate that CX-3543 interacts strongly with propeller quadruplexes tested (i.e., c-myc, TGF-β, and H-RAS), and less strongly with chair-eller and basket quadruplexes tested (i.e., BCl-2 and Hum Tel). CX-3543 interacts weakly with heptad-tetrad (SRC and HMGA-2) and i-motif quadruplexes tested. These results parallel results obtained in competition assays, as shown in FIG. 4.

TABLE 5

| Insert | $IC_{50}$ μm |
|---|---|
| c-MYC | 0.6 |
| TGF-β | 1.3 |
| H-RAS | 1.1 |
| BCL-2 | 2 |
| SRC | >10 |
| HMGA | >10 |
| HumTel | 3.3 |
| I-Motif | >10 |

Example 53

CX-3092 and CX-1535 Antitumor Activity

Figure 5:
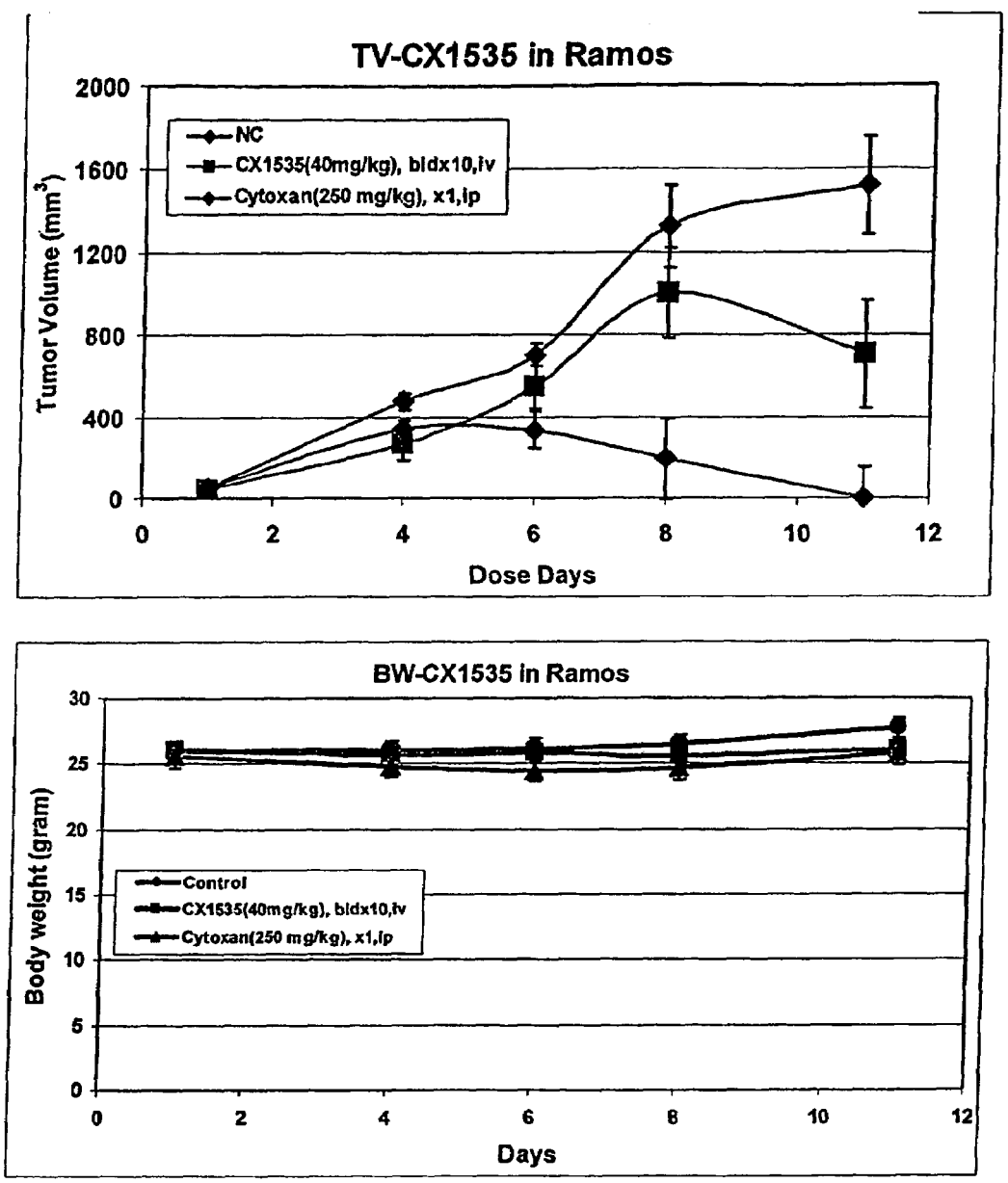
FIGS. 5 and 6 show the activity of a compound having formula 1 against Ramos and HCT-116 xenograft models respectively.
Figure 6:
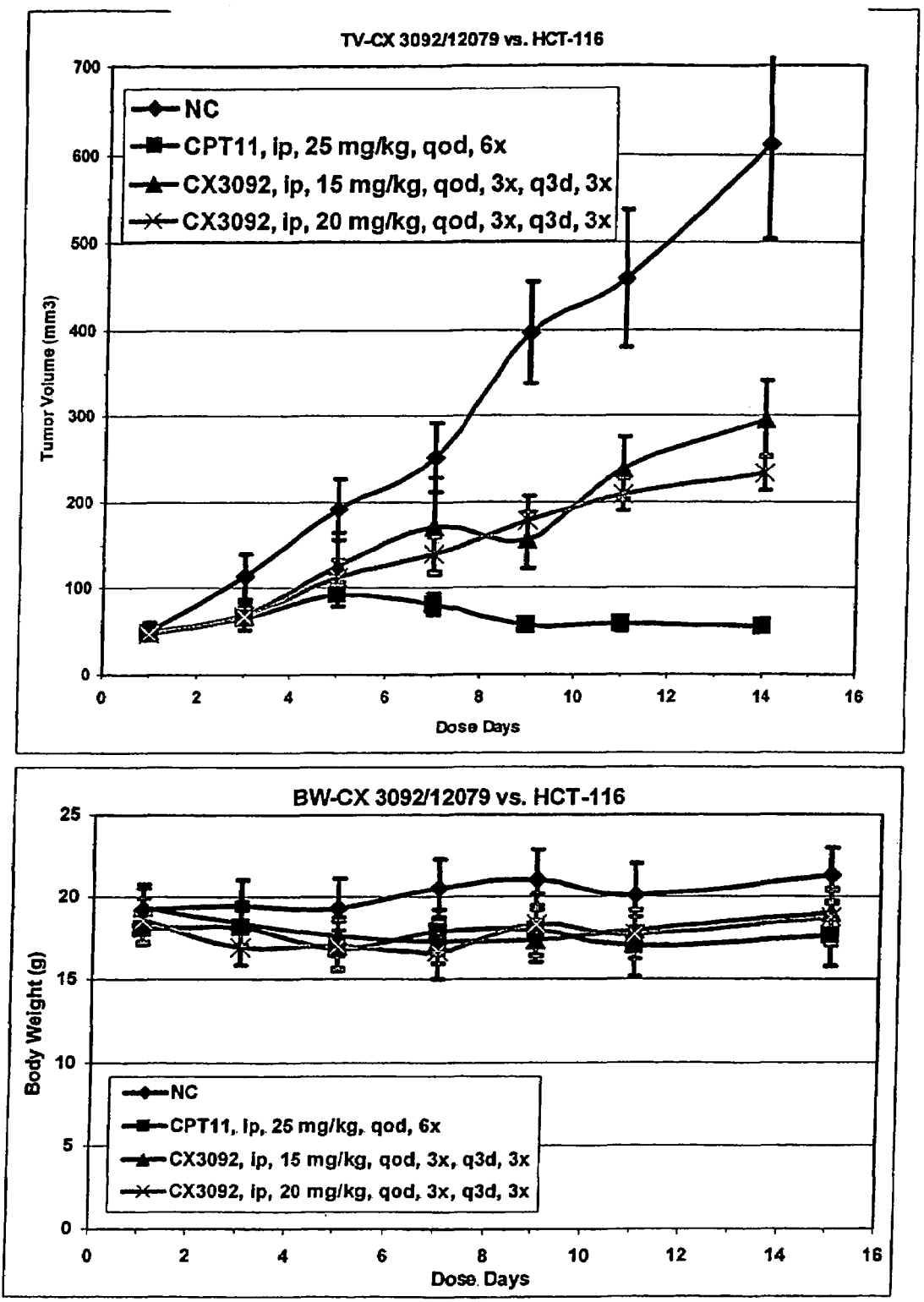

Antitumor activities for compounds CX-3092 (compound 1204) and CX-1535 (compound 494) are shown in a Ramos childhood leukemia model (FIG. 5) and HCT-116 colorectal cancer model (FIG. 6) respectively, indicating efficacy (slow tumor weight gain) and a lack of toxicity (little body weight change). Two xenograft models for inoculation were harvested and diluted to a concentration of $50 \times 10^6$ cells/ml or $100 \times 10^6$ cells/ml. Four to six week old nude mice were injected with 0.1 ml of the cell suspension containing between $5 \times 10^6$ and $10 \times 10^6$ cells. When tumors are of a suit-

Example 54

CX-3543 In Vitro Activity Against Tumor Cell Lines

The antitumor range of action of CX-3543 was tested in vitro using a panel of cancer cell-lines and evaluated using an MTS cell survival assay. Cells were exposed to CX3543 at various concentrations over a four day period, and $IC_{50}$ values were calculated. Generally, 2,000 to 5,000 cells were seeded in each well of a 96-well plate and incubated overnight. A serial dilution of testing compounds was added to cells and further incubated for 4 days at 37° C., in a 5% $CO_2$ humidified incubator. The survival cell numbers were evaluated by the MTS method as described in the manufacturer's protocol (Promega). $IC_{50}$ values (i.e., concentrations of test drug required to induce 50% cell death) were calculated as the concentration of testing compounds that decrease 505 of the cell number compared to that of the control group without compounds. In particular examples, $IC_{50}$ values were measured by Alamar Blue.

In vitro, CX-3543 displayed antitumor activity over a broad range of tumor types ($IC_{50}$ ranging from submicromolar to single digit micromolar levels in MTS assays, as shown in Table 5).

adding 50 μL of acetonitrile to 100 μL of cofactor solution to inactivate the enzymes, then adding 100 μL of enzyme/substrate solution. A control reaction with no inhibitor was also prepared. After a suitable incubation at 37° C., the reactions were terminated by the addition of 50 μL of acetonitrile. The reactions were analyzed for the metabolite forms of the probe substrate using LC/MS/MS. Each assay was performed in duplicate. Table 6 shows a summary of $IC_{50}$ values.

TABLE 6

| | | | $IC_{50}$ (μM) | |
|---|---|---|---|---|
| Isoform | Substrate | Control Inhibitor | Control | CX-3543 |
| 1A2 | Phenacetin | Furafylline | 0.99 | NI |
| 2C9 | Diclofenac | Sulfaphenazole | 0.62 | >10 |
| 2C19 | S-Mephenytoin | Tranylcypromine | 13.2 | NI |
| 2D6 | Dextro-methorphan | Quinidine | 0.072 | >25 |
| 3A4 Midazolam | Midazolam | Ketoconazole | 0.17 | 1.4 |
| 3A4 Testosterone | Testosterone | Ketoconazole | 0.20 | 3.3 |

No significant inhibition was apparent with four of the five isoenzymes: CYP1A2, CYP2C9, CYP2C19 and CYP2D6. In the case of CYP3A4, only minor and partial inhibition in the 1-3 μM range was evident. These results suggest that at clinical levels of drug exposure, there is a low likelihood of drug-

TABLE 5A

| Cell Line | A549 | HCT-116 (Colorectal) | HeLa (cervical) | HT-29 | MDA-MB-231 (Breast) | MDA-MB-468 (Breast) | MiaPaca | PC3 (Prostate) | Ramos (Burkitt's Lymphoma) | HepG2 | 786-O |
|---|---|---|---|---|---|---|---|---|---|---|---|
| $IC_{50}$ (μM) | 2.9 | 3.3 | 3.3 | 5.5 | 2.4 | 1.5 | 2.8 | 3.2 | 0.3 | 2.5 | 2.1 |

Figure 7:
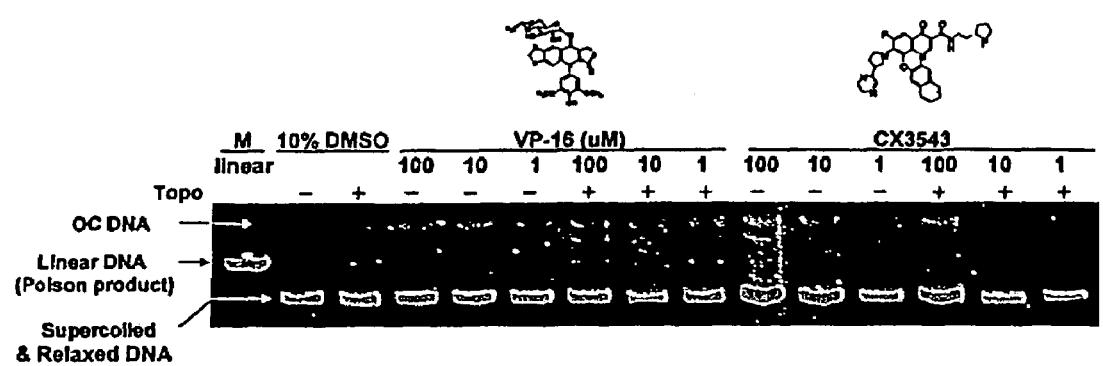
FIG. 7 shows the topoisomerase II assay for CX-3543.

Furthermore, CX-3543 was evaluated for potential inhibitory activity against topoisomerase I and topoisomerase II enzymes, and was determined not to be an inhibitor or poison of either enzyme. FIG. 7 illustrates data from a topoisomerase-II poison assay, using VP-16 (Etoposide) as a control Topoisomerase-II poison. In the presence of 1 μM VP-16, topoisomerase-II mediates the formation of double-strand breaks within the supercoiled DNA, giving rise to linear DNA product. CX-3543 did not induce topoisomerase dependent strand breaks at concentrations as high as 100 μM.

Example 55

Drug Metabolism of CX-3543

Cytochrome P450 (CYP450) Inhibition Assay. CX-3543 was evaluated for potential inhibitory activity against cytochrome P450 isoenzymes, using an in vitro inhibition assay with six CYP450 isoenzymes: CYP1A2, CYP2C9, CYP2C19, CYP2D6 and CYP3A4. Generally, six reaction tubes with 100 μL of a solution containing 50 mM potassium phosphate, pH 7.4, 2.6 mM NADP+, 6.6 mM glucose 6-phosphate, 0.8 U of glucose 6-phosphate dehydrogenase/mL, and 1:6 serial dilutions of the test compound were prepared along with six tubes of 1:6 serial dilutions of a suitable positive control inhibitor. The reactions were initiated by adding 100 μL of a pre-warmed enzyme/substrate solution to the reaction tubes. A zero time-point control reaction was prepared by drug interactions with the liver metabolism of co-administered drugs. As this example shows, CX3543 may be co-administered with anticancer cancer drugs that are principally metabolized by the CYP450 isoenzyme system (e.g., docetaxel).

Example 56

Metabolic Stability of CX-3543

Metabolic Stability Assay and Metabolite Profiling. A human hepatocyte assay to profile metabolites was carried out using commercially available kits and following standard procedures. The metabolic stability of CX-3543 with human hepatocytes was evaluated following incubation at 0, 30, 60, and 120 minutes at 1 and 20 μM. Consumption of the parent compound and the appearance of metabolites were carefully monitored, and mass spectrometer product ion scans were conducted on potential metabolite peaks to define the metabolite fragmentation pattern.

CX-3543 is consumed moderately to quickly at concentrations from about 12-20 uM, while it is consumed more slowly at or below 12 uM (about 60% of original drug remaining) and very slowly at 1 uM. These observations suggest that CX-3543 is consumed by hepatocytes at an apparent $K_m$ that is higher than 20 uM. Although the mechanism is not necessary to practice the invention, the high $K_m$ would explain the biphasic kinetics (i.e., a second enzyme component with a low $K_m$ may be involved).

Four potential metabolites with m/z 303, 347, 348 and 391 were identified by comparing the zero time point to the 120 min time point and looking for peak in the 120 min point that were not in the zero point. Attempts were made to collect product ion spectra of these species, and only the spectrum for m/z 348 was obtained, though the sensitivity was very low. Comparing the product ion spectrum of m/z 348 to that of the parent does not reveal any obvious molecular similarity, suggesting that none of the four metabolites are related to CX-3543, although this observation does not exclude them from being metabolites.

The peak heights of the potential metabolites are relatively small, though the significance of the size cannot be determined due to the possible difference in ionization potentials between the parent and the metabolites. This observation suggests that no single major metabolite is present in the hepatocyte incubation medium with CX-3543, but rather several minor metabolites. The minor role of hepatic elimination minimizes the likelihood of drug-drug interactions with co-administered compounds that are inducers or inhibitors of liver enzymes.

Example 57

CX-3543 In Vivo Activity

CX-3543 was tested against a number of cancer xenograft models to determine the in vivo efficacy. HCT-116 and PC-3 tumor-bearing nu/nu or MiaPaCa tumor-bearing SCID mice were administered reference and testing compounds on schedules indicated in figure legends. Tumor measurements were taken with calipers every other day or twice a week starting from the first day of dosing and body weights were measured at the same time points. Tumor volumes were calculated from the standard formula, $W^2 \times L/2$. c-MYC mRNA expression was measured with QPCR from all tumor samples following the final dose. 18S ribosomal RNA was used as a housekeeper and also quantified with QPCR.

Figure 9:
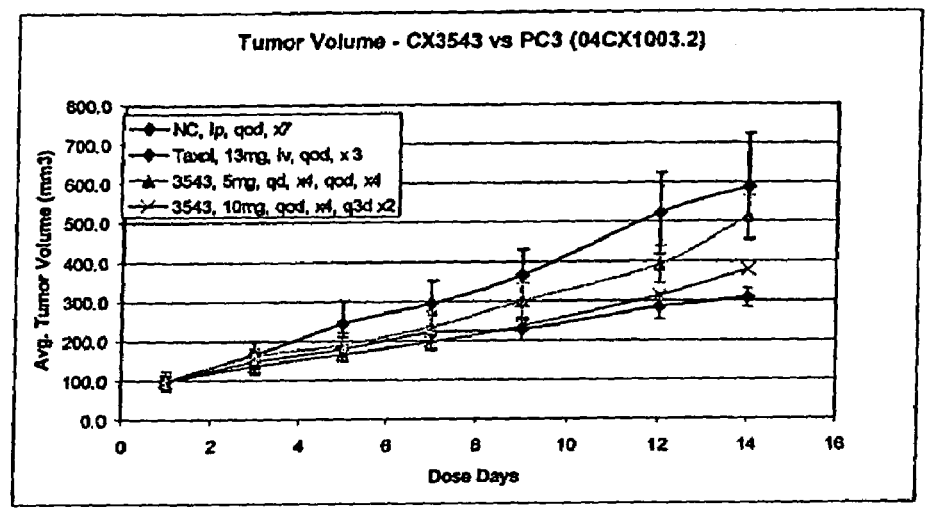
FIGS. 9 and 10 show the antitumor activity of CX-3543 in PC3 prostate cancer and MiaPaCa xenograft models respectively.
Figure 10:
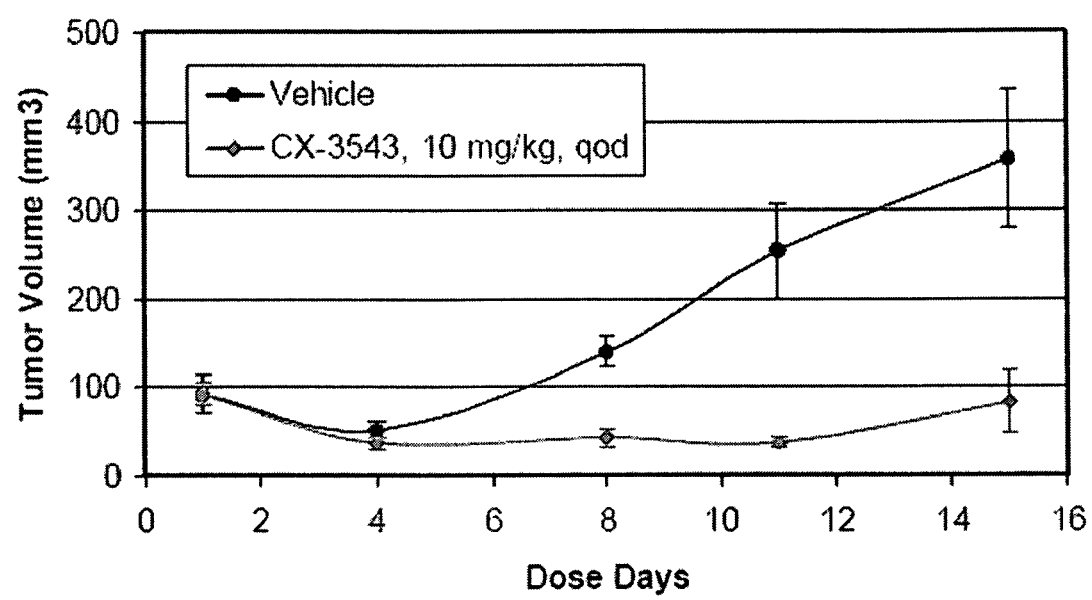

In vivo, CX-3543 induced significant tumor growth inhibition in refractory prostate cancer (PC-3), colorectal cancer (HCT-116) and pancreatic cancer (MiaPaCa) xenograft models, all of which express high levels of c-Myc. Efficacy in the HCT-116 colorectal tumor model was observed with doses of 10, 15 and 20 mg/kg (FIG. 8), and dose-dependent lowering of c-Myc mRNA expression relative to control (18s rRNA) was observed in tumor tissue isolated from the treated animal groups, with 85% lowering in the 20 mg/kg group. Significant tumor growth inhibition was also observed in the PC-3 (FIG. 9) and MiaPaCa (FIG. 10) models with 5, 10 and 15 mg/kg administered i.p. on a q.o.d. schedule.

Example 58

Evaluation of Compound Efficacy in Tumor Suppression

An experiment for evaluating the efficacy of compounds of the present invention in athymic nude mouse models of human carcinoma is designed as follows. Male or female animals (mouse, Sim) (NCR, nu/nu) aged five to six weeks and weighing more than 20 grams will be used. The animals are purposely bred and will be experimentally naive at the outset of the study. Tumors will propagate either from injected cells or from the passage of tumor fragments. Cell lines to be used include, but are not limited to, MiaPaca, PC3, HCT116, HT29 and BT474.

Cell implantation. One to ten million cells suspended in 0.1 ml culture media with or without Matrigel (Collaborative Biomedical Products, Inc, Bedford, Mass.) will be inoculated subcutaneously in the right flank of sixty animals. There will only be one injection per animal. Within 7-14 days of injection tumors will develop to a study use size of approximately 1.0 cm³. A small subset (<10/60) animals will be considered Donors and tumors will be grown 10-28 days and to a size of 1.5 cm³ in order to be used for serial transplantation. For estrogen dependent tumor lines (i.e. BT474), female mice will have estrogen pellets implanted subcutaneously between the shoulder blades via 10 gauge trocar three days before cells or tumor fragments are injected/implanted.

Fragment transplantation. Donor animals with be euthanized and tumors surgically excised and cut into 2 mm³ size fragments using aseptic technique. Animals to be implanted will be lightly anesthetized with isoflurane. The area to implanted will be cleansed with 70% alcohol and betadine. A single fragment will then be implanted subcutaneously using a trocar.

Efficacy studies. Groups of 50-60 tumor bearing animals will be randomly divided into three to eight groups containing 7 animals each, as described in Table 7.

TABLE 7

| Group No. | Number of Males/Females | Dose Level | Dose Vol. (µL) | Dose Solution Conc. (mg/mL) | Number Euthanized on: Day 28-42 |
|---|---|---|---|---|---|
| 1 | N = 7 | Negative Control* | 250 | | all |
| 2 | N = 7 | Positive Control** | 10-400 IP<br>10-250 IV<br>125-500 PO | 2 to 5 IP<br>2.5 to 5 IV<br>≦10 PO | all |
| Groups 3-8 | N = 7/grp <56 total | Test Compound 1 to 25 IP 1 to 50 IV 50 to 200 PO | 10-400 IP<br>10-250 IV<br>125-500 PO | 2.5 to 5 IP<br>2.5 to 5 IV<br>10 PO | all |

*Vehicle/Diluent
**Commercially available anticancer compounds including, but not limited to, Taxol, CPT11 and Gemcitabine will be used as positive controls.

Dosing Procedure. Compounds will be administered QD, QOD, Q3D or once weekly via IP, IV (lateral tail vein) or PO. Animals will be dosed in a systematic order that distributes the time of dosing similarly across all groups. For bolus IP and PO dosing, animals will be manually restrained. For IV bolus dosing or short term IV infusion (one minute), animals will be mechanically restrained but not sedated. Disposable sterile syringes will be used for each animal/dose.

Figure 8:
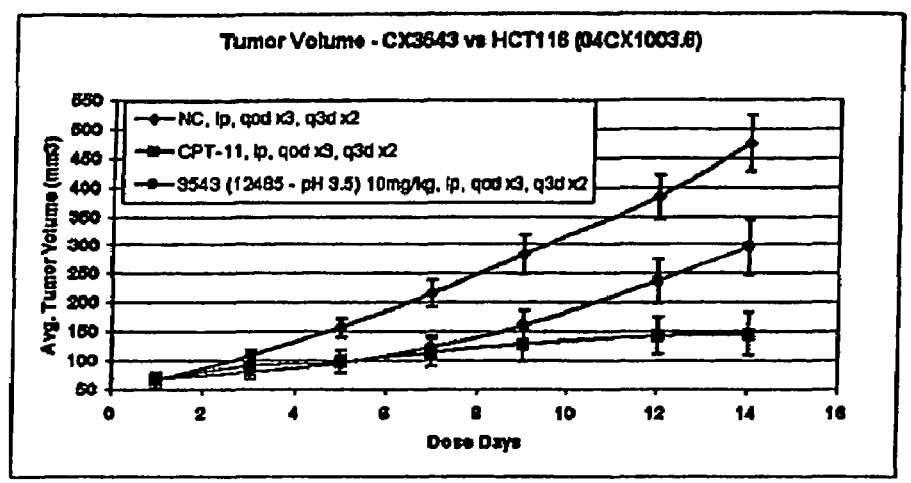
FIG. 8 shows the antitumor activity of CX-3543 in HCT-116 colorectal cancer xenograft model.

As indicated in FIG. 8, efficacy was observed in the HCT-116 colorectal model with doses of 10, 15 and 20 mg/kg. Efficacy was also observed in the PC-3 (FIG. 9) and MiaPaCa (FIG. 10) models with doses of 5, 10 and 15 mg/kg.

Example 59

Evaluation of Maximum Tolerated Doses

An experiment for evaluating the maximum tolerate dose (MTD) of compounds of the present invention is designed as follows. Selection for animal models is as previously described in Example 58.

Acute Toxicity Studies. To determine the MTD after a single dose, sixty naive animals will be randomly divided into groups containing 10 animals (5 male and 5 female) and will receive either one compound via two routes of administration or two compounds via a single route of administration. A single 50 mg/kg IV dose has been shown to be tolerated, and is used as the preliminary low dose levels. The low dose for oral studies is based on projected tolerability and will be adjusted downward if necessary. Designed dose levels, dose volumes and dose solution concentration are described in Table 8.

TABLE 8

| Group No. | Number of Males and Females | Dose Level (mg/kg) | Dose Vol. (µL) | Dose Solution Conc. (mg/mL) | Number Euthanized on: Day 7 |
|---|---|---|---|---|---|
| 1 | N = 5 M<br>N = 5 F | Test Compound #1<br>50 IV<br>100 PO | 250 IV<br>500 PO | 5 IV<br>5 PO | all |
| 2 | N = 5 M<br>N = 5 F | Test Compound #1<br>75 IV<br>200 PO | 250 IV<br>500 PO | 8.25 IV<br>10 PO | all |
| 3 | N = 5 M<br>N = 5 F | Test Compound #1<br>100 IV<br>300 PO | 250 IV<br>500 PO | 10 IV<br>15 PO | all |
| 4 | N = 5 M<br>N = 5 F | Test Compound #2<br>50 IV<br>100 PO | 250 IV<br>500 PO | 5 IV<br>5 PO | all |
| 5 | N = 5 M<br>N = 5 F | Test Compound #2<br>75 IV<br>200 PO | 250 IV<br>500 PO | 8.25 IV<br>10 PO | all |
| 6 | N = 5 M<br>N = 5 F | Test Compound #2<br>100 IV<br>300 PO | 250 IV<br>500 PO | 10 IV<br>15 PO | all |

SubChronic Studies. To characterize dose-response relationships following repeated dosing, twenty-five naive animals will be randomly divided into groups containing 5 animals each as described in Table 9. Each two week study will test only one compound via a single routes of administration at an optimal dose derived from data collected in prior acute toxicity studies.

TABLE 9

| Group No. | Number of Males or Females | Dose Level (mg/kg) | Dose Vol. (µL) | Dose Solution Conc. (mg/mL) | Number Euthanized on: Day 14 |
|---|---|---|---|---|---|
| 1 | N = 5 | Negative Control | 250 IV<br>500 PO | Depends on Dose Level | all |
| 2 QD | N = 5 | Test Compound As Determined in MTD Studies | 250 IV<br>500 PO | Depends on Dose Level | all |
| 3 QOD | N = 5 | Test Compound As Determined in MTD Studies | 250 IV<br>500 PO | Depends on Dose Level | all |
| 4 Q3D | N = 5 | Test Compound As Determined in MTD Studies | 250 IV<br>500 PO | Depends on Dose Level | all |
| 5 Q7D | N = 5 | Test Compound As Determined in MTD Studies | 250 IV<br>500 PO | Depends on Dose Level | all |

Dosing Procedure. Compounds will be administered QD, QOD, Q3D or Q7D via IV (lateral tail vein) or PO. Animals will be dosed in a systematic order that distributes the time of dosing similarly across all groups. For PO dosing, animals will be manually restrained. For IV bolus dosing or short term IV infusion (one minute), animals will be mechanically restrained but not sedated. Disposable sterile syringes will be used for each animal/dose.

Example 60

Evaluation of Pharmacokinetic Properties

Pharmacokinetic studies for evaluating pharmacokinetic properties of compounds are designed as follows. Male animals (mouse, Balb/c or rat, SD) aged five to six weeks and/or rats weighing more than 200 grams will be used for testing. Twenty animals will randomly divided into 4 groups, as shown in Table 10. One group will be untreated and samples taken to be used as a base line. The other three groups will be treated and administered a single dose of compounds by intravenous injection.

TABLE 10

| Group No. | No. of Animals | Time followed by injection (h) |
|---|---|---|
| 1 | 2 | Naïve |
| 2 | 6 | .25, 2, 8 |
| 3 | 6 | .5, 4, 12 |
| 4 | 6 | 1, 6, 24 |

Dosing Procedure. Compounds will be administered via IV (lateral tail vein), IP or PO. Animals will be dosed in a systematic order that distributes the time of dosing similarly across all groups. For IP and PO dosing, animals will be manually restrained. For IV bolus dosing or short term IV infusion (one minute), animals will be mechanically restrained but not sedated. Disposable sterile syringes will be used for each animal/dose.

Approximately 0.5 ml of blood will be collected from the naive animals via cardiac puncture prior to the first dose. Terminal blood samples (0.5 ml) will be collected via cardiac puncture from two animals per group per time point according to the above chart. All samples will be placed in tubes containing lithium heparin as anticoagulant and mixed immediately by inverting. They will be centrifuged and the plasma flash frozen in liquid nitrogen, stored at −70° C. or greater and analyzed for drug levels.

Figure 11:
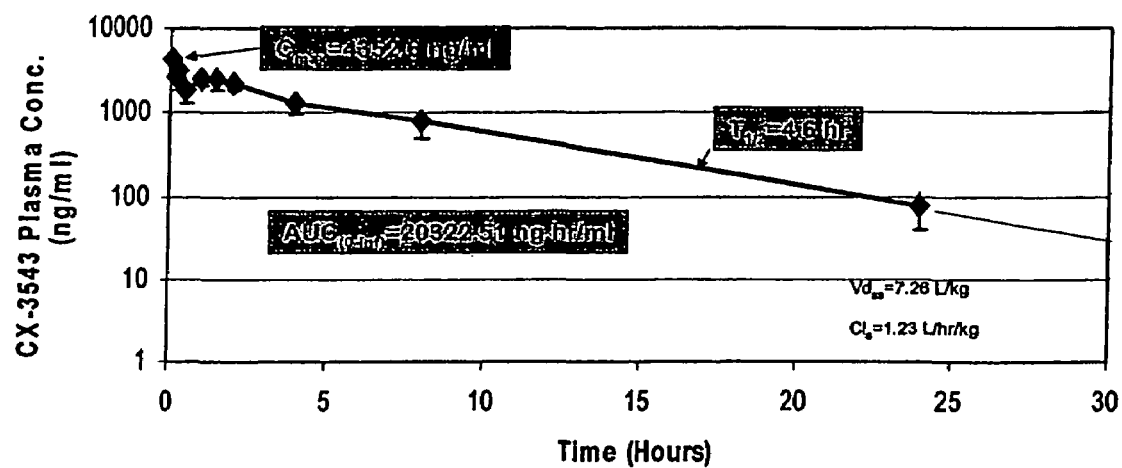
FIG. 11 shows a pharmacokinetic profile of CX-3543 in mice.

A pharmacokinetic study to determine the time course of CX-3543 disposition was conducted in mice following intravenous administered of 25 mg/kg of CX-3543. Regular sampling was undertaken throughout a 24 hour period after IV dose administration, and the key derived pharmacokinetic parameters were derived. FIG. 11 provides the graphical representation of the pharmacokinetic profile of CX-3543 from which key parameters (Table 11) were obtained.

In FIG. 11, $C_{max}$ is the maximum CX-3543 plasma concentration attained (expressed in ng/ml); $AUC_{0-inf}$ is the area under the CX-3543 plasma concentration versus time curve, extrapolated from time zero to infinity (expressed in ng.hr/ml); $T_{1/2}$ is the terminal half life of CX-3543 (expressed in hr); $Vd_{ss}$ is the volume of distribution of CX-3543 at steady state (expressed in L/kg); and $Cl_S$ is the systemic clearance of CX-3543 (expressed in L/hr/kg). As shown in FIG. 11, CX-3543 has a $C_{max}$ of about 5353 ng/mL; an $AUC_{0-inf}$ of about 20332.5 ng.hr/ml; and a $T_{1/2}$ of about 4.6 hr.

TABLE 11

| Parameter | value | Units |
|---|---|---|
| $C_{max}$ | 4353.0 | ng/mL |
| $AUC_{0\text{-}inf}$ | 20322.5 | ng·hr/mL |
| $T_{1/2}$ | 4.6 | hr |
| $Vd_{ss}$ | 7.26 | L/kg |
| $Cl_S$ | 1.23 | L/hr/kg |

Example 61

Determination of In Vitro Metabolic Stability in Hepatocytes

The protocol is designed to determine the stability of a new chemical entity in the presence of hepatocytes (human, rat, dog, monkey) in in vitro incubations. The test article will be incubated with hepatocytes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls are tolbutamide, desipramine and naloxone, and these compounds have defined pharmacokinetics corresponding to low, moderate and high in vivo clearance values, respectively.

Metabolic Stability Study. Generally, solutions of the test compounds are prepared along with a cocktail solution of metabolism controls that are intended to provide a reference for enzyme activity. The reactions are initiated by combining these pre-warmed solutions with hepatocyte suspensions and with a media control solution. Control zero samples are taken from these reactions immediately after initiation. Additional samples are taken at appropriate time points. Each sample is immediately placed in a terminating solution (acidified acetonitrile containing internal standard) to stop the reaction. Hepatocyte blank suspensions and test compound standard solutions are prepared.

Samples and standards for the test compound as well as appropriate blanks are subjected to a custom sample preparation procedure and analyzed for the parent and/or metabolite form of the test compound using high-performance liquid chromatography coupled with tandem mass spectrometry. Samples and standards for the metabolism controls are subjected to the analytical method described herein. Where Krebs Henseleit buffer is added, the buffer is bubbled with 5% $CO_2$ in air at room temperature for 5-10 minutes before adding BSA to a final concentration of 0.2% w/v. The volume of terminating solution and the method of sample preparation will be determined for the test article during method development.

Test Article/Media Solution. A solution of the test article will be prepared by adding an appropriate volume of the stock solution to 0.2% BSA in Krebs Henseleit buffer equilibrated with 5% $CO_2$ in air. The final concentration will be 20 µM and the final assay concentration at initiation of the reactions will be 10 PM.

Metabolism Controls/Media Solution. A solution of tolbutamide, desipramine and naloxone will be prepared by adding an appropriate volume of each 10 mM stock solution to 0.2% BSA in Krebs Henseleit buffer equilibrated with 5% $CO_2$ in air. The final concentration will be 20 µM for each metabolism control and the final assay concentration will be 10 µM at initiation of the reactions.

Hepatocyte Suspension Solution. The hepatocytes will be thawed and isolated according to the vendor (Invitrotech, Inc.) instructions. During the final step of the procedure, the viability of the cells will be determined using the method of trypan blue exclusion. Then, the hepatocytes will be resuspended with 0.2% BSA in Krebs Henseleit buffer equilibrated with 5% $CO_2$ in air so the final concentration is 0.5 million viable cells/mL. The concentration at the initiation of the reactions will be 0.25 million viable cells/mL.

Initiating Test Article Incubation. Equal volumes of the test article solution prepared will be dispensed into four polypropylene scintillation vials. The vials are pre-warmed for 5-10 minutes at 37° C. with 95% humidity and 5% $CO_2$. Equal volumes of 0.2% BSA in Krebs Henseleit buffer equilibrated with 5% $CO_2$ in air will be added to two of the vials and mixed thoroughly. Immediately after initiating the reaction, a timer is started and a 100 µL sample is removed from each vial and placed into a 1.7-mL centrifuge tube containing a suitable volume of terminating solution. These samples will serve as media controls to check for non-enzymatic degradation and non-specific binding to the vessel.

Equal volumes of the hepatocyte suspension prepared will be added to two of the vials and mixed thoroughly. Immediately after initiating the reaction, a timer is started and a 100 µL sample is removed from each vial and placed into a 1.7-mL centrifuge tube containing a suitable volume of terminating solution. All vials are placed in an incubator maintained at 37° C., 95% humidity and 5% $CO_2$.

Initiating Metabolism Control Incubation. Equal volumes of the metabolism control solution prepared will be dispensed into two polypropylene scintillation vials. The vials are pre-warmed for 5-10 minutes at 37° C. with 95% humidity and 5% $CO_2$. Equal volumes of the hepatocyte suspension prepared will be added to each of the two vials and mixed thoroughly. Immediately after initiating the reaction, a timer is started and a 100 µL sample is removed from each vial and placed into a 1.7-mL centrifuge tube containing an equal volume of terminating solution. All vials are placed in an incubator maintained at 37° C., 95% humidity and 5% $CO_2$.

Sample Collection. The vials will be gently shaken and samples (100 µL) will be removed and placed into a 1.7-mL centrifuge tube containing an appropriate volume of terminating solution according to the following schedule: Test article samples are taken after 5, 10, 15, 30, 60, 90 and 120 minutes; metabolism control samples are taken after 30, 60, 90 and 120 minutes. Immediately after removal of the samples, the vials are placed back in the incubator until the last sample is collected.

Blank Preparation. A sample (100 µL) of the hepatocyte suspension will be added to an equal volume of 0.2% BSA in Krebs Henseleit buffer and mixed thoroughly. A 100 µL sample of this solution will be removed and placed into a 1.7-mL centrifuge tube containing the same volume of terminating solution used for the test article reaction. A sample of the incubation medium (0.2% BSA in Krebs Henseleit buffer) will be placed into a 1.7-mL centrifuge tube containing the same volume of terminating solution used for the test article reaction.

Sample Preparation and Analysis. All vials will be centrifuged at 16,000 g for 3 minutes. The supernatants will be placed into polypropylene autosampler vials and stored at 4° C. (<1 day) or −70° C. (>1 day) until analysis. The test article solutions will be analyzed using HPLC/MS/MS conditions according to standard procedures. In one example, the following HPLC conditions may be used: column (Phenomenex Synergi Hydro-RP, 100.0×2.0 mm, 5 µm); guard column (Phenomenex C18, 4.0×2.0 mm, 5 µm); flow rate (0.3 mL/min); column temperature at 45° C.; injection volume at 10 µL; and ambient autosampler temperature.

Example 62

Determination of In Vitro Metabolic Stability in Microsomes

The protocol is designed to determine the stability of a new chemical entity in the presence of liver microsomes (human, rat, dog, monkey) in in vitro incubations. The test article will be incubated with microsomes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls are tolbutamide, desipramine and testosterone, and these compounds have defined pharmacokinetics corresponding to low, moderate and high in vivo clearance values, respectively.

Metabolic Stability Study. Generally, six pre-warmed reaction vials with 100 µL of a solution containing 50 mM potassium phosphate, pH 7.4, 2.6 mM $NADP^+$, 6.6 mM glucose 6-phosphate, 0.8 U/mL of glucose 6-phosphate dehydrogenase and 1, 10 or 50 µM of the test compound were prepared. Similar reactions with metabolic controls representing low (tolbutamide), moderate (desipramine), and high (testosterone) clearance compounds were run simultaneously with the same enzyme solution. The reactions were initiated by adding 100 µL of a pre-warmed enzyme solution and incubated at 37° C. The zero time-point reaction was prepared by adding 50 µL of acetonitrile (containing internal standard) to the test compound/cofactor solution prior to adding the enzyme solution. After 15, 30, 60, 90 and 120 minutes, a reaction tube was removed from the water bath and the reaction was terminated with 50 µL of acetonitrile containing internal standard. The reactions were extracted and the samples were analyzed for the parent form of the test compound and one metabolite using a C18 column with MS/MS detection. Each assay was performed in duplicate.

Cofactor/Test Compound Solution Concentrations. A stock solution of 10 mM NCE will be prepared in 10% DMSO (v/v). For all assays, a 2, 20 or 100 µM solution of the test article will be prepared in 50 mM potassium phosphate, pH 7.4, 2.6 mM $NADP^+$, 6.6 mM glucose 6-phosphate and 0.8 U/mL of glucose 6-phosphate dehydrogenase (cofactor solution).

Cofactor/Metabolism Control Solution Concentrations. Stock solutions of the metabolism controls (tolbutamide, desipramine, and testosterone) will be used to prepare a 6 µM solution of the metabolism control in cofactor solution.

Enzyme Solution Concentrations. The enzyme solutions will be prepared by adding liver microsomes to 50 mM potassium phosphate, pH 7.4, to a final concentration of 1 mg/mL. All microsomes were purchased from XenoTech or InvitroTech, Inc.

Initiating the Reactions. All the reaction tubes will be pre-warmed at 37° C. in a water bath for about 3-5 minutes. The zero time-point control reaction will be prepared for each replicate by adding 50 µL of acetonitrile containing 15.9 µM nebularine (internal standard) to 100 µL of cofactor solution to inactivate the enzymes, and then vortex mixing. The reactions will be initiated by adding 100 µL of the enzyme solution to each of the tubes and vortex mixing. All the tubes, including the zero time-point control, will be incubated in a 37° C. water bath. The final concentrations of all components in the tubes after initiating the reactions are 50 mM potassium phosphate, pH 7.4, 1.3 mM $NADP^+$, 3.3 mM glucose 6-phosphate, 0.4 U/mL of glucose 6-phosphate dehydrogenase, 0.5 mg/mL liver microsomes and 1, 10 or 50 µM test article.

Terminating and Extracting the Reactions. After 15, 30, 60, 90 and 120 minutes at 37° C., the reactions will be terminated by the addition of 150 µL of acetonitrile containing 15.9 µM nebularine (internal standard). The zero time-point control was removed from the water bath after 120 minutes. All vials will be centrifuged at 16,000 g for 3 minutes. The supernatants will be placed into polypropylene autosampler vials and stored at 4° C. (<1 day) or −70° C. (>1 day) until analysis.

Analysis of Test Article Solutions. The test article solutions will be analyzed using HPLC/MS/MS conditions according to standard procedures, such as those described in Example 60.

Example 63

Bacterial Mutagenicity Test

This Mutagenicity Assessment (Ames Assay) evaluated the potential of the test article extracts to induce histidine (his) reversion in *S. typhimurium* (his− to his+) or tryptophan (trp) reversion in *E. coli* (trp− to trp+) caused by base changes or frameshift mutations in the genome of tester organisms.

This plate incorporation assay was conducted with five strains of *Salmonella typhimurium* (TA97a, TA98, TA100, TA102, and TA1535) and one strain of *Escherichia coli* (WP2-uvrA$^-$) in the presence and absence of an exogenous mammalian activation system (S9). The test article was dissolved in 5% dextrose. A series of dilutions were then prepared in saline just prior to testing. A Range Finding Study was conducted for this assay to determine the appropriate doses for definitive mutagenicity assessment.

All negative controls were within or slightly below normal ranges and all positive controls showed suitably increased reversion rates, indicating a valid assay. Therefore, this assay was capable of correctly identifying potential mutagens and non-mutagens. In this assay, the test article did not induce substantial increases in reversion rates of the type that are associated with mutagenesis. Although some test article toxicity was noted, it was at moderate levels. However, as the revertant colony counts appeared normal, the toxicity was not causing interference. As none of the tester strains showed an increase in reversion rates when treated with the test article, the test article is determined not to have caused an increase in point mutations, exchanges or deletions. Based on these assay conditions, CX-3543 is considered non-mutagenic in this assay.

Test Material Preparation

A stock solution of test article was prepared at 20.0 mg/mL as follows: 1.0 g test article was added to 15.0 mL of 0.1 HCl for 1 minute. The test article was stirred for 15 minutes at room temperature. Next 33.0 mL of deionized water was added and allowed to stir for 30 minutes. The pH was then adjusted to 3.53. Lower doses were prepared by dilution in 5% dextrose from this stock immediately prior to use. To minimize any change of degradation, the test article solutions were kept on ice after preparation and until just prior to dosing procedures. The test article was administered in vitro, through a solvent compatible with the test system.

Genotypic Characterization of the Test Strains

Working stocks of test strains will be confirmed for genotypic markers and acceptable spontaneous reversion rates. All working stocks should demonstrate a requirement for histidine or tryptophan (*E. coli* only). Additionally, the following conformations will be made with each assay, as appropriate: sensitivity to crystal violet due to the rfa wall mutation (strains: TA100, TA98, TA97a, TA102, TA1535 and WP2-uvrA⁻); sensitivity to ultraviolet light due to the deletion of the uvrB gene (uvrA in *E. coli*) (strains: TA97a, TA98, TA100, TA1535 and WP2-uvrA⁻); resistance to ampicillin due to the presence of the pKM101 plasmid (strains: TA97a, TA98, TA100, TA102); resistance to tetracycline due to the presence of the pAQ1 plasmid (strain: TA102) and spontaneous reversion rates for the strains will be determined using the negative controls.

Test articles that are water-soluble will be dissolved in isotonic saline. Test articles that are not water-soluble will be dissolved in dimethylsulfoxide (DMSO). If DMSO is anticipated to cause adverse reactions with the test article, the test article will be suspended in carboxymethylcellulose. To aid in dissolution, heating, vigorous vortexing or alternative solvents may be employed.

Test System

This study was conducted in accordance with the plate incorporation methodology originally described by Ames (Ames et al., *Mutation Research* (1975) 31:347-364) and updated by Maron and Ames (Maron et al, *Mutation Research* (1983) 113:173-215). This assay has historically been used to detect mutation in a gene of a histidine requiring strain to produce a histidine independent strain or concordantly, to detect mutation in a gene of a tryptophan requiring strain to produce a tryptophan independent strain. In addition, it has been shown to detect diverse classes of chemical mutagens which produce heritable DNA mutations of a type which are associated with adverse effects.

The *Salmonella typhimurium* strains used in this assay, TA97a, TA98, TA100, and TA102 (as described by Maron and Ames, supra; Green (Green et al., *Mutation Research* (1976) 38:33-42); and Brusick (Brusick et al., *Mutation Research* (1980) 76:169-190)) were received from The Ames Laboratory, Department of Biochemistry, University of California, Berkeley, Calif. 94720. *S. typhimurium* strain TA1535 and *E. coli* strain Wp2-uvrA⁻ were received from American Type Culture Collection, Manassas, Va. (ATCC numbers: 29629 and 49979, respectively). All working stocks of test strains will be confirmed for genotypic markers and acceptable reversion rates. Working stocks should demonstrate a requirement for histidine or tryptophan (*E. coli* only).

Experimental Methods

Master plates of the tester strains were prepared from frozen working stocks. To create working cultures for each bacterial strain used in the assay, a single colony was transferred from the master plate into Oxoid nutrient broth and incubated, with shaking, at 37±2° C. until an optical density (at 650 nm) of 0.6-1.6 was reached. This overnight culture was used for the mutagenicity test and for genotypic confirmation. Genotype tests were performed.

For both the dose range and mutagenicity test, a top agar consisting of 0.6% Difco agar in 0.5% NaCl was melted and a solution of 0.5 mM L-histidine/0.5 mM biotin or 0.5 mM L-tryptophan was added to the melted top agar at a ratio of 10 mL per 100 mL agar, as required. The supplemented agar was aliquotted, 2 mL per tube and held at 45-47° C. To prepare the top agar for treatment, 0.1 mL of the test article or control, 0.1 mL of the bacterial culture and 0.5 mL of phosphate buffered saline were added to the molten agar. The mixture was briefly vortexed and poured onto a room temperature minimal glucose agar plate (1.5% Difco agar, 2% glucose, in Vogel-Bonner medium E). Metabolic activation was provided by adding 0.5 mL of the S9 mix in place of the PBS. The plates were allowed to harden and then incubated 48-72 hours at 37±2° C. All plates were counted using an automatic image analysis system. Negative control and test article treated plates were also examined for the presence of a bacterial lawn.

Exogenous Metabolic Activation

The in vitro metabolic activation system used in this assay was comprised of Sprague Dawley rat liver enzymes and a cofactor pool. The enzymes are contained in a preparation of liver microsomes (S9 fraction) from rates treated with Arochlor to induce the production of enzymes capable of transforming chemicals to more active forms. Immediately prior to use, the S9 was thawed and mixed with a cofactor pool to contain 5% S9, 5 mM glucose 6-phosphate, 4 mM β-nicotine-adenine dinucleotide phosphate, 8 mM $MgCl_2$ and 33 mM KCl in a 200 mM phosphate buffer at pH 7.4. The S9 was purchased from Moltox (Boone, N.C.) and maintained frozen at less than −70° C.

Dose Levels and Replicates

The test article was tested in triplicate at five dose levels (20.0, 10.0, 5.0, 2.5, and 1.25 mg/mL) along with appropriate vehicle (5% dextrose) and positive controls in the dose range assay. This was equivalent to 2.0, 1.0, 0.5, 0.25, and 0.125 mg/plate.

For the definitive assay, three dose levels were chosen (10.0, 10.0, and 5.0 mg/mL). This was equivalent to 2.0, 1.0, and 0.5 mg/plate. All treatments, including negative and positive control, were plated in triplicate against test strains TA97a, TA98, TA100, TA102, TA1535, and WP2-uvrA⁻ in the presence and absence of metabolic activation. These doses were chosen based on inducing a range of test article toxicity and maximizing the applied dose. No interfering reductions were noted in the background lawn of the test article treated plates during the course of the dose range assay, nor were there marked reductions in the number of spontaneous mutations on these plates. Both endpoints serve as toxicity indicators in this assay.

Control Substances

Control substances were prepared and used in the mutagenicity assay as described in Table 12.

TABLE 12

| Control | Strain | Metabolic Activation | Concentration |
|---|---|---|---|
| ICR-191 Acridine | TA97a | No | 1.0 μg/plate |
| 2-nitrofluorene | A98 | No | 10.0 μg/plate |
| Sodium azide | TA100 and TA1535 | No | 1.5 μg/plate |
| 1-methyl-3-nitro-1-nitrosoguanidine | WP2-uvrA⁻ | No | 4.0 μg/plate |
| 2-aminoanthracene | all strains (except TA1535) | Yes | 10.0 μg/plate |
| 2-aminoanthracene | TA1535 | Yes | 1.6 μg/plate |

Negative (Vehicle) Control

Tester strains were plated with untreated dextrose solution at the corresponding maximum concentration (0.1-1 mL), with and without S9. These plates served as the negative controls and provided information regarding background lawn and revertant colony formation.

Dose Range Assay

The initial dose range assay started at the maximum concentration of 2.0 mg/plate. The four lower doses tested were diluted in a 1:2 dilution series. No interfering levels of toxicity were noted at any dose or as a result of metabolic activation. Strain TA100 also met all of the characteristic genotypic qualifications; it retained its characteristic sensitivity to positive controls, was resistant to ampicillin, sensitive to crystal violet, tetracycline and UV irradiation. Based on the information from this range finding study, three doses were chosen for the definitive assay (2.0, 1.0, and 0.5 mg/plate). The results are presented in Table 13.

TABLE 13

TA100 Colony Count Data (Dose Range)

| | With S9 Activation | | | | | | | Without S9 Activation | | | | | | |
|---|---|---|---|---|---|---|---|---|---|---|---|---|---|---|
| | 2.0 mg/ plate | 1.0 mg/ plate | 0.5 mg/ plate | 0.25 mg/ plate | 0.125 mg/plate | Dextrose | 2-AA | 2.0 mg/ plate | 1.0 mg/ plate | 0.5 mg/ plate | 0.25 mg/ plate | 0.125 mg/plate | Dextrose | Sodium Azide |
| Rep 1 | 131 | 147 | 190 | 177 | 177 | 108 | 857 | 117 | 120 | 154 | 148 | 144 | 139 | 631 |
| Rep 2 | 137 | 168 | 193 | 189 | 175 | 124 | 949 | 122 | 134 | 137 | 146 | 135 | 121 | 702 |
| Rep 3 | 111 | 175 | 182 | 185 | 175 | 128 | 655 | 126 | 147 | 161 | 154 | 153 | 137 | 615 |
| Mean | 126.3 | 163.3 | 188.3 | 183.7 | 175.7 | 120.0 | 820.3 | 121.7 | 133.7 | 150.7 | 149.3 | 144.0 | 132.3 | 649.3 |
| SD | 13.6 | 14.6 | 5.7 | 6.1 | 1.2 | 10.6 | 150.4 | 4.5 | 13.5 | 12.3 | 4.2 | 9.0 | 9.9 | 46.3 |
| FI | 1.1 | 1.4 | 1.6 | 1.5 | 1.5 | NA | 6.8 | 0.9 | 1.0 | 1.1 | 1.1 | 1.1 | NA | 4.9 |

*Positive control response is two fold or greater than the negative control: TRUE Reverse Mutation Assay Each separate bacterial strain, with and without S9, was considered a separate experiment with its own concurrent positive and vehicle controls. All plates were scored with an automated colony counter and a printout of the data was made. The positive controls consisted of direct-acting mutagens and mutagens requiring metabolic transformation. A two-fold or greater increase in reversion rates was observed for all strains with the appropriate positive control. The negative control article reversion rates for each strain were within or slightly below the expected ranges from laboratory historical data. Accordingly, this assay met the criteria for a valid assay.

An induced positive result for any strain would be demonstrated by at least a two-fold increase in the number of revertant colonies per plate over the negative control values. The test article did not cause this type of increase in revertant colonies for any strain. In general, the top dose caused moderate levels of toxicity, as was noted by a reduction in the background lawn.

Genotypic Characterization of the Test Strains

Each test strain was confirmed for genotypic markers and acceptable spontaneous reversion rates to ensure the strains maintained the characteristics which make them sensitive to mutagenic activity. All strains demonstrated acceptable levels of sensitivity to crystal violet (due to the rfa wall mutation) and tetracycline (due to the absence of the pAQ1 plasmid) with the exception of TA102. Strain TA102 is known to be resistant to tetracycline (due to the presence of the pAQ1 plasmid) and appropriately grew in this genotype test (serving as a control for this test). Strains TA97a, TA100, TA98, TA1535, and WP2-uvrA⁻ demonstrated appropriate sensitivity to ultraviolet light (due to the deletion of the uvrB/uvrA gene). Again, TA102 was plated as a control for the test and did appropriately grow despite exposure to ultraviolet irradiation. Strains TA97a, TA98, and TA100 demonstrated appropriate resistance to ampicillin (due to the presence of the pKM101 plasmid). Strain WP2-uvrA⁻ demonstrated sensitivity to ampicillin. Spontaneous reversion rates were within or slightly below historical in-house ranges, proving that the working stocks retained their characteristic requirement for histidine.

Example 64

In Vitro Chromosome Aberration Assay in CHO Cells

The Chromosomal Aberration Assay is one of several in vitro tests that can be used to screen materials for their potential genetic toxicity. Chromosome aberrations are mutations which have been associated with carcinogenesis. Therefore, the chromosome aberration assay is relevant for testing potential mutagens and carcinogens (Galloway et al., *Environ. Mut.* (1985) 7:1-51; Galloway et al., *Environ. Mut.* (1987) 10:1-175). This Chromosome Aberration Assay evaluated the potential of the test article extracts to induce damage in Chinese Hamster Ovary Cells (CHO). This test was conducted in the presence and absence of an exogenous mammalian activation system (S9) over three treatment periods.

All negative control treated preparations demonstrated normal levels of spontaneously occurring aberrations while positive control treated cultures demonstrated dramatic, dose dependent increases in aberrant chromosomes. Substantial levels of cytotoxicity were noted at the three highest treatment levels. Test article precipitates were noted in cultures treated with the highest dose level. The levels of aberrant chromosomes were not outside of normal negative ranges. Based on these study conditions, the test article is considered non-mutagenic in this test system.

This assay is designed to determine whether a test material is clastogenic, i.e., whether it has the capacity to break chromosomes. Clastogenicity is an important endpoint because it is through chromosomal breakage and inappropriate rejoining that certain oncogenes (e.g., myc) can be activated and certain tumor suppressor genes (e.g., those suppressing retinoblastoma) can be inactivated). In this test, mammalian Chinese Hamster Ovary (CHO) cells are exposed to the test material and blocked in metaphase using a spindle poison. Visualization of chromosomes is performed microscopically after hypotonic swelling, fixing and staining the treated CHO cells. Agents found to be capable of inducing chromosome breakage have a high probability of being carcinogens and also have the potential for inducing heritable chromosomal defects.

The CHO-K, cell line (ATCC number: CCL-61) is a pro-line auxotroph with a modal chromosome number of 20 and a population doubling time of 10-14 hours. This system has been shown to be sensitive to the clastogenic activity of a variety of chemicals (Preston et al., *Mutation Res*. (1981) 87:143-188). CHO cells were grown and maintained in McCoy's 5A medium supplemented with 10% fetal calf serum, 1% L-glutamine (2 mM), penicillin (100 units/mL), and streptomycin (100 µg/mL). Cultures are incubated in 5-7% $CO_2$ with loose caps in a humidified incubator at 37±2° C.

Test Material Preparation

A stock solution was prepared at 50 mg/mL. Lower doses were prepared by dilution in 5% dextrose from this stock immediately prior to use. To minimize any chance of degradation, the test article solutions were kept on ice after preparation and until just prior to dosing procedures.

Test Procedures

Cells were seeded at approximately $1-1.5 \times 10^6$ cells per 75 $cm^2$ tissue culture flask in 10 mL fresh medium one day prior to treatment. For treatment, spent medium was replaced with fresh growth medium and the test article extract, negative or positive control was added to each flask. Positive controls were dosed in 0.1 mL volumes to minimize vehicle toxicity. The test article dilutions and negative control were dosed in 1 mL volumes. Fresh medium was added to bring the total treatment volume to 10 mL. For the portion of the test with metabolic activation, the S9 activation mix was added to serum free medium at 1.5%, (v/v) final concentration. All treatments were carried out in duplicate. The cells were incubated at 37±2° C. in the presence of the test article extract, the S9 reaction mixture (metabolic activation portion of the study only) and growth medium. The assay was divided into three treatment periods: 3 hours, 3 hours with S9 activation, and 20 hours.

After the treatment period, all flasks were evaluated microscopically for gross manifestations of toxicity (i.e., morphological changes in cells or significant cell detachment). All flasks were washed twice with phosphate buffered saline (PBS). Normal growth medium containing 10% fetal bovine serum (FBS) was added to the freshly washed cells and the flasks were returned to the incubator for an additional 14.5-15.5 hours. Those flasks treated for 20 hours were not washed prior to harvest. Microscopic evaluation was performed immediately prior to harvest. Two hours prior to harvest, 1 µg of colcemid was added (0.1 µg/mL final concentration) to all flasks to accumulate dividing cells.

Metabolic Activation System

The use of a metabolic activation system is an important aspect for evaluation of a test article, as some compounds exist only in a promutagenic state. That is, they become mutagenic only after being acted upon by an outside metabolic source. In vitro test systems lack this ability to metabolize compounds unless an outside system such as S9 is added.

The in vitro metabolic activation system used in this assay was comprised of Sprague Dawley rat liver enzymes and an energy producing system necessary for their function (NADP and isocitric acid; core reaction mixture). The enzymes are contained in a preparation of liver microsomes (S9 fraction) from rats treated with Arochlor 1254 to induce enzymes capable of transforming chemicals to more active forms. The S9 is purchased from Moltox (Boone, N.C.) and retained frozen at less than −70° C. until use. This S9 fraction is thawed immediately before use and added to the core reaction mixture.

Dose Levels

The test article extracts were tested in duplicate at six dose levels (0.5, 0.16, 0.05, 0.016, 0.005, and 0.0016 ml/mL final concentration in culture) along with appropriate vehicle and positive controls.

Cell Fixation

Metaphase cells were collected by mitotic shake off, swollen with 75 mM KCl, fixed in methanol:glacial acetic acid (3:1 v/v). Cells were pipetted onto glass slides after resuspension in fresh fixative and air dried. The slides were labeled with a blind code. Three slides were prepared from each treatment flask.

Cell Staining and Scoring

Slides were stained with Giemsa and permanently mounted. All slides were read under blind code with the exception of the high dose positive controls, which were evaluated first to ensure the aberration frequency was adequate. Two hundred cells per dose (100 from each of the duplicate flasks) were read from each of the doses. One hundred cells were read from each of the high dose positive controls in accordance with the following definitions and were scored as such.

Chromatid Type

TG (Chromatid Gap): "Tid Gap". An achromatic (unstained) region in one chromatid, the size of which is equal to or smaller than the width of a chromatid. These are noted but not usually included in final totals of aberrations, as they may not all be true breaks.

IG (Isochromatid Gap): "Chromosome Gap". The gaps are at the same locus in both sister chromatids. These are noted but are not usually included in final totals of aberrations, as they may not all be true breaks.

TB (Chromatid Break): An achromatic region in one chromatid, larger than the width of a chromatid. The associated fragment may be partially or completely displaced, or missing.

ID (Chromatid Deletion): Length of chromatid "cut" from midregion of a chromatid resulting in a small fragment or ring lying beside a shortened chromatid or a gap in the chromatid.

TR (Triradial): An exchange between two chromosomes, which results in a three-armed configuration. May have an associated acentric fragment.

QR (Quadriradial): The same as the triradial, but resulting in a four-armed configuration.

CR (Complex Rearrangement): An exchange among more than two chromosomes which is the result of several breaks and exchanges.

TI (Chromatid Interchange): Exchange within a chromosome involving one or both arms.

Chromosome Type

SB (Chromosome Break): Terminal deletion. Chromosome has a clear break forming an abnormal (deleted) chromosome with an acentric fragment that is dislocated and may remain associated or may appear anywhere in the cell.

DM (Double Minute Fragment): Chromosome interstitial deletion. These appear as small double "dots" or may be paired rings. In some cases, they cannot be distinguished from acentric fragments that result from exchanges or terminal deletions.

D (Dicentric): An exchange between two chromosomes that results in a chromosome with two centromeres. This is often associated with an acentric fragment in which it is classified as Dicentric with Fragment (DF).

MC (Multi-centric Chromosome): An exchange among chromosomes that results in a chromosome with more than two centromeres.

R (Ring): A chromosome that forms a circle containing a centromere. This is often associated with an acentric fragment, in which case it is classified as Ring with Fragment (RF). Acentric rings are also included in this category.

Ab (Abnormal Monocentric Chromosome): This is a chromosome whose morphology is abnormal for the karyotype, and often the result of such things as a translocation or pericentric inversion. Classification used if abnormally cannot be ascribed to, e.g., a reciprocal translocation.

T (Translocation): Obvious transfer of material between two chromosomes resulting in two abnormal chromosomes. When identifiable, scored at "T", not as "2 Ab".

Other

SD (Severely Damaged Cell): A cell with 10 or more aberrations of any type. A heavily damaged cell should be analyzed to identify the type of aberrations and may not have 10 or more, e.g., because of multiple fragments such as those found associated with a tricentric.

PU (Pulverized Chromosome): Despiralized or fragmented chromosome. This may simply be at a different stage of chromosome condensation.

P (+Pulverized Cell): More than one chromosome, up to the whole nucleus, is "pulverized".

PP (Polyploid Cell): A cell containing multiple copies of the haploid number of chromosomes. Polyploid cells are occasionally observed in normal bone marrow or cell culture. These are recorded but are not included in final totals of structural aberrations.

Control Substances

Control substances were prepared and used in this assay as described in published reports. Positive Controls: cyclophosphamide—high dose 15 µg/mL; cyclophosphamide—low dose 5 µg/mL; mitomycin C—high dose 1.0 µg/mL; and mitomycin C—low dose 0.25 µg/mL.

Negative (Vehicle) Control

CHO cells were treated with the 5% dextrose negative controls with and without S9 activation. These treatments provided information regarding background numbers of aberrant cells.

Assay Validity Evaluation

The total number of aberrations (% CA) of the solvent control culture(s) should fall within 1-14%. High dose positive controls should produce a statistically significant increase in the number of aberrations at the 95% confidence level ($p<0.05$) as determined by statistical analysis.

Statistical Analysis and Data Presentation

Analysis of Variance (ANOVA) was used to identify significant differences between positive and negative control groups or test article and negative control groups. A difference was considered significant when the p value obtained was less than 0.05. The type of aberrations found, frequencies of aberrations, and percentages of cells bearing aberrations are presented in Table 14. Historical control values are presented in Table 15. Chromatid and isochromatid gaps are noted but were not included in the totals for aberration assessment, as they may not represent true breaks.

Negative controls were run with this assay to determine the rates of spontaneously occurring aberrations (background). When spontaneously occurring aberrations reach excessively high proportions, this assay loses sensitivity. As shown in Table 14, the spontaneous aberration rates in the negative controls fall within normal ranges (5% dextrose 3 hrs.: 3.0%, 5% dextrose 3 hrs.+S9: 3.0%, 5% dextrose 20 hrs.: 3.0%).

The high dose positive control doses induced aberration rates greater than or equal to 39%; all of the low doses induced rates of at least 20%. The numerical increase and obvious dose response (Tables 14 and 16) is supported by statistically significant differences at all time periods when compared to the negative control. These profound increases observed in positive control treated preparations indicate that the assay retained its characteristic sensitivity. When the validation criteria were considered together with the results of the positive and negative controls, this assay was determined to be valid.

TABLE 14

| DOSE | % CA 3 HRS | FI 3 HRS | % CA 3 HRS + S9 | FI 3 HRS + S9 | % CA 20 HRS | FI 20 HRS |
|---|---|---|---|---|---|---|
| 0.5 mg/mL | NA | NA | NA | NA | NA | NA |
| 0.16 mg/mL | NA | NA | NA | NA | NA* | NA |
| 0.05 mg/mL | NA | NA | NA | NA | NA | NA |
| 0.016 mg/mL | NA | NA | 9.0% | 2.0 | NA | NA |
| 0.005 mg/mL | 5.5% | 1.8 | 8.4% | 2.8 | 5.0% | 1.7 |
| 0.0016 mg/mL | 6.0% | 2.0 | 4.5% | 1.5 | 4.5% | 1.5 |
| Negative | 3.0% | NA | 3.0% | NA | 3.0% | NA |
| MMC H | 42.0% | 14.0 | NA | NA | NA | NA |
| MMC L | 20.3% | 6.8 | NA | NA | 26.5% | 8.8 |
| CP H | NA | NA | 39.0% | 13.0 | NA | NA |
| CP L | NA | NA | 21.5% | 7.2 | NA | NA |

% CA = (total number of cells bearing aberrations excluding gaps/total number of spreads scored) * 100
FI = Fold Increase compared the test group with the concurrent negative control group
NA - no valid data available
*A total of six spreads were found and scored for this group. One cell did display evidence of damage. However, due to the extremely small sample size, estimations of damage cannot be accurately made.

TABLE 15

Historical Aberration Rates

|  | Negative (Spontaneously Induced) | Positive, Low Dose- (Directly Induced) | Positive, High Dose- (Directly Induced) |
|---|---|---|---|
| Range | 3.5-14% | 26-183% | 39-194% |
| Average | 10% | 54% | 111% |

*Data pooled from 2001-2002 studies

Test Article Data

The types of aberrations found, as well as the frequencies of aberrations and percentages of cells bearing aberrations, are summarized in Table 14. Chromatid and isochromatid gaps were noted but were not included in the totals for aberrations assessment, as they may not be true breaks. Endoreduplication and polyploidy occurred at normal background levels.

Several endpoints exist within this assay to determine the extent of test article induced toxicity. In this assay, the cultures were evaluated microscopically for evidence of gross morphological changes immediately after treatment. In all cases, the 0.5 mg/mL dose induced heavy levels of precipitates which obscured the monolayers. During the three hour treatment, doses 0.16, 0.05 and 0.016 mg/mL exhibited moderate to severe levels of cytotoxicity. Low to background levels of toxicity were noted at 0.005 and 0.0016 mg/mL treatments. During the course of the twenty hour treatment, cytotoxicity was more marked. The 0.16 mg/mL dose was highly cytotoxic. Mild levels of cytotoxicity were not noted until the 0.005 mg/mL dose. As an additional marker of cytotoxicity and potential cell cycle delays, the mitotic index was calculated for each slide scored. (Table 16)

TABLE 16

Average Mitotic Index

| DOSE | % MI | % MI 3 HRS + S9 | % MI 20 HRS |
|---|---|---|---|
| 0.5 mg/mL | 0% | 0% | 0% |
| 0.16 mg/mL | 0% | 0% | 1% |
| 0.05 mg/mL | 0% | 0% | 0% |
| 0.016 mg/mL | 1% | 1% | 0% |
| 0.005 mg/mL | 8% | 9% | 4% |
| 0.0016 mg/mL | 6% | 12% | 8% |
| Negative | 10% | 12% | 8% |
| MMC L | 6% | NA | 5% |
| CP L | NA | 9% | NA |

Due to the high levels of toxicity, no metaphase spreads were available to count in the highest three doses. At the 0.016 mg/mL dose, metaphase were noted, but were not of sufficient quality to be scored. The spreads were densely packed and the chromosomes not substantially elongated. At the 0.005 and 0.016 doses, metaphase spreads of sufficient quality were found and scored. When compared to the negative controls, none of these test article treated groups exhibits significant increases in the incidence of aberrations. In fact, the aberration rates were within normal negative ranges. No relevant dose response trends in aberration rates were noted.

Analysis and Conclusion

The Chromosome Aberration assay evaluates the potential of a test article to induce chromosome aberrations in the CHO-$K_1$ cell line in the presence and absence of S9 exogenous mammalian activation. The induction of aberrations has been linked to carcinogenesis, as damage can lead to inactivation of tumor suppressor genes or activation of oncogenes. The use of a metabolic activation system is an important component to the evaluation of a test article, as some compounds exist as promutagens and must be completely or partially metabolized before becoming mutagenic. The S9 metabolic activation system is intended to mimic the body's metabolic systems.

To fully assess the mutagenic potential of the test articles, three treatment periods were used. The shorter three hour treatment was performed with and without metabolic activation. To determine if the test article was mutagenic after an extended treatment time, due to delayed reactions or slower mutagenic mechanisms, a twenty hour treatment was also evaluated. Because metabolic activation systems become toxic when in extended contact with cells, the cells were only treated in the absence of metabolic activation for the twenty hour treatment. Additionally, cells were allowed an extended expression period (approximately 15 cell cycles, OECD 1995) to take into account any potential cell cycle delay caused by the test article and permit affected cells to reach metaphase.

As all of the negative controls showed aberration rates within normal parameters and all high dose positive controls induced statistically significant increases in aberration rates, this assay met the criteria for a valid assay. Statistical analysis did not show significant increases in the aberration rates in the cells treated with the test article dilutions as compared to the negative control. The absence of significant increases in aberrations in the test article treated preparations indicate that CX-3543 is not mutagenic in this test system.

Example 65

Subacute Study of Intravenously Administered CX-3543 in Dogs

This study determines the safety and tolerance of CX-3543 at three dose levels administered intravenously once daily to beagle dogs for five consecutive days. Safety parameters were monitored through observation, clinical pathology, and microscopic histopathology assessments. Selected animals also underwent blood sample collection for pharmacokinetic/toxicokinetic evaluation. All animals were also assessed with ECG evaluations to detect heart rhythm and/or conduction abnormalities.

Experimental Design

Table 17 summarizes the study design. The study was conducted using three (3) test article and one (1) control article group. The control article was the solution (5% dextrose in water) used to dilute the test article prior to administration and was administered at the same volume as the high dose. The test article dosage levels for this study were approximately 12, 3.8, and 1.2 mg/kg. Test and control articles were administered once by intravenous (IV) infusion over approximately a one hour period on five consecutive days. Blood samples for test article blood level analysis was taken as follows (i.e., pk/tk sampling): approximately 1 mL of blood was taken from three male and three female dogs in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth doses. Also, prior to and immediately after Dose 1 and after Dose 5 for all animals, and for recovery animals prior to necropsy, approximately 5-10 second ECG tracings in a lead II configuration were obtained. Animals were terminated one (1) or 15 days after the last dose. Blood for hematology and clinical chemistry analysis was drawn pre-dose and prior to euthanasia at termination. Following euthanasia, a necropsy was performed to include collection of major organs for microscopic evaluation.

TABLE 17

| GROUP NO. | ARTICLE[a] | DOSAGE (MG/KG) | PRIMARY NO. ANIMALS (MALE/FEMALE) | RECOVERY (15 DAY) NO. ANIMALS (MALE/FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

[a]Delivered as an approximate 1 hour infusion

Test Methods

Animals were systematically assigned to groups as follows: The heaviest dog for a sex was assigned to Group 1, the next heaviest for that sex was assigned to Group 2, the next heaviest to Group 3, the next heaviest to Group 4, then continue with Groups 2, 3, 4, and 1, then Groups 3, 4, 1, and 2, continuing with this pattern until each group had a full complement of animals. The test and control article were administered at each dosing as an intravenous infusion into a cephalic or saphenous vein over approximately one hour.

Animals were weighed daily prior to dosing and prior to necropsy. All animals were observed for signs of pharmacological activity, behavioral changes, and toxicity immediately and one hour after dosing. Recovery animals were also observed once daily during the recovery period. Prior to and immediately after Doses 1 and 5 for all animals, and for recovery animals prior to necropsy, approximately five second ECG tracings in a lead II configuration were obtained. These tracings were used to provide data for interpretation of the rhythm and amplitude changes of the QRS-complex and T-wave and to measure QT intervals on a number of segments per tracing (approximately 5-10).

Blood Collection

PK/TK: Blood samples for test article blood level analysis were taken. Approximately 1 mL of blood was taken from three males and three females in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth dose. Plasma (lithium heparin anticoagulant) samples were prepared and analyzed.

Clinical Pathology: After overnight fasting and prior to the first dose (baseline; all animals) and then prior to each necropsy, blood samples are taken for hematology and clinical chemistry. For hematology assays, blood collected at baseline and prior to necropsy (fasted) are analyzed for erythrocyte count, hematocrit, MCH, leukocyte count, differential WC, MCHC, hemoglobin, MCV, platelet count, PT, and APTT. For clinical chemistry assays, blood collected at baseline and prior to necropsy (fasted) are tested for: aspartate aminotransferase (ASP), globulin & A/G ratio, Alanine aminotransferase (ALT), sodium, alkaline phosphatase, potassium, gamma glutamyltransferase (GGT), chloride, glucose, calcium, blood urea nitrogen (BUN), total bilirubin, creatinine, inorganic phosphorus, total protein, cholesterol, albumin, and triglycerides.

Termination: Primary treatment and recovery group animals were euthanized at their respective time of necropsy by exsanguinations while anesthetized.

Necropsy

Following blood sample collection, primary treatment and recovery group animals were sacrificed at their respective termination times and were necropsied. Major organs were collected, weighed, and preserved for microscopic evaluation. Necropsy included examination of the cranial, thoracic, abdominal and pelvic cavities, their viscera, the tissues, organs, and the carcass.

Following blood sample collection, primary treatment and recovery group animals are sacrificed at their respective termination times and are necropsied. Major organs are collected, weighed, and preserved for microscopic evaluation. Necropsy included examination of the cranial, thoracic, abdominal and pelvic cavities, their viscera, the tissues, organs, and the carcass.

From the primary and recovery group animals, the following tissues were taken and weighed: brain, thymus, liver, kidneys (paired), adrenals (paired), spleen, and gonads (paired). From the primary and recovery group animals, the following tissues were fixed in 10% neutral buffered formalin (with the exception of the testes—where Bouin's fixative was used): all gross lesions, injection site vein, thymus, brain, caudal vena cava, pancreas, kidney, spleen, lymph note—mesenteric, lymph node—prescapular, liver, gonads, lungs, heart, and adrenals. Initially, tissues from only the control and the high dose animals were evaluated. Target tissues from the other treatment groups were also evaluated to further investigate observations.

Statistical Methods

Statistical analysis of the clinical chemistry and hematology values and organ and body weight data will be performed to compare the test article groups to the control group. The statistical methods used for the data will be selected as appropriate: parametric data will be analyzed using a one way Analysis of Variance, non-parametric data will be analyzed using the Kurskai-Wallis test. A paired t-test will also be used to compare baseline and post treatment clinical chemistry and hematology values for each animal. Probability (p) values of 0.05 or less will be considered significant for all statistical tests.

Results

Figure 12A:
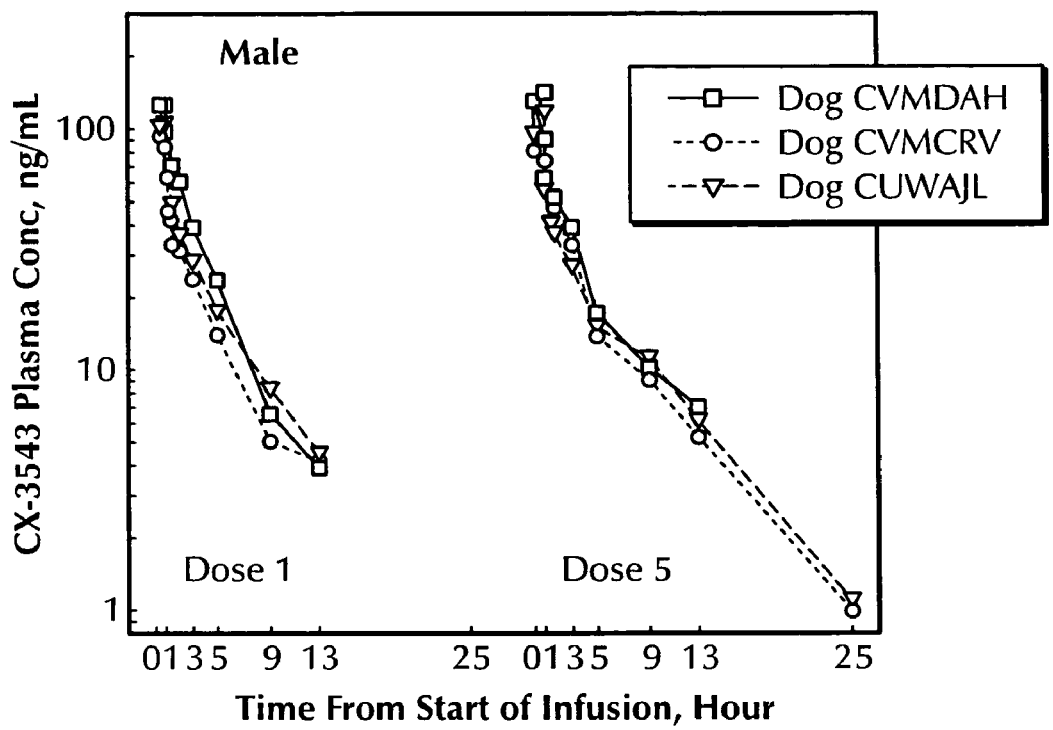
FIGS. 12 and 13 show CX-3543 plasma concentrations in dogs and rats respectively following intravenous administration of CX-3543.
Figure 12B:
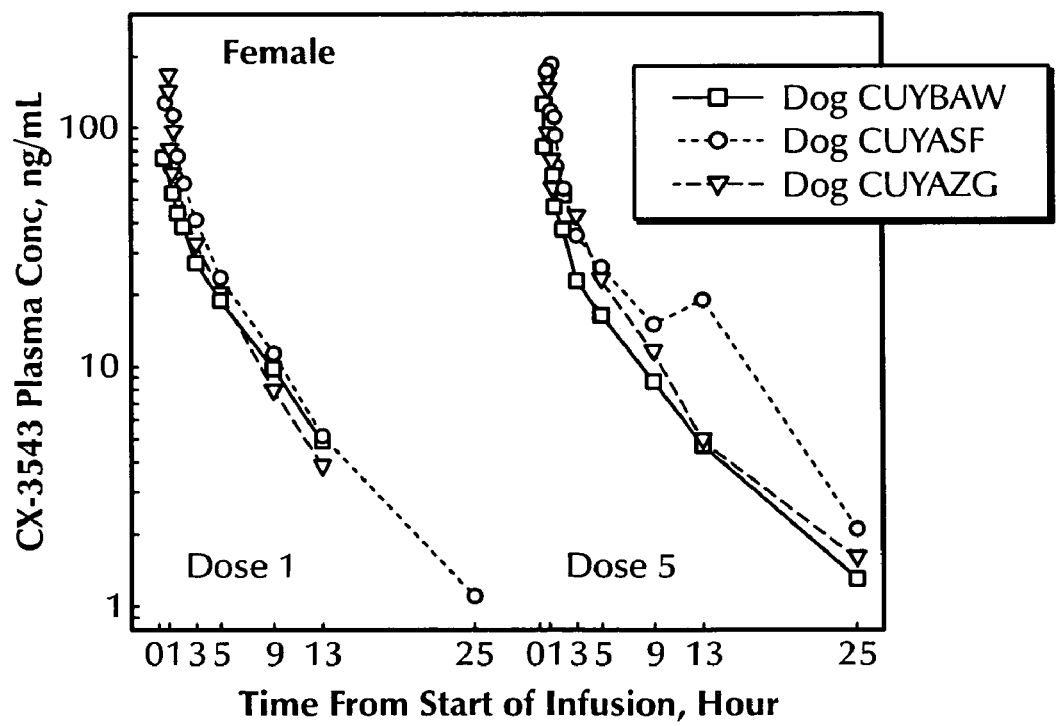

Table 18 provides a summary of CX-3543 pharmacokinetic parameters in dogs following intravenous administration of 1.2 mg/kg CX-3543 once daily for five days. FIG. 12 described CX-3543 plasma concentrations in docs following intravenous administration of 1.2 mg/kg CX-3543 once daily for five days. Following intravenous administration of CX-3543 for Dose 1, maximum plasma concentrations were generally achieved at or near the end of the one hour infusion. Following the infusion, plasma concentrations declined in a multi-exponential fashion with mean terminal half-lives of 3.2 and 3.8 hours in male and female dogs, respectively. Dose I Mean Cmax values were 108.3 and 138.9 ng/mL for males and females, respectively. Dose I Mean AUC(0-24) and AUC (0-inf) values were 313.6 and 316.9 ng·h/mL in males and 381.4 and 386.3 ng·h/mL in females.

Following once daily dosing of CX-3543 for five days, minimal accumulation was noted with mean Cmax values of 126.4 and 145.1 ng/mL in males and females, respectively. Dose 5 Mean AUC(0-24) values were 362.9 and 443.7 ng h/mL. Dose 5 to Dose 1 ratios for AUC(0-24) were 1.2 and 1.1 for males and females, respectively. The mean terminal half-lives for males and females for Dose 5 were both 5.2 hours.

Over the 5-day course of treatment, no mortality was noted and the males and females had only slight fluctuations in their body weight. Clinical observations for the males and females were dose dependent and predominantly noted during dosing and immediately and one hour post dosing. The principal observations were wheals, facial swelling, anxiety or agitation, lethargy, and swelling/erythema at previously dosed cephalic/saphenous regions, with vomiting and tachypnea being noted occasionally in the high dose group only. The only notable necropsy observations were limited to observations associated with vascular and perivascular lesions at or near to the injection site that appeared to be resolving in the recovery animals. No abnormalities were detected during ECG monitoring pre and post doses 1 and 5. No toxicologically significant changes in clinical pathology parameters were observed when comparing treated groups with control, with the exception of elevated white cell counts in the high dose group, possibly related to a local inflammatory response. Paired comparisons of hematology and clinical chemistry parameters at baseline with post-treatment results revealed no toxicologically relevant findings.

The histological evaluation of tissues indicated that the test article caused a dose dependent (i.e., more marked in the high dose than the mid and low dose groups) local inflammation, with necrosis and hemorrhage at the injection site, and an associated inflammatory response in the draining lymph nodes. All of these changes were noted to be resolving in the recovery animals. A mild decrease in lymphocytes in the spleen and the thymus was evident in the high dose group, but no differences were apparent when comparing the spleen and thymus of animals in the mid dose with those in the control group.

Under the conditions of this study, five consecutive daily doses of CX-3543 (lot#2591) at 12, 3.8, or 1.2 mg/kg, each administered as an intravenous, one-hour infusion, appeared to be toxicologically well tolerated with the exception of transient, dose dependent vascular and perivascular inflammation and necrosis at the injection site. Other dose dependent clinical observations, noted predominantly during dosing and immediately and one hour post dosing, included wheals, facial swelling, anxiety or agitation, lethargy, and swelling/erythema at previously dosed cephalic/saphenous regions, with vomiting and tachypnea being noted occasionally in the high dose group only.

TABLE 18

CX-3543 Pharmacokinetic Parameters in Dogs Following Intravenous Administration of 1.2 mg/kg CX-3543 Once Daily for 5 Days

| Parameter | Male | | Female | |
|---|---|---|---|---|
| | Mean | SD | Mean | SD |
| Dose 1 | | | | |
| Cmax, ng/mL | 108.3 | 16.1 | 138.9 | 50.7 |
| Tmax$^a$, h | 0.67 | (0.67-1.0) | 0.67 | (0.67-1.0) |
| AUC(0-24), ng · h/mL | 313.6 | 74.9 | 381.4 | 80.0 |
| AUC(0-inf), ng · h/mL | 316.9 | 74.1 | 386.3 | 82.1 |
| $T_{1/2}{}^b$, h | 3.2 | 0.8 | 3.8 | 0.8 |
| Dose 5 | | | | |
| Cmax, ng/mL | 126.4 | 12.6 | 145.1 | 47.5 |
| Tmax$^a$, h | 1.00 | (0.67-1.0) | 1.00 | (0.67-1.0) |
| AUC(0-24), ng · h/mL | 362.9 | 52.5 | 443.7 | 145.9 |
| $T_{1/2}{}^b$, h | 5.2 | 0.6 | 5.2 | 0.7 |
| Accumulation Ratio | 1.2 | 0.2 | 1.1 | 0.1 |

$^a$Expressed as median and range
$^b$Expressed as harmonic mean and pseudo SD based on jackknife variance Example 66

Subacute Study of Intravenously Administered CX-3543 in Rats

This study determines the safety and tolerance of CX-3543 at three dose levels administered intravenously once daily to rats for five consecutive days. Safety parameters will be monitored through observation, clinical pathology, and microscopic histopathology assessments. Selected animals will also undergo blood sample collection for pharmacokinetic/toxicokinetic evaluation.

Experimental Methods

Table 19 summarizes the Study Design. The study was conducted using three (3) test and one (1) control article groups. The high and low test article groups and the control group consisted of 28 animals each and were used to assess tolerance. The medium test article group consisted of 64 animals of which 28 animals were used to assess tolerance and 36 animals were used to determine the level of test article in the blood at various time points after the first and fifth doses in the PK/TK portion of the study. The control article was the solution (5% dextrose in water; D5W) used to dilute the test article prior to administration and was administered at the same volume as the high dose test article group. The test article dosage levels for this study were 24, 7.6, and 2.4 mg/kg. Test and control articles were administered by intravenous (IV) injection into a tail vein over one minute on five consecutive days.

Blood samples for test article blood level analysis were taken as follows. Approximately 0.3-0.5 mL of blood was taken from three male and three female rats under anesthesia at each sample time point of pre-dose and at the end of injection (Time 0) and at approximately 0.08, 0.25, 0.5, 1, 2, 4, 8, 12, and 24 hours from the end of the injection after the first and fifth doses. Animals used to assess tolerance were terminated one day (for the primary group) or 15 days (for the recovery group) after the last dose. At termination of the tolerance test animals, blood for hematology and clinical chemistry analysis was drawn prior to euthanasia and following euthanasia. A necropsy was performed to include collection of major organs for microscopic evaluation. The animals used for the pk/tk blood sampling only to determine the level of test article were euthanized after the final blood sample was collected without any further sampling or observations.

TABLE 19

| GROUP NO. | ARTICLE$^a$ | DOSAGE (MG/KG) | PRIMARY NO. ANIMALS (MALE/FEMALE) | RECOVERY (15 DAY) NO. ANIMALS (MALE/FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

$^a$Delivered as an approximate 1 hour infusion

Test Methods

The test and control article were administered at each dosing as an intravenous infusion into a tail vein over approximately one minute. Animals were weighed daily prior to dosing and prior to necropsy. All animals were observed for signs of pharmacological activity, behavioral changes, and toxicity immediately and one hour after dosing. Recovery animals were also observed once daily during the recovery period.

Blood Collection

PK/TK: Blood samples for test article blood level analysis were taken. Utilizing 18 male and 18 female medium dose animals, approximately 0.3-0.5 mL of blood was taken from three male and three female rats under anesthesia at each sampling time point of pre-dose and at the end of injection (Time 0) and at approximately 0.08, 0.25, 0.5, 1, 2, 4, 8, 12, and 24 hours from the end of the injection after the first and fifth dose. Blood sampling was via retro-orbital bleeding or cardiac puncture bleeding for an animal's terminal sample. Plasma (lithium heparin anticoagulant) samples were prepared and analyzed. General procedures for chemical pathology, necropsy, and histopathology, and statistical methods, for example as described in Example 65, were followed.

Dose Administration

The control animals were dosed with approximately 6 mL/kg of D5W. The high, mid, and low dose test article animals were administered dosages of approximately 24 mg/kg, 7.6 mg/kg, and 2.4 mg/kg, respectively. To generate 14 males and 14 females per group with successfully administered control or test article for five consecutive daily doses, the total number of animals dosed per study group by sex were Control: 14 males and 14 females, High Dose: 44 males and 34 females, Mid Dose: 17 males and 16 females, Low Dose: 16 males and 15 females.

Results

Figure 13:
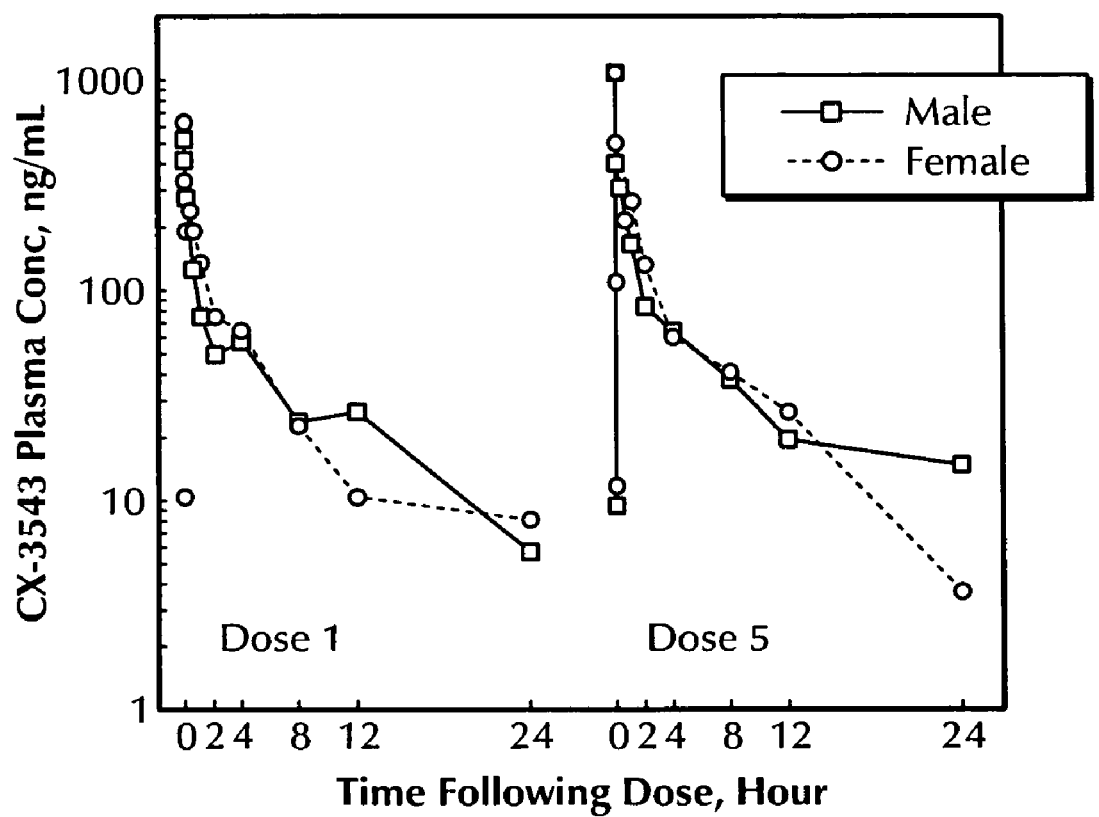

Table 20 provides a summary of CX-3543 pharmacokinetic parameters in rats following intravenous administration of CX-3543 once daily for five days. FIG. 13 describes CX-3543 plasma concentrations in rats following intravenous administration of CX-3543 once daily for five days. Following intravenous administration of CX-3543 for Dose 1, plasma concentrations declined in a multi-exponential fashion with terminal half-lives of 6.8 and 6.6 hours in male and female rats, respectively. Dose 1 Cmax values were 513.8 and 598.2 ng/mL for males and females, respectively. Dose 1 AUC(0-24) and AUC(0-inf) values were 778.7 and 833.3 ng·h/mL in males and 784.3 and 860.8 ng·h/mL in females.

Following once daily dosing of CX-3543 for five days, modest accumulation was noted with Cmax values of 485.3 and 1050.0 ng/mL in males and females, respectively. Corresponding Dose 5 AUC(0-24) values were 1008.6 and 1204.1 ng·h/mL. Dose 5 to Dose 1 ratios for AUC(0-24) were 1.3 and 1.5 for males and females, respectively. The terminal half-lives for males and females on Dose 5 were 8.8 and 4.8 hours, respectively.

All control animals appeared normal through the study. Over the five day course of treatment, approximately 5% mortality occurred in the high dose animals and these animals died within minutes of receiving the first dose. Clinical observations for the males and females were dose dependent and predominantly in the high dose animals. Most animals in the high dose group exhibited one or more of the following observations immediately after the first dose: salivation, labored breathing, head shaking, rapid respiration, wobbly gait, rearing, twitching, chewing, lethargy, hunched posture, piloerection, red nose, or red substance around the eyes. These observations in the high dose animals were mostly resolved within one hour after each dose and decreased in incidence and severity with subsequent dose administrations. However, severe tail irritation was noted in nearly all high dose animals, and this resulted in approximately 60-70% attrition (i.e., an inability to continue dosing the remainder of the five doses according to plan). Observations in the mid-dose group were predominantly limited to heavy breathing in one female, red substance around the eyes (40% of the animals), piloerection in five males, and tail observations (approximately 50% of the animals). The observations for low-dose animals were limited to occasional piloerection (four males), red substance around the eyes (approximately 30% of the animals), and tail observations (approximately 30% of the animals).

Overall, weight changes in animals treated with test article were minimal, and predominantly noted in the high-dose animals, and no toxicologically relevant changes in hematology or clinical chemistry were observed. Necropsy findings were predominantly from the high-dose group, and included observations in lungs, iliac lymph nodes, cranial contents, and tails. The histopathology observations included: I) local inflammation, necrosis, vascular necrosis, thrombosis, edema, and hemorrhage at the site of the injection at the mid and high doses, 2) inflammation and necrosis in the draining lymph nodes at the high dose, 3) histocytic inflammation in the lungs (histiocytic pneumonia) at the high dose, and 4) decreased lymphocytes in the thymus at the high dose.

Under the conditions of this study, five consecutive daily doses of CX-3543 at 24, 7.6, or 2.4 mg/kg, each administered as an intravenous, one-hour injection, appeared to be toxicologically well tolerated at the mid-and low-dose levels (i.e., 7.6 and 2.4 mg/kg, respectively). In the high-dose animals, a low incidence of mortality was observed, along with severe tail irritation, and histopathologic changes predominantly in the tail vein, lungs, draining lymph note, and thymus.

TABLE 20

CX-3543 Pharmacokinetic Parameters in Rats Following Intravenous Administration of CX-3543 Once Daily for 5 Days

| Parameter | Male Dose 1 | Male Dose 5 | Female Dose 1 | Female Dose 5 |
|---|---|---|---|---|
| Dose, mg/kg | 7.1 | 7.1 | 7.2 | 7.2 |
| Cmax. ng/mL | 513.8 | 485.3 | 598.2 | 1050.0 |
| AUC(0-24), ng · h/mL | 778.7 | 1008.6 | 784.3 | 1204.1 |
| AUC(0-inf), ng · h/mL | 833.3 | — | 860.8 | — |
| $T_{1/2}$, h | 6.8 | 8.8 | 6.6 | 4.8 |
| Accumulation Ratio | — | 1.3 | — | 1.5 |

Example 67

Effect of CX-3543 on phosphorylated and Total p53

Figure 14A:
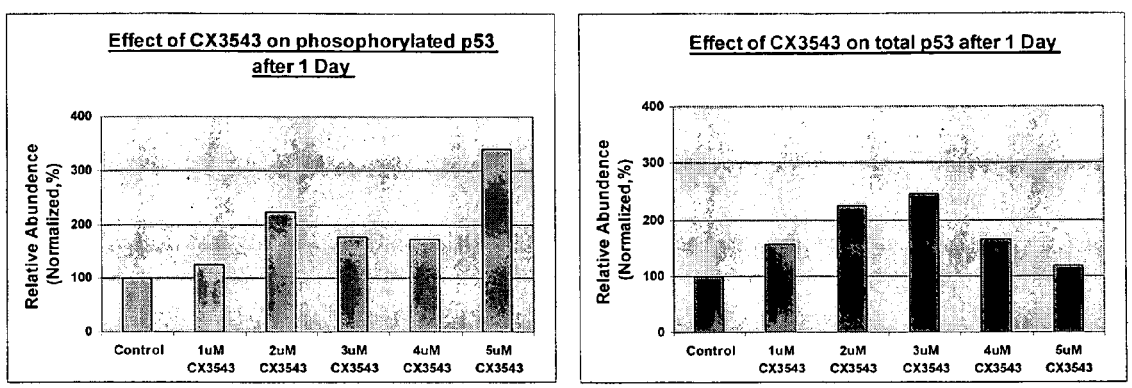
FIGS. 14A and 14B show the effect of CX-3543 on p53 status.
Figure 14B:
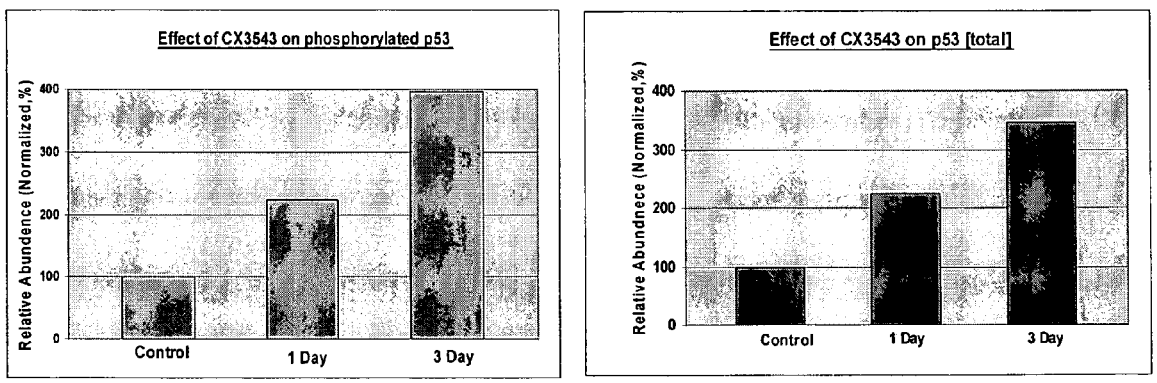

FIGS. 14A and 14B show the effect of CX-3543 (2-5 µM) on phosphorylated and total p53. The population of the protein p53 and phosphorylated p53, a known regulator of apoptotic cell death, is shown to be enhanced by treatment of HCT-116 cells for 24 hr, using a dose range of 1-5 uM CX-3543.

The protocol for this assay is described as follows. On Day 1, cells were seeded at $2 \times 10^6$ cells/10 cm dish/10 mL medium. On day two, cells were treated as follows: control=0.05% DMSO (5 µl DMSO stock/10 ml medium); 1 µM CX3543 (1 µl Stock (10 mM)/10 ml medium); 2 µM CX3543 (2 µl Stock (10 mM)/10 ml medium); 3 µM CX3543 (3 µl Stock (10 mM)/10 ml medium); 4 µM CX3543 (4 µl Stock (10 mM)/10 ml medium) and 5 µM CX3543 (5 µl Stock (10 mM)/10 ml medium).

On Day 3, cells were harvested and attached and floating cells were collected. Cells were washed twice with PBS, counted and collected at $4 \times 10^6$ cells/sample. The cell pellet was frozen at −80° C. until further use. On the same day or on Day 4, cells were extracted using a cell extraction buffer (3 mL cell extraction buffer, 300 µl protease inhibitor and 10 µl 0.3M PMSF. To each sample was added 200 µl Buffer, and the solution was vortexed and set on ice for 30 minutes, and subsequently vortexed after every 10 mins. The solution was then centrifuged at 13,000 rpm for 10 min, and 100 µl supernatant per tube were aliquoted and stored at −80° C.

Assay preparation (Day 5). An anti-rabbit IgG HRP solution was prepared by diluting 10 µl of 100× concentrate solution with 1 ml HRP diluent for each 8-well strip. A wash buffer solution is prepared by diluting the original vial (×25) using distilled water to make a ×1 solution. Dilutions of p53 standard solution or p53 total solution were prepared as described in Table 21. To ensure complete reconstitution, standard 1 was mixed gently and allowed to sit for 10 minutes at room temperature.

TABLE 21

| | Conc. | Standard Soln. | Dilution Buffer |
|---|---|---|---|
| Standard 1 | 100 Units/ml | Reconstitute 1 Vial worth | 0.7 ml of standard Dil. Buffer* |
| Standard 2 | 50 Units/ml | 250 µl of Standard 1 | 250 µl |
| Standard 3 | 25 Units/ml | 250 µl of Standard 2 | 250 µl |
| Standard 4 | 12.5 Units/ml | 250 µl of Standard 3 | 250 µl |
| Standard 5 | 6.25 Units/ml | 250 µl of Standard 4 | 250 µl |
| Standard 6 | 3.12 Units/ml | 250 µl of Standard 5 | 250 µl |

TABLE 21-continued

|  | Conc. | Standard Soln. | Dilution Buffer |
|---|---|---|---|
| Standard 7 | 1.6 Units/ml | 250 µl of Standard 6 | 250 µl |
| Standard 8 | 0 |  | 250 µl |

Test Procedure. Allow all solution to reach RT and mix gently before use. Take out and insert 8-well strips. Add 100 µl of standard dilution buffer to standard 8 well (0 ng/ml/well or 0 Units/well). Add nothing to the chromogen blank well. Add 100 µl of standard or diluted sample to the appropriate microtiter wells. Generally, the sample should be diluted with standard dilution buffer at least 1:10 or greater. Each sample is run in duplicates. Gently tap the side of the plate to thoroughly mix. Cover plate with plate cover and incubate for 2 hours at RT or o/n at 4C. Wash wells with 400 µl working wash buffer 4 times. Let soak for 15-30 sec., and then aspirate the liquid. After washing, the plate is inverted and tapped dry on absorbance tissue. Add 100 µl of anti-p53 [pS15] or anti-p53 (total) (detection antibody) to each well except chromogen blank. Tap gently to mix; cover plate and incubate 1 hour at RT. Aspirate solution from wells thoroughly.

Wash wells with 400 µl working wash buffer four times. Let soak for 15-30 sec., and then aspirate the liquid. After washing, the plate is inverted and tapped try on absorbance tissue. Add 100 µl of anti-rabbit IgG HRP working soln. to each well except chromogen blank. Cover plate and incubate 30 min at RT. Wash wells with 400 µl working wash buffer four times. Let soak for 15-30 sec., and then aspirate the liquid. After washing, the plate is inverted and tapped try on absorbance tissue. Add 100 µl of TMB (stabilized chromogen substrate) to each well and incubate for 30 min. at RT in the dark. The color will change to blue. Add 100 µl Stop soln. Tap plate gently to mix. The color should change to yellow. Read the plate at A450 nm by setting chromogen blank (=100 µl TMB+100 µl Stop soln) as blank. Read absorbance within 2 hours of assay completion.

Example 68

Caspase-3/7 Assay Protocol

Figure 15:
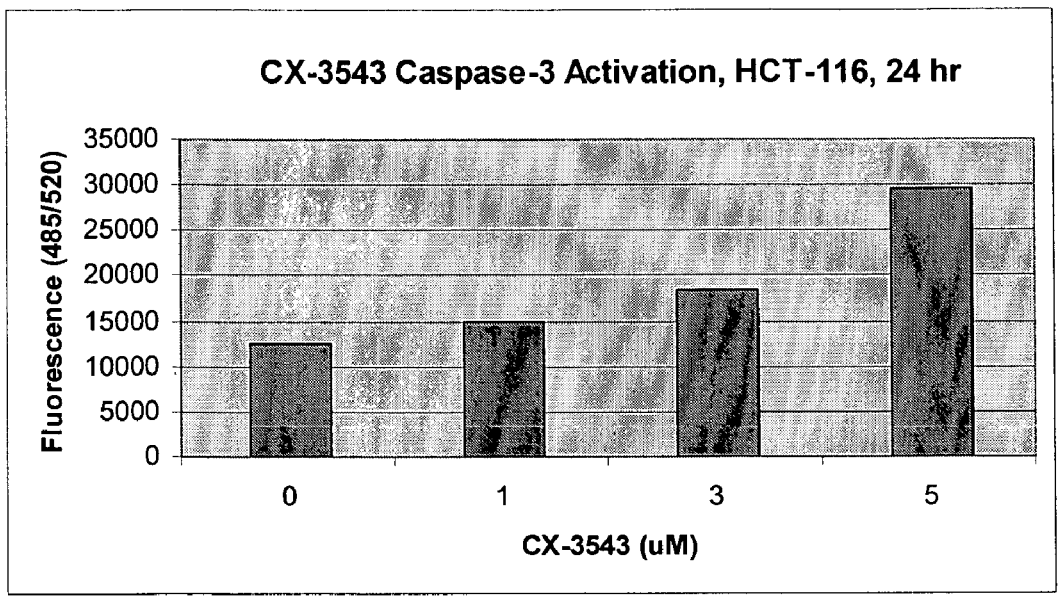
FIG. 15 shows the effect of CX-3543 on caspase-3 activation in HCT-116.

FIG. 15 shows the effect of CX-3543 on caspase-3 activation in HCT-116. Treatment of HCT-116 cells for 24 hr, using a dose range of 1,3 and 5 uM CX-3543 produces a dose responsive increase in caspase-3 levels. Caspase-3 is a major effector caspase in apoptotic induction, and this data is consistent with the induction of apoptosis.

The following protocol was followed (24 hr). On Day 1, seed $0.015 \times 10_6$ HCT-116 cells/50 ul/well. Incubate o/n in 37° C. $CO_2$ incubator. On Day 2, remove 25 ul of medium from wells. Treat HCT-116 cells with 1, 3, 5 uM CX-3543. Treat positive control group with Staurosporin 0.01, 0.1, 1 uM. Keep six negative control wells treated with medium only (add 25 ul of diluted sample to appropriate wells). Incubate for 24 h at 37° C. in a $CO_2$ incubator. On Day 3, prepare Apo-ONE Homogeneous Caspase-3/7 assay reagent (Promega) at 10 ul reagent/1 ml buffer. Add 50 ul of diluted reagent. Incubate one hour at room temp. Measure fluorescence at 485/520.

Example 68

Annexin V-Alexa 488 Staining Protocol

Using Annexin V externalization, a widely used marker of apoptotic response, this study demonstrates the apoptosis inducing capability of CX-3543. Treatment of HCT-116 cells with CX-3543 at 2 uM and 4 uM for 24 hr, gives significant increased staining by a dye positive for Annexin V externalization (X-axis). Camptotlhecin (CPT) was used as the control in the Annexin V experiment. At 0.5 uM CPT, a mixed apoptotic/necrotic response was seen (dye specific for Annexin V—x-axis; dye specific for duplex DNA binding—y-axis).

The following protocol was followed for this example. Seed $1.5-2.0 \times 10^6$ HCT-116 cells/10 cm dish/10 ml medium. Incubate o/n or up to 24 hrs at 37° C. in $CO_2$ incubator. The following day, treat cells with 1, 2, 3, 4 and 5 µM CX-3543. Keep one or two untreated plates (medium only) as control plates. The following controls are used: untreated samples (no Alexa or propidium iodide), controls treated with propidium iodide or Alexa 488 only, and controls treated with both Alexa 488 and propidium iodide. Harvest cells (collect attached as well as floating cells). Wash cells twice with cold PBS. Re-suspend cells in 1× Annexin binding buffer.

Count cells and dilute in 1× Annexin binding buffer to ~$1 \times 10^6$ cells/0.1 ml, preparing a sufficient volume to have 100 µl per assay. Add 5 µl of the Annexin V conjugate to each 100 µl of cell suspension. Add 4 µl of propidium iodide solution (stock=1 mg/ml) to each 100 µl of cell suspension. Incubate sample at RT for 15 minutes. Add 400 µl Annexin binding buffer, mix gently and keep samples on ice. Analyze stained cells immediately by flow cytometry.

Example 69

DNA Cell Cycle Analysis Protocol

Figure 16:
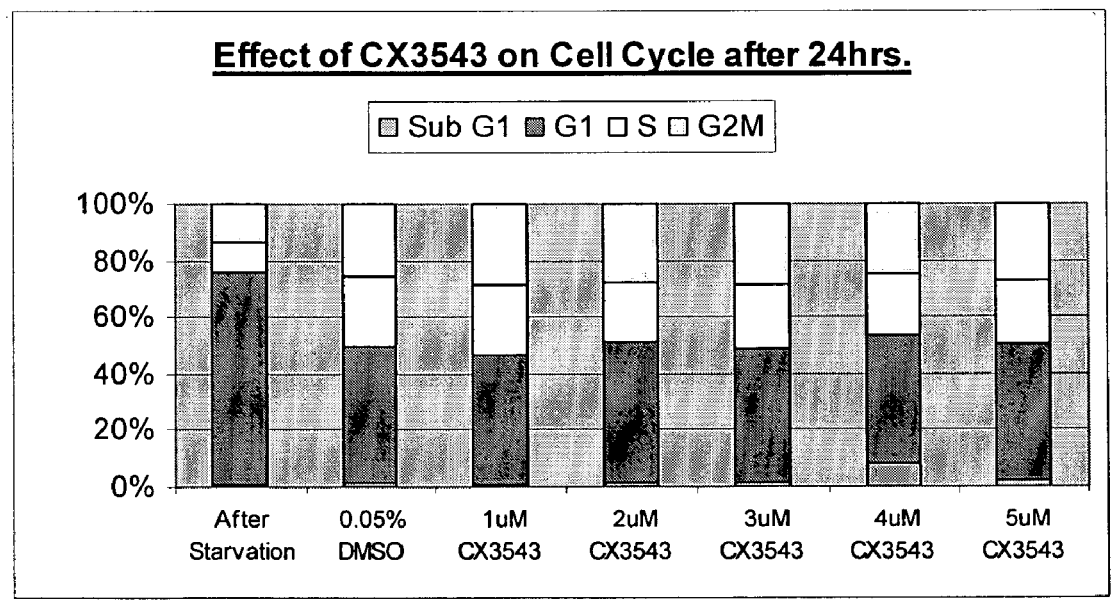
FIG. 16 shows the effect of CX-3543 on cell cycle.

FIG. 16 shows the effect of CX-3543 on cell cycle after 24 hours following a DNA cell cycle analysis. Treating HCT-116 cells (initially serum-starved to synchronize the cells within the cell-cycle) for 24 hr with 1 to 5 um CX-3543 had no observable effect on the distribution of cells throughout the cell cycle.

The following protocol was followed in this example. Seed $1.5-2.0 \times 10^6$ cells/10 cm dish (seed one extra dish for unstained cells). Incubate cells in 37° C. humidified 5% $CO_2$ incubator for 24 hours. For synchronizing cells in a low growth state to make cells quiescent, remove media and rinse once with serum-free media, add 10 ml of serum-free media to each dish. Incubate the cells for 24 hr in a 37° C. humidified 5% $CO_2$ incubator. Remove media and add treatment (diluted in serum contained media, 10 ml): 1-5 µM CX-3543 plus control. Incubate the cells for 24 hr in a 37° C. humidified 5% $CO_2$ incubator.

To trypsinize/isolate cells, remove treatment. Add 3 ml trypsin/EDTA solution. Keep floating cells and combine with attached cells. Incubate for 5 min in a 37° C. humidified 5% $CO_2$ incubator. Add 3 ml media (containing FBS) to wells and pipette into centrifuge tube. Centrifuge at 1000 rpm for 5 minutes. Decant supernatant and re-suspend pellet in 2-3 ml PBS. Count cells and wash cells once by putting $2 \times 10^6$ cells/ tube, adding 2 ml PBS and centrifuging at 1000 rpm for 5 minutes. Re-suspend pelleted cells in 0.3 ml cold PBS.

To fix cells, gently add 0.7 ml ice cold 70% ethanol drop wise to tube containing 0.3 ml of cell suspension in PBS while vortexing. Leave on Ice for one hour (or up to a few days at 4C). Centrifuge at 1000 rpm for 5 minutes. Wash one time with cold PBS (1-2 ml). Centrifuge at 1000 rpm for 5 minutes. Re-suspend cell pellet in 0.25 ml cold PBS, add 5 µl of 10 mg/ml RNAse A (the final concentration being 0.2-0.5 mg/ml). Incubate at 37C for 1 hour. Add 10 µl of 1 mg/ml of propidium iodide solution in deionized water (the final concentration being 10 µl/ml), and keep in the dark and at 4° C. until analysis. Analyze on FACS by reading on cytometer at 488 nm. Cells may be stained with propidium iodide on the same day of analysis.

Example 70

This example describes a method for preparing a substituted benzoxazine analog from reaction of the corresponding ester with an amine, and aluminum chloride.

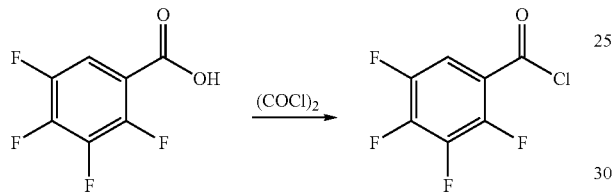

To a solution of 2,3,4,5-tetrafluorobenzoic acid (100 g, 510 mmol), in methylene chloride (0.5 L) was added oxalyl chloride (68 g, 540 mmol) and DMF (ca 3 drops) and the reaction mixture was allowed to stir at room temperature overnight allowing for the produced gasses to escape. The solvent was removed in vacuo and the vessel was placed on high vacuum (ca 0.5 mm Hg) for 2 hours to afford the acid chloride as a viscous oil (105 g) and was used in the subsequent reaction without further purification.

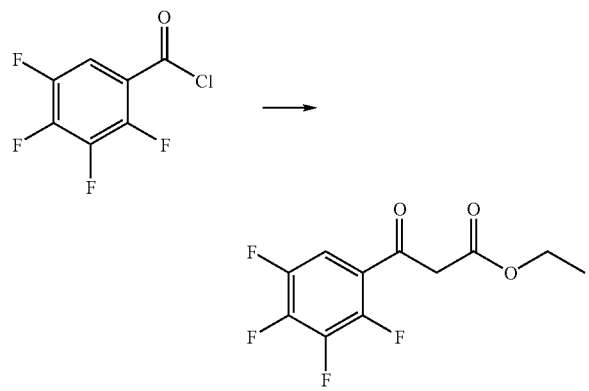

To a suspension of potassium ethyl malonate (97 g, 570 mmol) and magnesium chloride (55 g, 570 mmol) in acetonitrile and the suspension was chilled to 0° C. To this suspension was added the crude 2,3,4,5-benzoyl chloride (105 g, 520 mmol) over 5 minutes. Triethylamine was slowly added at a rate sufficient to keep the reaction temperature below 10° C. and the mixture was allowed to warm to room temperature and was stirred overnight. The solvent was removed in vacuo and replaced with toluene (300 mL) and 1N HCl (500 mL) was added and the mixture was allowed to stir for 1 hour. The organic layer was separated and washed with 1N HCl (100 mL) and brine (100 mL) and dried over sodium sulfate, filtering over a pad of silica gel (50×100 mm), eluting with ethyl acetate. The solvent was removed in vacuo and the resulting oil was dissolved in ethanol/water (9:1) and was allowed to crystallize overnight. The resulting crystals were Isolated by filtration, washing with ethanol/water (8:2) to afford the ketoester (43.75 g, 166 mmol) as a white crystalline solid.

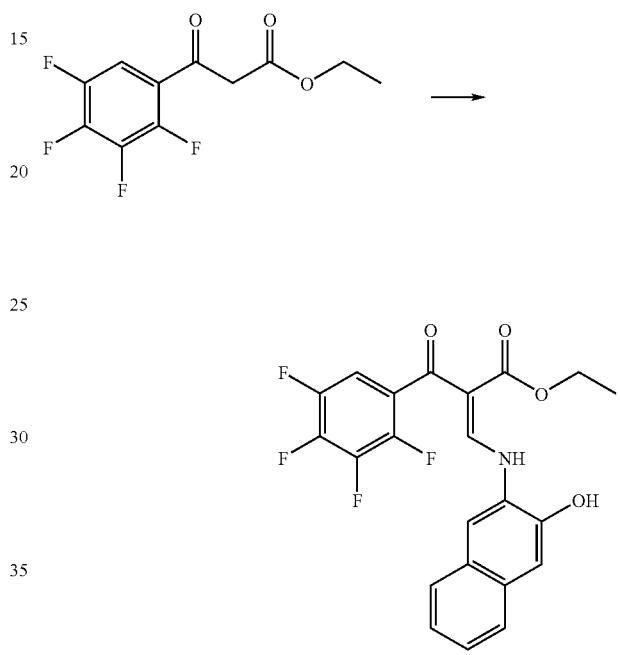

To a 250 mL round bottom flask was added the tetrafluoroketoester (10.0 g, 37.9 mmol), triethylorthoformate (8.6 mL, 56.8 mmol) and acetic anhydride (7.15 mL, 75.8 mmol) and the reaction mixture was heated to 145° C. for 2 hours. The reaction was allowed to cool to room temperature and placed on high vacuum (ca 0.5 mm Hg) for 1 hour. The resulting oil was dissolved in ethanol (100 mL) and 2-amino-1-naphthol (6.02 g, 37.9 mmol) was added at room temperature and the solution became briefly clear and then product began to precipitate. The reaction was allowed to stir for 2 hours and was then filtered and washed with ethanol (100 mL) to afford the enamine as a yellow solid (12.5 g, 28.9 mmol).

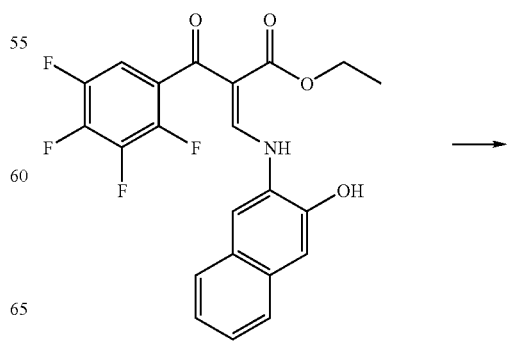

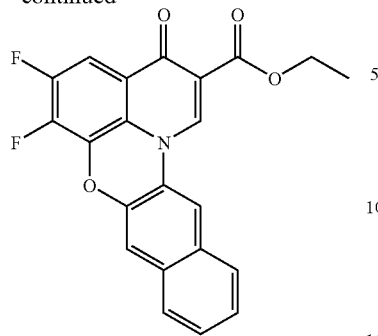

To a solution of the enamine (12.13 g, 27.95 mmol) in dry DMF (50 mL) was added potassium carbonate (4.24 g, 1.1 eq.) and the mixture was heated to 90° C., with constant stirring, for 2 hours. The mixture was allowed to cool to room temperature without stirring and was allowed to remain at room temperature for an additional hour. The crystalline solid was collected by filtration, washing with water. Recrystallization from THF afforded the difluoroester as a white crystalline solid (9.3 g, 23.6 mmol).

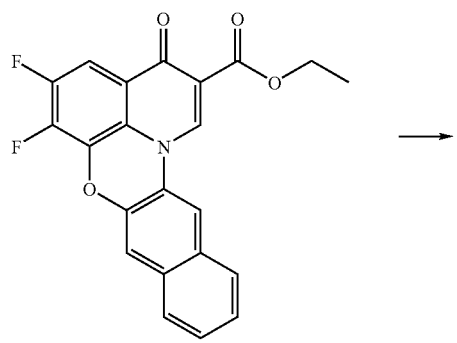

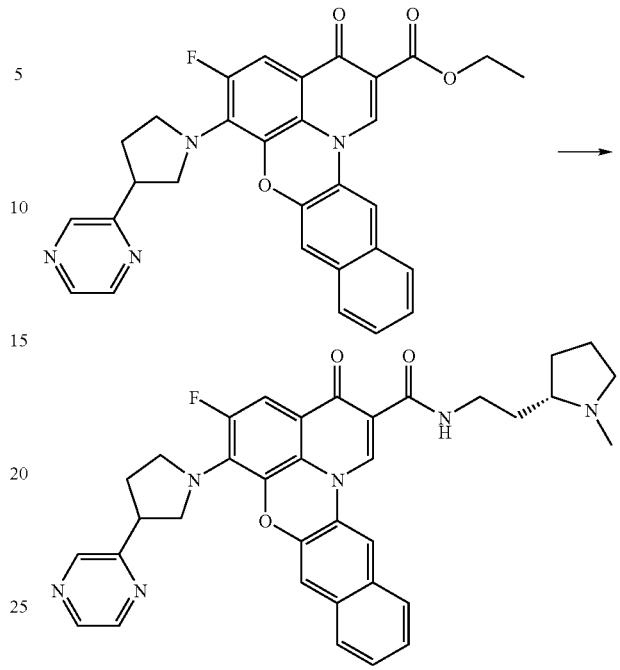

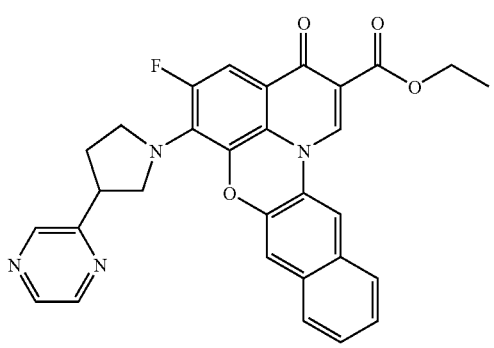

To a solution of the difluoroester (1.0 g, 2.5 mmol) in NMP (10 mL) was added N-Boc-3-(2-pyrazino)pyrrolidine (870 mg, 3.5 mmol) and the mixture was heated to reflux for 3 hours. The reaction mixture was then allowed to cool to room temperature and the product was collected by filtration. Crystallization from THF afforded the pyrazine ester as a yellow solid (910 mg, 1.74 mmol).

To a solution of the pyrazine ester (250 mg, 0.48 mmol) and 2-(2-aminoethyl)-1-methylpyrrolidine (80 mg, 0.63 mmol) in methylene chloride at room temperature was added aluminum chloride (83 mg, 0.63 mmol) and the reaction mixture was allowed to stir for 2 hours. The solvent was removed in vacuo and saturated L-tartaric acid was added (5 mL) and the mixture was allowed to stir for 1 hour. Methylene chloride (10 mL) was then added and the mixture was basified with 1N NaOH. The organic layer was separated and washed with a saturated solution of Rochelle's salt, brine and dried over sodium sulfate. The solvent was removed in vacuo and the resulting solid was dissolved in THF and filtered and the solvent was removed again. The crude solid was recrystallized in ethyl acetate to afford the amide as a yellow solid (225 mg, 0.37 mmol, 98.5% pure).

Example 71

This example describes a method for preparing a substituted benzoxazine analog from reaction of the corresponding carboxylic acid with an amine, and aluminum chloride.

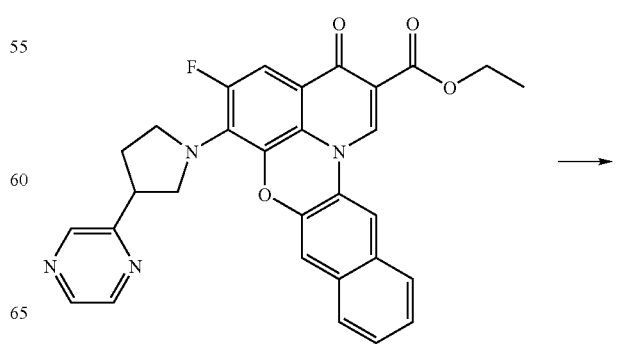

1011

-continued

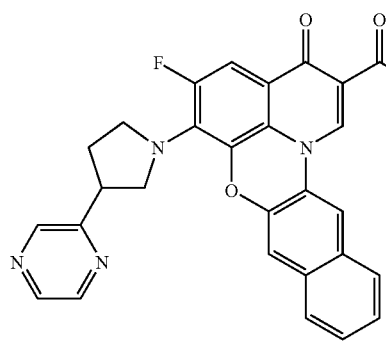

The pyrazinoester (2.0 g, 3.8 mmol) was dissolved in ethanol (100 mL) and conc HCl was added (20 mL) and the mixture was refluxed overnight. The mixture was allowed to cool to room temperature and the solid was collected by vacuum filtration, washing with ethanol to afford the pyrazinoacid as a light tan powder (1.6 g, 3.2 mmol).

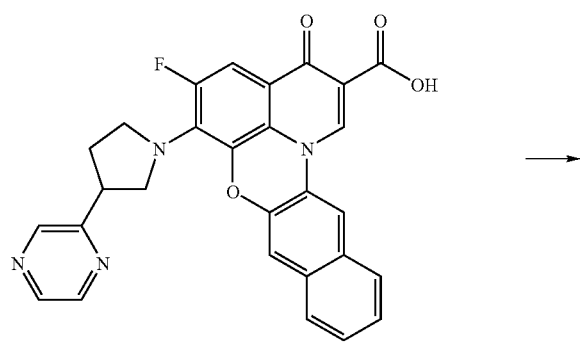

→

1012

-continued

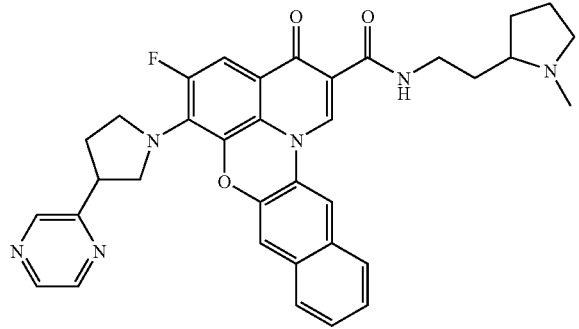

To a mixture of the fluoroaminoacid (1.6 g, 3.2 mmol) and HBTU (2.0 g, 5.3 mmol) in NMP (20 mL) was added N,N-diisopropyl-N-ethylamine (1.0 mL, 6 mmol) and the mixture was allowed to stir at room temperature, under argon, for 1 hour (the solution became clear). (S)-2-(2-aminoethyl)-1-methylpyrrolidine (Mizuno, A.; Hamada, Y.; Shioiri, T., Synthesis, 1980, 12 1007)(1.0 mL, 6.9 mmol) was added and the mixture was allowed to stir for 30 minutes. Water (200 mL) was added and the resulting solid was collected by vacuum filtration, washing with water, and dried to afford the pyrazine as a yellow solid. The yellow solid was purified on silica gel (10% MeOH/CH$_2$Cl$_2$ first eluting off impurities followed by eluting with 5% NH$_4$OH/15% MeOH/CH$_2$Cl$_2$. The combined fractions were evaporated to afford the compound as a yellow solid. (1.2 g, 2.0 mmol, 85% pure).

It is understood that the foregoing detailed description and accompanying examples are merely administrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A method for inducing apoptosis, comprising administering to a system or a subject in need thereof an effective amount of a compound having formula (1A),

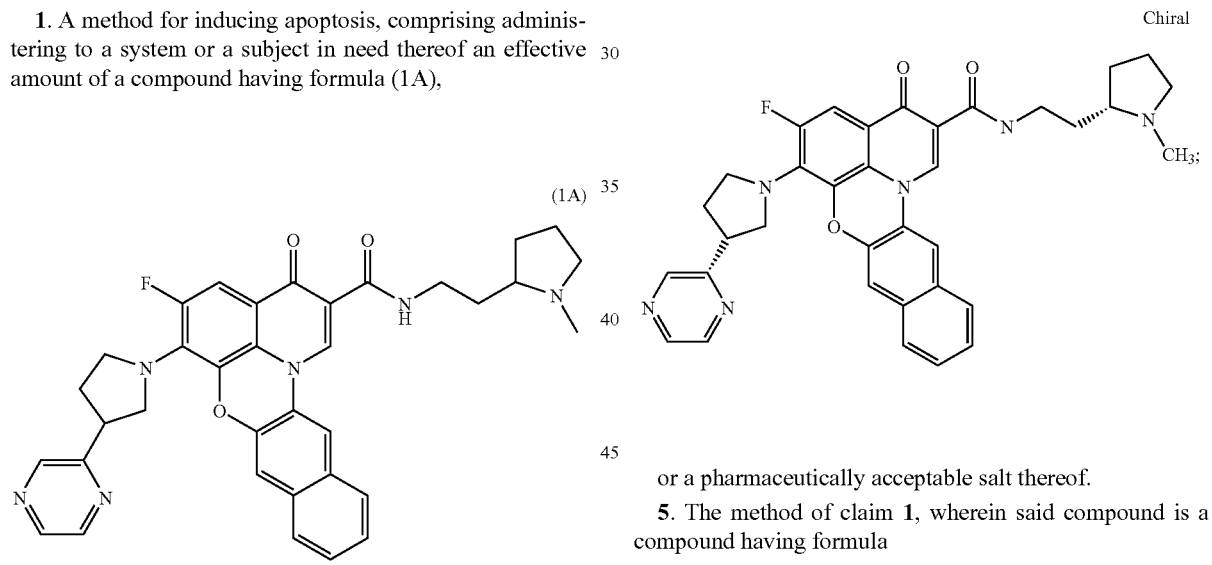

(1A)

or pharmaceutically acceptable salts or pharmaceutical compositions thereof, and optionally with a chemotherapeutic agent.

2. The method of claim 1, wherein said subject is human or an animal.

3. The method of claim 1, wherein said system is a cell or tissue.

4. The method of claim 1, wherein said compound is a compound having formula

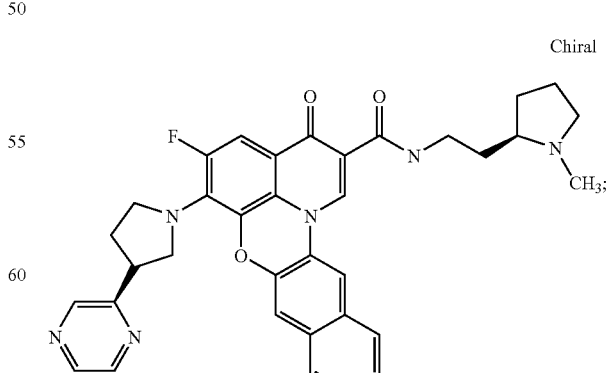

or a pharmaceutically acceptable salt thereof.

5. The method of claim 1, wherein said compound is a compound having formula or a pharmaceutically acceptable salt thereof.

6. The method of claim 1, wherein said compound is a compound having formula

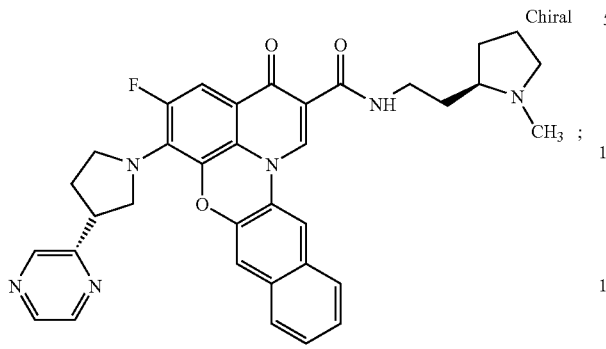

or a pharmaceutically acceptable salt thereof.

7. The method of claim 1, wherein said compound is a compound having formula

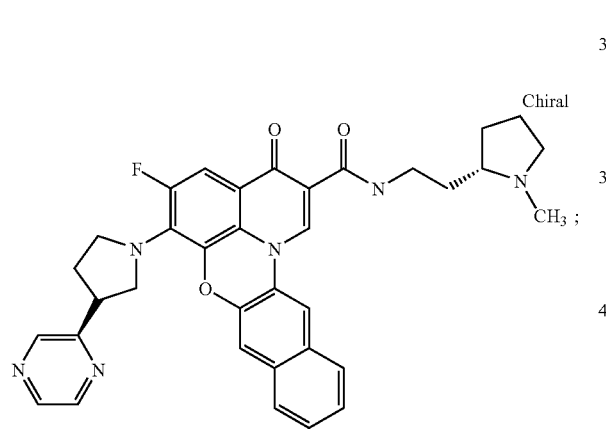

or a pharmaceutically acceptable salt thereof.

8. The method of claim 1, wherein said compound is a compound having formula (1A)

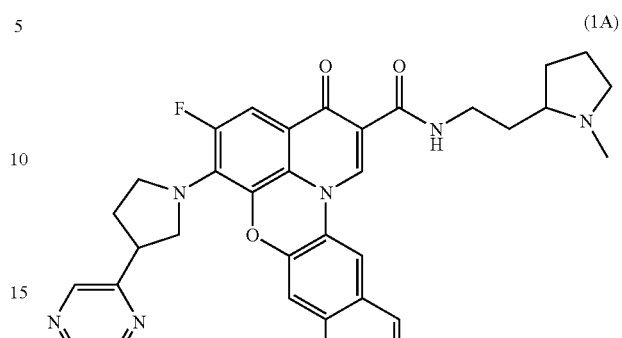

or a pharmaceutically acceptable salt thereof, which has a 50:50 ratio of RS and SS isomers.

9. A method for inducing apoptosis in a cancer cell, comprising contacting said cancer cell with an effective amount of a compound having formula (1A),

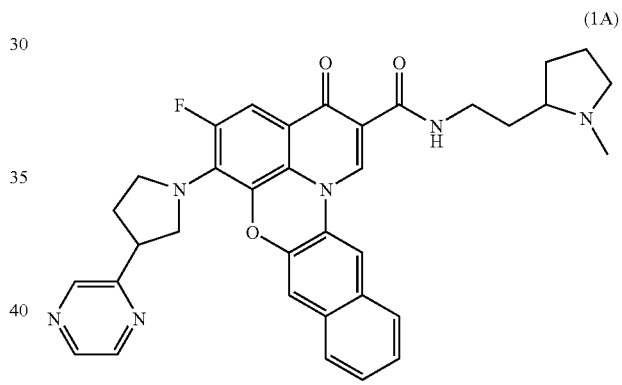

or pharmaceutically acceptable salts or pharmaceutical compositions thereof, and optionally with a chemotherapeutic agent, thereby inducing apoptosis;
wherein said cancer cell is a lymphoma cell, a colorectal cancer cell, a renal cancer cell, a lung cancer cell, a prostate cancer cell, an ovarian cancer cell, a pancreatic cancer cell, a breast cancer cell, or a leukemia cell.

* * * * *

SEQUENCE LISTING

```
<160> NUMBER OF SEQ ID NOS: 29

<210> SEQ ID NO 1
<211> LENGTH: 27
<212> TYPE: DNA
<213> ORGANISM: Homo sapiens

<400> SEQUENCE: 1
tggggagggt ggggagggtg gggaagg                                          27

<210> SEQ ID NO 2
<211> LENGTH: 37
<212> TYPE: DNA
<213> ORGANISM: Homo sapiens

<400> SEQUENCE: 2
gggggggggg gggcgggggc ggggcgggg gagggc                                 37

<210> SEQ ID NO 3
```

```
<211> LENGTH: 57
<212> TYPE: DNA
<213> ORGANISM: Homo sapiens

<400> SEQUENCE: 3 gggggggggac gcgggagctg ggggagggct tggggccagg gcgggcgct taggggg         57

<210> SEQ ID NO 4
<211> LENGTH: 28
<212> TYPE: DNA
<213> ORGANISM: Homo sapiens

<400> SEQUENCE: 4
aggaagggga gggccggggg gaggtggc                                          28

<210> SEQ ID NO 5
<211> LENGTH: 22
<212> TYPE: DNA
<213> ORGANISM: Homo sapiens

<400> SEQUENCE: 5
aggggcgggg cggggcgggg gc                                                22

<210> SEQ ID NO 6
<211> LENGTH: 25
<212> TYPE: DNA
<213> ORGANISM: Homo sapiens

<400> SEQUENCE: 6
gggaggaagg gggcgggagc ggggc                                             25

<210> SEQ ID NO 7
<211> LENGTH: 32
<212> TYPE: DNA
<213> ORGANISM: Homo sapiens

<400> SEQUENCE: 7 gggggggcggg ggcgggcgca gggggagggg gc                                    32

<210> SEQ ID NO 8
<211> LENGTH: 23
<212> TYPE: DNA
<213> ORGANISM: Homo sapiens

<400> SEQUENCE: 8
cggggcgggg cggggcggg ggc                                                23

<210> SEQ ID NO 9
<211> LENGTH: 46
<212> TYPE: DNA
<213> ORGANISM: Homo sapiens

<400> SEQUENCE: 9
```

-continued

```
agaggaggag gaggtcacgg aggaggagga gaaggaggag gaggaa                    46

<210> SEQ ID NO 10
<211> LENGTH: 12
<212> TYPE: DNA
<213> ORGANISM: Homo sapiens

<400> SEQUENCE: 10
ggaggaggag ga                                                         12

<210> SEQ ID NO 11
<211> LENGTH: 38
<212> TYPE: DNA
<213> ORGANISM: Homo sapiens

<400> SEQUENCE: 11
agagaagagg ggaggaggag gaggagagga ggaggcgc                             38

<210> SEQ ID NO 12
<211> LENGTH: 13
<212> TYPE: DNA
<213> ORGANISM: Homo sapiens

<400> SEQUENCE: 12 ggaggggggag ggg                                                       13

<210> SEQ ID NO 13
<211> LENGTH: 27
<212> TYPE: DNA
<213> ORGANISM: Homo sapiens

<400> SEQUENCE: 13
aggagaagga ggaggtggag gaggagg                                         27

<210> SEQ ID NO 14
<211> LENGTH: 33
<212> TYPE: DNA
<213> ORGANISM: Homo sapiens

<400> SEQUENCE: 14
aggaggagga gaatgcgagg aggagggagg aga                                  33

<210> SEQ ID NO 15
<211> LENGTH: 36
<212> TYPE: DNA
<213> ORGANISM: Homo sapiens

<400> SEQUENCE: 15
ggggcgggcc gggggcgggg tcccggcggg gcggag                               36

<210> SEQ ID NO 16
<211> LENGTH: 27
```

```
<212> TYPE: DNA
<213> ORGANISM: Homo sapiens

<400> SEQUENCE: 16
cgggaggagg aggaaggagg aagcgcg                                              27

<210> SEQ ID NO 17
<211> LENGTH: 45
<212> TYPE: DNA
<213> ORGANISM: Homo sapiens
<220> FEATURE:
<223> OTHER INFORMATION: Primer

<400> SEQUENCE: 17
agtctgactg actgtacgta gctaatacga ctcactatag caatt                         45

<210> SEQ ID NO 18
<211> LENGTH: 99
<212> TYPE: DNA
<213> ORGANISM: Homo sapiens
<220> FEATURE:
<223> OTHER INFORMATION: Primer

<400> SEQUENCE: 18
tccaactatg tatactgggg agggtgggga gggtggggaa ggttagcgac acgcaattgc         60
tatagtgagt cgtattagct acgtacagtc agtcagact                                99

<210> SEQ ID NO 19
<211> LENGTH: 15
<212> TYPE: DNA
<213> ORGANISM: Homo sapiens

<400> SEQUENCE: 19
tccaactatg tatac                                                          15

<210> SEQ ID NO 20
<211> LENGTH: 35
<212> TYPE: DNA
<213> ORGANISM: Homo sapiens

<400> SEQUENCE: 20
ttagcgacac gcaattgcta tagtgagtcg tatta                                    35

<210> SEQ ID NO 21
<211> LENGTH: 80
<212> TYPE: DNA
<213> ORGANISM: Homo sapiens

<400> SEQUENCE: 21
tatacggggt gggggaggga gggattagcg acacgcaatt gctatagtga gtcgtattag         60
ctacgtacag tcagtcagac                                                     80

<210> SEQ ID NO 22
<211> LENGTH: 86
```

```
<212> TYPE: DNA
<213> ORGANISM: Homo sapiens

<400> SEQUENCE: 22
ttataccggg gcggggcggg ggcgggggct tagcgacacg caattgctat agtgagtcgt      60
attagctacg tacagtcagt cagact                                          86

<210> SEQ ID NO 23
<211> LENGTH: 97
<212> TYPE: DNA
<213> ORGANISM: Homo sapiens

<400> SEQUENCE: 23 tagggggcggg cgcgggagga aggggggcggg agcggggctg ttagcgacac gcaattgcta    60
tagtgagtcg tattagctac gtacagtcag tcagact                              97

<210> SEQ ID NO 24
<211> LENGTH: 97
<212> TYPE: DNA
<213> ORGANISM: Homo sapiens

<400> SEQUENCE: 24
ttagagaaga ggggaggagg aggaggagag gaggaggcgc ttagcgacac gcaattgcta     60
tagtgagtcg tattagctac gtacagtcag tcagact                              97

<210> SEQ ID NO 25
<211> LENGTH: 99
<212> TYPE: DNA
<213> ORGANISM: Homo sapiens

<400> SEQUENCE: 25
tccaactatg tatactgggg agggtgggga gggtggggaa ggttagcgac acgcaattgc    60
tatagtgagt cgtattagct acgtacagtc agtcagact                            99

<210> SEQ ID NO 26
<211> LENGTH: 99
<212> TYPE: DNA
<213> ORGANISM: Homo sapiens

<400> SEQUENCE: 26
tccaactatg tataccctcc cccaccctcc ccaccctccc cattagcgac acgcaattgc     60
tatagtgagt cgtattagct acgtacagtc agtcagact                            99

<210> SEQ ID NO 27
<211> LENGTH: 95
<212> TYPE: DNA
<213> ORGANISM: Homo sapiens

<400> SEQUENCE: 27
tcatatatga ctacttaggg ttagggttag ggttaggggtt actgccacgc aattgctata    60
gtgagtcgta ttagctacgt acagtcagtc agact                                95
```

-continued

```
<210> SEQ ID NO 28
<211> LENGTH: 89
<212> TYPE: DNA
<213> ORGANISM: Homo sapiens

<400> SEQUENCE: 28
atgatcaccg ggaggaggag gaaggaggaa gcgcgctgcc acgcaattgc tatagtgagt      60
cgtattagct acgtacagtc agtcagact                                        89

<210> SEQ ID NO 29
<211> LENGTH: 45
<212> TYPE: DNA
<213> ORGANISM: Homo sapiens
<220> FEATURE:
<223> OTHER INFORMATION: Primer

<400> SEQUENCE: 29
agtctgactg actgtacgta gctaatacga ctcactatag caatt                      45
```